(12) United States Patent
Kasai et al.

(10) Patent No.: US 9,353,108 B2
(45) Date of Patent: May 31, 2016

(54) TETRAHYDRONAPHTHYRIDINE SOMATOSTATIN RECEPTOR 5 ANTAGONISTS

(71) Applicant: Takeda Pharmaceutical Company Limited, Chuo-ku, Osaka-shi, Osaka (JP)

(72) Inventors: Shizuo Kasai, Kanagawa (JP); Hideki Hirose, Kanagawa (JP); Takeshi Yamasaki, Kanagawa (JP); Tohru Yamashita, Kanagawa (JP); Asato Kina, Kanagawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 14/505,907

(22) Filed: Oct. 3, 2014

(65) Prior Publication Data
US 2015/0099777 A1 Apr. 9, 2015

(30) Foreign Application Priority Data

Oct. 7, 2013 (JP) ................................. 2013-209826

(51) Int. Cl.
*C07D 471/04* (2006.01)

(52) U.S. Cl.
CPC .................................... *C07D 471/04* (2013.01)

(58) Field of Classification Search
CPC .................................................... C07D 471/04
See application file for complete search history.

(56) References Cited

U.S. PATENT DOCUMENTS

| | | | |
|---|---|---|---|
| 2003/0212054 | A1 | 11/2003 | Quan et al. |
| 2004/0224970 | A1 | 11/2004 | Smith et al. |
| 2006/0178399 | A1 | 8/2006 | Nishizawa et al. |
| 2009/0004195 | A1 | 1/2009 | Vranic et al. |

FOREIGN PATENT DOCUMENTS

| | | | |
|---|---|---|---|
| WO | WO 93/22310 A1 | 11/1993 | |
| WO | WO 03/027114 A1 | 4/2003 | |
| WO | WO 03/047520 A2 | 6/2003 | |
| WO | WO 2004/080966 A1 | 9/2004 | |
| WO | WO 2005/047249 A1 | 5/2005 | |
| WO | WO 2008/019967 A2 | 2/2008 | |
| WO | WO 2008/122510 A1 | 10/2008 | |
| WO | WO 2008/148710 A2 | 12/2008 | |
| WO | WO 2009/036117 A1 | 3/2009 | |
| WO | WO 2010/129729 A1 | 11/2010 | |
| WO | WO 2012/024183 A1 | 2/2012 | |
| WO | WO 2012/069917 A1 | 5/2012 | |
| WO | WO 2014/142363 A1 | 9/2014 | |

OTHER PUBLICATIONS

Johnson, A. W. Invitation to Organic Chemistry 1999 Jones and Bartlett: Mississauga, Canada, p. 24.*
Jones, Maitland Organic Chemistry Norton: New York, 1997, p. 84-99.*
Alker "Piperidinyl-nicotinamides as potent and selective somatostatin receptor subtype 5 antagonists" Bioorganic & Medicinal Chemistry Letters 20 (2010) 4521-4525.*
Martin "Discovery of the First Nonpeptidic, Small-Molecule, Highly Selective Somatostatin Receptor Subtype 5 Antagonists: A Chemogenomics Approach" Journal of Medicinal Chemistry, 2007, vol. 50, No. 25 6291.*
Schwetz "Neuropeptide Y and somatostatin inhibit insulin secretion through different mechanisms" Am J Physiol Endocrinol Metab 304: E211-E221, 2013.*
Rai "Therapeutic uses of somatostatin and its analogues: Current view and potential applications" Pharmacology & Therapeutics 152 (2015) 98-110.*
Chisholm et al., "Somatostatin-28 regulates GLP-1 secretion via somatostatin receptor subtype 5 in rat intestinal cultures," Am. J. Physiol. Endocrinol. Metab., 2002, 283:E311-E317.
Patel, Y.C., "Molecular pharmacology of somatostatin receptor subtypes," J. Endocrinol., Invest., 1997, 20:348-367.
Touŕ'e et al., "The Role of the Acidity of N-Heteroaryl Sulfonamides as Inhibitors of Bcl-2 Family Protein-Protein Interactions," ACS Medicinal Chemistry Letters, 2013, 4(2):186-190.
Qiao et al., "Pyrazole-based factor Xa inhibitors containing N-arylpiperidinyl P4 residues," Bioorganic & Medicinal Chemistry Letters, 2007, 17(5):1432-1437.
Registry Compound No. 778571-82-7, ACS on STN (American Chemical Society, Scientific & Technical Information Network), entered Nov. 11, 2004.
Registry Compound No. 768356-31-6, ACS on STN (American Chemical Society, Scientific & Technical Information Network), entered Oct. 25, 2004.
U.S. Appl. No. 14/525,593, filed Oct. 28, 2014, Kasai et al.

* cited by examiner

*Primary Examiner* — David K. O'Dell
(74) *Attorney, Agent, or Firm* — Foley & Lardner LLP

(57) ABSTRACT

A compound having an SSTR5 antagonist action and use of the compound as a medicament are provided. Specifically, a compound represented by the following formula:

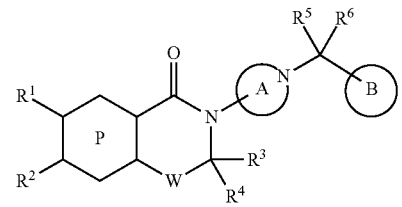

wherein each symbol is as defined herein, or a salt thereof, a medicament comprising the compound or a salt thereof, and use of the compound or a salt thereof as an agent for the prophylaxis or treatment of diabetes mellitus are provided.

8 Claims, No Drawings

TETRAHYDRONAPHTHYRIDINE SOMATOSTATIN RECEPTOR 5 ANTAGONISTS

The present application claims a priority right based on Japanese Patent Application No. 2013-209826 (filed Oct. 7, 2013), the content of which is incorporated herein by reference.

TECHNICAL FIELD

The present invention relates to a heterocyclic compound that has a somatostatin receptor subtype 5 (hereinafter sometimes to be abbreviated as "SSTR5") antagonist action and is useful in the treatment, improvement, or prophylaxis of diseases or states such as diabetes mellitus, insulin resistance, dyslipidemia, obesity, atherosclerosis, cardiovascular disease, metabolic syndrome, neurosis, and the like.

BACKGROUND OF THE INVENTION

Diabetes mellitus (DM) is a disease that causes a pathologic elevation in blood glucose level (glucose concentration in blood) due to impaired insulin secretion or insulin resistance and is known to serve as a risk factor for various serious complications. Diabetes mellitus is reportedly developed by the involvement of various environmental factors (a lack of exercise, overeating, and obesity, etc.) on the basis of genetic factors. The number of diabetes mellitus patients is expected to increase in the future with increases in obese population. Diabetes mellitus is classified into insulin-dependent diabetes mellitus (IDDM) (type 1 diabetes mellitus) and non-insulin-dependent diabetes mellitus (type 2 diabetes mellitus). The great part (about 90%) of diabetes mellitus patients is classified as type 2 diabetes mellitus patients.

Type 1 diabetes mellitus is a disease in which β cells, which secrete insulin in the pancreatic islets of Langerhans, are killed due to various genetic factors and acquired factors. Type 2 diabetes mellitus is a disease that is caused by insufficient amounts of insulin secreted in response to glucose in β cells and by reduction in insulin sensitivity in peripheral tissues (liver, muscle, and fat, etc.).

As for the treatment and prophylaxis of diabetes mellitus, diet therapy and exercise therapy as well as medication is practiced.

Examples of current typical medication include medication involving subcutaneously administering insulin, an insulin analog, or a GLP-1 (glucagon-like peptide-1) analog or the like, and medication using an orally administrable hypoglycemic drug. The orally administrable hypoglycemic drug includes sulfonylureas (SU drugs) such as glimepiride and the like; biguanides (BG drugs) such as metformin and the like; α-glucosidase inhibitors (αGI drugs) such as voglibose, miglitol, and the like; thiazolidine derivatives (TZD drugs) such as pioglitazone and the like; DPP-IV (dipeptidyl peptidase-IV) inhibitors such as Sitagliptin, Alogliptin, and the like; etc.

Somatostatin is widely distributed in the central nervous system including the hypothalamus and the like, the pancreatic islets of Langerhans, and the intestinal mucosa, etc., and plays an important role in the control of gastrointestinal motility, digestive juice secretion, and glucose or lipid metabolism. Particularly, in living organisms, somatostatin is known to suppressively act on the production or secretion of various hormones, growth factors, and biologically active substances. The hormones on which somatostatin suppressively acts include growth hormone (GH), thyroid stimulating hormone (TSH), prolactin, insulin, glucagon, gastrin, secretin, peptide YY (PYY), gastric inhibitory polypeptide (GIP), GLP-1, cholecystokinin (CCK), vasoactive intestinal peptide (VIP), oxyntomodulin, and the like. In addition, somatostatin also acts as paracrine in the pancreatic islets of Langerhans or the mucosa of gastrointestinal tract where δ cells are in contact with α cells and β cells. Somatostatin therefore has diverse biological functions in the endocrine system, the exocrine system, and the nervous system, etc.

Somatostatin receptor is a seven-transmembrane G protein-coupled receptor. Five subtypes have been found so far and respectively designated as SSTR1, SSTR2, SSTR3, SSTR4, and SSTR5 (Non Patent Literature 1). Among them, SSTR5 has been shown to participate in the regulation of insulin and incretin secretions (Non Patent Literature 2).

Meanwhile, Patent Literature 1 has reported that the following compound has an SSTR5 antagonist action:

[Formula 1]

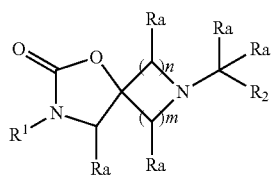

I wherein each Ra is independently selected from the group consisting of a hydrogen atom, a halogen atom, a $C_{1-10}$ alkyl group, and a halogen atom-substituted $C_{1-10}$ alkyl group; $R^1$ is selected from the group consisting of a hydrogen atom, substituted phenyl, and a substituted heterocyclic ring; $R^2$ is selected from the group consisting of substituted aryl and a substituted heterocyclic ring; and n and m are each independently selected from the group consisting of 1, 2, and 3.

Toure et al. describe, as a Bcl-2 antagonist, a compound represented by the following formula:

[Formula 2]

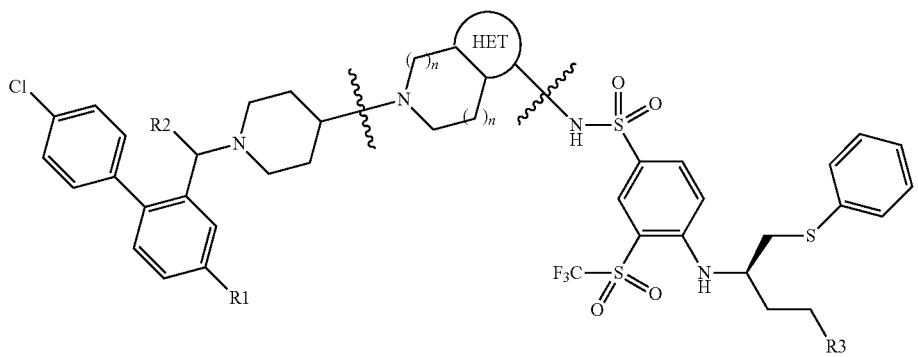

n = 0, 1, or 2 and disclose, as one example thereof, Compound 20 represented by the above-mentioned formula wherein R1 is F, R2 is H, R3 is NMe₂, and HET has the following structure (Non Patent Literature 3):

[Formula 3]

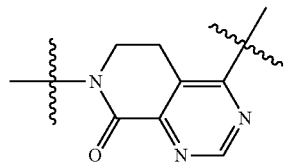

Qiao et al. have reported that the following compound has Factor Xa inhibitory activity and may be used as an antithrombotic agent (Non Patent Literature 4):

[Formula 4]

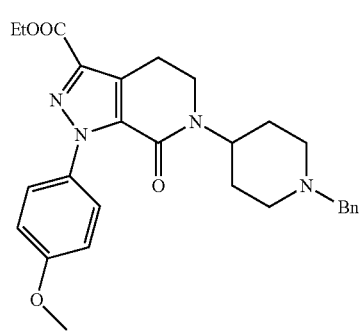

Patent Literature 2 describes a compound substituted by substituted aminomethyl, which is a Factor Xa inhibitor, and discloses the following compound as a preferable form thereof:

[Formula 5]

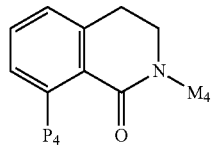

wherein $P_4$ represents a particular cyclic moiety such as 4-methoxyphenyl, 2-aminomethylphenyl, 2-naphthyl, or the like; and $M_4$ represents a particular cyclic moiety represented by A-B (A: a 5-membered or 6-membered carbocyclic or nitrogen-containing heterocyclic ring, B: a 5-membered or 6-membered carbocyclic or nitrogen-containing heterocyclic ring having a substituted aminomethyl group).

Also, Patent Literature 3 has reported that the following compound may be used as a therapeutic drug for obesity and obesity-related disorders:

[Formula 6]

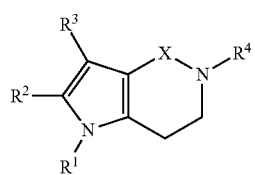

wherein $R^1$ represents optionally substituted phenyl; $R^2$ represents hydrogen or optionally substituted phenyl; $R^3$ represents hydrogen, $C_{1-6}$ alkyl, or benzyl; $R^4$ represents hydrogen, optionally substituted (e.g., benzyl-substituted) piperidin-3-yl, piperidin-4-yl, or the like; and X represents —C(=O)— or methylene.

In addition to those mentioned above, the following compounds are known under CAS Registration Nos. 778571-82-7 and 768356-31-6:

[Formula 7]

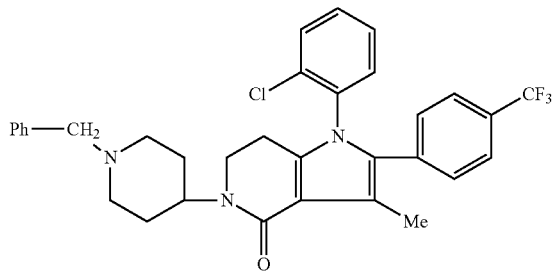

RN: 778571-82-7

[Formula 8]

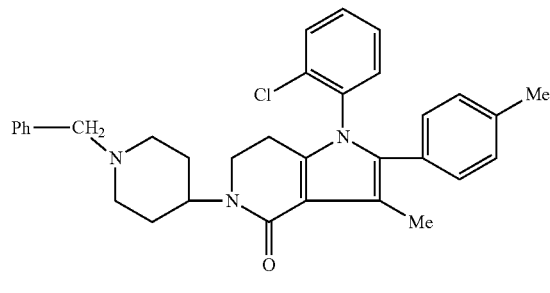

RN: 768356-31-6

CITATION LIST

Patent Literature

[Patent Literature 1] International Publication No. WO 2012/024183
[Patent Literature 2] International Publication No. WO 2003/047520
[Patent Literature 3] International Publication No. WO 2003/027114

Non Patent Literature

[Non Patent Literature 1] Patel Y C: "Molecular pharmacology of somatostatin receptor subtypes." J Endocrinol Invest 20: 348-367, 1997
[Non Patent Literature 2] Chisholm C et al.: "Somatostatin-28 regulates GLP-1 secretion via somatostatin receptor subtype 5 in rat intestinal cultures." Am J Physiol Endocrinol Metab 283: E311-317, 2002

[Non Patent Literature 3] B. Barry Toure et al.: "The Role of the Acidity of N-Heteroaryl Sulfonamides as Inhibitors of Bcl-2 Family Protein-Protein Interactions." ACS Medicinal Chemistry Letters 4 (2): 186-190, 2013

[Non Patent Literature 4] Qiao J X et al.: "Pyrazole-based factor Xa inhibitors containing N-arylpiperidinyl P4 residues." Bioorganic & Medicinal Chemistry Letters 17 (5): 1432-1437, 2007

SUMMARY OF INVENTION

Technical Problem

There has been a demand for the development of a compound that has an SSTR5 antagonist action and is useful in the treatment, improvement, or prophylaxis of diseases or states such as diabetes mellitus, insulin resistance, dyslipidemia, obesity, atherosclerosis, cardiovascular disease, metabolic syndrome, neurosis, and the like.

Solution to Problem

The present inventors have found for the first time a compound represented by the following formula:

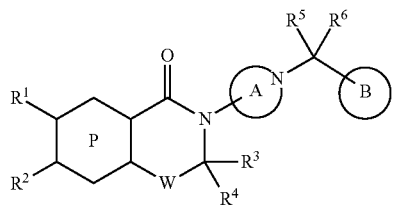

[Formula 9]

wherein ring P represents a 6-membered aromatic heterocyclic ring;

ring A represents an optionally substituted 4- to 7-membered nitrogen-containing saturated heterocyclic ring;

ring B represents an optionally substituted benzene ring or an optionally substituted heterocyclic ring:

$R^1$ and $R^2$ each independently represent a hydrogen atom, an optionally substituted $C_{1-6}$ alkyl group, a $C_{3-10}$ cycloalkyl group, or $CO_2R$ (wherein R represents a hydrogen atom or an optionally substituted $C_{1-6}$ alkyl group);

either one of $R^1$ and $R^2$ is $CO_2R$;

W represents a $C_{1-2}$ alkylene group optionally substituted by a $C_{1-6}$ alkyl group; and $R^3$, $R^4$, $R^5$, and $R^6$ each independently represent a hydrogen atom or a $C_{1-6}$ alkyl group, or a salt thereof (hereinafter sometimes to be referred to as compound (I)) has a superior SSTR5 antagonist action, is useful in the treatment, improvement, or prophylaxis of diseases or states such as diabetes mellitus, insulin resistance, metabolic syndrome, dyslipidemia, obesity, atherosclerosis, cardiovascular disease, neurosis, and the like, and has superior efficacy. On the basis of this finding, the present inventors have conducted intensive studies, which resulted in the completion of the present invention.

Accordingly, the present invention relates to

[1] a compound represented by the following formula:

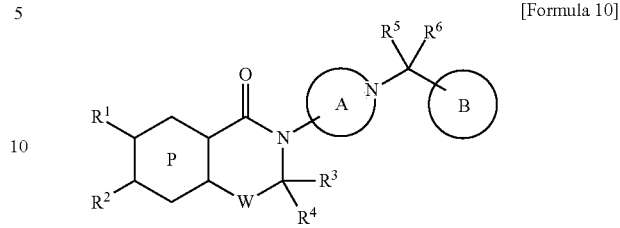

[Formula 10]

wherein ring P represents a 6-membered aromatic heterocyclic ring;

ring A represents an optionally substituted 4- to 7-membered nitrogen-containing saturated heterocyclic ring;

ring B represents an optionally substituted benzene ring or an optionally substituted heterocyclic ring;

$R^1$ and $R^2$ each independently represent a hydrogen atom, an optionally substituted $C_{1-6}$ alkyl group, a $C_{3-10}$ cycloalkyl group, or $CO_2R$ (wherein R represents a hydrogen atom or an optionally substituted $C_{1-6}$ alkyl group);

either one of $R^1$ and $R^2$ is $CO_2R$;

W represents a $C_{1-2}$ alkylene group optionally substituted by a $C_{1-6}$ alkyl group; and $R^3$, $R^4$, $R^5$, and $R^6$ each independently represent a hydrogen atom or a $C_{1-6}$ alkyl group, or a salt thereof;

[2] The compound according to the above-mentioned [1] or a salt thereof, wherein ring P is pyridine;

[3] The compound according to any one of the above-mentioned [1] and [2] or a salt thereof, wherein ring A is piperidine, azetidine, or pyrrolidine;

[4] The compound according to any one of the above-mentioned [1] to [3] or a salt thereof, wherein ring B is (1) a benzene ring optionally substituted by 1 to 4 substituents selected from:

a halogen atom; a $C_{3-10}$ cycloalkyl group; a $C_{1-6}$ alkoxy group; and a $C_{6-14}$ aryl group optionally substituted by 1 to 3 halogen atom(s), or (2) pyridine, indole, or pyrazole each optionally substituted by 1 to 3 substituents selected from:

a $C_{1-6}$ alkyl group; a $C_{3-10}$ cycloalkyl group; a $C_{1-6}$ alkoxy group; and a $C_{6-14}$ aryl group optionally substituted by 1 to 3 halogen atom(s);

[5] The compound according to any one of the above-mentioned [1] to [4] or a salt thereof, wherein $R^1$ is a hydrogen atom or COOH, $R^2$ is a hydrogen atom, a $C_{1-6}$ alkyl group optionally substituted by a $C_{1-6}$ alkoxy group, a $C_{3-10}$ cycloalkyl group, or COOH, and either one of $R^1$ and $R^2$ is COOH;

[6] The compound according to any one of the above-mentioned [1] to [5] or a salt thereof, wherein W is methylene;

[7] The compound according to any one of the above-mentioned [1] to [6] or a salt thereof, wherein each of $R^3$, $R^4$, $R^5$, and $R^6$ is a hydrogen atom;

[8] The compound according to the above-mentioned [1] or a salt thereof, wherein ring P is pyridine; W is methylene; the pyridine constitutes optionally substituted tetrahydronaphthyridine together with the adjacent ring;

ring A is piperidine, azetidine, or pyrrolidine;

ring B is (1) a benzene ring optionally substituted by 1 to 4 substituents selected from:

a halogen atom; a $C_{3-10}$ cycloalkyl group; a $C_{1-6}$ alkoxy group; and a $C_{6-14}$ aryl group optionally substituted by 1 to 3 halogen atom(s), or (2) pyridine, indole, or pyrazole each optionally substituted by 1 to 3 substituents selected from: a $C_{1-6}$ alkyl group; a $C_{3-10}$ cycloalkyl group; a $C_{1-6}$ alkoxy group; and a $C_{6-14}$ aryl group optionally substituted by 1 to 3 halogen atom(s), $R^1$ is a hydrogen atom or COOH; $R^2$ is a hydrogen atom, a $C_{1-6}$ alkyl group optionally substituted by a $C_{1-6}$ alkoxy group, a $C_{3-10}$ cycloalkyl group, or COOH; and either one of $R^1$ and $R^2$ is COOH, and each of $R^3$, $R^4$, $R^5$, and $R^6$ is a hydrogen atom;

[9] 6-(1-((2-Cyclopropyl-5-ethoxy-2',4'-difluorobiphenyl-4-yl)methyl)piperidin-4-yl)-5-oxo-2-propyl-5,6,7,8-tetrahydro-1,6-naphthyridine-3-carboxylic acid or a salt thereof;

[10] 6-(1-((6-Cyclopropyl-3-ethoxy-2,4'-difluorobiphenyl-4-yl)methyl)piperidin-4-yl)-5-oxo-2-propyl-5,6,7,8-tetrahydro-1,6-naphthyridine-3-carboxylic acid or a salt thereof;

[11] 6-(1-((6-Cyclopropyl-2,4'-difluoro-3-isopropoxybiphenyl-4-yl)methyl)piperidin-4-yl)-2-ethyl-5-oxo-5,6,7,8-tetrahydro-1,6-naphthyridine-3-carboxylic acid or a salt thereof;

[12] 6-(1-((6-Cyclopropyl-3-ethoxy-2,4'-difluorobiphenyl-4-yl)methyl)piperidin-4-yl)-2-ethyl-5-oxo-5,6,7,8-tetrahydro-1,6-naphthyridine-3-carboxylic acid or a salt thereof;

[13] A medicament comprising the compound of the above-mentioned [1] or a salt thereof;

[14] The medicament of the above-mentioned [13], which is a somatostatin receptor 5 antagonist;

[15] The medicament of the above-mentioned [13], which is an agent for the prophylaxis or treatment of diabetes mellitus;

[16] A method for preventing or treating diabetes mellitus in a mammal, comprising administering to the mammal an effective amount of the compound according to the above-mentioned [1] or a salt thereof;

[17] A method for antagonizing somatostatin receptor subtype 5 in a mammal, comprising administering to the mammal an effective amount of the compound according to the above-mentioned [1] or a salt thereof;

[18] Use of the compound according to the above-mentioned [1] or a salt thereof in the production of an agent for the prophylaxis or treatment of diabetes mellitus;

[19] The compound according to the above-mentioned [1] or a salt thereof for use in the prohylaxis or treatment of diabetes mellitus.

Advantageous Effects of Invention

Compound (I) has a superior SSTR5 antagonist action, is useful in the treatment, improvement, and prophylaxis of diseases or states such as diabetes mellitus, insulin resistance, metabolic syndrome, dyslipidemia, obesity, atherosclerosis, cardiovascular disease, neurosis, and the like, and has superior efficacy.

DETAILED DESCRIPTION OF THE INVENTION

The definition of each substituent used in the present specification is described in detail in the following. Unless otherwise specified, each substituent has the following definition.

In the present specification, examples of the "halogen atom" include fluorine, chlorine, bromine and iodine.

In the present specification, examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

In the present specification, examples of the "optionally halogenated $C_{1-6}$ alkyl group" include a $C_{1-6}$ alkyl group optionally having 1 to 7, preferably 1 to 5, halogen atoms. Specific examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl.

In the present specification, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.

In the present specification, examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl.

In the present specification, examples of the "$C_{3-10}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl and adamantyl.

In the present specification, examples of the "optionally halogenated $C_{3-10}$ cycloalkyl group" include a $C_{3-10}$ cycloalkyl group optionally having 1 to 7, preferably 1 to 5, halogen atoms. Specific examples thereof include cyclopropyl, 2,2-difluorocyclopropyl, 2,3-difluorocyclopropyl, cyclobutyl, difluorocyclobutyl, cyclopentyl, cyclohexyl, cycloheptyl and cyclooctyl.

In the present specification, examples of the "$C_{3-10}$ cycloalkenyl group" include cyclopropenyl, cyclobutenyl, cyclopentenyl, cyclohexenyl, cycloheptenyl and cyclooctenyl.

In the present specification, examples of the "$C_{6-14}$ aryl group" include phenyl, 1-naphthyl, 2-naphthyl, 1-anthryl, 2-anthryl and 9-anthryl.

In the present specification, examples of the "$C_{7-16}$ aralkyl group" include benzyl, phenethyl, naphthylmethyl and phenylpropyl.

In the present specification, examples of the "$C_{1-6}$ alkoxy group" include methoxy, ethoxy, propoxy, isopropoxy, butoxy, isobutoxy, sec-butoxy, tert-butoxy, pentyloxy and hexyloxy.

In the present specification, examples of the "optionally halogenated $C_{1-6}$ alkoxy group" include a $C_{1-6}$ alkoxy group optionally having 1 to 7, preferably 1 to 5, halogen atoms. Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.

In the present specification, examples of the "$C_{3-10}$ cycloalkyloxy group" include cyclopropyloxy, cyclobutyloxy, cyclopentyloxy, cyclohexyloxy, cycloheptyloxy and cyclooctyloxy.

In the present specification, examples of the "$C_{1-6}$ alkylthio group" include methylthio, ethylthio, propylthio, isopropylthio, butylthio, sec-butylthio, tert-butylthio, pentylthio and hexylthio.

In the present specification, examples of the "optionally halogenated $C_{1-6}$ alkylthio group" include a $C_{1-6}$ alkylthio group optionally having 1 to 7, preferably 1 to 5, halogen atoms. Specific examples thereof include methylthio, difluoromethylthio, trifluoromethylthio, ethylthio, propylthio, isopropylthio, butylthio, 4,4,4-trifluorobutylthio, pentylthio and hexylthio.

In the present specification, examples of the "$C_{1-6}$ alkyl-carbonyl group" include acetyl, propanoyl, butanoyl, 2-methylpropanoyl, pentanoyl, 3-methylbutanoyl, 2-methylbutanoyl, 2,2-dimethylpropanoyl, hexanoyl and heptanoyl.

In the present specification, examples of the "optionally halogenated $C_{1-6}$ alkyl-carbonyl group" include a $C_{1-6}$ alkyl-carbonyl group optionally having 1 to 7, preferably 1 to 5, halogen atoms. Specific examples thereof include acetyl, chloroacetyl, trifluoroacetyl, trichloroacetyl, propanoyl, butanoyl, pentanoyl and hexanoyl.

In the present specification, examples of the "$C_{1-6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

In the present specification, examples of the "$C_{6-14}$ aryl-carbonyl group" include benzoyl, 1-naphthoyl and 2-naphthoyl.

In the present specification, examples of the "$C_{7-16}$ aralkyl-carbonyl group" include phenylacetyl and phenylpropionyl.

In the present specification, examples of the "5- to 14-membered aromatic heterocyclylcarbonyl group" include nicotinoyl, isonicotinoyl, thenoyl and furoyl.

In the present specification, examples of the "3- to 14-membered non-aromatic heterocyclylcarbonyl group" include morpholinylcarbonyl, piperidinylcarbonyl and pyrrolidinylcarbonyl.

In the present specification, examples of the "mono- or di-$C_{1-6}$alkyl-carbamoyl group" include methylcarbamoyl, ethylcarbamoyl, dimethylcarbamoyl, diethylcarbamoyl and N-ethyl-N-methylcarbamoyl.

In the present specification, examples of the "mono- or di-$C_{7-16}$ aralkyl-carbamoyl group" include benzylcarbamoyl and phenethylcarbamoyl.

In the present specification, examples of the "$C_{1-6}$ alkylsulfonyl group" include methylsulfonyl, ethylsulfonyl, propylsulfonyl, isopropylsulfonyl, butylsulfonyl, sec-butylsulfonyl and tert-butylsulfonyl.

In the present specification, examples of the "optionally halogenated $C_{1-6}$ alkylsulfonyl group" include a $C_{1-6}$ alkylsulfonyl group optionally having 1 to 7, preferably 1 to 5, halogen atoms. Specific examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl and hexylsulfonyl.

In the present specification, examples of the "$C_{6-14}$ arylsulfonyl group" include phenylsulfonyl, 1-naphthylsulfonyl and 2-naphthylsulfonyl.

In the present specification, examples of the "substituent" include a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group and an optionally substituted silyl group.

In the present specification, examples of the "hydrocarbon group" (including "hydrocarbon group" of "optionally substituted hydrocarbon group") include a $C_{1-6}$ alkyl group, a $C_{2-6}$ alkenyl group, a $C_{2-6}$ alkynyl group, a $C_{3-10}$ cycloalkyl group, a $C_{3-10}$ cycloalkenyl group, a $C_{6-14}$ aryl group and a $C_{7-16}$ aralkyl group.

In the present specification, examples of the "optionally substituted hydrocarbon group" include a hydrocarbon group optionally having substituent(s) selected from the following substituent group A.

[Substituent Group A]
(1) a halogen atom,
(2) a nitro group,
(3) a cyano group,
(4) an oxo group,
(5) a hydroxy group,
(6) an optionally halogenated $C_{1-6}$ alkoxy group,
(7) a $C_{6-14}$ aryloxy group (e.g., phenoxy, naphthoxy),
(8) a $C_{7-16}$ aralkyloxy group (e.g., benzyloxy),
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a $C_{1-6}$ alkyl-carbonyloxy group (e.g., acetoxy, propanoyloxy),
(12) a $C_{6-14}$ aryl-carbonyloxy group (e.g., benzoyloxy, 1-naphthoyloxy, 2-naphthoyloxy),
(13) a $C_{1-6}$ alkoxy-carbonyloxy group (e.g., methoxycarbonyloxy, ethoxycarbonyloxy, propoxycarbonyloxy, butoxycarbonyloxy),
(14) a mono- or di-$C_{1-6}$alkyl-carbamoyloxy group (e.g., methylcarbamoyloxy, ethylcarbamoyloxy, dimethylcarbamoyloxy, diethylcarbamoyloxy),
(15) a $C_{6-14}$ aryl-carbamoyloxy group (e.g., phenylcarbamoyloxy, naphthylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy),
(19) a $C_{6-14}$ arylsulfonyloxy group optionally substituted by a $C_{1-6}$ alkyl group (e.g., phenylsulfonyloxy, toluenesulfonyloxy),
(20) an optionally halogenated $C_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1-6}$ alkyl-carbonyl group,
(26) a $C_{6-14}$ aryl-carbonyl group,
(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,
(30) a $C_{6-14}$ aryloxy-carbonyl group (e.g., phenyloxycarbonyl, 1-naphthyloxycarbonyl, 2-naphthyloxycarbonyl),
(31) a $C_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-$C_{1-6}$alkyl-carbamoyl group,
(35) a $C_{6-14}$ aryl-carbamoyl group (e.g., phenylcarbamoyl),
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(39) a $C_{6-14}$ arylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,
(42) a $C_{6-14}$ arylsulfinyl group (e.g., phenylsulfinyl, 1-naphthylsulfinyl, 2-naphthylsulfinyl),

(43) a 5- to 14-membered aromatic heterocyclylsulfinyl group (e.g., pyridylsulfinyl, thienylsulfinyl),
(44) an amino group,
(45) a mono- or di-$C_{1-6}$alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-$C_{6-14}$ arylamino group (e.g., phenylamino),
(47) a 5- to 14-membered aromatic heterocyclylamino group (e.g., pyridylamino),
(48) a $C_{7-16}$ aralkylamino group (e.g., benzylamino),
(49) a formylamino group,
(50) a $C_{1-6}$ alkyl-carbonylamino group (e.g., acetylamino, propanoylamino, butanoylamino),
(51) a ($C_{1-6}$ alkyl) ($C_{1-6}$ alkyl-carbonyl)amino group (e.g., N-acetyl-N-methylamino),
(52) a $C_{6-14}$ aryl-carbonylamino group (e.g., phenylcarbonylamino, naphthylcarbonylamino),
(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(54) a $C_{7-16}$ aralkyloxy-carbonylamino group (e.g., benzyloxycarbonylamino),
(55) a $C_{1-6}$ alkylsulfonylamino group (e.g., methylsulfonylamino, ethylsulfonylamino),
(56) a $C_{6-14}$ arylsulfonylamino group optionally substituted by a $C_{1-6}$ alkyl group (e.g., phenylsulfonylamino, toluenesulfonylamino),
(57) an optionally halogenated $C_{1-6}$ alkyl group,
(58) a $C_{2-6}$ alkenyl group,
(59) a $C_{2-6}$ alkynyl group,
(60) a $C_{3-10}$ cycloalkyl group,
(61) a $C_{3-10}$ cycloalkenyl group and
(62) a $C_{6-14}$ aryl group.

The number of the above-mentioned substituents in the "optionally substituted hydrocarbon group" is, for example, 1 to 5, preferably 1 to 3. When the number of the substituents is two or more, the respective substituents may be the same or different.

In the present specification, examples of the "heterocyclic group" (including "heterocyclic group" of "optionally substituted heterocyclic group") include (i) an aromatic heterocyclic group, (ii) a non-aromatic heterocyclic group and (iii) a 7- to 10-membered bridged heterocyclic group, each containing, as a ring-constituting atom besides carbon atom, 1 to 4 hetero atoms selected from a nitrogen atom, a sulfur atom and an oxygen atom.

In the present specification, examples of the "aromatic heterocyclic group" (including "5- to 14-membered aromatic heterocyclic group") include a 5- to 14-membered (preferably 5- to 10-membered) aromatic heterocyclic group containing, as a ring-constituting atom besides carbon atom, 1 to 4 hetero atoms selected from a nitrogen atom, a sulfur atom and an oxygen atom. Preferable examples of the "aromatic heterocyclic group" include 5- or 6-membered monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like; and 8- to 14-membered fused polycyclic (preferably bi or tricyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, β-carbolinyl, phenanthridinyl, acridinyl, phenazinyl, phenothiazinyl, phenoxazinyl and the like.

In the present specification, examples of the "non-aromatic heterocyclic group" (including "3- to 14-membered non-aromatic heterocyclic group") include a 3- to 14-membered (preferably 4- to 10-membered) non-aromatic heterocyclic group containing, as a ring-constituting atom besides carbon atom, 1 to 4 hetero atoms selected from a nitrogen atom, a sulfur atom and an oxygen atom.

Preferable examples of the "non-aromatic heterocyclic group" include 3- to 8-membered monocyclic non-aromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and
9- to 14-membered fused polycyclic (preferably bi or tricyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacrydinyl, tetrahydrophenazinyl, tetrahydrothioxanthenyl, octahydroisoquinolyl and the like.

In the present specification, preferable examples of the "7- to 10-membered bridged heterocyclic group" include quinuclidinyl and 7-azabicyclo[2.2.1]heptanyl.

In the present specification, examples of the "nitrogen-containing heterocyclic group" include a "heterocyclic group" containing at least one nitrogen atom as a ring-constituting atom.

In the present specification, examples of the "optionally substituted heterocyclic group" include a heterocyclic group optionally having substituent(s) selected from the aforementioned substituent group A.

The number of the substituents in the "optionally substituted heterocyclic group" is, for example, 1 to 3. When the number of the substituents is two or more, the respective substituents may be the same or different.

In the present specification, examples of the "acyl group" include a formyl group, a carboxy group, a carbamoyl group, a thiocarbamoyl group, a sulfino group, a sulfo group, a sulfamoyl group and a phosphono group, each optionally having "1 or 2 substituents selected from a $C_{1-6}$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-16}$ aralkyl group, a 5- to 14-membered aromatic heterocyclic group and a 3- to 14-membered non-aromatic heterocyclic group, each of which optionally has 1 to 3 substituents selected from a halogen atom, an optionally halogenated $C_{1-6}$ alkoxy group, a hydroxy group, a nitro group, a cyano group, an amino group and a carbamoyl group".

Examples of the "acyl group" also include a hydrocarbon-sulfonyl group, a heterocyclylsulfonyl group, a hydrocarbon-sulfinyl group and a heterocyclylsulfinyl group.

Here, the hydrocarbon-sulfonyl group means a hydrocarbon group-bonded sulfonyl group, the heterocyclylsulfonyl group means a heterocyclic group-bonded sulfonyl group, the hydrocarbon-sulfinyl group means a hydrocarbon group-bonded sulfinyl group and the heterocyclylsulfinyl group means a heterocyclic group-bonded sulfinyl group.

Preferable examples of the "acyl group" include a formyl group, a carboxy group, a $C_{1-6}$ alkyl-carbonyl group, a $C_{2-6}$ alkenyl-carbonyl group (e.g., crotonoyl), a $C_{3-10}$ cycloalkyl-carbonyl group (e.g., cyclobutanecarbonyl, cyclopentanecarbonyl, cyclohexanecarbonyl, cycloheptanecarbonyl), a $C_{3-10}$ cycloalkenyl-carbonyl group (e.g., 2-cyclohexenecarbonyl), a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a $C_{6-14}$ aryloxy-carbonyl group (e.g., phenyloxycarbonyl, naphthyloxycarbonyl), a $C_{7-16}$ aralkyloxy-carbonyl group (e.g., benzyloxycarbonyl, phenethyloxycarbonyl), a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl), a mono- or di-$C_{6-14}$ aryl-carbamoyl group (e.g., phenylcarbamoyl), a mono- or di-$C_{7-16}$ aralkyl-carbamoyl group, a 5- to 14-membered aromatic heterocyclylcarbamoyl group (e.g., pyridylcarbamoyl), a thiocarbamoyl group, a mono- or di-$C_{1-6}$alkyl-thiocarbamoyl group (e.g., methylthiocarbamoyl, N-ethyl-N-methylthiocarbamoyl), a mono- or di-$C_{2-6}$alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a 5- to 14-membered aromatic heterocyclylthiocarbamoyl group (e.g., pyridylthiocarbamoyl), a sulfino group, a $C_{1-6}$ alkylsulfinyl group (e.g., methylsulfinyl, ethylsulfinyl), a sulfo group, a $C_{1-6}$ alkylsulfonyl group, a $C_{6-14}$ arylsulfonyl group, a phosphono group and a mono- or di-$C_{1-6}$ alkylphosphono group (e.g., dimethylphosphono, diethylphosphono, diisopropylphosphono, dibutylphosphono).

In the present specification, examples of the "optionally substituted amino group" include an amino group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from substituent group A".

Preferable examples of the optionally substituted amino group include an amino group, a mono- or di-(optionally halogenated $C_{1-6}$ alkyl)amino group (e.g., methylamino, trifluoromethylamino, dimethylamino, ethylamino, diethylamino, propylamino, dibutylamino), a mono- or di-$C_{2-6}$alkenylamino group (e.g., diallylamino), a mono- or di-$C_{3-10}$ cycloalkylamino group (e.g., cyclopropylamino, cyclohexylamino), a mono- or di-$C_{6-14}$ arylamino group (e.g., phenylamino), a mono- or di-$C_{7-16}$ aralkylamino group (e.g., benzylamino, dibenzylamino), a mono- or di-(optionally halogenated $C_{1-6}$ alkyl)-carbonylamino group (e.g., acetylamino, propionylamino), a mono- or di-$C_{6-14}$ aryl-carbonylamino group (e.g., benzoylamino), a mono- or di-$C_{7-16}$ aralkyl-carbonylamino group (e.g., benzylcarbonylamino), a mono- or di-5- to 14-membered aromatic heterocyclylcarbonylamino group (e.g., nicotinoylamino, isonicotinoylamino), a mono- or di-3- to 14-membered non-aromatic heterocyclyl-carbonylamino group (e.g., piperidinylcarbonylamino), a mono- or di-$C_{1-6}$alkoxy-carbonylamino group (e.g., tert-butoxycarbonylamino), a 5- to 14-membered aromatic heterocyclylamino group (e.g., pyridylamino), a carbamoylamino group, a (mono- or di-$C_{1-6}$ alkyl-carbamoyl)amino group (e.g., methylcarbamoylamino), a (mono- or di-$C_{7-16}$ aralkyl-carbamoyl)amino group (e.g., benzylcarbamoylamino), a $C_{1-6}$ alkylsulfonylamino group (e.g., methylsulfonylamino, ethylsulfonylamino), a $C_{6-14}$ arylsulfonylamino group (e.g., phenylsulfonylamino), a ($C_{1-6}$ alkyl) ($C_{1-6}$ alkyl-carbonyl) amino group (e.g., N-acetyl-N-methylamino) and a ($C_{1-6}$ alkyl) ($C_{6-14}$ aryl-carbonyl)amino group (e.g., N-benzoyl-N-methylamino).

In the present specification, examples of the "optionally substituted carbamoyl group" include a carbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$alkyl-carbamoyl group and a mono- or di-$C_{7-16}$ aralkyl-carbamoyl group, each of which optionally has 1 to 3 substituents selected from substituent group A".

Preferable examples of the optionally substituted carbamoyl group include a carbamoyl group, a mono- or di-$C_{1-6}$ alkyl-carbamoyl group, a mono- or di-$C_{2-6}$alkenyl-carbamoyl group (e.g., diallylcarbamoyl), a mono- or di-$C_{3-10}$ cycloalkyl-carbamoyl group (e.g., cyclopropylcarbamoyl, cyclohexylcarbamoyl), a mono- or di-$C_{6-14}$ aryl-carbamoyl group (e.g., phenylcarbamoyl), a mono- or di-$C_{7-16}$ aralkyl-carbamoyl group, a mono- or di-$C_{1-6}$ alkyl-carbonyl-carbamoyl group (e.g., acetylcarbamoyl, propionylcarbamoyl), a mono- or di-$C_{6-14}$ aryl-carbonyl-carbamoyl group (e.g., benzoylcarbamoyl) and a 5- to 14-membered aromatic heterocyclylcarbamoyl group (e.g., pyridylcarbamoyl).

In the present specification, examples of the "optionally substituted thiocarbamoyl group" include a thiocarbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted thiocarbamoyl group include a thiocarbamoyl group, a mono- or di-$C_{1-6}$ alkyl-thiocarbamoyl group (e.g., methylthiocarbamoyl, ethylthiocarbamoyl, dimethylthiocarbamoyl, diethylthiocarbamoyl, N-ethyl-N-methylthiocarbamoyl), a mono- or di-$C_{2-6}$alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a mono- or di-$C_{1-6}$ alkyl-carbonyl-thiocarbamoyl group (e.g., acetylthiocarbamoyl, propionylthiocarbamoyl), a mono- or di-$C_{6-14}$ aryl-carbonyl-thiocarbamoyl group (e.g., benzoylthiocarbamoyl) and a 5- to 14-membered aromatic heterocyclylthiocarbamoyl group (e.g., pyridylthiocarbamoyl).

In the present specification, examples of the "optionally substituted sulfamoyl group" include a sulfamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$alkyl-carbamoyl group and a mono- or di-$C_{7-16}$ aralkyl-carbamoyl group, each of which optionally has 1 to 3 substituents selected from substituent group A".

Preferable examples of the optionally substituted sulfamoyl group include a sulfamoyl group, a mono- or di-$C_{1-6}$ alkyl-sulfamoyl group (e.g., methylsulfamoyl, ethylsulfamoyl, dimethylsulfamoyl, diethylsulfamoyl, N-ethyl-N-methylsulfamoyl), a mono- or di-$C_{2-6}$alkenyl-sulfamoyl group (e.g., diallylsulfamoyl), a mono- or di-$C_{3-10}$ cycloalkyl-sulfamoyl group (e.g., cyclopropylsulfamoyl, cyclohexylsulfamoyl), a mono- or di-$C_{6-14}$ aryl-sulfamoyl group (e.g., phenylsulfamoyl), a mono- or di-$C_{7-16}$ aralkyl-sulfamoyl group (e.g., benzylsulfamoyl, phenethylsulfamoyl), a mono- or di-$C_{1-6}$ alkyl-carbonyl-sulfamoyl group (e.g., acetylsulfamoyl, propionylsulfamoyl), a mono- or di-$C_{6-14}$ aryl-carbonyl-sulfamoyl group (e.g., benzoylsulfamoyl) and a 5- to 14-membered aromatic heterocyclylsulfamoyl group (e.g., pyridylsulfamoyl).

In the present specification, examples of the "optionally substituted hydroxy group" include a hydroxyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from substituent group A".

Preferable examples of the optionally substituted hydroxy group include a hydroxy group, a $C_{1-6}$ alkoxy group, a $C_{2-6}$ alkenyloxy group (e.g., allyloxy, 2-butenyloxy, 2-pentenyloxy, 3-hexenyloxy), a $C_{3-10}$ cycloalkyloxy group (e.g., cyclohexyloxy), a $C_{6-14}$ aryloxy group (e.g., phenoxy, naphthyloxy), a $C_{7-16}$ aralkyloxy group (e.g., benzyloxy, phenethyloxy), a $C_{1-6}$ alkyl-carbonyloxy group (e.g., acetyloxy, propionyloxy, butyryloxy, isobutyryloxy, pivaloyloxy), a $C_{6-14}$ aryl-carbonyloxy group (e.g., benzoyloxy), a $C_{7-16}$ aralkyl-carbonyloxy group (e.g., benzylcarbonyloxy), a 5- to 14-membered aromatic heterocyclylcarbonyloxy group (e.g., nicotinoyloxy), a 3- to 14-membered non-aromatic heterocyclylcarbonyloxy group (e.g., piperidinylcarbonyloxy), a $C_{1-6}$ alkoxy-carbonyloxy group (e.g., tert-butoxycarbonyloxy), a 5- to 14-membered aromatic heterocyclyloxy group (e.g., pyridyloxy), a carbamoyloxy group, a $C_{1-6}$ alkyl-carbamoyloxy group (e.g., methylcarbamoyloxy), a $C_{7-16}$ aralkyl-carbamoyloxy group (e.g., benzylcarbamoyloxy), a $C_{1-6}$ alkyl-sulfonyloxy group (e.g., methylsulfonyloxy, ethylsulfonyloxy) and a $C_{6-14}$ arylsulfonyloxy group (e.g., phenylsulfonyloxy).

In the present specification, examples of the "optionally substituted sulfanyl group" include a sulfanyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group and a 5- to 14-membered aromatic heterocyclic group, each of which optionally has 1 to 3 substituents selected from substituent group A" and a halogenated sulfanyl group.

Preferable examples of the optionally substituted sulfanyl group include a sulfanyl (—SH) group, a $C_{1-6}$ alkylthio group, a $C_{2-6}$ alkenylthio group (e.g., allylthio, 2-butenylthio, 2-pentenylthio, 3-hexenylthio), a $C_{3-10}$ cycloalkylthio group (e.g., cyclohexylthio), a $C_{6-14}$ arylthio group (e.g., phenylthio, naphthylthio), a $C_{7-16}$ aralkylthio group (e.g., benzylthio, phenethylthio), a $C_{1-6}$ alkyl-carbonylthio group (e.g., acetylthio, propionylthio, butyrylthio, isobutyrylthio, pivaloylthio), a $C_{6-14}$ aryl-carbonylthio group (e.g., benzoylthio), a 5- to 14-membered aromatic heterocyclylthio group (e.g., pyridylthio) and a halogenated thio group (e.g., pentafluorothio).

In the present specification, examples of the "optionally substituted silyl group" include a silyl group optionally having "1 to 3 substituents selected from a $C_{1-6}$ alkyl group, a $C_{2-6}$ alkenyl group, a $C_{3-10}$ cycloalkyl group, a $C_{6-14}$ aryl group and a $C_{7-16}$ aralkyl group, each of which optionally has 1 to 3 substituents selected from substituent group A".

Preferable examples of the optionally substituted silyl group include a tri-$C_{1-6}$alkylsilyl group (e.g., trimethylsilyl, tert-butyl(dimethyl)silyl).

In the present specification, examples of the "$C_{1-6}$ alkylene group" include —$CH_2$—, —$(CH_2)_2$—, —$(CH_2)_3$—, —$(CH_2)_4$—, —$(CH_2)_5$—, —$(CH_2)_6$—, —$CH(CH_3)$—, —$C(CH_3)_2$—, —$CH(C_2H_5)$—, —$CH(C_3H_7)$—, —$CH(CH(CH_3)_2)$—, —$(CH(CH_3))_2$—, —$CH_2$—$CH(CH_3)$—, —$CH(CH_3)$—$CH_2$—, —$CH_2$—$CH_2$—$C(CH_3)_2$—, —$C(CH_3)_2$—$CH_2$—$CH_2$—, —$CH_2$—$CH_2$—$CH_2$—$C(CH_3)_2$— and —$C(CH_3)_2$—$CH_2$—$CH_2$—$CH_2$—.

In the present specification, examples of the "$C_{2-6}$ alkenylene group" include —CH=CH—, —$CH_2$—CH=CH—, —CH=CH—$CH_2$—, —$C(CH_3)_2$—CH=CH—, —CH=CH—$C(CH_3)_2$—, —$CH_2$—CH=CH—$CH_2$—, —$CH_2$—$CH_2$—CH=CH—, —CH=CH—$CH_2$—$CH_2$—, —CH=CH—CH=CH—, —CH=CH—$CH_2$—$CH_2$—$CH_2$— and —$CH_2$—$CH_2$—$CH_2$—CH=CH—.

In the present specification, examples of the "$C_{2-6}$ alkynylene group" include —C≡C—, —$CH_2$—C≡C—, —C≡C—$CH_2$—, —$C(CH_3)_2$—C≡C—, —C≡C—$C(CH_3)_2$—, —$CH_2$—C≡C—$CH_2$—, —$CH_2$—$CH_2$—C≡C—, —C≡C—$CH_2$—$CH_2$—, —C≡C—C≡C—, —C≡C—$CH_2$—$CH_2$—$CH_2$— and —$CH_2$—$CH_2$—$CH_2$—C≡C—.

In the present specification, examples of the "hydrocarbon ring" include a $C_{6-14}$ aromatic hydrocarbon ring, $C_{3-10}$ cycloalkane and $C_{3-10}$ cycloalkene.

In the present specification, examples of the "$C_{6-14}$ aromatic hydrocarbon ring" include benzene and naphthalene.

In the present specification, examples of the "C$_{3-10}$ cycloalkane" include cyclopropane, cyclobutane, cyclopentane, cyclohexane, cycloheptane and cyclooctane.

In the present specification, examples of the "C$_{3-10}$ cycloalkene" include cyclopropene, cyclobutene, cyclopentene, cyclohexene, cycloheptene and cyclooctene. In the present specification, examples of the "heterocycle" include an aromatic heterocycle and a non-aromatic heterocycle, each containing, as a ring-constituting atom besides carbon atom, 1 to 4 hetero atoms selected from a nitrogen atom, a sulfur atom and an oxygen atom.

In the present specification, examples of the "aromatic heterocycle" include a 5- to 14-membered (preferably 5- to 10-membered) aromatic heterocycle containing, as a ring-constituting atom besides carbon atom, 1 to 4 hetero atoms selected from a nitrogen atom, a sulfur atom and an oxygen atom. Preferable examples of the "aromatic heterocycle" include 5- or 6-membered monocyclic aromatic heterocycles such as thiophene, furan, pyrrole, imidazole, pyrazole, thiazole, isothiazole, oxazole, isoxazole, pyridine, pyrazine, pyrimidine, pyridazine, 1,2,4-oxadiazole, 1,3,4-oxadiazole, 1,2,4-thiadiazole, 1,3,4-thiadiazole, triazole, tetrazole, triazine and the like; and 8- to 14-membered fused polycyclic (preferably bi or tricyclic) aromatic heterocycles such as benzothiophene, benzofuran, benzimidazole, benzoxazole, benzisoxazole, benzothiazole, benzisothiazole, benzotriazole, imidazopyridine, thienopyridine, furopyridine, pyrrolopyridine, pyrazolopyridine, oxazolopyridine, thiazolopyridine, imidazopyrazine, imidazopyrimidine, thienopyrimidine, furopyrimidine, pyrrolopyrimidine, pyrazolopyrimidine, oxazolopyrimidine, thiazolopyrimidine, pyrazolopyrimidine, pyrazolotriazine, naphtho[2,3-b]thiophene, phenoxathiine, indole, isoindole, 1H-indazole, purine, isoquinoline, quinoline, phthalazine, naphthyridine, quinoxaline, quinazoline, cinnoline, carbazole, β-carboline, phenanthridine, acridine, phenazine, phenothiazine, phenoxathiine and the like.

In the present specification, examples of the "non-aromatic heterocycle" include a 3- to 14-membered (preferably 4- to 10-membered) non-aromatic heterocycle containing, as a ring-constituting atom besides carbon atom, 1 to 4 hetero atoms selected from a nitrogen atom, a sulfur atom and an oxygen atom. Preferable examples of the "non-aromatic heterocycle" include 3- to 8-membered monocyclic non-aromatic heterocycles such as aziridine, oxirane, thiirane, azetidine, oxetane, thietane, tetrahydrothiophene, tetrahydrofuran, pyrroline, pyrrolidine, imidazoline, imidazolidine, oxazoline, oxazolidine, pyrazoline, pyrazolidine, thiazoline, thiazolidine, tetrahydroisothiazole, tetrahydrooxazole, tetrahydroisoxazole, piperidine, piperazine, tetrahydropyridine, dihydropyridine, dihydrothiopyran, tetrahydropyrimidine, tetrahydropyridazine, dihydropyran, tetrahydropyran, tetrahydrothiopyran, morpholine, thiomorpholine, azepanine, diazepane, azepine, azocane, diazocane, oxepane and the like; and 9- to 14-membered fused polycyclic (preferably bi or tricyclic) non-aromatic heterocycles such as dihydrobenzofuran, dihydrobenzimidazole, dihydrobenzoxazole, dihydrobenzothiazole, dihydrobenzisothiazole, dihydronaphtho[2,3-b]thiophene, tetrahydroisoquinoline, tetrahydroquinoline, 4H-quinolizine, indoline, isoindoline, tetrahydrothieno[2,3-c]pyridine, tetrahydrobenzazepine, tetrahydroquinoxaline, tetrahydrophenanthridine, hexahydrophenothiazine, hexahydrophenoxazine, tetrahydrophthalazine, tetrahydronaphthyridine, tetrahydroquinazoline, tetrahydrocinnoline, tetrahydrocarbazole, tetrahydro-β-carboline, tetrahydroacridine, tetrahydrophenazine, tetrahydrothioxanthene, octahydroisoquinoline and the like.

In the present specification, examples of the "nitrogen-containing heterocycle" include a "heterocycle" containing at least one nitrogen atom as a ring-constituting atom.

The definition of each symbol in compound (I) is described in detail in the following.

Ring P represents a 6-membered aromatic heterocyclic ring.

Examples of the "6-membered aromatic heterocyclic ring" represented by ring P include 6-membered aromatic heterocyclic rings among the above-mentioned "aromatic heterocyclic rings".

The "6-membered aromatic heterocyclic ring" represented by ring P is preferably pyridine.

When ring P is pyridine, this ring P preferably constitutes optionally substituted tetrahydronaphthyridine (particularly, optionally substituted 1,6-tetrahydronaphthyridine or optionally substituted 1,7-tetrahydronaphthyridine) together with the adjacent ring. In other words, the partial formula:

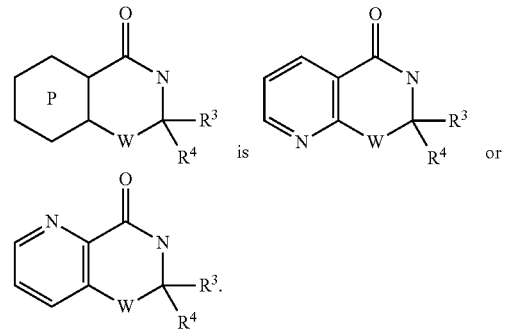

The partial formula:

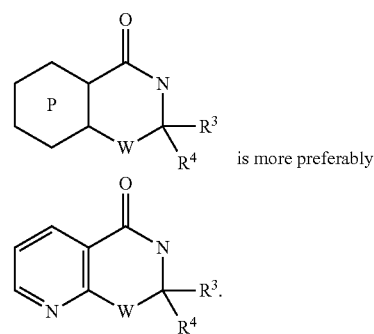

is more preferably

Ring A represents an optionally substituted 4- to 7-membered nitrogen-containing saturated heterocyclic ring.

Examples of the "4- to 7-membered nitrogen-containing saturated heterocyclic ring" in the "optionally substituted 4- to 7-membered nitrogen-containing saturated heterocyclic ring" represented by ring A include 4- to 7-membered nitrogen-containing saturated heterocyclic rings among the above-mentioned "heterocyclic rings".

The "4- to 7-membered nitrogen-containing saturated heterocyclic ring" in the "optionally substituted 4- to 7-membered nitrogen-containing saturated heterocyclic ring" represented by ring A is preferably piperidine, azetidine, or pyrrolidine, more preferably piperidine.

The "4- to 7-membered nitrogen-containing saturated heterocyclic ring" may have 1 to 5, preferably 1 to 3 substituents at substitutable positions. When the number of the substituents is two or more, the respective substituents may be the same or different.

Ring A is preferably piperidine, azetidine, or pyrrolidine, more preferably piperidine.

Ring B represents an optionally substituted benzene ring or an optionally substituted heterocyclic ring.

The "benzene ring" in the "optionally substituted benzene ring" represented by ring B may have 1 to 5, preferably 1 to 4, more preferably 3 or 4 substituents at substitutable positions. When the number of the substituents is two or more, the respective substituents may be the same or different.

Preferable examples of such substituents include a halogen atom (preferably fluorine, chlorine, bromine, iodine); a $C_{3-10}$ cycloalkyl group (preferably cyclopropyl, cyclobutyl, cyclopentyl); a $C_{1-6}$ alkoxy group (preferably methoxy, ethoxy, propoxy, isopropoxy); and a $C_{6-14}$ aryl group (preferably phenyl) optionally substituted by 1 to 3 halogen atoms (preferably fluorine).

The "heterocyclic ring" in the "optionally substituted heterocyclic ring" represented by ring B is preferably a 5- to 14-membered heterocyclic ring, more preferably a 5- to 14-membered nitrogen-containing heterocyclic ring.

The "heterocyclic ring" in the "optionally substituted heterocyclic ring" represented by ring B is particularly preferably pyridine, indole, or pyrazole.

The "heterocyclic ring" may have 1 to 5, preferably 1 to 3, more preferably 3 substituents at substitutable positions. When the number of the substituents is two or more, the respective substituents may be the same or different.

Preferable examples of such substituents include a halogen atom (preferably fluorine, chlorine, bromine, iodine); a $C_{1-6}$ alkyl group (preferably methyl, ethyl, isopropyl, tert-butyl); a $C_{3-10}$ cycloalkyl group (preferably cyclopropyl); a $C_{1-6}$ alkoxy group (preferably methoxy, ethoxy, isopropoxy); and a $C_{6-14}$ aryl group (preferably phenyl) optionally substituted by 1 to 3 halogen atoms (preferably fluorine, chlorine).

Ring B is preferably an optionally substituted benzene ring, optionally substituted pyridine, optionally substituted indole, or optionally substituted pyrazole.

More preferable examples of ring B include (1) a benzene ring optionally substituted by 1 to 4 substituents selected from:
a halogen atom (preferably fluorine, chlorine); a $C_{3-10}$ cycloalkyl group (preferably cyclopropyl, cyclobutyl, cyclopentyl); a $C_{1-6}$ alkoxy group (preferably methoxy, ethoxy, propoxy, isopropoxy); and a $C_{6-14}$ aryl group (preferably phenyl) optionally substituted by 1 to 3 halogen atoms (preferably chlorine, fluorine), or
(2) pyridine, indole, or pyrazole each optionally substituted by 1 to 3 substituents selected from:
a $C_{1-6}$ alkyl group (preferably isobutyl); a $C_{3-10}$ cycloalkyl group (preferably cyclopropyl); a $C_{1-6}$ alkoxy group (preferably methoxy, ethoxy, isopropoxy); and a $C_{6-14}$ aryl group (preferably phenyl) optionally substituted by 1 to 3 halogen atoms (preferably chlorine, fluorine).

Particularly preferable examples of ring B include a benzene ring optionally substituted by 1 to 4 substituents selected from:
a halogen atom (preferably fluorine, chlorine); a $C_{3-10}$ cycloalkyl group (preferably cyclopropyl, cyclobutyl, cyclopentyl); a $C_{1-6}$ alkoxy group (preferably methoxy, ethoxy, propoxy, isopropoxy); and a $C_{6-14}$ aryl group (preferably phenyl) optionally substituted by 1 to 3 halogen atoms (preferably chlorine, fluorine).

$R^1$ and $R^2$ each independently represent a hydrogen atom, an optionally substituted $C_{1-6}$ alkyl group (preferably methyl, ethyl, propyl, methoxymethyl), a $C_{3-10}$ cycloalkyl group (preferably cyclopropyl), or $CO_2R$ (wherein R represents a hydrogen atom or an optionally substituted $C_{1-6}$ alkyl group, preferably a hydrogen atom). Either one of $R^1$ and $R^2$ is $CO_2R$ (preferably COOH).

$R^1$ and $R^2$ are each independently, preferably, a hydrogen atom, a $C_{1-6}$ alkyl group optionally substituted by a $C_{1-6}$ alkoxy group (e.g., methyl, ethyl, propyl, methoxymethyl), a $C_{3-10}$ cycloalkyl group (e.g., cyclopropyl), or $CO_2R$ (wherein R represents a hydrogen atom or a $C_{1-6}$ alkyl group, preferably a hydrogen atom).

Furthermore, $R^1$ is preferably a hydrogen atom or COOH, $R^2$ is preferably a hydrogen atom, a $C_{1-6}$ alkyl group optionally substituted by a $C_{1-6}$ alkoxy group, a $C_{3-10}$ cycloalkyl group, or COOH, and either one of $R^1$ and $R^2$ preferably is COOH. Particularly preferably, $R^1$ is COOH, and $R^2$ is a $C_{1-6}$ alkyl group (preferably ethyl or propyl)

$R^3$, $R^4$, $R^5$, and $R^6$ each independently represent a hydrogen atom or a $C_{1-6}$ alkyl group.

Each of $R^3$, $R^4$, $R^5$, and $R^6$ is preferably a hydrogen atom.

W represents a $C_{1-2}$ alkylene group optionally substituted by a $C_{1-6}$ alkyl group (preferably methylene).

W is preferably a $C_{1-2}$ alkylene group, more preferably methylene.

Preferable examples of compound (I) include the following compound:

[Compound A]

Compound (I) wherein ring P is pyridine; W is methylene; the pyridine constitutes optionally substituted tetrahydronaphthyridine (preferably, optionally substituted 1,6-tetrahydronaphthyridine or optionally substituted 1,7-tetrahydronaphthyridine) together with the adjacent ring;

ring A is piperidine, azetidine, or pyrrolidine;

ring B is (1) a benzene ring optionally substituted by 1 to 4 substituents selected from a halogen atom (preferably fluorine, chlorine), a $C_{3-10}$ cycloalkyl group (preferably cyclopropyl, cyclobutyl, cyclopentyl), a $C_{1-6}$ alkoxy group (preferably methoxy, ethoxy, propoxy, isopropoxy), and a $C_{6-14}$ aryl group (preferably phenyl) optionally substituted by 1 to 3 halogen atoms (preferably chlorine, fluorine), or (2) pyridine, indole, or pyrazole each optionally substituted by 1 to 3 substituents selected from a $C_{1-6}$ alkyl group (preferably isobutyl), a $C_{3-10}$ cycloalkyl group (preferably cyclopropyl), a $C_{1-6}$ alkoxy group (preferably ethoxy, isopropoxy), and a $C_{6-14}$ aryl group (preferably phenyl) optionally substituted by halogen atom(s) (preferably fluorine);

$R^1$ is a hydrogen atom or COOH;

$R^2$ is a hydrogen atom, a $C_{1-6}$ alkyl group optionally substituted by a $C_{1-6}$ alkoxy group (preferably methyl, ethyl, propyl, methoxymethyl), a $C_{3-10}$ cycloalkyl group (preferably cyclopropyl), or COOH;

either one of $R^1$ and $R^2$ is COOH; and each of $R^3$, $R^4$, $R^5$, and $R^6$ is a hydrogen atom.

[Compound A-1]
Compound A wherein
the partial formula

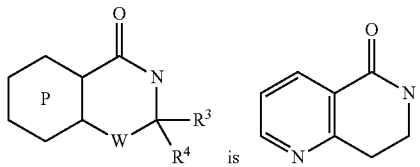

[Compound A-2]
Compound A-1 wherein
ring A is piperidine.
[Compound A-3]
Compound A-1 or compound A-2, in each of which ring B is a benzene ring optionally substituted by 1 to 4 substituents selected from
a halogen atom (preferably fluorine, chlorine), a $C_{3-10}$ cycloalkyl group (preferably cyclopropyl, cyclobutyl, cyclopentyl), a $C_{1-6}$ alkoxy group (preferably methoxy, ethoxy, propoxy, isopropoxy), and a $C_{6-14}$ aryl group (preferably phenyl) optionally substituted by 1 to 3 halogen atoms (preferably chlorine, fluorine).
[Compound A-4]
Compound A-1, compound A-2 or compound A-3, in each of which
$R^1$ is COOH and $R^2$ is a $C_{1-6}$ alkyl group (preferably ethyl or propyl).

The salt of compound (I) is preferably a pharmacologically acceptable salt.

Examples of such salt include salts with inorganic bases, salts with organic base, salts with inorganic acid, salts with organic acid, salts with basic or acidic amino acid, and the like.

Preferable examples of the salt with inorganic base include alkali metal salts such as sodium salt, potassium salt and the like; alkaline earth metal salts such as calcium salt, magnesium salt and the like; aluminum salt; ammonium salt and the like.

Preferable examples of the salt with organic base include salts with trimethylamine, triethylamine, pyridine, picoline, ethanolamine, diethanolamine, triethanolamine, tromethamine [tris(hydroxymethyl)methylamine], tert-butylamine, cyclohexylamine, benzylamine, dicyclohexylamine, N,N-dibenzylethylenediamine and the like.

Preferable examples of the salt with inorganic acid include salts with hydrochloric acid, hydrobromic acid, nitric acid, sulfuric acid, phosphoric acid and the like.

Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salt with basic amino acid include salts with arginine, lysine, ornithine and the like.

Preferable examples of the salt with acidic amino acid include salts with aspartic acid, glutamic acid and the like.

Compound (I) may be used as a prodrug.

A prodrug of compound (I) is a compound which is converted to compound (I) with a reaction due to an enzyme, gastric acid, etc. under the physiological condition in the living body, that is, a compound which is converted to compound (I) with oxidation, reduction, hydrolysis, etc. according to an enzyme; a compound which is converted to compound (I) by hydrolysis etc. due to gastric acid, etc.

Examples of a prodrug of compound (I) include:
a compound wherein an amino group of compound (I) is acylated, alkylated or phosphorylated (e.g., compound wherein an amino group of compound (I) is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated or tert-butylated, and the like);

a compound wherein a hydroxy group of compound (I) is acylated, alkylated, phosphorylated or borated (e.g., a compound wherein a hydroxy group of compound (I) is acetylated, palmitoylated, propanoylated, pivaloylated, succinylated, fumarylated, alanylated or dimethylaminomethylcarbonylated);

a compound wherein a carboxy group of compound (I) is esterified or amidated (e.g., a compound wherein a carboxy group of compound (I) is ethyl esterified, phenyl esterified, carboxymethyl esterified, dimethylaminomethyl esterified, pivaloyloxymethyl esterified, ethoxycarbonyloxyethyl esterified, phthalidyl esterified, (5-methyl-2-oxo-1,3-dioxolen-4-yl)methyl esterified, cyclohexyloxycarbonylethyl esterified or methylamidated); and the like. These compounds can be produced from compound (I) by a method known per se.

A prodrug of compound (I) may also be one which is converted into compound (I) under a physiological condition, such as those described in IYAKUHIN no KAIHATSU (Development of Pharmaceuticals), Vol. 7, Design of Molecules, p. 163-198, Published by HIROKAWA SHOTEN (1990).

In the present specification, the prodrug may form a salt. Examples of such a salt include those exemplified as the above-mentioned salt of compound (I).

Alternatively, compound (I) may be labeled with an isotope (e.g., $^3H$, $^{13}C$, $^{14}C$, $^{18}F$, $^{35}S$, $^{125}I$) or the like.

Furthermore, compound (I) may be a hydrate, a non-hydrate, a non-solvate, or a solvate.

In addition, a deuterium conversion form wherein $^1H$ is converted to $^2H(D)$ is also included in compound (I).

Compound (I) labeled or substituted with an isotope can be used as, for example, a tracer (PET tracer) for use in Positron Emission Tomography (PET), and is useful in the fields of medical diagnosis and the like.

In addition, compound (I) may be a pharmaceutically acceptable cocrystal or cocrystal salt. Here, the cocrystal or cocrystal salt means a crystalline substance consisting of two or more particular substances which are solids at room temperature, each having different physical properties (e.g., structure, melting point, heat of melting, hygroscopicity, solubility, stability etc.). The cocrystal and cocrystal salt can be produced by cocrystallization known per se.

Compound (I) or a prodrug thereof (hereinafter to be sometimes abbreviated simply as the compound of the present invention) shows low toxicity. Thus, the compound of the present invention can be prepared into a pharmaceutical composition alone or in admixture with a pharmacologically acceptable carrier or the like and thereby used as an agent for the prophylaxis or treatment of various diseases mentioned below in a mammal (e.g., human, mouse, rat, rabbit, dog, cat, bovine, horse, pig, monkey).

In this context, any of various organic or inorganic carrier materials that are conventionally used as preparation materials can be used as the pharmacologically acceptable carrier. These are formulated as an excipient, a lubricant, a binding agent, and a disintegrant for solid preparations or as a solvent, a solubilizing agent, a suspending agent, an isotonic agent, a buffering agent, a soothing agent, and the like for liquid preparations. Further, if necessary, formulation additives such as preservative, antioxidant, colorant, sweetening agent, and the like can also be used.

Preferable examples of the excipient include lactose, sucrose, D-mannitol, D-sorbitol, starch, pregelatinized starch, dextrin, crystalline cellulose, low-substituted hydroxypropylcellulose, carboxymethylcellulose sodium, gum arabic, pullulan, light anhydrous silicic acid, synthetic aluminum silicate, and magnesium alumino metasilicate.

Preferable examples of the lubricant include magnesium stearate, calcium stearate, talc, and colloidal silica.

Preferable examples of the binding agent include pregelatinized starch, sucrose, gelatin, gum arabic, methylcellulose, carboxymethylcellulose, carboxymethylcellulose sodium, crystalline cellulose, sucrose, D-mannitol, trehalose, dextrin, pullulan, hydroxypropylcellulose, hydroxypropylmethylcellulose, and polyvinylpyrrolidone.

Preferable examples of the disintegrant include lactose, sucrose, starch, carboxymethylcellulose, carboxymethylcellulose calcium, croscarmellose sodium, carboxymethyl starch sodium, light anhydrous silicic acid, and low-substituted hydroxypropylcellulose.

Preferable examples of the solvent include water for injection, physiological saline, Ringer's solution, alcohol, propylene glycol, polyethylene glycol, sesame oil, corn oil, olive oil, and cottonseed oil.

Preferable examples of the solubilizing agent include polyethylene glycol, propylene glycol, D-mannitol, trehalose, benzyl benzoate, ethanol, trisaminomethane, cholesterol, triethanolamine, sodium carbonate, sodium citrate, sodium salicylate, and sodium acetate.

Preferable examples of the suspending agent include surfactants such as stearyl triethanolamine, sodium lauryl sulfate, laurylaminopropionic acid, lecithin, benzalkonium chloride, benzethonium chloride, glycerin monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like; polysorbates, and polyoxyethylene hydrogenated castor oil.

Preferable examples of the isotonic agent include sodium chloride, glycerin, D-mannitol, D-sorbitol, and glucose.

Preferable examples of the buffering agent include buffer solutions such as phosphates, acetates, carbonates, citrates and the like.

Preferable examples of the soothing agent include benzyl alcohol.

Preferable examples of the preservative include parahydroxybenzoic acid esters, chlorobutanol, benzyl alcohol, phenethyl alcohol, dehydroacetic acid, and sorbic acid.

Preferable examples of the antioxidant include sulfites and ascorbates.

Preferable examples of the colorant include water-soluble Food coal tar dyes (e.g., Food dyes such as Food Red No. 2 and No. 3, Food Yellow No. 4 and No. 5, Food Blue No. 1 and No. 2, and the like), water-insoluble lake dyes (e.g., aluminum salts of the aforementioned water-soluble Food coal tar dyes), and natural dyes (e.g., β-carotene, chlorophyll, ferric oxide red).

Preferable examples of the sweetening agent include saccharin sodium, dipotassium glycyrrhizinate, aspartame, and stevia.

A medicament comprising the compound of the present invention can be obtained using the compound of the present invention alone or in admixture with a pharmacologically acceptable carrier, and safely administered orally or parenterally (e.g., administered intravenously, intramuscularly, subcutaneously, into an organ, into a nasal cavity, intracutaneously, through ocular instillation, intracerebrally, rectally, vaginally, intraperitoneally, to the inside of tumor, to the proximity of tumor, and the like, and administered directly to a lesion) to a mammal as a pharmaceutical composition, for example, tablets (inclusive of sugar-coated tablets, film-coated tablets, sublingual tablets, orally disintegrating tablets, buccal tablets, and the like), pills, powders, granules, capsules (inclusive of soft capsules, microcapsules), troches, syrups, liquids, emulsions, suspensions, aerosols, films, (e.g., orally disintegrating films, patch films for application to the oral mucosa), injections (e.g., subcutaneous injections, intravenous injections, intramuscular injections, intraperitoneal injections), transfusions, dermal preparations, ointments, lotions, patches, suppositories (e.g., rectal suppositories, vaginal suppositories), pellets, nasal preparations, pulmonary preparations (inhalants), eye drops, and the like.

The pharmaceutical composition may be a controlled release preparation such as a rapid release preparation, a sustained release preparation, and the like (e.g., a sustained release microcapsule).

The pharmaceutical composition can be produced by a method that is conventionally used in the field of formulation technology, for example, the method described in the Japanese Pharmacopoeia and the like.

The content of the compound of the present invention in the pharmaceutical composition differs depending on the dosage form, the dose of the compound of the present invention, etc. and is, for example, about 0.1 to 100 wt %.

During production of an oral preparation, coating may be applied as necessary for the purpose of masking of taste, enteric property or durability.

Examples of the coating base to be used for coating include sugar coating base, aqueous film coating base, enteric film coating base and sustained-release film coating base.

As the sugar coating base, sucrose is used. Moreover, one or more kinds selected from talc, precipitated calcium carbonate, gelatin, gum arabic, pullulan, carnauba wax and the like may be used in combination.

Examples of the aqueous film coating base include cellulose polymers such as hydroxypropyl cellulose, hydroxypropylmethyl cellulose, hydroxyethyl cellulose, methylhydroxyethyl cellulose etc.; synthetic polymers such as polyvinylacetal diethylaminoacetate, aminoalkyl methacrylate copolymer E [Eudragit E (trade name)], polyvinylpyrrolidone etc.; and polysaccharides such as pullulan etc.

Examples of the enteric film coating base include cellulose polymers such as hydroxypropylmethyl cellulose phthalate, hydroxypropylmethyl cellulose acetate succinate, carboxymethylethyl cellulose, cellulose acetate phthalate etc.; acrylic polymers such as methacrylic acid copolymer L [Eudragit L (trade name)], methacrylic acid copolymer LD [Eudragit L-30D55 (trade name)], methacrylic acid copolymer S [Eudragit S (trade name)] etc.; and naturally occurring substances such as shellac etc.

Examples of the sustained-release film coating base include cellulose polymers such as ethyl cellulose etc.; and acrylic polymers such as aminoalkyl methacrylate copolymer RS [Eudragit RS (trade name)], ethyl acrylate-methyl methacrylate copolymer suspension [Eudragit NE (trade name)] etc.

The above-mentioned coating bases may be used after mixing with two or more kinds thereof at appropriate ratios. For coating, for example, a light shielding agent such as titanium oxide, red ferric oxide and the like can be used.

The compound of the present invention is low in its toxicity (e.g., acute toxicity, chronic toxicity, genetic toxicity, reproductive toxicity, pulmonary toxicity, carcinogenicity), shows a few side effects, and can be used for a mammal as an agent for the prophylaxis or treatment of various diseases or as a diagnostic drug for various diseases.

The compound of the present invention has a superior SSTR5 antagonist action.

The compound of the present invention can be used as an agent for the prophylaxis or treatment of, for example, diabetes mellitus (e.g., type 1 diabetes mellitus, type 2 diabetes mellitus, gestational diabetes mellitus, obese diabetes mellitus), obesity (e.g., malignant mastocytosis, exogenous obesity, hyperinsulinar obesity, hyperplasmic obesity, hypophyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity and the like), hyperphagia, hyperlipidemia/dyslipidemia (e.g., hypertriglyceridemia, hypercholesterolemia, high LDL-cholesterolemia, low HDL-cholesterolemia, postprandial hyperlipemia), hypertension, cardiovascular disease, (e.g., cardiac failure, arrhythmia, ischemic heart disease, valvular heart disease, arteriosclerosis), diabetic complications [e.g., neuropathy, nephropathy, retinopathy, diabetic cardiomyopathy, cataract, macroangiopathy, osteopenia, hyperosmolar diabetic coma, infectious disease (e.g., respiratory infection, urinary tract infection, gastrointestinal infection, dermal soft tissue infections, inferior limb infection), diabetic gangrene, xerostomia, hypacusis, cerebrovascular disorder, peripheral blood circulation disorder], metabolic syndrome (disease states having 3 or more selected from hypertriglycerid(TG)emia, low HDL cholesterol(HDL-C)emia, hypertension, abdominal obesity and impaired glucose tolerance), sarcopenia, affective disorder, sexual dysfunction, depression, anxiety, neurosis, arteriosclerosis, knee arthritis and the like.

"Report of the Committee on the classification and diagnostic criteria of diabetes mellitus" was reported by The Japan Diabetes Society in 2010 about the diagnostic criteria of diabetes mellitus.

According to this report, diabetes mellitus refers to a state that meets any of a fasting blood glucose level (glucose concentration in venous plasma) of 126 mg/dL or more, a 2-hr value (glucose concentration in venous plasma) of 200 mg/dL or more in the 75 g oral glucose tolerance test (75 g OGTT), a casual blood glucose level (glucose concentration in venous plasma) of 200 mg/dL or more, and HbA1c (international standard value) of 6.5% or more. However, HbA1c (international standard value) (%) is indicated as an internationally standardized value corresponding to NGSP (National Glycohemoglobin Standardization Program) by 0.4% plus the conventional JDS (Japan Diabetes Society) value of HbA1c (JDS value) (%). Also, a state that does not apply to the above-mentioned diabetes mellitus, and is not a state exhibiting "a fasting blood glucose level (glucose concentration in venous plasma) less than 110 mg/dL or a 2-hr value (glucose concentration in venous plasma) less than 140 mg/dL in the 75 g oral glucose tolerance test (75 g OGTT)" (normal type) is called "borderline type".

According to the report by World Health Organization (WHO) in 2006, diabetes mellitus refers to a state that meets a fasting blood glucose level (glucose concentration in venous plasma) of 126 mg/dL or more or a 2-hr value (glucose concentration in venous plasma) of 200 mg/dL or more in the 75 g oral glucose tolerance test.

According to the above-mentioned reports, impaired glucose tolerance (IGT) refers to a state that meets a fasting blood glucose level (glucose concentration in venous plasma) less than 126 mg/dL and a 2-hr value (glucose concentration in venous plasma) of 140 mg/dL or more and less than 200 mg/dL in the 75 g oral glucose tolerance test. According to the report of WHO, a state exhibiting a fasting blood glucose level (glucose concentration in venous plasma) of 110 mg/dL or more and less than 126 mg/dL and a 2-hr value (glucose concentration in venous plasma) less than 140 mg/dL in the 75 g oral glucose tolerance test, if it has been measured, is called IFG (Impaired Fasting Glucose).

The compound of the present invention is also used as an agent for the prophylaxis or treatment of diabetes mellitus, borderline type diabetes mellitus, impaired glucose tolerance or IFG (Impaired Fasting Glucose) determined according to the above-mentioned reports. Moreover, the compound of the present invention can prevent progress of borderline type, impaired glucose tolerance or IFG (Impaired Fasting Glucose) into diabetes mellitus.

The compound of the present invention is also useful as an agent for the prophylaxis or treatment of metabolic syndrome. The incidence of cardiovascular disease is significantly high in metabolic syndrome patients, compared with patients with a single lifestyle-related disease. Thus, the prophylaxis or treatment of metabolic syndrome is exceedingly important for preventing cardiovascular disease.

The diagnostic criteria of metabolic syndrome were announced by WHO in 1999 and by NCEP in 2001. According to the diagnostic criteria of WHO, an individual having hyperinsulinemia or abnormal glucose tolerance as a requirement and two or more of visceral obesity, dyslipidemia (high TG or low HDL) and hypertension is diagnosed as having metabolic syndrome (World Health Organization: Definition, Diagnosis and Classification of Diabetes Mellitus and Its Complications. Part I: Diagnosis and Classification of Diabetes Mellitus, World Health Organization, Geneva, 1999). According to the diagnostic criteria of the Adult Treatment Panel III of the National Cholesterol Education Program (guideline of ischemic heart disease) in USA, an individual having three or more of visceral obesity, hypertriglyceridemia, low HDL-cholesterolemia, hypertension and abnormal glucose tolerance is diagnosed as having metabolic syndrome (National Cholesterol Education Program: Executive Summary of the Third Report of National Cholesterol Education Program (NCEP) Expert Panel on Detection, Evaluation, and Treatment of High Blood Cholesterol in Adults (Adults Treatment Panel III). The Journal of the American Medical Association, Vol. 285, 2486-2497, 2001).

The compound of the present invention can also be used as an agent for the prophylaxis or treatment of, for example, osteoporosis, cachexia (e.g., cancerous cachexia, tuberculous cachexia, diabetic cachexia, cachexia associated with blood disease, cachexia associated with endocrine disease, cachexia associated with infectious disease or cachexia caused by acquired immunodeficiency syndrome), fatty liver, polycystic ovary syndrome, renal disease (e.g., diabetic nephropathy, glomerulonephritis, glomerulosclerosis, Nephrotic syndrome, hypertensive nephrosclerosis, end-stage renal disease), muscular dystrophy, myocardial infarction, angina pectoris, cerebrovascular disorder (e.g., cerebral infarction, stroke), Alzheimer's disease, Parkinson's disease, dementia, insulin resistant syndrome, syndrome X, hyperinsulinemia, paresthesia caused by hyperinsulinemia, acute or chronic diarrhea, inflammatory disease (e.g., chronic rheumatoid arthritis, spondylitis deformans, arthritis deformans, lumbago, gout, post-operational or post-traumatic inflammation, bloating, neuralgia, laryngopharyngitis, cystitis, hepatitis (including non-alcoholic steatohepatitis), pneumonia, pancreatitis, enteritis, inflammatory bowel disease (including inflammatory large bowel disease), colitis ulcerosa, gastric mucosal injury (including gastric mucosal injury caused by aspirin)), small intestinal mucosal injury, malabsorption, testicular dysfunction, visceral obesity syndrome and sarcopenia.

Moreover, the compound of the present invention can also be used as an agent for the prophylaxis or treatment of various cancers (particularly, breast cancer (e.g., invasive ductal breast cancer, noninvasive ductal breast cancer, inflammatory breast cancer, etc.), prostate cancer (e.g., hormone-dependent prostate cancer, hormone-independent prostate cancer, etc.), pancreatic cancer (e.g., ductal pancreatic cancer, etc.), gastric cancer (e.g., papillary adenocarcinoma, mucous adenocarcinoma, adenosquamous carcinoma, etc.), lung cancer (e.g., non-small cell lung cancer, small-cell lung cancer, malignant mesothelioma, etc.), colon cancer (e.g., gastrointestinal stromal tumor, etc.), rectal cancer (e.g., gastrointestinal stromal tumor, etc.), colorectal cancer (e.g., familial colorectal cancer, hereditary non-polyposis colorectal cancer, gastrointestinal stromal tumor, etc.), small intestinal cancer (e.g., non-Hodgkin's lymphoma, gastrointestinal stromal tumor, etc.), esophageal cancer, duodenal cancer, tongue cancer, pharyngeal cancer (e.g., nasopharyngeal cancer, oropharynx cancer, hypopharyngeal cancer, etc.), salivary gland cancer, brain tumor (e.g., pineal astrocytoma, pilocytic astrocytoma, diffuse astrocytoma, anaplastic astrocytoma, etc.), neurilemmoma, liver cancer (e.g., primary liver cancer, extrahepatic bile duct cancer, etc.), renal cancer (e.g., renal cell cancer, transitional cell cancer of the renal pelvis and ureter, etc.), bile duct cancer, endometrial cancer, uterine cervical cancer, ovarian cancer (e.g., epithelial ovarian cancer, extragonadal germ cell tumor, ovarian germ cell tumor, ovarian tumor of low malignant potential, etc.), bladder cancer, urethral cancer, skin cancer (e.g., intraocular (ocular) melanoma, Merkel cell carcinoma, etc.), hemangioma, malignant lymphoma, malignant melanoma, thyroid cancer (e.g., medullary thyroid cancer, etc.), parathyroid cancer, nasal cavity cancer, sinus cancer, bone tumor (e.g., osteosarcoma, Ewing tumor, uterine sarcoma, soft tissue sarcoma, etc.), angiofibroma, sarcoma of the retina, penis cancer, testicular tumor, pediatric solid tumor (e.g., Wilms' tumor, childhood kidney tumor, etc.), Kaposi's sarcoma, Kaposi's sarcoma caused by AIDS, tumor of maxillary sinus, fibrous histiocytoma, leiomyosarcoma, rhabdomyosarcoma, leukemia (e.g., acute myeloid leukemia, acute lymphoblastic leukemia, etc.), etc.).

The compound of the present invention can also be used for secondary prevention or suppression of progression of the above-mentioned various diseases (e.g., cardiovascular events such as myocardial infarction and the like).

The dosage of the compound of the present invention is appropriately determined according to the subject of administration, administration route, target disease, symptom and the like. For example, when the compound of the present invention is administered orally to an adult obesity patient, a single dose is typically about 0.01 to 100 mg/kg body weight, preferably about 0.05 to 30 mg/kg body weight, more preferably about 0.5 to 10 mg/kg body weight. The single dose of the compound is preferably administered once to three times a day.

The compound of the present invention can be used in combination with a drug (hereinafter abbreviated as a concomitant drugs) such as therapeutic agents for diabetes mellitus, therapeutic agents for diabetic complications, therapeutic agents for hyperlipidemia, antihypertensive agents, antiobesity agents, diuretics, antithrombotic agents and the like for the purpose of promoting the action of the compound, reducing the dose of the compound, or the like. In this respect, the time of administration of the compound of the present invention and that of the concomitant drug are not limited. These concomitant drugs may be low-molecular-weight compounds or may be macromolecules such as proteins, polypeptides, antibodies, vaccines, and the like. The compound of the present invention and the concomitant drug may be administered simultaneously or in a staggered manner to the administration subject.

Furthermore, the compound of the present invention and the concomitant drug may be administered as two types of preparations respectively comprising the active ingredients or as a single preparation comprising both of the active ingredients.

The dose of the concomitant drug can be appropriately determined based on the dose employed in clinical situations. The mixing ratio of the compound of the present invention and a concomitant drug can be appropriately determined depending on the administration subject, administration route, target disease, symptom, combination and the like. When the subject of administration is human, for example, a concomitant drug can be used in 0.01 to 100 parts by weight relative to 1 part by weight of the compound of the present invention.

Here, as the therapeutic agent for diabetes mellitus, for example, insulin preparations (e.g., animal insulin preparations extracted from the pancreas of bovine or swine; human insulin preparations genetically synthesized using *Escherichia coli* or yeast; zinc insulin; protamine zinc insulin; fragment or derivative of insulin (e.g., INS-1), oral insulin preparation), insulin sensitizers (e.g., pioglitazone or a salt thereof (preferably, hydrochloride), rosiglitazone or a salt thereof (preferably, maleate), Metaglidasen, AMG-131, Balaglitazone, MBX-2044, Rivoglitazone, Aleglitazar, Chiglitazar, Lobeglitazone, PLX-204, PN-2034, GFT-505, THR-0921, compound described in WO2007/013694, WO2007/018314, WO2008/093639 or WO2008/099794), a-glucosidase inhibitors (e.g., voglibose, acarbose, miglitol, emiglitate), biguanides (e.g., metformin or a salt thereof (preferably, hydrochloride), buformin or a salt thereof (e.g., hydrochloride, fumarate, succinate)), insulin secretagogues [sulfonylurea (e.g., tolbutamide, glibenclamide, gliclazide, chlorpropamide, tolazamide, acetohexamide, glyclopyramide, glimepiride, glipizide, glybuzole), repaglinide, nateglinide, mitiglinide or calcium salt hydrate thereof], dipeptidyl peptidase IV inhibitors (e.g., Alogliptin or a salt thereof (preferably, benzoate), Vildagliptin, Sitagliptin, Saxagliptin, Teneligliptin, Linagliptin, Anagliptin, Melogliptin, Dutogliptin, PF-00734200, ALS2-0426, TA-6666, TS-021, KRP-104, Trelagliptin or a salt thereof (preferably, succinate)), β3 agonists (e.g., N-5984), GPR40 agonists (e.g., fasiglifam, compound described in WO2004/041266, WO2004/106276, WO2005/063729, WO2005/063725, WO2005/087710, WO2005/095338, WO2007/013689 or WO2008/001931), GLP-1 receptor agonists [e.g., GLP-1, GLP-1 MR preparations, liraglutide, exenatide, AVE-0010, BIM-51077, Aib(8, 35)hGLP-1 (7,37)NH$_2$, CJC-1131, albiglutide], amylin agonists (e.g., pramlintide), phosphotyrosine phosphatase inhibitors (e.g., sodium vanadate), gluconeogenesis inhibitors (e.g., glycogen phosphorylase inhibitors, glucose-6-phosphatase inhibitors, glucagon antagonists, FBPase inhibitors), SGLT2 (sodium-glucose cotransporter 2) inhibitors (e.g., dapagliflozin, AVE2268, TS-033, YM543, TA-7284, Remogliflozin, ASP1941), SGLT1 inhibitors, 11β-hydroxysteroid dehydrogenase inhibitors (e.g., BVT-3498), adiponectin or agonist thereof, IKK inhibitors (e.g., AS-2868), leptin resistance improving drugs, somatostatin receptor agonists, glucokinase activators (e.g., Piragliatin, AZD1656, AZD6370, TTP-355, compound described in WO006/112549, WO007/028135, WO008/047821, WO008/050821, WO008/136428 or WO008/156757), GIP (Glucose-dependent insulinotropic peptide) and the like can be mentioned.

As the therapeutic agent for diabetic complications, for example, aldose reductase inhibitors (e.g., tolrestat, epalrestat, zopolrestat, fidarestat, CT-112, ranirestat (AS-3201), lidorestat), neurotrophic factor and increasing agents thereof (e.g., NGF, NT-3, BDNF, neurotrophic production/secretion promoting agent described in WO01/14372 (e.g., 4-(4-chlorophenyl)-2-(2-methyl-1-imidazolyl)-5-[3-(2-methylphenoxy)propyl]oxazole), compound described in WO2004/039365), nerve regeneration-promoting drugs (e.g., Y-128), PKC inhibitors (e.g., ruboxistaurin mesylate), AGE inhibitors (e.g., ALT946, pyratoxatin, N-phenacylthiazolium bromide (ALT766), ALT-711, EXO-226, Pyridorin, pyridoxamine), GABA receptor agonists (e.g., gabapentin, pregabalin), serotonin and noradrenalin reuptake inhibitors (e.g., duloxetine), sodium channel inhibitors (e.g., lacosamide), active oxygen scavengers (e.g., thioctic acid), cerebral vasodilators (e.g., tiapuride, mexiletine), somatostatin receptor agonists (e.g., BIM23190), apoptosis signal regulating kinase-1 (ASK-1) inhibitors and the like can be mentioned.

As the therapeutic agent for hyperlipidemia, for example, statin compounds (e.g., pravastatin, simvastatin, lovastatin, atorvastatin, fluvastatin, rosuvastatin, pitavastatin, cerivastatin or a salt thereof (e.g., sodium salt, calcium salt)), squalene synthase inhibitors (e.g., compound described in WO97/10224, for example, N-[[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepin-3-yl]acetyl]piperidin-4-acetic acid), fibrate compounds (e.g., bezafibrate, clofibrate, simfibrate, clinofibrate), anion exchange resin (e.g., colestyramine), probucol, nicotinic acid drugs (e.g., nicomol, niceritrol, niaspan), ethyl icosapentate, phytosterol (e.g., soysterol, gamma oryzanol (γ-oryzanol)), cholesterol absorption inhibitors (e.g., zechia), CETP inhibitors (e.g., dalcetrapib, anacetrapib), ω-3 fatty acid preparations (e.g., ω-3-fatty acid ethyl esters 90 (ω-3-acid ethyl esters 90)) and the like can be mentioned.

Examples of the antihypertensive agent include angiotensin converting enzyme inhibitors (e.g., captopril, enalapril, delapril, etc.), angiotensin II antagonists (e.g., candesartan cilexetil, candesartan, losartan, losartan potassium, eprosartan, valsartan, telmisartan, irbesartan, tasosartan, olmesartan, olmesartan medoxomil, azilsartan, azilsartan medoxomil), calcium antagonists (e.g., manidipine, nifedipine, amlodipine, efonidipine, nicardipine, amlodipine, cilnidipine, etc.), β blockers (e.g., metoprolol, atenolol, propranolol, carvedilol, pindolol), renin inhibitors (e.g., aliskiren), clonidine and the like.

Examples of the antiobesity agent include monoamine uptake inhibitors (e.g., phentermine, sibutramine, mazindol, fluoxetine, tesofensine), serotonin 2C receptor agonists (e.g., lorcaserin), serotonin 6 receptor antagonists, histamine H3 receptor, GABA modulator (e.g., topiramate), MCH receptor antagonists (e.g., SB-568849; SNAP-7941; the compounds described in WO01/82925 or WO01/87834), neuropeptide Y antagonists (e.g., velneperit), cannabinoid receptor antagonists (e.g., rimonabant, taranabant), ghrelin antagonists, ghrelin receptor antagonists, ghrelinacylation enzyme inhibitors, opioid receptor antagonists (e.g., GSK-1521498), orexin receptor antagonists (e.g., almorexant), melanocortin 4 receptor agonists, 11β-hydroxysteroid dehydrogenase inhibitors (e.g., AZD-4017), pancreatic lipase inhibitors (e.g., orlistat, cetilistat), β3 agonists (e.g., N-5984), diacylglycerol acyltransferase 1 (DGAT1) inhibitors, acetylCoA carboxylase (ACC) inhibitors, stearoyl-CoA desaturated enzyme inhibitors, microsomal triglyceride transfer protein inhibitors (e.g., R-256918), Na-glucose cotransporter inhibitors (e.g., JNJ-28431754, dapagliflozin, canagliflozin, remogliflozin), NFκ inhibitory (e.g., HE-3286), PPAR agonists (e.g., GFT-505, DRF-11605), phosphotyrosine phosphatase inhibitors (e.g., sodium vanadate, Trodusquemin), GPR119 agonists (e.g., PSN-821), glucokinase activators (e.g., AZD-1656), leptin, leptin derivatives (e.g., metreleptin), CNTF (ciliary neurotrophic factor), BDNF (brain-derived neurotrophic factor), cholecystokinin agonists, glucagon-like peptide-1 (GLP-1) preparations (e.g., animal GLP-1 preparations extracted from the pancreas of bovine or swine; human GLP-1 preparations genetically synthesized by using *Escherichia coli* or yeast; fragments or derivatives of GLP-1 (e.g., exenatide, liraglutide)), amylin preparations (e.g., pramlintide, AC-2307), neuropeptide Y agonists (e.g., PYY3-36, derivatives of PYY3-36, obineptide, TM-30339, TM-30335), oxyntomodulin preparations: FGF21 preparations (e.g., animal FGF21 preparations extracted from the pancreas of bovine or swine; human FGF21 preparations genetically synthesized using *Escherichia coli* or yeast; fragments or derivatives of FGF21), combination of a sustained release preparation of naltrexone hydrochloride and a sustained release preparation of bupropion hydrochloride, anorexigenic agents (e.g., P-57) and the like.

As the diuretic, for example, xanthine derivatives (e.g., theobromine sodium salicylate, theobromine calcium salicylate), thiazide preparations (e.g., ethiazide, cyclopenthiazide, trichloromethiazide, hydrochlorothiazide, hydroflumethiazide, benzylhydrochlorothiazide, penfluthiazide, polythiazide, methyclothiazide), antialdosterone preparations (e.g., spironolactone, triamterene, potassium canrenoate), carbonic anhydrase inhibitors (e.g., acetazolamide), chlorobenzenesulfonamide agents (e.g., chlortalidone, mefruside, indapamide), azosemide, isosorbide, ethacrynic acid, piretanide, bumetanide, furosemide and the like can be mentioned.

As the antithrombotic agent, for example, heparin (e.g., heparin sodium, heparin calcium, enoxaparin sodium, dalteparin sodium), warfarin (e.g., warfarin potassium), antithrombin drugs (e.g., aragatroban, dabigatran), thrombolytic agents (e.g., urokinase, tisokinase, alteplase, nateplase, monteplase, pamiteplase), platelet aggregation inhibitors (e.g., ticlopidine hydrochloride, clopidogrel, E5555, SHC530348, cilostazol, ethyl icosapentate, beraprost sodium, sarpogrelate hydrochloride, prasugrel, ticagrelor), Fxa inhibitors (e.g., rivaroxaban, apixaban, edoxaban, YM150, compound described in WO02/06234, WO2004/048363, WO2005/030740, WO2005/058823 or WO2005/113504) and the like can be mentioned.

The time of administration of the above-mentioned concomitant drug is not limited, and the compound of the present invention and the concomitant drug may be administered simultaneously or in a staggered manner to the administration subject. The dose of the concomitant drug can conform to the dose employed in clinical situations and can be appropriately determined depending on the administration subject, administration route, disease, combination and the like.

The administration mode of the concomitant drug is not particularly limited, and it is only required that the compound of the present invention and the concomitant drug should be combined at the time of administration. Examples of such administration mode include the following:
1) administration of a single preparation obtained by simultaneously processing the compound of the present invention and the concomitant drug, 2) simultaneous administration of two kinds of preparations of the compound of the present invention and the concomitant drug, which have been separately produced, by the same administration route,
3) administration of two kinds of preparations of the compound of the present invention and the concomitant drug, which have been separately produced, by the same administration route in a staggered manner,
4) simultaneous administration of two kinds of preparations of the compound of the present invention and the concomitant drug, which have been separately produced, by different administration routes,
5) administration of two kinds of preparations of the compound of the present invention and the concomitant drug, which have been separately produced, by different administration routes in a staggered manner (e.g., administration in the order of the compound of the present invention and the concomitant drug, or in the reverse order) and the like.

The mixing ratio of the compound of the present invention and a concomitant drug can be appropriately determined depending on the administration subject, administration route, disease and the like.

Methods for producing the compound of the present invention are described in the following.

In production methods given below, starting materials or reagents used in each step and obtained compounds may each form a salt. Examples of such salt include the same as the above-mentioned salt of the compound of the present invention and the like.

When the compound obtained in each step is a free compound, it can be converted to a salt of interest by a method known per se. On the contrary, when the compound obtained in each step is a salt, it can be converted to a free form or a different type of salt of interest by a method known per se.

The compound obtained in each step may be used in subsequent reaction directly in the form of a reaction solution thereof or after being obtained as a crude product. Alternatively, the compound obtained in each step can be isolated and/or purified from the reaction mixture by separation means such as concentration, crystallization, recrystallization, distillation, solvent extraction, fractionation, chromatography, and the like according to a conventional method.

When compounds of starting materials or reagents for each step are commercially available, these commercially available products can be used directly.

For reaction in each step, the reaction time may differ depending on the reagent or solvent used and is usually 1 minute to 48 hours, preferably 10 minutes to 8 hours, unless otherwise specified.

For reaction in each step, the reaction temperature may differ depending on the reagent or solvent used and is usually −78° C. to 300° C., preferably −78° C. to 150° C., unless otherwise specified.

For reaction in each step, the pressure may differ depending on the reagent or solvent used and is usually 1 atm to 20 atm, preferably 1 atm to 3 atm, unless otherwise specified.

For reaction in each step, for example, a microwave synthesis apparatus such as Initiator manufactured by Biotage Japan Ltd. and the like may be used. The reaction temperature may differ depending on the reagent or solvent used and is usually room temperature to 300° C., preferably 50° C. to 250° C., unless otherwise specified. The reaction time may differ depending on the reagent or solvent used and is usually 1 minute to 48 hours, preferably 1 minute to 8 hours, unless otherwise specified.

For reaction in each step, a reagent is used at 0.5 equivalents to 20 equivalents, preferably 0.8 equivalents to 5 equivalents, relative to a substrate, unless otherwise specified. When a reagent is used as a catalyst, the reagent is used at 0.001 equivalents to 1 equivalent, preferably 0.01 equivalents to 0.2 equivalents, relative to a substrate. When a reagent also serves as a reaction solvent, the reagent is used in the amount of the solvent.

For reaction in each step, the reaction is performed without a solvent or after dissolution or suspension in an appropriate solvent, unless otherwise specified. Specific examples of the solvent include the solvents described in Examples and the following:

Alcohols: methanol, ethanol, tert-butyl alcohol, 2-methoxyethanol, etc.;
Ethers: diethyl ether, diphenyl ether, tetrahydrofuran, 1,2-dimethoxyethane, etc.;
Aromatic hydrocarbons: chlorobenzene, toluene, xylene, etc.;
Saturated hydrocarbons: cyclohexane, hexane, etc.;
Amides: N,N-dimethylformamide, N-methylpyrrolidone, etc.;
Halogenated hydrocarbons: dichloromethane, carbon tetrachloride, etc.;
Nitriles: acetonitrile, etc.;
Sulfoxides: dimethyl sulfoxide, etc.;
Aromatic organic bases: pyridine, etc.;
Acid anhydrides: acetic anhydride, etc.;
Organic acids: formic acid, acetic acid, trifluoroacetic acid, etc.;
Inorganic acids: hydrochloric acid, sulfuric acid, etc.;
Esters: ethyl acetate, etc.;
Ketones: acetone, methyl ethyl ketone, etc.; and Water.

These solvents may be used as a mixture of two or more thereof at an appropriate ratio.

When a base is used for reaction in each step, any of the following bases or the bases described in Examples, for example, is used.

Inorganic bases: sodium hydroxide, magnesium hydroxide, etc.;
Basic salts: sodium carbonate, calcium carbonate, sodium bicarbonate, etc.;
Organic bases: triethylamine, diethylamine, pyridine, 4-dimethylaminopyridine, N,N-dimethylaniline, 1,4-diazabicyclo[2.2.2]octane, 1,8-diazabicyclo[5.4.0]-7-undecene, imidazole, piperidine, etc.;
Metal alkoxides: sodium ethoxide, potassium tert-butoxide, etc.;
Alkali metal hydrides: sodium hydride, etc.;
Metal amides: sodium amide, lithium diisopropylamide, lithium hexamethyldisilazide, etc.; and
Organic lithiums: n-butyllithium, etc.

When an acid or acidic catalyst is used for reaction in each step, any of the following acids or acidic catalysts or the acids or acidic catalysts described in Examples, for example, is used.

Inorganic acids: hydrochloric acid, sulfuric acid, nitric acid, hydrobromic acid, phosphoric acid, etc.;
Organic acids: acetic acid, trifluoroacetic acid, citric acid, p-toluenesulfonic acid, 10-camphorsulfonic acid, etc.; and
Lewis acids: boron trifluoride-diethyl ether complex, zinc iodide, anhydrous aluminum chloride, anhydrous zinc chloride, anhydrous iron chloride, etc.

Reaction in each step is performed in accordance with a method known per se, for example, the method described in Jikken Kagaku Koza (Encyclopedia of Experimental Chemistry in English), 5th Ed., Vol. 13-19 (edited by The Chemical Society of Japan); Shin Jikken Kagaku Koza (New Encyclopedia of Experimental Chemistry in English), Vol. 14-15

(edited by The Chemical Society of Japan); Reactions and Syntheses in the Organic Chemistry Laboratory, Revised, 2nd Ed. (L. F. Tietze, Th. Eicher, Nankodo Co., Ltd.); Revised Organic Name Reactions; The Reaction Mechanism and Essence (Hideo Togo, Kodansha Ltd.); ORGANIC SYNTHESES Collective Volume I-VII (John Wiley & Sons Inc.); Modern Organic Synthesis in the Laboratory A Collection of Standard Experimental Procedures (Jie Jack Li, OXFORD UNIVERSITY Press); Comprehensive Heterocyclic Chemistry III, Vol. 1-14 (Elsevier B. V.); Strategic Applications of Named Reactions in Organic Synthesis (translated by Kiyoshi Tomioka, published by Kagaku-Dojin Publishing Company, INC); Comprehensive Organic Transformations (VCH Publishers Inc.) (1989), etc., or the method described in Examples, unless otherwise specified.

The protection or deprotection reaction of a functional group in each step is performed in accordance with a method known per se, for example, the method described in "Protective Groups in Organic Synthesis, 4th Ed." (Theodora W. Greene, Peter G. M. Wuts), Wiley-Interscience (2007); "Protecting Groups 3rd Ed." (P. J. Kocienski), Thieme Medical Publishers (2004), etc., or the method described in Examples.

Examples of protecting groups for the hydroxyl group or phenolic hydroxyl group of an alcohol or the like include ether type protecting groups such as methoxymethyl ether, benzyl ether, t-butyldimethylsilyl ether, tetrahydropyranyl ether, and the like; carboxylic acid ester type protecting groups such as acetic acid ester and the like; sulfonic acid ester type protecting groups such as methanesulfonic acid ester and the like; carbonic acid ester type protecting groups such as t-butyl carbonate and the like; etc.

Examples of protecting groups for the carbonyl group of an aldehyde include acetal type protecting groups such as dimethyl acetal and the like; cyclic acetal type protecting groups such as cyclic 1,3-dioxane and the like; etc.

Examples of protecting groups for the carbonyl group of a ketone include ketal type protecting groups such as dimethyl ketal and the like; cyclic ketal type protecting groups such as cyclic 1,3-dioxane and the like; oxime type protecting groups such as O-methyloxime and the like; hydrazone type protecting groups such as N,N-dimethylhydrazone and the like; etc.

Examples of protecting groups for the carboxyl group include ester type protecting groups such as methyl ester and the like; amide type protecting groups such as N,N-dimethylamide and the like; etc.

Examples of protecting groups for thiol include ether type protecting groups such as benzylthio ether and the like; ester type protecting groups such as thioacetic acid ester, thiocarbonate, thiocarbamate, and the like; etc.

Examples of protecting groups for the amino group or an aromatic heterocyclic ring such as imidazole, pyrrole, indole, or the like include carbamate type protecting groups such as benzyl carbamate and the like; amide type protecting groups such as acetamide and the like; alkylamine type protecting groups such as N-triphenylmethylamine and the like; sulfonamide type protecting groups such as methanesulfonamide and the like; etc.

A protecting group can be removed by a method known per se, for example, a method using acid, base, ultraviolet light, hydrazine, phenylhydrazine, sodium N-methyldithiocarbamate, tetrabutylammonium fluoride, palladium acetate, or trialkylsilyl halide (e.g., trimethylsilyl iodide, trimethylsilyl bromide), a reduction method, or the like.

In the case of performing reduction reaction in each step, examples of the reducing agent used include metal hydrides such as lithium aluminum hydride, sodium triacetoxy borohydride, sodium cyanoborohydride, diisobutyl aluminum hydride (DIBAL-H), sodium borohydride, tetramethylammonium triacetoxy borohydride, and the like; boranes such as borane-tetrahydrofuran complex and the like; Raney nickel; Raney cobalt; hydrogen; formic acid; etc. A catalyst such as palladium-carbon, a Lindlar's catalyst, or the like may be used in a method for reducing a carbon-carbon double bond or triple bond.

In the case of performing oxidation reaction in each step, examples of the oxidizing agent used include peracids such as m-chloroperbenzoic acid (MCPBA), hydrogen peroxide, t-butyl hydroperoxide, and the like; perchlorates such as tetrabutylammonium perchlorate and the like; chlorates such as sodium chlorate and the like; chlorites such as sodium chlorite and the like; periodates such as sodium periodate and the like; high-valent iodine reagents such as iodosylbenzene and the like; manganese-containing reagents such as manganese dioxide, potassium permanganate, and the like; leads such as lead tetraacetate and the like; chromium-containing reagents such as pyridinium chlorochromate (PCC), pyridinium dichromate (PDC), Jones reagents, and the like; halogen compounds such as N-bromosuccinimide (NBS) and the like; oxygen; ozone; sulfur trioxide-pyridine complex; osmium tetraoxide; selenium dioxide; 2,3-dichloro-5,6-dicyano-1,4-benzoquinone (DDQ); etc.

In the case of performing radical cyclization reaction in each step, examples of the radical initiator used include azo compounds such as azobisisobutyronitrile (AIBN) and the like; water-soluble radical initiators such as 4-4'-azobis-4-cyanopentanoic acid (ACPA) and the like; triethylboron in the presence of air or oxygen; benzoyl peroxide; etc. Examples of the radical reagent used include tributylstannane, tristrimethylsilylsilane, 1,1,2,2-tetraphenyldisilane, diphenylsilane, samarium iodide, and the like.

In the case of performing Wittig reaction in each step, examples of the Wittig reagent used include alkylidene phosphoranes. The alkylidene phosphoranes can be prepared by a method known per se, for example, the reaction of a phosphonium salt with a strong base.

In the case of performing Horner-Emmons reaction in each step, examples of the reagent used include phosphonoacetic acid esters such as methyl dimethylphosphonoacetate, ethyl diethylphosphonoacetate, and the like; and bases such as alkali metal hydrides, organic lithiums, and the like.

In the case of performing Friedel-Crafts reaction in each step, examples of the reagent used include a Lewis acid and an acid chloride or an alkylating agent (e.g., alkyl halides, alcohols, olefins, etc.). Alternatively, an organic or inorganic acid may be used instead of the Lewis acid, and an acid anhydride such as acetic anhydride or the like may be used instead of the acid chloride.

In the case of aromatic nucleophilic substitution reaction in each step, a nucleophile (e.g., amines, imidazole, etc.) and a base (e.g., basic salts, organic bases, etc.) are used as reagents.

In the case of performing carbanion-mediated nucleophilic addition reaction, carbanion-mediated nucleophilic 1,4-addition reaction (Michael addition reaction), or carbanion-mediated nucleophilic substitution reaction in each step, examples of the base used for generating a carbanion include organic lithiums, metal alkoxides, inorganic bases, organic bases, and the like.

In the case of performing Grignard reaction in each step, examples of the Grignard reagent include aryl magnesium halides such as phenyl magnesium bromide and the like; and alkyl magnesium halides such as methyl magnesium bromide and the like. The Grignard reagent can be prepared by a method known per se, for example, the reaction of alkyl halide or aryl halide with metal magnesium in the presence of ether or tetrahydrofuran as a solvent.

In the case of performing Knoevenagel condensation reaction in each step, an active methylene compound flanked by two electron withdrawing groups (e.g., malonic acid, diethyl malonate, malononitrile, etc.) and a base (e.g., organic bases, metal alkoxides, inorganic bases) are used as reagents.

In the case of performing Vilsmeier-Haack reaction in each step, phosphoryl chloride and an amide derivative (e.g., N,N-dimethylformamide, etc.) are used as reagents.

In the case of performing the azidation reaction of alcohols, alkyl halides, or sulfonic acid esters in each step, examples of the azidation agent used include diphenylphosphorylazide (DPPA), trimethylsilyl azide, sodium azide, and the like. For the azidation of alcohols, for example, a method using diphenylphosphorylazide and 1,8-diazabicyclo[5,4,0]undec-7-ene (DBU), a method using trimethylsilyl azide and a Lewis acid, or the like is used.

In the case of performing reductive amination reaction in each step, examples of the reducing agent used include sodium triacetoxy borohydride, sodium cyanoborohydride, hydrogen, formic acid, and the like. When a substrate is an amine compound, examples of the carbonyl compound used include paraformaldehyde as well as aldehydes such as acetaldehyde and the like and ketones such as cyclohexanone and the like. When a substrate is a carbonyl compound, examples of the amines used include primary amines such as ammonia, methylamine, and the like; secondary amines such as dimethylamine and the like; etc.

In the case of performing Mitsunobu reaction in each step, azodicarboxylic acid esters (e.g., diethyl azodicarboxylate (DEAD), diisopropyl azodicarboxylate (DIAD), etc.) and triphenylphosphine are used as reagents.

In the case of performing esterification reaction, amidation reaction, or urea formation reaction in each step, examples of the reagent used include acyl halides such as acid chloride, acid bromide, and the like; acid anhydrides, active esters, and activated carboxylic acids such as sulfuric acid ester and the like. Examples of the activator for carboxylic acids include carbodiimide condensing agents such as 1-ethyl-3-(3-dimethylaminopropyl)carbodiimide hydrochloride (WSCD) and the like; triazine condensing agents such as 4-(4,6-dimethoxy-1,3,5-triazin-2-yl)-4-methylmorpholinium chloride n-hydrate (DMT-MM) and the like; carbonic acid ester condensing agents such as 1,1-carbonyldiimidazole (CDI) and the like; diphenylphosphorylazide (DPPA); benzotriazol-1-yloxy-trisdimethylamino phosphonium salt (BOP reagent); 2-chloro-1-methyl-pyridinium iodide (Mukaiyama reagent); thionyl chloride; lower alkyl halo-formates such as ethyl chloroformate and the like; O-(7-azabenzotriazol-1-yl)-N,N,N',N'-tetramethyluronium hexafluorophosphate (HATU); sulfuric acid; combinations thereof; etc. In the case of using a carbodiimide condensing agent, an additive such as 1-hydroxybenzotriazole (HOBt), N-hydroxysuccinimide (HOSu), dimethylaminopyridine (DMAP), or the like may be further added to the reaction.

In the case of performing coupling reaction in each step, examples of the metal catalyst used include palladium compounds such as palladium(II) acetate, tetrakis(triphenylphosphine)palladium(0), dichlorobis(triphenylphosphine)palladium(II), dichlorobis(triethylphosphine)palladium(II), tris(dibenzylideneacetone)dipalladium(0), 1,1'-bis(diphenylphosphino)ferrocene palladium(II) chloride, and the like; nickel compounds such as tetrakis(triphenylphosphine)nickel(0) and the like; rhodium compounds such as tris(triphenylphosphine)rhodium(III) chloride and the like; cobalt compounds; copper compounds such as copper oxide, copper(I) iodide, and the like; platinum compounds; etc. A base may be further added to the reaction. Examples of such a base include inorganic bases, basic salts, and the like.

In the case of performing thiocarbonylation reaction in each step, typically, diphosphorus pentasulfide is used as a thiocarbonylation agent. In addition to diphosphorus pentasulfide, a reagent having a 1,3,2,4-dithiadiphosphetane-2,4-disulfide structure, such as 2,4-bis(4-methoxyphenyl-1,3,2,4-dithiadiphosphetane-2,4-disulfide (Lawesson's reagent) or the like may be used.

In the case of performing Wohl-Ziegler reaction in each step, examples of the halogenating agent used include N-iodosuccinimide, N-bromosuccinimide (NBS), N-chlorosuccinimide (NCS), bromine, sulfuryl chloride, and the like. Heat, light, or a radical initiator such as benzoyl peroxide, azobisisobutyronitrile, or the like can be added to the reaction to thereby accelerate the reaction.

In the case of performing the halogenation reaction of a hydroxy group in each step, examples of the halogenating agent used include a hydrohalic acid and an acid halide of an inorganic acid, specifically, hydrochloric acid, thionyl chloride, phosphorus oxychloride, or the like for chlorination, and 48% hydrobromic acid or the like for bromination. Also, a method for obtaining an alkyl halide from an alcohol by the action of triphenylphosphine and carbon tetrachloride or carbon tetrabromide, etc. may be used. Alternatively, a method for synthesizing an alkyl halide through two reaction steps involving the conversion of an alcohol to sulfonic acid ester and subsequent reaction with lithium bromide, lithium chloride, or sodium iodide, may be used.

In the case of performing Arbuzov reaction in each step, examples of the reagent used include alkyl halides such as ethyl bromoacetate and the like; and phosphites such as triethylphosphite, tri(isopropyl)phosphite, and the like.

In the case of performing sulfone esterification reaction in each step, examples of the sulfonating agent used include methanesulfonyl chloride, p-toluenesulfonyl chloride, methanesulfonic anhydride, p-toluenesulfonic anhydride, and the like.

In the case of performing hydrolysis reaction in each step, an acid or a base is used as a reagent. For the acid hydrolysis reaction of t-butyl ester, formic acid, triethylsilane, or the like may be added in order to reductively trap t-butyl cation by-products.

In the case of performing dehydration reaction in each step, examples of the dehydrating agent used include sulfuric acid, diphosphorus pentaoxide, phosphorus oxychloride, N,N'-dicyclohexylcarbodiimide, alumina, polyphosphoric acid, and the like.

Compound (1) and compound (1') can be produced by a method mentioned below from compound (2).

[Formula 11]

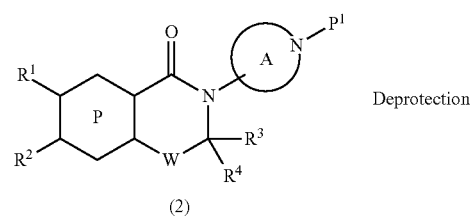

Deprotection

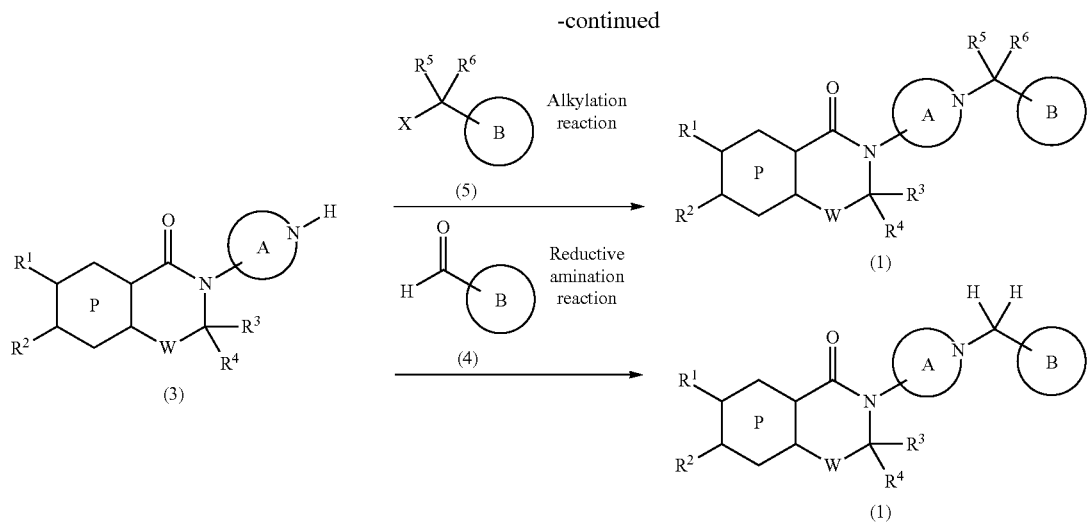

wherein $P^1$ represents a protecting group for the amino group; and X represents a sulfonate group or a halogen atom.

Compound (1) can also be produced by alkylation reaction using compound (5) and a base.

Compound (4) and compound (5) can be produced by a method known per se.

Of compounds (1), compound (1-2) can be produced by a method mentioned below from compound (1-1).

[Formula 12]

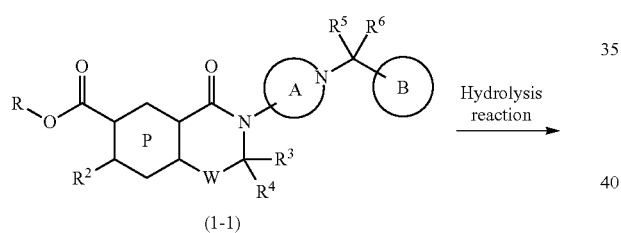

Of compounds (1), compound (1-4) can be produced by a method mentioned below from compound (1-3).

[Formula 13]

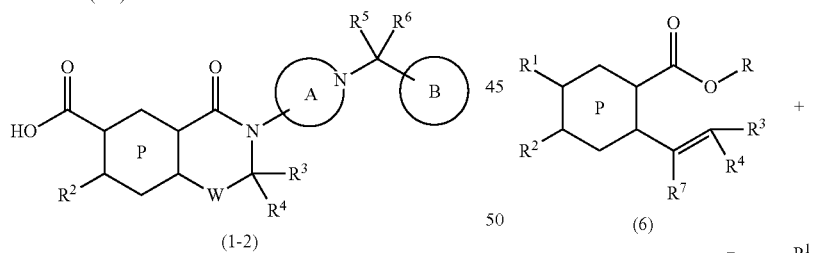

Of compounds (2), compound (2-1) can be produced by a method mentioned below from compound (6) and compound (7).

[Formula 14]

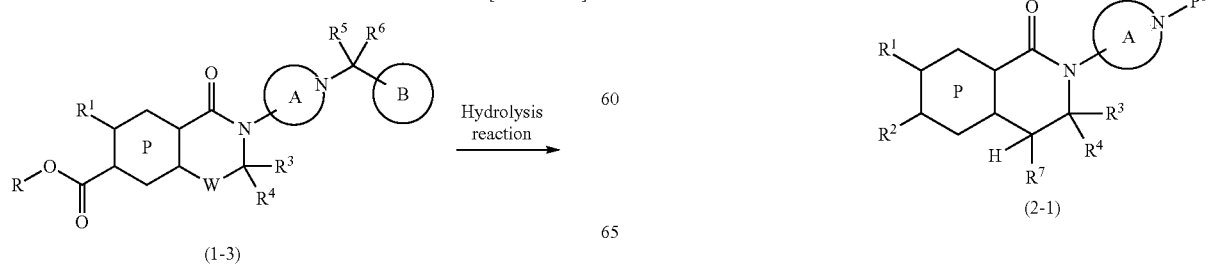

wherein $R^7$ represents H or $C_{1-6}$ alkyl.

Compound (2-1) can be produced by cycloaddition reaction using compound (6), compound (7) and a base. Examples of the solvent include dimethylacetamide, methanol, acetonitrile, and the like. These may be used in admixture at an appropriate ratio. Examples of the base include triethylamine, diisopropylethylamine, and the like.

Compound (7) can be produced by a method known per se.

Of compounds (6), compound (6-1) can be produced by a method mentioned below from compound (8).

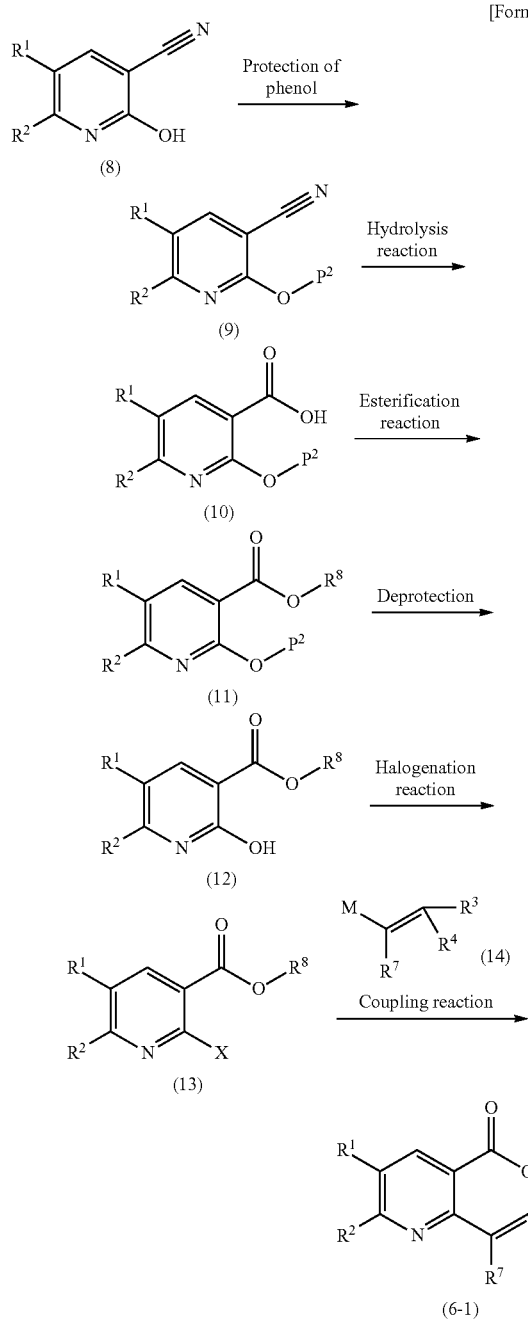

wherein $P^2$ represents a protecting group for the phenolic hydroxyl group; and M represents trialkyltin or boronic acid (B (OR) 2 or $B^-F_3K^+$).

Compound (13) can be produced by the halogenation reaction of compound (12) with a halogenating agent. Examples of the halogenating agent include phosphorus oxychloride, oxalyl chloride, thionyl chloride, and the like.

Compound (6-1) can be produced by the coupling reaction of compound (13) and compound (14). Examples of the compound (14) include potassium vinyl trifluoroborate, 4,4,5,5-tetramethyl-2-vinyl-1,3,2-dioxaborolane, tributylvinyltin, and the like.

Compound (8) and compound (14) can be produced by a method known per se.

Of compounds (12), compound (12-1) can be produced by a method mentioned below from compound (15), compound (16), and compound (17).

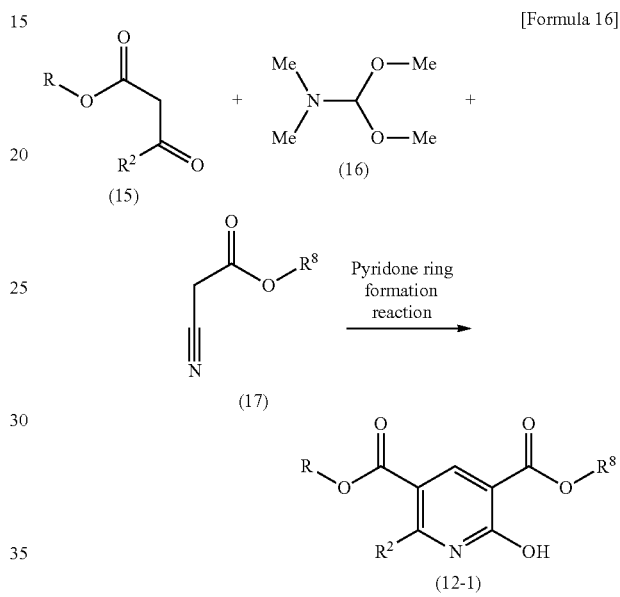

Compound (12-1) can be produced by pyridone ring formation reaction from compound (15), compound (16), and compound (17). An active intermediate is obtained from compound (15) and compound (16) and then reacted with compound (17) using a base to form a pyridone ring.

Compound (15), compound (16), and compound (17) can be produced by a method known per se.

Of compounds (2), compound (2-2) can be produced by a method mentioned below from compound (18) and compound (7).

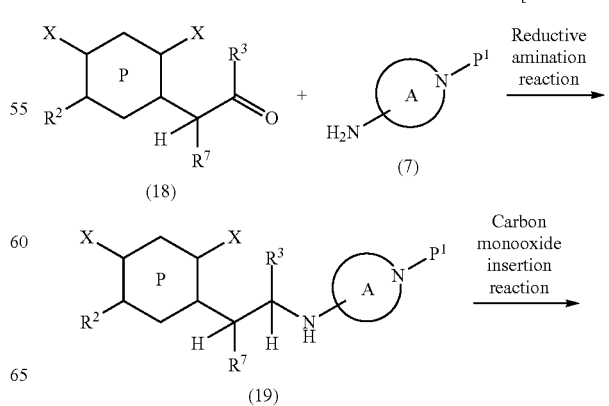

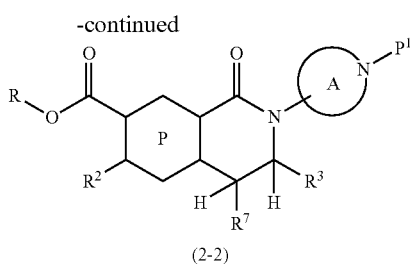

(2-2)

Compound (2-2) can be produced by carbon monooxide insertion reaction using compound (19), carbon monooxide, a base, and a palladium catalyst. Examples of the palladium catalyst include palladium acetate, a dichloromethane adduct of [1,1'-bis(diphenylphosphino)ferrocene]dichloropalladium (II), tris(dibenzylideneacetone)dipalladium, and the like. Compound (18) can be produced by a method known per se.

The present invention is explained in detail in the following by referring to the following Examples, TestExamples and Formulation Examples, which are not to be construed as limitative. In addition, the present invention may be modified without departing from the scope of invention.

The term "room temperature" in the following Examples indicates the range of generally from about 10° C. to about 35° C. A ratio used for a mixed solvent indicates a volume ratio, unless otherwise specified. % indicates wt %, unless otherwise specified.

The term "NH" in silica gel column chromatography indicates that an aminopropylsilane-bound silica gel was used. The term "C18" in HPLC (high-performance liquid chromatography) indicates that an octadecyl-bound silica gel was used. A ratio used for elution solvents indicates a volume ratio, unless otherwise specified.

Abbreviations described below are used in the following Examples.
THF: tetrahydrofuran
DMF: dimethylformamide
DMA: dimethylacetamide
DME: 1,2-dimethoxyethane
DMSO: dimethyl sulfoxide
$^1$H NMR (proton nuclear magnetic resonance spectrum) was measured by Fourier transform type NMR. ACD/Spec-Manager (trade name) or the like was used in analysis. No mention was made about the very broad peaks of protons of a carboxy group, a hydroxyl group, an amino group, and the like.

Other abbreviations used herein indicate meanings described below.
s: singlet
d: doublet
t: triplet
q: quartet
quin: quintet
m: multiplet
br: broad
J: coupling constant
Hz: Hertz
$CDCl_3$: deuterated chloroform
$DMSO-d_6$: $d_6$-dimethyl sulfoxide
$CD_3OD$: deuterated methanol
$^1$H-NMR: proton nuclear magnetic resonance
TFA: trifluoroacetic acid MS (mass spectrum) was measured using LC/MS (liquid chromatograph mass spectrometer). ESI (ElectroSpray Ionization) or APCI (Atmospheric Pressure Chemical Ionization) was used as an ionization method. Both or either one of a positive mode (ESI+) and a negative mode (ESI−) was used as an ionization mode, and any data was described. Data was indicated by actual measurement value (found). In general, molecular ion peaks are observed. In the case of a compound having a tert-butoxycarbonyl group (—Boc), a fragment ion peak derived from the elimination of the tert-butoxycarbonyl group or the tert-butyl group may be observed. In the case of a compound having a hydroxyl group (—OH), a fragment ion peak derived from the elimination of $H_2O$ may be observed. In the case of salt, a molecular ion peak or fragment ion peak of a free form is generally observed.

Example 1

6-(1-((2-Cyclopropyl-6-ethoxy-4'-fluorobiphenyl-4-yl)methyl)piperidin-4-yl)-2-methyl-5-oxo-5,6,7,8-tetrahydro-1,6-naphthyridine-3-carboxylic acid

[Formula 18]

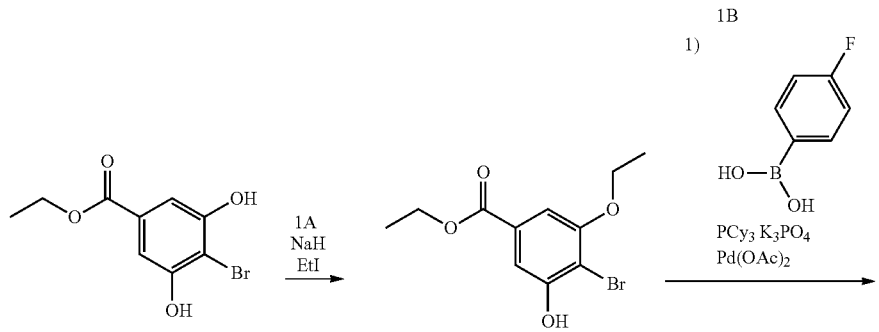

-continued
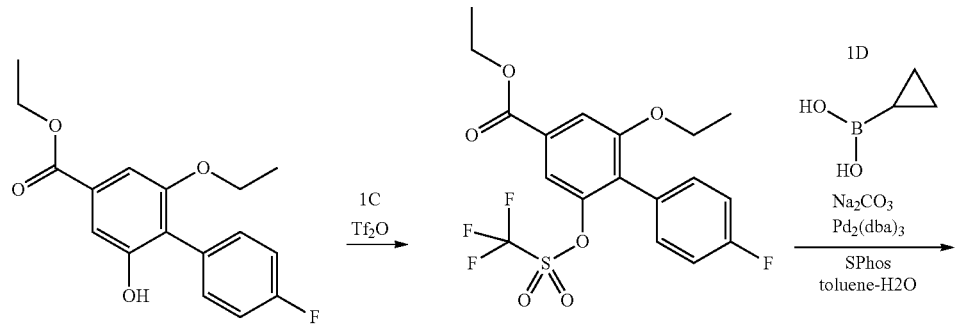
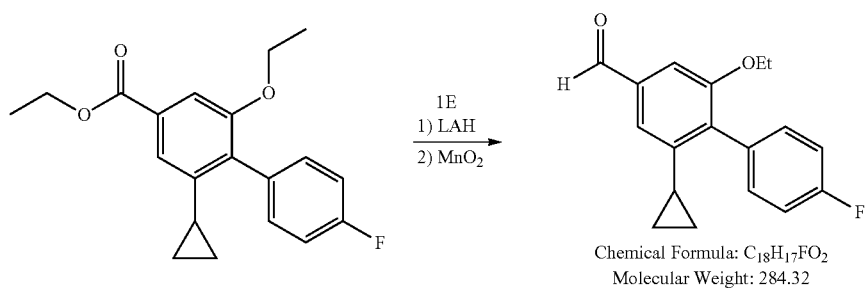
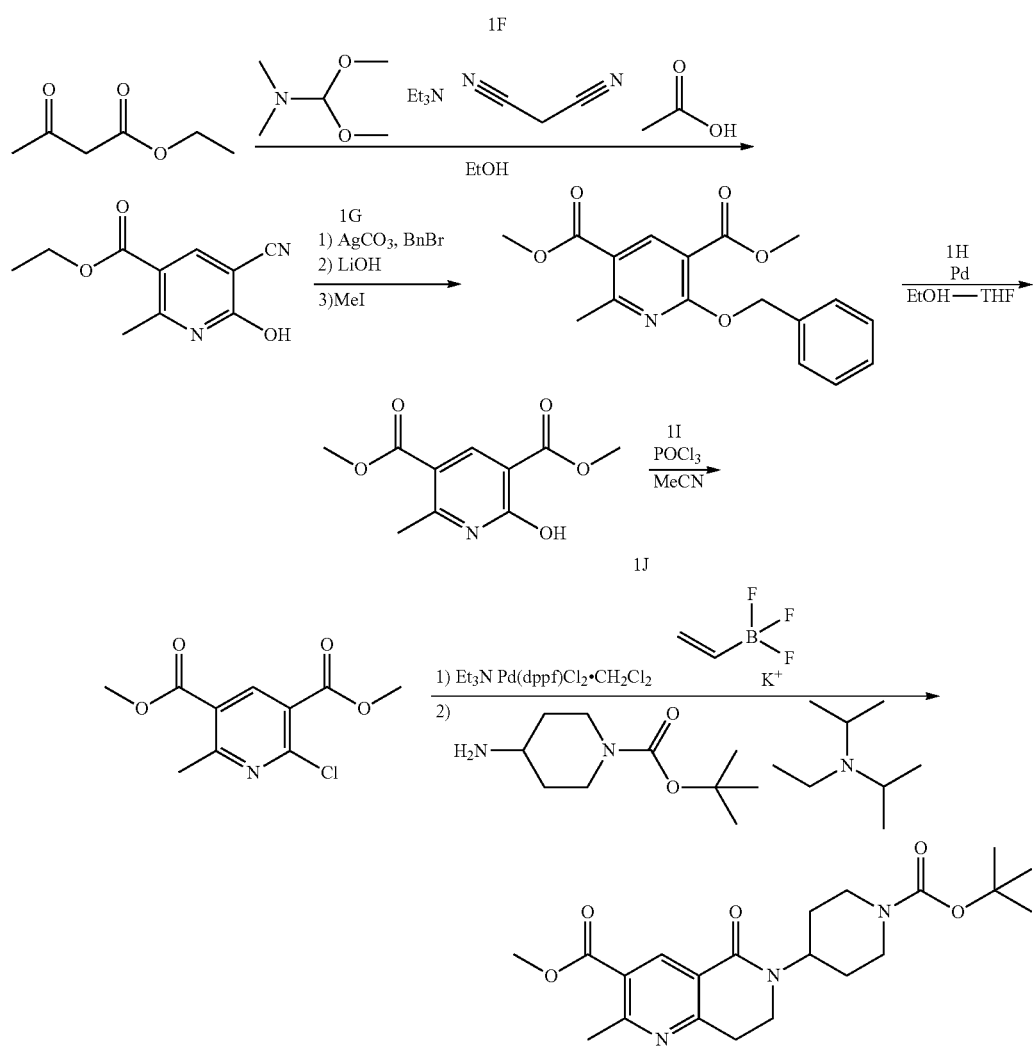

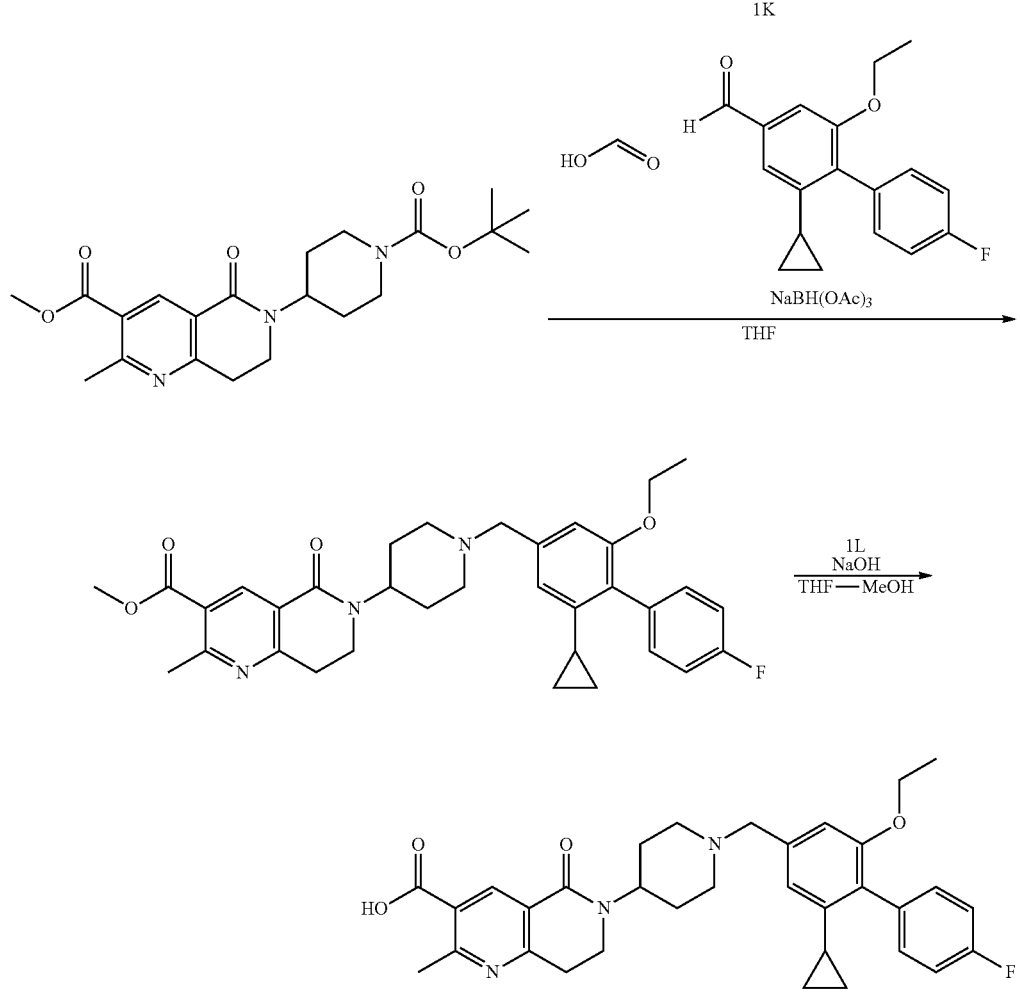

A) Ethyl 4-bromo-3-ethoxy-5-hydroxybenzoate

Sodium hydride (60% oil, 3.86 g) was added to a DMF (100 mL) solution of ethyl 4-bromo-3,5-dihydroxybenzoate (12.3 g), and the mixture was stirred at 00° C. for 30 minutes in a nitrogen atmosphere. Iodoethane (4.15 mL) was added to the reaction mixture, and the mixture was stirred at room temperature for 2 hours. Water was added to the reaction mixture, followed by extraction with ethyl acetate. The obtained organic layer was washed with saturated saline and dried over anhydrous magnesium sulfate, and then, the solvent was distilled off under reduced pressure. The obtained residue was purified by silica gel column chromatography (hexane/ethyl acetate) to obtain the title compound (8.87 g).
$^1$H NMR (300 MHz, CDCl$_3$) δ 1.35-1.43 (3H, m), 1.49 (3H, t, J=7.0 Hz), 4.13-4.22 (2H, m), 4.37 (2H, q, J=7.2 Hz), 5.75 (1H, s), 7.13 (1H, d, J=1.7 Hz), 7.34 (1H, d, J=1.8 Hz).

B) Ethyl 2-ethoxy-4'-fluoro-6-hydroxybiphenyl-4-carboxylate

Palladium acetate (344 mg) was added to a mixture of ethyl 4-bromo-3-ethoxy-5-hydroxybenzoate (8.87 g), tripotassium phosphate (19.5 g), (4-fluorophenyl)boronic acid (10.7 g), tricyclohexylphosphine (20% toluene solution, 5.45 mL), toluene (80 mL), and water (40 mL), and the resultant mixture was stirred overnight at 90° C. in an argon atmosphere. The reaction mixture was allowed to cool to room temperature, then diluted with ethyl acetate, and washed with water and saturated saline in this order. The organic layer was dried over anhydrous magnesium sulfate, and then, the solvent was distilled off under reduced pressure. The obtained residue was purified by silica gel column chromatography (hexane/ethyl acetate) to obtain the title compound (9.34 g).
$^1$H NMR (300 MHz, CDCl$_3$) δ 1.26 (3H, t, J=7.1 Hz), 1.40 (3H, t, J=7.1 Hz), 4.04 (2H, q, J=7.0 Hz), 4.39 (2H, q, J=7.2 Hz), 5.06 (1H, s), 7.14-7.23 (3H, m), 7.30-7.39 (3H, m).

C) Ethyl 2-ethoxy-4'-fluoro-6-(((trifluoromethyl)sulfonyl)oxy)biphenyl-4-carboxylate Trifluoromethanesulfonic anhydride (8.66 mL) was added at 0° C. to a mixture of ethyl 2-ethoxy-4'-fluoro-6-hydroxybiphenyl-4-carboxylate (13.0 g) and pyridine (80 mL), and the resultant mixture was stirred at the same temperature as above for 20 minutes. The reaction mixture was passed through a short silica gel (NH) column, and the solvent was distilled off under reduced pressure. The obtained residue was purified by silica gel column chromatography (hexane/ethyl acetate) to obtain the title compound (15.6 g).

¹H NMR (300 MHz, CDCl₃) δ 1.31 (3H, t, J=7.0 Hz), 1.42 (3H, t, J=7.1 Hz), 4.10 (2H, q, J=7.0 Hz), 4.43 (2H, q, J=7.2 Hz), 7.10-7.19 (2H, m), 7.28-7.38 (2H, m), 7.64 (2H, s).

D) Ethyl 2-cyclopropyl-6-ethoxy-4'-fluorobiphenyl-4-carboxylate

A mixture of ethyl 2-ethoxy-4'-fluoro-6-(((trifluoromethyl)sulfonyl)oxy)biphenyl-4-carboxylate (15.6 g), cyclopropylboronic acid (7.67 g), dicyclohexyl(2',6'-dimethoxybiphenyl-2-yl)phosphine (2.20 g), a 2 M aqueous sodium carbonate solution (53.6 mL), tris(dibenzylideneacetone)dipalladium(0) (2.29 g), and toluene (60 mL) was stirred at 100° C. for 2 hours in an argon atmosphere. The reaction mixture was allowed to cool to room temperature and then poured to water, followed by extraction with ethyl acetate. The obtained organic layer was washed with saturated saline and dried over anhydrous magnesium sulfate, and then, the solvent was distilled off under reduced pressure. The obtained residue was purified by silica gel column chromatography (hexane/ethyl acetate) to obtain the title compound (10.5 g).

¹H NMR (300 MHz, CDCl₃) δ 0.65-0.73 (2H, m), 0.73-0.83 (2H, m), 1.18-1.26 (3H, m), 1.40 (3H, t, J=7.1 Hz), 1.56-1.67 (1H, m), 4.01 (2H, q, J=7.0 Hz), 4.39 (2H, q, J=7.2 Hz), 7.05-7.16 (2H, m), 7.20-7.31 (3H, m), 7.42 (1H, d, J=1.4 Hz).

E) 2-Cyclopropyl-6-ethoxy-4'-fluorobiphenyl-4-carbaldehyde

A THF (50 mL) solution of ethyl 2-cyclopropyl-6-ethoxy-4'-fluorobiphenyl-4-carboxylate (10.5 g) was added to a THF (50 mL) suspension of lithium aluminum hydride (1.21 g) under ice cooling in a nitrogen atmosphere. After stirring at the same temperature as above for 30 minutes, water (1.2 mL) and a 15% aqueous sodium hydroxide solution (1.2 mL) were added thereto, and the mixture was stirred for 5 minutes. Water (3.6 mL) was further added to the reaction mixture, and the mixture was stirred for 30 minutes and then filtered. The filtrate was concentrated under reduced pressure. Manganese dioxide (13.9 g) was added to a toluene (60 mL) solution of the obtained residue, and the mixture was stirred at 60° C. for 1 hour in a nitrogen atmosphere. The reaction mixture was filtered, and then, the solvent was distilled off under reduced pressure. The obtained residue was purified by silica gel column chromatography (hexane/ethyl acetate) to obtain the title compound (7.79 g).

¹H NMR (300 MHz, CDCl₃) δ 0.66-0.77 (2H, m), 0.80-0.91 (2H, m), 1.24 (3H, t, J=6.9 Hz), 1.60-1.74 (1H, m), 4.03 (2H, q, J=6.9 Hz), 7.03 (1H, d, J=1.1 Hz), 7.08-7.18 (2H, m), 7.22-7.31 (3H, m), 9.94 (1H, s).

F) Ethyl 5-cyano-6-hydroxy-2-methylnicotinate

A mixed solution of ethyl 3-oxobutanoate (40.0 mL) and N,N-dimethylformamide dimethyl acetal (46.1 mL) in ethanol (80 mL) was stirred at 41° C. to 43° C. for 5 hours. The reaction mixture was cooled to 20° C., and then, triethylamine (4.40 mL) was added thereto. While the reaction mixture was cooled to keep the temperature at 25° C. to 36° C., a mixture of malononitrile (22.9 mL) and ethanol (177 mL) was added dropwise thereto, and the mixture was stirred overnight at room temperature. Acetic acid (21.7 mL) was added to the reaction mixture at 20° C. to 25° C., and then, water (560 mL) was added thereto under heating at 70° C. to 75° C. The reaction mixture was cooled in ice, and then, the deposited solid was collected and washed with water to obtain the title compound (54.8 g).

¹H NMR (300 MHz, DMSO-d₆) δ 1.29 (3H, t, J=7.1 Hz), 2.60 (3H, s), 4.22 (2H, q, J=7.1 Hz), 8.44 (1H, s), 12.99 (1H, brs).

G) Dimethyl 2-(benzyloxy)-6-methylpyridine-3,5-dicarboxylate

Benzyl bromide (6.92 mL) was added to a toluene (120 mL) suspension of ethyl 5-cyano-6-hydroxy-2-methylnicotinate (10.0 g) and silver carbonate (14.7 g), and the mixture was stirred at room temperature for 2 days. The reaction mixture was passed through a short silica gel (NH) column, and the solvent was distilled off under reduced pressure. Lithium hydroxide monohydrate (25.2 g) was added to a mixture of the obtained residue in ethanol (60 mL) and water (60 mL), and the resultant mixture was stirred overnight at 100° C. in a nitrogen atmosphere. The reaction mixture was neutralized with 6 M hydrochloric acid, followed by extraction with ethyl acetate. The obtained organic layer was dried over anhydrous magnesium sulfate, and then, the solvent was distilled off under reduced pressure. Potassium carbonate (21.8 g) and iodomethane (9.86 mL) were added to a mixture of the obtained residue and DMF (20 mL), and the resultant mixture was stirred at 50° C. for 1 hour. The reaction mixture was allowed to cool to room temperature and then poured to water, followed by extraction with ethyl acetate. The obtained organic layer was washed with saturated saline and dried over anhydrous magnesium sulfate, and then, the solvent was distilled off under reduced pressure. The obtained residue was purified by silica gel column chromatography (NH, hexane/ethyl acetate) to obtain the title compound (14.4 g).

¹H NMR (300 MHz, CDCl₃) δ 2.80 (3H, s), 3.89 (3H, s), 3.91 (3H, s), 5.59 (2H, s), 7.29-7.43 (3H, m), 7.53 (2H, d, J=7.3 Hz), 8.74 (1H, s).

H) Dimethyl 2-hydroxy-6-methylpyridine-3,5-dicarboxylate

A mixture of dimethyl 2-(benzyloxy)-6-methylpyridine-3,5-dicarboxylate (14.4 g), 10% palladium carbon (containing 55% water, 9.00 g), THF (20 mL), and ethanol (20 mL) was stirred at room temperature for 1 hour in a hydrogen atmosphere. The catalyst was filtered off, and then, the obtained filtrate was concentrated under reduced pressure. The obtained solid was washed with ethyl acetate to obtain the title compound (4.96 g).

¹H NMR (300 MHz, CDCl₃) δ 2.83 (3H, s), 3.88 (3H, s), 3.92 (3H, s), 8.83 (1H, s), 12.85 (1H, brs).

I) Dimethyl 2-chloro-6-methylpyridine-3,5-dicarboxylate

Phosphorus oxychloride (4.11 mL) was added to a mixture of dimethyl 2-hydroxy-6-methylpyridine-3,5-dicarboxylate (4.96 g) and acetonitrile (30 mL), and the resultant mixture was stirred overnight at 90° C. in a nitrogen atmosphere. The reaction mixture was allowed to cool to room temperature, and then, a saturated aqueous solution of sodium bicarbonate was added thereto, followed by extraction with ethyl acetate. The obtained organic layer was dried over anhydrous magnesium sulfate, and then, the solvent was distilled off under reduced pressure. The obtained residue was purified by silica gel column chromatography (hexane/ethyl acetate) to obtain the title compound (4.97 g).

$^1$H NMR (300 MHz, CDCl$_3$) δ 2.87 (3H, s), 3.95 (3H, s), 3.97 (3H, s), 8.70 (1H, s).

J) Methyl 6-(1-(tert-butoxycarbonyl)piperidin-4-yl)-2-methyl-5-oxo-5,6,7,8-tetrahydro-1,6-naphthyridine-3-carboxylate A dichloromethane adduct of (1,1'-bis(diphenylphosphino)ferrocene)dichloropalladium(II) (0.804 g) was added to a mixture of dimethyl 2-chloro-6-methylpyridine-3,5-dicarboxylate (2.40 g), potassium vinyl trifluoroborate (2.64 g), triethylamine (2.75 mL), and ethanol (20 mL), and the resultant mixture was stirred at 95° C. for 1 hour in an argon atmosphere. The solvent in the reaction mixture was distilled off under reduced pressure, and the obtained residue was purified by silica gel column chromatography (hexane/ethyl acetate). A mixture of the obtained purified product, tert-butyl 4-aminopiperidine-1-carboxylate (3.95 g), N,N'-diisopropylethylamine (2.57 mL), acetonitrile (7.5 mL), and methanol (7.5 mL) was stirred at 150° C. for 4 hours under microwave irradiation. The reaction mixture was allowed to cool to room temperature, and then, the solvent was distilled off under reduced pressure. The obtained residue was purified by silica gel column chromatography (hexane/ethyl acetate) to obtain the title compound (3.29 g).

$^1$H NMR (300 MHz, CDCl$_3$) δ 1.48 (9H, s), 1.59-1.79 (4H, m), 2.73-2.96 (5H, m), 3.14 (2H, t, J=6.6 Hz), 3.46-3.58 (2H, m), 3.93 (3H, s), 4.18-4.37 (2H, m), 4.70-4.94 (1H, m), 8.80 (1H, s).

K) Methyl 6-(1-((2-cyclopropyl-6-ethoxy-4'-fluorobiphenyl-4-yl)methyl)piperidin-4-yl)-2-methyl-5-oxo-5,6,7,8-tetrahydro-1,6-naphthyridine-3-carboxylate Methyl 6-(1-(tert-butoxycarbonyl)piperidin-4-yl)-2-methyl-5-oxo-5,6,7,8-tetrahydro-1,6-naphthyridine-3-carboxylate (630 mg) was added to formic acid (5 mL), and the mixture was stirred at 60° C. for 30 minutes. Then, the solvent was distilled off under reduced pressure. Toluene was added to the residue, and the solvent was further distilled off under reduced pressure. 2-Cyclopropyl-6-ethoxy-4'-fluorobiphenyl-4-carbaldehyde (533 mg) was added to a mixture of the obtained residue and THF (20 mL), and the resultant mixture was stirred for 10 minutes. Then, sodium triacetoxy borohydride (496 mg) was added thereto, and the mixture was stirred at room temperature for 2 hours. A saturated aqueous solution of sodium bicarbonate was added to the reaction mixture, followed by extraction with ethyl acetate twice. The obtained organic layer was dried over anhydrous magnesium sulfate, and then, the solvent was distilled off under reduced pressure. The obtained residue was purified by silica gel column chromatography (hexane/ethyl acetate/methanol) to obtain the title compound (772 mg).

MS (ESI+): [M+H]$^+$ 572.5.

L) 6-(1-((2-Cyclopropyl-6-ethoxy-4'-fluorobiphenyl-4-yl)methyl)piperidin-4-yl)-2-methyl-5-oxo-5,6,7,8-tetrahydro-1,6-naphthyridine-3-carboxylic acid A 2 M aqueous sodium hydroxide solution (1.50 mL) was added at room temperature to a methanol (2 mL)-THF (2 mL) solution of methyl 6-(1-((2-cyclopropyl-6-ethoxy-4'-fluorobiphenyl-4-yl)methyl)piperidin-4-yl)-2-methyl-5-oxo-5,6,7,8-tetrahydro-1,6-naphthyridine-3-carboxylate (770 mg), and the mixture was stirred at 50° C. for 1 hour. The reaction mixture was neutralized with hydrochloric acid at room temperature. Then, ethyl acetate was added thereto, and the solvent was distilled off under reduced pressure. The deposited solid was collected by filtration and washed with diethyl ether. The obtained solid was recrystallized (DMSO/ethanol/hexane) to obtain the title compound (221 mg).

$^1$H NMR (300 MHz, DMSO-d$_6$) δ 0.52-0.63 (2H, m), 0.66-0.79 (2H, m), 1.12 (3H, t, J=6.9 Hz), 1.43-1.54 (1H, m), 1.58 (2H, d, J=11.0 Hz), 1.74-1.94 (2H, m), 2.03-2.21 (2H, m), 2.75 (3H, s), 2.97 (2H, d, J=11.0 Hz), 3.06 (2H, t, J=6.5 Hz), 3.51 (2H, s), 3.58 (2H, s), 3.93 (2H, d, J=7.1 Hz), 4.30-4.56 (1H, m), 6.49 (1H, s), 6.85 (1H, s), 7.15-7.33 (4H, m), 8.51 (1H, s).

Example 2

6-(1-((2-Cyclopropyl-5-ethoxy-4'-fluorobiphenyl-4-yl)methyl)piperidin-4-yl)-2-ethyl-5-oxo-5,6,7,8-tetrahydro-1,6-naphthyridine-3-carboxylic acid

[Formula 19]

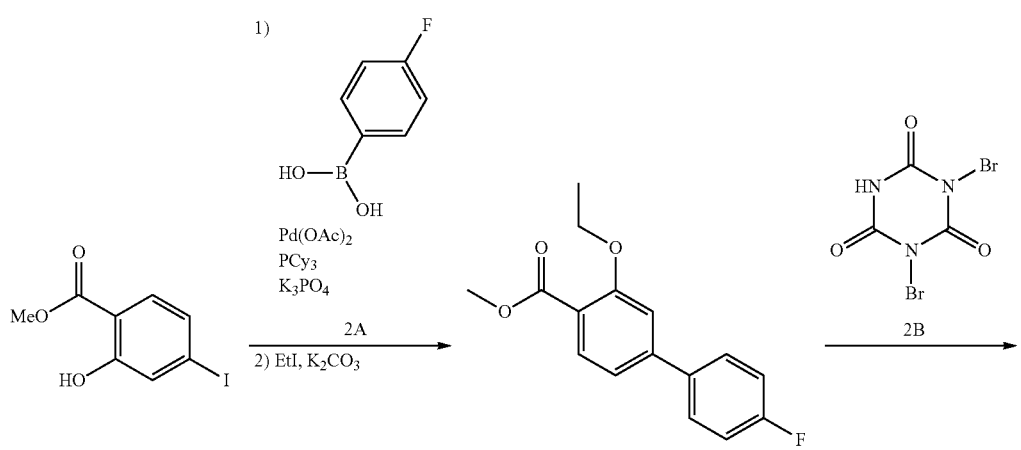

-continued
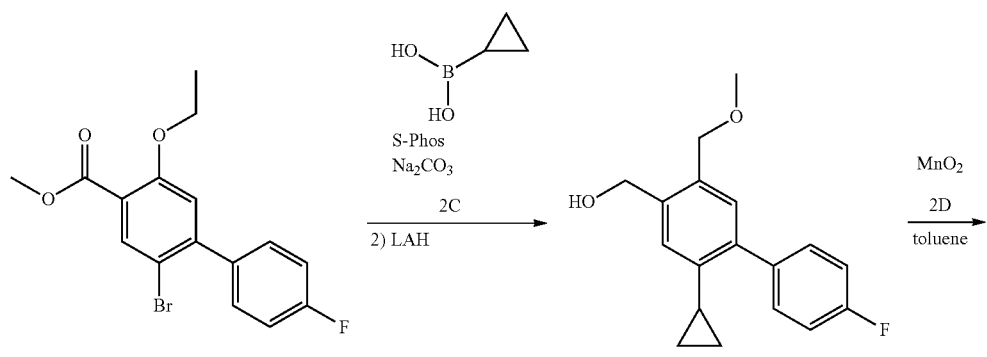
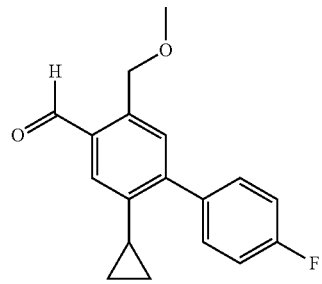
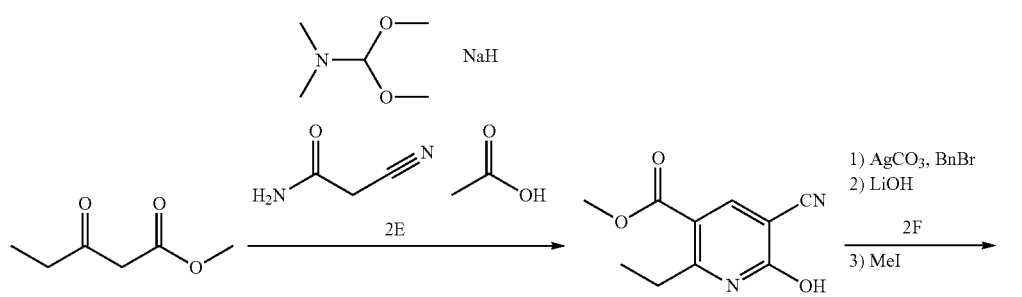
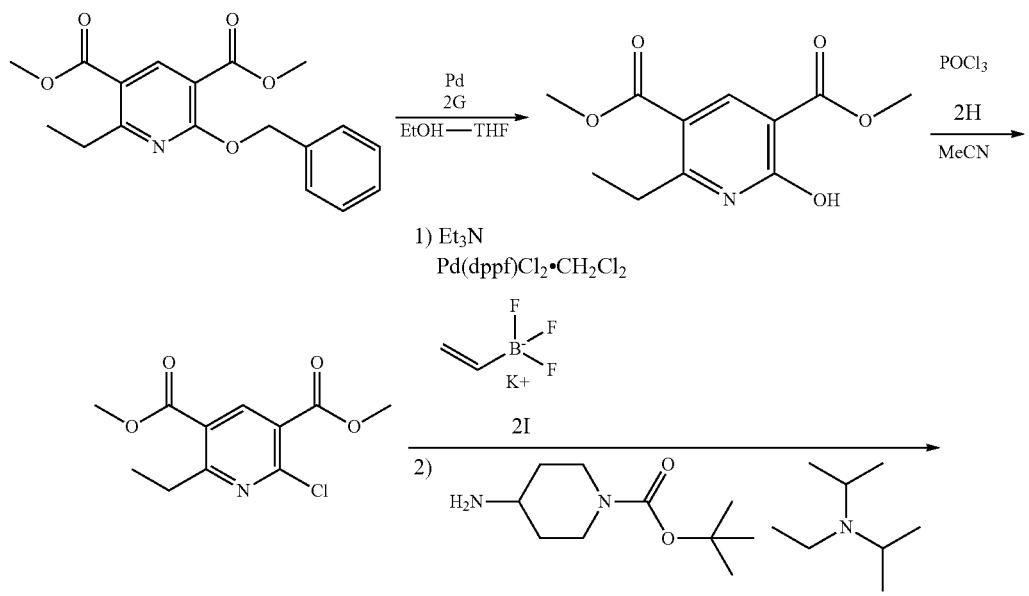

-continued

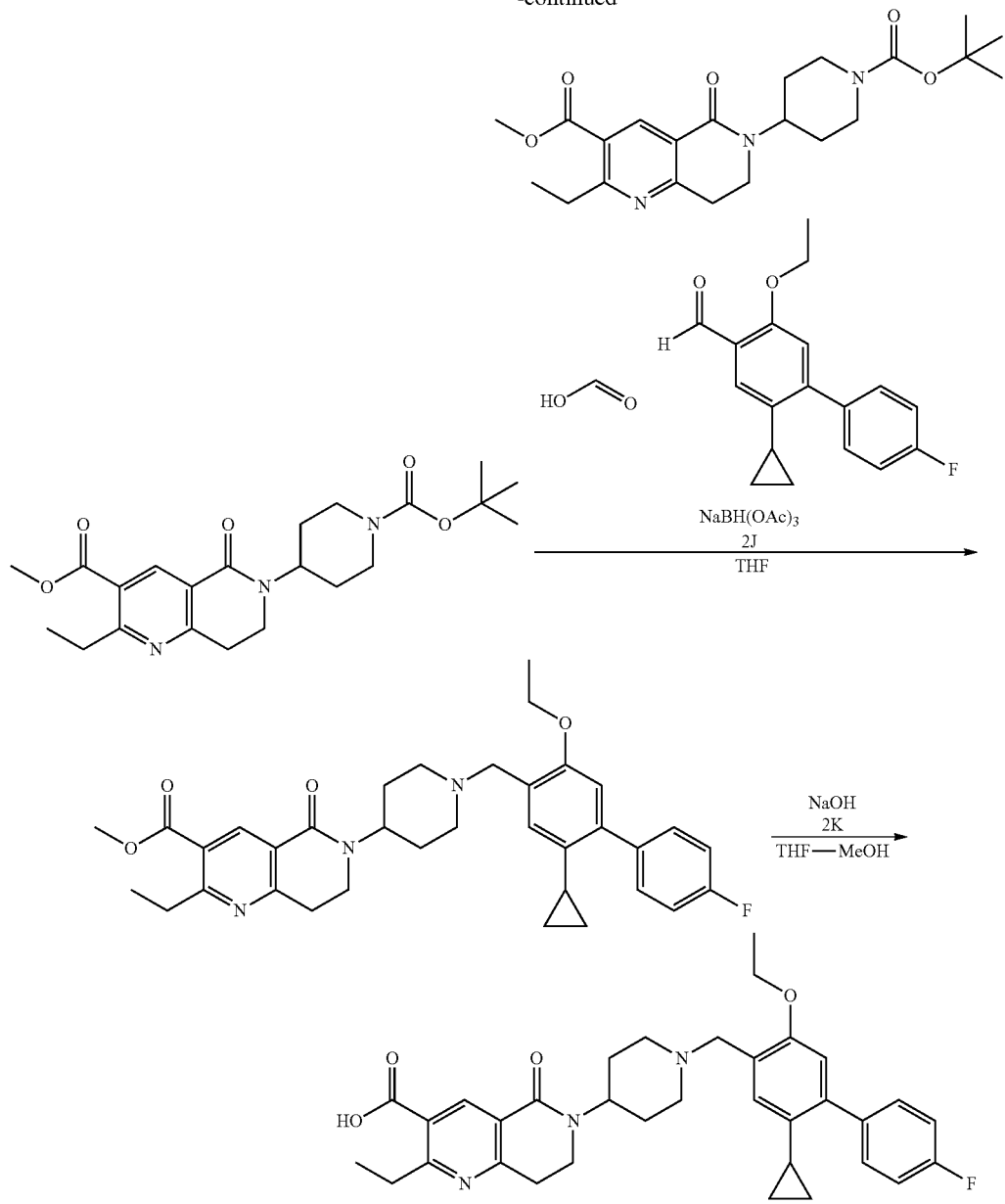

A) Methyl 3-ethoxy-4'-fluorobiphenyl-4-carboxylate

Palladium acetate (0.484 g) was added to a mixture of methyl 2-hydroxy-4-iodobenzoate (6.00 g), tripotassium phosphate (13.7 g), (4-fluorophenyl)boronic acid (6.04 g), tricyclohexylphosphine (20% toluene solution, 7.66 mL), toluene (30 mL), and water (15 mL), and the resultant mixture was stirred at 90° C. for 1.5 hours in an argon atmosphere. The reaction mixture was allowed to cool to room temperature, and then, the organic layer was separated. The aqueous layer was subjected to extraction with ethyl acetate. Combined organic layers were washed with saturated saline, then dried over anhydrous magnesium sulfate, and then passed through a short silica gel (NH) column, and the solvent was distilled off under reduced pressure. Iodoethane (2.59 mL) was added to a DMF (50 mL) suspension of the obtained residue and potassium carbonate (4.47 g), and the mixture was stirred at 80° C. for 1 hour. Water was added to the reaction mixture, followed by extraction with ethyl acetate. The obtained organic layer was washed with saturated saline and passed through a short silica gel (NH) column, and the solvent was distilled off under reduced pressure. The obtained residue was purified by silica gel column chromatography (hexane/ethyl acetate) to obtain the title compound (5.92 g).

$^1$H NMR (300 MHz, CDCl$_3$) δ 1.50 (3H, t, J=7.0 Hz), 3.91 (3H, s), 4.19 (2H, q, J=7.1 Hz), 7.04-7.21 (4H, m), 7.46-7.63 (2H, m), 7.86 (1H, d, J=8.0 Hz).

B) Methyl 2-bromo-5-ethoxy-4'-fluorobiphenyl-4-carboxylate

Dibromoisocyanuric acid (3.28 g) was added to a mixture of methyl 3-ethoxy-4'-fluorobiphenyl-4-carboxylate (5.92 g) and DMF (40 mL), and the resultant mixture was stirred overnight at room temperature. Water was added to the reaction mixture at room temperature, followed by extraction with ethyl acetate. The obtained organic layer was washed with saturated saline and dried over anhydrous magnesium sulfate, and then, the solvent was distilled off under reduced pressure. The obtained residue was purified by silica gel column chromatography (hexane/ethyl acetate) to obtain the title compound (7.62 g).
$^1$H NMR (300 MHz, CDCl$_3$) δ 1.46 (3H, t, J=6.9 Hz), 3.82-3.97 (3H, m), 4.11 (2H, q, J=7.0 Hz), 6.89 (1H, s), 7.13 (2H, t, J=8.7 Hz), 7.32-7.45 (2H, m), 8.07 (1H, s).

C) (2-Cyclopropyl-5-ethoxy-4'-fluorobiphenyl-4-yl) methanol

A mixture of methyl 2-bromo-5-ethoxy-4'-fluorobiphenyl-4-carboxylate (7.62 g), cyclopropylboronic acid (5.56 g), dicyclohexyl(2',6'-dimethoxybiphenyl-2-yl)phosphine (1.33 g), a 2 M aqueous sodium carbonate solution (32.4 mL), tris(dibenzylideneacetone)dipalladium(0) (1.38 g), and toluene (50 mL) was stirred at 100° C. for 2 hours in an argon atmosphere. The reaction mixture was allowed to cool to room temperature, and then, water was added thereto. The reaction mixture was washed with saturated saline and dried over anhydrous magnesium sulfate, and then, the solvent was distilled off under reduced pressure. A THF (50 mL) solution of the obtained residue was added to a THF (50 mL) suspension of lithium aluminum hydride (0.819 g) under ice cooling. After stirring at the same temperature as above for 30 minutes, water (1 mL) and a 15% aqueous sodium hydroxide solution (1 mL) were added thereto, and the mixture was stirred for 5 minutes. Water (3 mL) was further added to the reaction mixture, and the mixture was stirred for 30 minutes and then filtered. The filtrate was concentrated under reduced pressure. The obtained residue was purified by silica gel column chromatography (hexane/ethyl acetate) to obtain the title compound (5.65 g).
$^1$H NMR (300 MHz, CDCl$_3$) δ 0.54-0.65 (2H, m), 0.72-0.82 (2H, m), 1.43 (3H, t, J=7.0 Hz), 1.67-1.81 (1H, m), 2.42 (1H, t, J=6.5 Hz), 4.02-4.12 (2H, m), 4.69 (2H, d, J=6.5 Hz), 6.72 (1H, s), 6.87 (1H, s), 7.05-7.16 (2H, m), 7.34-7.47 (2H, m).

D) 2-Cyclopropyl-5-ethoxy-4'-fluorobiphenyl-4-carbaldehyde

Manganese dioxide (17.2 g) was added to a toluene (30 mL) solution of (2-cyclopropyl-5-ethoxy-4'-fluorobiphenyl-4-yl)methanol (5.65 g), and the mixture was stirred at 60° C. for 1 hour in a nitrogen atmosphere. The reaction mixture was filtered, and then, the solvent was distilled off under reduced pressure. The obtained residue was purified by silica gel column chromatography (hexane/ethyl acetate) to obtain the title compound (4.66 g).
$^1$H NMR (300 MHz, CDCl$_3$) δ 0.62-0.70 (2H, m), 0.74-0.84 (2H, m), 1.46 (3H, t, J=7.0 Hz), 1.62-1.80 (1H, m), 4.14 (2H, q, J=7.0 Hz), 6.81 (1H, s), 7.06-7.21 (2H, m), 7.34-7.49 (3H, m), 10.48 (1H, s).

E) Methyl 5-cyano-2-ethyl-6-hydroxynicotinate

A mixture of methyl 3-oxopentanoate (15 mL) and N,N-dimethylformamide dimethyl acetal (19.1 mL) was stirred overnight at room temperature. The reaction mixture was concentrated under reduced pressure. Sodium hydride (60% oil, 5.27 g) was added to a mixture of 2-cyanoacetamide (10.6 g) and THF (200 mL), then the residue obtained above was added thereto, and the mixture was stirred at room temperature for 18 hours. The reaction mixture was concentrated under reduced pressure, and then, the obtained residue was dissolved in water. The solution was rendered acidic by the addition of 6 M hydrochloric acid, and the deposited solid was collected and washed with water and hexane to obtain the title compound (17.5 g).
$^1$H NMR (300 MHz, DMSO-d$_6$) δ 1.17 (3H, t, J=7.5 Hz), 2.95 (2H, q, J=7.5 Hz), 3.78 (3H, s), 8.45 (1H, s), 12.92-13.10 (1H, m).

F) Dimethyl 2-(benzyloxy)-6-ethylpyridine-3,5-dicarboxylate

Benzyl bromide (3.46 mL) was added to a mixture of methyl 5-cyano-2-ethyl-6-hydroxynicotinate (5.00 g), silver carbonate (7.36 g), and toluene (60 mL), and the resultant mixture was stirred overnight at room temperature. The reaction mixture was passed through a short silica gel (NH) column, and the solvent was distilled off under reduced pressure. The obtained solid was washed with diethyl ether-hexane. Lithium hydroxide monohydrate (7.92 g) was added to a mixture of the obtained solid, ethanol (20 mL), and water (20 mL), and the resultant mixture was stirred overnight at 100° C. in a nitrogen atmosphere. The reaction mixture was neutralized with 6 M hydrochloric acid at 0° C., followed by extraction with ethyl acetate twice. The obtained organic layer was dried over anhydrous magnesium sulfate, and then, the solvent was distilled off under reduced pressure. Potassium carbonate (6.85 g) and iodomethane (7.04 g) were added to a mixture of the obtained residue and DMF (20 mL), and the resultant mixture was stirred at 50° C. for 1 hour. The reaction mixture was allowed to cool to room temperature and then poured to water, followed by extraction with ethyl acetate. The obtained organic layer was washed with saturated saline and dried over anhydrous magnesium sulfate, and then, the solvent was distilled off under reduced pressure. The obtained residue was purified by silica gel column chromatography (hexane/ethyl acetate) to obtain the title compound (2.37 g).
$^1$H NMR (300 MHz, CDCl$_3$) δ 1.25-1.32 (3H, m), 3.18 (2H, q, J=7.5 Hz), 3.89 (3H, s), 3.91 (3H, s), 5.61 (2H, s), 7.28-7.42 (3H, m), 7.52 (2H, d, J=7.3 Hz), 8.72 (1H, s)

G) Dimethyl 2-ethyl-6-hydroxypyridine-3,5-dicarboxylate

A mixture of dimethyl 2-(benzyloxy)-6-ethylpyridine-3,5-dicarboxylate (2.37 g), 10% palladium carbon (containing 55% water, 2.00 g), THF (20 mL), and ethanol (20 mL) was stirred at room temperature for 1 hour in a hydrogen atmosphere. The catalyst was filtered off, and then, the obtained filtrate was concentrated under reduced pressure. The obtained solid was washed with ethyl acetate to obtain the title compound (1.25 g).
$^1$H NMR (300 MHz, CDCl$_3$) δ 1.36 (3H, t, J=7.5 Hz), 3.18 (2H, q, J=7.5 Hz), 3.88 (3H, s), 3.92 (3H, s), 8.81 (1H, s), 11.81 (1H, brs).

H) Dimethyl 2-chloro-6-ethylpyridine-3,5-dicarboxylate

Phosphorus oxychloride (0.731 mL) was added to a mixture of dimethyl 2-ethyl-6-hydroxypyridine-3,5-dicarboxylate (1.25 g) and acetonitrile (15 mL), and the resultant mixture was stirred overnight at 90° C. in a nitrogen atmosphere. The reaction mixture was allowed to cool to room temperature, and then, a saturated aqueous solution of sodium bicarbonate was added thereto, followed by extraction with ethyl acetate. The obtained organic layer was dried over anhydrous magnesium sulfate, and then, the solvent was distilled off under reduced pressure. The obtained residue was purified by silica gel column chromatography (hexane/ethyl acetate) to obtain the title compound (1.35 g).

$^1$H NMR (300 MHz, CDCl$_3$) δ 1.31 (3H, t, J=7.5 Hz), 3.21 (2H, q, J=7.5 Hz), 3.95 (3H, s), 3.97 (3H, s), 8.66 (1H, s).

I) Methyl 6-(1-(tert-butoxycarbonyl)piperidin-4-yl)-2-ethyl-5-oxo-5,6,7,8-tetrahydro-1,6-naphthyridine-3-carboxylate A dichloromethane adduct of (1,1'-bis(diphenylphosphino)ferrocene)dichloropalladium(II) (0.428 g) was added to a mixture of dimethyl 2-chloro-6-ethylpyridine-3,5-dicarboxylate (1.35 g), potassium vinyl trifluoroborate (1.40 g), triethylamine (1.46 mL), and ethanol (10 mL), and the resultant mixture was stirred at 95° C. for 1 hour in an argon atmosphere. The solvent in the reaction mixture was distilled off under reduced pressure, and the obtained residue was purified by silica gel column chromatography (hexane/ethyl acetate). A mixture of the obtained purified product, tert-butyl 4-aminopiperidine-1-carboxylate (2.10 g), N,N'-diisopropylethylamine (1.37 mL), acetonitrile (7.5 mL), and methanol (7.5 mL) was stirred at 150° C. for 4 hours under microwave irradiation. The reaction mixture was allowed to cool to room temperature, and then, the solvent was distilled off under reduced pressure. The obtained residue was purified by silica gel column chromatography (hexane/ethyl acetate) to obtain the title compound (1.53 g).

$^1$H NMR (300 MHz, CDCl$_3$) δ 1.30 (3H, t, J=7.5 Hz), 1.48 (9H, s), 1.62-1.79 (4H, m), 2.75-2.95 (2H, m), 3.09-3.27 (4H, m), 3.54 (2H, t, J=6.7 Hz), 3.93 (3H, s), 4.17-4.37 (2H, m), 4.73-4.92 (1H, m), 8.76 (1H, s)

J) Methyl 6-(1-((2-cyclopropyl-5-ethoxy-4'-fluorobiphenyl-4-yl)methyl)piperidin-4-yl)-2-ethyl-5-oxo-5,6,7,8-tetrahydro-1,6-naphthyridine-3-carboxylate Methyl 6-(1-(tert-butoxycarbonyl)piperidin-4-yl)-2-ethyl-5-oxo-5,6,7,8-tetrahydro-1,6-naphthyridine-3-carboxylate (527 mg) was added to formic acid (5 mL), and the mixture was stirred at 60° C. for 30 minutes. Then, the solvent was distilled off under reduced pressure. Toluene was added to the residue, and the solvent was further distilled off under reduced pressure. 2-Cyclopropyl-5-ethoxy-4'-fluorobiphenyl-4-carbaldehyde (359 mg) was added to a mixture of the obtained residue and THF (5 mL), and the resultant mixture was stirred for 10 minutes. Then, sodium triacetoxy borohydride (401 mg) was added thereto, and the mixture was stirred at room temperature for 2 hours. A saturated aqueous solution of sodium bicarbonate was added to the reaction mixture, followed by extraction with ethyl acetate. The obtained organic layer was dried over anhydrous magnesium sulfate, and then, the solvent was distilled off under reduced pressure. The obtained residue was purified by silica gel column chromatography (hexane/ethyl acetate/methanol) to obtain the title compound (267 mg).

MS (ESI+): [M+H]$^+$ 586.5

K) 6-(1-((2-Cyclopropyl-5-ethoxy-4'-fluorobiphenyl-4-yl)methyl)piperidin-4-yl)-2-ethyl-5-oxo-5,6,7,8-tetrahydro-1,6-naphthyridine-3-carboxylic acid A 2 M aqueous sodium hydroxide solution (1.50 mL) was added at room temperature to a methanol (2 mL)-THF (2 mL) solution of methyl 6-(1-((2-cyclopropyl-5-ethoxy-4'-fluorobiphenyl-4-yl)methyl)piperidin-4-yl)-2-ethyl-5-oxo-5,6,7,8-tetrahydro-1,6-naphthyridine-3-carboxylate (260 mg), and the mixture was stirred at 50° C. for 1 hour. The reaction mixture was neutralized with hydrochloric acid at room temperature. Then, ethyl acetate was added thereto, and the mixture was concentrated. The deposited solid was collected by filtration and washed with diethyl ether. The obtained solid was recrystallized (ethanol/hexane) to obtain the title compound (149 mg).

$^1$H NMR (300 MHz, DMSO-d$_6$) δ 0.52-0.61 (2H, m), 0.69-0.82 (2H, m), 1.21 (3H, t, J=7.5 Hz), 1.33 (3H, t, J=6.9 Hz), 1.59 (2H, d, J=11.7 Hz), 1.68-2.00 (3H, m), 2.25 (2H, t, J=11.5 Hz), 2.93-3.19 (6H, m), 3.50-3.66 (4H, m), 4.04 (2H, q, J=6.9 Hz), 4.40-4.56 (1H, m), 6.77 (1H, s), 7.01 (1H, s), 7.27 (2H, t, J=8.9 Hz), 7.49 (2H, dd, J=8.6, 5.6 Hz), 8.47 (1H, s).

Example 3

2-Cyclopropyl-6-(1-((2-cyclopropyl-5-ethoxy-4'-fluorobiphenyl-4-yl)methyl)piperidin-4-yl)-5-oxo-5,6,7,8-tetrahydro-1,6-naphthyridine-3-carboxylic acid

[Formula 20]

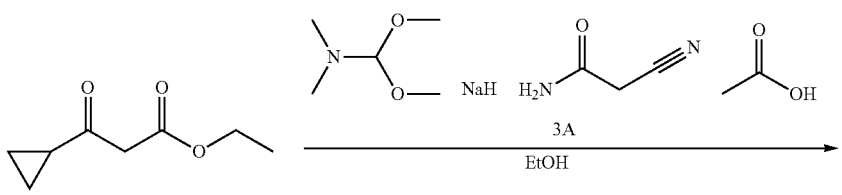

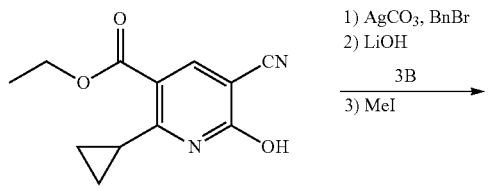

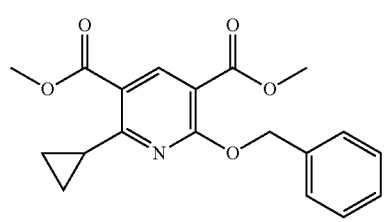
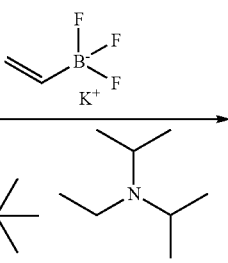
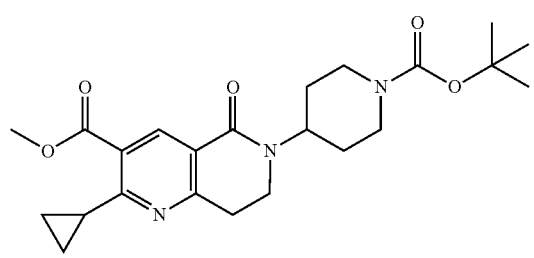
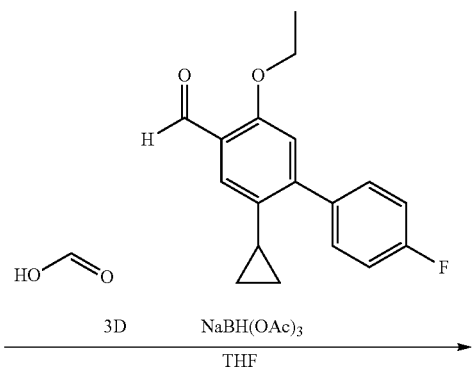
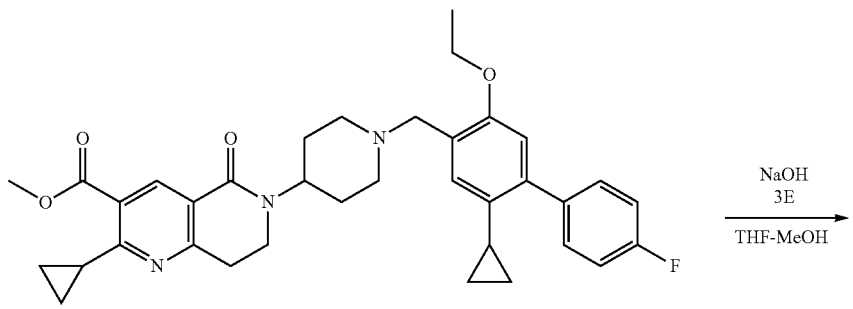
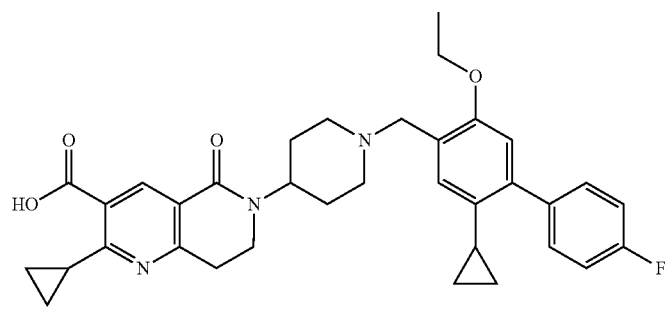

A) Ethyl 5-cyano-2-cyclopropyl-6-hydroxynicotinate

A mixture of ethyl 3-cyclopropyl-3-oxopropanoate (20 mL) and N,N-dimethylformamide dimethyl acetal (21.6 mL) was stirred at 75° C. for 3 hours. The reaction mixture was concentrated under reduced pressure. Sodium hydride (60% oil, 5.96 g) was added to a mixture of 2-cyanoacetamide (12.0 g) and THF (200 mL), then the residue obtained above was added thereto, and the mixture was stirred overnight at room temperature in a nitrogen atmosphere. The reaction mixture was concentrated under reduced pressure, and then, water was added to the obtained residue. The mixture was further rendered acidic by the addition of 6 M hydrochloric acid and stirred at 0° C. for 10 minutes, and the deposited solid was collected and washed with water and hexane in this order to obtain the title compound (26.4 g).

¹H NMR (300 MHz, DMSO-d₆) δ 1.12-1.22 (2H, m), 1.24-1.35 (5H, m), 3.03-3.17 (1H, m), 4.24 (2H, q, J=7.1 Hz), 8.42 (1H, s), 11.95 (1H, brs).

B) Dimethyl 2-(benzyloxy)-6-cyclopropylpyridine-3,5-dicarboxylate

Benzyl bromide (3.07 mL) was added to a toluene (60 mL) suspension of ethyl 5-cyano-2-cyclopropyl-6-hydroxynicotinate (5.00 g) and silver carbonate (6.53 g), and the mixture was stirred overnight at room temperature. The reaction mixture was passed through a short silica gel (NH) column, and the solvent was distilled off under reduced pressure. The obtained solid was washed with diethyl ether-hexane. Lithium hydroxide monohydrate (9.35 g) was added to a mixture of the obtained solid, ethanol (20 mL), and water (20 mL), and the resultant mixture was stirred overnight at 100° C. in a nitrogen atmosphere. The reaction mixture was neutralized with 6 M hydrochloric acid at 0° C., followed by extraction with ethyl acetate twice. The obtained organic layer was dried over anhydrous magnesium sulfate, and then, the solvent was distilled off under reduced pressure. Potassium carbonate (8.09 g) and iodomethane (3.66 mL) were added to a mixture of the obtained residue and DMF (20 mL), and the resultant mixture was stirred at 50° C. for 1 hour. The reaction mixture was allowed to cool to room temperature and then poured to water, followed by extraction with ethyl acetate. The obtained organic layer was washed with saturated saline and dried over anhydrous magnesium sulfate, and then, the solvent was distilled off under reduced pressure. The obtained residue was purified by silica gel column chromatography (hexane/ethyl acetate) to obtain the title compound (5.80 g).

¹H NMR (300 MHz, CDCl₃) δ 1.00-1.11 (2H, m), 1.12-1.19 (2H, m), 3.18-3.32 (1H, m), 3.90 (6H, s), 5.48 (2H, s), 7.27-7.39 (3H, m), 7.42-7.48 (2H, m), 8.70 (1H, s).

C) Methyl 6-(1-(tert-butoxycarbonyl)piperidin-4-yl)-2-cyclopropyl-5-oxo-5,6,7,8-tetrahydro-1,6-naphthyridine-3-carboxylate A mixture of dimethyl 2-(benzyloxy)-6-cyclopropylpyridine-3,5-dicarboxylate (5.80 g), 10% palladium carbon (containing 55% water, 2.00 g), THF (20 mL), and ethanol (20 mL) was stirred at room temperature for 1 hour in a hydrogen atmosphere. The catalyst was filtered off, and then, the obtained filtrate was concentrated under reduced pressure. The obtained solid was washed with diethyl ether. Phosphorus oxychloride (1.79 mL) was added to a mixture of this solid and acetonitrile (15 mL), and the resultant mixture was stirred at 90° C. for 3 hours in a nitrogen atmosphere. The reaction mixture was allowed to cool to room temperature, and then, a saturated aqueous solution of sodium bicarbonate was added thereto, followed by extraction with ethyl acetate. The obtained organic layer was dried over anhydrous magnesium sulfate, and then, the solvent was distilled off under reduced pressure. The obtained residue was purified by silica gel column chromatography (hexane/ethyl acetate). A dichloromethane adduct of (1,1'-bis(diphenylphosphino)ferrocene) dichloropalladium(II) (0.718 g) was added to a mixture of this purified product, potassium vinyl trifluoroborate (2.35 g), triethylamine (2.45 mL), and ethanol (10 mL), and the resultant mixture was stirred at 95° C. for 1 hour in an argon atmosphere. The solvent in the reaction mixture was distilled off under reduced pressure, and the obtained residue was purified by silica gel column chromatography (hexane/ethyl acetate). A mixture of the obtained purified product, tert-butyl 4-aminopiperidine-1-carboxylate (3.53 g), N,N'-diisopropylethylamine (2.30 mL), acetonitrile (7.5 mL), and methanol (7.5 mL) was stirred at 150° C. for 8 hours under microwave irradiation. The reaction mixture was allowed to cool to room temperature, and then, the solvent was distilled off under reduced pressure. The obtained residue was purified by silica gel column chromatography (hexane/ethyl acetate) to obtain the title compound (0.980 g).

¹H NMR (300 MHz, CDCl₃) δ 1.00-1.12 (2H, m), 1.17-1.25 (2H, m, J=3.6 Hz), 1.47 (9H, s), 1.55-1.77 (4H, m), 2.78-2.93 (2H, m), 3.02 (2H, t, J=6.6 Hz), 3.09-3.20 (1H, m), 3.49 (2H, t, J=6.6 Hz), 3.94 (3H, s), 4.18-4.35 (2H, m), 4.67-4.94 (1H, m), 8.69 (1H, s).

D) Methyl 2-cyclopropyl-6-(1-((2-cyclopropyl-5-ethoxy-4'-fluorobiphenyl-4-yl)methyl)piperidin-4-yl)-5-oxo-5,6,7,8-tetrahydro-1,6-naphthyridine-3-carboxylate Methyl 6-(1-(tert-butoxycarbonyl)piperidin-4-yl)-2-cyclopropyl-5-oxo-5,6,7,8-tetrahydro-1,6-naphthyridine-3-carboxylate (480 mg) was added to formic acid (5 mL), and the mixture was stirred at 60° C. for 30 minutes. Then, the solvent was distilled off under reduced pressure. Toluene was added to the obtained residue, and the solvent was further distilled off under reduced pressure. 2-Cyclopropyl-5-ethoxy-4'-fluorobiphenyl-4-carbaldehyde (350 mg) was added to a mixture of the obtained residue and THF (5 mL), and the resultant mixture was stirred for 10 minutes. Then, sodium triacetoxy borohydride (355 mg) was added thereto, and the mixture was stirred at room temperature for 2 hours. A saturated aqueous solution of sodium bicarbonate was added to the reaction mixture, followed by extraction with ethyl acetate. The obtained organic layer was dried over anhydrous magnesium sulfate, and then, the solvent was distilled off under reduced pressure. The obtained residue was purified by silica gel column chromatography (hexane/ethyl acetate/methanol) to obtain the title compound (486 mg).

MS (ESI+): [M+H]⁺ 598.5

E) 2-Cyclopropyl-6-(1-((2-cyclopropyl-5-ethoxy-4'-fluorobiphenyl-4-yl)methyl)piperidin-4-yl)-5-oxo-5,6,7,8-tetrahydro-1,6-naphthyridine-3-carboxylic acid A 2 M aqueous sodium hydroxide solution (1.50 mL) was added at room temperature to a methanol (2 mL)-THF (2 mL) solution of methyl 2-cyclopropyl-6-(1-((2-cyclopropyl-5-ethoxy-4'-fluorobiphenyl-4-yl)methyl)piperidin-4-yl)-5-oxo-5,6,7,8-tetrahydro-1,6-naphthyridine-3-carboxylate (480 mg), and the mixture was stirred at 50° C. for 1 hour. The reaction mixture was neutralized with hydrochloric acid at room temperature. Then, ethyl acetate was added thereto, and the mixture was concentrated. The deposited solid was collected by filtration and washed with diethyl ether. The obtained solid was recrystallized (ethanol/hexane) to obtain the title compound (320 mg).

¹H NMR (300 MHz, DMSO-d₆) δ 0.54 (2H, q, J=5.1 Hz), 0.70-0.82 (2H, m), 0.96-1.18 (4H, m), 1.32 (3H, t, J=6.9 Hz), 1.58 (2H, d, J=12.8 Hz), 1.68-1.98 (3H, m), 2.15-2.35 (2H, m), 2.91-3.07 (4H, m), 3.11-3.27 (1H, m), 3.53 (2H, t, J=6.6 Hz), 3.59 (2H, s), 4.04 (2H, q, J=7.0 Hz), 4.24-4.56 (1H, m), 6.77 (1H, s), 7.00 (1H, s), 7.27 (2H, t, J=8.9 Hz), 7.49 (2H, dd, J=8.7, 5.7 Hz), 8.43 (1H, s).

Example 4
6-(1-((2-Cyclopropyl-5-ethoxy-4'-fluorobiphenyl-4-yl)methyl)piperidin-4-yl)-5-oxo-2-propyl-5,6,7,8-tetrahydro-1,6-naphthyridine-3-carboxylic acid
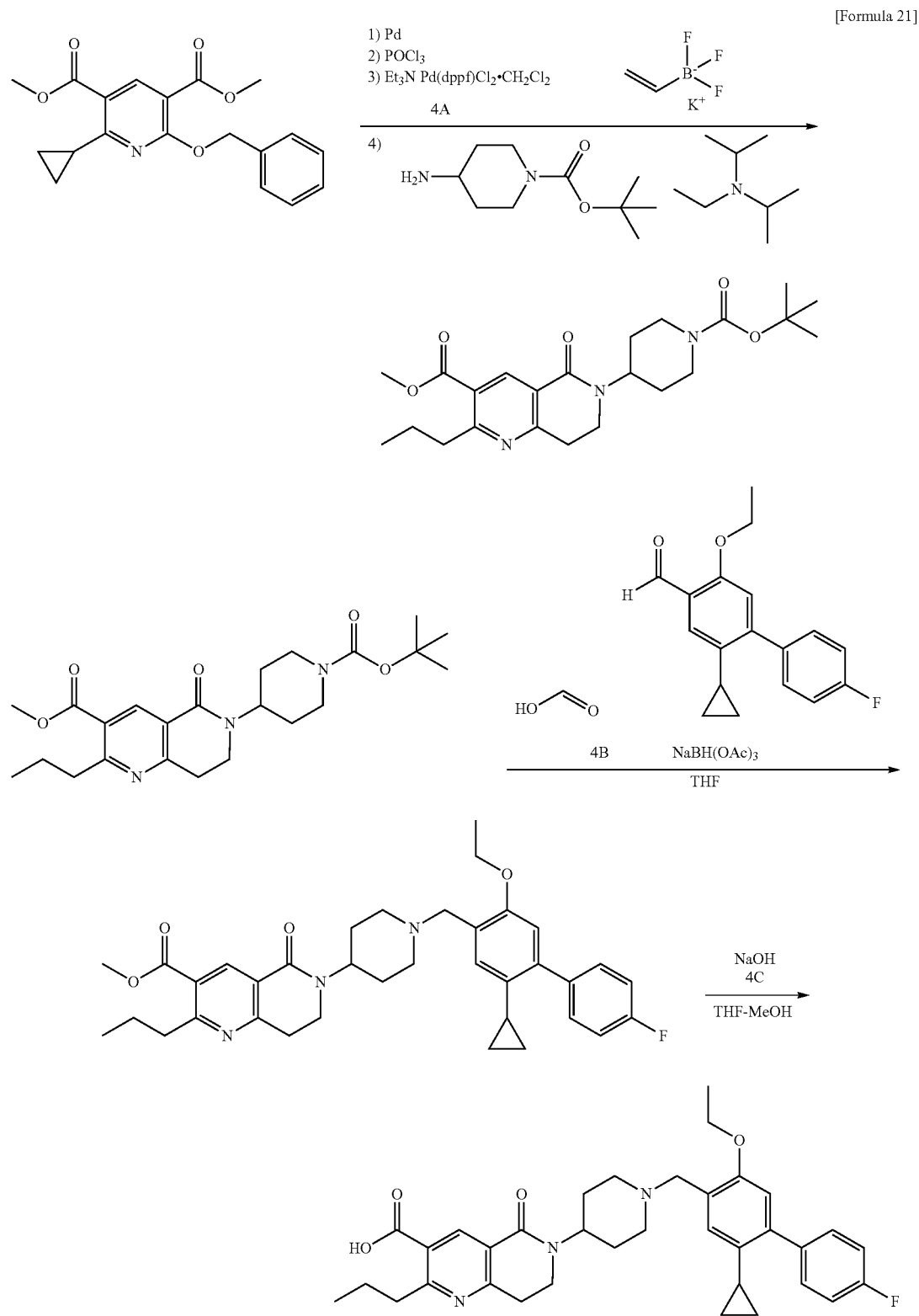

A) Methyl 6-(1-(tert-butoxycarbonyl)piperidin-4-yl)-5-oxo-2-propyl-5,6,7,8-tetrahydro-1,6-naphthyridine-3-carboxylate A mixture of dimethyl 2-(benzyloxy)-6-cyclopropylpyridine-3,5-dicarboxylate (5.80 g), 10% palladium carbon (containing 55% water, 2.00 g), THF (20 mL), and ethanol (20 mL) was stirred at room temperature for 1 hour in a hydrogen atmosphere. The catalyst was filtered off, and then, the obtained filtrate was concentrated under reduced pressure. The obtained solid was washed with diethyl ether. Phosphorus oxychloride (1.79 mL) was added to a mixture of this solid and acetonitrile (15 mL), and the resultant mixture was stirred at 90° C. for 3 hours in a nitrogen atmosphere. The reaction mixture was allowed to cool to room temperature, and then, a saturated aqueous solution of sodium bicarbonate was added thereto, followed by extraction with ethyl acetate. The obtained organic layer was dried over anhydrous magnesium sulfate, and then, the solvent was distilled off under reduced pressure. The obtained residue was purified by silica gel column chromatography (hexane/ethyl acetate). A dichloromethane adduct of (1,1'-bis(diphenylphosphino)ferrocene)dichloropalladium(II) (0.718 g) was added to a mixture of this purified product, potassium vinyl trifluoroborate (2.35 g), triethylamine (2.45 mL), and ethanol (10 mL), and the resultant mixture was stirred at 95° C. for 1 hour in an argon atmosphere. The solvent in the reaction mixture was distilled off under reduced pressure, and the obtained residue was purified by silica gel column chromatography (hexane/ethyl acetate). A mixture of the obtained purified product, tert-butyl 4-aminopiperidine-1-carboxylate (3.53 g), N,N'-diisopropylethylamine (2.30 mL), acetonitrile (7.5 mL), and methanol (7.5 mL) was stirred at 150° C. for 8 hours under microwave irradiation. The reaction mixture was allowed to cool to room temperature, and then, the solvent was distilled off under reduced pressure. The obtained residue was purified by silica gel column chromatography (hexane/ethyl acetate) to obtain the title compound (1.46 g).

$^1$H NMR (300 MHz, CDCl$_3$) δ 1.01 (3H, t, J=7.3 Hz), 1.48 (9H, s), 1.61-1.84 (6H, m), 2.70-3.00 (2H, m), 3.09-3.21 (4H, m), 3.54 (2H, t, J=6.6 Hz), 3.93 (3H, s), 4.18-4.40 (2H, m), 4.75-4.91 (1H, m), 8.76 (1H, s).

B) Methyl 6-(1-((2-cyclopropyl-5-ethoxy-4'-fluorobiphenyl-4-yl)methyl)piperidin-4-yl)-5-oxo-2-propyl-5,6,7,8-tetrahydro-1,6-naphthyridine-3-carboxylate Methyl 6-(1-(tert-butoxycarbonyl)piperidin-4-yl)-5-oxo-2-propyl-5,6,7,8-tetrahydro-1,6-naphthyridine-3-carboxylate (532 mg) was added to formic acid (5 mL), and the mixture was stirred at 60° C. for 30 minutes. Then, the solvent was distilled off under reduced pressure. Toluene was added to the obtained residue, and the solvent was further distilled off under reduced pressure. 2-Cyclopropyl-5-ethoxy-4'-fluorobiphenyl-4-carbaldehyde (351 mg) was added to a mixture of the obtained residue and THF (5 mL), and the resultant mixture was stirred at room temperature for 10 minutes. Then, sodium triacetoxy borohydride (392 mg) was added thereto, and the mixture was stirred at room temperature for 2 hours. A saturated aqueous solution of sodium bicarbonate was added to the reaction mixture, followed by extraction with ethyl acetate twice. The obtained organic layer was dried over anhydrous magnesium sulfate, and then, the solvent was distilled off under reduced pressure. The obtained residue was purified by silica gel column chromatography (hexane/ethyl acetate/methanol) to obtain the title compound (679 mg).

MS (ESI+): [M+H]$^+$ 600.5

C) 6-(1-((2-Cyclopropyl-5-ethoxy-4'-fluorobiphenyl-4-yl)methyl)piperidin-4-yl)-5-oxo-2-propyl-5,6,7,8-tetrahydro-1,6-naphthyridine-3-carboxylic acid A 2 M aqueous sodium hydroxide solution (1.50 mL) was added at room temperature to a methanol (2 mL)-THF (2 mL) solution of methyl 6-(1-((2-cyclopropyl-5-ethoxy-4'-fluorobiphenyl-4-yl)methyl)piperidin-4-yl)-5-oxo-2-propyl-5,6,7,8-tetrahydro-1,6-naphthyridine-3-carboxylate (670 mg), and the mixture was stirred at 50° C. for 1 hour. The reaction mixture was neutralized with hydrochloric acid at room temperature. Then, ethyl acetate was added thereto, and the mixture was concentrated. Then, the deposited solid was collected by filtration and washed with diethyl ether. The obtained solid was recrystallized (ethanol/hexane) to obtain the title compound (442 mg).

$^1$H NMR (300 MHz, DMSO-d$_6$) δ 0.48-0.59 (2H, m), 0.72-0.83 (2H, m), 0.92 (3H, t, J=7.4 Hz), 1.32 (3H, t, J=6.9 Hz), 1.50-1.95 (7H, m), 2.22 (2H, t, J=11.4 Hz), 2.90-3.15 (6H, m), 3.18-3.66 (4H, m), 4.03 (2H, q, J=6.9 Hz), 4.37-4.53 (1H, m), 6.77 (1H, s), 6.99 (1H, s), 7.27 (2H, t, J=8.9 Hz), 7.49 (2H, dd, J=8.6, 5.6 Hz), 8.46 (1H, s).

Example 5

6-(1-((2-Cyclopropyl-5-ethoxy-4'-fluorobiphenyl-4-yl)methyl)piperidin-4-yl)-2-methyl-5-oxo-5,6,7,8-tetrahydro-1,6-naphthyridine-3-carboxylic acid

[Formula 22]

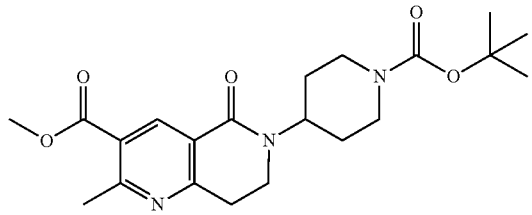

5(Same as Examples 1K and 1L)

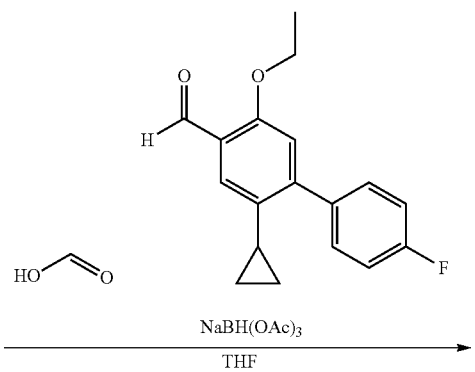

NaBH(OAc)$_3$
THF

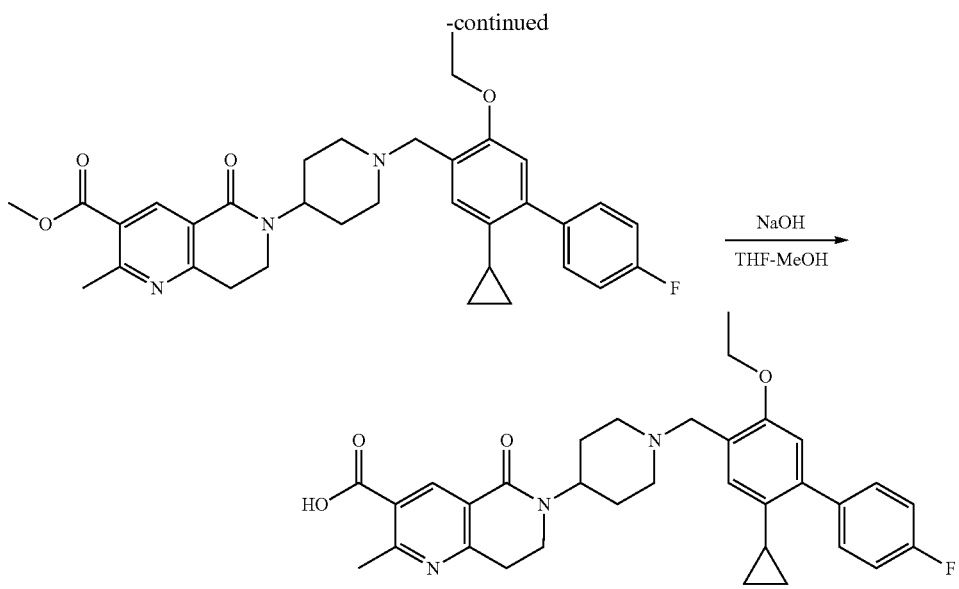

The title compound was obtained in the same way as in steps K and L of Example 1 using methyl 6-(1-(tert-butoxycarbonyl)piperidin-4-yl)-2-methyl-5-oxo-5,6,7,8-tetrahydro-1,6-naphthyridine-3-carboxylate and 2-cyclopropyl-5-ethoxy-4'-fluorobiphenyl-4-carbaldehyde.

Example 6

6-(1-((5-Cyclopropyl-6-(4-fluorophenyl)-2-isopropoxypyridin-3-yl)methyl)piperidin-4-yl)-2-methyl-5-oxo-5,6,7,8-tetrahydro-1,6-naphthyridine-3-carboxylic acid

[Formula 23]

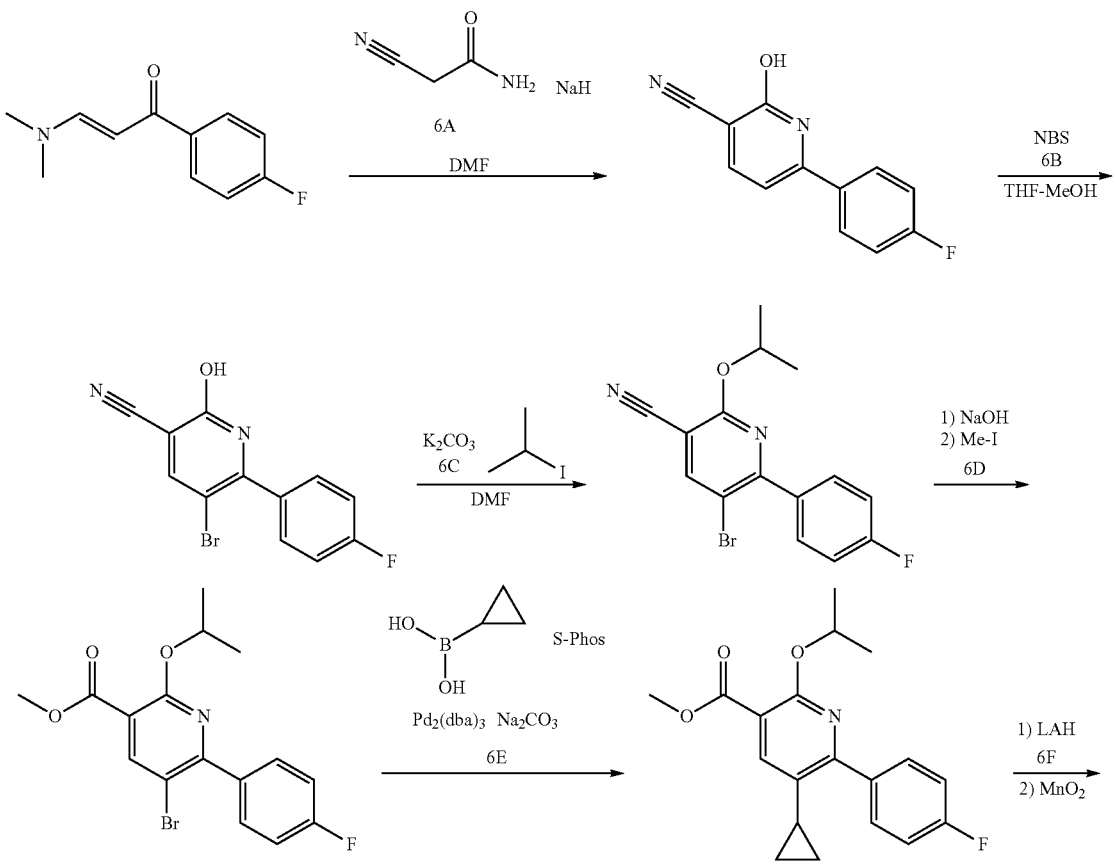

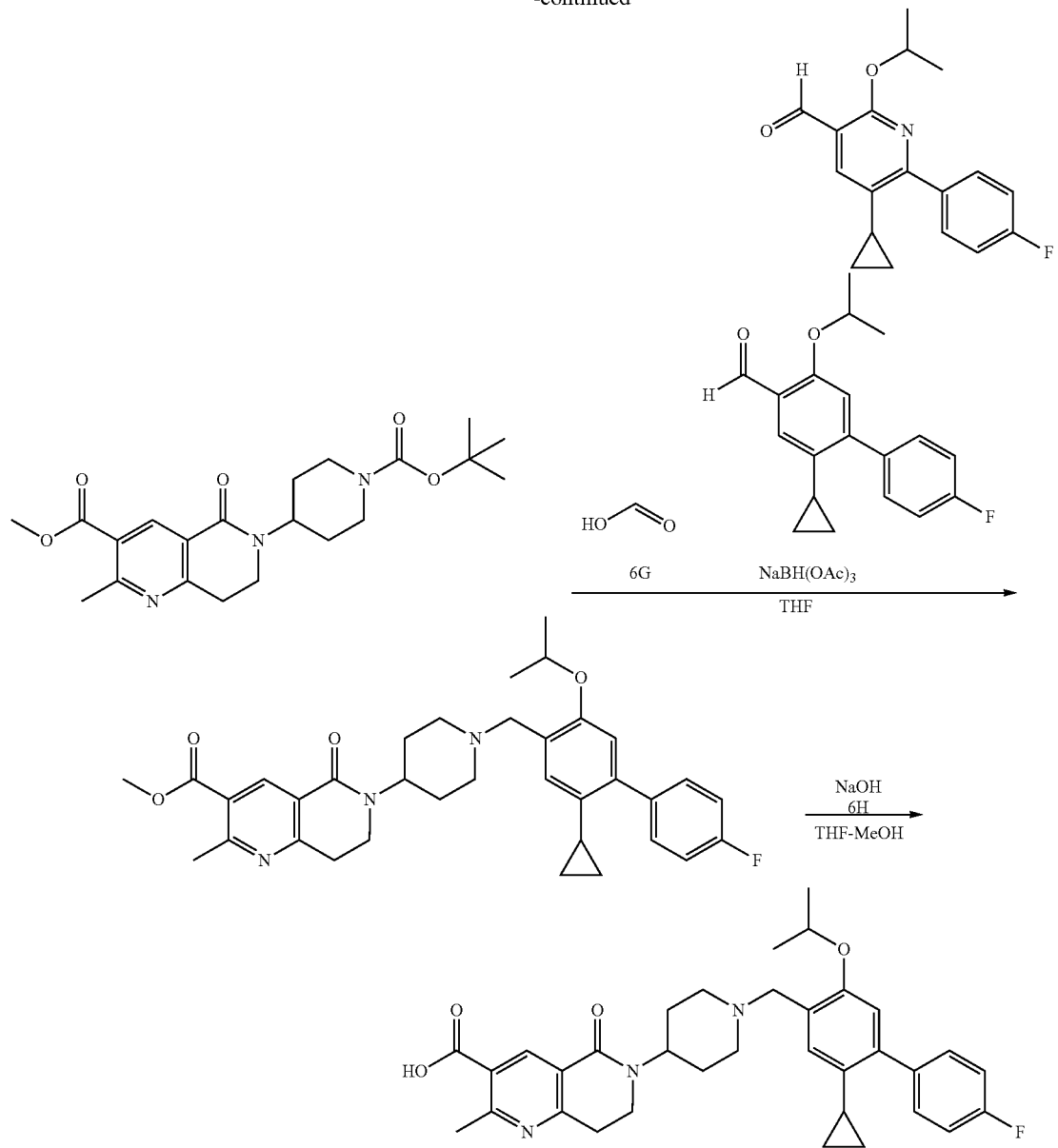

A) 6-(4-Fluorophenyl)-2-hydroxynicotinonitrile

2-Cyanoacetamide (4.31 g) and 3-(dimethylamino)-1-(4-fluorophenyl)prop-2-en-1-one (9.00 g) were added in this order to a mixture of sodium hydride (60% oil, 4.10 g) and DMF (90 mL), and the resultant mixture was stirred at 105° C. for 2 hours. The solvent was distilled off. Water was added to the obtained residue, and then, the mixture was rendered acidic by the addition of acetic acid and stirred at 70° C. for 15 minutes. Methanol was added to the reaction mixture for suspension, and the deposited solid was washed with ethyl acetate to obtain the title compound (9.98 g).

$^1$H NMR (300 MHz, DMSO-$d_6$) δ 6.78 (1H, d, J=7.2 Hz), 7.38 (2H, t, J=8.9 Hz), 7.89 (2H, dd, J=8.8, 5.4 Hz), 8.19 (1H, d, J=7.6 Hz).

B) 5-Bromo-6-(4-fluorophenyl)-2-hydroxynicotinonitrile

N-Bromosuccinimide (3.66 g) was added to a mixture of 6-(4-fluorophenyl)-2-hydroxynicotinonitrile (4.00 g), THF (30 mL), and methanol (30 mL), and the resultant mixture was stirred at room temperature for 10 minutes. The solvent was distilled off, and the obtained residue was suspended in a mixed solvent of water, ethyl acetate, and hexane. Then, the obtained solid was washed with hexane to obtain the title compound (5.18 g).

$^1$H NMR (300 MHz, DMSO-$d_6$) δ 7.28-7.44 (2H, m), 7.63 (2H, dd, J=8.6, 5.5 Hz), 8.54 (1H, s), 13.11 (1H, brs).

C) 5-Bromo-6-(4-fluorophenyl)-2-isopropoxynicotinonitrile

2-Bromopropane (3.32 mL) was added to a mixture of 5-bromo-6-(4-fluorophenyl)-2-hydroxynicotinonitrile (5.18 g), potassium carbonate (4.89 g), and DMF (30 mL), and the resultant mixture was stirred at 80° C. for 30 minutes. Water was added to the reaction mixture, followed by extraction with ethyl acetate. The organic layer was washed with saturated saline and dried over anhydrous magnesium sulfate, and then, the solvent was distilled off under reduced pressure. The obtained residue was purified by silica gel column chromatography (hexane/ethyl acetate) to obtain the title compound (5.92 g).

$^1$H NMR (300 MHz, CDCl$_3$) δ 1.41 (6H, d, J=6.2 Hz), 5.27-5.56 (1H, m), 7.16 (2H, t, J=8.7 Hz), 7.66-7.82 (2H, m), 8.08 (1H, s).

D) Methyl 5-bromo-6-(4-fluorophenyl)-2-isopropoxynicotinate

An 8 M aqueous potassium hydroxide solution (22.1 mL) was added to a mixture of 5-bromo-6-(4-fluorophenyl)-2-isopropoxynicotinonitrile (5.92 g) and ethanol (50 mL), and the resultant mixture was stirred overnight at 100° C. The reaction mixture was neutralized with 6 M hydrochloric acid at 0° C., followed by extraction with ethyl acetate. The organic layer was dried over anhydrous magnesium sulfate, and then, the solvent was distilled off under reduced pressure. Potassium carbonate (4.88 g) and iodomethane (1.66 mL) were added to a mixture of the obtained residue and DMF (30 mL), and the mixture was stirred at 60° C. for 30 minutes. Water was added to the reaction mixture, followed by extraction with ethyl acetate. The organic layer was washed with saturated saline and dried over anhydrous magnesium sulfate, and then, the solvent was distilled off under reduced pressure. The obtained residue was purified by silica gel column chromatography (hexane/ethyl acetate) to obtain the title compound (3.65 g).

$^1$H NMR (300 MHz, CDCl$_3$) δ 1.40 (6H, d, J=6.1 Hz), 3.91 (3H, s), 5.35-5.51 (1H, m), 7.14 (2H, t, J=8.7 Hz), 7.78 (2H, dd, J=8.9, 5.4 Hz), 8.38 (1H, s).

E) Methyl 5-cyclopropyl-6-(4-fluorophenyl)-2-isopropoxynicotinate

Tris(dibenzylideneacetone)dipalladium(0) (635 mg) was added to a mixture of methyl 5-bromo-6-(4-fluorophenyl)-2-isopropoxynicotinate (3.65 g), cyclopropylboronic acid (2.55 g), dicyclohexyl(2',6'-dimethoxybiphenyl-2-yl)phosphine (610 mg), a 2 M aqueous sodium carbonate solution (14.9 mL), and toluene (25 mL), and the resultant mixture was stirred at 100° C. for 2 hours in an argon atmosphere. The reaction mixture was allowed to cool to room temperature and poured to water, followed by extraction with ethyl acetate. The obtained organic layer was washed with saturated saline and dried over anhydrous magnesium sulfate, and then, the solvent was distilled off under reduced pressure. The obtained residue was purified by silica gel column chromatography (hexane/ethyl acetate) to obtain the title compound (3.18 g).

$^1$H NMR (300 MHz, CDCl$_3$) δ 0.60-0.68 (2H, m), 0.79-0.99 (2H, m), 1.39 (6H, d, J=6.1 Hz), 1.87-2.00 (1H, m), 3.89 (3H, s), 5.37-5.53 (1H, m), 7.14 (2H, t, J=8.7 Hz), 7.71-7.80 (2H, m), 7.82 (1H, s).

F) 5-Cyclopropyl-6-(4-fluorophenyl)-2-isopropoxynicotinaldehyde

A THF (20 mL) solution of methyl 5-cyclopropyl-6-(4-fluorophenyl)-2-isopropoxynicotinate (3.17 g) was added to a THF (20 mL) suspension of lithium aluminum hydride (365 mg) under ice cooling in a nitrogen atmosphere. After stirring at the same temperature as above for 30 minutes, water (0.35 mL) and a 15% aqueous sodium hydroxide solution (0.35 mL) were added thereto, and the mixture was stirred for 5 minutes. Then, water (1.05 mL) was further added thereto. The reaction mixture was stirred for 30 minutes and then filtered. The filtrate was concentrated under reduced pressure. Manganese dioxide (8.36 g) was added to a toluene (30 mL) solution of the obtained residue, and the mixture was stirred at 60° C. for 1 hour in a nitrogen atmosphere. The reaction mixture was filtered, and then, the solvent was distilled off under reduced pressure. The obtained residue was purified by silica gel column chromatography (hexane/ethyl acetate) to obtain the title compound (2.45 g).

$^1$H NMR (300 MHz, CDCl$_3$) δ 0.58-0.72 (2H, m), 0.87-0.99 (2H, m), 1.40 (6H, d, J=6.2 Hz), 1.81-2.01 (1H, m), 5.35-5.66 (1H, m), 7.15 (2H, t, J=8.7 Hz), 7.69-7.84 (3H, m), 10.36 (1H, s).

G) Methyl 6-(1-((5-cyclopropyl-6-(4-fluorophenyl)-2-isopropoxypyridin-3-yl)methyl)piperidin-4-yl)-2-methyl-5-oxo-5,6,7,8-tetrahydro-1,6-naphthyridine-3-carboxylate Methyl 6-(1-(tert-butoxycarbonyl)piperidin-4-yl)-2-methyl-5-oxo-5,6,7,8-tetrahydro-1,6-naphthyridine-3-carboxylate (600 mg) was added to formic acid (5 mL), and the mixture was stirred at 60° C. for 30 minutes. Then, the solvent was distilled off under reduced pressure. Toluene was added to the obtained residue, and the solvent was further distilled off under reduced pressure. 5-Cyclopropyl-6-(4-fluorophenyl)-2-isopropoxynicotinaldehyde (534 mg) was added to a mixture of the obtained residue and THF (5 mL), and the resultant mixture was stirred at room temperature for 10 minutes. Then, sodium triacetoxy borohydride (473 mg) was added thereto, and the mixture was stirred at room temperature for 2 hours. A saturated aqueous solution of sodium bicarbonate was added to the reaction mixture, followed by extraction with ethyl acetate. The obtained organic layer was dried over anhydrous magnesium sulfate, and then, the solvent was distilled off under reduced pressure. The obtained residue was purified by silica gel column chromatography (hexane/ethyl acetate/methanol) to obtain the title compound (810 mg).

MS (ESI+): [M+H]$^+$ 587.5

H) 6-(1-((5-Cyclopropyl-6-(4-fluorophenyl)-2-isopropoxypyridin-3-yl)methyl)piperidin-4-yl)-2-methyl-5-oxo-5,6,7,8-tetrahydro-1,6-naphthyridine-3-carboxylic acid A 2 M aqueous sodium hydroxide solution (1.50 mL) was added at room temperature to a methanol (2 mL)-THF (2 mL) solution of methyl 6-(1-((5-cyclopropyl-6-(4-fluorophenyl)-2-isopropoxypyridin-3-yl)methyl)piperidin-4-yl)-2-methyl-5-oxo-5,6,7,8-tetrahydro-1,6-naphthyridine-3-carboxylate (800 mg), and the mixture was stirred at 50° C. for 1 hour. The reaction mixture was neutralized with hydrochloric acid at room temperature. Then, ethyl acetate was added thereto, and the mixture was concentrated. Then, the deposited solid was collected by filtration and washed with diethyl ether. The obtained solid was recrystallized (ethanol/hexane) to obtain the title compound (727 mg).

$^1$H NMR (300 MHz, DMSO-d$_6$) δ 0.51-0.62 (2H, m), 0.81-0.94 (2H, m), 1.30 (6H, d, J=6.1 Hz), 1.58 (2H, d, J=12.0 Hz), 1.73-2.00 (3H, m), 2.10-2.26 (2H, m), 2.75 (3H, s), 2.96 (2H, d, J=11.1 Hz), 3.06 (2H, t, J=6.5 Hz), 3.49 (2H, s), 3.58 (2H, t, J=6.5 Hz), 4.27-4.52 (1H, m), 5.16-5.33 (1H, m), 7.29 (2H, t, J=8.9 Hz), 7.37 (1H, s), 7.70-7.82 (2H, m), 8.50 (1H, s).

Example 7
6-(1-((2-Cyclopropyl-4'-fluoro-5-isopropoxybiphenyl-4-yl)methyl)piperidin-4-yl)-2-methyl-5-oxo-5,6,7,8-tetrahydro-1,6-naphthyridine-3-carboxylic acid
[Formula 24]
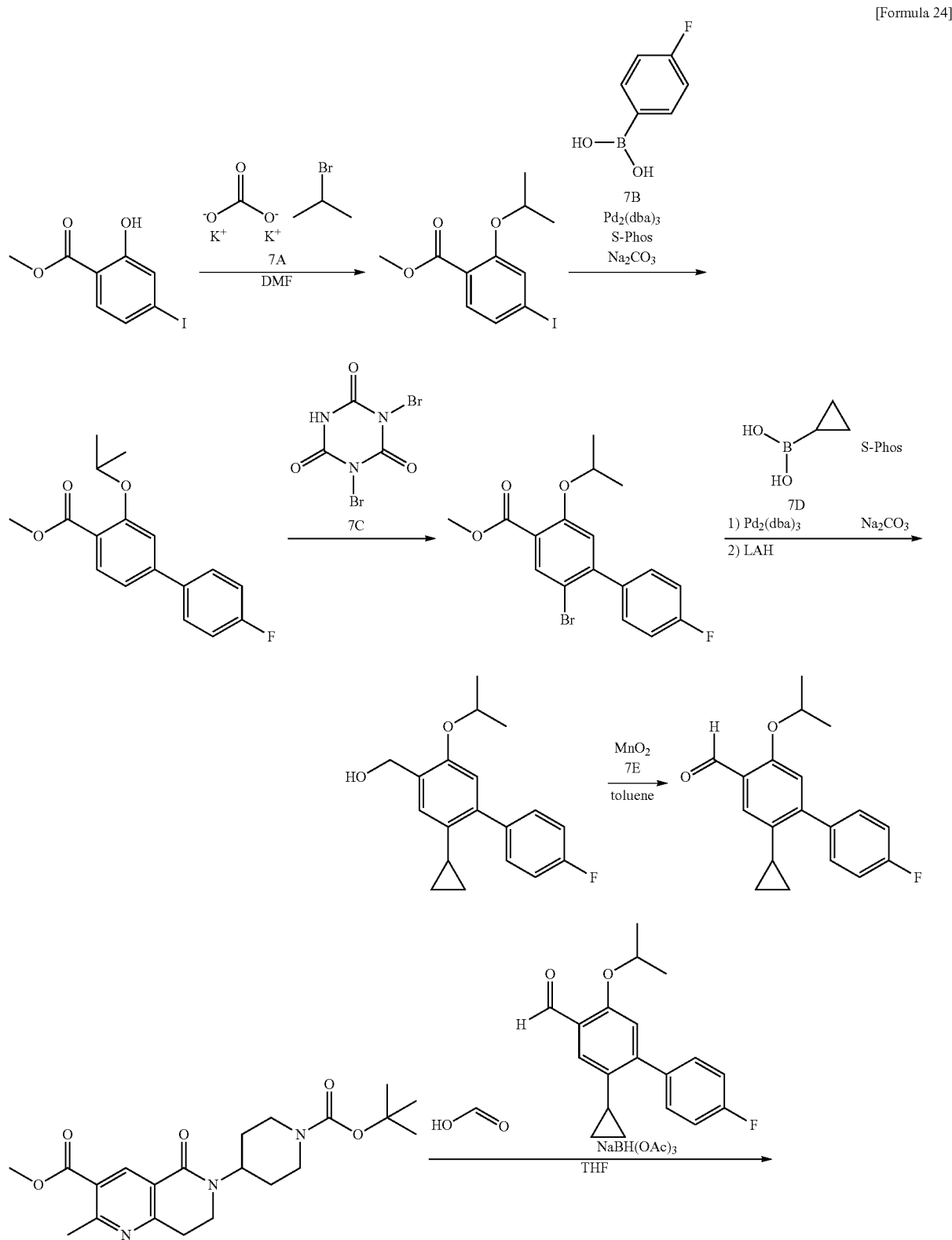

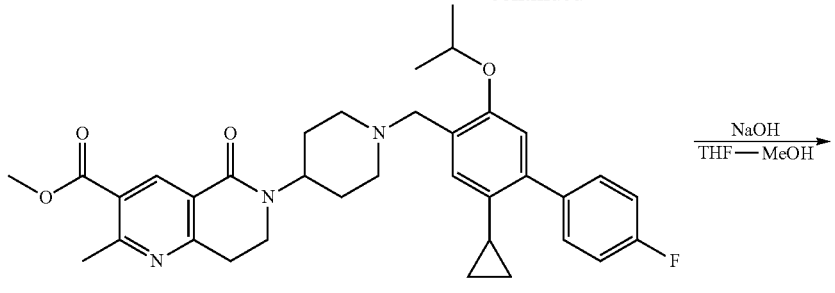

7F (Same as Examples 1K and 1L)

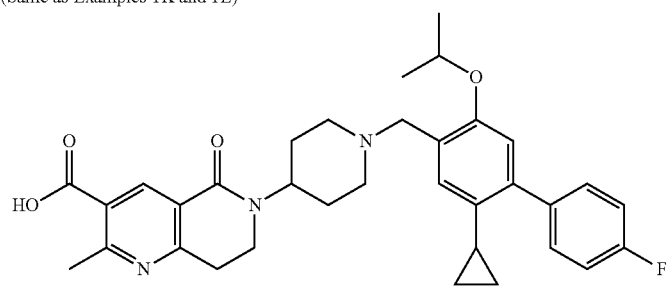

A) Methyl 4-iodo-2-isopropoxybenzoate

2-Bromopropane (6.49 mL) was added to a DMF (70 mL) suspension of methyl 2-hydroxy-4-iodobenzoate (12.8 g) and potassium carbonate (12.7 g), and the mixture was stirred at 60° C. for 2 hours. The reaction mixture was allowed to cool to room temperature, and then, water was added thereto, followed by extraction with ethyl acetate. The obtained organic layer was washed with saturated saline and dried over anhydrous magnesium sulfate, and then, the solvent was distilled off under reduced pressure. The obtained residue was purified by silica gel column chromatography (NH, hexane/ethyl acetate) to obtain the title compound (14.0 g).

$^1$H NMR (300 MHz, CDCl$_3$) δ 1.37 (6H, d, J=6.0 Hz), 3.86 (3H, s), 4.41-4.67 (1H, m), 7.29-7.35 (2H, m), 7.46 (1H, d, J=8.6 Hz).

B) Methyl 4'-fluoro-3-isopropoxybiphenyl-4-carboxylate

A mixture of methyl 4-iodo-2-isopropoxybenzoate (7.50 g), (4-fluorophenyl)boronic acid (6.56 g), dicyclohexyl(2',6'-dimethoxybiphenyl-2-yl)phosphine (1.44 g), a 2 M aqueous sodium carbonate solution (35.1 mL), tris(dibenzylideneacetone)dipalladium(0) (1.50 g), and toluene (50 mL) was stirred at 100° C. for 2 hours in an argon atmosphere. The reaction mixture was allowed to cool to room temperature. Then, the organic layer was separated and passed through a short silica gel (NH) column, and the solvent was distilled off under reduced pressure. The obtained residue was purified by silica gel column chromatography (hexane/ethyl acetate) to obtain the title compound (6.61 g).

$^1$H NMR (300 MHz, CDCl$_3$) δ 1.41 (6H, d, J=6.0 Hz), 3.90 (3H, s), 4.56-4.78 (1H, m), 7.07-7.19 (4H, m), 7.49-7.59 (2H, m), 7.80-7.90 (1H, m).

C) Methyl 2-bromo-4'-fluoro-5-isopropoxybiphenyl-4-carboxylate

Dibromoisocyanuric acid (4.60 g) was added to a mixture of methyl 4'-fluoro-3-isopropoxybiphenyl-4-carboxylate (6.61 g) and DMF (60 mL), and the resultant mixture was stirred at room temperature for 5 hours. Water was added to the reaction mixture, followed by extraction with ethyl acetate. The obtained organic layer was washed with saturated saline and dried over anhydrous magnesium sulfate, and then, the solvent was distilled off under reduced pressure. The obtained residue was purified by silica gel column chromatography (hexane/ethyl acetate) to obtain the title compound (7.53 g).

$^1$H NMR (300 MHz, CDCl$_3$) δ 1.37 (6H, d, J=6.0 Hz), 3.90 (3H, s), 4.45-4.69 (1H, m), 6.91 (1H, s), 7.06-7.18 (2H, m), 7.32-7.44 (2H, m), 8.05 (1H, s).

D) (2-Cyclopropyl-4'-fluoro-5-isopropoxybiphenyl-4-yl)methanol

A mixture of methyl 2-bromo-4'-fluoro-5-isopropoxybiphenyl-4-carboxylate (7.53 g), cyclopropylboronic acid (4.40 g), dicyclohexyl(2',6'-dimethoxybiphenyl-2-yl)phosphine (1.26 g), a 2 M aqueous sodium carbonate solution (30.8 mL), tris(dibenzylideneacetone)dipalladium(0) (1.31 g), and toluene (150 mL) was stirred overnight at 100° C. in an argon atmosphere. The reaction mixture was allowed to cool to room temperature. Then, the organic layer was separated, washed with saturated saline, and passed through a short silica gel (NH) column, and the solvent was distilled off under reduced pressure. A THF (50 mL) solution of the obtained residue was added to a THF (50 mL) suspension of lithium aluminum hydride (2.00 g) under ice cooling in a nitrogen atmosphere. After stirring at the same temperature as above for 30 minutes, water (2 mL) and a 15% aqueous sodium hydroxide solution (2 mL) were added thereto, and the mixture was stirred for 5 minutes. Water (6 mL) was further added to the reaction mixture, and the mixture was stirred for 30 minutes and then filtered. The filtrate was concentrated under reduced pressure. The obtained residue was purified by silica gel column chromatography (hexane/ethyl acetate) to obtain the title compound (5.75 g).

$^1$H NMR (300 MHz, CDCl$_3$) δ 0.55-0.64 (2H, m), 0.68-0.83 (2H, m), 1.31-1.40 (6H, m), 1.67-1.89 (1H, m), 2.45 (1H, t, J=6.6 Hz), 4.51-4.64 (1H, m), 4.66 (2H, d, J=6.6 Hz), 6.73 (1H, s), 6.86 (1H, s), 7.05-7.15 (2H, m), 7.34-7.45 (2H, m).

E) 2-Cyclopropyl-4'-fluoro-5-isopropoxybiphenyl-4-carbaldehyde

Manganese dioxide (16.6 g) was added to a toluene (80 mL) solution of (2-cyclopropyl-4'-fluoro-5-isopropoxybiphenyl-4-yl)methanol (5.75 g), and the mixture was stirred at 60° C. for 1 hour in a nitrogen atmosphere. The reaction mixture was filtered, and then, the solvent was distilled off under reduced pressure. The obtained residue was purified by silica gel column chromatography (hexane/ethyl acetate) to obtain the title compound (4.54 g).

$^1$H NMR (300 MHz, CDCl$_3$) δ 0.61-0.72 (2H, m), 0.75-0.85 (2H, m), 1.39 (6H, d, J=6.0 Hz), 1.71 (1H, tt, J=8.4, 5.4 Hz), 4.54-4.76 (1H, m), 6.83 (1H, s), 7.07-7.20 (2H, m), 7.35-7.50 (3H, m), 10.46 (1H, s).

F) 6-(1-((2-Cyclopropyl-4'-fluoro-5-isopropoxybiphenyl-4-yl)methyl)piperidin-4-yl)-2-methyl-5-oxo-5,6,7,8-tetrahydro-1,6-naphthyridine-3-carboxylic acid The title compound was obtained in the same way as in steps K and L of Example 1 using methyl 6-(1-(tert-butoxycarbonyl)piperidin-4-yl)-2-methyl-5-oxo-5,6,7,8-tetrahydro-1,6-naphthyridine-3-carboxylate and 2-cyclopropyl-4'-fluoro-5-isopropoxybiphenyl-4-carbaldehyde.

Example 8

6-(1-((2-Cyclopropyl-6-ethoxy-3',4'-difluorobiphenyl-4-yl)methyl)piperidin-4-yl)-2-methyl-5-oxo-5,6,7,8-tetrahydro-1,6-naphthyridine-3-carboxylic acid

[Formula 25]

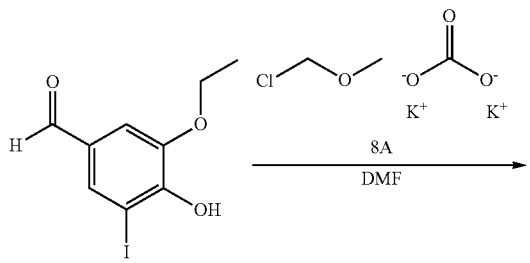

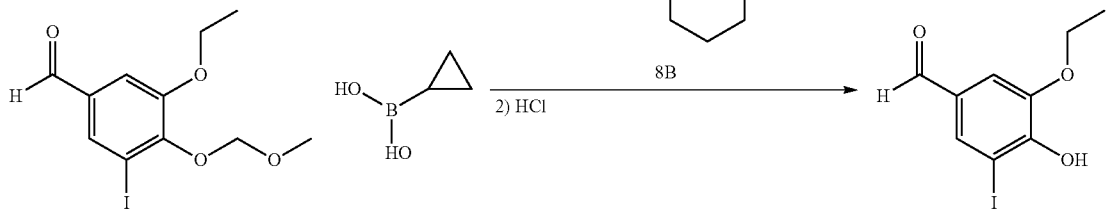

-continued
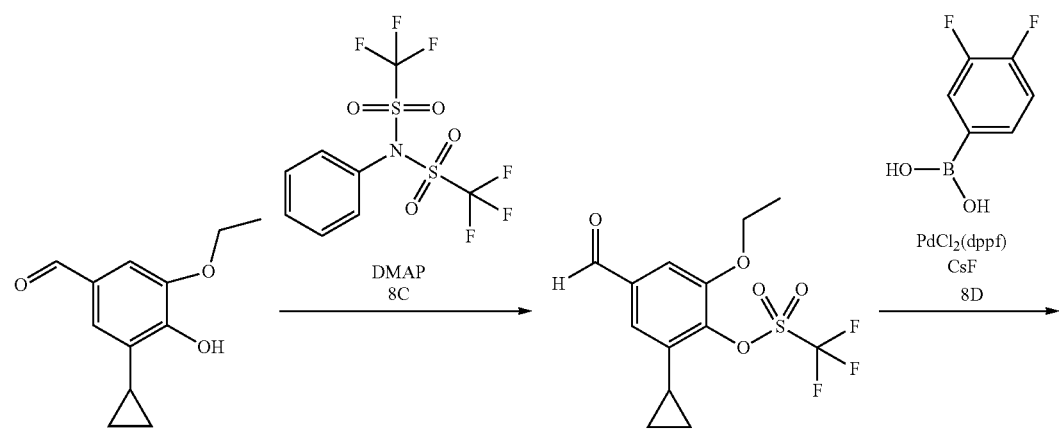
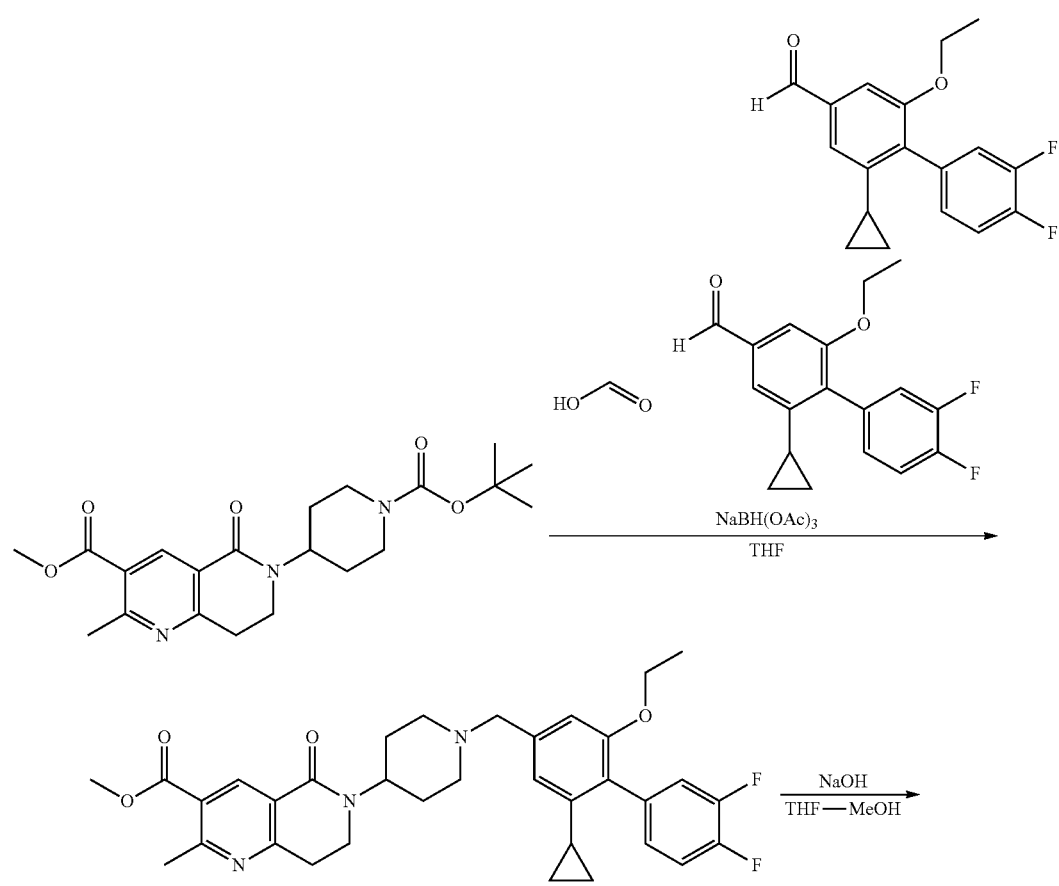
8E
(Same as Example 1K and 1L)
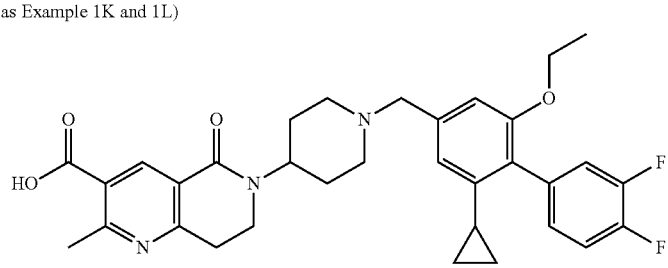

A) 3-Ethoxy-5-iodo-4-(methoxymethoxy)benzaldehyde

Chloro(methoxy)methane (6.27 mL) was added to a mixture of 3-ethoxy-4-hydroxy-5-iodobenzaldehyde (16.1 g), potassium carbonate (15.2 g), and DMF (120 mL), and the resultant mixture was stirred at room temperature for 3 hours. Water was added to the reaction mixture, followed by extraction with ethyl acetate. The obtained organic layer was washed with water and saturated saline and dried over anhydrous magnesium sulfate, and then, the solvent was distilled off under reduced pressure. The obtained residue was purified by silica gel column chromatography (hexane/ethyl acetate) to obtain the title compound (12.1 g).

$^1$H NMR (300 MHz, CDCl$_3$) δ 1.47 (3H, t, J=7.0 Hz), 3.67 (3H, s), 4.04-4.19 (2H, m), 5.33 (2H, s), 7.39 (1H, d, J=1.6 Hz), 7.87 (1H, d, J=1.7 Hz), 9.82 (1H, s).

B) 3-Cyclopropyl-5-ethoxy-4-hydroxybenzaldehyde

Tris(dibenzylideneacetone)dipalladium(0) (2.30 g) and dicyclohexyl(2',6'-dimethoxybiphenyl-2-yl)phosphine (2.21 g) were added to a mixture of 3-ethoxy-5-iodo-4-(methoxymethoxy)benzaldehyde (12.1 g), cyclopropylboronic acid (9.25 g), a 2 M aqueous sodium carbonate solution (53.9 mL), and toluene (60 mL), and the resultant mixture was stirred at 100° C. for 2 hours in an argon atmosphere. Water was added to the reaction mixture, followed by extraction with ethyl acetate. The obtained organic layer was dried over anhydrous magnesium sulfate, and then, the solvent was distilled off under reduced pressure. The obtained residue was purified by silica gel column chromatography (hexane/ethyl acetate) to obtain a purified product. 6 M hydrochloric acid (50 mL) was added to a methanol (100 mL) solution of the obtained purified product, and the mixture was stirred at 70° C. for 3 hours, and then, the solvent was distilled off under reduced pressure, followed by extraction with ethyl acetate. The obtained organic layer was washed with water and saturated saline and dried over anhydrous magnesium sulfate, and then, the solvent was distilled off under reduced pressure. The obtained residue was purified by silica gel column chromatography (hexane/ethyl acetate) to obtain the title compound (6.60 g).

$^1$H NMR (300 MHz, CDCl$_3$) δ 0.68-0.79 (2H, m), 0.95-1.06 (2H, m), 1.48 (3H, t, J=7.0 Hz), 2.12-2.24 (1H, m), 4.20 (2H, q, J=7.0 Hz), 6.36 (1H, s), 7.02 (1H, d, J=1.5 Hz), 7.23 (1H, d, J=1.7 Hz), 9.76 (1H, s).

C) 2-Cyclopropyl-6-ethoxy-4-formylphenyl trifluoromethanesulfonate

4-Dimethylaminopyridine (0.237 g) and N-phenyltrifluoromethanesulfonimide (9.70 g) were added to a mixture of 3-cyclopropyl-5-ethoxy-4-hydroxybenzaldehyde (4.00 g), N,N'-diisopropylethylamine (6.77 mL), and THF (100 mL), and the resultant mixture was stirred at 70° C. for 3 hours. 1 M hydrochloric acid was added to the reaction mixture, followed by extraction with ethyl acetate. The obtained organic layer was washed with saturated saline and dried over anhydrous magnesium sulfate, and then, the solvent was distilled off under reduced pressure. The obtained residue was purified by silica gel column chromatography (hexane/ethyl acetate) to obtain the title compound (6.24 g).

$^1$H NMR (300 MHz, CDCl$_3$) δ 0.78-0.87 (2H, m), 1.10-1.19 (2H, m), 1.49 (3H, t, J=7.0 Hz), 2.06-2.20 (1H, m), 4.20 (2H, q, J=7.0 Hz), 7.05 (1H, d, J=1.7 Hz), 7.32 (1H, d, J=1.7 Hz), 9.90 (1H, s).

D) 2-Cyclopropyl-6-ethoxy-3',4'-difluorobiphenyl-4-carbaldehyde (1,1'-Bis(diphenylphosphino)ferrocene)dichloropalladium(II) (1.30 g) was added to a mixture of 2-cyclopropyl-6-ethoxy-4-formylphenyl trifluoromethanesulfonate (3.00 g), (3,4-difluorophenyl)boronic acid (5.60 g), cesium fluoride (5.39 g), and DME (15 mL), and the resultant mixture was stirred at 100° C. for 15 hours in an argon atmosphere. Water was added to the reaction mixture, and the mixture was filtered through celite. The filtrate was subjected to extraction with ethyl acetate. The organic layer was washed with water and saturated saline and dried over anhydrous magnesium sulfate, and then, the solvent was distilled off under reduced pressure. The obtained residue was purified by silica gel column chromatography (hexane/ethyl acetate) to obtain the title compound (1.57 g).

$^1$H NMR (300 MHz, DMSO-d$_6$) δ 0.67-0.77 (2H, m), 0.79-0.92 (2H, m), 1.26 (3H, t, J=7.0 Hz), 1.58-1.70 (1H, m), 4.04 (2H, q, J=7.0 Hz), 6.95-7.06 (2H, m), 7.08-7.19 (1H, m), 7.20-7.24 (1H, m), 7.27-7.44 (1H, m), 9.94 (1H, s).

E) 6-(1-((2-Cyclopropyl-6-ethoxy-3',4'-difluorobiphenyl-4-yl)methyl)piperidin-4-yl)-2-methyl-5-oxo-5,6,7,8-tetrahydro-1,6-naphthyridine-3-carboxylic acid The title compound was obtained in the same way as in steps K and L of Example 1 using methyl 6-(1-(tert-butoxycarbonyl)piperidin-4-yl)-2-methyl-5-oxo-5,6,7,8-tetrahydro-1,6-naphthyridine-3-carboxylate and 2-cyclopropyl-6-ethoxy-3',4'-difluorobiphenyl-4-carbaldehyde.

Example 9

6-(1-((2-Cyclopropyl-4'-fluoro-6-propoxybiphenyl-4-yl)methyl)piperidin-4-yl)-2-methyl-5-oxo-5,6,7,8-tetrahydro-1,6-naphthyridine-3-carboxylic acid

[Formula 26]

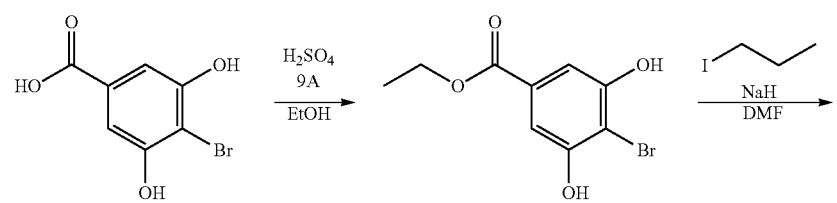

-continued
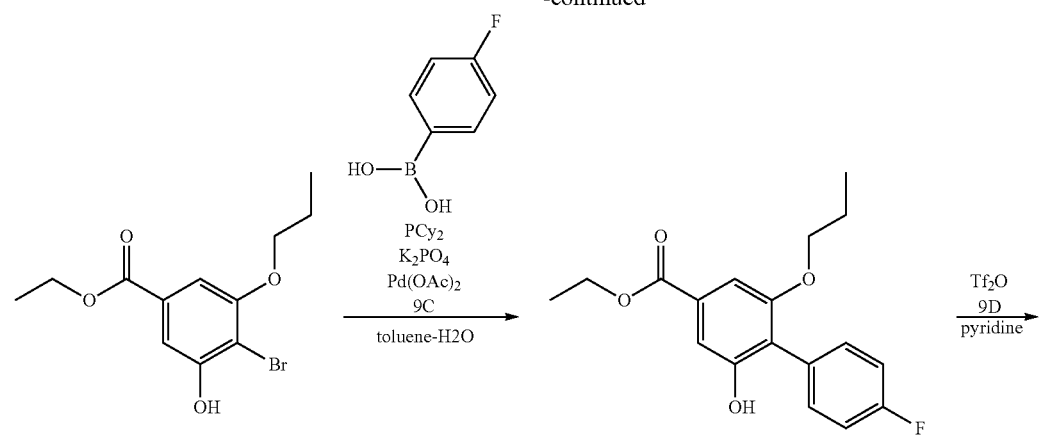
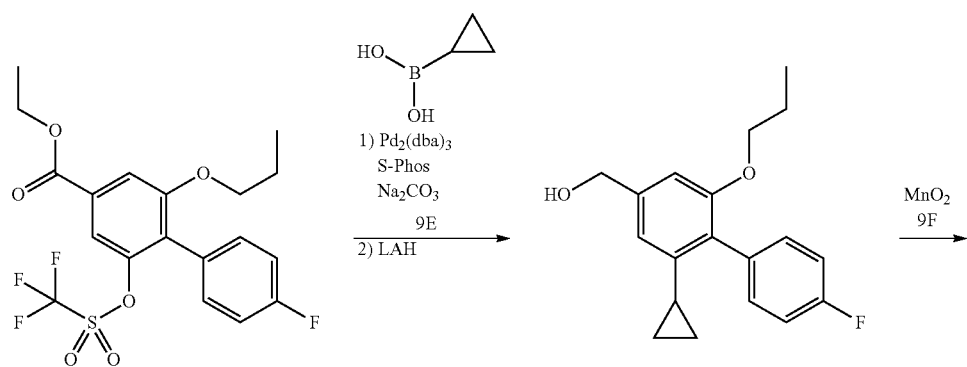
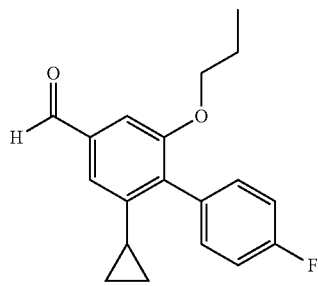
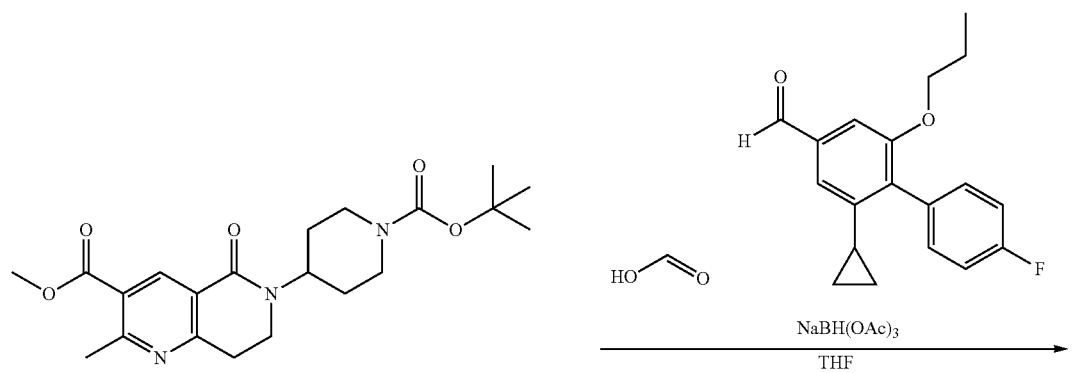
9G (Same as Examples 1K and 1L)

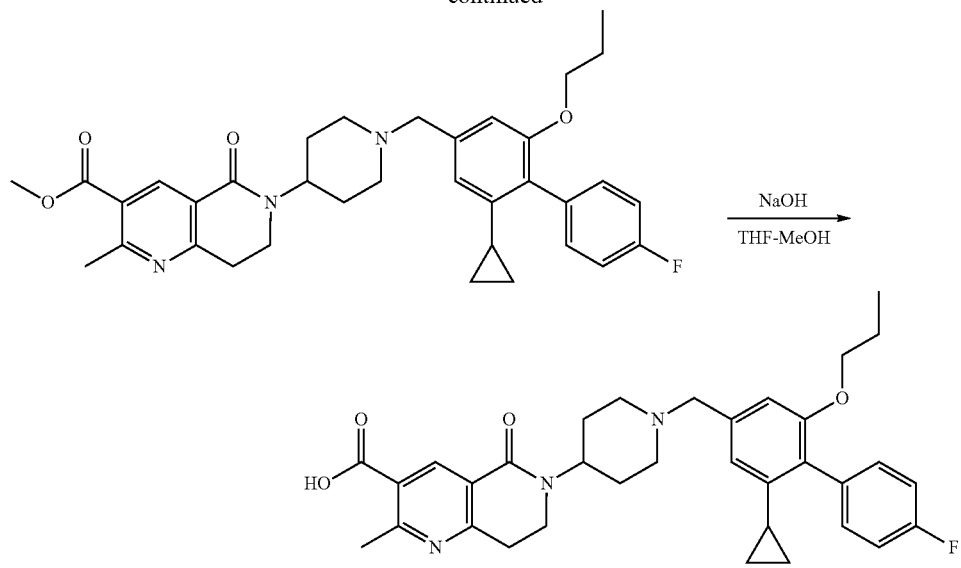

A) Ethyl 4-bromo-3,5-dihydroxybenzoate

A mixture of 4-bromo-3,5-dihydroxybenzoic acid (45.0 g), concentrated sulfuric acid (5 mL), and ethanol (300 mL) was heated to reflux for 24 hours. The solvent was distilled off under reduced pressure. The residue was diluted with ethyl acetate and washed with water, a saturated aqueous solution of sodium bicarbonate, and saturated saline in this order. The obtained organic layer was dried over anhydrous magnesium sulfate, and then, the solvent was distilled off under reduced pressure. The obtained solid was washed with hexane to obtain the title compound (48.3 g).

$^1$H NMR (300 MHz, CDCl$_3$) δ 1.39 (3H, t, J=7.1 Hz), 4.37 (2H, q, J=7.1 Hz), 5.82 (2H, brs), 7.31 (2H, s).

B) Ethyl 4-bromo-3-hydroxy-5-propoxybenzoate

Sodium hydride (60% oil, 10.1 g) was added to a mixture of ethyl 4-bromo-3,5-dihydroxybenzoate (30.0 g) and DMF (200 mL), and the resultant mixture was stirred at 0° C. for 30 minutes in a nitrogen atmosphere. 1-Iodopropane (11.2 mL) was added to the reaction mixture, and the mixture was stirred at room temperature for 2 hours. Water was added to the reaction mixture, followed by extraction with ethyl acetate. The obtained organic layer was washed with saturated saline and dried over anhydrous magnesium sulfate, and then, the solvent was distilled off under reduced pressure. The obtained residue was purified by silica gel column chromatography (hexane/ethyl acetate) to obtain the title compound (14.1 g).

$^1$H NMR (300 MHz, CDCl$_3$) δ 1.08 (3H, t, J=7.4 Hz), 1.39 (3H, t, J=7.1 Hz), 1.78-1.95 (2H, m), 4.05 (2H, t, J=6.4 Hz), 4.37 (2H, q, J=7.1 Hz), 5.74 (1H, s), 7.13 (1H, d, J=1.8 Hz), 7.34 (1H, d, J=1.8 Hz).

C) Ethyl 4'-fluoro-2-hydroxy-6-propoxybiphenyl-4-carboxylate

Palladium acetate (1.11 g) was added to a mixture of ethyl 4-bromo-3-hydroxy-5-propoxybenzoate (30.0 g), tripotassium phosphate (63.0 g), (4-fluorophenyl)boronic acid (34.6 g), and tricyclohexylphosphine (20% toluene solution, 17.6 mL) in toluene (200 mL) and water (100 mL), and the resultant mixture was heated with stirring overnight at 90° C. in an argon atmosphere. The reaction mixture was allowed to cool to room temperature, then diluted with ethyl acetate, and washed with water and saturated saline in this order. The organic layer was dried over anhydrous magnesium sulfate, and then, the solvent was distilled off under reduced pressure. The obtained residue was purified by silica gel column chromatography (hexane/ethyl acetate) to obtain the title compound (31.5 g).

$^1$H NMR (300 MHz, CDCl$_3$) δ 0.86 (3H, t, J=7.4 Hz), 1.40 (3H, t, J=7.1 Hz), 1.58-1.71 (2H, m), 3.92 (2H, t, J=6.4 Hz), 4.39 (2H, q, J=7.1 Hz), 5.03 (1H, s), 7.10-7.23 (3H, m), 7.30-7.41 (3H, m).

D) Ethyl 4'-fluoro-2-propoxy-6-(((trifluoromethyl)sulfonyl)oxy)biphenyl-4-carboxylate Trifluoromethanesulfonic anhydride (20.1 mL) was added at 0° C. to a mixture of ethyl 4'-fluoro-2-hydroxy-6-propoxybiphenyl-4-carboxylate (31.5 g) and pyridine (200 mL), and the resultant mixture was stirred at the same temperature as above for 20 minutes. The reaction mixture was passed through a short silica gel (NH) column, and the solvent was distilled off under reduced pressure. The obtained residue was purified by silica gel column chromatography (hexane/ethyl acetate) to obtain the title compound (44.6 g).

$^1$H NMR (300 MHz, CDCl$_3$) δ 0.81-0.96 (3H, m), 1.43 (3H, t, J=7.1 Hz), 1.62-1.76 (2H, m), 3.99 (2H, t, J=6.3 Hz), 4.43 (2H, q, J=7.2 Hz), 7.09-7.18 (2H, m), 7.28-7.38 (2H, m), 7.63 (2H, s).

E) (2-Cyclopropyl-4'-fluoro-6-propoxybiphenyl-4-yl)methanol

Tris(dibenzylideneacetone)dipalladium(0) (6.65 g) was added to a mixture of ethyl 4'-fluoro-2-propoxy-6-(((trifluoromethyl)sulfonyl)oxy)biphenyl-4-carboxylate (44.6 g), cyclopropylboronic acid (22.3 g), dicyclohexyl(2',6'-dimethoxybiphenyl-2-yl)phosphine (6.38 g), a 2 M aqueous sodium carbonate solution (156 mL), and toluene (250 mL), and the resultant mixture was stirred at 100° C. for 4 hours in an argon atmosphere. The reaction mixture was allowed to cool to room temperature, followed by extraction with ethyl acetate. The obtained organic layer was washed with saturated saline and dried over anhydrous magnesium sulfate, and then, the solvent was distilled off under reduced pressure. The obtained residue was purified by silica gel chromatography (hexane/ethyl acetate). A THF (150 mL) solution of the obtained purified product was added to a THF (150 mL) suspension of lithium aluminum hydride (3.50 g) under ice cooling in a nitrogen atmosphere. After stirring at the same temperature as above for 30 minutes, water (3.5 mL) and a 15% aqueous sodium hydroxide solution (3.5 mL) were added thereto, and the mixture was stirred for 5 minutes. Then, water (10.5 mL) was further added thereto, and the mixture was stirred for 30 minutes. The reaction mixture was filtered, and the filtrate was concentrated under reduced pressure. The obtained residue was purified by silica gel column chromatography (hexane/ethyl acetate) to obtain the title compound (29.8 g).

$^1$H NMR (300 MHz, CDCl$_3$) δ 0.58-0.69 (2H, m), 0.72-0.78 (2H, m), 0.82 (3H, t, J=7.4 Hz), 1.50-1.76 (3H, m), 3.84 (2H, t, J=6.3 Hz), 4.66 (2H, d, J=5.9 Hz), 6.51 (1H, s), 6.80 (1H, s), 7.03-7.13 (2H, m), 7.20-7.31 (2H, m).

F) 2-Cyclopropyl-4'-fluoro-6-propoxybiphenyl-4-carbaldehyde

Manganese dioxide (60.4 g) was added to a mixture of (2-cyclopropyl-4'-fluoro-6-propoxybiphenyl-4-yl)methanol (29.8 g) and toluene (200 mL), and the resultant mixture was stirred at 60° C. for 1 hour in a nitrogen atmosphere. The reaction mixture was filtered, and then, the filtrate was concentrated. The obtained residue was purified by silica gel column chromatography (hexane/ethyl acetate) to obtain the title compound (22.1 g).

$^1$H NMR (300 MHz, CDCl$_3$) δ 0.67-0.76 (2H, m), 0.78-0.93 (5H, m), 1.57-1.73 (3H, m), 3.91 (2H, t, J=6.3 Hz), 7.03 (1H, d, J=1.2 Hz), 7.07-7.18 (2H, m), 7.22-7.33 (3H, m), 9.94 (1H, s).

G) 6-(1-((2-Cyclopropyl-4'-fluoro-6-propoxybiphenyl-4-yl)methyl)piperidin-4-yl)-2-methyl-5-oxo-5,6,7,8-tetrahydro-1,6-naphthyridine-3-carboxylic acid The title compound was obtained in the same way as in steps K and L of Example 1 using methyl 6-(1-(tert-butoxycarbonyl)piperidin-4-yl)-2-methyl-5-oxo-5,6,7,8-tetrahydro-1,6-naphthyridine-3-carboxylate and 2-cyclopropyl-4'-fluoro-6-propoxybiphenyl-4-carbaldehyde.

Example 10

6-(1-(4-Cyclobutyl-3-cyclopropyl-5-ethoxybenzyl)piperidin-4-yl)-2-methyl-5-oxo-5,6,7,8-tetrahydro-1,6-naphthyridine-3-carboxylic acid

[Formula 27]

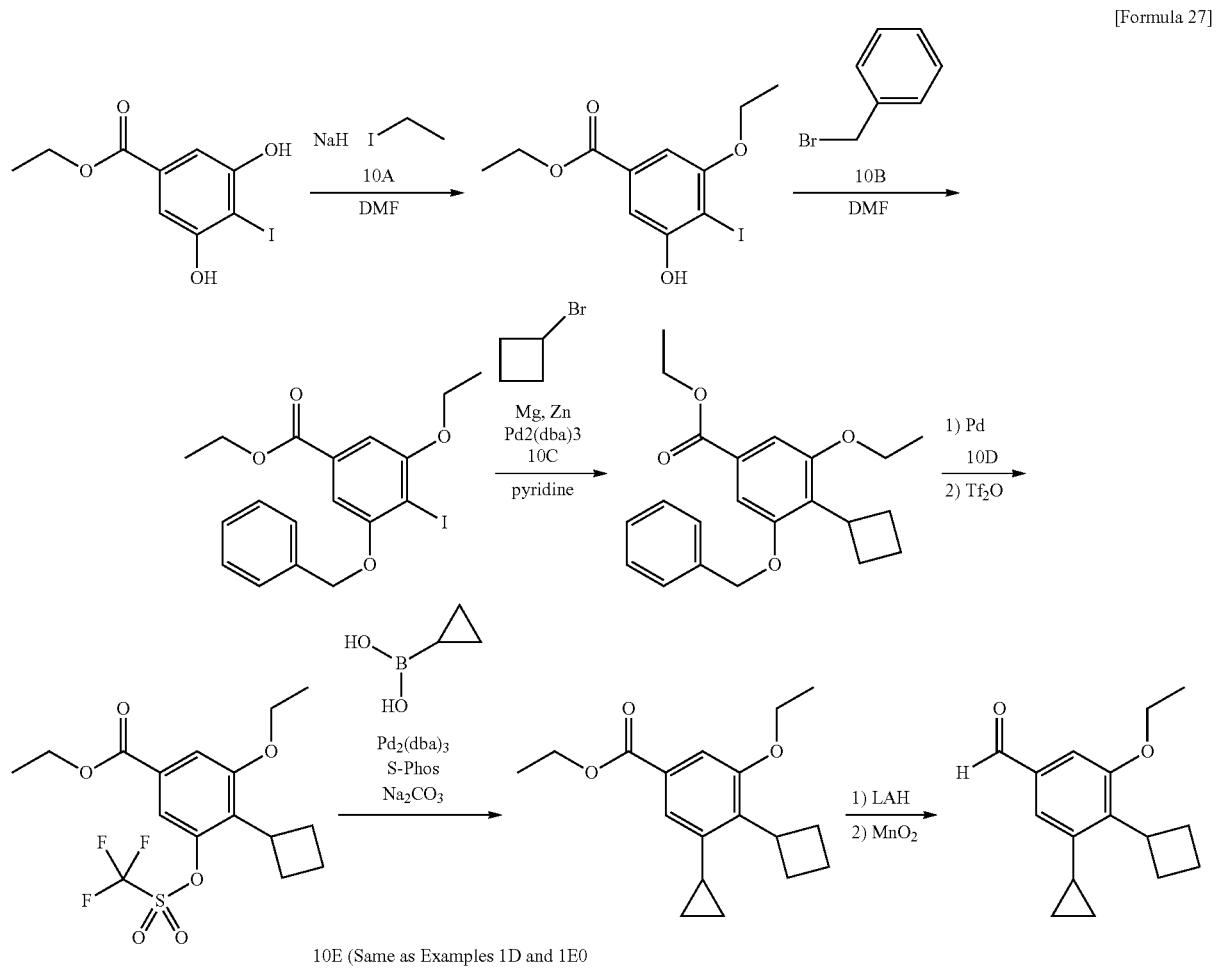

10E (Same as Examples 1D and 1E0)

-continued

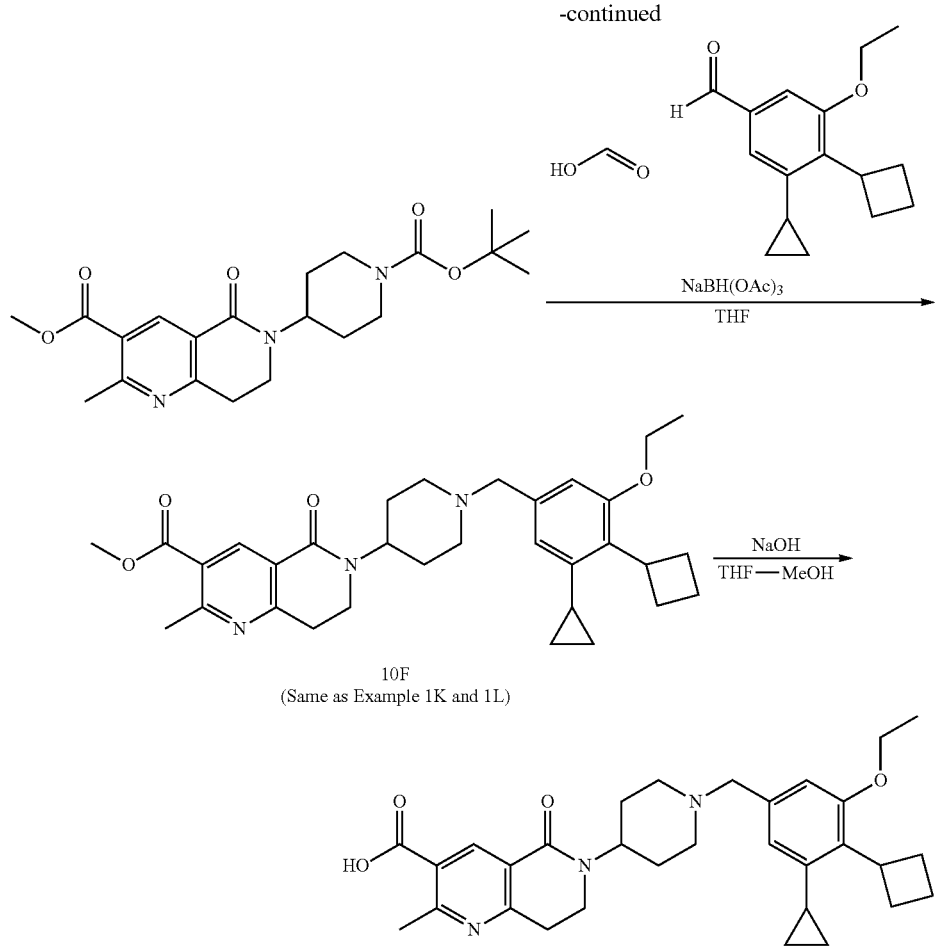

10F
(Same as Example 1K and 1L)

A) Ethyl 3-ethoxy-5-hydroxy-4-iodobenzoate

Sodium hydride (60% oil, 3.99 g) was added to a DMF (100 mL) solution of ethyl 3,5-dihydroxy-4-iodobenzoate (15.0 g), and the mixture was stirred at 0° C. for 30 minutes in a nitrogen atmosphere. Iodoethane (4.09 mL) was added to the reaction mixture, and the mixture was stirred at room temperature for 2 hours. Water was added to the reaction mixture, followed by extraction with ethyl acetate. The obtained organic layer was washed with saturated saline and dried over anhydrous magnesium sulfate, and then, the solvent was distilled off under reduced pressure. The obtained residue was purified by silica gel column chromatography (hexane/ethyl acetate) to obtain the title compound (7.59 g).
$^1$H NMR (300 MHz, CDCl$_3$) δ 1.39 (3H, t, J=7.1 Hz), 1.50 (3H, t, J=7.0 Hz), 4.16 (2H, q, J=6.9 Hz), 4.37 (2H, q, J=7.2 Hz), 5.59 (1H, s), 7.02 (1H, d, J=1.6 Hz), 7.31 (1H, d, J=1.7 Hz).

B) Ethyl 3-(benzyloxy)-5-ethoxy-4-iodobenzoate

Benzyl bromide (2.95 mL) was added to a DMF (200 mL) suspension of ethyl 3-ethoxy-5-hydroxy-4-iodobenzoate (7.59 g) and potassium carbonate (4.68 g), and the mixture was stirred at 60° C. for 2 hours. The reaction mixture was allowed to cool to room temperature, and then, water was added thereto, followed by extraction with ethyl acetate. The obtained organic layer was washed with saturated saline and passed through a short silica gel (NH) column, and the solvent was distilled off under reduced pressure. The obtained residue was purified by silica gel column chromatography (hexane/ethyl acetate) to obtain the title compound (7.09 g).
$^1$H NMR (300 MHz, CDCl$_3$) δ 1.40 (3H, t, J=7.1 Hz), 1.51 (3H, t, J=7.0 Hz), 4.17 (2H, q, J=7.1 Hz), 4.38 (2H, q, J=7.1 Hz), 5.22 (2H, s), 7.14 (1H, d, J=1.4 Hz), 7.20 (1H, d, J=1.4 Hz), 7.31-7.46 (3H, m), 7.54 (2H, d, J=7.2 Hz).

C) Ethyl 3-(benzyloxy)-4-cyclobutyl-5-ethoxybenzoate

A catalytic amount of iodine was added to a mixture of magnesium (10.8 g) and THF (180 mL), then a THF (90 mL) solution of cyclobutyl bromide (30 g) was slowly added thereto at room temperature, and the mixture was stirred at the same temperature as above for 2 hours. A THF (120 mL) solution of zinc bromide (50.0 g) was added to the reaction mixture at 0° C., and the mixture was stirred at the same temperature as above for 2 hours. The zinc reagent (140 mL) prepared above was added to a mixture of ethyl 3-(benzyloxy)-5-ethoxy-4-iodobenzoate (10 g), tris(dibenzylideneacetone)dipalladium(0) (0.644 g), dicyclohexyl(2',6'-dimethoxybiphenyl-2-yl)phosphine (0.482 g), and DMF (100 mL), and the resultant mixture was stirred at 100° C. for 16 hours in an argon atmosphere. The reaction mixture was allowed to cool to room temperature. Then, ethyl acetate was added thereto, and the mixture was filtered through celite. The filtrate was washed with water and saturated saline and dried over anhydrous sodium sulfate, and then, the solvent was distilled off under reduced pressure. The obtained residue was purified by silica gel column chromatography (hexane/ethyl acetate) to obtain the title compound (3.5 g).

MS (ESI+): [M+H]$^+$ 355.

D) Ethyl 4-cyclobutyl-3-ethoxy-5-(((trifluoromethyl)sulfonyl)oxy)benzoate

10% palladium carbon (2.55 g) was added to a mixture of ethyl 3-(benzyloxy)-4-cyclobutyl-5-ethoxybenzoate (8.5 g) and methanol (100 mL), and the resultant mixture was stirred at room temperature for 5 hours in a hydrogen atmosphere. The reaction mixture was filtered through celite, and then, the filtrate was concentrated. Triethylamine (6.1 mL) was added at 0° C. to a mixture of the obtained residue and dichloromethane (60 mL), and the resultant mixture was stirred at room temperature for 20 minutes. Trifluoromethanesulfonic anhydride (5.56 mL) was added to the reaction mixture, and the mixture was stirred at room temperature for 12 hours. Water was added to the reaction mixture, followed by extraction with dichloromethane three times. Then, combined organic layers were washed with water and saturated saline and dried over anhydrous sodium sulfate, and then, the solvent was distilled off under reduced pressure. The obtained residue was purified by silica gel column chromatography (hexane/ethyl acetate) to obtain the title compound (6 g).

MS (ESI+): [M+H]$^+$ 397.

E) 4-Cyclobutyl-3-cyclopropyl-5-ethoxybenzaldehyde

The title compound was obtained in the same way as in steps D and E of Example 1 using ethyl 4-cyclobutyl-3-ethoxy-5-(((trifluoromethyl)sulfonyl)oxy)benzoate.

MS (ESI+): [M+H]$^+$ 245.

F) 6-(1-(4-Cyclobutyl-3-cyclopropyl-5-ethoxybenzyl)piperidin-4-yl)-2-methyl-5-oxo-5,6,7,8-tetrahydro-1,6-naphthyridine-3-carboxylic acid The title compound was obtained in the same way as in steps K and L of Example 1 using methyl 6-(1-(tert-butoxycarbonyl)piperidin-4-yl)-2-methyl-5-oxo-5,6,7,8-tetrahydro-1,6-naphthyridine-3-carboxylate and 4-cyclobutyl-3-cyclopropyl-5-ethoxybenzaldehyde.

Example 11

6-(1-(3-Cyclopropyl-4-(cyclopropylmethoxy)-5-ethoxybenzyl)piperidin-4-yl)-2-methyl-5-oxo-5,6,7,8-tetrahydro-1,6-naphthyridine-3-carboxylic acid

[Formula 28]

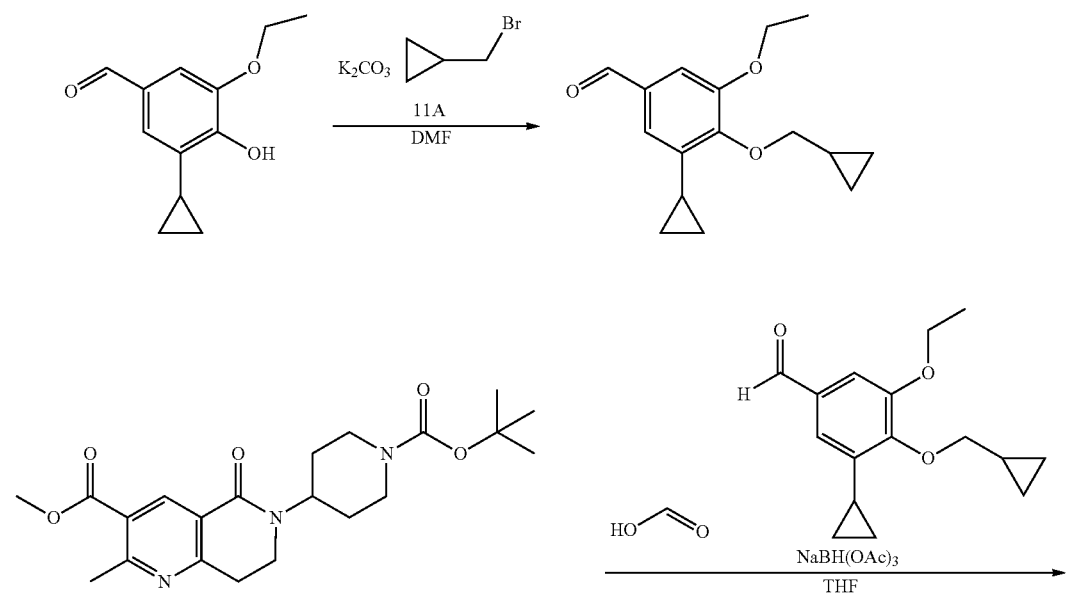

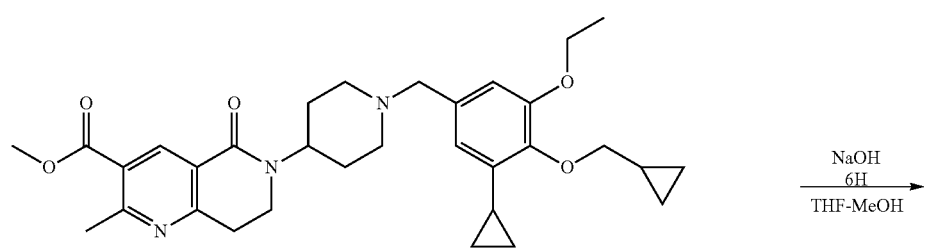

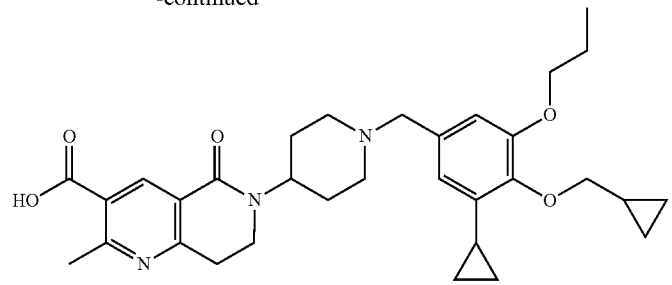

A) 3-Cyclopropyl-4-(cyclopropylmethoxy)-5-ethoxybenzaldehyde (Bromomethyl)cyclopropane (0.781 mL) was added to a DMF (10 mL) suspension of 3-cyclopropyl-5-ethoxy-4-hydroxybenzaldehyde (830 mg) and potassium carbonate (1.11 g), and the mixture was stirred at 70° C. for 5 hours. The reaction mixture was allowed to cool to room temperature, and then, water was added thereto, followed by extraction with ethyl acetate. The obtained organic layer was washed with saturated saline and dried over anhydrous magnesium sulfate, and then, the solvent was distilled off under reduced pressure. The obtained residue was purified by silica gel column chromatography (hexane/ethyl acetate) to obtain the title compound (1.03 g).

$^1$H NMR (300 MHz, CDCl$_3$) δ 0.27-0.38 (2H, m), 0.54-0.65 (2H, m), 0.68-0.78 (2H, m), 0.97-1.11 (2H, m), 1.21-1.38 (1H, m), 1.47 (3H, t, J=7.0 Hz), 2.30-2.45 (1H, m), 3.95 (2H, d, J=7.3 Hz), 4.11 (2H, q, J=7.0 Hz), 6.91 (1H, d, J=1.8 Hz), 7.22 (1H, d, J=1.8 Hz), 9.81 (1H, s).

B) 6-(1-(3-Cyclopropyl-4-(cyclopropylmethoxy)-5-ethoxybenzyl)piperidin-4-yl)-2-methyl-5-oxo-5,6,7,8-tetrahydro-1,6-naphthyridine-3-carboxylic acid The title compound was obtained in the same way as in steps K and L of Example 1 using methyl 6-(1-(tert-butoxycarbonyl)piperidin-4-yl)-2-methyl-5-oxo-5,6,7,8-tetrahydro-1,6-naphthyridine-3-carboxylate and 3-cyclopropyl-4-(cyclopropylmethoxy)-5-ethoxybenzaldehyde.

Example 12

6-(1-(4-Cyclopentyl-3-cyclopropyl-5-ethoxybenzyl)piperidin-4-yl)-2-methyl-5-oxo-5,6,7,8-tetrahydro-1,6-naphthyridine-3-carboxylic acid

[Formula 29]

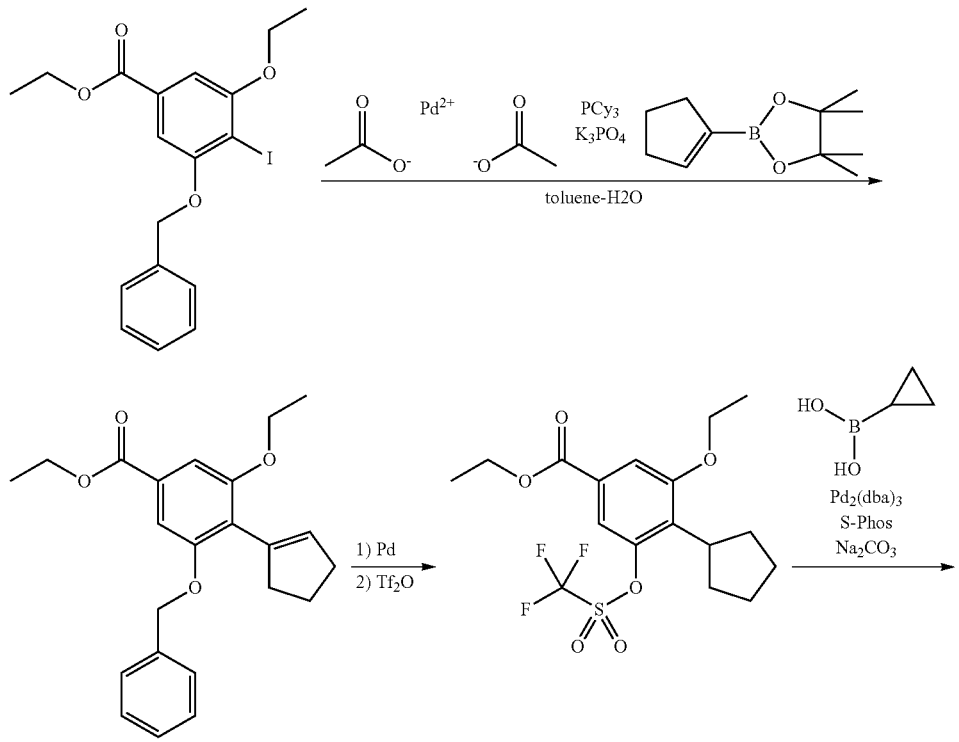

12A
(Same as Example 1B, 1H, 1C, 1D and 1E)

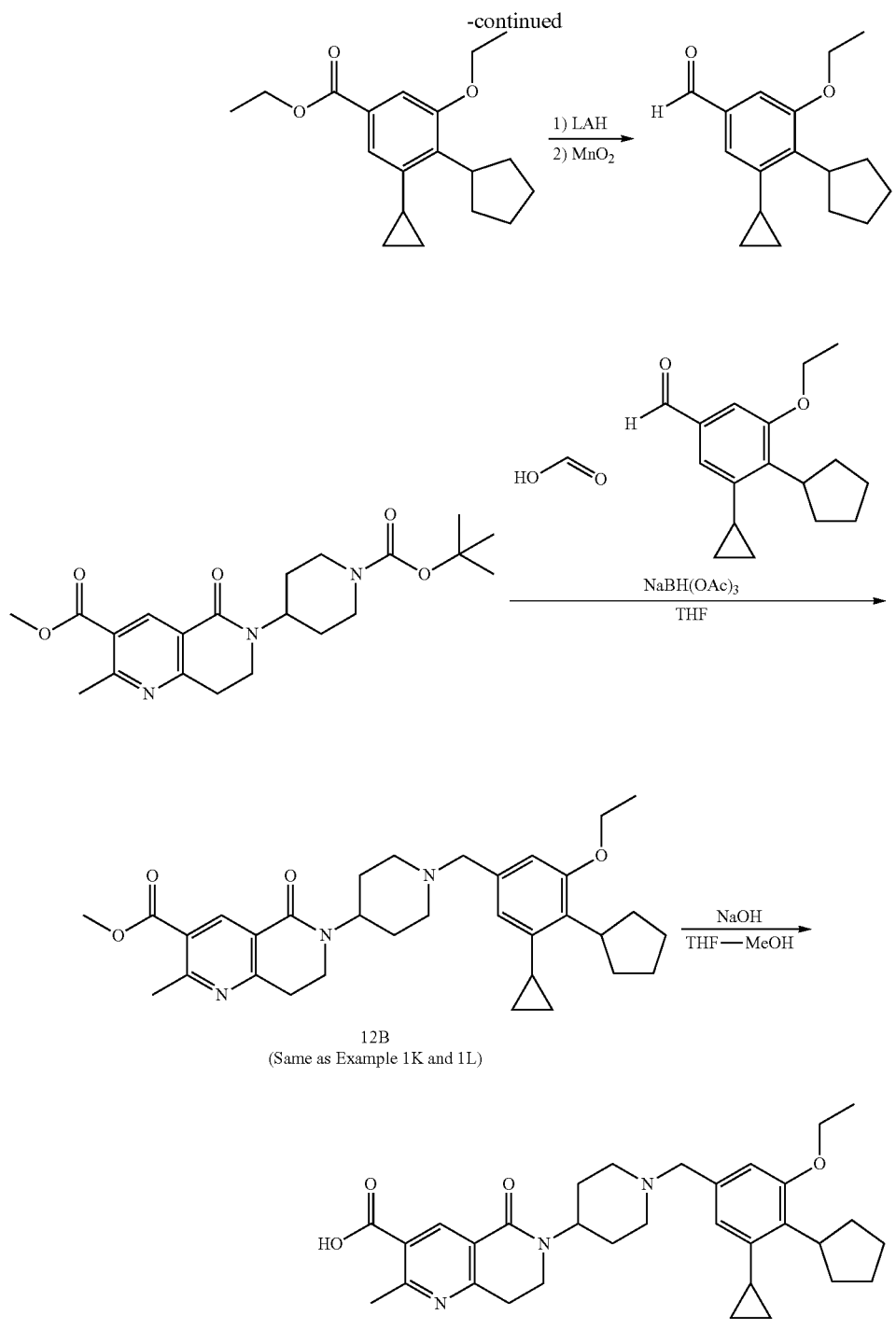

A)
4-Cyclopentyl-3-cyclopropyl-5-ethoxybenzaldehyde

The title compound was obtained in the same way as in steps B, H, C, D, and E of Example 1 using ethyl 3-(benzyloxy)-5-ethoxy-4-iodobenzoate and 2-(cyclopent-1-en-1-yl)-4,4,5,5-tetramethyl-1,3,2-dioxaborolane.

$^1$H NMR (300 MHz, CDCl$_3$) δ 0.52-0.73 (2H, m), 0.91-1.02 (2H, m), 1.45 (3H, t, J=6.9 Hz), 1.61-2.14 (9H, m), 3.72-3.97 (1H, m), 4.09 (2H, q, J=7.0 Hz), 7.22 (2H, s), 9.87 (1H, s).

B) 6-(1-(4-Cyclopentyl-3-cyclopropyl-5-ethoxybenzyl)piperidin-4-yl)-2-methyl-5-oxo-5,6,7,8-tetrahydro-1,6-naphthyridine-3-carboxylic acid The title compound was obtained in the same way as in steps K and L of Example 1 using methyl 6-(1-(tert-butoxycarbonyl)piperidin-4-yl)-2-methyl-5-oxo-5,6,7,8-tetrahydro-1,6-naphthyridine-3-carboxylate and 4-cyclopentyl-3-cyclopropyl-5-ethoxybenzaldehyde.

Example 13
6-(1-((1-tert-Butyl-3-(3-chloro-4-fluorophenyl)-1H-pyrazol-4-yl)methyl)piperidin-4-yl)-2-methyl-5-oxo-5,6,7,8-tetrahydro-1,6-naphthyridine-3-carboxylic acid
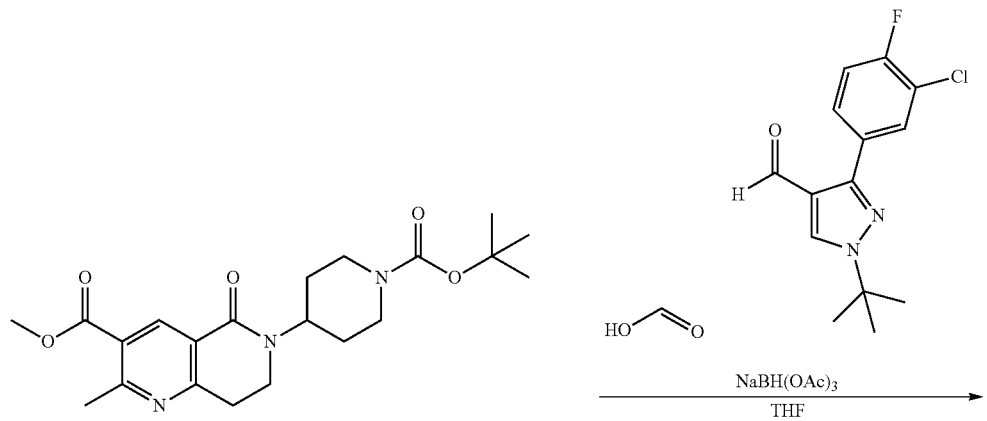
13 (Same as Examples 1K and 1L)
[Formula 30]
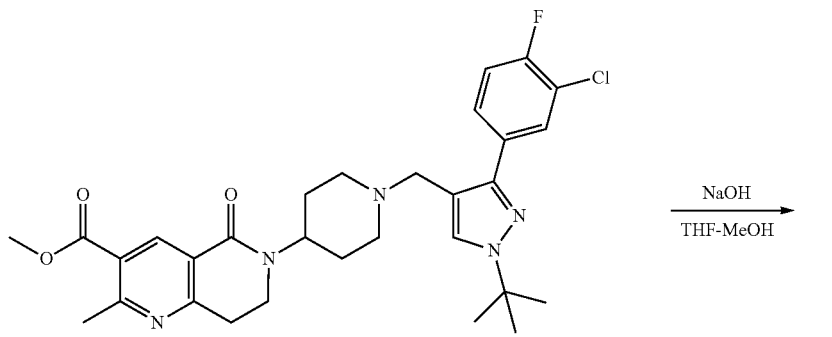
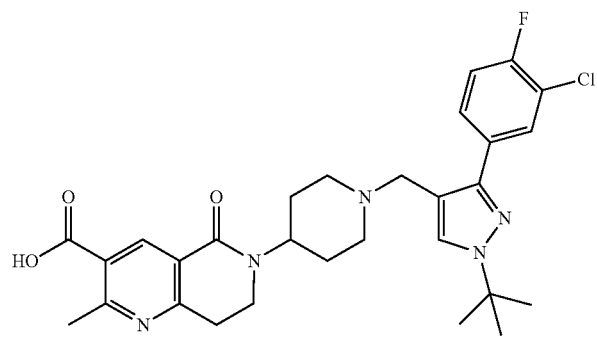

The title compound was obtained in the same way as in steps K and L of Example 1 using methyl 6-(1-(tert-butoxycarbonyl)piperidin-4-yl)-2-methyl-5-oxo-5,6,7,8-tetrahydro-1,6-naphthyridine-3-carboxylate and 1-tert-butyl-3-(3-chloro-4-fluorophenyl)-1H-pyrazole-4-carbaldehyde.

Example 14

6-(1-((2-Cyclopropyl-6-ethoxy-2',4'-difluorobiphenyl-4-yl)methyl)piperidin-4-yl)-2-methyl-5-oxo-5,6,7,8-tetrahydro-1,6-naphthyridine-3-carboxylic acid

[Formula 31]

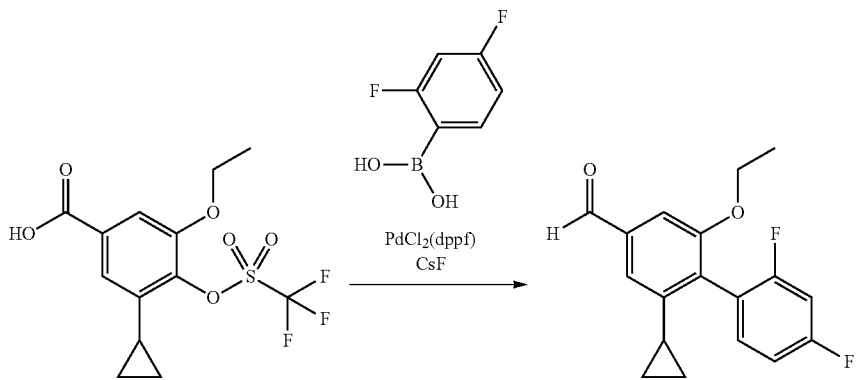

14A
(Same as Example 8D)

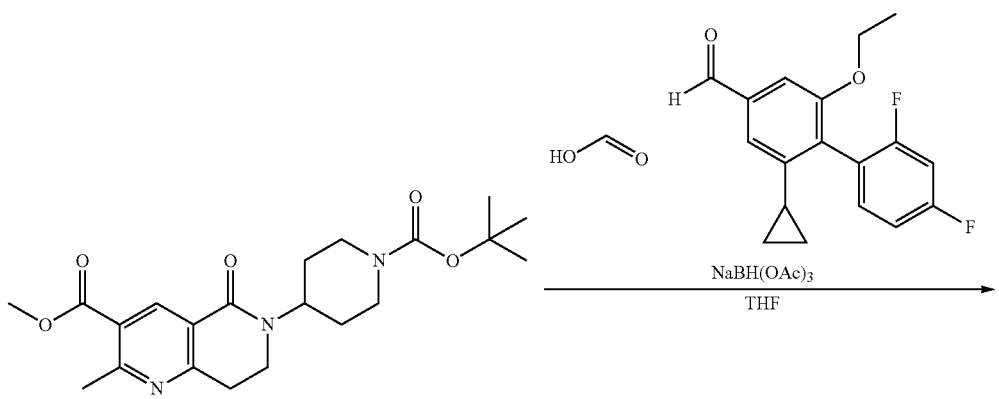

14B
(Same as Example 1K and 1L)

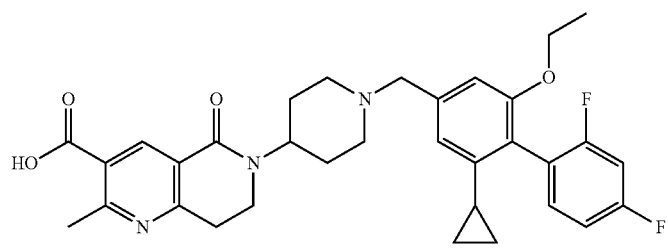

101

A) 2-Cyclopropyl-6-ethoxy-2',4'-difluorobiphenyl-4-carbaldehyde

The title compound was obtained in the same way as in step D of Example 8 using 2-cyclopropyl-6-ethoxy-4-formylphenyl trifluoromethanesulfonate and (2,4-difluorophenyl)boronic acid.

$^1$H NMR (300 MHz, CDCl$_3$) δ 0.54-0.92 (4H, m), 1.25 (3H, t, J=6.9 Hz), 1.58-1.71 (1H, m), 4.06 (2H, q, J=7.0 Hz), 6.83-7.01 (2H, m), 7.07 (1H, d, J=1.1 Hz), 7.18-7.25 (1H, m), 7.27 (1H, d, J=1.2 Hz), 9.95 (1H, s).

102

B) 6-(1-((2-Cyclopropyl-6-ethoxy-2',4'-difluorobiphenyl-4-yl)methyl)piperidin-4-yl)-2-methyl-5-oxo-5,6,7,8-tetrahydro-1,6-naphthyridine-3-carboxylic acid The title compound was obtained in the same way as in steps K and L of Example 1 using methyl 6-(1-(tert-butoxycarbonyl)piperidin-4-yl)-2-methyl-5-oxo-5,6,7,8-tetrahydro-1,6-naphthyridine-3-carboxylate and 2-cyclopropyl-6-ethoxy-2',4'-difluorobiphenyl-4-carbaldehyde.

Example 15

6-(1-((2-Chloro-6-cyclopropyl-4'-fluoro-3-isopropoxybiphenyl-4-yl)methyl)piperidin-4-yl)-2-methyl-5-oxo-5,6,7,8-tetrahydro-1,6-naphthyridine-3-carboxylic acid

[Formula 32]

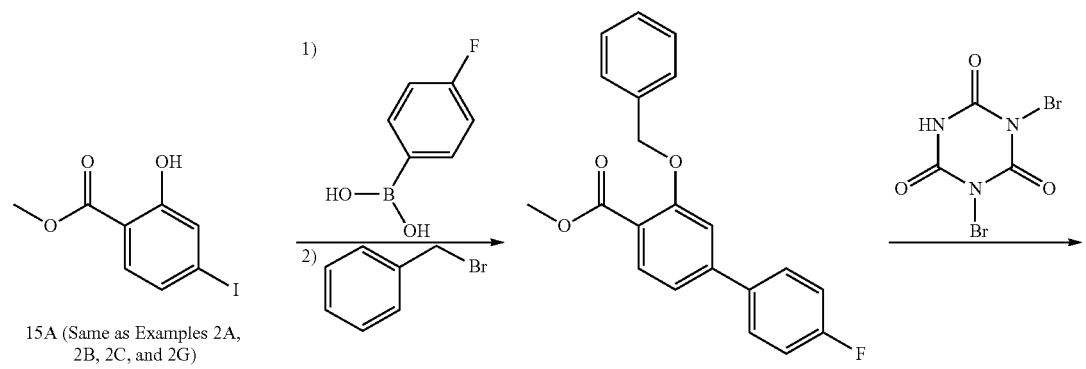

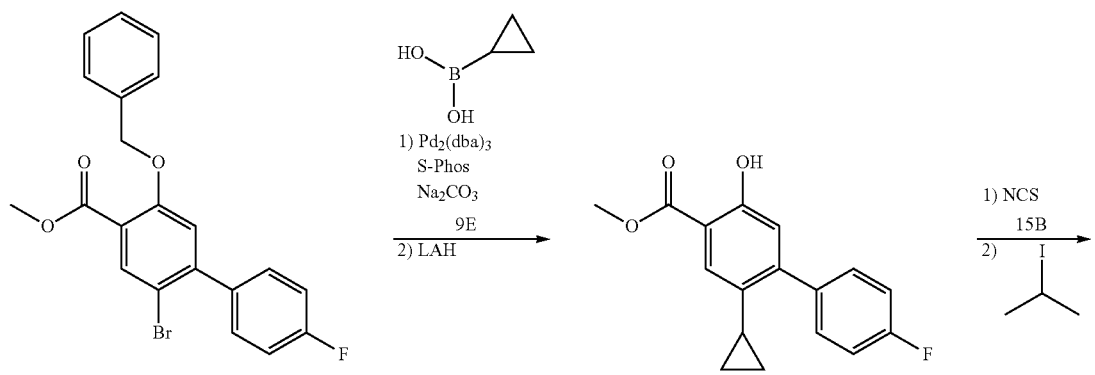

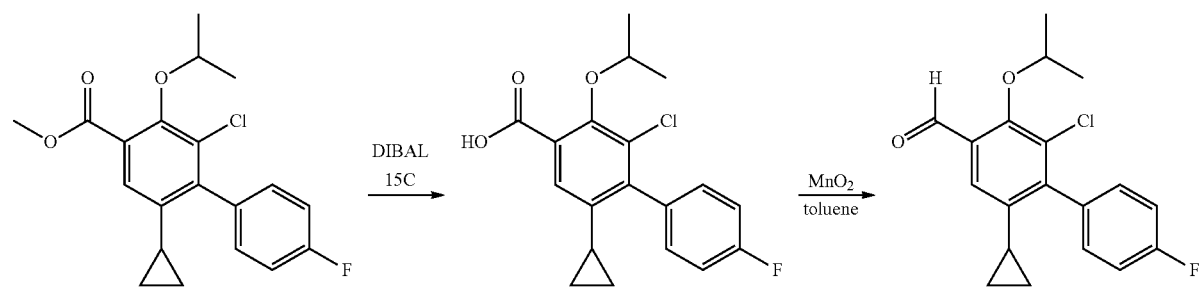

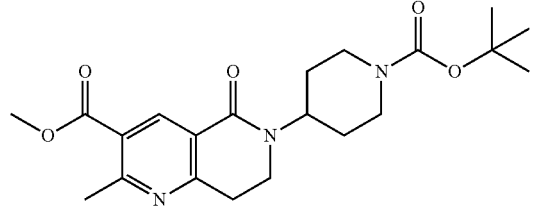

15E (Same as Examples 1K and 1L)

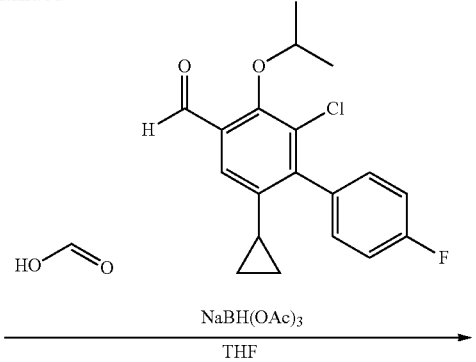

NaBH(OAc)₃ / THF

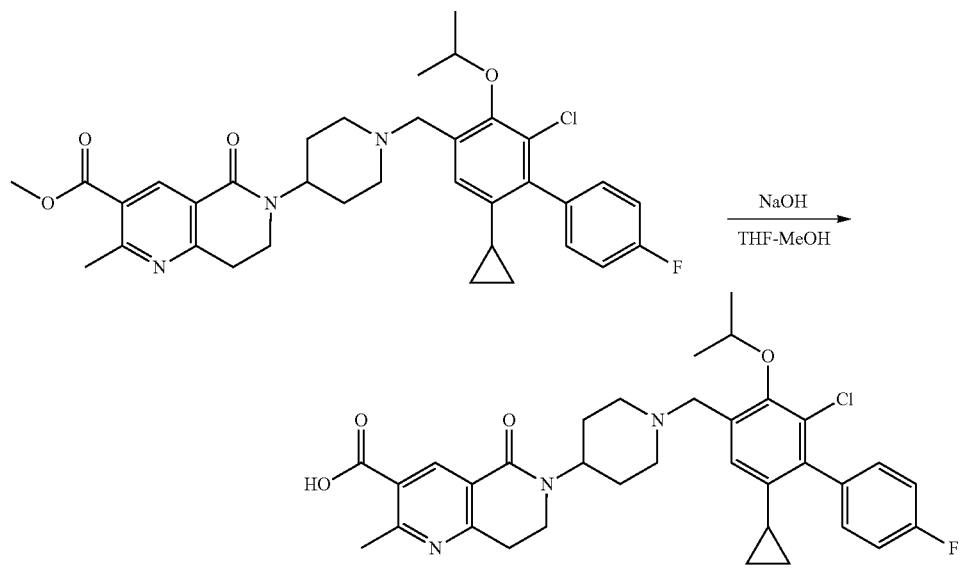

NaOH / THF-MeOH

A) Methyl 2-cyclopropyl-4'-fluoro-5-hydroxybiphenyl-4-carboxylate

The title compound was obtained in the same way as in steps A, B, C, and G of Example 2 using methyl 2-hydroxy-4-iodobenzoate and benzyl bromide.

¹H NMR (300 MHz, CDCl₃) δ 0.53-0.64 (2H, m), 0.73-0.85 (2H, m), 1.65-1.78 (1H, m), 3.96 (3H, s), 6.86 (1H, s), 7.11 (2H, t, J=8.7 Hz), 7.35-7.44 (2H, m), 7.46 (1H, s), 10.57 (1H, s).

B) Methyl 2-chloro-6-cyclopropyl-4'-fluoro-3-isopropoxybiphenyl-4-carboxylate N-Chlorosuccinimide (2.17 g) was added to a mixture of methyl 2-cyclopropyl-4'-fluoro-5-hydroxybiphenyl-4-carboxylate (3.88 g) and DMF (40 mL), and the resultant mixture was stirred at room temperature for 2 hours. Water was added to the reaction mixture, followed by extraction with ethyl acetate. The obtained organic layer was washed with water and saturated saline and dried over anhydrous magnesium sulfate, and then, the solvent was distilled off under reduced pressure. Potassium carbonate (5.62 g) and 2-iodopropane (4.06 mL) were added to a mixture of the residue and DMF (40 mL), and the resultant mixture was stirred at 80° C. for 1 hour. The reaction mixture was allowed to cool to room temperature, and then, water was added thereto, followed by extraction with ethyl acetate. The obtained organic layer was washed with saturated saline and dried over anhydrous magnesium sulfate, and then, the solvent was distilled off under reduced pressure. The obtained residue was purified by silica gel column chromatography (NH, hexane/ethyl acetate) to obtain the title compound (3.45 g).

¹H NMR (300 MHz, CDCl₃) δ 0.58-0.68 (2H, m), 0.70-0.80 (2H, m), 1.32 (6H, d, J=6.1 Hz), 1.41-1.54 (1H, m), 3.92 (3H, s), 4.28-4.47 (1H, m), 7.09-7.25 (5H, m)

C) (2-Chloro-6-cyclopropyl-4'-fluoro-3-isopropoxybiphenyl-4-yl)methanol

Diisobutyl aluminum hydride (1.5 M toluene solution, 19.0 mL) was added at 0° C. to a mixture of methyl 2-chloro-6-cyclopropyl-4'-fluoro-3-isopropoxybiphenyl-4-carboxylate (3.45 g) and THF (40 mL), and the resultant mixture was stirred at the same temperature as above for 20 minutes in a nitrogen atmosphere. Sodium sulfate decahydrate was added to the reaction mixture, and the mixture was stirred at room temperature for 1 hour. The reaction mixture was filtered, and then, the solvent in the filtrate was distilled off under reduced pressure. The obtained residue was purified by silica gel column chromatography (hexane/ethyl acetate) to obtain the title compound (2.82 g).

¹H NMR (300 MHz, CDCl₃) δ 0.58-0.65 (2H, m), 0.68-0.77 (2H, m), 1.35 (6H, d, J=6.1 Hz), 1.41-1.53 (1H, m), 2.25 (1H, t, J=6.3 Hz), 4.48-4.63 (1H, m), 4.73 (2H, d, J=6.2 Hz), 6.85 (1H, s), 7.06-7.25 (4H, m).

D) 2-Chloro-6-cyclopropyl-4'-fluoro-3-isopropoxybiphenyl-4-carbaldehyde

The title compound was obtained in the same way as in step D of Example 2 using (2-chloro-6-cyclopropyl-4'-fluoro-3-isopropoxybiphenyl-4-yl)methanol.

¹H NMR (300 MHz, CDCl₃) δ 0.63-0.70 (2H, m), 0.71-0.82 (2H, m), 1.39 (6H, d, J=6.1 Hz), 1.47 (1H, t, J=8.4 Hz), 4.45-4.64 (1H, m), 7.12-7.25 (4H, m), 7.34 (1H, s), 10.38 (1H, s).

E) 6-(1-((2-Chloro-6-cyclopropyl-4'-fluoro-3-isopropoxybiphenyl-4-yl)methyl)piperidin-4-yl)-2-methyl-5-oxo-5,6,7,8-tetrahydro-1,6-naphthyridine-3-carboxylic acid The title compound was obtained in the same way as in steps K and L of Example 1 using methyl 6-(1-(tert-butoxycarbonyl)piperidin-4-yl)-2-methyl-5-oxo-5,6,7,8-tetrahydro-1,6-naphthyridine-3-carboxylate and 2-chloro-6-cyclopropyl-4'-fluoro-3-isopropoxybiphenyl-4-carbaldehyde.

Example 16

6-(1-((2-Cyclopropyl-2',4'-difluoro-5-isopropoxybiphenyl-4-yl)methyl)piperidin-4-yl)-2-methyl-5-oxo-5,6,7,8-tetrahydro-1,6-naphthyridine-3-carboxylic acid

[Formula 33]

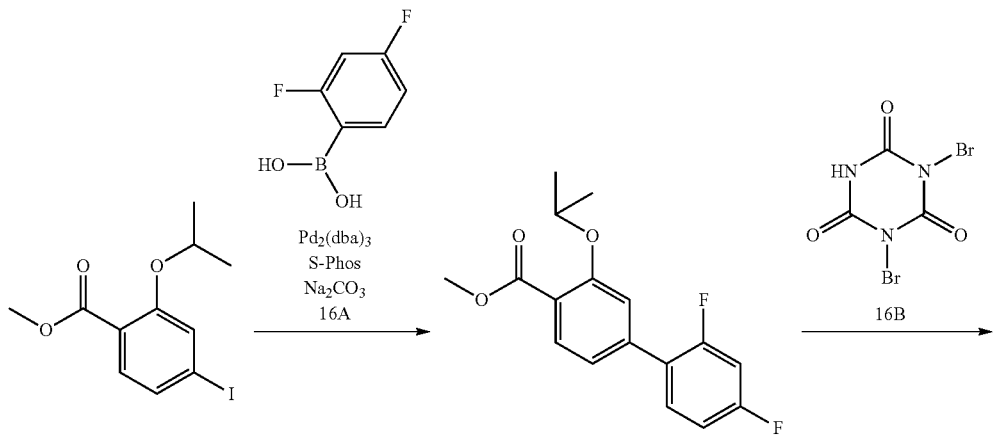

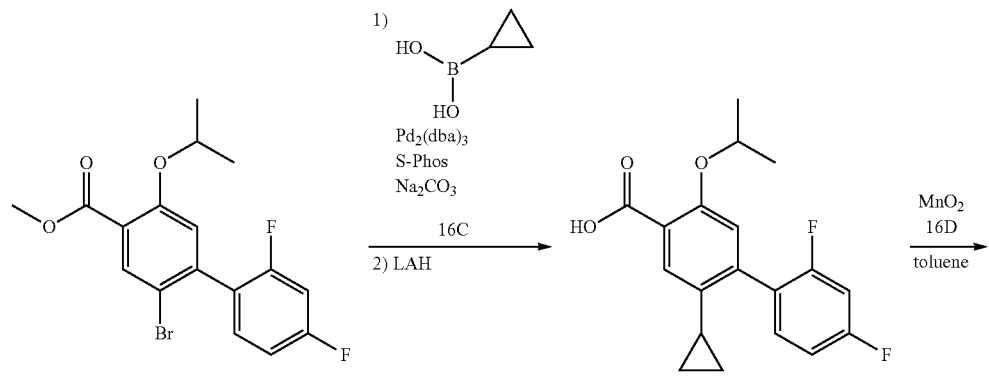

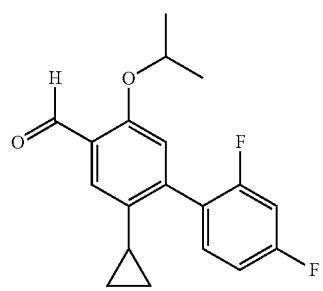

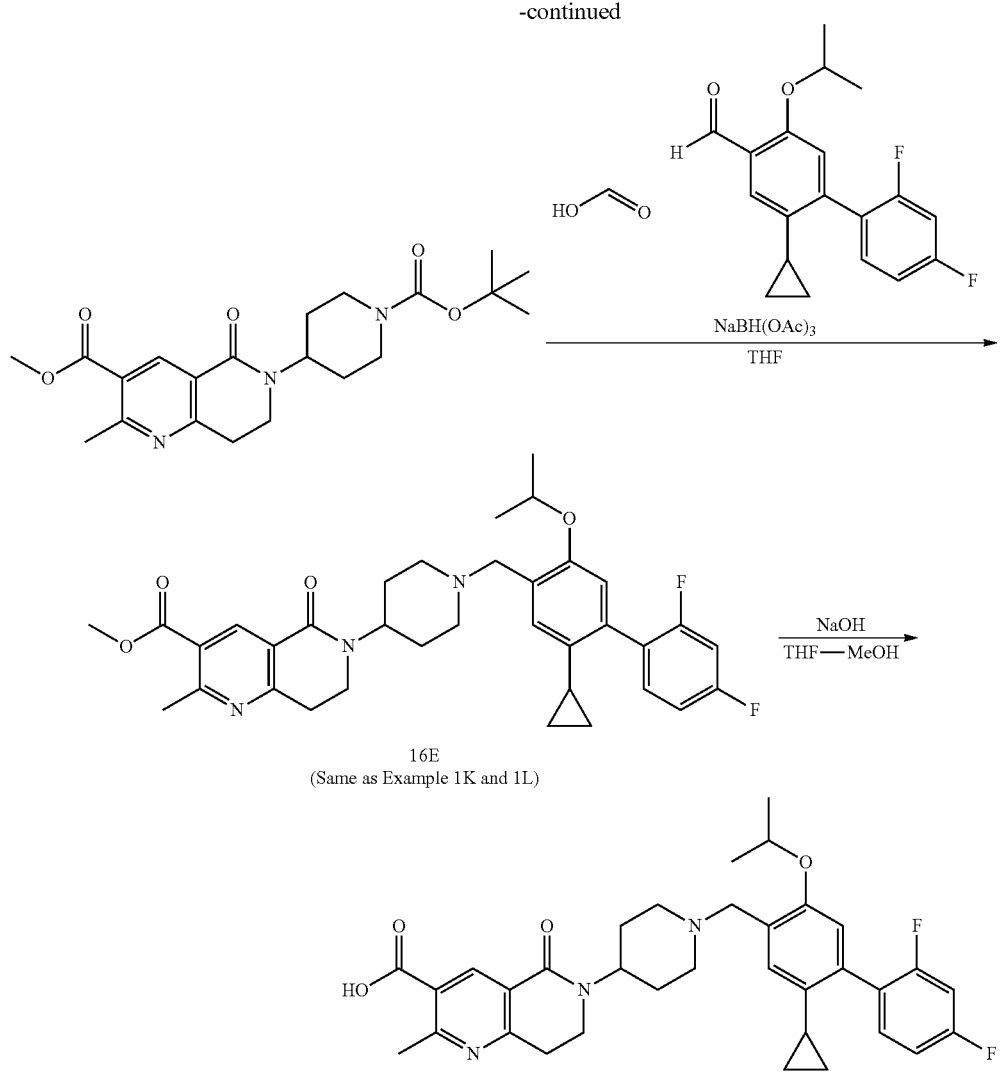

16E
(Same as Example 1K and 1L)

A) Methyl 2',4'-difluoro-3-isopropoxybiphenyl-4-carboxylate

A mixture of methyl 4-iodo-2-isopropoxybenzoate (4.10 g), (2,4-difluorophenyl)boronic acid (4.04 g), dicyclohexyl (2',6'-dimethoxybiphenyl-2-yl)phosphine (0.789 g), a 2 M aqueous sodium carbonate solution (19.2 mL), tris(dibenzylideneacetone)dipalladium(0) (0.821 g), and toluene (50 mL) was stirred at 100° C. for 2 hours in an argon atmosphere. The reaction mixture was allowed to cool to room temperature. Then, the organic layer was separated and passed through a short silica gel (NH) column, and the solvent was distilled off under reduced pressure. The obtained residue was purified by silica gel column chromatography (hexane/ethyl acetate) to obtain the title compound (3.90 g).

$^1$H NMR (300 MHz, CDCl$_3$) δ 1.40 (6H, d, J=6.0 Hz), 3.90 (3H, s), 4.52-4.70 (1H, m), 6.83-7.01 (2H, m), 7.04-7.15 (2H, m), 7.33-7.49 (1H, m, J=6.4 Hz), 7.83 (1H, d, J=8.0 Hz).

B) Methyl 2-bromo-2',4'-difluoro-5-isopropoxybiphenyl-4-carboxylate

Dibromoisocyanuric acid (2.19 g) was added to a mixture of methyl 2',4'-difluoro-3-isopropoxybiphenyl-4-carboxylate (3.90 g) and DMF (40 mL), and the resultant mixture was stirred at room temperature for 3 hours. Water was added to the reaction mixture, followed by extraction with ethyl acetate. The obtained organic layer was washed with saturated saline and dried over anhydrous magnesium sulfate, and then, the solvent was distilled off under reduced pressure. The obtained residue was purified by silica gel column chromatography (hexane/ethyl acetate) to obtain the title compound (4.90 g).

$^1$H NMR (300 MHz, CDCl$_3$) δ 1.37 (6H, d, J=6.0 Hz), 3.90 (3H, s), 4.41-4.63 (1H, m), 6.85-7.02 (3H, m), 7.17-7.33 (1H, m), 8.04 (1H, s).

C) (2-Cyclopropyl-2',4'-difluoro-5-isopropoxybiphenyl-4-yl)methanol

A mixture of methyl 2-bromo-2',4'-difluoro-5-isopropoxybiphenyl-4-carboxylate (4.90 g), cyclopropylboronic acid (3.28 g), dicyclohexyl(2',6'-dimethoxybiphenyl-2-yl)phosphine (0.783 g), a 2 M aqueous sodium carbonate solution (30.8 mL), tris(dibenzylideneacetone)dipalladium(0) (0.815 g), and toluene (50 mL) was stirred overnight at 100° C. in an argon atmosphere. The reaction mixture was allowed to cool to room temperature. Then, the organic layer was separated, washed with saturated saline, and passed through a short silica gel (NH) column, and the solvent was distilled off under reduced pressure. The obtained residue was purified by silica gel column chromatography (hexane/ethyl acetate). A THF (50 mL) solution of this purified product was added to a THF (50 mL) suspension of lithium aluminum hydride (0.474 g) under ice cooling in a nitrogen atmosphere. After stirring at the same temperature as above for 30 minutes, water (0.5 mL) and a 15% aqueous sodium hydroxide solution (0.5 mL) were added thereto, and the mixture was stirred for 5 minutes. Water (1.5 mL) was further added to the reaction mixture, and the mixture was stirred for 30 minutes and then filtered. The filtrate was concentrated under reduced pressure. The obtained residue was purified by silica gel column chromatography (hexane/ethyl acetate) to obtain the title compound (3.97 g).

$^1$H NMR (300 MHz, CDCl$_3$) δ 0.48-0.60 (2H, m), 0.66-0.79 (2H, m), 1.35 (6H, d, J=6.0 Hz), 1.59-1.72 (1H, m), 2.45 (1H, t, J=6.5 Hz), 4.47-4.63 (1H, m), 4.67 (2H, d, J=6.4 Hz), 6.71 (1H, s), 6.86-6.99 (3H, m), 7.19-7.36 (1H, m)

D) 2-Cyclopropyl-2',4'-difluoro-5-isopropoxybiphenyl-4-carbaldehyde

Manganese dioxide (10.8 g) was added to a toluene (30 mL) solution of (2-cyclopropyl-2',4'-difluoro-5-isopropoxybiphenyl-4-yl)methanol (3.97 g), and the mixture was stirred at 60° C. for 1 hour in a nitrogen atmosphere. The reaction mixture was filtered, and then, the solvent was distilled off under reduced pressure. The obtained residue was purified by silica gel column chromatography (hexane/ethyl acetate) to obtain the title compound (3.53 g).

$^1$H NMR (300 MHz, CDCl$_3$) δ 0.56-0.66 (2H, m), 0.70-0.80 (2H, m), 1.39 (6H, d, J=6.1 Hz), 1.58-1.70 (1H, m), 4.52-4.74 (1H, m), 6.82 (1H, s), 6.87-7.04 (2H, m), 7.28-7.35 (1H, m), 7.48 (1H, s), 10.47 (1H, s).

E) 6-(1-((2-Cyclopropyl-2',4'-difluoro-5-isopropoxy-biphenyl-4-yl)methyl)piperidin-4-yl)-2-methyl-5-oxo-5,6,7,8-tetrahydro-1,6-naphthyridine-3-carboxylic acid The title compound was obtained in the same way as in steps K and L of Example 1 using methyl 6-(1-(tert-butoxycarbonyl)piperidin-4-yl)-2-methyl-5-oxo-5,6,7,8-tetrahydro-1,6-naphthyridine-3-carboxylate and 2-cyclopropyl-2',4'-difluoro-5-isopropoxybiphenyl-4-carbaldehyde.

Example 17

6-(1-((2-Cyclopropyl-4'-fluoro-6-isopropoxybiphenyl-4-yl)methyl)piperidin-4-yl)-2-methyl-5-oxo-5,6,7,8-tetrahydro-1,6-naphthyridine-3-carboxylic acid

[Formula 34]

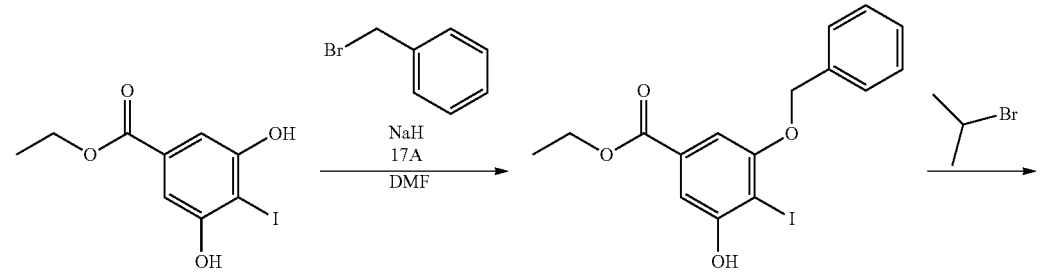

17B (Same as Examples 7A, 1B, 2G, 8C, 1D, and 1E)

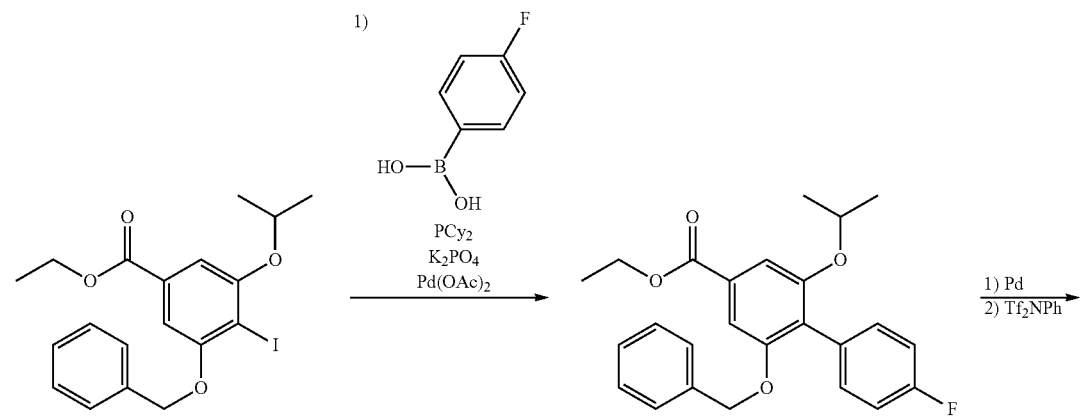

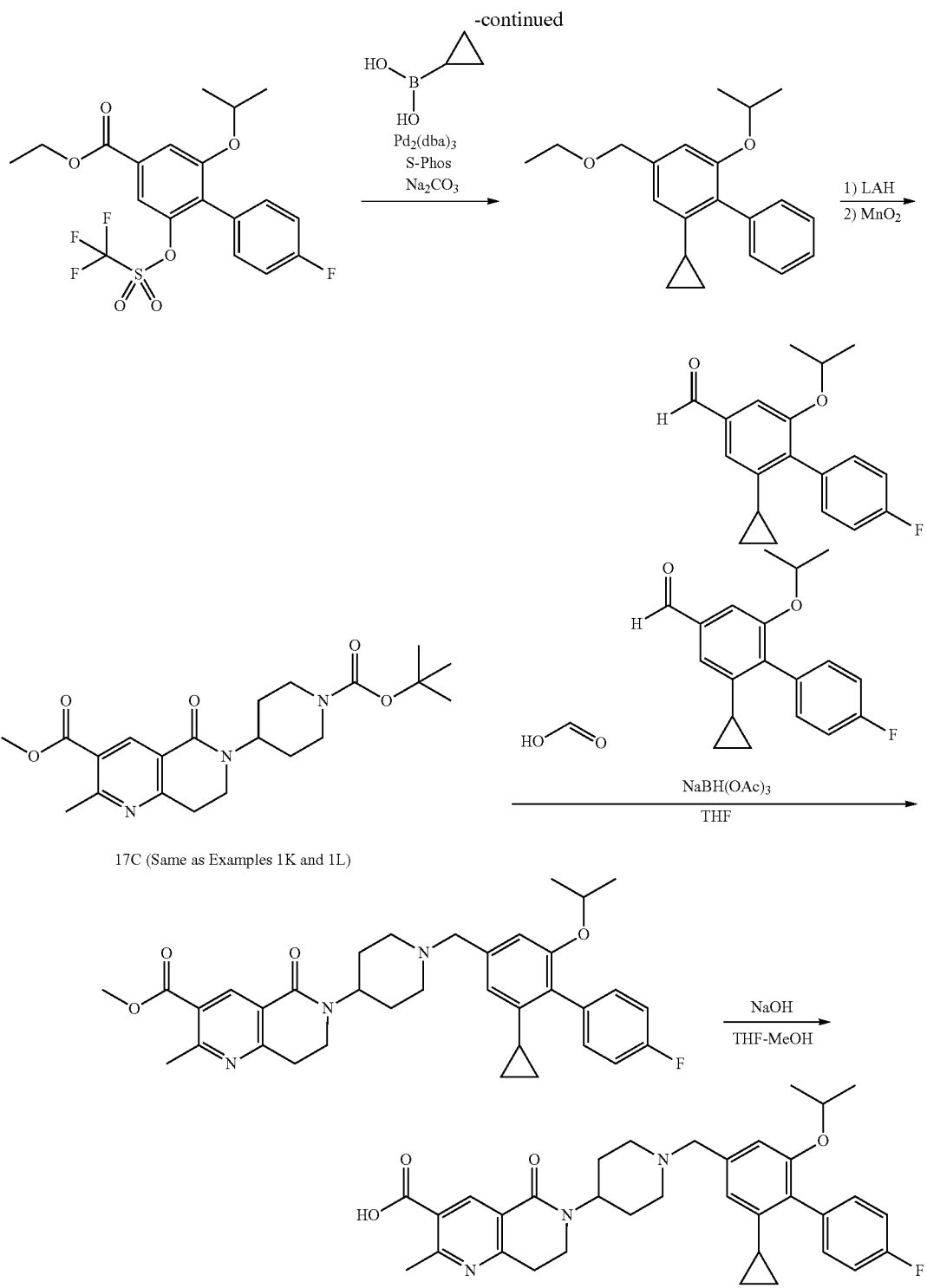

A) Ethyl 3-(benzyloxy)-5-hydroxy-4-iodobenzoate

Sodium hydride (60% oil, 1.33 g) was added to a mixture of ethyl 3,5-dihydroxy-4-iodobenzoate (5.00 g) and DMF (50 mL), and the resultant mixture was stirred at 0° C. for 30 minutes in a nitrogen atmosphere. Benzyl bromide (2.78 mL) was added to the reaction mixture, and the mixture was stirred at room temperature for 2 hours. Water was added to the reaction mixture, followed by extraction with ethyl acetate. The obtained organic layer was washed with saturated saline and dried over anhydrous magnesium sulfate, and then, the solvent was distilled off under reduced pressure. The obtained residue was purified by silica gel column chromatography (hexane/ethyl acetate) to obtain the title compound (2.94 g).

$^1$H NMR (300 MHz, CDCl$_3$) δ 1.26 (3H, t, J=7.2 Hz), 4.37 (2H, q, J=7.2 Hz), 5.20 (2H, s), 7.12 (1H, d, J=1.6 Hz), 7.31-7.45 (4H, m), 7.47-7.55 (2H, m).

113

B) 2-Cyclopropyl-4'-fluoro-6-isopropoxybiphenyl-4-carbaldehyde

The title compound was obtained in the same way as in step A of Example 7, step B of Example 1, step G of Example 2, step C of Example 8, and steps D and E of Example 1 using ethyl 3-(benzyloxy)-5-hydroxy-4-iodobenzoate.

$^1$H NMR (300 MHz, CDCl$_3$) δ 0.66-0.74 (2H, m), 0.79-0.92 (2H, m), 1.18 (6H, d, J=6.0 Hz), 1.64 (1H, tt, J=8.4, 5.3 Hz), 4.43-4.59 (1H, m), 7.02 (1H, d, J=1.1 Hz), 7.06-7.16 (2H, m), 7.20-7.31 (3H, m), 9.93 (1H, s).

114

C) 6-(1-((2-Cyclopropyl-4'-fluoro-6-isopropoxybiphenyl-4-yl)methyl)piperidin-4-yl)-2-methyl-5-oxo-5,6,7,8-tetrahydro-1,6-naphthyridine-3-carboxylic acid The title compound was obtained in the same way as in steps K and L of Example 1 using methyl 6-(1-(tert-butoxycarbonyl)piperidin-4-yl)-2-methyl-5-oxo-5,6,7,8-tetrahydro-1,6-naphthyridine-3-carboxylate and 2-cyclopropyl-4'-fluoro-6-isopropoxybiphenyl-4-carbaldehyde.

Example 18

6-(1-(4-Cyclobutyl-5-cyclopropyl-2-isopropoxybenzyl)piperidin-4-yl)-2-methyl-5-oxo-5,6,7,8-tetrahydro-1,6-naphthyridine-3-carboxylic acid

[Formula 35]

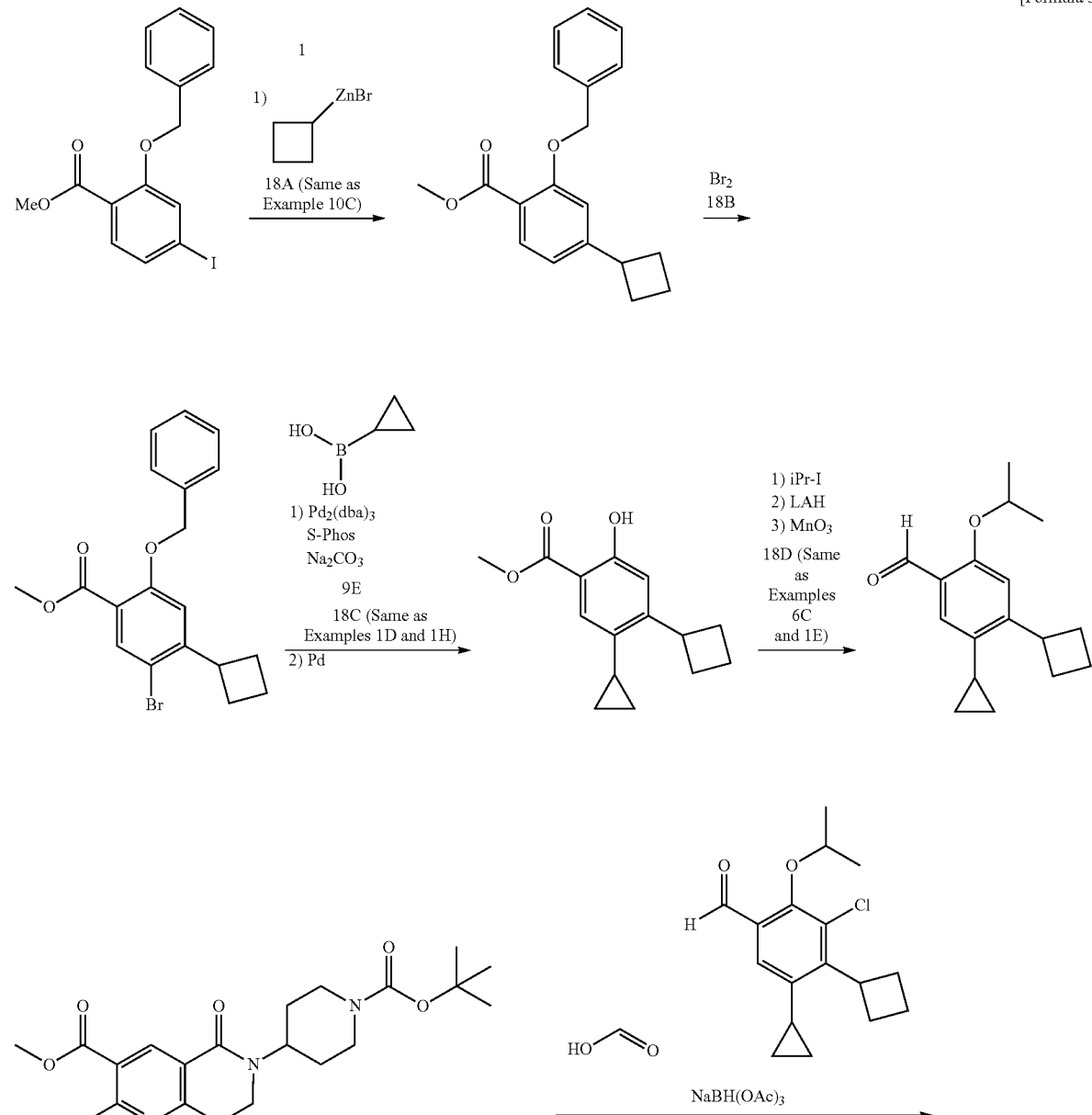

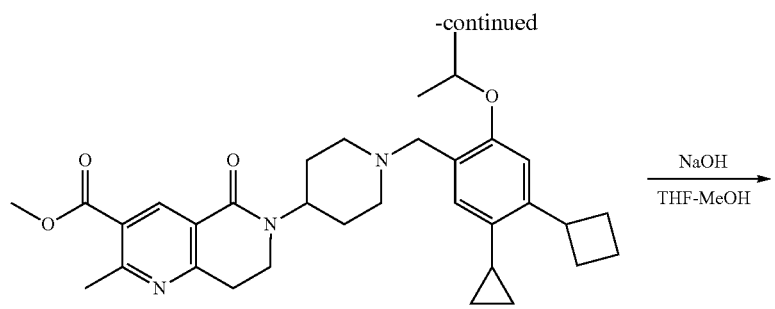

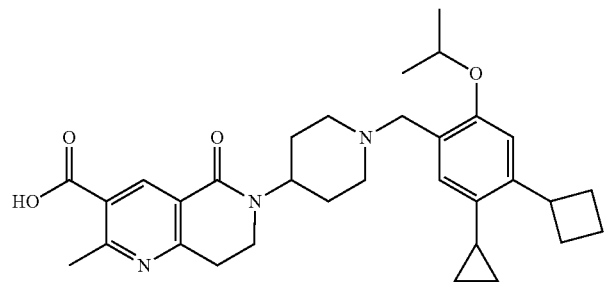

A) Methyl 2-(benzyloxy)-4-cyclobutylbenzoate

The title compound was obtained in the same way as in step C of Example 10 using methyl 2-(benzyloxy)-4-iodobenzoate.

MS (ESI+): [M+H]$^+$ 297.3.

B) Methyl 2-(benzyloxy)-5-bromo-4-cyclobutylbenzoate

Sodium bicarbonate (7.51 g) was added to a mixture of methyl 2-(benzyloxy)-4-cyclobutylbenzoate (14 g) and dichloromethane, then a dichloromethane (25 mL) solution of bromine (3.17 mL) was slowly added thereto at 10° C., and the mixture was stirred at the same temperature as above for 1 hour. A saturated aqueous solution of sodium bicarbonate was added to the reaction mixture, followed by extraction with ethyl acetate. The organic layer was washed with a saturated aqueous solution of sodium bisulfite and saturated saline and then dried over anhydrous sodium sulfate, and then, the solvent was distilled off under reduced pressure. The obtained residue was purified by silica gel column chromatography (hexane/ethyl acetate) to obtain the title compound (12.2 g).

MS (ESI+): [M+H]$^+$ 375.1.

C) Methyl 4-cyclobutyl-5-cyclopropyl-2-hydroxybenzoate

The title compound was obtained in the same way as in steps D and H of Example 1 using methyl 2-(benzyloxy)-5-bromo-4-cyclobutylbenzoate.

MS (ESI+): [M+H]$^+$ 247.2.

D) 4-Cyclobutyl-5-cyclopropyl-2-isopropoxybenzaldehyde

The title compound was obtained in the same way as in step C of Example 6 and step E of Example 1 using methyl 4-cyclobutyl-5-cyclopropyl-2-hydroxybenzoate.

$^1$H NMR (400 MHz, CDCl$_3$) δ 0.58-0.63 (2H, m), 0.84-0.88 (2H, m), 1.39 (6H, d, J=6.1 Hz), 1.71-1.77 (1H, m), 1.83-1.89 (1H, m), 2.02-2.18 (3H, m), 2.38-2.44 (2H, m), 3.91-3.96 (1H, m), 4.65-4.71 (1H, m), 6.86 (1H, s), 7.43 (1H, s), 10.38 (1H, s).

E) 6-(1-(4-Cyclobutyl-5-cyclopropyl-2-isopropoxybenzyl)piperidin-4-yl)-2-methyl-5-oxo-5,6,7,8-tetrahydro-1,6-naphthyridine-3-carboxylic acid The title compound was obtained in the same way as in steps K and L of Example 1 using methyl 6-(1-(tert-butoxycarbonyl)piperidin-4-yl)-2-methyl-5-oxo-5,6,7,8-tetrahydro-1,6-naphthyridine-3-carboxylate and 4-cyclobutyl-5-cyclopropyl-2-isopropoxybenzaldehyde.

Example 19
6-(1-((2-Cyclopropyl-3',4'-difluoro-5-isopropoxybiphenyl-4-yl)methyl)piperidin-4-yl)-2-methyl-5-oxo-5,6,7,8-tetrahydro-1,6-naphthyridine-3-carboxylic acid
[Formula 36]
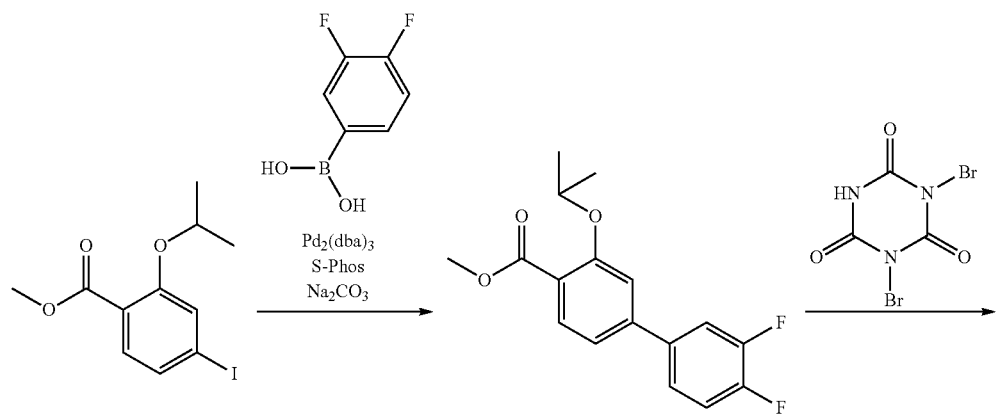
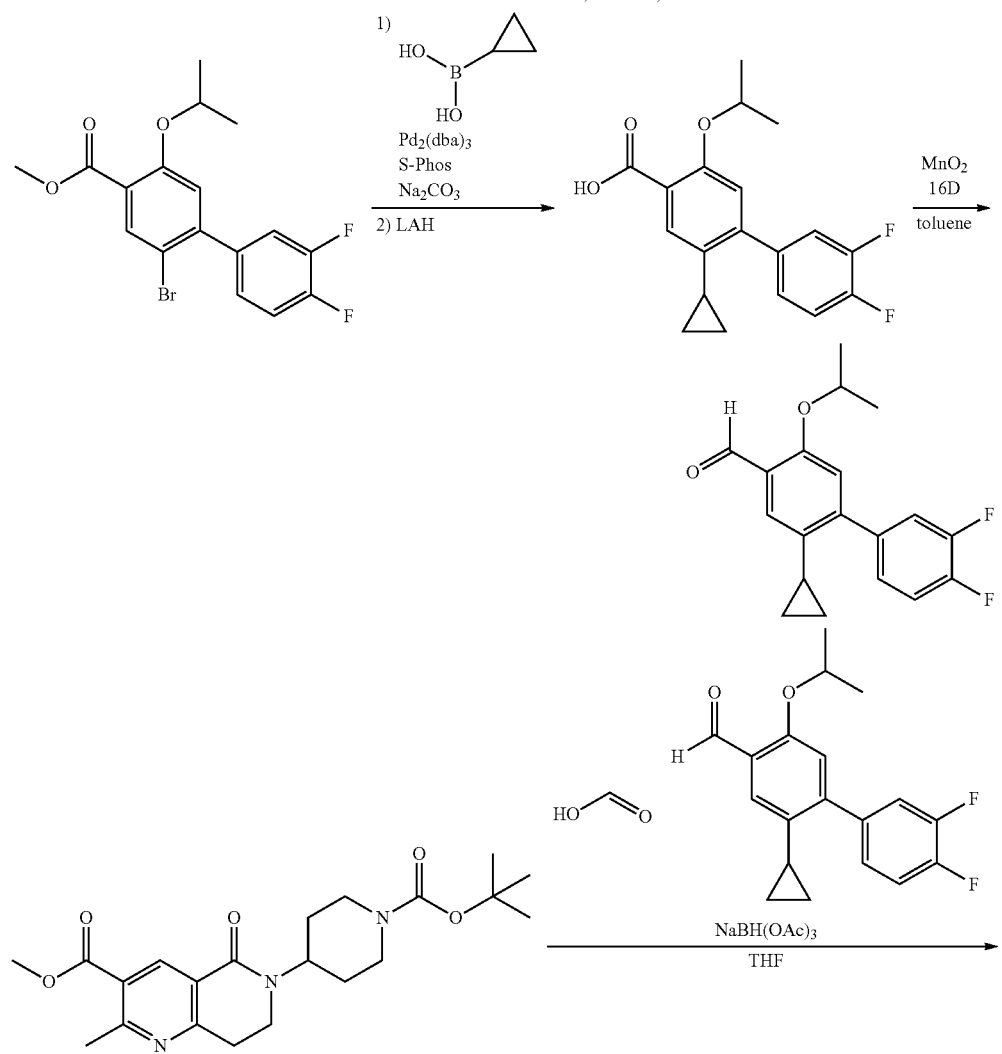

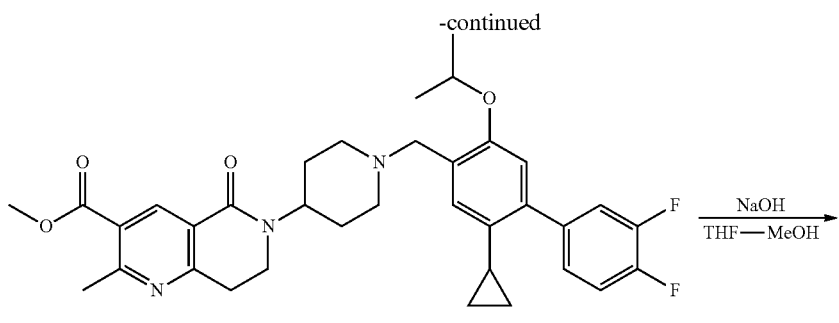

19B
(Same as Example 1K and 1L)

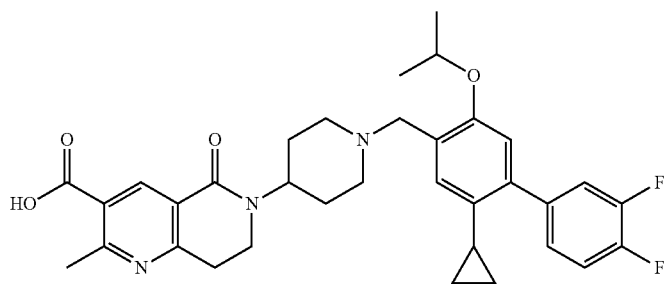 [SMILES: Cc1nc2c(cc1C(=O)O)C(=O)N(C1CCN(Cc3cc(C4CC4)c(-c4ccc(F)cc4)cc3OC(C)C)CC1)CC2]

A) 2-Cyclopropyl-3',4'-difluoro-5-isopropoxybiphenyl-4-carbaldehyde

The title compound was obtained in the same way as in steps A, B, C, and D of Example 16 using methyl 4-iodo-2-isopropoxybenzoate.

$^1$H NMR (300 MHz, CDCl$_3$) δ 0.56-0.66 (2H, m), 0.70-0.80 (2H, m), 1.39 (6H, d, J=6.1 Hz), 1.58-1.70 (1H, m), 4.52-4.74 (1H, m), 6.82 (1H, s), 6.87-7.04 (2H, m), 7.28-7.35 (1H, m), 7.48 (1H, s), 10.47 (1H, s).

B) 6-(1-((2-Cyclopropyl-3',4'-difluoro-5-isopropoxybiphenyl-4-yl)methyl)piperidin-4-yl)-2-methyl-5-oxo-5,6,7,8-tetrahydro-1,6-naphthyridine-3-carboxylic acid The title compound was obtained in the same way as in steps K and L of Example 1 using methyl 6-(1-(tert-butoxycarbonyl)piperidin-4-yl)-2-methyl-5-oxo-5,6,7,8-tetrahydro-1,6-naphthyridine-3-carboxylate and 2-cyclopropyl-3',4'-difluoro-5-isopropoxybiphenyl-4-carbaldehyde.

Example 20

6-(1-((2,6-diethoxy-4'-fluorobiphenyl-4-yl)methyl)piperidin-4-yl)-2-methyl-5-oxo-5,6,7,8-tetrahydro-1,6-naphthyridine-3-carboxylic acid

[Formula 37]

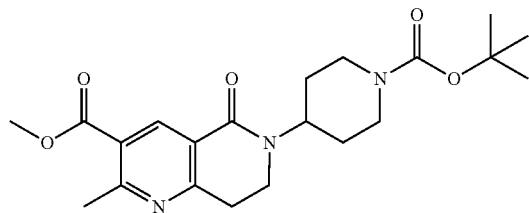

20 (Same as Examples 1K and 1L)

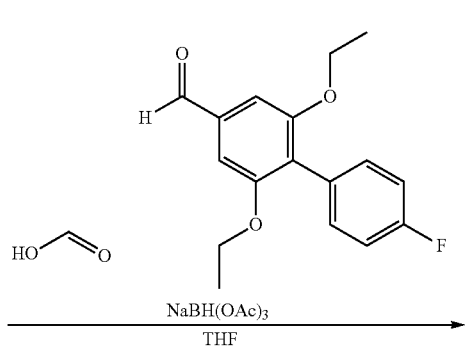

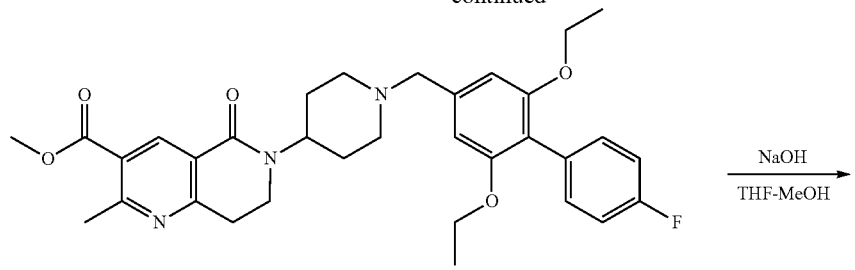
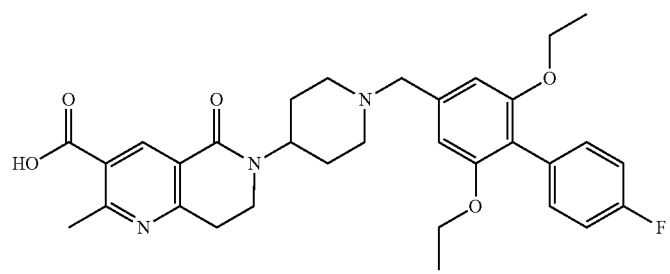
The title compound was obtained in the same way as in steps K and L of Example 1 using methyl 6-(1-(tert-butoxycarbonyl)piperidin-4-yl)-2-methyl-5-oxo-5,6,7,8-tetrahydro-1,6-naphthyridine-3-carboxylate and 2,6-diethoxy-4'-fluorobiphenyl-4-carbaldehyde.
Example 21
6-(1-(4-Cyclopentyl-5-cyclopropyl-2-isopropoxybenzyl)piperidin-4-yl)-2-methyl-5-oxo-5,6,7,8-tetrahydro-1,6-naphthyridine-3-carboxylic acid
[Formula 38]
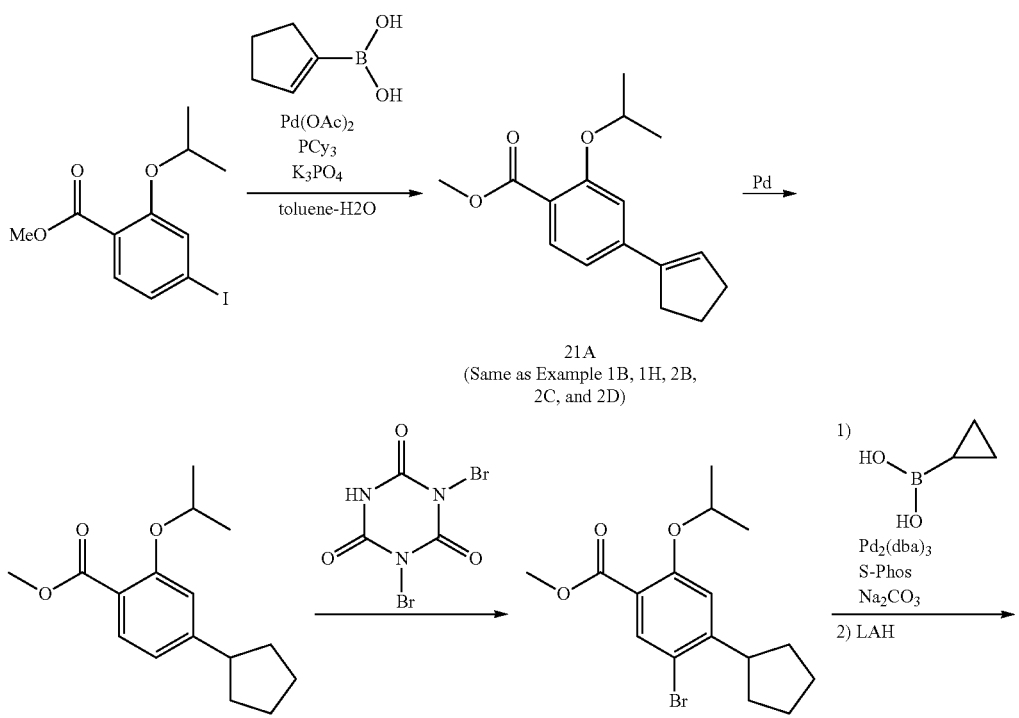

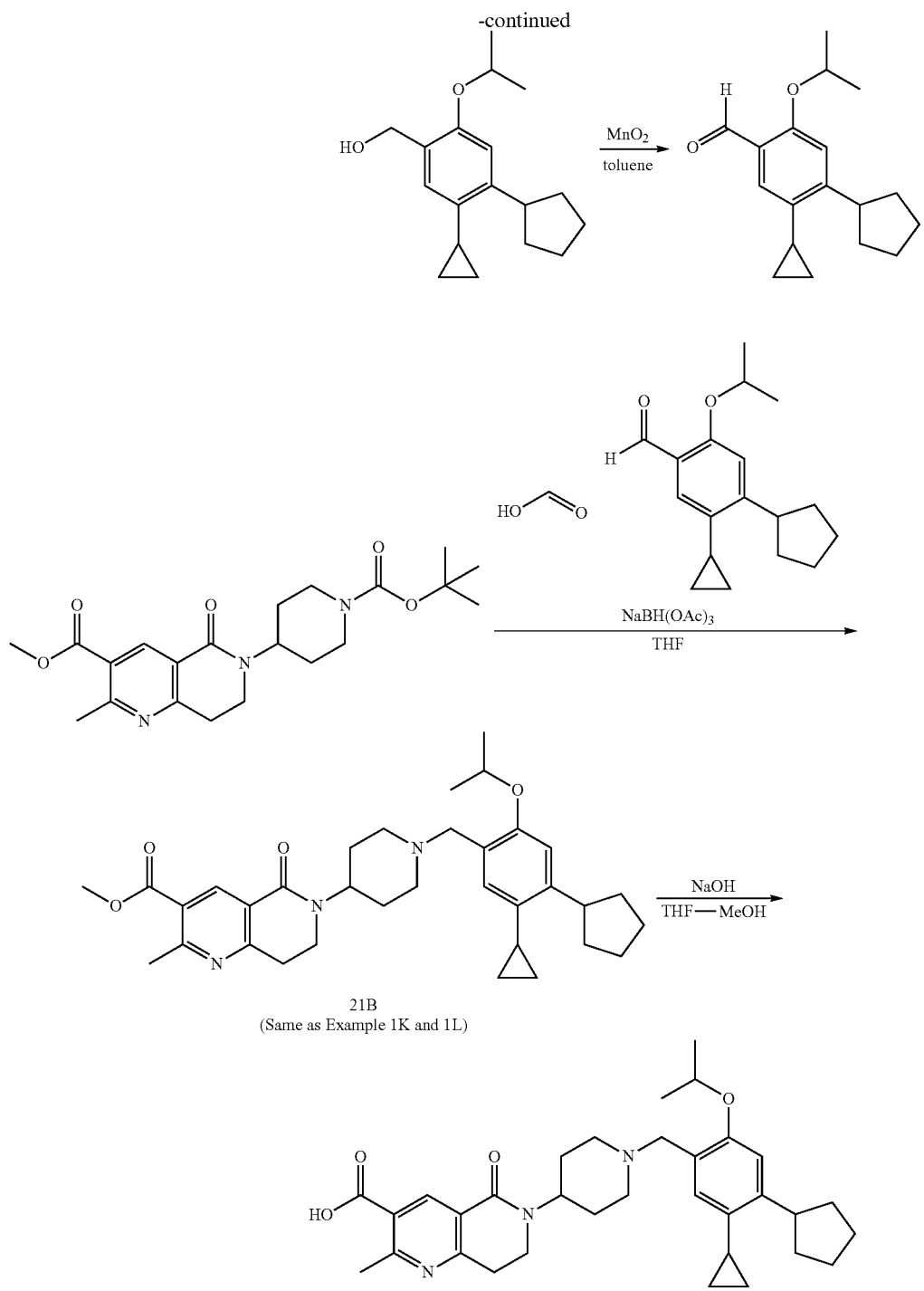

A) 4-Cyclopentyl-5-cyclopropyl-2-isopropoxybenzaldehyde

The title compound was obtained in the same way as in steps B and H of Example 1 and steps B, C, and D of Example 2 using methyl 4-iodo-2-isopropoxybenzoate and cyclopent-1-en-1-ylboronic acid.

$^1$H NMR (400 MHz, CDCl$_3$) δ 0.61-0.70 (2H, m), 0.84-0.95 (2H, m), 1.38 (6H, d, J=6.0 Hz), 1.50-1.65 (2H, m), 1.68-1.97 (5H, m), 2.05-2.19 (2H, m), 3.54-3.73 (1H, m), 4.54-4.72 (1H, m), 6.86 (1H, s), 7.49 (1H, s), 10.38 (1H, s).

B) 6-(1-(4-Cyclopentyl-5-cyclopropyl-2-isopropoxybenzyl)piperidin-4-yl)-2-methyl-5-oxo-5,6,7,8-tetrahydro-1,6-naphthyridine-3-carboxylic acid The title compound was obtained in the same way as in steps K and L of Example 1 using methyl 6-(1-(tert-butoxycarbonyl)piperidin-4-yl)-2-methyl-5-oxo-5,6,7,8-tetrahydro-1,6-naphthyridine-3-carboxylate and 4-cyclopentyl-5-cyclopropyl-2-isopropoxybenzaldehyde.

Example 22
6-(1-((2-Ethoxy-4'-fluoro-6-isopropoxybiphenyl-4-yl)methyl)piperidin-4-yl)-2-methyl-5-oxo-5,6,7,8-tetrahydro-1,6-naphthyridine-3-carboxylic acid
A) 2-Ethoxy-4'-fluoro-6-isopropoxybiphenyl-4-carbaldehyde
The title compound was obtained in the same way as in step C of Example 6 and step E of Example 1 using ethyl 2-ethoxy-
[Formula 39]
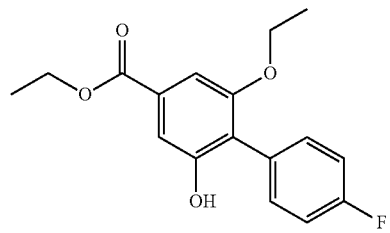
22A (Same as Examples 6C and 1E)
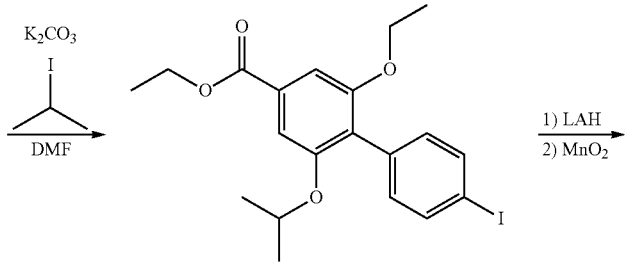
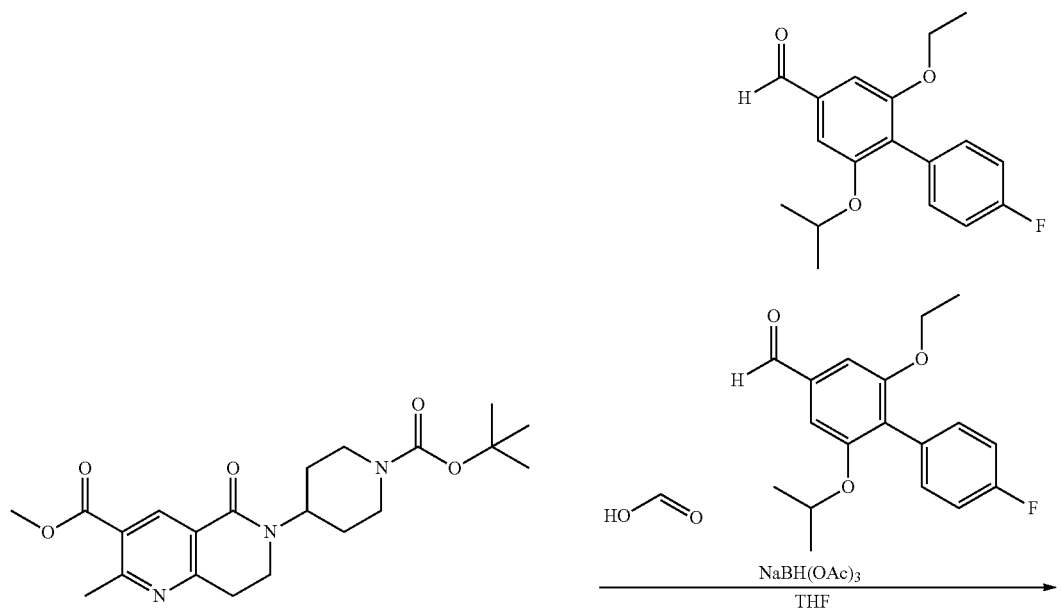
22B (Same as Examples 1K and 1L)
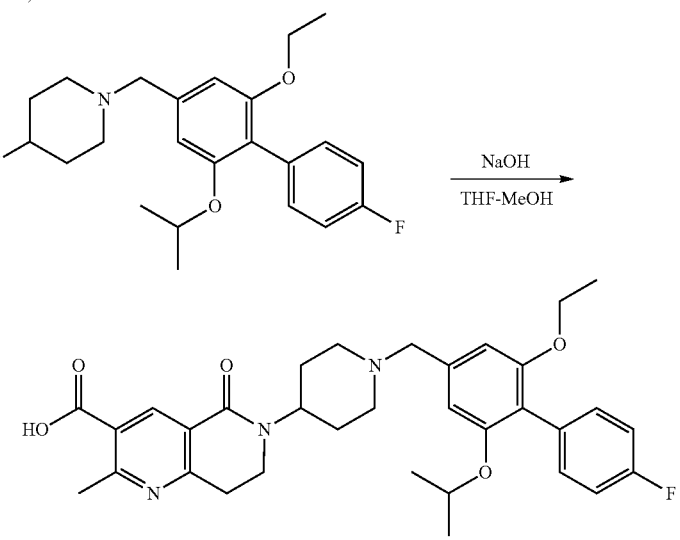

4'-fluoro-6-hydroxybiphenyl-4-carboxylate. ¹H NMR (300 MHz, CDCl₃) δ 1.21 (6H, d, J=6.0 Hz), 1.29 (3H, t, J=7.0 Hz), 4.05 (2H, q, J=7.0 Hz), 4.39-4.62 (1H, m), 6.97-7.18 (4H, m), 7.29-7.39 (2H, m), 9.94 (1H, s).

B) 6-(1-((2-Ethoxy-4'-fluoro-6-isopropoxybiphenyl-4-yl)methyl)piperidin-4-yl)-2-methyl-5-oxo-5,6,7,8-tetrahydro-1,6-naphthyridine-3-carboxylic acid The title compound was obtained in the same way as in steps K and L of Example 1 using methyl 6-(1-(tert-butoxycarbonyl)piperidin-4-yl)-2-methyl-5-oxo-5,6,7,8-tetrahydro-1,6-naphthyridine-3-carboxylate and 2-ethoxy-4'-fluoro-6-isopropoxybiphenyl-4-carbaldehyde.

Example 23

6-(1-((2-Ethoxy-4'-fluoro-6-propoxybiphenyl-4-yl)methyl)piperidin-4-yl)-2-methyl-5-oxo-5,6,7,8-tetrahydro-1,6-naphthyridine-3-carboxylic acid

[Formula 40]

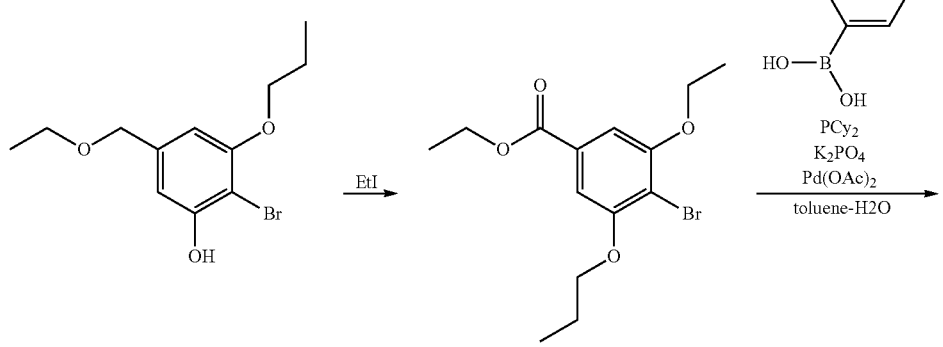

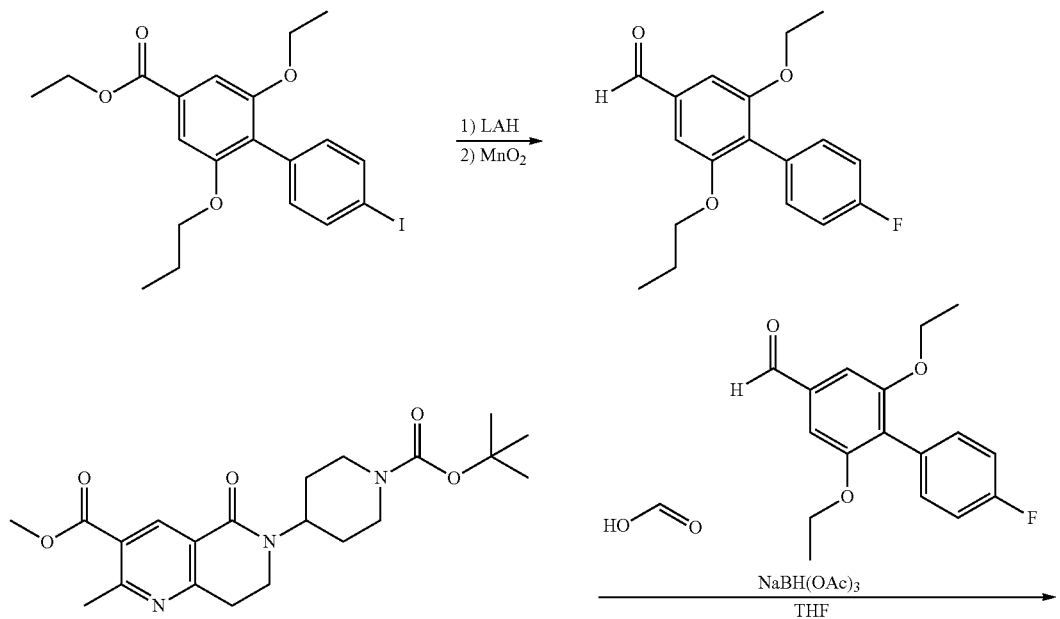

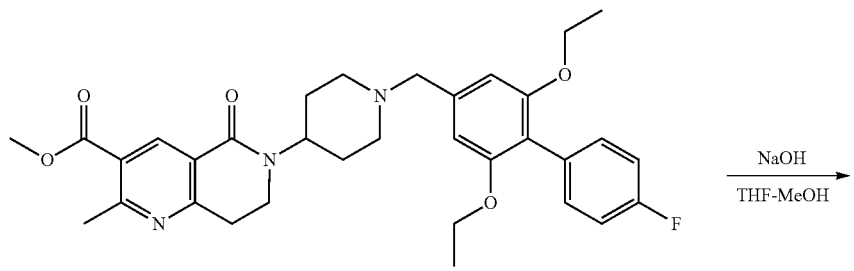

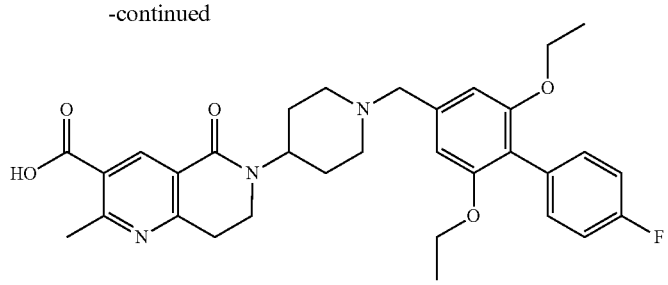

A) 2-Ethoxy-4'-fluoro-6-propoxybiphenyl-4-carbaldehyde

The title compound was obtained in the same way as in step C of Example 6 and steps B and E of Example 1 using ethyl 4-bromo-3-hydroxy-5-propoxybenzoate.

$^1$H NMR (300 MHz, CDCl$_3$) δ 0.89 (3H, t, J=7.4 Hz), 1.29 (3H, t, J=6.9 Hz), 1.59-1.78 (2H, m), 3.94 (2H, t, J=6.4 Hz), 4.06 (2H, q, J=6.9 Hz), 7.04-7.11 (2H, m), 7.12 (2H, s), 7.30-7.38 (2H, m), 9.94 (1H, s).

B) 6-(1-((2-Ethoxy-4'-fluoro-6-propoxybiphenyl-4-yl)methyl)piperidin-4-yl)-2-methyl-5-oxo-5,6,7,8-tetrahydro-1,6-naphthyridine-3-carboxylic acid The title compound was obtained in the same way as in steps K and L of Example 1 using methyl 6-(1-(tert-butoxycarbonyl)piperidin-4-yl)-2-methyl-5-oxo-5,6,7,8-tetrahydro-1,6-naphthyridine-3-carboxylate and 2-ethoxy-4'-fluoro-6-propoxybiphenyl-4-carbaldehyde.

Example 24

6-(1-(4,5-Dicyclopropyl-2-isopropoxybenzyl)piperidin-4-yl)-2-methyl-5-oxo-5,6,7,8-tetrahydro-1,6-naphthyridine-3-carboxylic acid

[Formula 41]

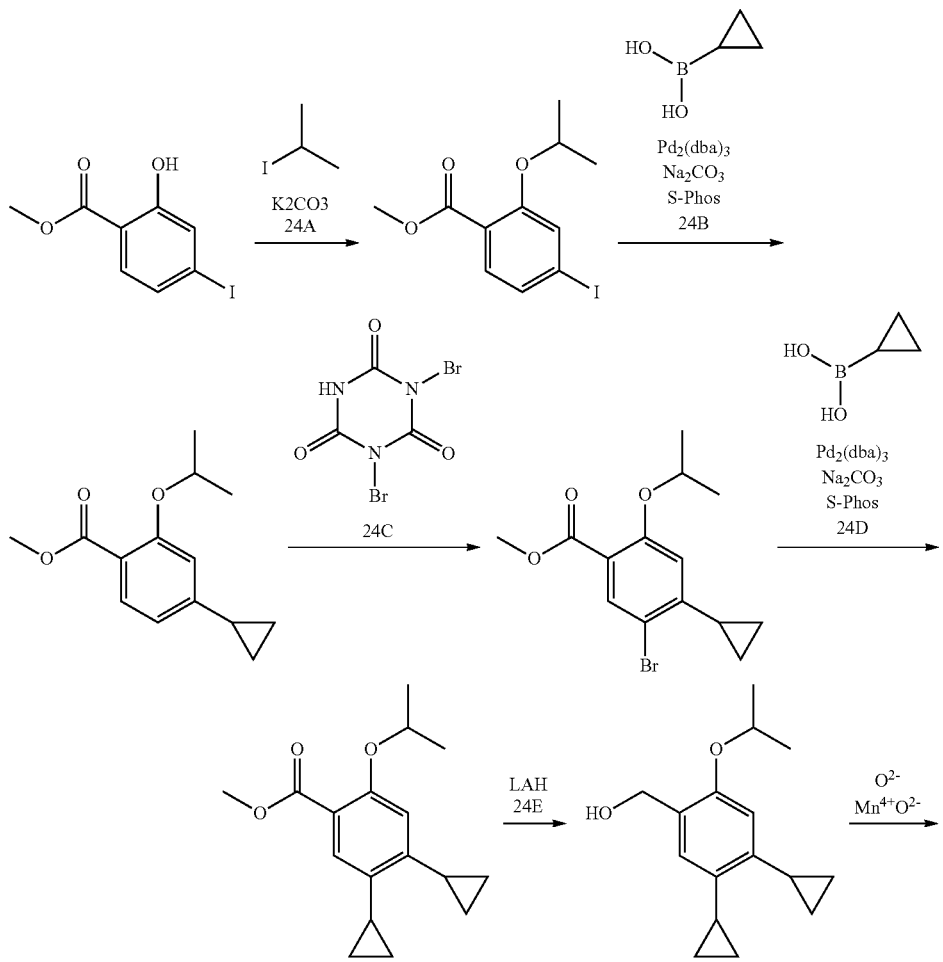

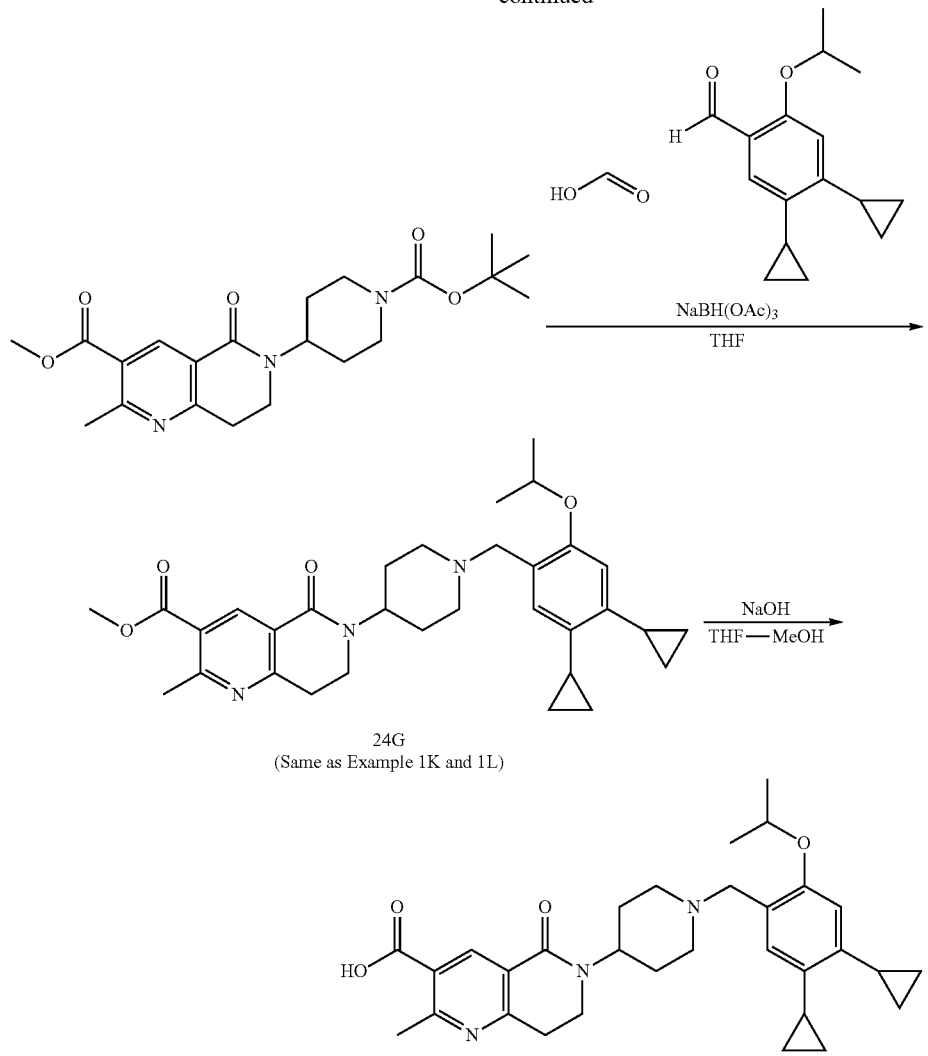

24G
(Same as Example 1K and 1L)

A) Methyl 4-iodo-2-isopropoxybenzoate

2-Iodopropane (6.42 g) was added at room temperature to a mixture of methyl 2-hydroxy-4-iodobenzoate (7.00 g), potassium carbonate (6.96 g), and DMF (100 mL), and the resultant mixture was stirred at 70° C. for 2 days in a nitrogen atmosphere. Water was added to the reaction mixture at room temperature, followed by extraction with ethyl acetate. The obtained organic layer was washed with water and saturated saline in this order and dried over anhydrous magnesium sulfate, and then, the solvent was distilled off under reduced pressure. The obtained residue was purified by silica gel column chromatography (hexane/ethyl acetate) to obtain the title compound (7.92 g).

$^1$H NMR (300 MHz, CDCl$_3$) δ 1.37 (6H, d, J=6.0 Hz), 3.86 (3H, s), 4.49-4.63 (1H, m), 7.28-7.33 (2H, m), 7.46 (1H, d, J=8.5 Hz).

B) Methyl 4-cyclopropyl-2-isopropoxybenzoate

Cyclopropylboronic acid (3.19 g), a 2 M aqueous sodium carbonate solution (37 mL), tris(dibenzylideneacetone)dipalladium(0) (1.59 g), and dicyclohexyl(2',6'-dimethoxybiphenyl-2-yl)phosphine (1.52 g) were added at room temperature to a toluene (100 mL) solution of methyl 4-iodo-2-isopropoxybenzoate (7.92 g), and the mixture was stirred at 100° C. for 15 hours in an argon atmosphere. Water was added to the reaction mixture at room temperature. The mixture was filtered through celite, and then, the filtrate was subjected to extraction with ethyl acetate. The obtained organic layer was washed with water and saturated saline in this order and dried over anhydrous magnesium sulfate, and then, the solvent was distilled off under reduced pressure. The obtained residue was purified by silica gel column chromatography (hexane/ethyl acetate) to obtain the title compound (5.43 g).

$^1$H NMR (300 MHz, CDCl$_3$) δ 0.70-0.76 (2H, m), 0.98-1.05 (2H, m), 1.36 (6H, d, J=6.1 Hz), 1.82-1.93 (1H, m), 3.85 (3H, s), 4.49-4.63 (1H, m), 6.62 (1H, dd, J=8.1, 1.6 Hz), 6.69 (1H, d, J=1.5 Hz), 7.69 (1H, d, J=8.1 Hz).

C) Methyl 5-bromo-4-cyclopropyl-2-isopropoxybenzoate

Dibromoisocyanuric acid (3.99 g) was added at room temperature to a DMF (80 mL) solution of methyl 4-cyclopropyl-2-isopropoxybenzoate (5.43 g), and the mixture was stirred at 90° C. for 1 hour in a nitrogen atmosphere. An aqueous sodium thiosulfate solution was added to the reaction mixture at room temperature, followed by extraction with ethyl acetate. The obtained organic layer was washed with water and saturated saline in this order and dried over anhydrous magnesium sulfate, and then, the solvent was distilled off under reduced pressure. The obtained residue was purified by silica gel column chromatography (hexane/ethyl acetate) to obtain the title compound (6.89 g).

$^1$H NMR (300 MHz, CDCl$_3$) δ 0.65-0.72 (2H, m), 1.04-1.11 (2H, m), 1.34 (6H, d, J=6.1 Hz), 2.12-2.23 (1H, m), 3.86 (3H, s), 4.42-4.56 (1H, m), 6.50 (1H, s), 7.96 (1H, s).

D) Methyl 4,5-dicyclopropyl-2-isopropoxybenzoate

Cyclopropylboronic acid (2.83 g), a 2 M aqueous sodium carbonate solution (33 mL), tris(dibenzylideneacetone)dipalladium(0) (1.41 g), and dicyclohexyl(2',6'-dimethoxybiphenyl-2-yl)phosphine (1.36 g) were added at room temperature to a toluene (100 mL) solution of methyl 5-bromo-4-cyclopropyl-2-isopropoxybenzoate (6.89 g), and the mixture was stirred at 100° C. for 15 hours in an argon atmosphere. Water was added to the reaction mixture at room temperature. The mixture was filtered through celite, and then, the filtrate was subjected to extraction with ethyl acetate. The obtained organic layer was washed with water and saturated saline in this order and dried over anhydrous magnesium sulfate, and then, the solvent was distilled off under reduced pressure. The obtained residue was purified by silica gel column chromatography (hexane/ethyl acetate) to obtain the title compound (5.90 g).

$^1$H NMR (300 MHz, CDCl$_3$) δ 0.62-0.72 (4H, m), 0.88-0.96 (2H, m), 0.98-1.06 (2H, m), 1.33 (6H, d, J=6.1 Hz), 1.99-2.11 (1H, m), 2.21-2.32 (1H, m), 3.85 (3H, s), 4.40-4.53 (1H, m), 6.51 (1H, s), 7.43 (1H, d, J=0.4 Hz).

E) (4,5-Dicyclopropyl-2-isopropoxyphenyl)methanol

A THF (15 mL) solution of methyl 4,5-dicyclopropyl-2-isopropoxybenzoate (5.90 g) was added at 0° C. to a mixture of lithium aluminum hydride (1.71 g) and THF (85 mL), and the resultant mixture was stirred at room temperature for 30 minutes in a nitrogen atmosphere. Water (1.8 mL), a 1 M aqueous sodium hydroxide solution (1.8 mL), and water (5.4 mL) were added in this order to the reaction mixture at 0° C. The mixture was filtered through celite, and then, the filtrate was concentrated under reduced pressure. The obtained residue was purified by silica gel chromatography (hexane/ethyl acetate) to obtain the title compound (5.22 g).

$^1$H NMR (300 MHz, CDCl$_3$) δ 0.59-0.68 (4H, m), 0.86-1.00 (4H, m), 1.33 (6H, d, J=6.0 Hz), 2.02-2.13 (1H, m), 2.15-2.27 (1H, m), 2.41 (1H, t, J=6.5 Hz), 4.48-4.64 (3H, m), 6.49 (1H, s), 6.86 (1H, s).

F) 4,5-Dicyclopropyl-2-isopropoxybenzaldehyde

Manganese dioxide (14.7 g) was added at room temperature to a toluene (80 mL) solution of (4,5-dicyclopropyl-2-isopropoxyphenyl)methanol (5.22 g), and the mixture was stirred at 80° C. for 1 hour in a nitrogen atmosphere. The reaction mixture was filtered through celite, and then, the filtrate was concentrated. The obtained residue was purified by silica gel column chromatography (hexane/ethyl acetate) to obtain the title compound (4.88 g).

$^1$H NMR (300 MHz, CDCl$_3$) δ 0.64-0.76 (4H, m), 0.88-0.96 (2H, m), 1.03-1.11 (2H, m), 1.36 (6H, d, J=6.0 Hz), 1.98-2.09 (1H, m), 2.25-2.37 (1H, m), 4.53-4.66 (1H, m), 6.49 (1H, s), 7.47 (1H, d, J=0.6 Hz), 10.37 (1H, s).

G) 6-(1-(4,5-Dicyclopropyl-2-isopropoxybenzyl) piperidin-4-yl)-2-methyl-5-oxo-5,6,7,8-tetrahydro-1, 6-naphthyridine-3-carboxylic acid The title compound was obtained in the same way as in steps K and L of Example 1 using methyl 6-(1-(tert-butoxycarbonyl)piperidin-4-yl)-2-methyl-5-oxo-5,6,7,8-tetrahydro-1,6-naphthyridine-3-carboxylate and 4,5-dicyclopropyl-2-isopropoxybenzaldehyde.

Example 25

6-(1-((2,6-Diethoxy-4'-fluorobiphenyl-4-yl)methyl) piperidin-4-yl)-5-oxo-5,6,7,8-tetrahydro-1,6-naphthyridine-3-carboxylic acid

[Formula 42]

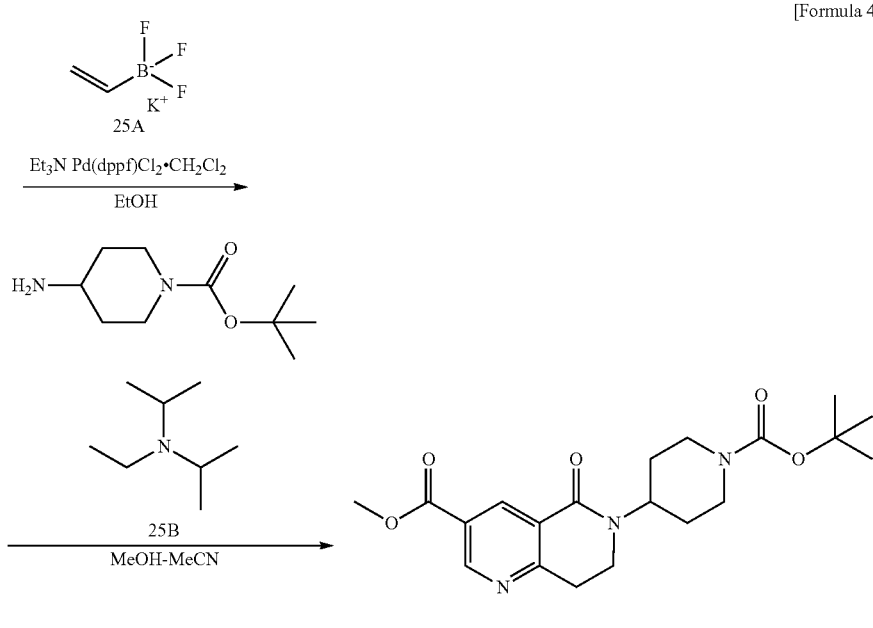

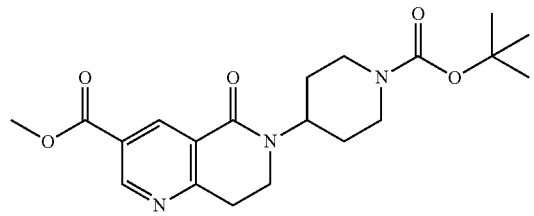

25C (Same as Examples 1K and 1L)

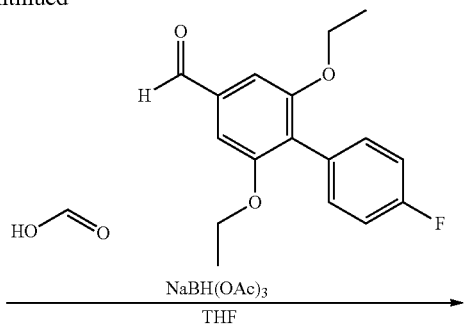

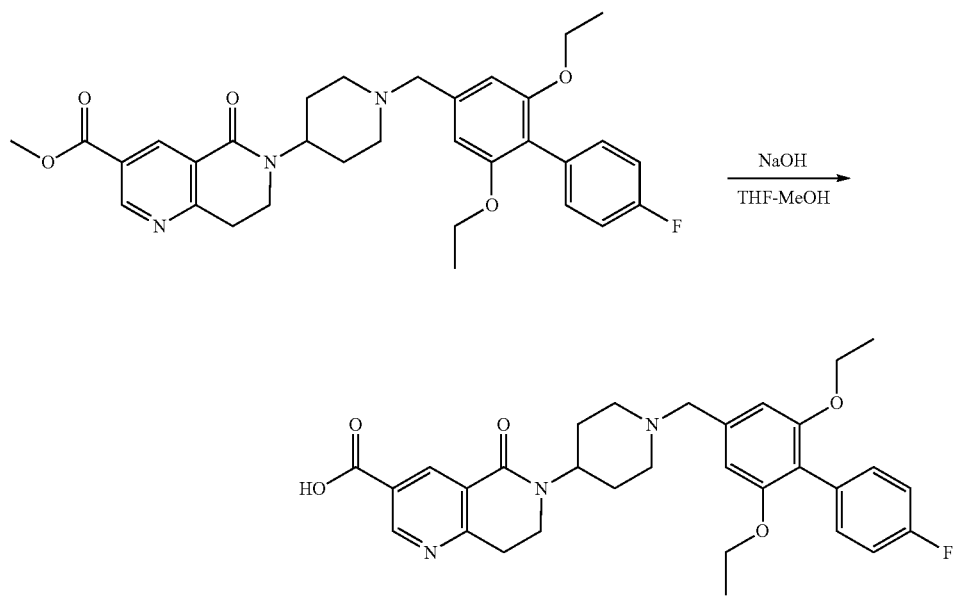

A) Dimethyl 2-vinylpyridine-3,5-dicarboxylate

A dichloromethane adduct of (1,1'-bis(diphenylphosphino)ferrocene)dichloropalladium(II) (0.359 g) was added to a mixture of dimethyl 2-chloropyridine-3,5-dicarboxylate (1.01 g), potassium vinyl trifluoroborate (1.18 g), triethylamine (1.22 mL), and ethanol (10 mL), and the resultant mixture was stirred at 95° C. for 1 hour in an argon atmosphere. The solvent in the reaction mixture was distilled off under reduced pressure, and the obtained residue was purified by silica gel column chromatography (hexane/ethyl acetate) to obtain the title compound (880 mg).

$^1$H NMR (300 MHz, CDCl$_3$) δ 3.90 (3H, s), 3.91 (3H, s), 5.74 (1H, dd, J=1.36 Hz, 10.68 Hz), 6.59 (1H, dd, J=1.36 Hz, 17.0 Hz), 7.51-7.58 (1H, m), 8.56 (1H, d, J=1.28 Hz), 9.16 (1H, s).

B) Methyl 6-(1-(tert-butoxycarbonyl)piperidin-4-yl)-5-oxo-5,6,7,8-tetrahydro-1,6-naphthyridine-3-carboxylate A mixture of dimethyl 2-vinylpyridine-3,5-dicarboxylate (1.8 g), tert-butyl 4-aminopiperidine-1-carboxylate (2.4 g), N,N'-diisopropylethylamine (2.13 mL), acetonitrile (10 mL), and methanol (10 mL) was stirred at 150° C. for 16 hours under microwave irradiation. The reaction mixture was allowed to cool to room temperature, and then, the solvent was distilled off under reduced pressure. The obtained residue was purified by silica gel column chromatography (hexane/ethyl acetate) to obtain the title compound (1.8 g).

MS (ESI+) [M+H]$^+$ 390.2.

C) 6-(1-((2,6-Diethoxy-4'-fluorobiphenyl-4-yl)methyl)piperidin-4-yl)-5-oxo-5,6,7,8-tetrahydro-1,6-naphthyridine-3-carboxylic acid The title compound was obtained in the same way as in steps K and L of Example 1 using methyl 6-(1-(tert-butoxycarbonyl)piperidin-4-yl)-5-oxo-5,6,7,8-tetrahydro-1,6-naphthyridine-3-carboxylate and 2,6-diethoxy-4'-fluorobiphenyl-4-carbaldehyde.

Example 26
6-(1-((2-Cyclopropyl-6-ethoxy-4'-fluorobiphenyl-4-yl)methyl)piperidin-4-yl)-5-oxo-5,6,7,8-tetrahydro-1,6-naphthyridine-3-carboxylic acid
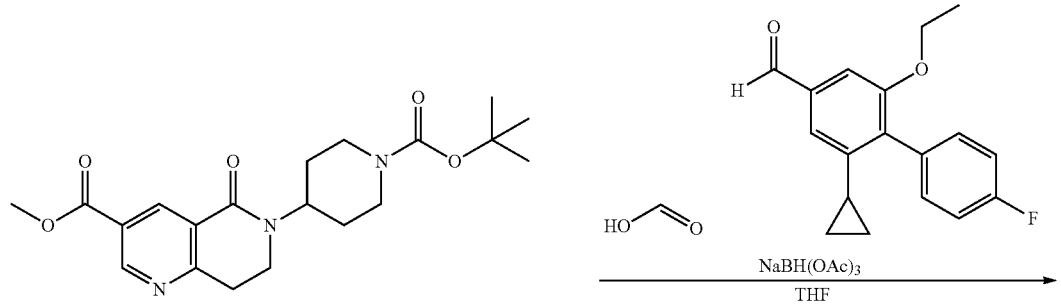
26 (Same as Examples 1K and 1L)
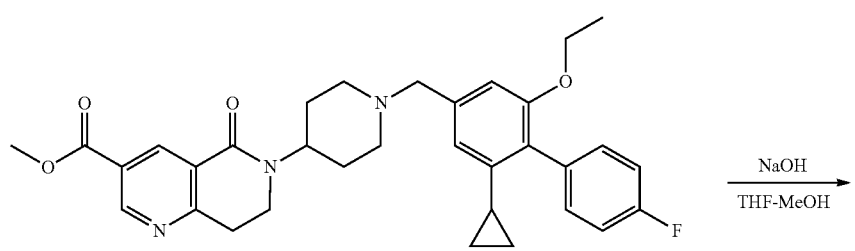
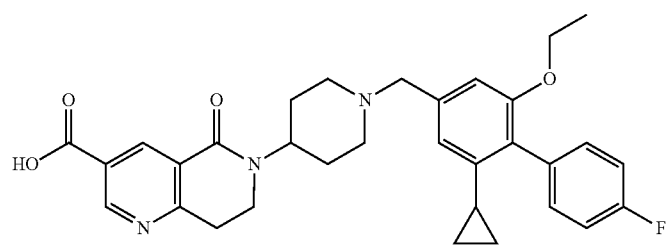

139

The title compound was obtained in the same way as in steps K and L of Example 1 using methyl 6-(1-(tert-butoxycarbonyl)piperidin-4-yl)-5-oxo-5,6,7,8-tetrahydro-1,6-naphthyridine-3-carboxylate and 2-cyclopropyl-6-ethoxy-4'-fluorobiphenyl-4-carbaldehyde.

Example 27

6-(1-((2-Cyclopropyl-5-ethoxy-4'-fluorobiphenyl-4-yl)methyl)piperidin-4-yl)-5-oxo-5,6,7,8-tetrahydro-1,6-naphthyridine-3-carboxylic acid

[Formula 44]

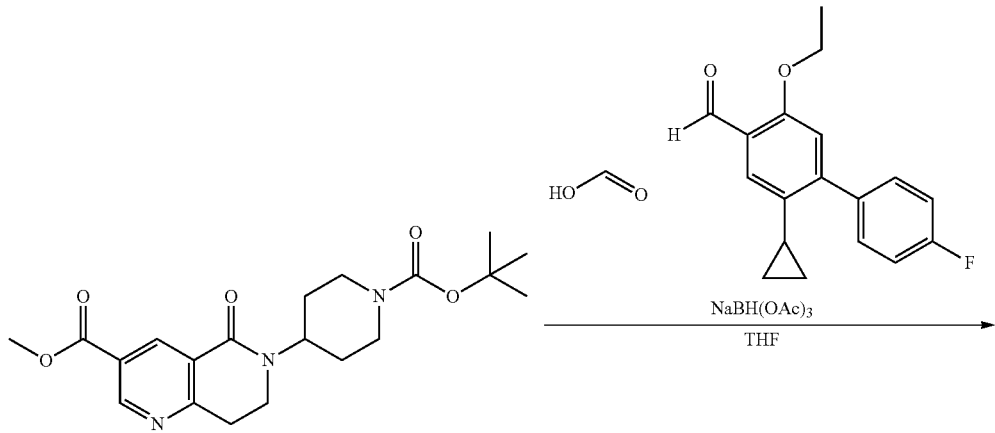

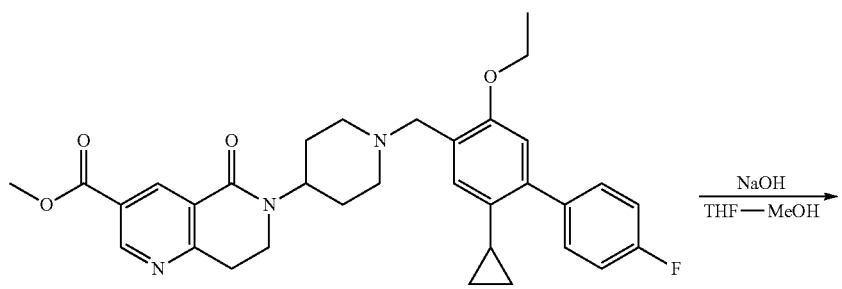

27
(Same as Example 1K and 1L)

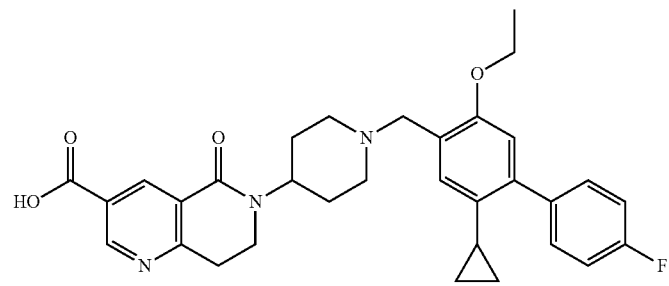

141
The title compound was obtained in the same way as in steps K and L of Example 1 using methyl 6-(1-(tert-butoxycarbonyl)piperidin-4-yl)-5-oxo-5,6,7,8-tetrahydro-1,6-naphthyridine-3-carboxylate and 2-cyclopropyl-5-ethoxy-4'-fluorobiphenyl-4-carbaldehyde.
142
Example 28
6-(1-((5-Cyclopropyl-2-ethoxy-6-(4-fluorophenyl)pyridin-3-yl)methyl)piperidin-4-yl)-5-oxo-5,6,7,8-tetrahydro-1,6-naphthyridine-3-carboxylic acid
[Formula 45]
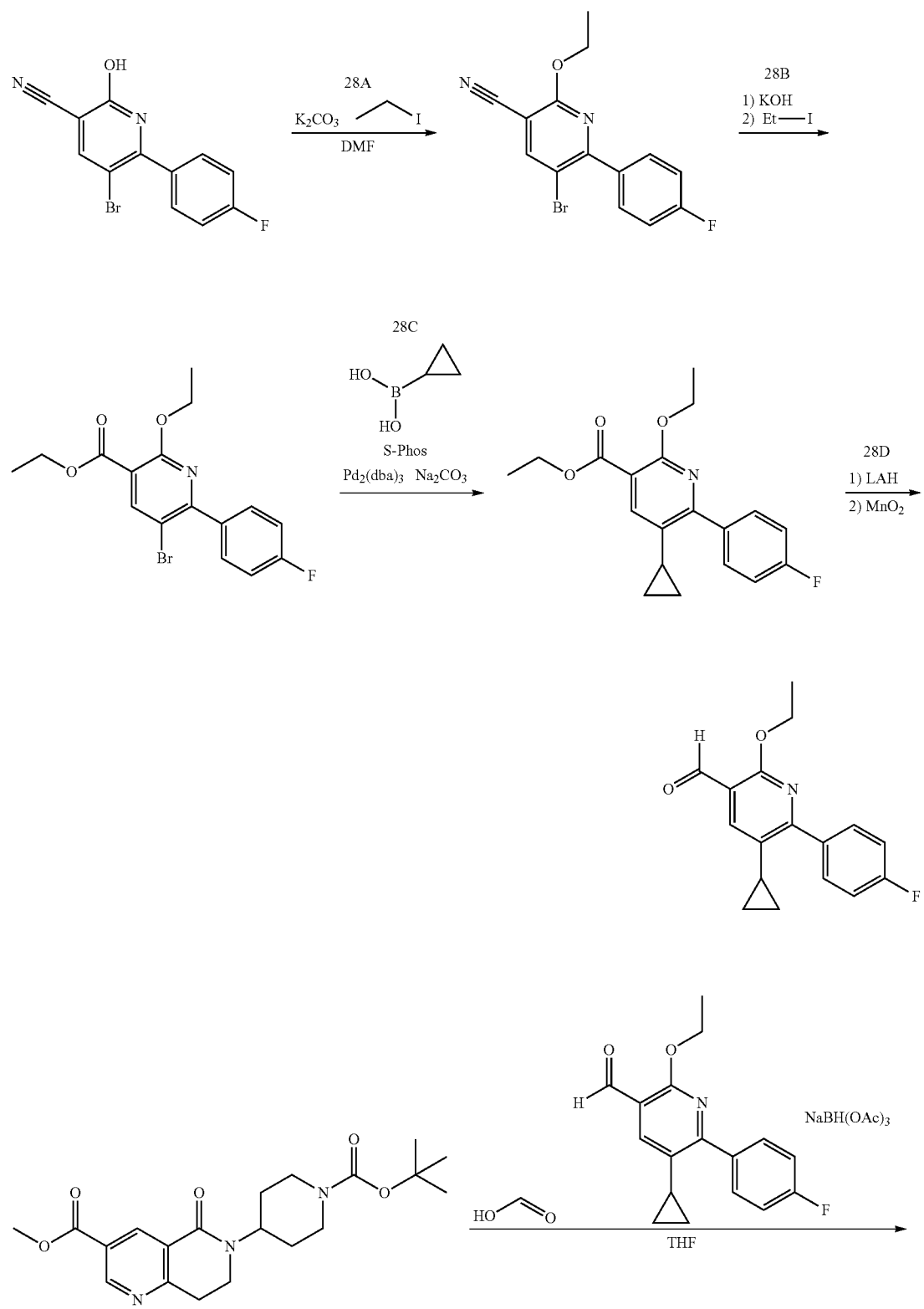

-continued

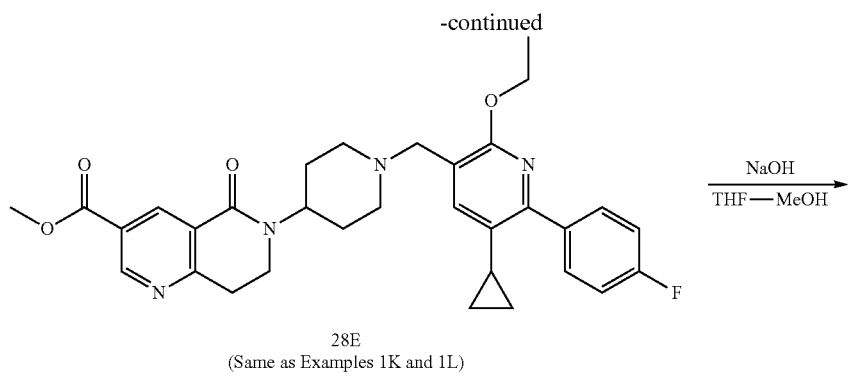

28E
(Same as Examples 1K and 1L)

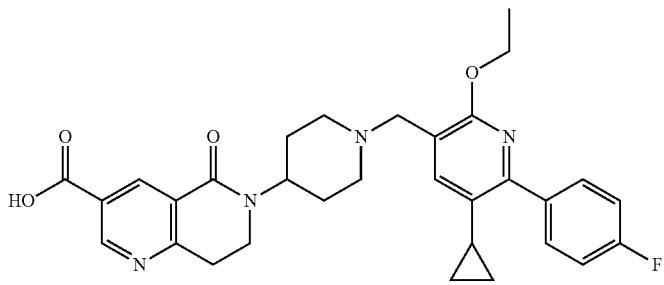 [SMILES: CCOc1cc(-c2ccc(F)cc2)c(C2CC2)cc1CN1CCC(N2CCc3ccc(C(=O)O)nc3C2=O)CC1]

A)
5-Bromo-2-ethoxy-6-(4-fluorophenyl)nicotinonitrile

Iodoethane (1.43 mL) was added to a mixture of 5-bromo-6-(4-fluorophenyl)-2-hydroxynicotinonitrile (3.49 g), potassium carbonate (3.29 g), and DMF (30 mL), and the resultant mixture was stirred at 80° C. for 30 minutes. Water was added to the reaction mixture, followed by extraction with ethyl acetate. The organic layer was washed with saturated saline and dried over anhydrous magnesium sulfate, and then, the solvent was distilled off under reduced pressure. The obtained residue was purified by silica gel column chromatography (hexane/ethyl acetate) to obtain the title compound (3.00 g).
$^1$H NMR (300 MHz, CDCl$_3$) δ 1.45 (3H, t, J=7.1 Hz), 4.51 (2H, q, J=7.0 Hz), 7.16 (2H, t, J=8.7 Hz), 7.77 (2H, dd, J=8.9, 5.3 Hz), 8.10 (1H, s).

B) Ethyl 5-bromo-2-ethoxy-6-(4-fluorophenyl)nicotinate

An 8 M aqueous potassium hydroxide solution (14.6 mL) was added to a mixture of 5-bromo-2-ethoxy-6-(4-fluorophenyl)nicotinonitrile (3.75 g), THF (10 mL), and ethanol (10 mL), and the resultant mixture was stirred overnight at 100° C. The reaction mixture was neutralized with 6 M hydrochloric acid, followed by extraction with ethyl acetate. The organic layer was dried over anhydrous magnesium sulfate, and then, the solvent was distilled off under reduced pressure. Potassium carbonate (3.23 g) and iodoethane (1.40 mL) were added to a mixture of the obtained residue and DMF (10 mL), and the resultant mixture was stirred at 60° C. for 30 minutes. Water was added to the reaction mixture, followed by extraction with ethyl acetate. The organic layer was washed with saturated saline and dried over anhydrous magnesium sulfate, and then, the solvent was distilled off under reduced pressure. The obtained residue was purified by silica gel column chromatography (hexane/ethyl acetate) to obtain the title compound (2.40 g).
$^1$H NMR (300 MHz, CDCl$_3$) δ 1.33-1.50 (6H, m), 4.38 (2H, q, J=7.1 Hz), 4.49 (2H, q, J=7.0 Hz), 7.14 (2H, t, J=8.8 Hz), 7.79 (2H, dd, J=8.9, 5.4 Hz), 8.38 (1H, s).

C) Ethyl 5-cyclopropyl-2-ethoxy-6-(4-fluorophenyl)nicotinate

Tris(dibenzylideneacetone)dipalladium(0) (418 mg) was added to a mixture of ethyl 5-bromo-2-ethoxy-6-(4-fluorophenyl)nicotinate (2.40 g), cyclopropylboronic acid (1.68 g), dicyclohexyl(2',6'-dimethoxybiphenyl-2-yl)phosphine (401 mg), a 2 M aqueous sodium carbonate solution (9.78 mL), and toluene (25 mL), and the resultant mixture was stirred at 100° C. for 2 hours in an argon atmosphere. The reaction mixture was allowed to cool to room temperature and poured to water, followed by extraction with ethyl acetate. The obtained organic layer was washed with saturated saline and dried over anhydrous magnesium sulfate, and then, the solvent was distilled off under reduced pressure. The obtained residue was purified by silica gel column chromatography (hexane/ethyl acetate) to obtain the title compound (2.06 g).
$^1$H NMR (300 MHz, CDCl$_3$) δ 0.60-0.68 (2H, m), 0.84-0.96 (2H, m), 1.33-1.47 (6H, m), 1.89-2.00 (1H, m), 4.37 (2H, q, J=7.2 Hz), 4.50 (2H, q, J=7.0 Hz), 7.14 (2H, t, J=8.7 Hz), 7.77 (2H, dd, J=8.8, 5.5 Hz), 7.82 (1H, s).

D) 5-Cyclopropyl-2-ethoxy-6-(4-fluorophenyl)nicotinaldehyde

A THF (20 mL) solution of ethyl 5-cyclopropyl-2-ethoxy-6-(4-fluorophenyl)nicotinate (2.06 g) was added to a THF (20 mL) suspension of lithium aluminum hydride (237 mg) under ice cooling in a nitrogen atmosphere. After stirring at the same temperature as above for 30 minutes, water (0.20 mL) and a 15% aqueous sodium hydroxide solution (0.20 mL) were added thereto, and the mixture was stirred for 5 minutes. Then, water (0.60 mL) was further added thereto. The reaction mixture was stirred for 1 hour and then filtered. The filtrate was concentrated under reduced pressure. Manganese dioxide (5.43 g) was added to a toluene (10 mL) solution of the obtained residue, and the mixture was stirred at 60° C. for 1 hour in a nitrogen atmosphere. The reaction mixture was filtered, and then, the solvent was distilled off under reduced pressure. The obtained residue was purified by silica gel column chromatography (hexane/ethyl acetate) to obtain the title compound (1.47 g).

$^1$H NMR (300 MHz, CDCl$_3$) δ 0.64-0.71 (2H, m), 0.88-0.99 (2H, m), 1.44 (3H, t, J=7.1 Hz), 1.86-2.01 (1H, m), 4.54 (2H, q, J=7.1 Hz), 7.15 (2H, t, J=8.8 Hz), 7.75-7.83 (3H, m), 10.38 (1H, s).

E) 6-(1-((5-Cyclopropyl-2-ethoxy-6-(4-fluorophenyl)pyridin-3-yl)methyl)piperidin-4-yl)-5-oxo-5,6,7,8-tetrahydro-1,6-naphthyridine-3-carboxylic acid The title compound was obtained in the same way as in steps K and L of Example 1 using methyl 6-(1-(tert-butoxycarbonyl)piperidin-4-yl)-5-oxo-5,6,7,8-tetrahydro-1,6-naphthyridine-3-carboxylate and 5-cyclopropyl-2-ethoxy-6-(4-fluorophenyl)nicotinaldehyde.

Example 29

6-(1-((2,6-Diethoxy-4'-fluorobiphenyl-4-yl)methyl)azetidin-3-yl)-5-oxo-5,6,7,8-tetrahydro-1,6-naphthyridine-3-carboxylic acid

[Formula 46]

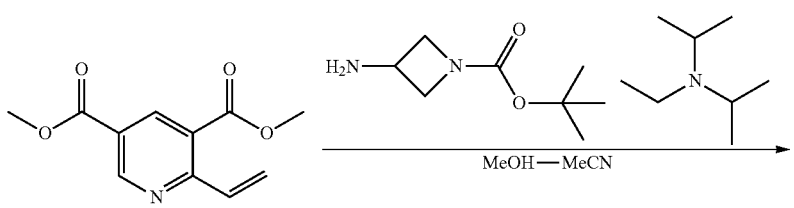

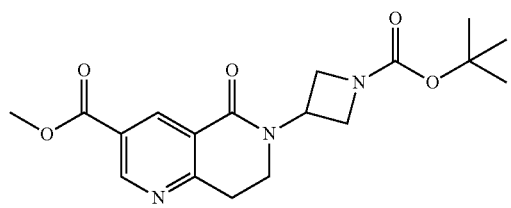

29A
(Same as Example 25B)

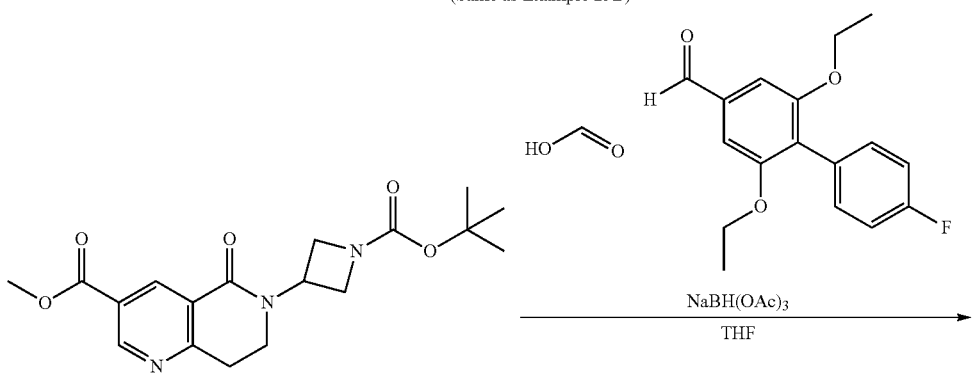

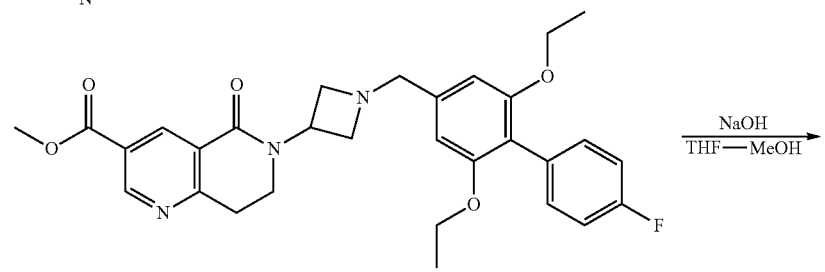

29B
(Same as Examples 1K and 1L)

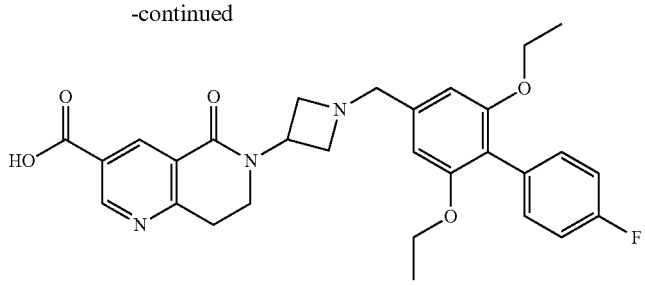

A) Methyl 6-(1-(tert-butoxycarbonyl)azetidin-3-yl)-5-oxo-5,6,7,8-tetrahydro-1,6-naphthyridine-3-carboxylate The title compound was obtained in the same way as in step B of Example 25 using dimethyl 2-vinylpyridine-3,5-dicarboxylate and tert-butyl 3-aminoazetidine-1-carboxylate. MS (ESI+): [M+H]$^+$ 362.2.

B) 6-(1-((2,6-Diethoxy-4'-fluorobiphenyl-4-yl)methyl)azetidin-3-yl)-5-oxo-5,6,7,8-tetrahydro-1,6-naphthyridine-3-carboxylic acid The title compound was obtained in the same way as in steps K and L of Example 1 using methyl 6-(1-(tert-butoxycarbonyl)azetidin-3-yl)-5-oxo-5,6,7,8-tetrahydro-1,6-naphthyridine-3-carboxylate and 2,6-diethoxy-4'-fluorobiphenyl-4-carbaldehyde.

Example 30

6-(1-(4-Cyclobutyl-5-cyclopropyl-2-ethoxybenzyl)piperidin-4-yl)-5-oxo-5,6,7,8-tetrahydro-1,6-naphthyridine-3-carboxylic acid

[Formula 47]

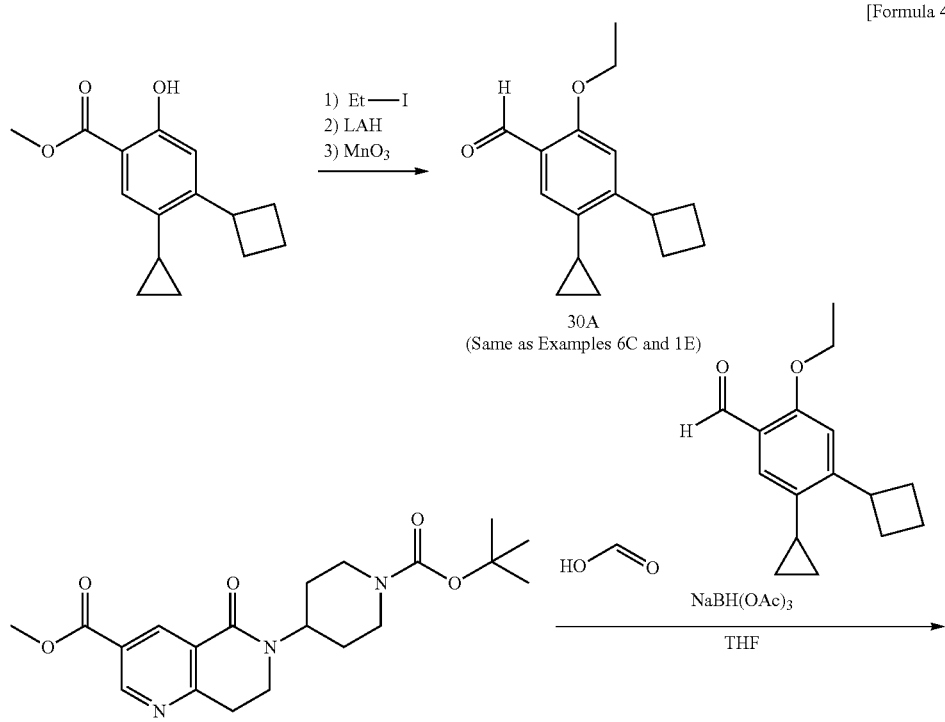

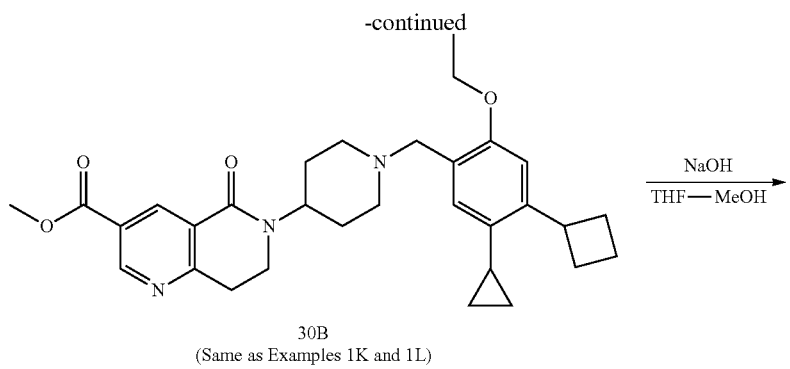

30B
(Same as Examples 1K and 1L)

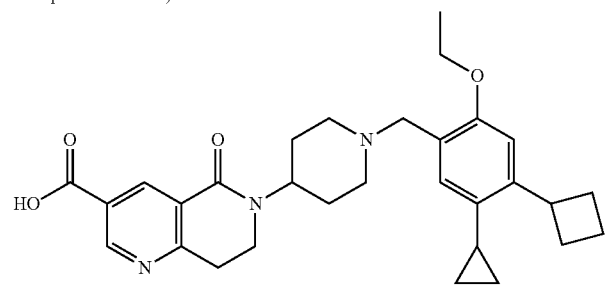

A) 4-Cyclobutyl-5-cyclopropyl-2-ethoxybenzaldehyde

The title compound was obtained in the same way as in step C of Example 6 and step E of Example 1 using methyl 4-cyclobutyl-5-cyclopropyl-2-hydroxybenzoate and ethyl iodide. MS (ESI+): [M+H]$^+$ 245.5.

B) 6-(1-(4-Cyclobutyl-5-cyclopropyl-2-ethoxybenzyl)piperidin-4-yl)-5-oxo-5,6,7,8-tetrahydro-1,6-naphthyridine-3-carboxylic acid The title compound was obtained in the same way as in steps K and L of Example 1 using methyl 6-(1-(tert-butoxycarbonyl)piperidin-4-yl)-5-oxo-5,6,7,8-tetrahydro-1,6-naphthyridine-3-carboxylate and 4-cyclobutyl-5-cyclopropyl-2-ethoxybenzaldehyde.

Example 31

7-(1-((2-Cyclopropyl-5-ethoxy-4'-fluorobiphenyl-4-yl)methyl)piperidin-4-yl)-8-oxo-5,6,7,8-tetrahydro-1,7-naphthyridine-2-carboxylic acid

[Formula 48]

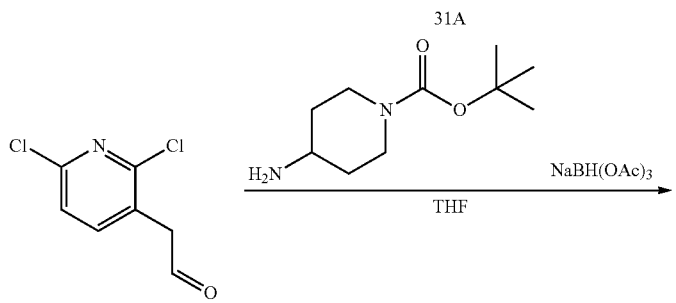

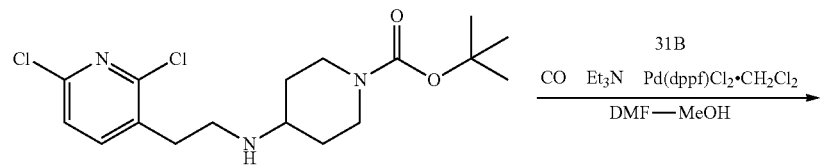

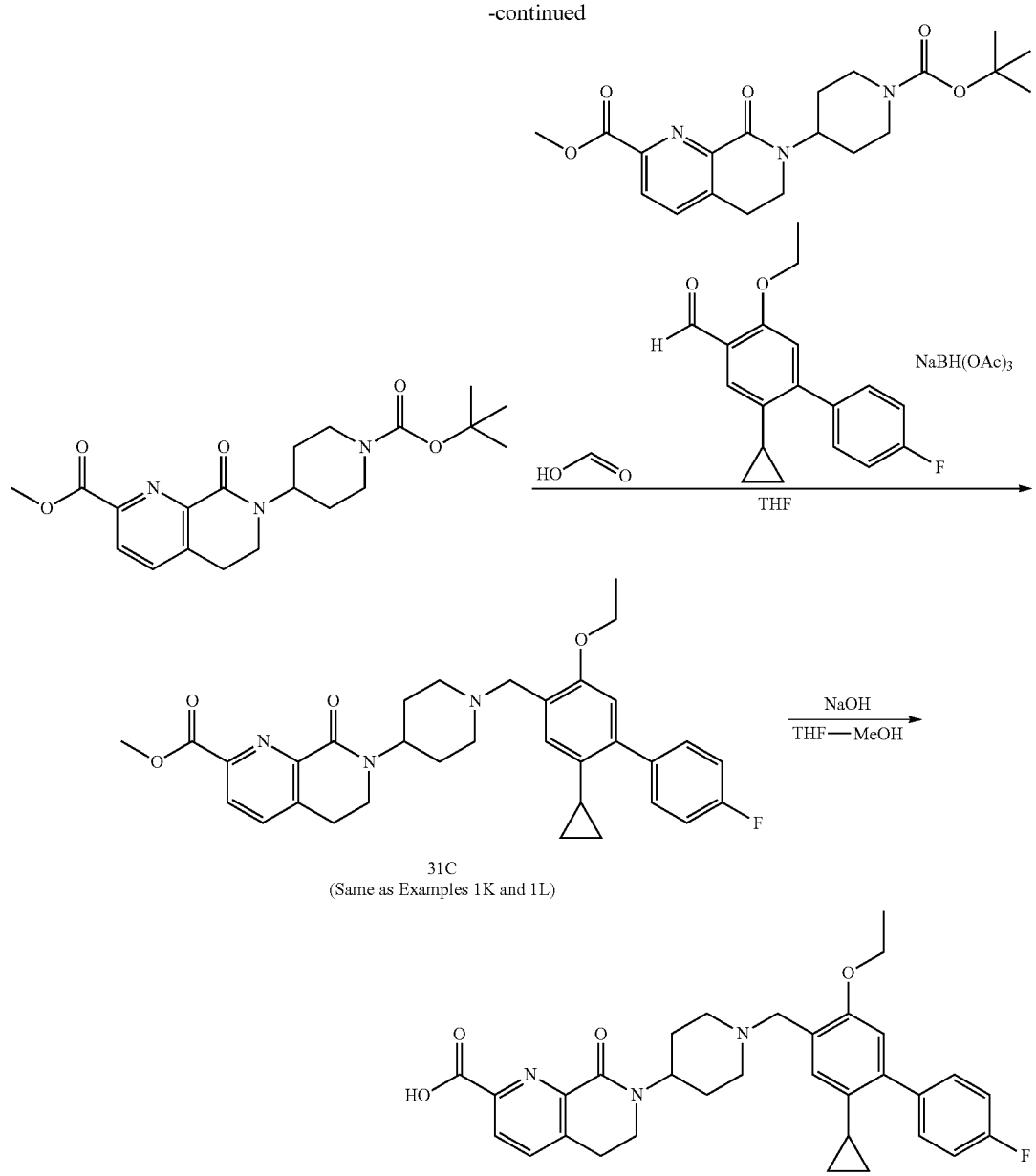

A) tert-Butyl 4-((2-(2,6-dichloropyridin-3-yl)ethyl)amino)piperidine-1-carboxylate Sodium triacetoxy borohydride (9.47 g) was added to a THF (60 mL) solution of (2,6-dichloropyridin-3-yl)acetaldehyde (5.66 g) and tert-butyl 4-aminopiperidine-1-carboxylate (7.16 g), and the mixture was stirred at room temperature for 1 hour. A saturated aqueous solution of sodium bicarbonate was added to the reaction mixture, followed by extraction with ethyl acetate. The obtained organic layer was dried over anhydrous magnesium sulfate, and then, the solvent was distilled off under reduced pressure. The obtained residue was purified by silica gel column chromatography (ethyl acetate/methanol) to obtain the title compound (10.5 g).

MS (ESI+): [M+H]$^+$ 374.2.

B) Methyl 7-(1-(tert-butoxycarbonyl)piperidin-4-yl)-8-oxo-5,6,7,8-tetrahydro-1,7-naphthyridine-2-carboxylate A mixture of tert-butyl 4-((2-(2,6-dichloropyridin-3-yl)ethyl)amino)piperidine-1-carboxylate (10.5 g), a dichloromethane adduct of [1,1'-bis(diphenylphosphino)ferrocene]dichloropalladium(II) (2.30 g), triethylamine (11.8 mL), methanol (20 mL), and DMF (60 mL) was stirred at 90° C. for 7 hours in a carbon monooxide (5 atm) atmosphere. Water was added to the reaction mixture, followed by extraction with ethyl acetate. The organic layer was washed with saturated saline and dried over anhydrous magnesium sulfate, and then, the solvent was distilled off under reduced pressure. The residue was purified by silica gel column chromatography (hexane/ethyl acetate) to obtain the title compound (4.01 g).

MS (ESI+): [M+H]$^+$ 390.3.

153

C) 7-(1-((2-Cyclopropyl-5-ethoxy-4'-fluorobiphenyl-4-yl)methyl)piperidin-4-yl)-8-oxo-5,6,7,8-tetrahydro-1,7-naphthyridine-2-carboxylic acid The title compound was obtained in the same way as in steps K and L of Example 1 using methyl 7-(1-(tert-butoxycarbonyl)piperidin-4-yl)-8-oxo-5,6,7,8-tetrahydro-1,7-

154 naphthyridine-2-carboxylate and 2-cyclopropyl-5-ethoxy-4'-fluorobiphenyl-4-carbaldehyde.

Example 32

6-(1-((4-Cyclopropyl-1-ethyl-1H-indol-6-yl)methyl)piperidin-4-yl)-5-oxo-5,6,7,8-tetrahydro-1,6-naphthyridine-3-carboxylic acid

[Formula 49]

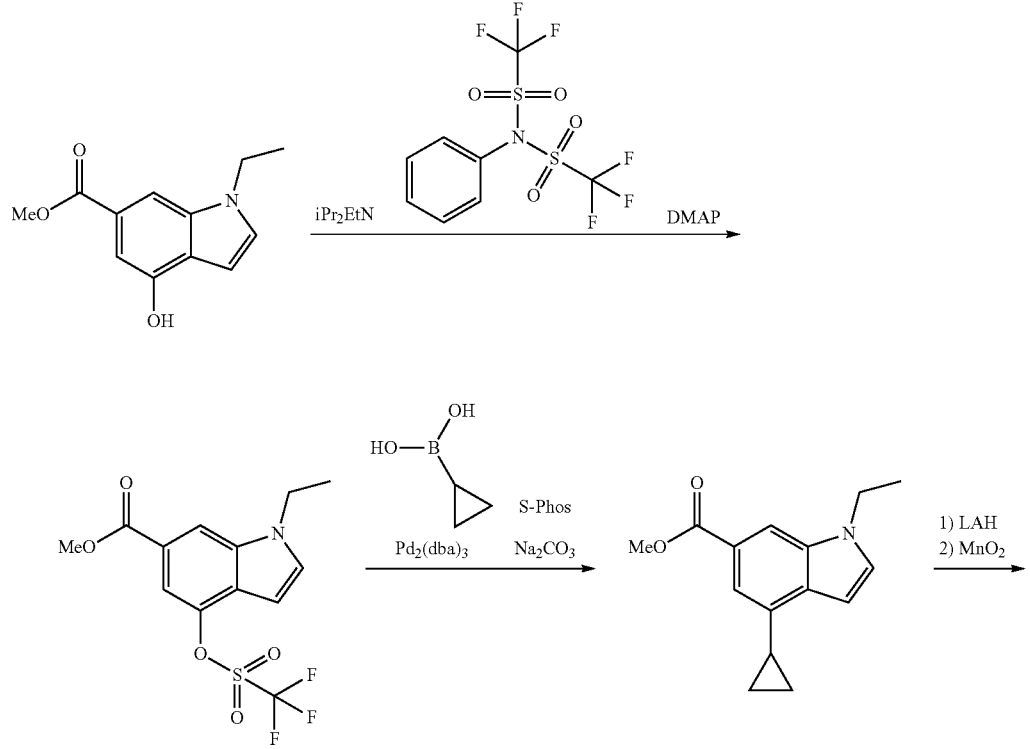

32A
(Same as Examples 8C, 1D, and 1E)

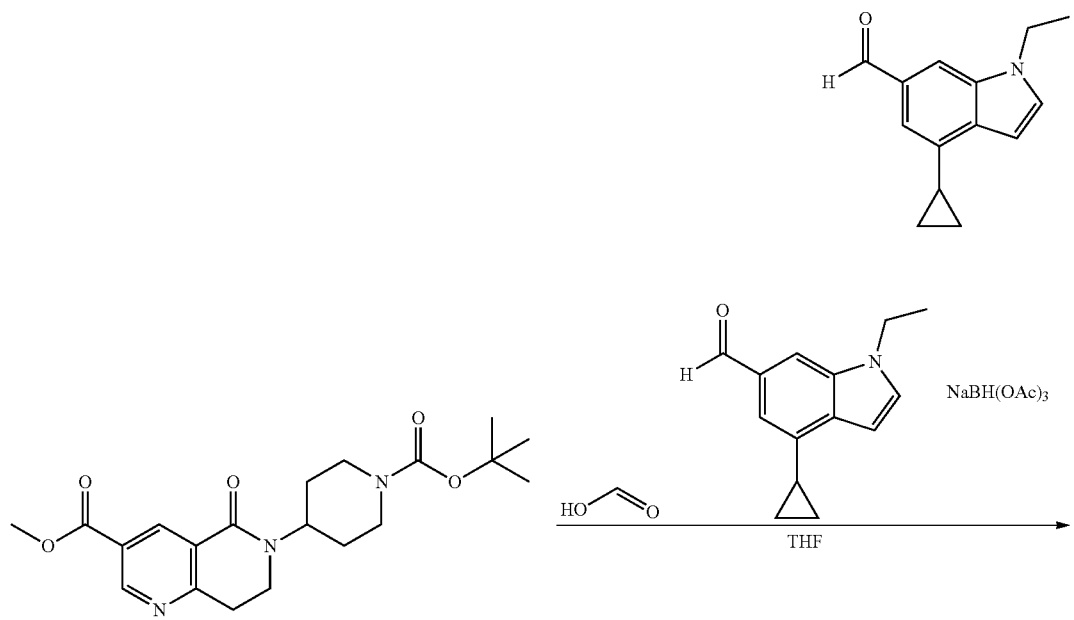

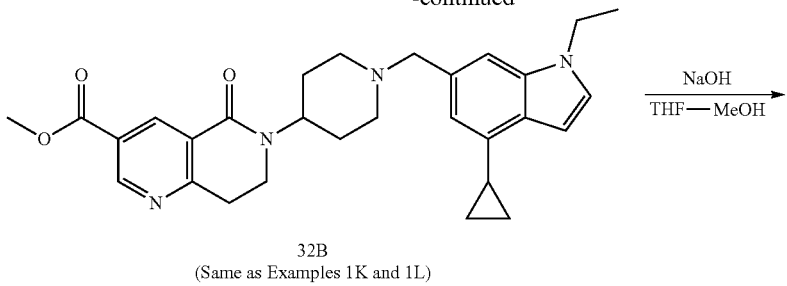

32B
(Same as Examples 1K and 1L)

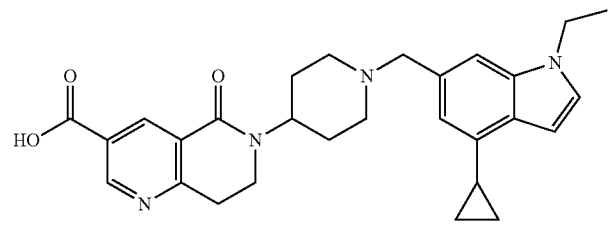 [SMILES: CCn1ccc2c(C3CC3)cc(CN3CCC(N4CCc5ncc(C(=O)O)cc5C4=O)CC3)cc21]

A) 4-Cyclopropyl-1-ethyl-1H-indole-6-carbaldehyde

The title compound was obtained in the same way as in step C of Example 8 and steps D and E of Example 1 using methyl 1-ethyl-4-hydroxy-1H-indole-6-carboxylate.

$^1$H NMR (300 MHz, CDCl$_3$) δ 0.85-0.93 (2H, m), 1.00-1.12 (2H, m), 1.50 (3H, t, J=7.3 Hz), 2.19-2.32 (1H, m), 4.25 (2H, q, J=7.3 Hz), 6.73 (1H, d, J=3.1 Hz), 7.23 (1H, s), 7.35 (1H, d, J=3.1 Hz), 7.73 (1H, s), 10.01 (1H, s)

B) 6-(1-((4-Cyclopropyl-1-ethyl-1H-indol-6-yl)methyl)piperidin-4-yl)-5-oxo-5,6,7,8-tetrahydro-1,6-naphthyridine-3-carboxylic acid The title compound was obtained in the same way as in steps K and L of Example 1 using methyl 6-(1-(tert-butoxycarbonyl)piperidin-4-yl)-5-oxo-5,6,7,8-tetrahydro-1,6-naphthyridine-3-carboxylate and 4-cyclopropyl-1-ethyl-1H-indole-6-carbaldehyde.

Example 33

6-(1-((5-Cyclopropyl-2-ethoxy-6-(4-fluorophenyl)pyridin-3-yl)methyl)piperidin-4-yl)-2-ethyl-5-oxo-5,6,7,8-tetrahydro-1,6-naphthyridine-3-carboxylic acid

[Formula 50]

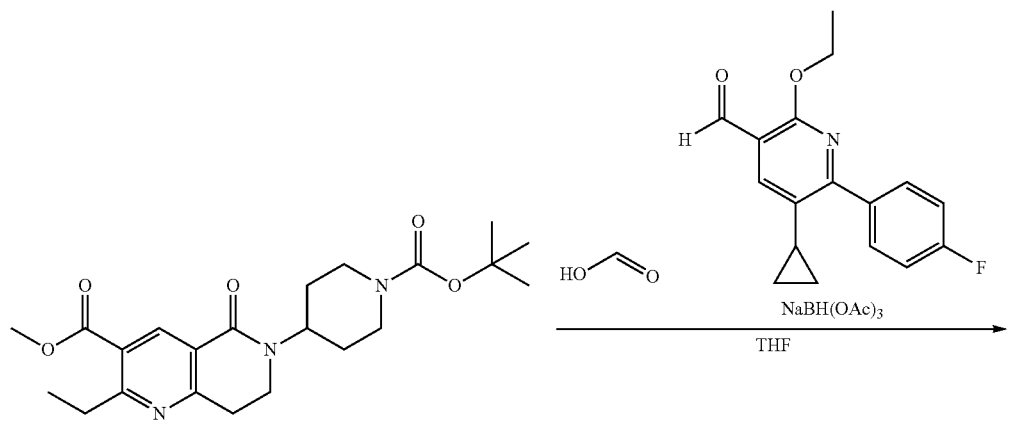

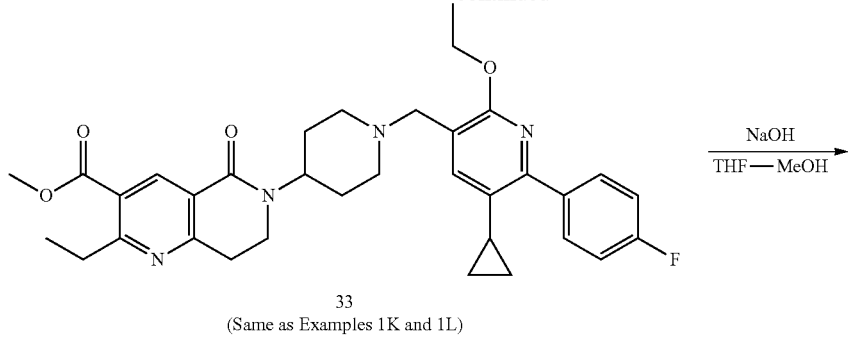

33
(Same as Examples 1K and 1L)

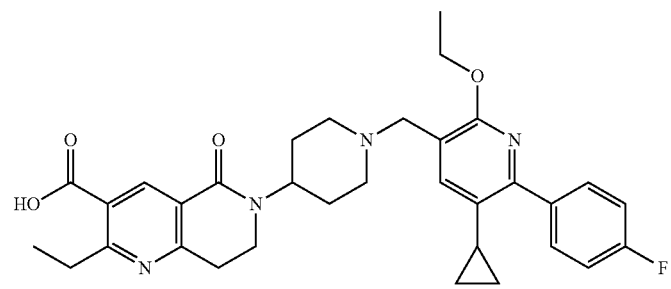

The title compound was obtained in the same way as in steps K and L of Example 1 using methyl 6-(1-(tert-butoxycarbonyl)piperidin-4-yl)-2-ethyl-5-oxo-5,6,7,8-tetrahydro-1,6-naphthyridine-3-carboxylate and 5-cyclopropyl-2-ethoxy-6-(4-fluorophenyl)nicotinaldehyde.

Example 34

6-(1-((2,6-Diethoxy-4'-fluorobiphenyl-4-yl)methyl)pyrrolidin-3-yl)-5-oxo-5,6,7,8-tetrahydro-1,6-naphthyridine-3-carboxylic acid

[Formula 51]

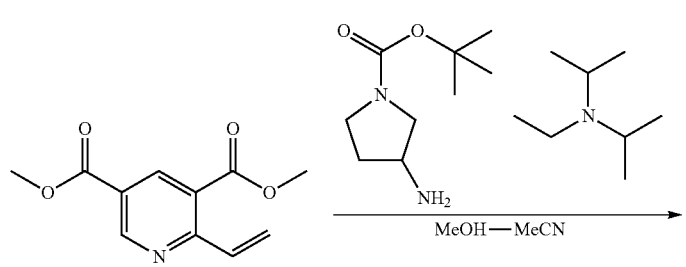

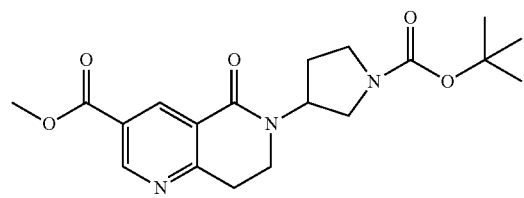

34A
(Same as Example 25B)

-continued

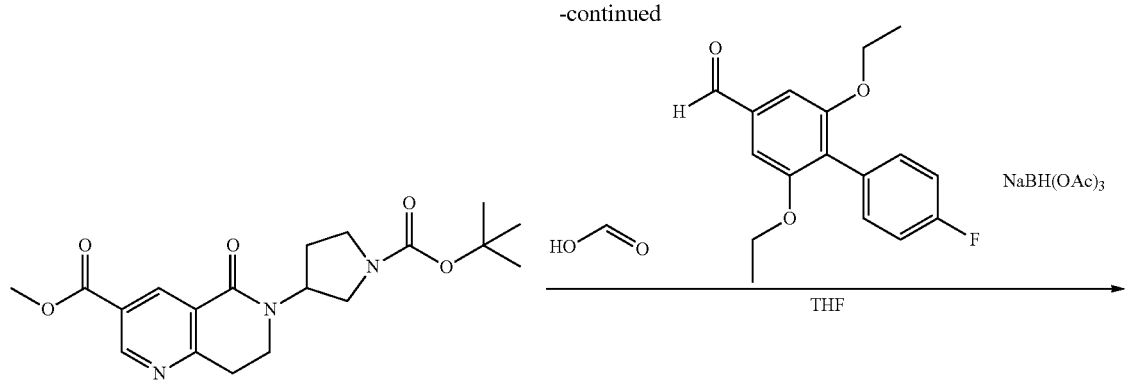

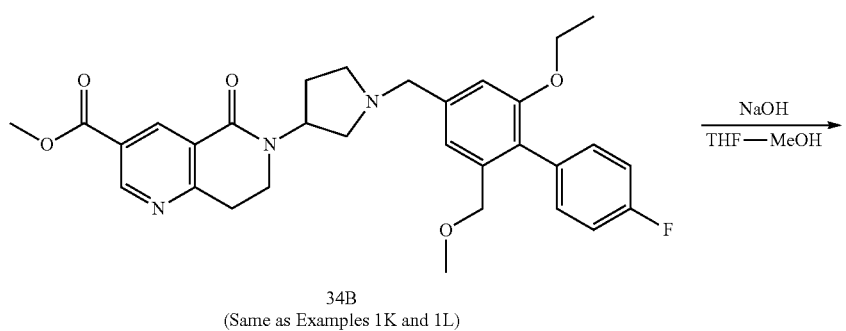

34B
(Same as Examples 1K and 1L)

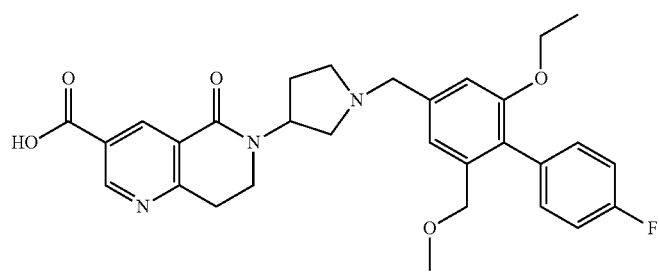

A) Methyl 6-(1-(tert-butoxycarbonyl)pyrrolidin-3-yl)-5-oxo-5,6,7,8-tetrahydro-1,6-naphthyridine-3-carboxylate The title compound was obtained in the same way as in step B of Example 25 using dimethyl 2-vinylpyridine-3,5-dicarboxylate and tert-butyl 3-aminopyrrolidine-1-carboxylate. MS (ESI+): [M+H]$^+$ 376.3.

B) 6-(1-((2,6-Diethoxy-4'-fluorobiphenyl-4-yl)methyl)pyrrolidin-3-yl)-5-oxo-5,6,7,8-tetrahydro-1,6-naphthyridine-3-carboxylic acid The title compound was obtained in the same way as in steps K and L of Example 1 using methyl 6-(1-(tert-butoxycarbonyl)pyrrolidin-3-yl)-5-oxo-5,6,7,8-tetrahydro-1,6-naphthyridine-3-carboxylate and 2,6-diethoxy-4'-fluorobiphenyl-4-carbaldehyde.

Example 35
6-(1-((2-Cyclopropyl-5-ethoxy-2',4'-difluorobiphenyl-4-yl)methyl)piperidin-4-yl)-5-oxo-2-propyl-5,6,7,8-tetrahydro-1,6-naphthyridine-3-carboxylic acid
[Formula 52]
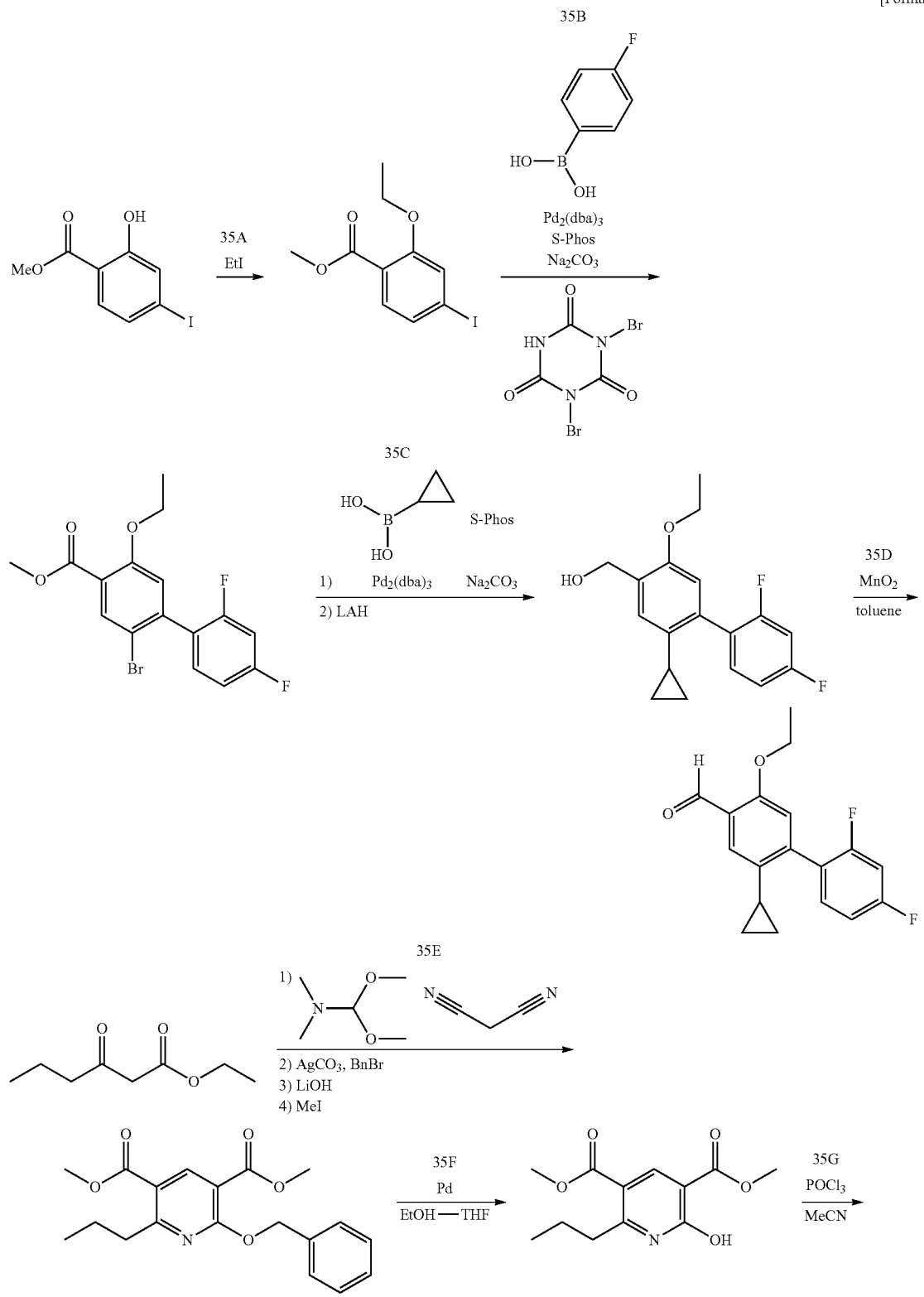

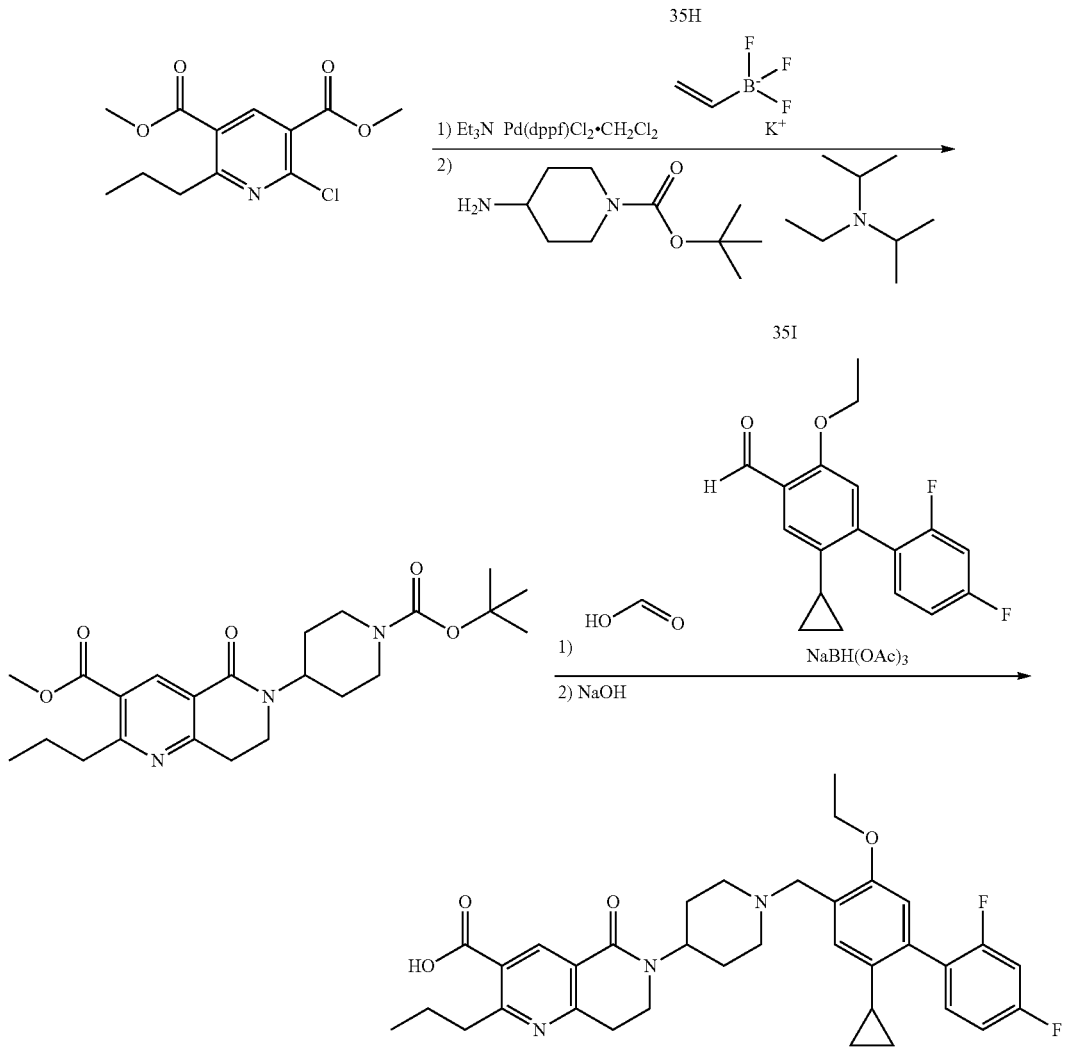

A) Methyl 2-ethoxy-4-iodobenzoate

Iodoethane (6.47 mL) was added to a mixture of methyl 2-hydroxy-4-iodobenzoate (15 g), potassium carbonate (14.9 g), and DMF (100 mL), and the resultant mixture was stirred at 70° C. for 1 hour in a nitrogen atmosphere. Water was added to the reaction mixture at room temperature, followed by extraction with ethyl acetate. The obtained organic layer was washed with saturated saline and dried over anhydrous magnesium sulfate, and then, the solvent was distilled off under reduced pressure. The obtained residue was purified by silica gel column chromatography (hexane/ethyl acetate) to obtain the title compound (16.5 g).

$^1$H NMR (300 MHz, CDCl$_3$) δ 1.46 (3H, t, J=7.0 Hz), 3.87 (3H, s), 4.09 (2H, q, J=6.9 Hz), 7.28-7.35 (2H, m), 7.48 (1H, d, J=8.1 Hz).

B) Methyl 2-bromo-5-ethoxy-2',4'-difluorobiphenyl-4-carboxylate

A mixture of methyl 2-ethoxy-4-iodobenzoate (16.5 g), dicyclohexyl(2',6'-dimethoxybiphenyl-2-yl)phosphine (3.32 g), a 2 M aqueous sodium carbonate solution (81 mL), tris(dibenzylideneacetone)dipalladium(0) (3.46 g), and toluene (100 mL) was stirred overnight at 100° C. in an argon atmosphere. The reaction mixture was allowed to cool to room temperature. Then, water was added thereto, and the mixture was filtered through celite, followed by extraction with ethyl acetate. The organic layer was washed with saturated saline and passed through a short silica gel (NH) column, and the solvent was distilled off under reduced pressure. The obtained residue was purified by silica gel column chromatography (hexane/ethyl acetate). Dibromoisocyanuric acid (12.5 g) was added to a mixture of the purified product and DMF (150 mL), and the resultant mixture was stirred at room temperature for 5 hours. Water was added to the reaction mixture, followed by extraction with ethyl acetate. The obtained organic layer was washed with saturated saline and dried over anhydrous magnesium sulfate, and then, the solvent was distilled off under reduced pressure. The obtained residue was purified by silica gel column chromatography (hexane/ethyl acetate) to obtain the title compound (22.6 g). This compound contained impurities, but was subjected to the subsequent reaction without being further purified.

$^1$H NMR (300 MHz, CDCl$_3$) δ 1.45 (3H, t, J=7.0 Hz), 3.91 (3H, s), 4.10 (2H, q, J=7.1 Hz), 6.74-7.03 (3H, m), 7.20-7.36 (1H, m), 8.06 (1H, s).

C) (2-Cyclopropyl-5-ethoxy-2',4'-difluorobiphenyl-4-yl)methanol

A mixture of methyl 2-bromo-5-ethoxy-2',4'-difluorobiphenyl-4-carboxylate (22.6 g), cyclopropylboronic acid (13.1 g), dicyclohexyl(2',6'-dimethoxybiphenyl-2-yl)phosphine (3.75 g), a 2 M aqueous sodium carbonate solution (91 mL), tris(dibenzylideneacetone)dipalladium(0) (3.91 g), and toluene (150 mL) was stirred overnight at 100° C. in an argon atmosphere. The reaction mixture was allowed to cool to room temperature, followed by extraction with ethyl acetate. The organic layer was washed with saturated saline and passed through a short silica gel (NH) column, and the solvent was distilled off under reduced pressure. The obtained residue was purified by silica gel column chromatography (hexane/ethyl acetate). A THF (50 mL) solution of the purified product was added to a THF (50 mL) suspension of lithium aluminum hydride (2.5 g) under ice cooling in a nitrogen atmosphere. After stirring at the same temperature as above for 30 minutes, water (2.5 mL) and a 15% aqueous sodium hydroxide solution (2.5 mL) were added thereto, and the mixture was stirred for 5 minutes. Water (7.5 mL) was further added to the reaction mixture, and the mixture was stirred for 30 minutes and then filtered. The filtrate was concentrated under reduced pressure. The obtained residue was purified by silica gel column chromatography (hexane/ethyl acetate) to obtain the title compound (16.1 g).

$^1$H NMR (300 MHz, CDCl$_3$) δ 0.51-0.59 (2H, m), 0.66-0.77 (2H, m), 1.37-1.46 (3H, m), 1.58-1.71 (1H, m), 2.39 (1H, t, J=6.6 Hz), 4.06 (2H, q, J=7.0 Hz), 4.69 (2H, d, J=6.5 Hz), 6.69 (1H, s), 6.84-7.00 (3H, m), 7.18-7.36 (1H, m).

D) 2-Cyclopropyl-5-ethoxy-2',4'-difluorobiphenyl-4-carbaldehyde

Manganese dioxide (45.9 g) was added to a toluene (80 mL) solution of (2-cyclopropyl-5-ethoxy-2',4'-difluorobiphenyl-4-yl)methanol (16.1 g), and the mixture was stirred at 60° C. for 1 hour in a nitrogen atmosphere. The reaction mixture was filtered, and then, the solvent was distilled off under reduced pressure. The obtained residue was purified by silica gel column chromatography (hexane/ethyl acetate) to obtain the title compound (12.8 g).

$^1$H NMR (300 MHz, CDCl$_3$) δ 0.57-0.64 (2H, m), 0.71-0.80 (2H, m), 1.46 (3H, t, J=7.0 Hz), 1.54-1.70 (1H, m), 4.13 (2H, q, J=7.0 Hz), 6.81 (1H, s), 6.87-7.04 (2H, m), 7.26-7.35 (1H, m), 7.48 (1H, s), 10.49 (1H, s).

E) Dimethyl 2-(benzyloxy)-6-propylpyridine-3,5-dicarboxylate

A mixed solution of ethyl butyrylacetate (40 g) and N,N-dimethylformamide dimethyl acetal (35.3 mL) in ethanol (80 mL) was stirred at 40° C. to 50° C. for 5 hours. The reaction mixture was cooled to 25° C., and then, triethylamine (3.52 mL) was added thereto. While the reaction mixture was cooled in ice to keep the temperature at 25° C. to 35° C., a mixture of malononitrile (18.4 g) and ethanol (160 mL) was added dropwise thereto, and the resultant mixture was stirred at room temperature for 16 hours. Acetic acid (17.4 mL) was added to the reaction mixture, and then, water (400 mL) was added thereto under heating at 50° C. The reaction mixture was cooled in ice, and then, the deposited solid was collected and washed with a water-ethanol mixed solvent. Benzyl bromide (38.9 mL) was added to a toluene (400 mL) suspension of the solid thus obtained and silver carbonate (83 g), and the mixture was stirred at room temperature for 2 days. The reaction mixture was filtered through celite, and then, the solvent was distilled off under reduced pressure. An ethyl acetate solution of the obtained residue was passed through a short silica gel (NH) column, and the solvent was distilled off under reduced pressure. Lithium hydroxide monohydrate (98 g) was added to a mixture of the obtained residue in ethanol (250 mL) and water (250 mL), and the resultant mixture was stirred over weekend at 100° C. in a nitrogen atmosphere. The reaction mixture was neutralized with hydrochloric acid at 0° C., followed by extraction with ethyl acetate twice. The obtained organic layer was dried over anhydrous magnesium sulfate, and then, the solvent was distilled off under reduced pressure. Potassium carbonate (113 g) and iodomethane (51.1 mL) were added to a mixture of the obtained residue and DMF (100 mL), and the resultant mixture was stirred at 50° C. for 1 hour. The reaction mixture was allowed to cool to room temperature and then poured to water, followed by extraction with ethyl acetate. The obtained organic layer was washed with saturated saline and dried over anhydrous magnesium sulfate, and then, the solvent was distilled off under reduced pressure. The obtained residue was purified by silica gel column chromatography (hexane/ethyl acetate) to obtain the title compound (53.8 g).

$^1$H NMR (300 MHz, CDCl$_3$) δ 0.98 (3H, t, J=7.4 Hz), 1.67-1.83 (2H, m), 3.08-3.18 (2H, m), 3.89 (3H, s), 3.91 (3H, s), 5.59 (2H, s), 7.27-7.42 (3H, m), 7.49-7.55 (2H, m), 8.72 (1H, s).

F) Dimethyl 2-hydroxy-6-propylpyridine-3,5-dicarboxylate

A mixture of dimethyl 2-(benzyloxy)-6-propylpyridine-3,5-dicarboxylate (53.8 g), 10% palladium carbon (containing 55% water, 20 g), THF (50 mL), and ethanol (50 mL) was stirred at room temperature for 1 hour in a hydrogen atmosphere. The catalyst was filtered off, and then, the obtained filtrate was concentrated under reduced pressure. The obtained solid was washed with diethyl ether to obtain the title compound (35.4 g).

$^1$H NMR (300 MHz, CDCl$_3$) δ 1.07 (3H, t, J=7.3 Hz), 1.69-1.87 (2H, m), 2.98-3.24 (2H, m), 3.88 (3H, s), 3.91 (3H, s), 8.82 (1H, s), 12.47 (1H, brs).

G) Dimethyl 2-chloro-6-propylpyridine-3,5-dicarboxylate

Phosphorus oxychloride (8.10 mL) was added to a mixture of dimethyl 2-hydroxy-6-propylpyridine-3,5-dicarboxylate (11 g) and acetonitrile (50 mL), and the resultant mixture was stirred overnight at 90° C. in a nitrogen atmosphere. The reaction mixture was allowed to cool to room temperature, and then, a saturated aqueous solution of sodium bicarbonate was added thereto, followed by extraction with ethyl acetate. The obtained organic layer was dried over anhydrous magnesium sulfate, and then, the solvent was distilled off under reduced pressure. The obtained residue was purified by silica gel column chromatography (hexane/ethyl acetate) to obtain the title compound (11.8 g).

$^1$H NMR (300 MHz, CDCl$_3$) δ 1.01 (3H, t, J=7.4 Hz), 1.65-1.85 (2H, m), 3.08-3.24 (2H, m), 3.94 (3H, s), 3.97 (3H, s), 8.66 (1H, s).

H) Methyl 6-(1-(tert-butoxycarbonyl)piperidin-4-yl)-5-oxo-2-propyl-5,6,7,8-tetrahydro-1,6-naphthyridine-3-carboxylate A dichloromethane adduct of (1,1'-bis(diphenylphosphino)ferrocene)dichloropalladium(II) (1.9 g) was added to a mixture of dimethyl 2-chloro-6-propylpyridine-3,5-dicarboxylate (11.8 g), potassium vinyl trifluoroborate (10.2 g), triethylamine (12.1 mL), and ethanol (50 mL), and the resultant mixture was stirred at 95° C. for 1 hour in an argon atmosphere. The solvent in the reaction mixture was distilled off under reduced pressure, and the obtained residue was purified by silica gel column chromatography (hexane/ethyl acetate). A mixture of the obtained purified product, tert-butyl 4-aminopiperidine-1-carboxylate (13.1 g), N,N'-diisopropylethylamine (11.4 mL), and DMA (80 mL) was stirred at 140° C. for 4 hours. The reaction mixture was allowed to cool to room temperature and then poured to water, followed by extraction with ethyl acetate twice. The obtained organic layer was washed with saturated saline and passed through a short silica gel (NH) column, and the solvent was distilled off under reduced pressure. The obtained residue was purified by silica gel column chromatography (hexane/ethyl acetate) to obtain the title compound (16.5 g).

$^1$H NMR (300 MHz, CDCl$_3$) δ 1.01 (3H, t, J=7.3 Hz), 1.48 (9H, s), 1.60-1.82 (6H, m), 2.72-2.99 (2H, m), 3.08-3.25 (4H, m), 3.54 (2H, t, J=6.6 Hz), 3.93 (3H, s), 4.19-4.35 (2H, m), 4.73-4.90 (1H, m), 8.76 (1H, s).

I) 6-(1-((2-Cyclopropyl-5-ethoxy-2',4'-difluorobiphenyl-4-yl)methyl)piperidin-4-yl)-5-oxo-2-propyl-5,6,7,8-tetrahydro-1,6-naphthyridine-3-carboxylic acid Methyl 6-(1-(tert-butoxycarbonyl)piperidin-4-yl)-5-oxo-2-propyl-5,6,7,8-tetrahydro-1,6-naphthyridine-3-carboxylate (15.2 g) was added to formic acid (50 mL), and the mixture was stirred at 60° C. for 30 minutes. Then, the solvent was distilled off under reduced pressure. Toluene was added to the obtained residue, and the solvent was further distilled off under reduced pressure. 2-Cyclopropyl-5-ethoxy-2',4'-difluorobiphenyl-4-carbaldehyde (10.6 g) was added to a mixture of the obtained residue and THF (60 mL), and the resultant mixture was stirred for 10 minutes. Then, sodium triacetoxy borohydride (11.2 g) was added thereto, and the mixture was stirred overnight at room temperature. A saturated aqueous solution of sodium bicarbonate was added to the reaction mixture, followed by extraction with ethyl acetate twice. The obtained organic layer was dried over anhydrous magnesium sulfate, and then, the solvent was distilled off under reduced pressure. The obtained residue was purified by silica gel column chromatography (hexane/ethyl acetate/methanol). A 2 M aqueous sodium hydroxide solution (70 mL) was added at room temperature to a methanol (30 mL)-THF (30 mL) solution of the obtained purified product, and the mixture was stirred at 50° C. for 1 hour. The reaction mixture was neutralized with 2 M hydrochloric acid at room temperature. Then, water was added thereto, and the mixture was stirred at 100° C. for 5 minutes. After cooling to 0° C., the deposited solid was collected by filtration and washed with water and diethyl ether. The obtained solid was recrystallized (DMSO/ethanol) to obtain the title compound (15.0 g).

$^1$H NMR (300 MHz, DMSO-d$_6$) δ 0.37-0.56 (2H, m), 0.68-0.77 (2H, m), 0.92 (3H, t, J=7.4 Hz), 1.31 (3H, t, J=6.9 Hz), 1.53-1.74 (5H, m), 1.75-1.93 (2H, m), 2.17 (2H, t, J=11.9 Hz), 2.98 (2H, d, J=11.3 Hz), 3.03-3.14 (4H, m), 3.50-3.63 (4H, m), 4.01 (2H, q, J=7.0 Hz), 4.34-4.51 (1H, m), 6.76 (1H, s), 6.99 (1H, s), 7.18 (1H, s), 7.28-7.38 (1H, m), 7.40-7.51 (1H, m), 8.47 (1H, s)

Example 36

6-(1-((2-Cyclopropyl-6-ethoxy-4'-fluorobiphenyl-4-yl)methyl)piperidin-4-yl)-5-oxo-2-propyl-5,6,7,8-tetrahydro-1,6-naphthyridine-3-carboxylic acid

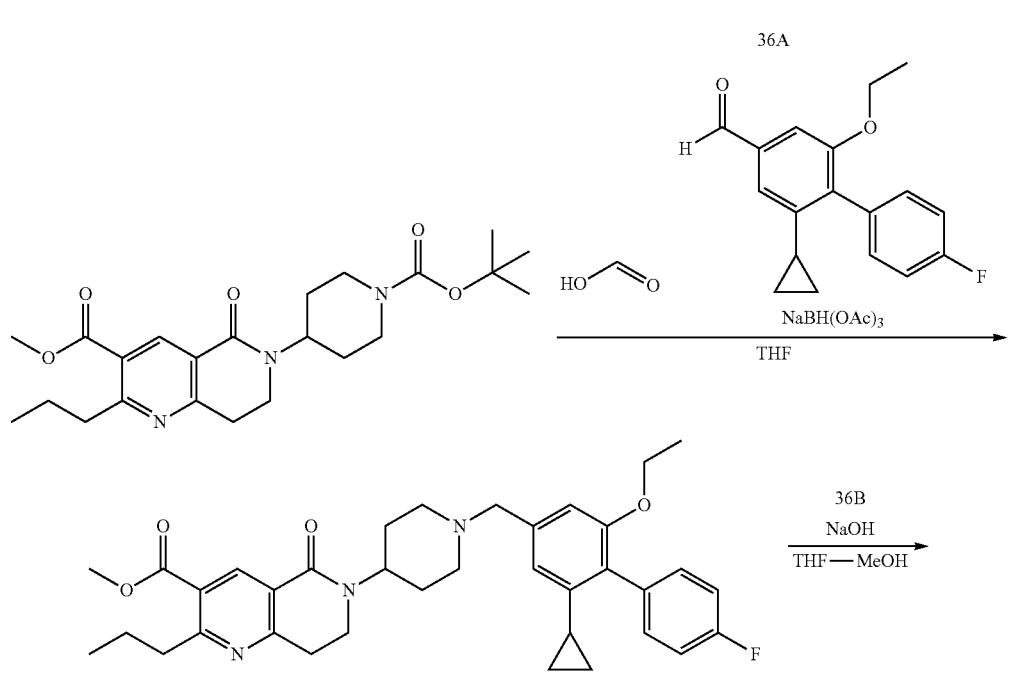

[Formula 53]

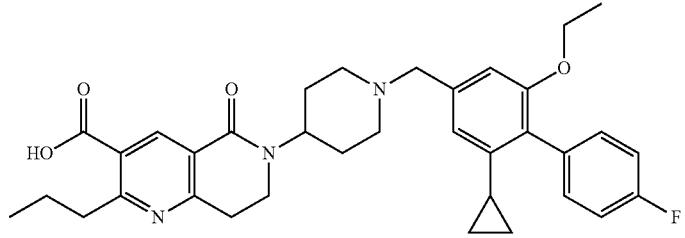

A) Methyl 6-(1-((2-cyclopropyl-6-ethoxy-4'-fluoro-biphenyl-4-yl)methyl)piperidin-4-yl)-5-oxo-2-propyl-5,6,7,8-tetrahydro-1,6-naphthyridine-3-carboxylate Methyl 6-(1-(tert-butoxycarbonyl)piperidin-4-yl)-5-oxo-2-propyl-5,6,7,8-tetrahydro-1,6-naphthyridine-3-carboxylate (530 mg) was added to formic acid (5 mL), and the mixture was stirred at 60° C. for 30 minutes. Then, the solvent was distilled off under reduced pressure. Toluene was added to the obtained residue, and the solvent was further distilled off under reduced pressure. 2-Cyclopropyl-6-ethoxy-4'-fluorobiphenyl-4-carbaldehyde (349 mg) was added to a mixture of the obtained residue and THF (5 mL), and the resultant mixture was stirred for 10 minutes. Then, sodium triacetoxy borohydride (390 mg) was added thereto, and the mixture was stirred at room temperature for 2 hours. A saturated aqueous solution of sodium bicarbonate was added to the reaction mixture, followed by extraction with ethyl acetate twice. The obtained organic layer was dried over anhydrous magnesium sulfate, and then, the solvent was distilled off under reduced pressure. The obtained residue was purified by silica gel column chromatography (hexane/ethyl acetate/methanol) to obtain the title compound (730 mg).

MS (ESI+): [M+H]⁺ 600.5.

B) 6-(1-((2-Cyclopropyl-6-ethoxy-4'-fluorobiphenyl-4-yl)methyl)piperidin-4-yl)-5-oxo-2-propyl-5,6,7,8-tetrahydro-1,6-naphthyridine-3-carboxylic acid A 2 M aqueous sodium hydroxide solution (1.50 mL) was added at room temperature to a methanol (2 mL)-THF (2 mL) solution of methyl 6-(1-((2-cyclopropyl-6-ethoxy-4'-fluoro-biphenyl-4-yl)methyl)piperidin-4-yl)-5-oxo-2-propyl-5,6,7,8-tetrahydro-1,6-naphthyridine-3-carboxylate (730 mg), and the mixture was stirred at 50° C. for 1 hour. The reaction mixture was neutralized with 6 M hydrochloric acid at room temperature. Then, ethyl acetate was added thereto, and the mixture was concentrated. The deposited solid was collected by filtration and washed with diethyl ether. The obtained solid was recrystallized (DMSO/ethanol) to obtain the title compound (486 mg).

¹H NMR (300 MHz, DMSO-$d_6$) δ 0.49-0.62 (2H, m), 0.66-0.77 (2H, m), 0.92 (3H, t, J=7.4 Hz), 1.12 (3H, t, J=6.9 Hz), 1.37-1.73 (5H, m), 1.75-1.94 (2H, m), 2.11 (2H, t, J=12.2 Hz), 2.96 (2H, d, J=11.1 Hz), 3.02-3.15 (4H, m, J=6.2 Hz), 3.50 (2H, s), 3.58 (2H, s), 3.93 (2H, q, J=6.9 Hz), 4.37-4.53 (1H, m), 6.49 (1H, s), 6.85 (1H, s), 7.16-7.32 (4H, m), 8.48 (1H, s).

Example 37

6-(1-((2-Cyclopropyl-4'-fluoro-5-isopropoxybiphenyl-4-yl)methyl)piperidin-4-yl)-5-oxo-2-propyl-5,6,7,8-tetrahydro-1,6-naphthyridine-3-carboxylic acid

[Formula 54]

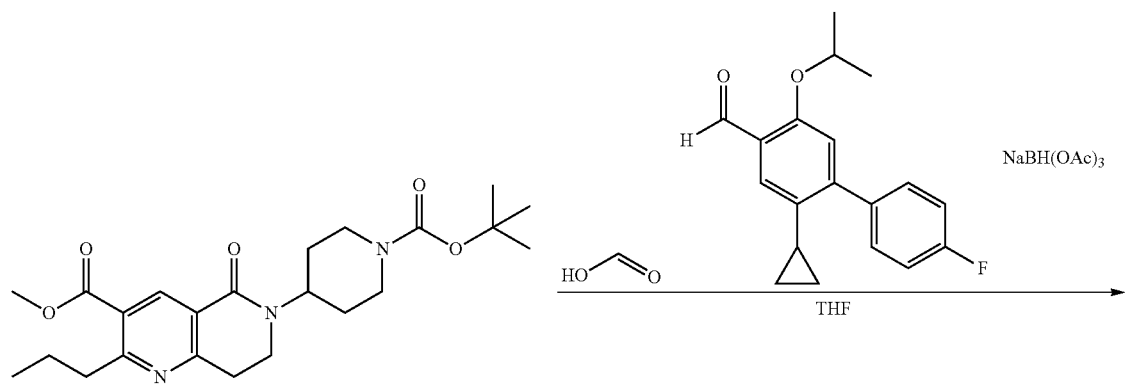

-continued

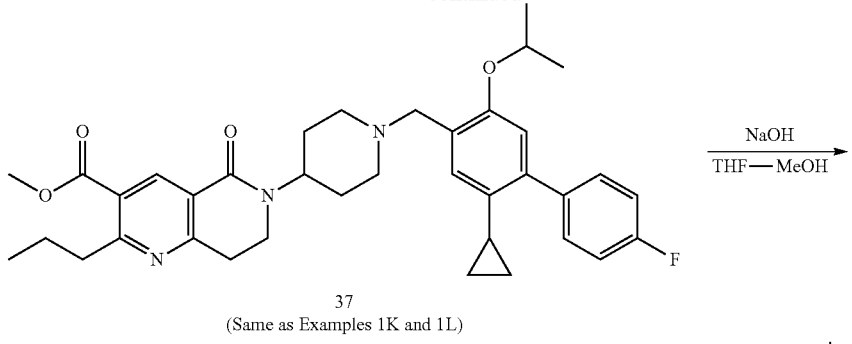

37
(Same as Examples 1K and 1L)

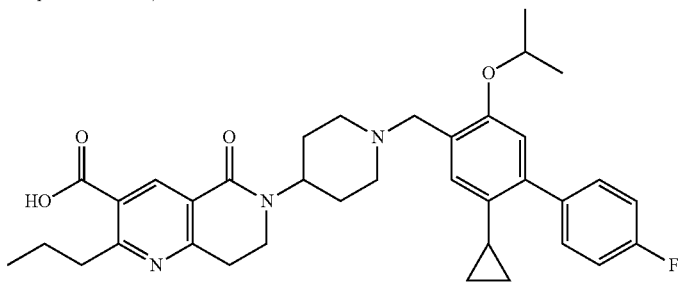

The title compound was obtained in the same way as in steps K and L of Example 1 using methyl 6-(1-(tert-butoxycarbonyl)piperidin-4-yl)-5-oxo-2-propyl-5,6,7,8-tetrahydro-1,6-naphthyridine-3-carboxylate and 2-cyclopropyl-4'-fluoro-5-isopropoxybiphenyl-4-carbaldehyde.

Example 38

6-(1-((2,6-Diethoxy-4'-fluorobiphenyl-4-yl)methyl)piperidin-4-yl)-5-oxo-2-propyl-5,6,7,8-tetrahydro-1,6-naphthyridine-3-carboxylic acid

[Formula 55]

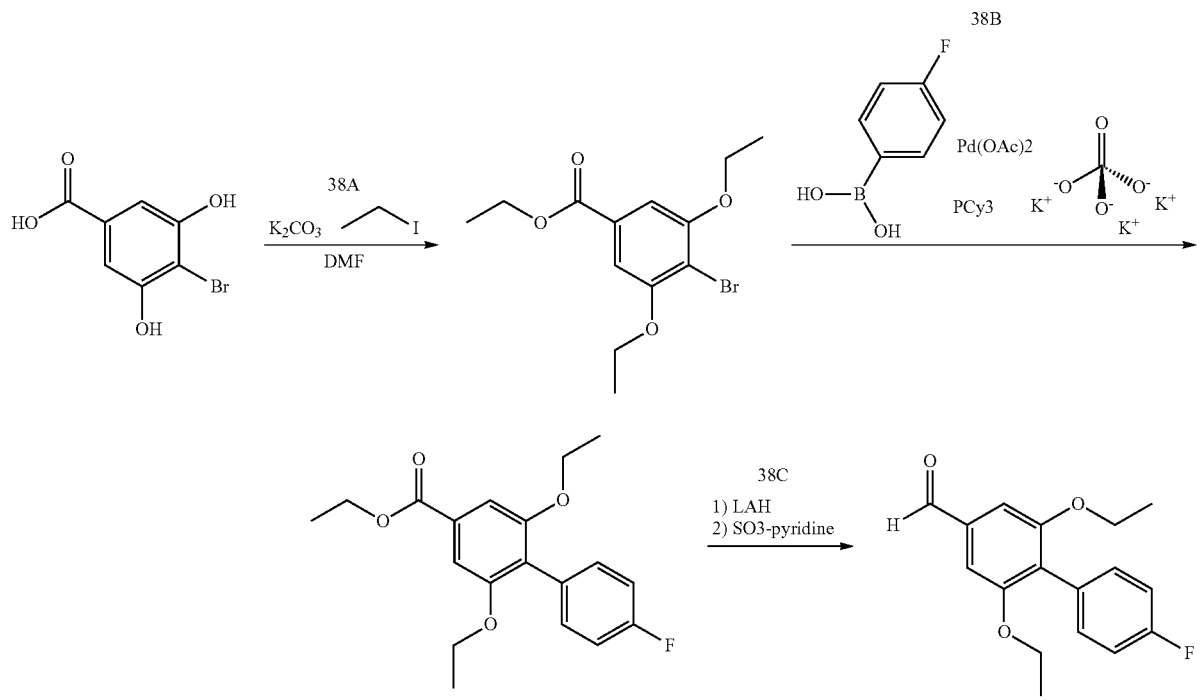

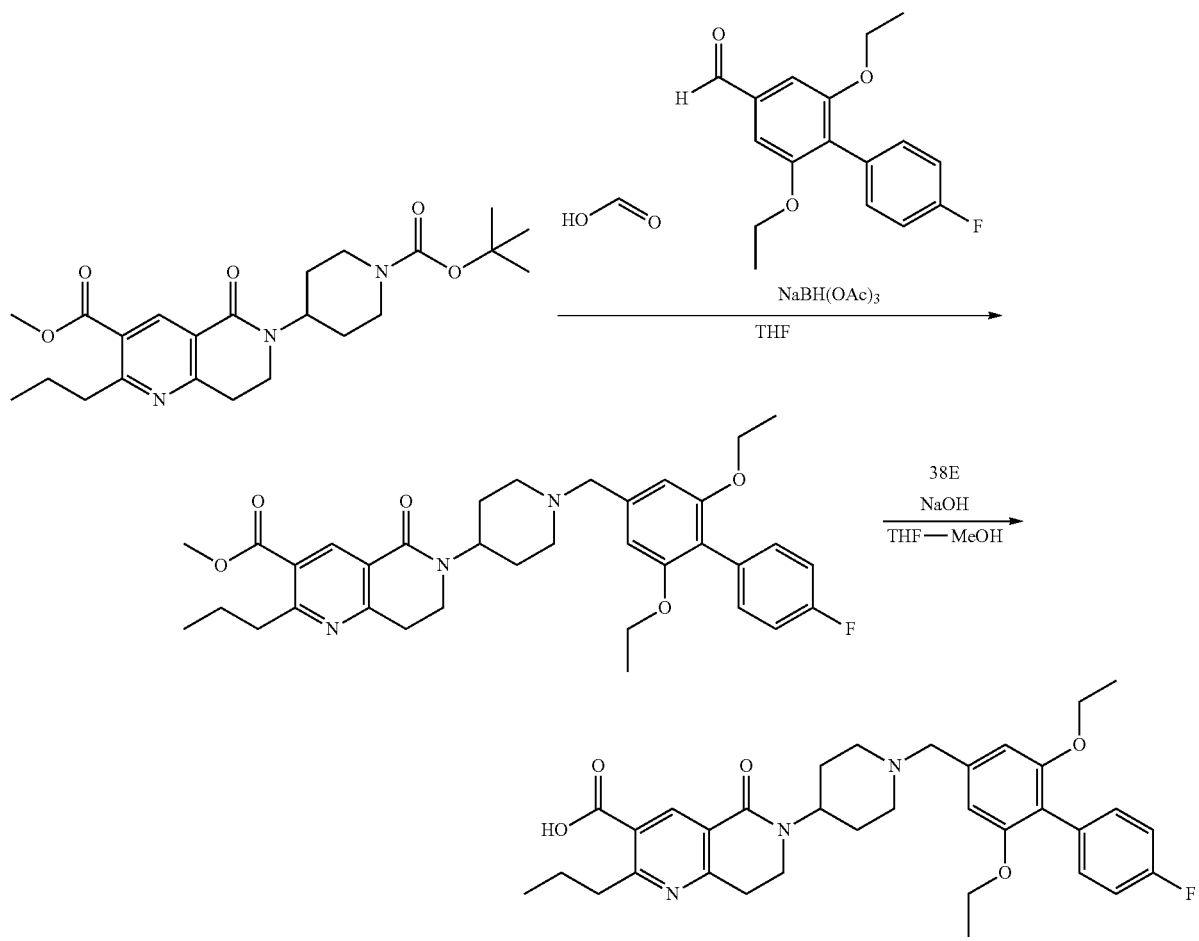

A) Ethyl 4-bromo-3,5-diethoxybenzoate

Potassium carbonate (89.0 g) and iodoethane (60.1 mL) were added to a DMF (300 mL) solution of 4-bromo-3,5-dihydroxybenzoic acid (50.0 g), and the mixture was stirred at 60° C. for 2 hours. The reaction mixture was allowed to cool to room temperature, and then, water was added thereto, followed by extraction with ethyl acetate. The organic layer was washed with saturated saline. The obtained organic layer was applied to silica gel chromatography (NH, ethyl acetate), and then, the solvent was distilled off under reduced pressure. The obtained solid was washed with diethyl ether and hexane to obtain the title compound (55.8 g).

$^1$H NMR (300 MHz, CDCl$_3$) δ 1.40 (3H, t, J=7.1 Hz), 1.49 (6H, t, J=7.0 Hz), 4.17 (4H, q, J=7.0 Hz), 4.38 (2H, q, J=7.1 Hz), 7.21 (2H, s).

B) Ethyl 2,6-diethoxy-4'-fluorobiphenyl-4-carboxylate

Palladium acetate (1.98 g), tripotassium phosphate (112 g), (4-fluorophenyl)boronic acid (43.1 g), and tricyclohexylphosphine (20% toluene solution, 31.2 mL) were added to a mixture of ethyl 4-bromo-3,5-diethoxybenzoate (55.8 g) in toluene (300 mL) and water (150 mL), and the resultant mixture was heated with stirring overnight at 90° C. in an argon atmosphere. The reaction mixture was allowed to cool to room temperature, and then, water was added thereto, followed by extraction with ethyl acetate. The organic layer was washed with water and saturated saline in this order. The organic layer was dried over anhydrous magnesium sulfate, and then, the solvent was distilled off under reduced pressure. The obtained residue was purified by silica gel column chromatography (hexane/ethyl acetate) to obtain the title compound (50.7 g).

$^1$H NMR (300 MHz, CDCl$_3$) δ 1.27 (6H, t, J=6.9 Hz), 1.41 (3H, t, J=7.1 Hz), 4.03 (4H, q, J=6.9 Hz), 4.40 (2H, q, J=7.1 Hz), 6.99-7.14 (2H, m), 7.28-7.41 (4H, m).

C) 2,6-Diethoxy-4'-fluorobiphenyl-4-carbaldehyde

A THF (200 mL) solution of ethyl 2,6-diethoxy-4'-fluorobiphenyl-4-carboxylate (50.7 g) was added to a THF (200 mL) suspension of lithium aluminum hydride (4.34 g) under ice cooling. After stirring at the same temperature as above for 30 minutes, water (4.5 mL) and a 1 M aqueous sodium hydroxide solution (4.5 mL) were added thereto, and the mixture was stirred for 5 minutes. Water (13.5 mL) was further added thereto. The reaction mixture was stirred for 1 hour and then filtered through celite, and the filtrate was concentrated under reduced pressure. A sulfur trioxide-pyridine complex (48.6 g) was added to a DMSO (250 mL) solution of the obtained residue and triethylamine (63.8 mL), and the mixture was stirred at room temperature for 30 minutes. Water (450 mL) was added to the reaction mixture, and the deposited solid was collected by filtration. The obtained solid was recrystallized (ethanol/water) to obtain the title compound (36.9 g).

$^1$H NMR (300 MHz, CDCl$_3$) δ 1.29 (6H, t, J=7.0 Hz), 4.06 (4H, q, J=6.9 Hz), 7.08 (2H, t, J=8.9 Hz), 7.13 (2H, s), 7.34 (2H, dd, J=9.0, 5.6 Hz), 9.94 (1H, s).

D) Methyl 6-(1-((2,6-diethoxy-4'-fluorobiphenyl-4-yl)methyl)piperidin-4-yl)-5-oxo-2-propyl-5,6,7,8-tetrahydro-1,6-naphthyridine-3-carboxylate Methyl 6-(1-(tert-butoxycarbonyl)piperidin-4-yl)-5-oxo-2-propyl-5,6,7,8-tetrahydro-1,6-naphthyridine-3-carboxylate (500 mg) was added to formic acid (5 mL), and the mixture was stirred at 60° C. for 30 minutes. Then, the solvent was distilled off under reduced pressure. Toluene was added to the obtained residue, and the solvent was further distilled off under reduced pressure. 2,6-Diethoxy-4'-fluorobiphenyl-4-carbaldehyde (334 mg) was added to a mixture of the obtained residue and THF (5 mL), and the resultant mixture was stirred for 10 minutes. Then, sodium triacetoxy borohydride (368 mg) was added thereto, and the mixture was stirred at room temperature for 2 hours. A saturated aqueous solution of sodium bicarbonate was added to the reaction mixture, followed by extraction with ethyl acetate twice. The obtained organic layer was dried over anhydrous magnesium sulfate, and then, the solvent was distilled off under reduced pressure. The obtained residue was purified by silica gel column chromatography (hexane/ethyl acetate/methanol) to obtain the title compound (565 mg).

MS (ESI+): [M+H]$^+$ 604.5

E) 6-(1-((2,6-Diethoxy-4'-fluorobiphenyl-4-yl)methyl)piperidin-4-yl)-5-oxo-2-propyl-5,6,7,8-tetrahydro-1,6-naphthyridine-3-carboxylic acid A 2 M aqueous sodium hydroxide solution (1.50 mL) was added at room temperature to a methanol (2 mL)-THF (2 mL) solution of methyl 6-(1-((2,6-diethoxy-4'-fluorobiphenyl-4-yl)methyl)piperidin-4-yl)-5-oxo-2-propyl-5,6,7,8-tetrahydro-1,6-naphthyridine-3-carboxylate (560 mg), and the mixture was stirred at 50° C. for 1 hour. The reaction mixture was neutralized with 6 M hydrochloric acid at room temperature. Then, ethyl acetate was added thereto, and the mixture was concentrated. The deposited solid was collected by filtration and washed with diethyl ether. The obtained solid was recrystallized (DMSO/ethanol/hexane) to obtain the title compound (141 mg).

$^1$H NMR (300 MHz, DMSO-d$_6$) δ 0.92 (3H, t, J=7.4 Hz), 1.16 (6H, t, J=6.9 Hz), 1.50-1.73 (4H, m, J=7.5 Hz), 1.74-1.95 (2H, m), 2.05-2.20 (2H, m), 2.91-3.15 (6H, m, J=7.4 Hz), 3.49-3.64 (4H, m), 3.96 (4H, q, J=7.0 Hz), 4.34-4.55 (1H, m, J=6.5 Hz), 6.68 (2H, s), 7.10-7.20 (2H, m), 7.25-7.35 (2H, m, J=5.8 Hz), 8.48 (1H, s).

Example 39

6-(1-((2-Cyclopropyl-3',4'-difluoro-5-isopropoxybiphenyl-4-yl)methyl)piperidin-4-yl)-5-oxo-2-propyl-5,6,7,8-tetrahydro-1,6-naphthyridine-3-carboxylic acid

[Formula 56]

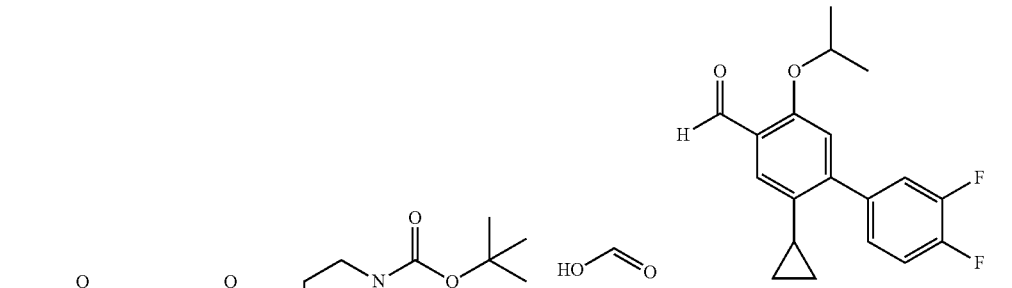

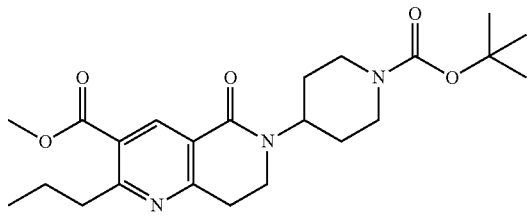

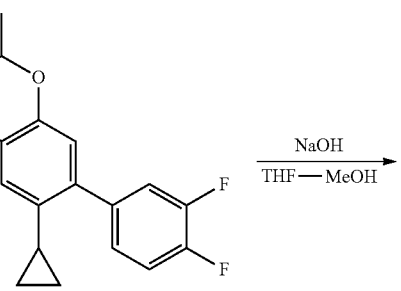

39
(Same as Examples 1K and 1L)

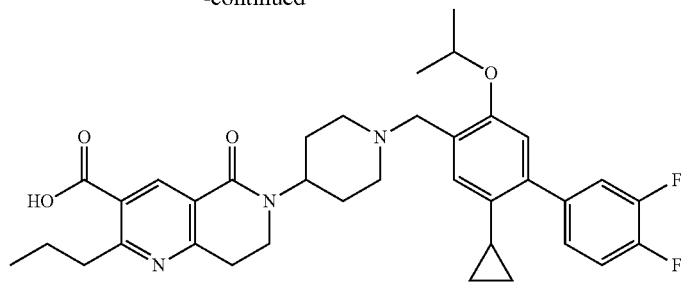

The title compound was obtained in the same way as in steps K and L of Example 1 using methyl 6-(1-(tert-butoxycarbonyl)piperidin-4-yl)-5-oxo-2-propyl-5,6,7,8-tetrahydro-1,6-naphthyridine-3-carboxylate and 2-cyclopropyl-3',4'-difluoro-5-isopropoxybiphenyl-4-carbaldehyde.

Example 40

6-(1-((2-Cyclopropyl-2',4'-difluoro-5-isopropoxybiphenyl-4-yl)methyl)piperidin-4-yl)-5-oxo-2-propyl-5,6,7,8-tetrahydro-1,6-naphthyridine-3-carboxylic acid

[Formula 57]

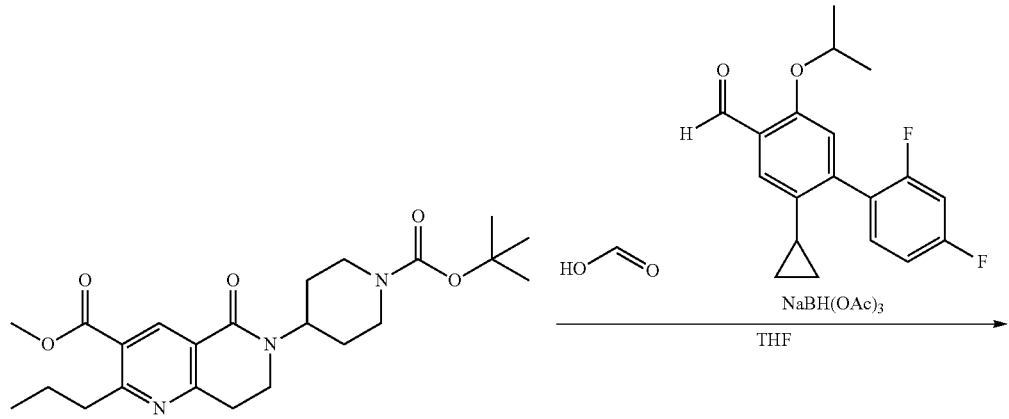

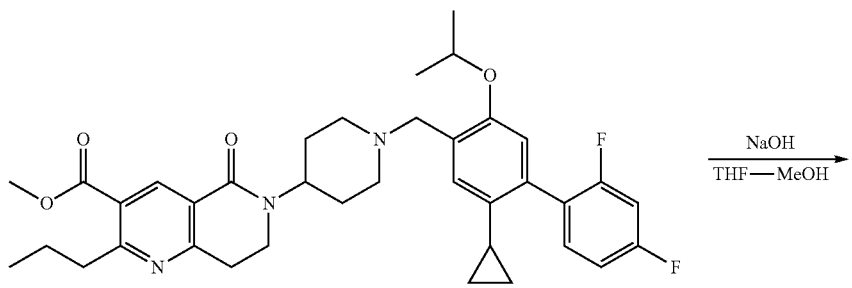

40
(Same as Examples 1K and 1L)

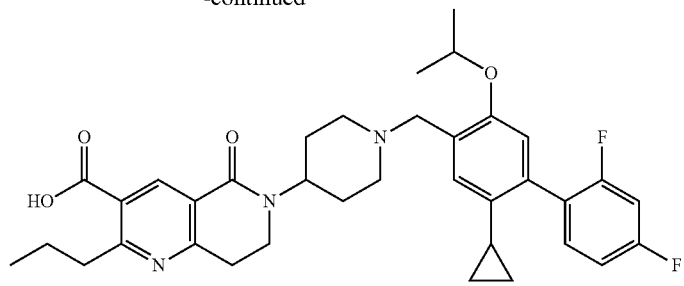

The title compound was obtained in the same way as in steps K and L of Example 1 using methyl 6-(1-(tert-butoxycarbonyl)piperidin-4-yl)-5-oxo-2-propyl-5,6,7,8-tetrahydro-1,6-naphthyridine-3-carboxylate and 2-cyclopropyl-2',4'-difluoro-5-isopropoxybiphenyl-4-carbaldehyde.

Example 41

6-(1-(4-Cyclobutyl-5-cyclopropyl-2-isopropoxybenzyl)piperidin-4-yl)-5-oxo-2-propyl-5,6,7,8-tetrahydro-1,6-naphthyridine-3-carboxylic acid

[Formula 58]

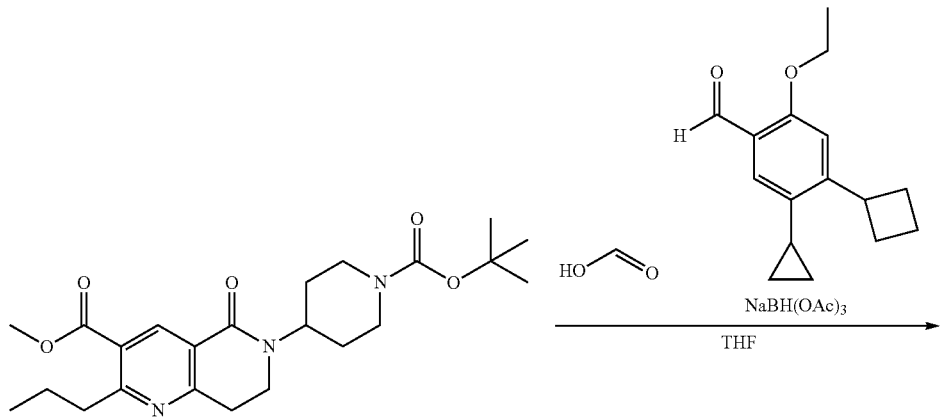

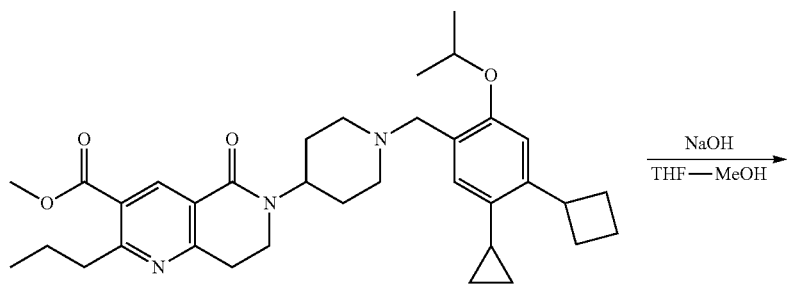

41
(Same as Examples 1K and 1L)

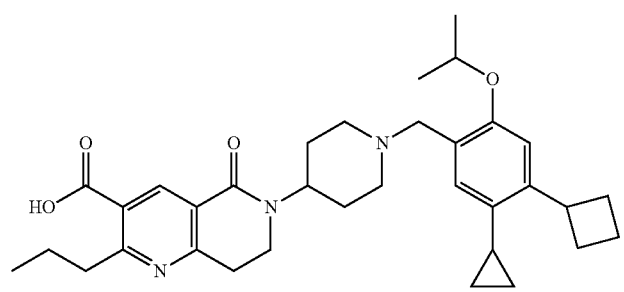

181

The title compound was obtained in the same way as in steps K and L of Example 1 using methyl 6-(1-(tert-butoxycarbonyl)piperidin-4-yl)-5-oxo-2-propyl-5,6,7,8-tetrahydro-1,6-naphthyridine-3-carboxylate and 4-cyclobutyl-5-cyclopropyl-2-isopropoxybenzaldehyde.

182

Example 42

6-(1-((2-Cyclopropyl-4'-fluoro-5-methoxybiphenyl-4-yl)methyl)piperidin-4-yl)-5-oxo-2-propyl-5,6,7,8-tetrahydro-1,6-naphthyridine-3-carboxylic acid

[Formula 59]

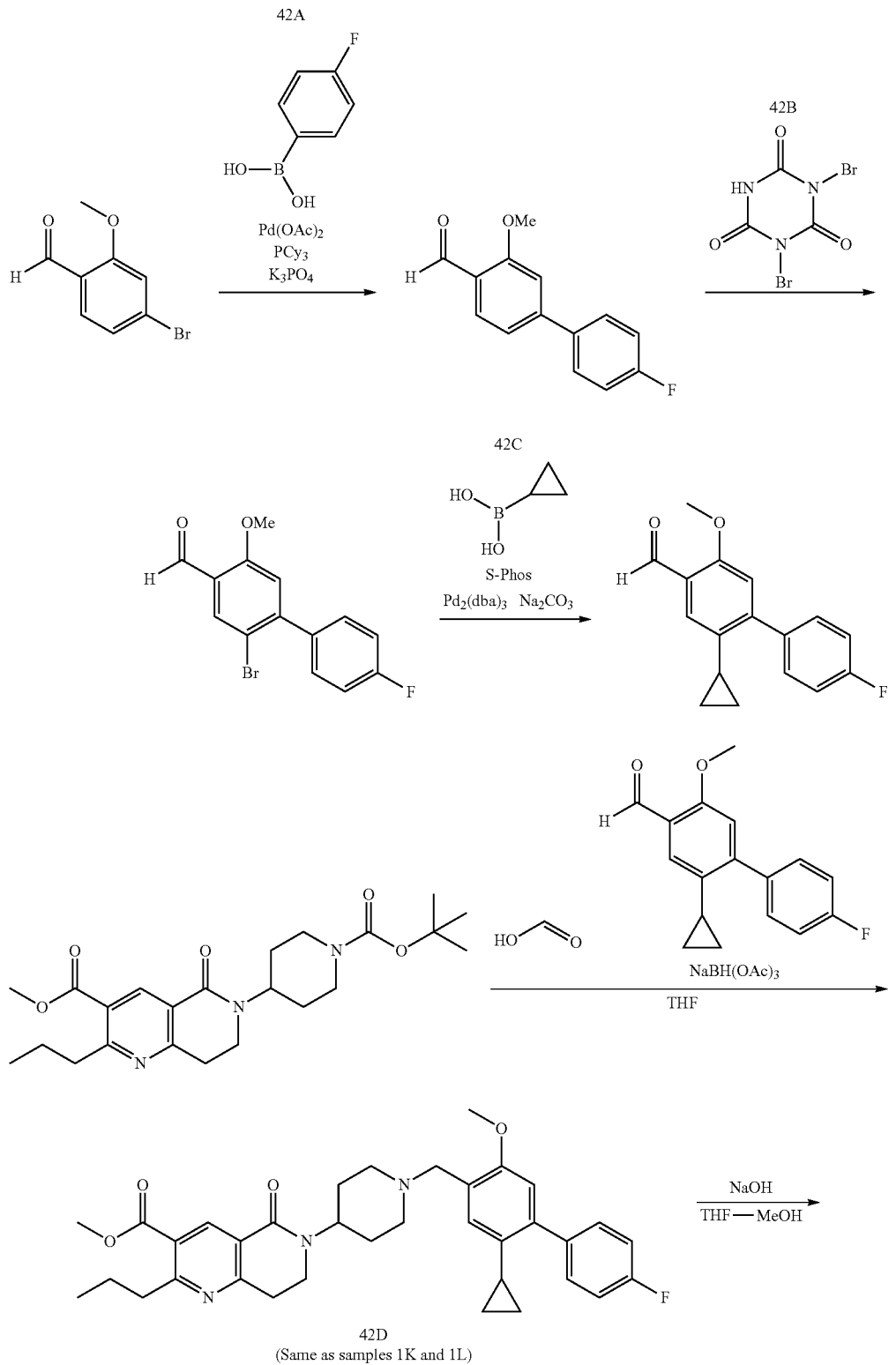

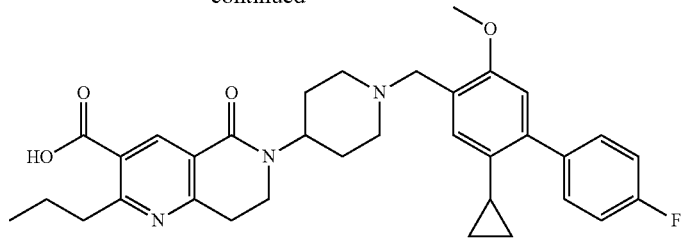

A) 4'-Fluoro-3-methoxybiphenyl-4-carbaldehyde

Palladium acetate (2.61 g) was added to a mixture of 4-bromo-2-methoxybenzaldehyde (25.0 g), tripotassium phosphate (74.0 g), (4-fluorophenyl)boronic acid (24.4 g), tricyclohexylphosphine (20% toluene solution, 41.3 mL), toluene (250 mL), and water (125 mL), and the resultant mixture was stirred at 90° C. for 3 hours in an argon atmosphere. The reaction mixture was allowed to cool to room temperature, and then, the organic layer was separated. The aqueous layer was subjected to extraction with ethyl acetate. Combined organic layers were washed with water and saturated saline in this order and dried over anhydrous magnesium sulfate, and then, the solvent was distilled off under reduced pressure. The obtained residue was crystallized from methanol (150 mL) to obtain the title compound (16.0 g).

$^1$H NMR (300 MHz, DMSO-$d_6$) δ 4.03 (3H, s), 7.31-7.41 (3H, m), 7.45 (1H, d, J=1.3 Hz), 7.77 (1H, d, J=8.0 Hz), 7.82-7.91 (2H, m), 10.37 (1H, s).

B) 2-Bromo-4'-fluoro-5-methoxybiphenyl-4-carbaldehyde

Dibromoisocyanuric acid (10.6 g) was added at 15° C. to 30° C. to a DMF (90 mL) solution of 4'-fluoro-3-methoxybiphenyl-4-carbaldehyde (16.0 g), and the mixture was stirred for 40 minutes. Then, water (30 mL) was added thereto, and the mixture was further stirred for 1 hour. The deposited solid was collected by filtration and washed with a mixed solution of DMF (15 mL) and water (15 mL) and water (30 mL) in this order to obtain the title compound (20.6 g).

$^1$H NMR (300 MHz, DMSO-$d_6$) δ 3.96 (3H, s), 7.25 (1H, s), 7.29-7.40 (2H, m), 7.54 (2H, dd, J=8.4, 5.6 Hz), 7.91 (1H, s), 10.30 (1H, s).

C) 2-Cyclopropyl-4'-fluoro-5-methoxybiphenyl-4-carbaldehyde

2-Bromo-4'-fluoro-5-methoxybiphenyl-4-carbaldehyde (20.6 g), cyclopropylboronic acid (10.3 g), dicyclohexyl(2', 6'-dimethoxybiphenyl-2-yl)phosphine (4.10 g), tris(dibenzylideneacetone)dipalladium(0) (4.27 g), and a 2 M aqueous sodium carbonate solution (100 mL) were added to toluene (250 mL) in an argon atmosphere, and the mixture was stirred at 100° C. for 2 hours. The reaction mixture was allowed to cool to room temperature and poured to water, followed by extraction with ethyl acetate. The obtained organic layer was washed with saturated saline and dried over anhydrous magnesium sulfate, and then, the solvent was distilled off under reduced pressure. The obtained residue was passed through a short silica gel column (hexane/ethyl acetate), and then, the filtrate was concentrated. The residue was crystallized from a mixed solution of ethanol (50 mL) and water (10 mL), and the obtained crystals were washed with ethanol (85 mL) to obtain the title compound (9.70 g).

$^1$H NMR (300 MHz, CDCl$_3$) δ0.62-0.71 (2H, m), 0.77-0.86 (2H, m), 1.66-1.79 (1H, m), 3.91 (3H, s), 6.82 (1H, s), 7.09-7.19 (2H, m), 7.38-7.48 (3H, m), 10.45 (1H, s).

D) 6-(1-((2-Cyclopropyl-4'-fluoro-5-methoxybiphenyl-4-yl)methyl)piperidin-4-yl)-5-oxo-2-propyl-5,6,7,8-tetrahydro-1,6-naphthyridine-3-carboxylic acid The title compound was obtained in the same way as in steps K and L of Example 1 using methyl 6-(1-(tert-butoxycarbonyl)piperidin-4-yl)-5-oxo-2-propyl-5,6,7,8-tetrahydro-1,6-naphthyridine-3-carboxylate and 2-cyclopropyl-4'-fluoro-5-methoxybiphenyl-4-carbaldehyde.

Example 43

6-(1-((2-Cyclopropyl-5-ethoxy-3',4'-difluorobiphenyl-4-yl)methyl)piperidin-4-yl)-5-oxo-2-propyl-5,6,7,8-tetrahydro-1,6-naphthyridine-3-carboxylic acid

[Formula 60]

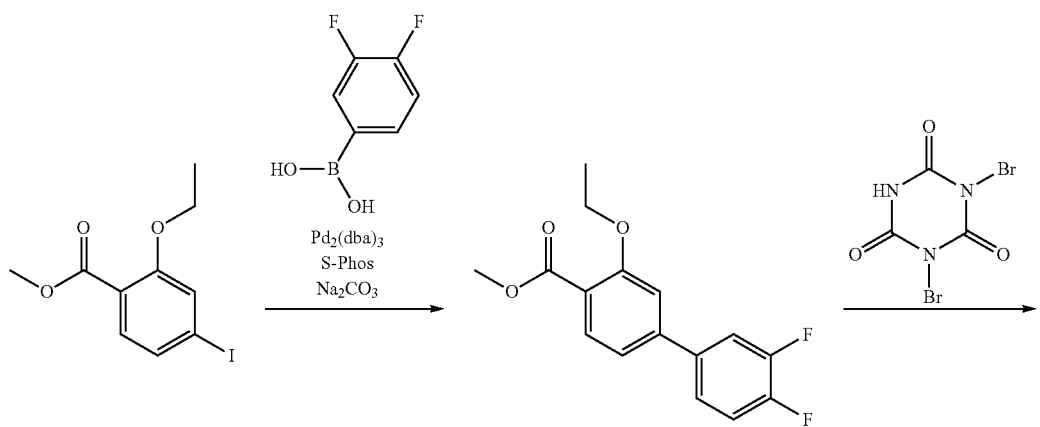

43A (Same as Examples 7B, 7C, 7D, and 7E)

185
186
-continued
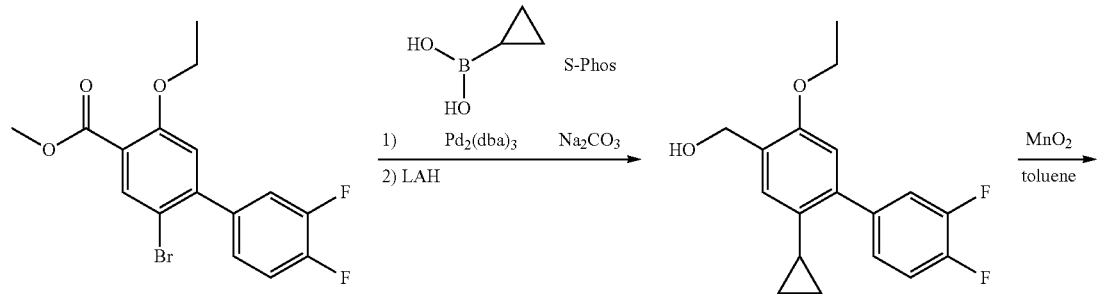
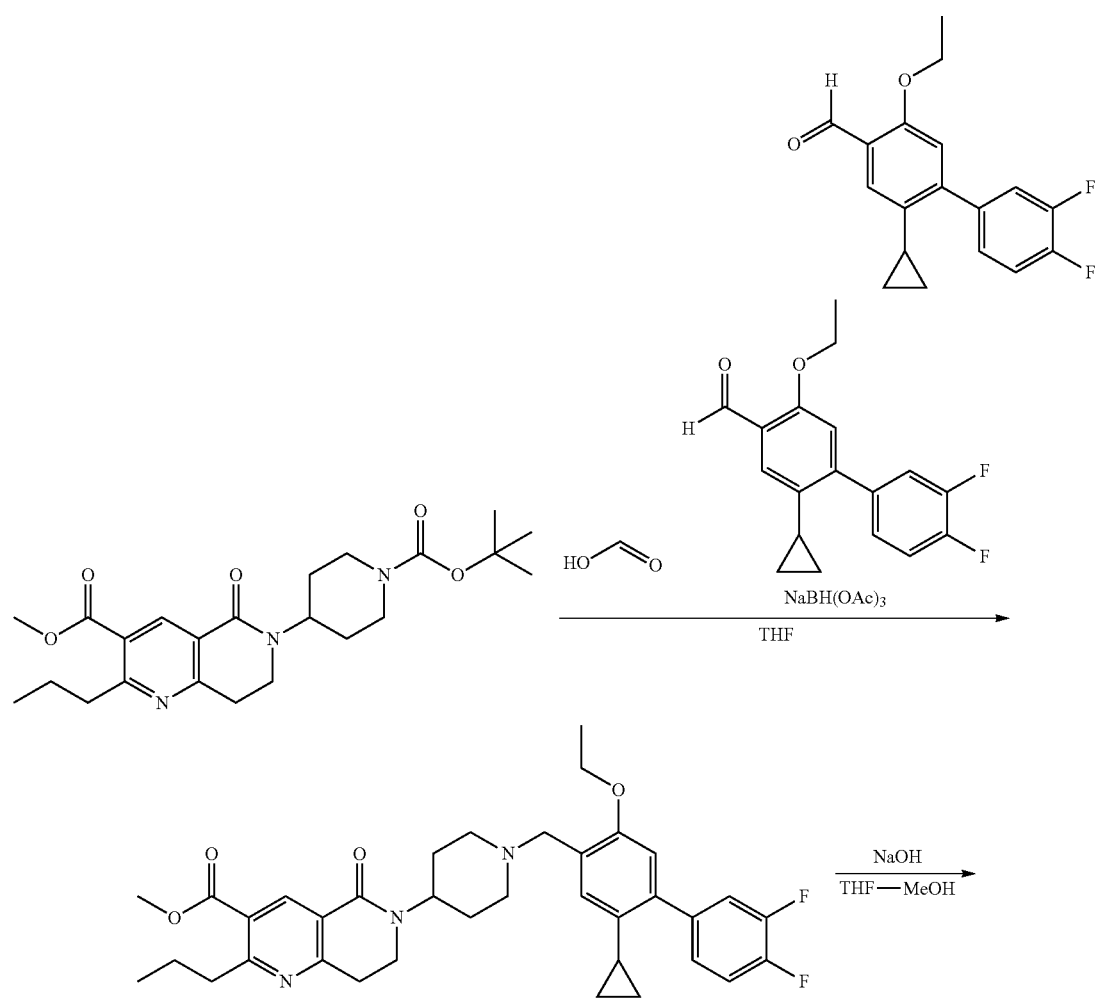
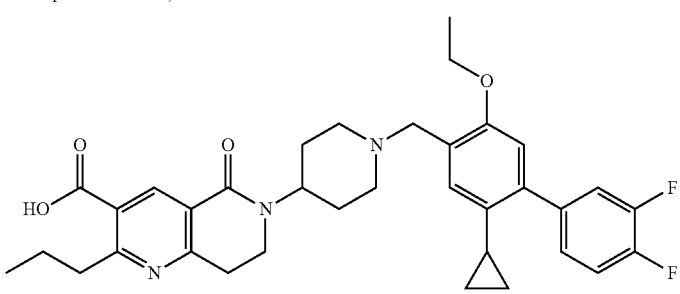

A) 2-Cyclopropyl-5-ethoxy-3',4'-difluorobiphenyl-4-carbaldehyde

The title compound was obtained in the same way as in steps B, C, D, and E of Example 7 using methyl 2-ethoxy-4-iodobenzoate and (3,4-difluorophenyl)boronic acid.

$^1$H NMR (300 MHz, CDCl$_3$) δ 0.59-0.72 (2H, m), 0.78-0.88 (2H, m), 1.47 (3H, t, J=7.0 Hz), 1.65-1.79 (1H, m), 4.14 (2H, q, J=7.0 Hz), 6.79 (1H, s), 7.08-7.34 (3H, m), 7.46 (1H, s), 10.48 (1H, s)

B) 6-(1-((2-Cyclopropyl-5-ethoxy-3',4'-difluorobiphenyl-4-yl)methyl)piperidin-4-yl)-5-oxo-2-propyl-5,6,7,8-tetrahydro-1,6-naphthyridine-3-carboxylic acid The title compound was obtained in the same way as in steps K and L of Example 1 using methyl 6-(1-(tert-butoxycarbonyl)piperidin-4-yl)-5-oxo-2-propyl-5,6,7,8-tetrahydro-1,6-naphthyridine-3-carboxylate and 2-cyclopropyl-5-ethoxy-3',4'-difluorobiphenyl-4-carbaldehyde.

Example 44

6-(1-((2-Cyclopropyl-4'-fluoro-5-isopropoxybiphenyl-4-yl)methyl)piperidin-4-yl)-2-ethyl-5-oxo-5,6,7,8-tetrahydro-1,6-naphthyridine-3-carboxylic acid

[Formula 61]

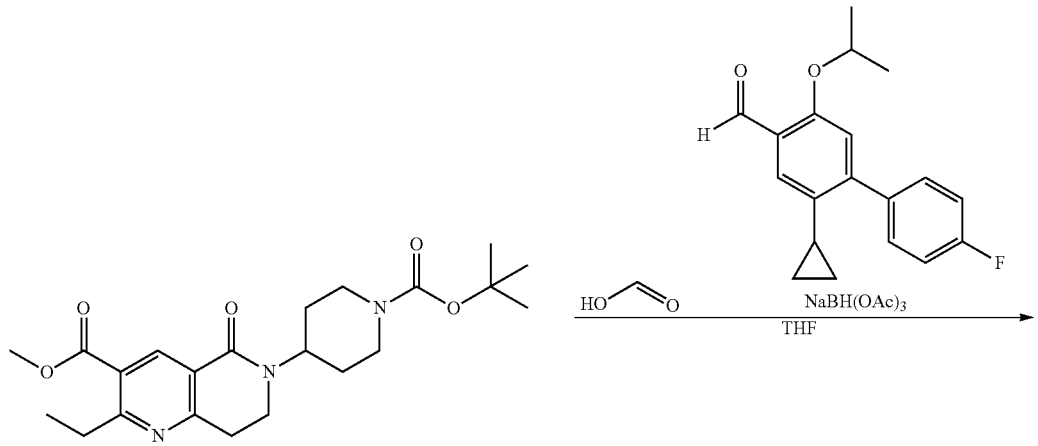

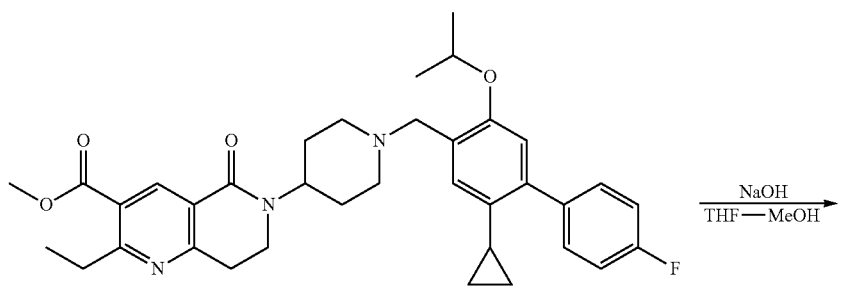

44 (Same as Examples 1K and 1L)

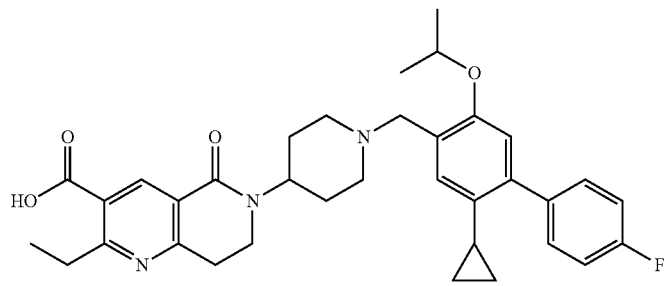

189

The title compound was obtained in the same way as in steps K and L of Example 1 using methyl 6-(1-(tert-butoxycarbonyl)piperidin-4-yl)-2-ethyl-5-oxo-5,6,7,8-tetrahydro-1,6-naphthyridine-3-carboxylate and 2-cyclopropyl-4'-fluoro-5-isopropoxybiphenyl-4-carbaldehyde.

190

Example 45

6-(1-((2-Cyclopropyl-6-ethoxy-4'-fluorobiphenyl-4-yl)methyl)piperidin-4-yl)-2-ethyl-5-oxo-5,6,7,8-tetrahydro-1,6-naphthyridine-3-carboxylic acid

[Formula 62]

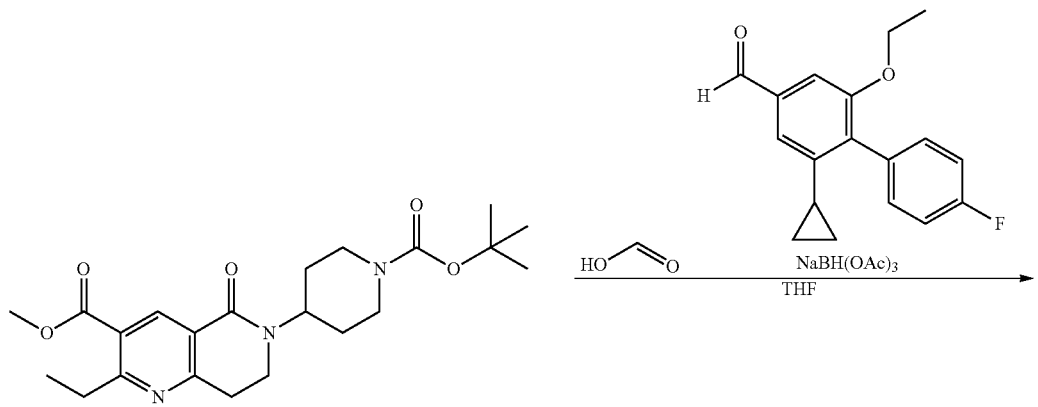

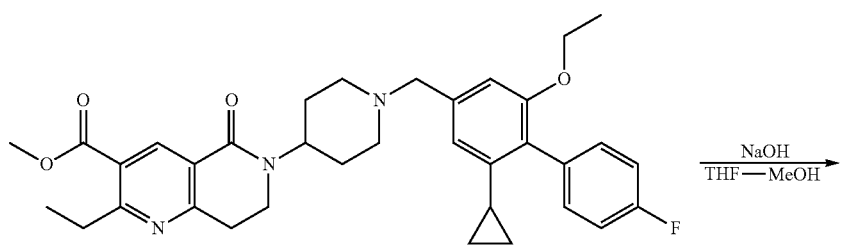

45 (Same as Examples 1K and 1L)

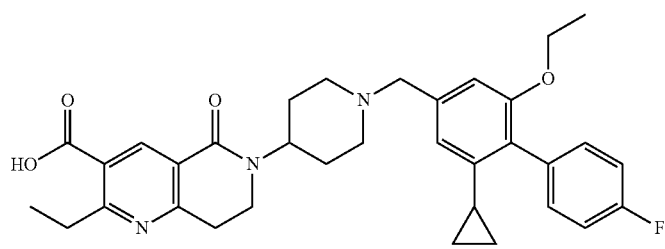

191

The title compound was obtained in the same way as in steps K and L of Example 1 using methyl 6-(1-(tert-butoxycarbonyl)piperidin-4-yl)-2-ethyl-5-oxo-5,6,7,8-tetrahydro-1,6-naphthyridine-3-carboxylate and 2-cyclopropyl-6-ethoxy-4'-fluorobiphenyl-4-carbaldehyde.

192

Example 46

6-(1-((2-Cyclopropyl-2',4'-difluoro-5-isopropoxybiphenyl-4-yl)methyl)piperidin-4-yl)-2-ethyl-5-oxo-5,6,7,8-tetrahydro-1,6-naphthyridine-3-carboxylic acid

[Formula 63]

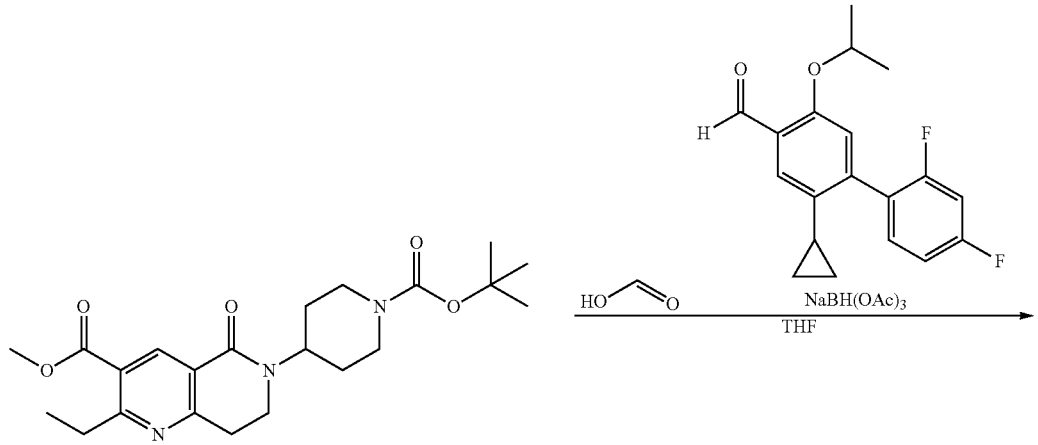

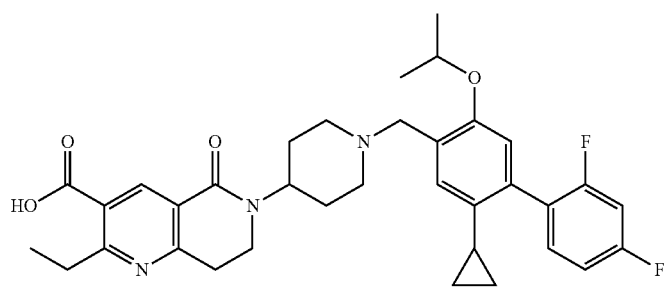

The title compound was obtained in the same way as in steps K and L of Example 1 using methyl 6-(1-(tert-butoxycarbonyl)piperidin-4-yl)-2-ethyl-5-oxo-5,6,7,8-tetrahydro-1,6-naphthyridine-3-carboxylate and 2-cyclopropyl-2',4'-difluoro-5-isopropoxybiphenyl-4-carbaldehyde.

Example 47

6-(1-((2-Cyclopropyl-5-ethoxy-4'-fluorobiphenyl-4-yl)methyl)piperidin-4-yl)-2-(methoxymethyl)-5-oxo-5,6,7,8-tetrahydro-1,6-naphthyridine-3-carboxylic acid

[Formula 64]

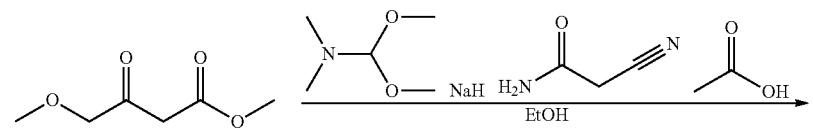

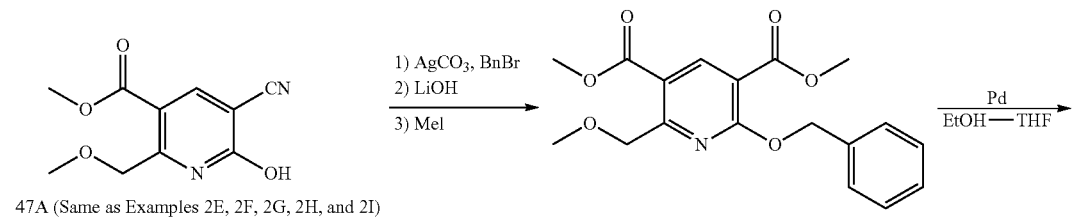

47A (Same as Examples 2E, 2F, 2G, 2H, and 2I)

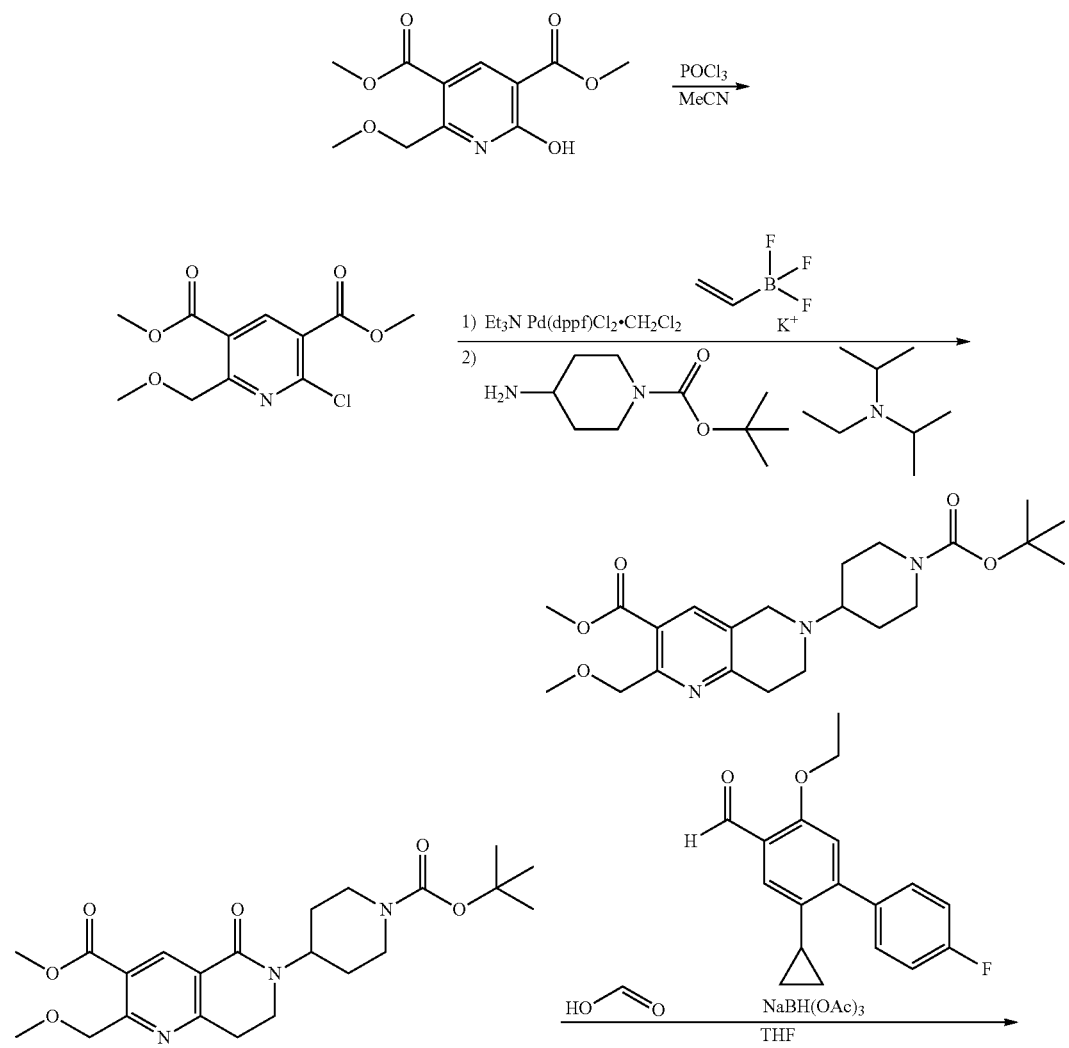

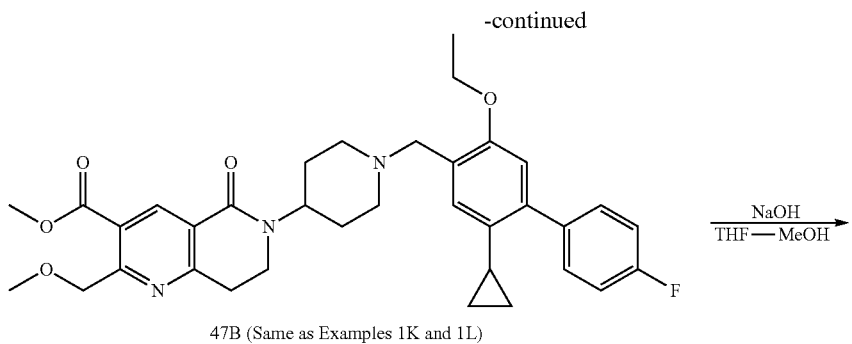

47B (Same as Examples 1K and 1L)

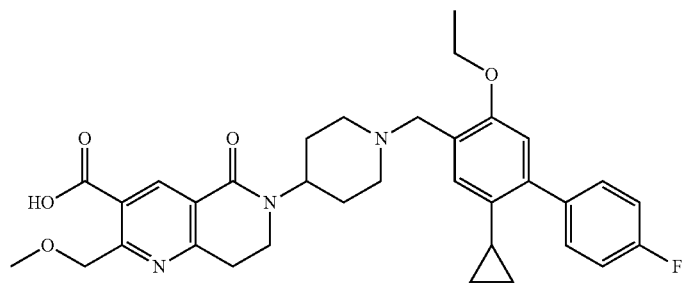

A) Methyl 6-(1-(tert-butoxycarbonyl)piperidin-4-yl)-2-(methoxymethyl)-5-oxo-5,6,7,8-tetrahydro-1,6-naphthyridine-3-carboxylate The title compound was obtained in the same way as in steps E, F, G, H, and I of Example 2 using methyl 4-methoxy-3-oxobutanoate.

$^1$H NMR (300 MHz, CDCl$_3$) δ 1.48 (9H, s), 1.59-1.82 (4H, m), 2.77-2.99 (2H, m), 3.16-3.27 (2H, m), 3.47-3.61 (5H, m), 3.94 (3H, s), 4.17-4.38 (2H, m), 4.69-4.89 (1H, m), 4.97 (2H, s), 8.81 (1H, s).

B) 6-(1-((2-Cyclopropyl-5-ethoxy-4'-fluorobiphenyl-4-yl)methyl)piperidin-4-yl)-2-(methoxymethyl)-5-oxo-5,6,7,8-tetrahydro-1,6-naphthyridine-3-carboxylic acid The title compound was obtained in the same way as in steps K and L of Example 1 using methyl 6-(1-(tert-butoxycarbonyl)piperidin-4-yl)-2-(methoxymethyl)-5-oxo-5,6,7,8-tetrahydro-1,6-naphthyridine-3-carboxylate and 2-cyclopropyl-5-ethoxy-4'-fluorobiphenyl-4-carbaldehyde.

Example 48

6-(1-((2-Cyclopropyl-5-ethoxy-2',4'-difluorobiphenyl-4-yl)methyl)piperidin-4-yl)-2-(methoxymethyl)-5-oxo-5,6,7,8-tetrahydro-1,6-naphthyridine-3-carboxylic acid

[Formula 65]

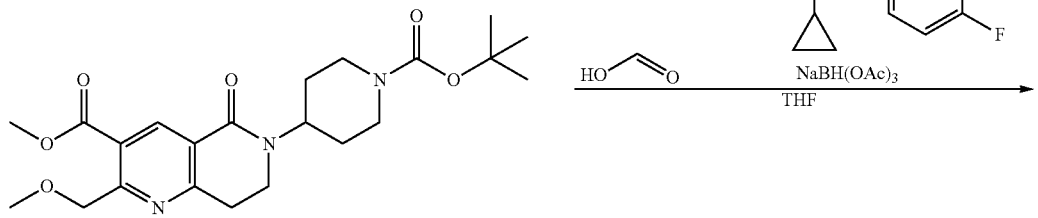

-continued

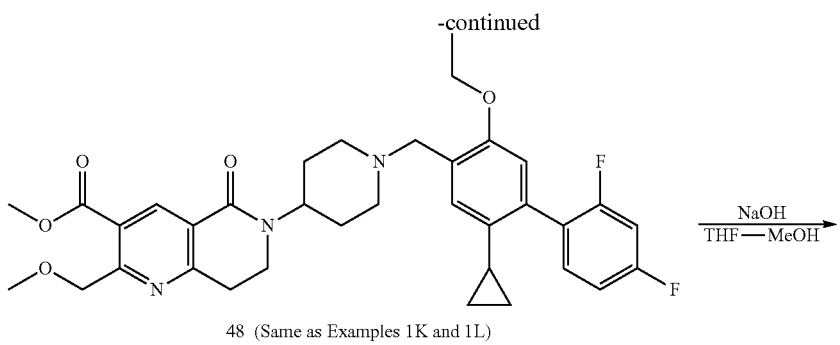

48 (Same as Examples 1K and 1L)

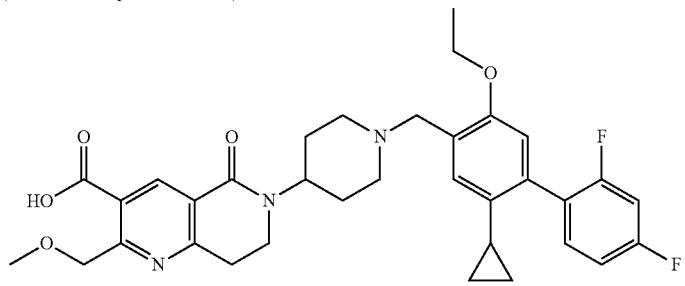

The title compound was obtained in the same way as in steps K and L of Example 1 using methyl 6-(1-(tert-butoxycarbonyl)piperidin-4-yl)-2-(methoxymethyl)-5-oxo-5,6,7,8-tetrahydro-1,6-naphthyridine-3-carboxylate and 2-cyclopropyl-5-ethoxy-2',4'-difluorobiphenyl-4-carbaldehyde.

Example 49

6-(1-((2-Cyclopropyl-5-ethoxy-4'-fluorobiphenyl-4-yl)methyl)piperidin-4-yl)-2-isopropyl-5-oxo-5,6,7,8-tetrahydro-1,6-naphthyridine-3-carboxylic acid

[Formula 66]

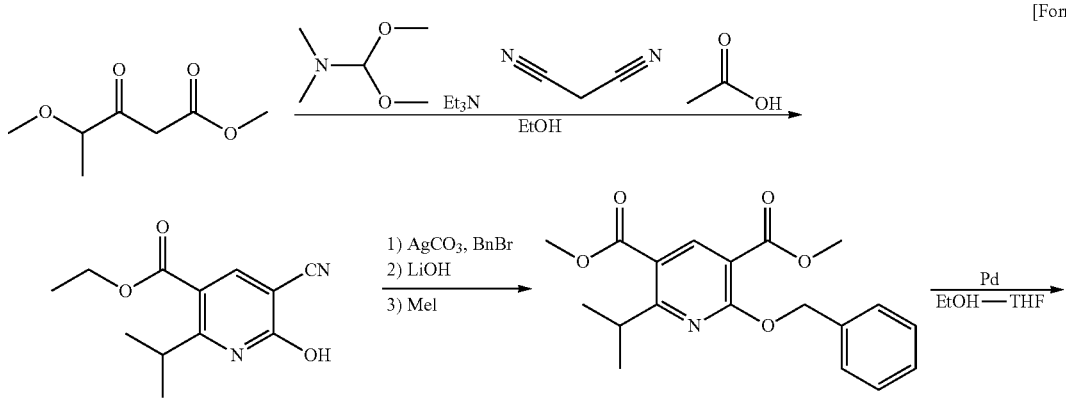

49A (Same as Examples 1F, 1G, 1H, 1I, and 1J)

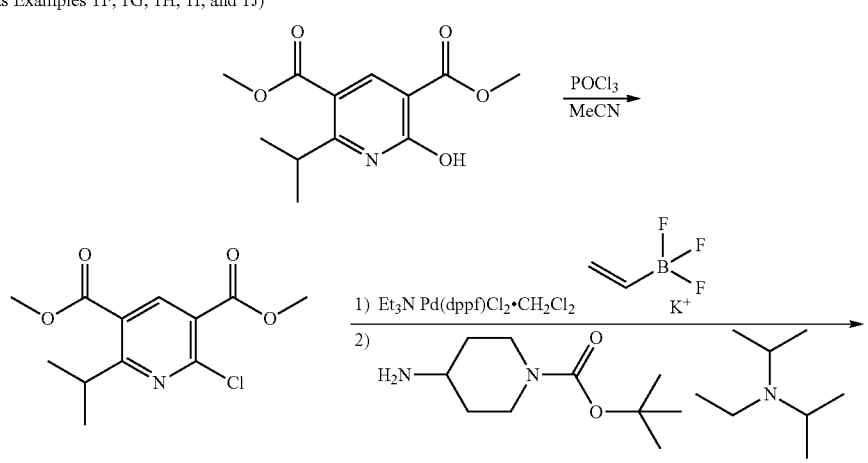

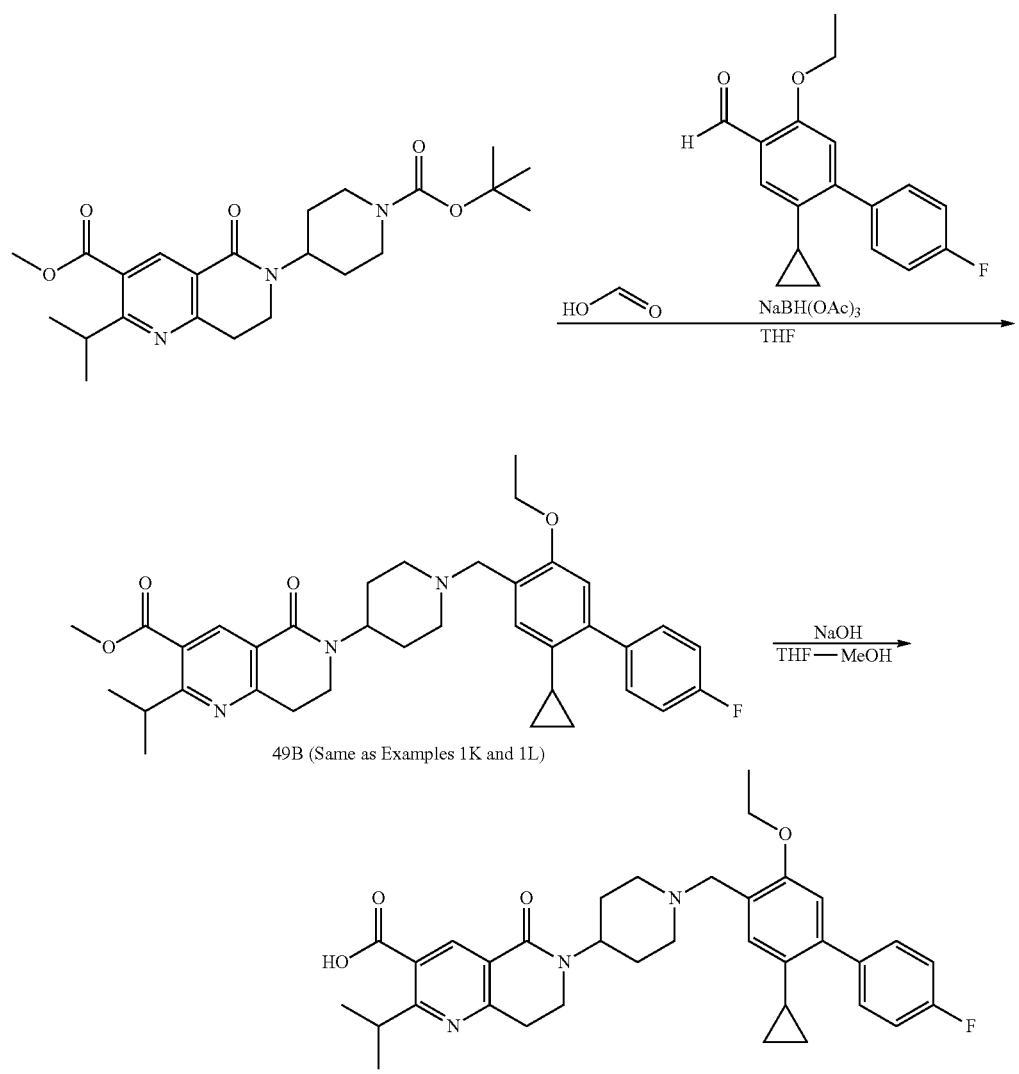

A) Methyl 6-(1-(tert-butoxycarbonyl)piperidin-4-yl)-2-isopropyl-5-oxo-5,6,7,8-tetrahydro-1,6-naphthyridine-3-carboxylate The title compound was obtained in the same way as in steps F, G, H, I, and J of Example 1 using ethyl 4-methyl-3-oxopentanoate.

$^1$H NMR (300 MHz, CDCl$_3$) δ 1.28 (6H, d, J=6.6 Hz), 1.44-1.52 (9H, m), 1.58-1.77 (4H, m), 2.75-2.99 (2H, m), 3.14 (2H, t, J=6.5 Hz), 3.53 (2H, t, J=6.5 Hz), 3.79-3.99 (4H, m), 4.17-4.35 (2H, m), 4.71-4.90 (1H, m), 8.66 (1H, s).

B) 6-(1-((2-Cyclopropyl-5-ethoxy-4'-fluorobiphenyl-4-yl)methyl)piperidin-4-yl)-2-isopropyl-5-oxo-5,6,7,8-tetrahydro-1,6-naphthyridine-3-carboxylic acid The title compound was obtained in the same way as in steps K and L of Example 1 using methyl 6-(1-(tert-butoxycarbonyl)piperidin-4-yl)-2-isopropyl-5-oxo-5,6,7,8-tetrahydro-1,6-naphthyridine-3-carboxylate and 2-cyclopropyl-5-ethoxy-4'-fluorobiphenyl-4-carbaldehyde.

Example 50
6-(1-((2-Cyclopropyl-4'-fluoro-5-isopropoxybiphenyl-4-yl)methyl)piperidin-4-yl)-2-isopropyl-5-oxo-5,6,7,8-tetrahydro-1,6-naphthyridine-3-carboxylic acid
[Formula 67]
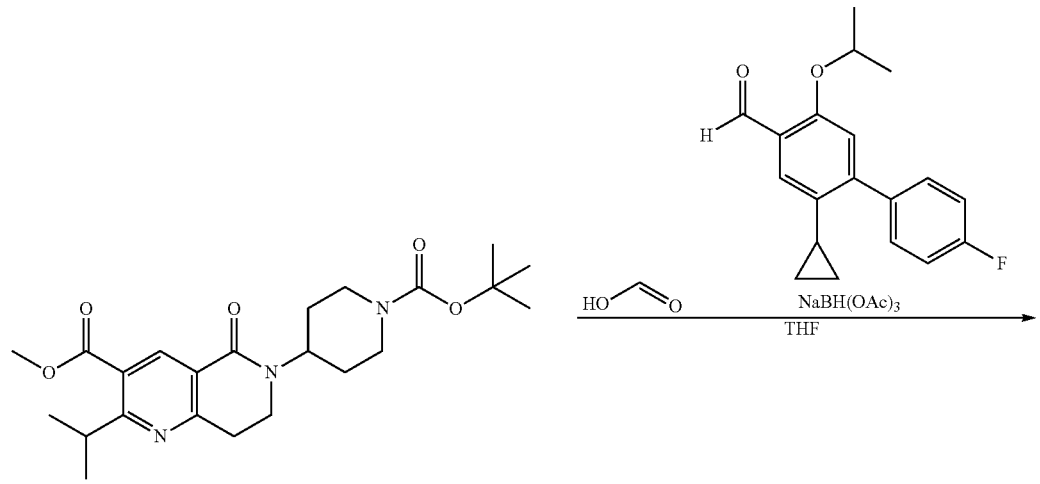
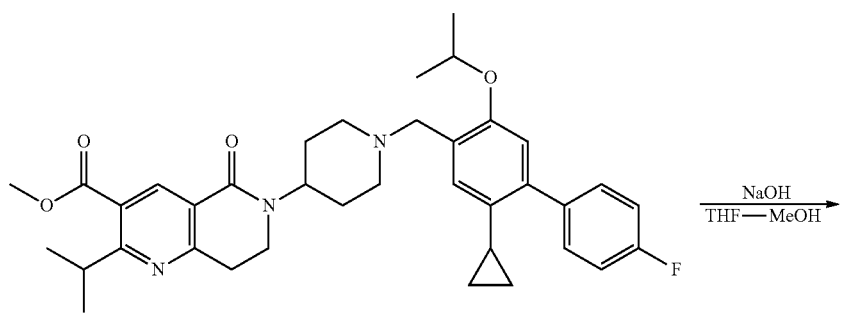
50 (Same as Examples 1K and 1L)
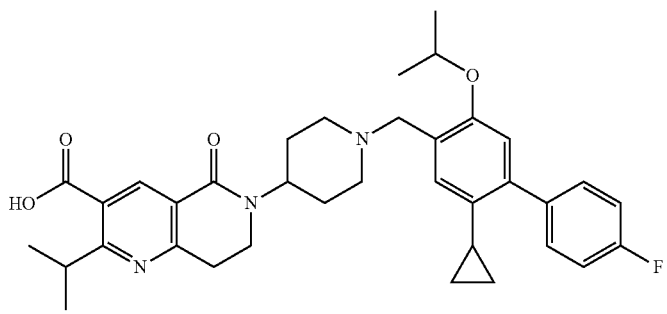

The title compound was obtained in the same way as in steps K and L of Example 1 using methyl 6-(1-(tert-butoxycarbonyl)piperidin-4-yl)-2-isopropyl-5-oxo-5,6,7,8-tetrahydro-1,6-naphthyridine-3-carboxylate and 2-cyclopropyl-4'-fluoro-5-isopropoxybiphenyl-4-carbaldehyde.
Example 51
6-(1-(4,5-Dicyclopropyl-2-ethoxybenzyl)piperidin-4-yl)-5-oxo-2-propyl-5,6,7,8-tetrahydro-1,6-naphthyridine-3-carboxylic acid
[Formula 68]
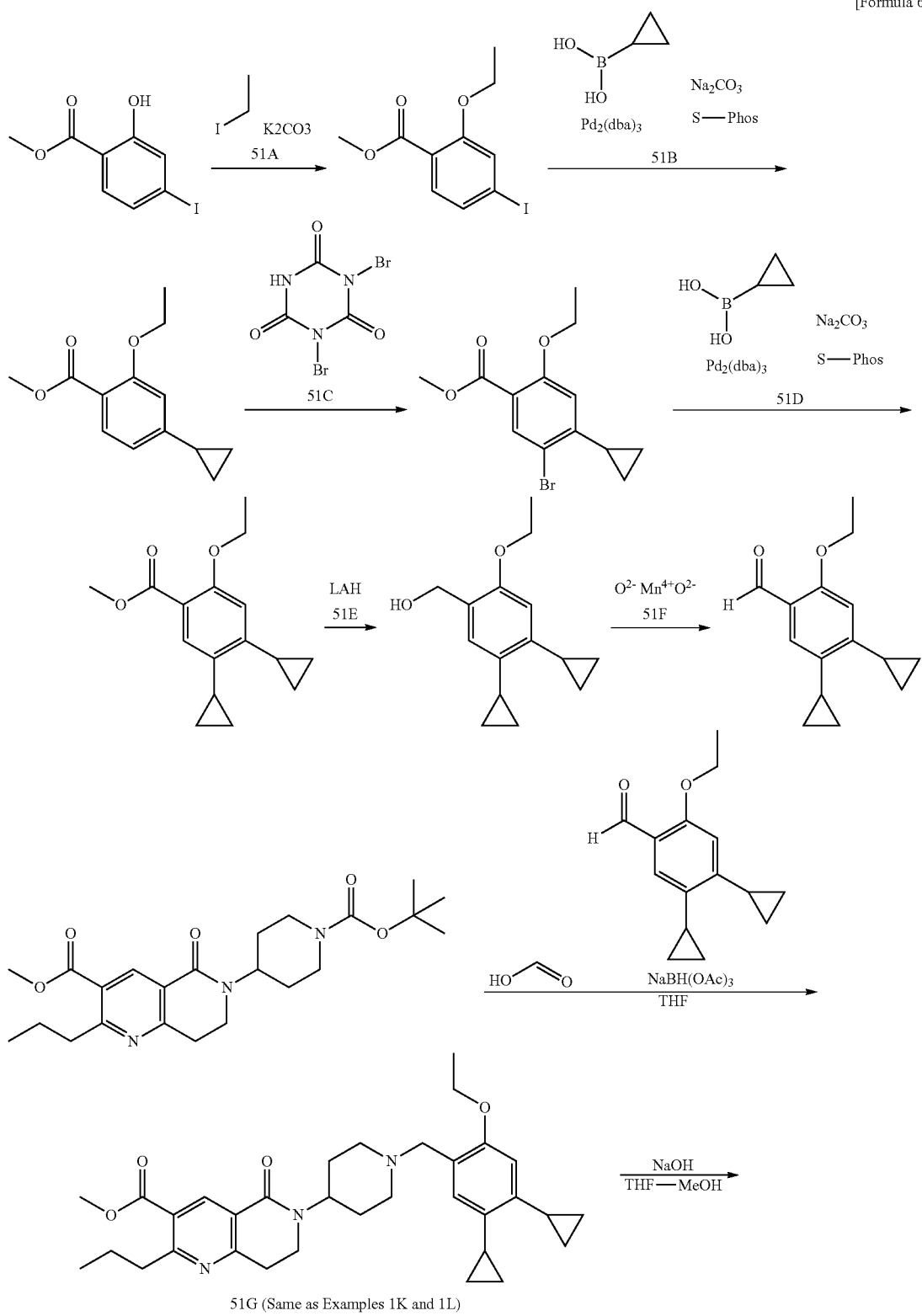

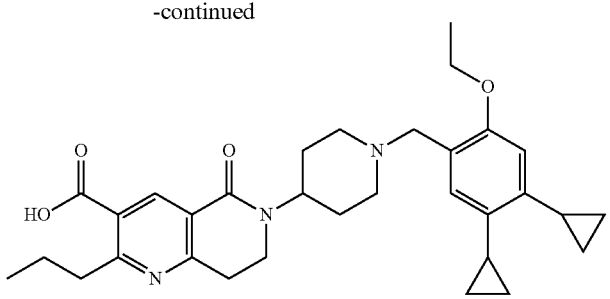

A) Methyl 2-ethoxy-4-iodobenzoate

2-Iodoethane (3.53 g) was added at room temperature to a mixture of methyl 2-hydroxy-4-iodobenzoate (4.19 g), potassium carbonate (4.17 g), and DMF (50 mL), and the resultant mixture was stirred at 70° C. for 1 hour in a nitrogen atmosphere. Water was added to the reaction mixture at room temperature, followed by extraction with ethyl acetate. The obtained organic layer was washed with water and saturated saline in this order and dried over anhydrous magnesium sulfate, and then, the solvent was distilled off under reduced pressure. The obtained residue was purified by silica gel column chromatography (hexane/ethyl acetate) to obtain the title compound (4.52 g).

$^1$H NMR (300 MHz, CDCl$_3$) δ 1.46 (3H, t, J=7.0 Hz), 3.87 (3H, s), 4.09 (2H, q, J=7.0 Hz), 7.29-7.34 (2H, m), 7.48 (1H, d, J=8.1 Hz).

B) Methyl 4-cyclopropyl-2-ethoxybenzoate

Cyclopropylboronic acid (1.90 g), a 2 M aqueous sodium carbonate solution (22 mL), tris(dibenzylideneacetone)dipalladium(0) (944 mg), and dicyclohexyl(2',6'-dimethoxybiphenyl-2-yl)phosphine (907 mg) were added at room temperature to a toluene (80 mL) solution of methyl 2-ethoxy-4-iodobenzoate (4.51 g), and the mixture was stirred at 100° C. for 18 hours in an argon atmosphere. Water was added to the reaction mixture at room temperature, and the mixture was filtered through celite. Then, the filtrate was subjected to extraction with ethyl acetate. The obtained organic layer was washed with water and saturated saline in this order and dried over anhydrous magnesium sulfate, and then, the solvent was distilled off under reduced pressure. The obtained residue was purified by silica gel column chromatography (hexane/ethyl acetate) to obtain the title compound (3.25 g).

$^1$H NMR (300 MHz, CDCl$_3$) δ 0.71-0.78 (2H, m), 0.98-1.06 (2H, m), 1.46 (3H, t, J=7.0 Hz), 1.83-1.94 (1H, m), 3.86 (3H, s), 4.11 (2H, q, J=6.9 Hz), 6.61 (1H, dd, J=8.1, 1.6 Hz), 6.67 (1H, d, J=1.5 Hz), 7.71 (1H, d, J=8.1 Hz).

C) Methyl 5-bromo-4-cyclopropyl-2-ethoxybenzoate

Dibromoisocyanuric acid (2.54 g) was added at room temperature to a DMF (60 mL) solution of methyl 4-cyclopropyl-2-ethoxybenzoate (3.25 g), and the mixture was stirred at 90° C. for 1 hour in a nitrogen atmosphere. Dibromoisocyanuric acid (423 mg) was added to the reaction mixture, and the mixture was stirred at 90° C. for 30 minutes in a nitrogen atmosphere. An aqueous sodium thiosulfate solution was added to the reaction mixture at room temperature, followed by extraction with ethyl acetate. The obtained organic layer was washed with water and saturated saline in this order and dried over anhydrous magnesium sulfate, and then, the solvent was distilled off under reduced pressure. The obtained residue was purified by silica gel column chromatography (hexane/ethyl acetate) to obtain the title compound (4.08 g).

$^1$H NMR (300 MHz, CDCl$_3$) δ 0.66-0.74 (2H, m), 1.04-1.12 (2H, m), 1.44 (3H, t, J=7.0 Hz), 2.12-2.24 (1H, m), 3.86 (3H, s), 4.06 (2H, q, J=7.0 Hz), 6.48 (1H, s), 7.97 (1H, s).

D) Methyl 4,5-dicyclopropyl-2-ethoxybenzoate

Cyclopropylboronic acid (1.76 g), a 2 M aqueous sodium carbonate solution (20 mL), tris(dibenzylideneacetone)dipalladium(0) (874 mg), and dicyclohexyl(2',6'-dimethoxybiphenyl-2-yl)phosphine (840 mg) were added at room temperature to a toluene (70 mL) solution of methyl 5-bromo-4-cyclopropyl-2-ethoxybenzoate (4.08 g), and the mixture was stirred at 100° C. for 18 hours in an argon atmosphere. Water was added to the reaction mixture at room temperature, and the mixture was filtered through celite. Then, the filtrate was subjected to extraction with ethyl acetate. The obtained organic layer was washed with water and saturated saline in this order and dried over anhydrous magnesium sulfate, and then, the solvent was distilled off under reduced pressure. The obtained residue was purified by silica gel column chromatography (hexane/ethyl acetate) to obtain the title compound (3.27 g).

$^1$H NMR (300 MHz, CDCl$_3$) δ 0.62-0.73 (4H, m), 0.88-0.96 (2H, m), 0.98-1.06 (2H, m), 1.42 (3H, t, J=7.0 Hz), 1.99-2.10 (1H, m), 2.22-2.33 (1H, m), 3.85 (3H, s), 4.06 (2H, q, J=7.0 Hz), 6.49 (1H, s), 7.45 (1H, s).

E) (4,5-Dicyclopropyl-2-ethoxyphenyl)methanol

A THF (15 mL) solution of methyl 4,5-dicyclopropyl-2-ethoxybenzoate (3.26 g) was added at 0° C. to a mixture of lithium aluminum hydride (1.09 g) and THF (65 mL), and the resultant mixture was stirred at room temperature for 1 hour in a nitrogen atmosphere. Water (1 mL), a 1 M aqueous sodium hydroxide solution (1 mL), and water (3 mL) were added in this order to the reaction mixture at 0° C., and the mixture was filtered through celite. Then, the filtrate was concentrated under reduced pressure. The obtained residue was purified by silica gel chromatography (hexane/ethyl acetate) to obtain the title compound (2.84 g).

$^1$H NMR (300 MHz, CDCl$_3$) δ 0.59-0.69 (4H, m), 0.86-1.00 (4H, m), 1.41 (3H, t, J=7.0 Hz), 2.02-2.14 (1H, m), 2.17-2.27 (1H, m), 2.35 (1H, t, J=6.5 Hz), 4.05 (2H, q, J=7.0 Hz), 4.61 (2H, d, J=6.3 Hz), 6.47 (1H, s), 6.87 (1H, s).

F) 4,5-Dicyclopropyl-2-ethoxybenzaldehyde

Manganese dioxide (8.50 g) was added at room temperature to a toluene (50 mL) solution of (4,5-dicyclopropyl-2-ethoxyphenyl)methanol (2.84 g) in a nitrogen atmosphere, and the mixture was stirred at 80° C. for 1 hour. The reaction mixture was filtered through celite, and then, the filtrate was concentrated. The obtained residue was purified by silica gel column chromatography (hexane/ethyl acetate) to obtain the title compound (2.68 g).

$^1$H NMR (300 MHz, CDCl$_3$) δ 0.63-0.70 (2H, m), 0.71-0.78 (2H, m), 0.89-0.96 (2H, m), 1.03-1.11 (2H, m), 1.44 (3H, t, J=6.9 Hz), 1.98-2.10 (1H, m), 2.27-2.37 (1H, m), 4.10 (2H, q, J=7.0 Hz), 6.47 (1H, s), 7.47 (1H, s), 10.39 (1H, s).

G) 6-(1-(4,5-Dicyclopropyl-2-ethoxybenzyl)piperidin-4-yl)-5-oxo-2-propyl-5,6,7,8-tetrahydro-1,6-naphthyridine-3-carboxylic acid The title compound was obtained in the same way as in steps K and L of Example 1 using methyl 6-(1-(tert-butoxycarbonyl)piperidin-4-yl)-5-oxo-2-propyl-5,6,7,8-tetrahydro-1,6-naphthyridine-3-carboxylate and 4,5-dicyclopropyl-2-ethoxybenzaldehyde.

Example 52

6-(1-(4-Cyclobutyl-5-cyclopropyl-2-ethoxybenzyl)piperidin-4-yl)-5-oxo-2-propyl-5,6,7,8-tetrahydro-1,6-naphthyridine-3-carboxylic acid

[Formula 69]

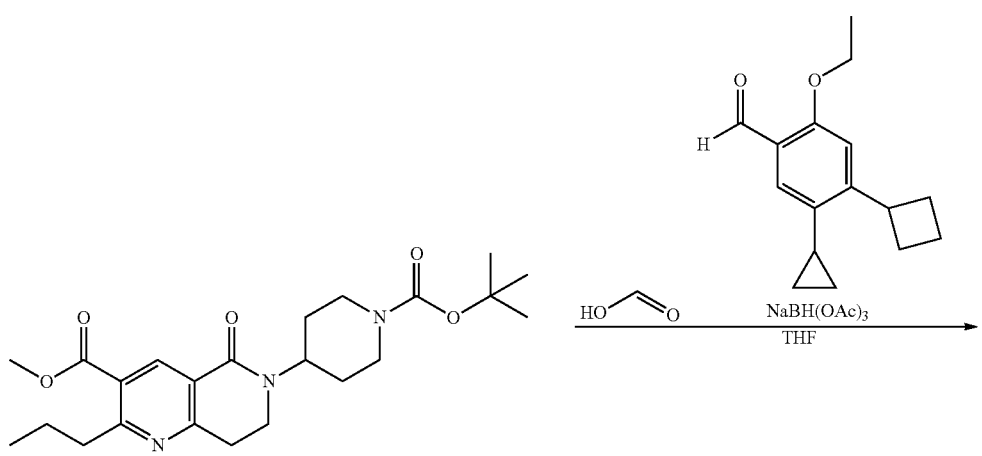

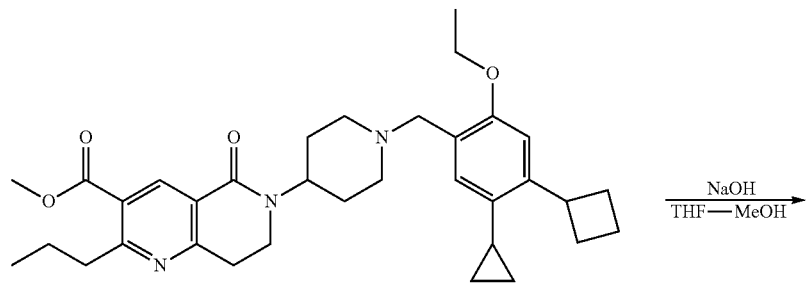

52 (Same as Examples 1K and 1L)

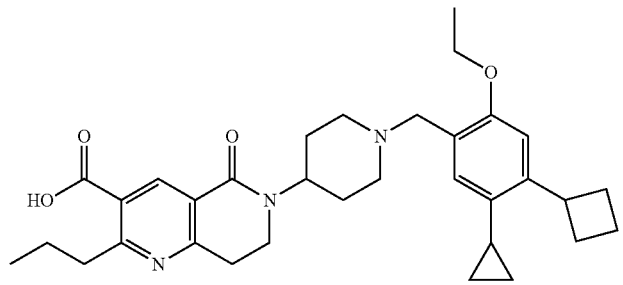

The title compound was obtained in the same way as in steps K and L of Example 1 using methyl 6-(1-(tert-butoxycarbonyl)piperidin-4-yl)-5-oxo-2-propyl-5,6,7,8-tetrahydro-1,6-naphthyridine-3-carboxylate and 4-cyclobutyl-5-cyclopropyl-2-ethoxybenzaldehyde.

Example 53

6-(1-((2,6-Diethoxy-4'-fluorobiphenyl-4-yl)methyl)piperidin-4-yl)-5-oxo-5,6,7,8-tetrahydro-1,6-naphthyridine-2-carboxylic acid

[Formula 70]

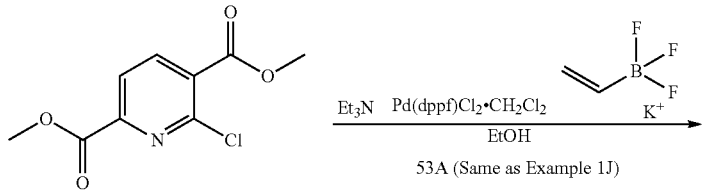

53A (Same as Example 1J)

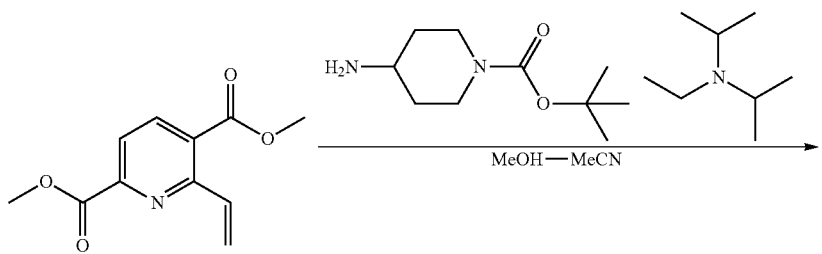

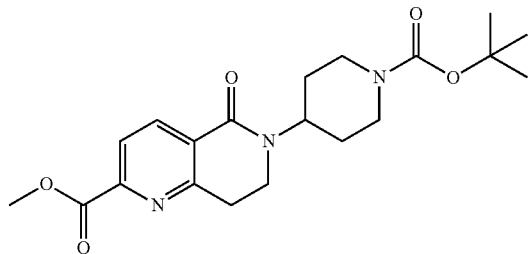

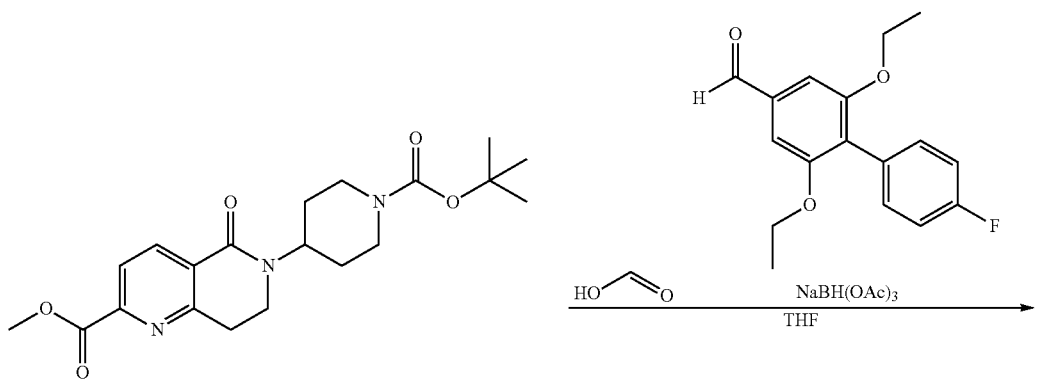

53B (Same as Examples 1K and 1L)

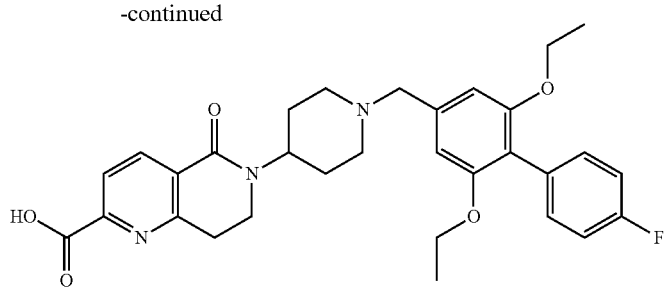

A) Methyl 6-(1-(tert-butoxycarbonyl)piperidin-4-yl)-5-oxo-5,6,7,8-tetrahydro-1,6-naphthyridine-2-carboxylate The title compound was obtained in the same way as in step J of Example 1 using dimethyl 6-chloropyridine-2,5-dicarboxylate.
MS (ESI+): [M+H]+ 390.3.

B) 6-(1-((2,6-Diethoxy-4'-fluorobiphenyl-4-yl)methyl)piperidin-4-yl)-5-oxo-5,6,7,8-tetrahydro-1,6-naphthyridine-2-carboxylic acid The title compound was obtained in the same way as in steps K and L of Example 1 using methyl 6-(1-(tert-butoxycarbonyl)piperidin-4-yl)-5-oxo-5,6,7,8-tetrahydro-1,6-naphthyridine-2-carboxylate and 2,6-diethoxy-4'-fluorobiphenyl-4-carbaldehyde.

Example 54

6-(1-((2-Cyclopropyl-5-ethoxy-4'-fluorobiphenyl-4-yl)methyl)piperidin-4-yl)-5-oxo-5,6,7,8-tetrahydro-1,6-naphthyridine-2-carboxylic acid

[Formula 71]

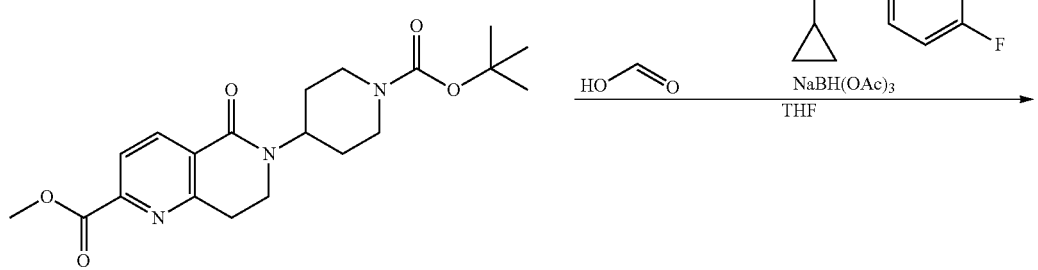

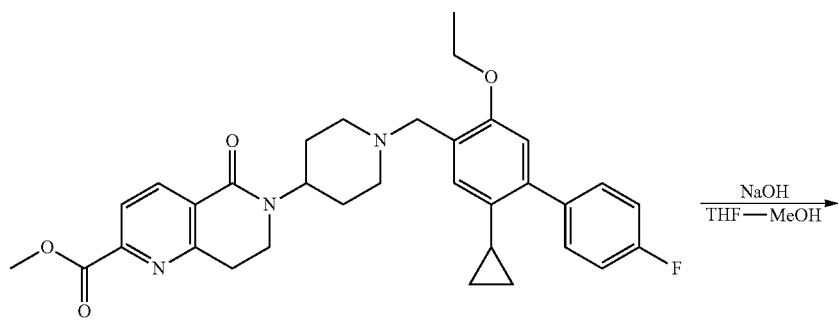

54 (Same as Examples 1K and 1L)

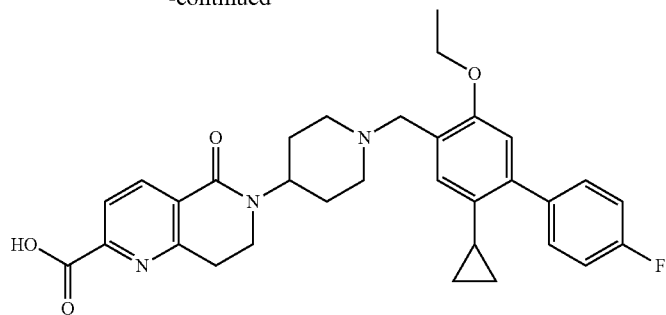

The title compound was obtained in the same way as in steps K and L of Example 1 using methyl 6-(1-(tert-butoxycarbonyl)piperidin-4-yl)-5-oxo-5,6,7,8-tetrahydro-1,6-naphthyridine-2-carboxylate and 2-cyclopropyl-5-ethoxy-4'-fluorobiphenyl-4-carbaldehyde.

Example 55

6-(1-((5-Cyclopropyl-6-(4-fluorophenyl)-2-isopropoxypyridin-3-yl)methyl)piperidin-4-yl)-5-oxo-5,6,7,8-tetrahydro-1,6-naphthyridine-2-carboxylic acid

[Formula 72]

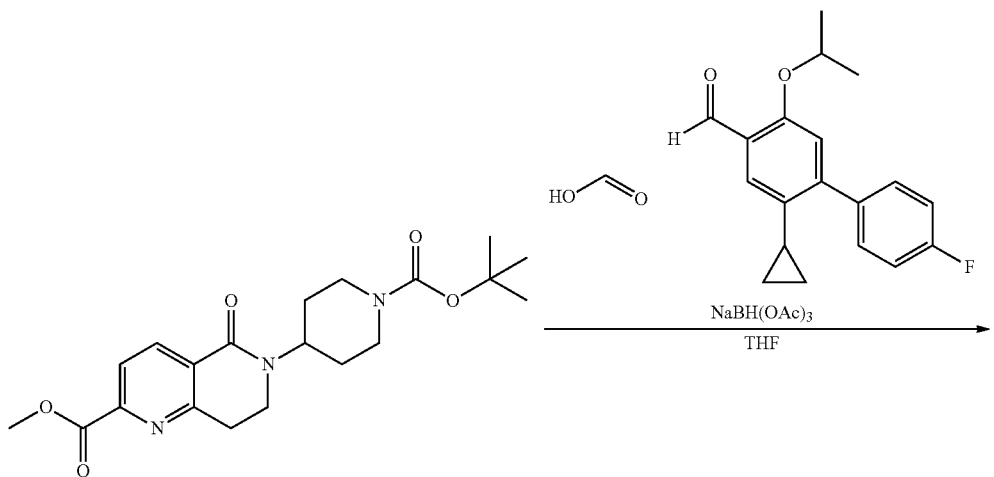

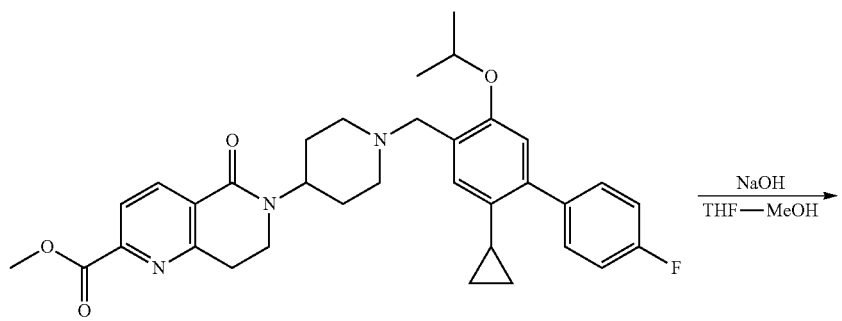

55
(Same as Example 1K and 1L)

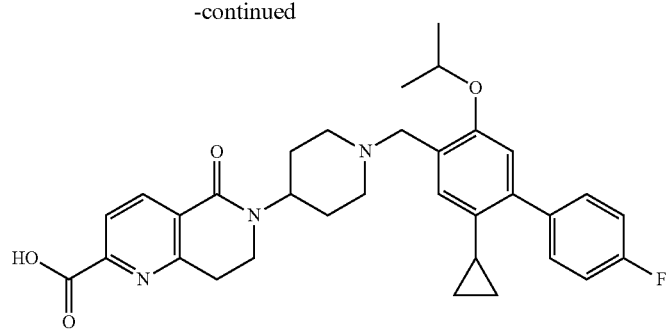

The title compound was obtained in the same way as in steps K and L of Example 1 using methyl 6-(1-(tert-butoxycarbonyl)piperidin-4-yl)-5-oxo-5,6,7,8-tetrahydro-1,6-naphthyridine-2-carboxylate and 5-cyclopropyl-6-(4-fluorophenyl)-2-isopropoxynicotinaldehyde.

Example 56

6-(1-((2-Cyclopropyl-4'-fluoro-5-isopropoxybiphenyl-4-yl)methyl)piperidin-4-yl)-5-oxo-5,6,7,8-tetrahydro-1,6-naphthyridine-2-carboxylic acid

[Formula 73]

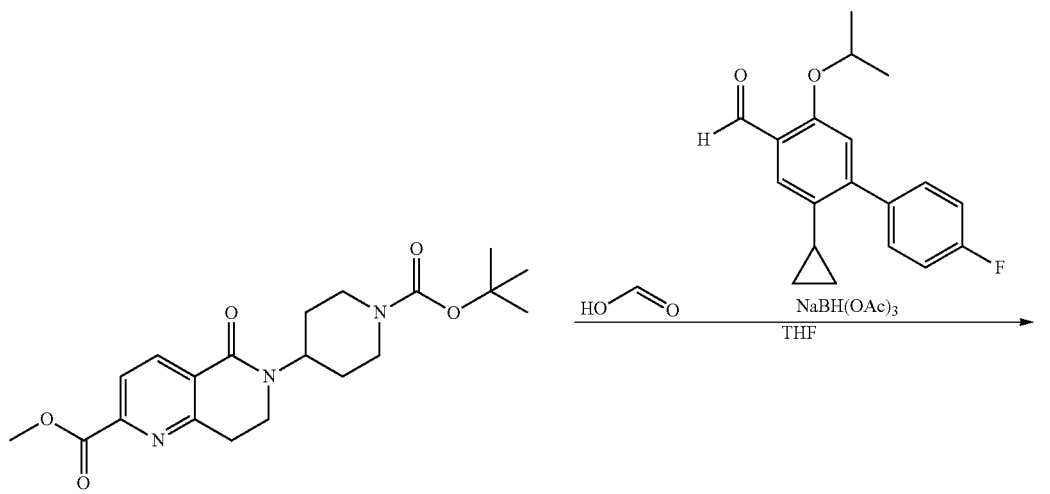

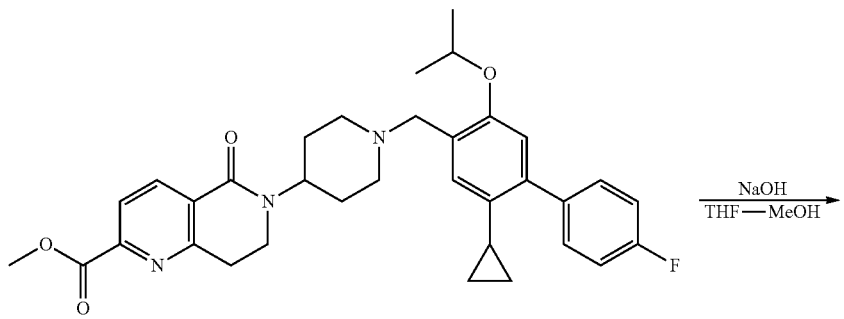

56 (Same as Examples 1K and 1L)

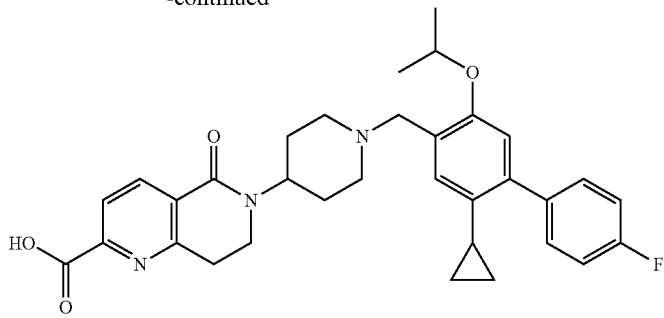

The title compound was obtained in the same way as in steps K and L of Example 1 using methyl 6-(1-(tert-butoxycarbonyl)piperidin-4-yl)-5-oxo-5,6,7,8-tetrahydro-1,6-naphthyridine-2-carboxylate and 2-cyclopropyl-4'-fluoro-5-isopropoxybiphenyl-4-carbaldehyde.

Example 57

6-(1-((2-Cyclopropyl-4'-fluoro-5-methoxybiphenyl-4-yl)methyl)piperidin-4-yl)-5-oxo-5,6,7,8-tetrahydro-1,6-naphthyridine-2-carboxylic acid

[Formula 74]

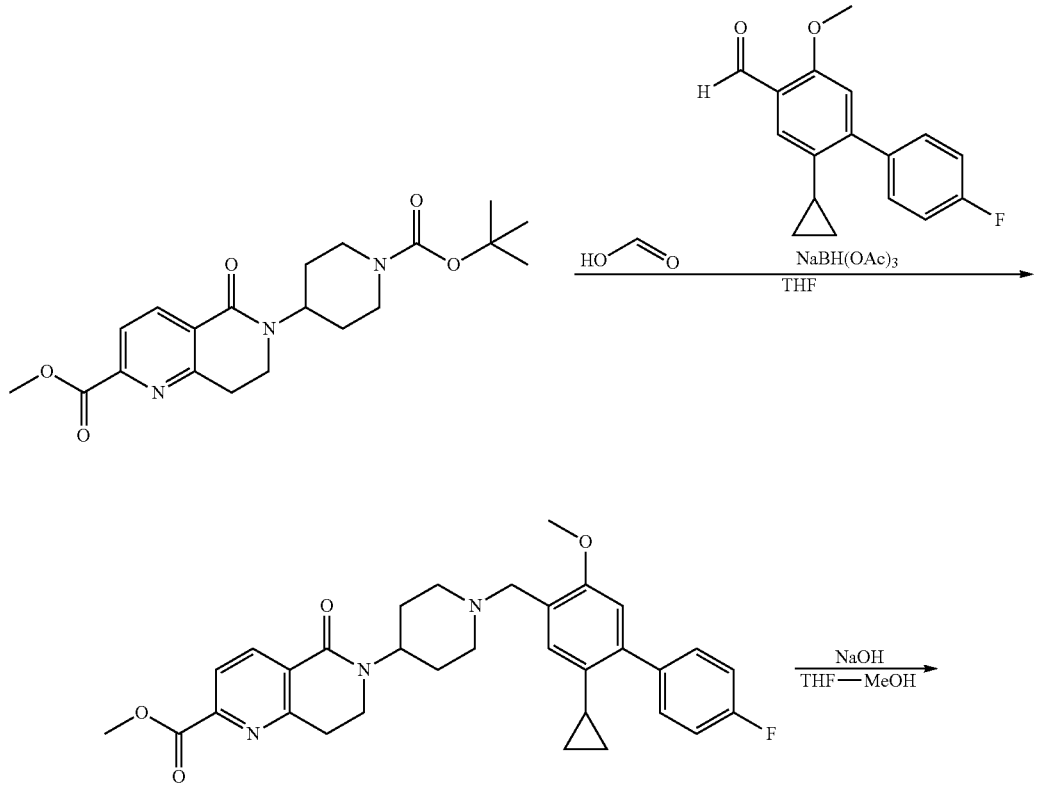

57 (Same as Examples 1K and 1L)

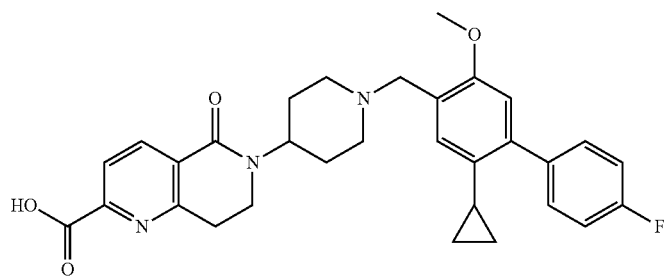

219

The title compound was obtained in the same way as in steps K and L of Example 1 using methyl 6-(1-(tert-butoxycarbonyl)piperidin-4-yl)-5-oxo-5,6,7,8-tetrahydro-1,6-naphthyridine-2-carboxylate and 2-cyclopropyl-4'-fluoro-5-methoxybiphenyl-4-carbaldehyde.

220

Example 58

6-(1-((5-Cyclopropyl-2-ethoxy-6-(4-fluorophenyl)pyridin-3-yl)methyl)piperidin-4-yl)-5-oxo-5,6,7,8-tetrahydro-1,6-naphthyridine-2-carboxylic acid

[Formula 75]

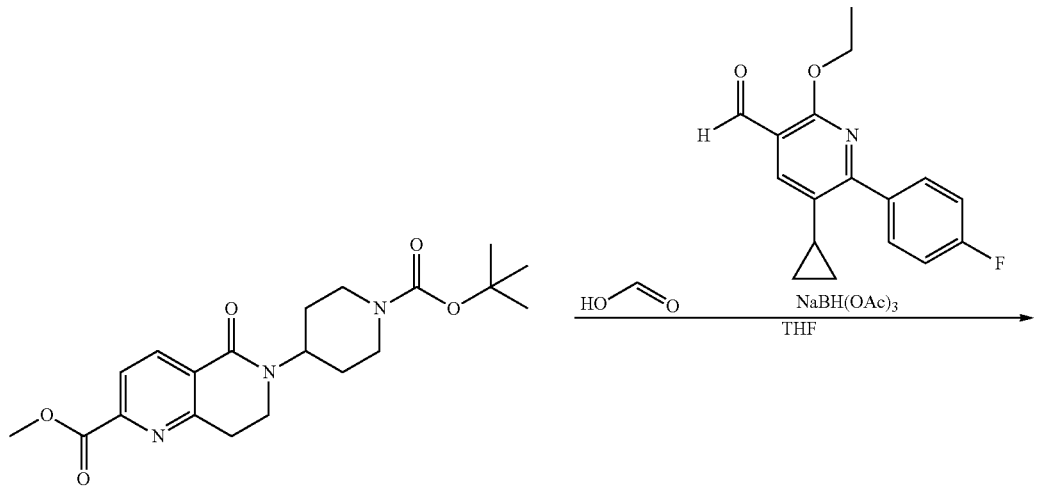

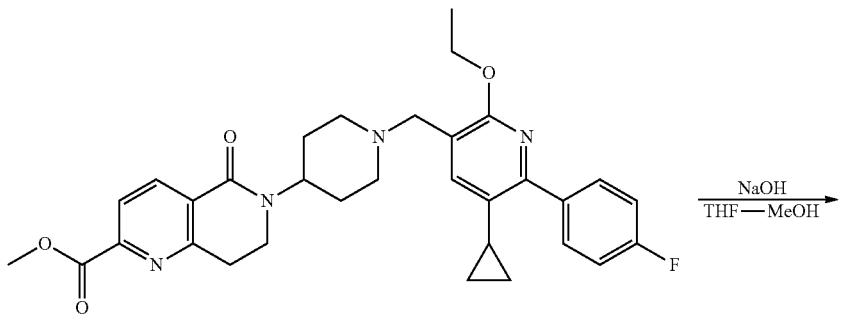

58 (Same as Examples 1K and 1L)

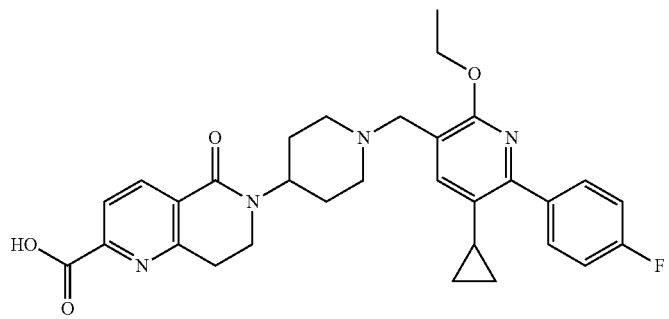

221

The title compound was obtained in the same way as in steps K and L of Example 1 using methyl 6-(1-(tert-butoxycarbonyl)piperidin-4-yl)-5-oxo-5,6,7,8-tetrahydro-1,6-naphthyridine-2-carboxylate and 5-cyclopropyl-2-ethoxy-6-(4-fluorophenyl)nicotinaldehyde.

222

Example 59

6-(1-((2-Cyclopropyl-6-ethoxy-4'-fluorobiphenyl-4-yl)methyl)piperidin-4-yl)-5-oxo-5,6,7,8-tetrahydro-1,6-naphthyridine-2-carboxylic acid

[Formula 76]

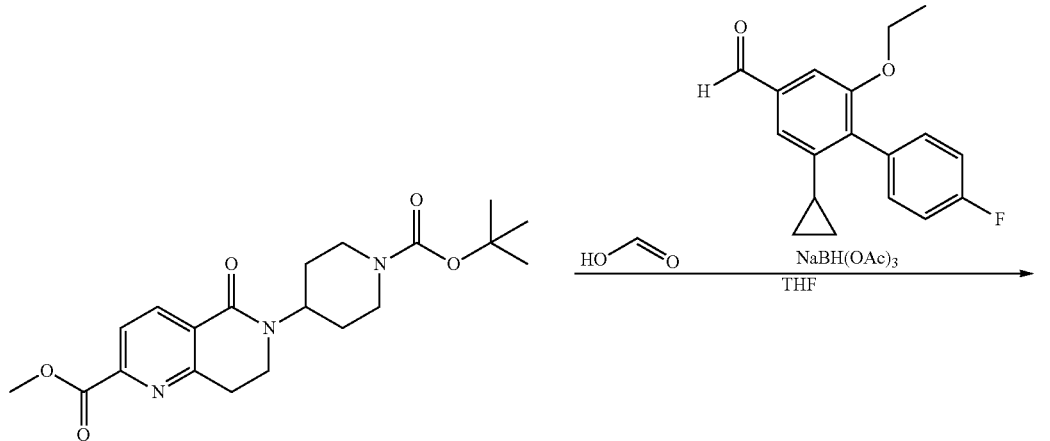

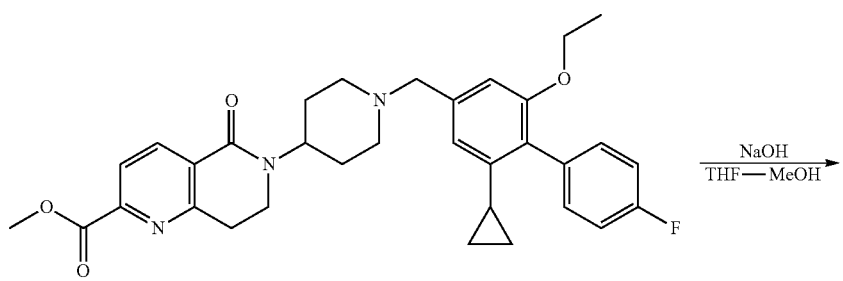

59 (Same as Examples 1K and 1L)

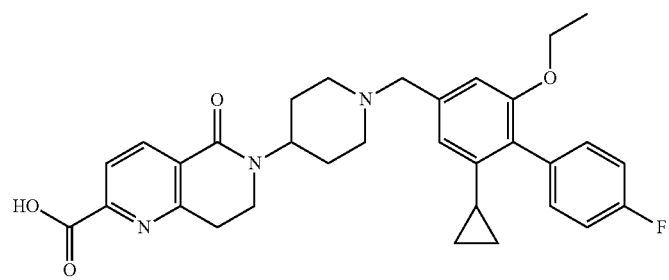

223
The title compound was obtained in the same way as in steps K and L of Example 1 using methyl 6-(1-(tert-butoxycarbonyl)piperidin-4-yl)-5-oxo-5,6,7,8-tetrahydro-1,6-naphthyridine-2-carboxylate and 2-cyclopropyl-6-ethoxy-4'-fluorobiphenyl-4-carbaldehyde.
224
Example 60
Methyl 6-(1-((2,6-diethoxy-4'-fluorobiphenyl-4-yl)methyl)piperidin-4-yl)-5-oxo-6,7,8,9-tetrahydro-5H-pyrido[3,2-c]azepine-2-carboxylate
[Formula 77]
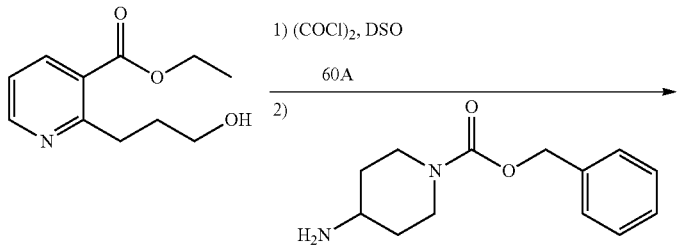
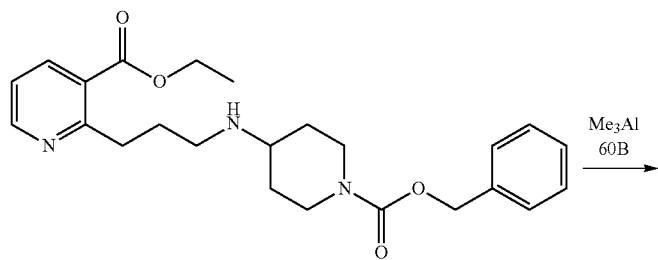
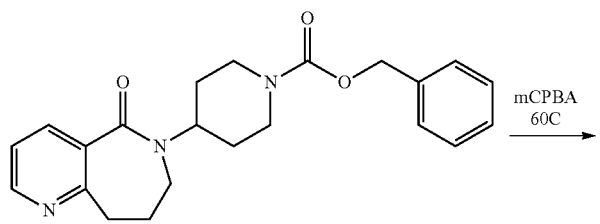
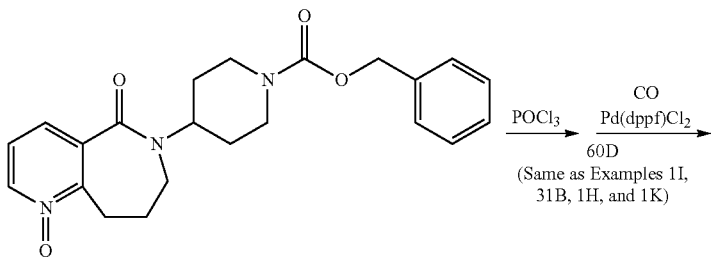
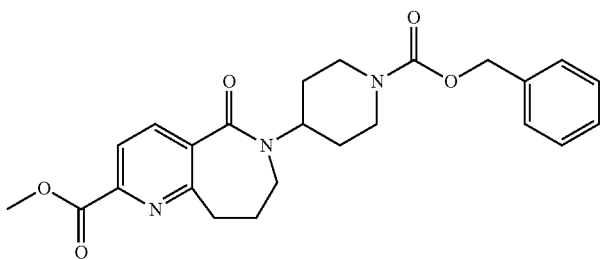

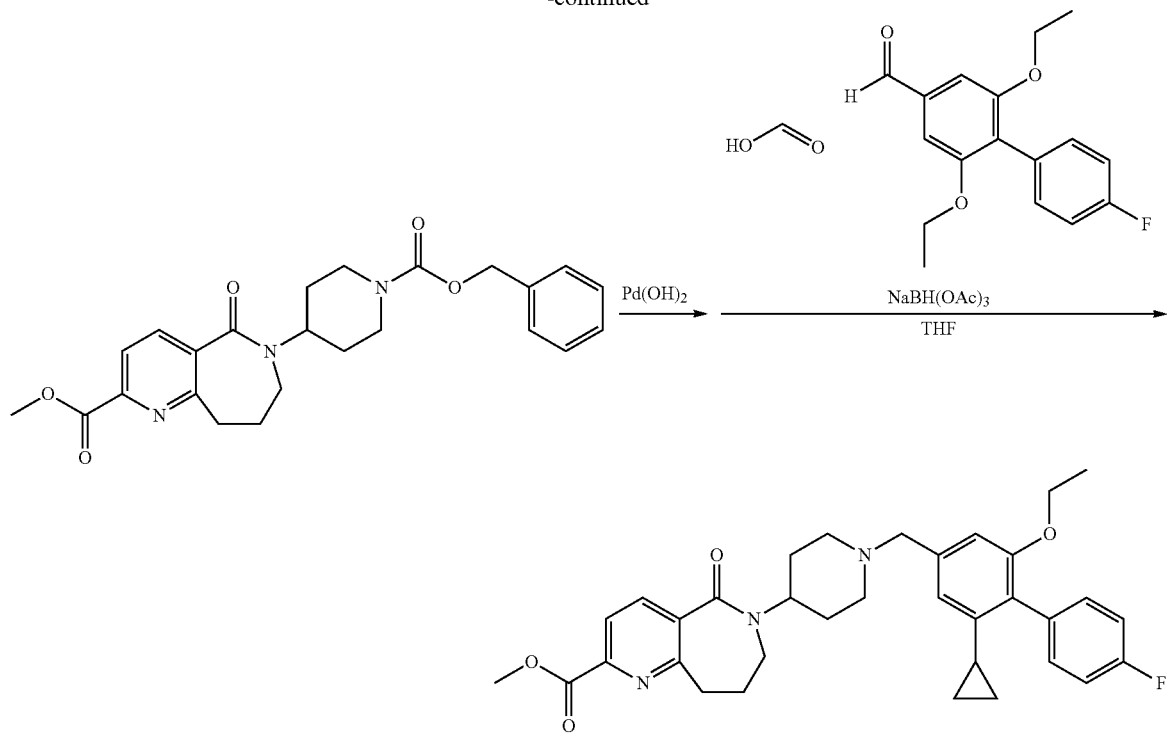

A) Ethyl 2-(3-((1-(((benzyloxy)carbonyl)piperidin-4-yl)amino)propyl)nicotinate A dichloromethane (10 mL) solution of DMSO (4.19 mL) was added at −65° C. to a mixture of oxalyl chloride (2.55 mL) and dichloromethane (50 mL), and the resultant mixture was stirred at the same temperature as above for 15 minutes. A dichloromethane solution (10 mL) of ethyl 2-(3-hydroxypropyl)nicotinate (4.8 g) was added to the reaction mixture, and the mixture was further stirred at the same temperature as above for 20 minutes. Triethylamine (10.4 mL) was added to the reaction mixture at −78° C., and the mixture was stirred at the same temperature as above for 25 minutes and then heated to room temperature. Water was added to the reaction mixture, followed by extraction with dichloromethane. The organic layer was washed with water and dried over sodium sulfate, and then, the solvent was distilled off under reduced pressure. Benzyl 4-aminopiperidine-1-carboxylate (5.65 g) was added to a mixture of the obtained residue and ethanol (80 mL), and the resultant mixture was stirred at room temperature for 2 hours. Sodium borohydride (0.92 g) was added to the reaction mixture at 0° C., and the mixture was stirred overnight at room temperature. The reaction mixture was neutralized with 1 M hydrochloric acid, followed by extraction with dichloromethane. Then, the organic layer was washed with water and saturated saline and dried over sodium sulfate, and then, the solvent was distilled off under reduced pressure. The obtained residue was purified by silica gel column chromatography (methanol/dichloromethane) to obtain the title compound (5.0 g).

MS (ESI+): [M+H]$^+$ 426.0.

B) Benzyl 4-(5-oxo-5,7,8,9-tetrahydro-6H-pyrido[3,2-c]azepin-6-yl)piperidine-1-carboxylate A 2 M toluene solution (14.6 mL) of trimethylaluminum was added at 0° C. to a mixture of ethyl 2-(3-((1-(((benzyloxy)carbonyl)piperidin-4-yl)amino)propyl)nicotinate (2.4 g) and dichloromethane (60 mL), and the resultant mixture was stirred at room temperature for 36 hours. Water was added to the reaction mixture, and then, the mixture was neutralized by the addition of hydrochloric acid. The organic layer was separated, and then, the aqueous layer was subjected to extraction with dichloromethane. Combined organic layers were washed with water and saturated saline and dried over sodium sulfate, and then, the solvent was distilled off under reduced pressure. The obtained residue was purified by silica gel column chromatography (methanol/dichloromethane) to obtain the title compound (1.2 g).

MS (ESI+): [M+H]$^+$ 380.2.

C) Benzyl 4-(1-oxido-5-oxo-5,7,8,9-tetrahydro-6H-pyrido[3,2-c]azepin-6-yl)piperidine-1-carboxylate m-Chloroperbenzoic acid (2.45 g) was added to a mixture of benzyl 4-(5-oxo-5,7,8,9-tetrahydro-6H-pyrido[3,2-c]azepin-6-yl)piperidine-1-carboxylate (1.8 g) and dichloromethane (50 mL), and the resultant mixture was stirred at room temperature for 3 hours. A 10% aqueous sodium disulfite solution was added to the reaction mixture, and the mixture was stirred for 20 minutes, followed by extraction with dichloromethane. The organic layer was washed with water and saturated saline and dried over sodium sulfate, and then, the solvent was distilled off under reduced pressure to obtain the title compound (1.0 g).

MS (ESI+): [M+H]$^+$ 396.2.

D) Methyl 6-(1-((2,6-diethoxy-4'-fluorobiphenyl-4-yl)methyl)piperidin-4-yl)-5-oxo-6,7,8,9-tetrahydro-5H-pyrido[3,2-c]azepine-2-carboxylate The title compound was obtained in the same way as in step I of Example 1, step B of Example 31, and steps H and K of Example 1 using benzyl 4-(1-oxido-5-oxo-5,7,8,9-tetrahydro-6H-pyrido[3,2-c]azepin-6-yl)piperidine-1-carboxylate.

Example 61

6-(1-((2-Cyclopropyl-4'-fluoro-6-propoxybiphenyl-4-yl)methyl)piperidin-4-yl)-5-oxo-2-propyl-5,6,7,8-tetrahydro-1,6-naphthyridine-3-carboxylic acid A) Methyl 6-(1-((2-cyclopropyl-4'-fluoro-6-propoxybiphenyl-4-yl)methyl)piperidin-4-yl)-5-oxo-2-propyl-5,6,7,8-tetrahydro-1,6-naphthyridine-3-carboxylate Methyl 6-(1-(tert-butoxycarbonyl)piperidin-4-yl)-5-oxo-2-propyl-5,6,7,8-tetrahydro-1,6-naphthyridine-3-carboxylate (500 mg) was added to formic acid (5 mL), and the mixture was stirred at 60° C. for 30 minutes. Then, the solvent was distilled off under reduced pressure. Toluene was added to the residue, and the solvent was further distilled off under reduced pressure. 2-Cyclopropyl-4'-fluoro-6-propoxybiphenyl-4-carbaldehyde (415 mg) was added to a mixture of the obtained residue and THF (5 mL), and the resultant mixture was stirred for 10 minutes. Then, sodium triacetoxy borohydride (368 mg) was added thereto, and the mixture was stirred at room temperature for 3 hours. A saturated aqueous solution of sodium bicarbonate was added to the reaction mixture, followed by extraction with ethyl acetate twice. The obtained organic layer was dried over anhydrous magnesium sulfate, and then, the solvent was distilled off under reduced pressure. The obtained residue was purified by silica gel column chromatography (hexane/ethyl acetate/methanol) to obtain the title compound (482 mg).
MS (ESI+): [M+H]$^+$ 614.3.

B) 6-(1-((2-Cyclopropyl-4'-fluoro-6-propoxybiphenyl-4-yl)methyl)piperidin-4-yl)-5-oxo-2-propyl-5,6,7,8-tetrahydro-1,6-naphthyridine-3-carboxylic acid A 2 M aqueous sodium hydroxide solution (1.50 mL) was added at room temperature to a methanol (5 mL)-THF (5 mL) solution of methyl 6-(1-((2-cyclopropyl-4'-fluoro-6-propoxybiphenyl-4-yl)methyl)piperidin-4-yl)-5-oxo-2-propyl-5,6,7,8-tetrahydro-1,6-naphthyridine-3-carboxylate (475 mg), and the mixture was stirred at 60° C. for 30 minutes. The reaction mixture was neutralized with hydrochloric acid at room temperature. Then, ethyl acetate was added thereto, and the solvent was distilled off under reduced pressure. The deposited solid was collected by filtration and washed with diethyl ether. The obtained solid was recrystallized (DMSO/ethanol/hexane) to obtain the title compound (360 mg).
$^1$H NMR (300 MHz, DMSO-d$_6$) δ 0.52-0.63 (2H, m), 0.66-0.82 (5H, m), 0.92 (3H, t, J=7.4 Hz), 1.44-1.74 (7H, m), 1.74-1.94 (2H, m), 2.03-2.17 (2H, m), 2.96 (2H, d, J=11.3 Hz), 3.03-3.15 (4H, m), 3.49 (2H, s), 3.58 (2H, t, J=6.6 Hz), 3.83 (2H, t, J=6.2 Hz), 4.33-4.54 (1H, m), 6.49 (1H, s), 6.83 (1H, s), 7.16-7.32 (4H, m), 8.48 (1H, s).

Example 62

6-(1-((2-Cyclopropyl-6-ethoxy-3',4'-difluorobiphenyl-4-yl)methyl)piperidin-4-yl)-5-oxo-2-propyl-5,6,7,8-tetrahydro-1,6-naphthyridine-3-carboxylic acid A) Methyl 6-(1-((2-cyclopropyl-6-ethoxy-3',4'-difluorobiphenyl-4-yl)methyl)piperidin-4-yl)-5-oxo-2-propyl-5,6,7,8-tetrahydro-1,6-naphthyridine-3-carboxylate Methyl 6-(1-(tert-butoxycarbonyl)piperidin-4-yl)-5-oxo-2-propyl-5,6,7,8-tetrahydro-1,6-naphthyridine-3-carboxylate (500 mg) was added to formic acid (5 mL), and the mixture was stirred at 60° C. for 30 minutes. Then, the solvent was distilled off under reduced pressure. Toluene was added to the residue, and the solvent was further distilled off under reduced pressure. 2-Cyclopropyl-6-ethoxy-3',4'-difluorobiphenyl-4-carbaldehyde (420 mg) was added to a mixture of the obtained residue and THF (5 mL), and the resultant mixture was stirred for 10 minutes. Then, sodium triacetoxy borohydride (368 mg) was added thereto, and the mixture was stirred at room temperature for 3 hours. A saturated aqueous solution of sodium bicarbonate was added to the reaction mixture, followed by extraction with ethyl acetate twice. The obtained organic layer was dried over anhydrous magnesium sulfate, and then, the solvent was distilled off under reduced pressure. The obtained residue was purified by silica gel column chromatography (hexane/ethyl acetate/methanol) to obtain the title compound (595 mg).
MS (ESI+): [M+H]$^+$ 618.3.

B) 6-(1-((2-Cyclopropyl-6-ethoxy-3',4'-difluorobiphenyl-4-yl)methyl)piperidin-4-yl)-5-oxo-2-propyl-5,6,7,8-tetrahydro-1,6-naphthyridine-3-carboxylic acid A 2 M aqueous sodium hydroxide solution (1.50 mL) was added at room temperature to methanol (5 mL)-THF (5 mL) solution of methyl 6-(1-((2-cyclopropyl-6-ethoxy-3',4'-difluorobiphenyl-4-yl)methyl)piperidin-4-yl)-5-oxo-2-propyl-5,6,7,8-tetrahydro-1,6-naphthyridine-3-carboxylate (580 mg), and the mixture was stirred at 60° C. for 30 minutes. The reaction mixture was neutralized with hydrochloric acid at room temperature. Then, ethyl acetate was added thereto, and the solvent was distilled off under reduced pressure. The deposited solid was collected by filtration and washed with diethyl ether. The obtained solid was recrystallized (DMSO/ethanol/hexane) to obtain the title compound (487 mg).
$^1$H NMR (300 MHz, DMSO-d$_6$) δ 0.54-0.62 (2H, m), 0.69-0.79 (2H, m), 0.92 (3H, t, J=7.4 Hz), 1.14 (3H, t, J=6.9 Hz), 1.44-1.73 (5H, m), 1.74-1.93 (2H, m), 2.11 (2H, t, J=11.2 Hz), 2.96 (2H, d, J=11.0 Hz), 3.03-3.15 (4H, m), 3.50 (2H, s), 3.58 (2H, t, J=6.7 Hz), 3.95 (2H, q, J=7.0 Hz), 4.31-4.53 (1H, m), 6.52 (1H, s), 6.86 (1H, s), 7.03-7.12 (1H, m), 7.24-7.35 (1H, m), 7.37-7.51 (1H, m), 8.48 (1H, s).

Example 63

6-(1-((2-Cyclopropyl-4'-fluoro-6-isopropoxybiphenyl-4-yl)methyl)piperidin-4-yl)-5-oxo-2-propyl-5,6,7,8-tetrahydro-1,6-naphthyridine-3-carboxylic acid A) Ethyl 3-(benzyloxy)-5-hydroxy-4-iodobenzoate Sodium hydride (60% oil, 1.33 g) was added to a mixture of ethyl 3,5-dihydroxy-4-iodobenzoate (5.00 g) and DMF (50 mL), and the resultant mixture was stirred at 0° C. for 30 minutes in a nitrogen atmosphere. Benzyl bromide (2.78 g) was added to the reaction mixture, and the mixture was stirred at room temperature for 2 hours. Water was added to the reaction mixture, followed by extraction with ethyl acetate. The obtained organic layer was washed with saturated saline and dried over anhydrous magnesium sulfate, and then, the solvent was distilled off under reduced pressure. The obtained residue was purified by silica gel column chromatography (hexane/ethyl acetate) to obtain the title compound (2.94 g).
$^1$H NMR (300 MHz, CDCl$_3$) δ 1.26 (3H, t, J=7.2 Hz), 4.37 (2H, q, J=7.2 Hz), 5.20 (2H, s), 7.12 (1H, d, J=1.6 Hz), 7.31-7.45 (4H, m), 7.47-7.55 (2H, m).

B) Ethyl 3-(benzyloxy)-4-iodo-5-isopropoxybenzoate

2-Iodopropane (1.47 mL) was added to a DMF (30 mL) suspension of ethyl 3-(benzyloxy)-5-hydroxy-4-iodobenzoate (2.94 g) and potassium carbonate (1.53 g), and the mixture was stirred at 60° C. for 2 hours. The reaction mixture was allowed to cool to room temperature, and then, water was added thereto, followed by extraction with ethyl acetate. The obtained organic layer was washed with saturated saline and dried over anhydrous magnesium sulfate, and then, the solvent was distilled off under reduced pressure. The obtained residue was purified by silica gel column chromatography (hexane/ethyl acetate) to obtain the title compound (2.72 g).

$^1$H NMR (300 MHz, CDCl$_3$) δ 1.36-1.47 (9H, m), 4.38 (2H, q, J=7.1 Hz), 4.68 (1H, dt, J=12.1, 6.1 Hz), 5.21 (2H, s), 7.12-7.22 (2H, m), 7.29-7.47 (3H, m), 7.54 (2H, d, J=7.2 Hz).

C) Ethyl 2-(benzyloxy)-4'-fluoro-6-isopropoxybiphenyl-4-carboxylate

Palladium acetate (72 mg) was added to a mixture of ethyl 3-(benzyloxy)-4-iodo-5-isopropoxybenzoate (2.72 g), tripotassium phosphate (4.06 g), (4-fluorophenyl)boronic acid (1.78 g), tricyclohexylphosphine (20% toluene solution, 1.13 mL), toluene (20 mL), and water (10 mL), and the resultant mixture was stirred at 100° C. for 2 hours in an argon atmosphere. The reaction mixture was allowed to cool to room temperature, then diluted with ethyl acetate, and washed with water and saturated saline in this order. The organic layer was dried over anhydrous magnesium sulfate, and then, the solvent was distilled off under reduced pressure. The obtained residue was purified by silica gel column chromatography (hexane/ethyl acetate) to obtain the title compound (2.03 g).

$^1$H NMR (300 MHz, CDCl$_3$) δ 1.15-1.23 (6H, m), 1.41 (3H, t, J=7.1 Hz), 4.40 (2H, q, J=7.1 Hz), 4.45-4.57 (1H, m), 5.06 (2H, s), 7.01-7.12 (2H, m), 7.16-7.40 (9H, m).

D) Ethyl 4'-fluoro-2-isopropoxy-6-(((trifluoromethyl)sulfonyl)oxy)biphenyl-4-carboxylate A mixture of ethyl 2-(benzyloxy)-4'-fluoro-6-isopropoxybiphenyl-4-carboxylate (2.03 g), 10% palladium carbon (containing 55% water, 1.6 g), THF (10 mL), and ethanol (5 mL) was stirred at room temperature for 1 hour in a hydrogen atmosphere. The catalyst was filtered off, and then, the obtained filtrate was concentrated under reduced pressure. The obtained residue was purified by silica gel column chromatography (hexane/ethyl acetate). 4-Dimethylaminopyridine (55 mg) and N-phenyltrifluoromethanesulfonimide (2.25 g) were added to a mixture of the obtained purified product, N,N'-diisopropylethylamine (1.57 mL), and THF (50 mL), and the resultant mixture was stirred at 70° C. for 4 hours. The solvent in the reaction mixture was distilled off under reduced pressure. The obtained residue was purified by silica gel column chromatography (hexane/ethyl acetate) to obtain the title compound (1.67 g).

$^1$H NMR (300 MHz, CDCl$_3$) δ 1.21-1.27 (6H, m), 1.42 (3H, t, J=7.1 Hz), 4.43 (2H, q, J=7.1 Hz), 4.52-4.74 (1H, m), 7.06-7.18 (2H, m), 7.27-7.35 (2H, m), 7.63 (2H, dd, J=10.2, 1.1 Hz).

E) Ethyl 2-cyclopropyl-4'-fluoro-6-isopropoxybiphenyl-4-carboxylate

A mixture of ethyl 4'-fluoro-2-isopropoxy-6-(((trifluoromethyl)sulfonyl)oxy)biphenyl-4-carboxylate (1.67 g), cyclopropylboronic acid (0.955 g), dicyclohexyl(2',6'-dimethoxybiphenyl-2-yl)phosphine (228 mg), a 2 M aqueous sodium carbonate solution (5.56 mL), tris(dibenzylideneacetone)dipalladium(0) (238 mg), and toluene (15 mL) was stirred at 100° C. for 2 hours in an argon atmosphere. The reaction mixture was filtered, and then, the filtrate was poured to water, followed by extraction with ethyl acetate. The obtained organic layer was dried over anhydrous magnesium sulfate, and then, the solvent was distilled off under reduced pressure. The obtained residue was purified by silica gel column chromatography (hexane/ethyl acetate) to obtain the title compound (1.22 g).

$^1$H NMR (300 MHz, CDCl$_3$) δ 0.64-0.83 (4H, m), 1.15 (6H, d, J=6.0 Hz), 1.40 (3H, t, J=7.1 Hz), 1.56-1.68 (1H, m), 4.29-4.54 (3H, m), 7.04-7.14 (2H, m), 7.20-7.30 (3H, m), 7.44 (1H, d, J=1.3 Hz).

F) 2-Cyclopropyl-4'-fluoro-6-isopropoxybiphenyl-4-carbaldehyde

A THF (10 mL) solution of ethyl 2-cyclopropyl-4'-fluoro-6-isopropoxybiphenyl-4-carboxylate (1.22 g) was added to a THF (20 mL) suspension of lithium aluminum hydride (0.3 g) under ice cooling in a nitrogen atmosphere. After stirring at the same temperature as above for 30 minutes, water (0.3 mL) and a 15% aqueous sodium hydroxide solution (0.3 mL) were added thereto, and the mixture was stirred for 5 minutes. Water (0.9 mL) was further added to the reaction mixture, and the mixture was stirred for 30 minutes and then filtered. The filtrate was concentrated under reduced pressure. The obtained residue was purified by silica gel column chromatography (hexane/ethyl acetate). Manganese dioxide (3.21 g) was added to a toluene (10 mL) solution of the obtained purified product, and the mixture was stirred at 70° C. for 30 minutes in a nitrogen atmosphere. The reaction mixture was filtered, and then, the solvent was distilled off under reduced pressure. The obtained residue was purified by silica gel column chromatography (hexane/ethyl acetate) to obtain the title compound (850 mg).

$^1$H NMR (300 MHz, CDCl$_3$) δ 0.66-0.74 (2H, m), 0.79-0.92 (2H, m), 1.18 (6H, d, J=6.0 Hz), 1.64 (1H, tt, J=8.4, 5.3 Hz), 4.43-4.59 (1H, m), 7.02 (1H, d, J=1.1 Hz), 7.06-7.16 (2H, m), 7.20-7.31 (3H, m), 9.93 (1H, s).

G) Methyl 6-(1-((2-cyclopropyl-4'-fluoro-6-isopropoxybiphenyl-4-yl)methyl)piperidin-4-yl)-5-oxo-2-propyl-5,6,7,8-tetrahydro-1,6-naphthyridine-3-carboxylate Methyl 6-(1-(tert-butoxycarbonyl)piperidin-4-yl)-5-oxo-2-propyl-5,6,7,8-tetrahydro-1,6-naphthyridine-3-carboxylate (500 mg) was added to formic acid (5 mL), and the mixture was stirred at 60° C. for 30 minutes. Then, the solvent was distilled off under reduced pressure. Toluene was added to the residue, and the solvent was further distilled off under reduced pressure. 2-Cyclopropyl-4'-fluoro-6-isopropoxybiphenyl-4-carbaldehyde (346 mg) was added to a mixture of the obtained residue and THF (5 mL), and the resultant mixture was stirred for 10 minutes. Then, sodium triacetoxy borohydride (368 mg) was added thereto, and the mixture was stirred at room temperature for 3 hours. A saturated aqueous solution of sodium bicarbonate was added to the reaction mixture, followed by extraction with ethyl acetate twice. The obtained organic layer was dried over anhydrous magnesium sulfate, and then, the solvent was distilled off under reduced pressure. The obtained residue was purified by silica gel column chromatography (hexane/ethyl acetate/methanol) to obtain the title compound (477 mg).
MS (ESI+): [M+H]$^+$ 614.3.

H) 6-(1-((2-Cyclopropyl-4'-fluoro-6-isopropoxybiphenyl-4-yl)methyl)piperidin-4-yl)-5-oxo-2-propyl-5,6,7,8-tetrahydro-1,6-naphthyridine-3-carboxylic acid A 2 M aqueous sodium hydroxide solution (1.50 mL) was added at room temperature to a methanol (5 mL)-THF (5 mL) solution of methyl 6-(1-((2-cyclopropyl-4'-fluoro-6-isopropoxybiphenyl-4-yl)methyl)piperidin-4-yl)-5-oxo-2-propyl-5,6,7,8-tetrahydro-1,6-naphthyridine-3-carboxylate (470 mg), and the mixture was stirred at 60° C. for 30 minutes. The reaction mixture was neutralized with hydrochloric acid at room temperature. Then, ethyl acetate was added thereto, and the solvent was distilled off under reduced pressure. The deposited solid was collected by filtration and washed with diethyl ether. The obtained solid was recrystallized (DMSO/ethanol/hexane) to obtain the title compound (389 mg).
$^1$H NMR (300 MHz, DMSO-d$_6$) δ 0.52-0.63 (2H, m), 0.68-0.78 (2H, m), 0.92 (3H, t, J=7.4 Hz), 1.05-1.11 (6H, m), 1.42-1.74 (5H, m), 1.75-1.94 (2H, m), 2.12 (2H, t, J=11.3 Hz), 2.96 (2H, d, J=10.8 Hz), 3.02-3.16 (4H, m), 3.50 (2H, s), 3.58 (2H, t, J=6.6 Hz), 4.27-4.58 (2H, m), 6.49 (1H, s), 6.85 (1H, s), 7.15-7.31 (4H, m), 8.48 (1H, s).

Example 64

6-(1-((2-Cyclopropyl-6-ethoxy-2',4'-difluorobiphenyl-4-yl)methyl)piperidin-4-yl)-5-oxo-2-propyl-5,6,7,8-tetrahydro-1,6-naphthyridine-3-carboxylic acid The title compound was obtained in the same way as in steps K and L of Example 1 using methyl 6-(1-(tert-butoxycarbonyl)piperidin-4-yl)-5-oxo-2-propyl-5,6,7,8-tetrahydro-1,6-naphthyridine-3-carboxylate and 2-cyclopropyl-6-ethoxy-2',4'-difluorobiphenyl-4-carbaldehyde.

Example 65

6-(1-((6-Cyclopropyl-2,2',4'-trifluoro-3-methoxybiphenyl-4-yl)methyl)piperidin-4-yl)-5-oxo-2-propyl-5,6,7,8-tetrahydro-1,6-naphthyridine-3-carboxylic acid A) 2,2',3,4'-Tetrafluorobiphenyl-4-carbaldehyde (2,4-Difluorophenyl)boronic acid (5.39 g), dicyclohexyl(2',6'-dimethoxybiphenyl-2-yl)phosphine (1.40 g), a 2 M aqueous sodium carbonate solution (34.1 mL), and tris(dibenzylideneacetone)dipalladium(0) (1.46 g) were added at room temperature to a toluene (150 mL) solution of 4-bromo-2,3-difluorobenzaldehyde (5.03 g), and the mixture was stirred at 100° C. for 16 hours in a nitrogen atmosphere. Water was added to the reaction mixture at room temperature, and the mixture was filtered through celite. Then, the filtrate was subjected to extraction with ethyl acetate. The obtained organic layer was washed with water and saturated saline in this order and dried over anhydrous magnesium sulfate, and then, the solvent was distilled off under reduced pressure. The obtained residue was purified by silica gel column chromatography (hexane/ethyl acetate) to obtain the title compound (5.49 g).
$^1$H NMR (300 MHz, CDCl$_3$) δ 6.93-7.06 (2H, m), 7.23-7.30 (1H, m), 7.35-7.44 (1H, m), 7.70 (1H, ddd, J=8.1, 6.2, 1.8 Hz), 10.39 (1H, d, J=0.6 Hz).

B) 2,2',4'-Trifluoro-3-methoxybiphenyl-4-carbaldehyde

Sodium methoxide (28% methanol solution, 5.64 g) was added at room temperature to a methanol (120 mL) solution of 2,2',3,4'-tetrafluorobiphenyl-4-carbaldehyde (4.95 g), and the mixture was heated to reflux for 16 hours in a nitrogen atmosphere. The reaction mixture was cooled to room temperature, and then, the solvent was distilled off under reduced pressure. The obtained residue was diluted with ethyl acetate and water, followed by extraction with ethyl acetate. The obtained organic layer was washed with water and saturated saline in this order and dried over anhydrous magnesium sulfate, and then, the solvent was distilled off under reduced pressure to obtain the title compound (5.14 g).
$^1$H NMR (300 MHz, CDCl$_3$) δ 4.13 (3H, d, J=2.6 Hz), 6.91-7.05 (2H, m), 7.09-7.16 (1H, m), 7.32-7.43 (1H, m), 7.67 (1H, dd, J=8.1, 1.4 Hz), 10.43 (1H, d, J=0.8 Hz).

C) 2,2',4'-Trifluoro-3-hydroxybiphenyl-4-carbaldehyde

48% hydrobromic acid (22.0 mL) was added at room temperature to an acetic acid (120 mL) solution of 2,2',4'-trifluoro-3-methoxybiphenyl-4-carbaldehyde (5.14 g), and the mixture was stirred at 120° C. for 16 hours in a nitrogen atmosphere. The reaction mixture was cooled to room temperature, and then, the solvent was distilled off under reduced pressure. The obtained residue was neutralized with a 1 M aqueous sodium hydroxide solution, followed by extraction with ethyl acetate. The obtained organic layer was washed with water and saturated saline in this order and dried over anhydrous magnesium sulfate, and then, the solvent was distilled off under reduced pressure. The obtained residue was passed through a short silica gel column (hexane/ethyl acetate) to obtain the title compound (4.60 g).
$^1$H NMR (300 MHz, CDCl$_3$) δ 6.91-7.05 (3H, m), 7.34-7.46 (2H, m), 9.96 (1H, d, J=1.8 Hz), 11.07 (1H, s).

D) 6-Bromo-2,2',4'-trifluoro-3-hydroxybiphenyl-4-carbaldehyde

Dibromoisocyanuric acid (2.25 g) was added at room temperature to a DMF (90 mL) solution of 2,2',4'-trifluoro-3-hydroxybiphenyl-4-carbaldehyde (3.29 g), and the mixture was stirred at the same temperature as above for 3 hours in a nitrogen atmosphere. A saturated aqueous solution of sodium thiosulfate was added to the reaction mixture at room temperature, followed by extraction with ethyl acetate. The obtained organic layer was washed with water and saturated saline in this order and dried over anhydrous magnesium sulfate, and then, the solvent was distilled off under reduced pressure. The obtained residue was purified by silica gel column chromatography (hexane/ethyl acetate) and diol-supported silica gel column chromatography (hexane/ethyl acetate) in this order to obtain the title compound (3.15 g).
$^1$H NMR (300 MHz, CDCl$_3$) δ 6.93-7.06 (2H, m), 7.22-7.32 (1H, m), 7.71 (1H, d, J=1.9 Hz), 9.92 (1H, d, J=1.9 Hz), 10.90 (1H, brs).

E) 6-Bromo-2,2',4'-trifluoro-3-methoxybiphenyl-4-carbaldehyde

Iodomethane (0.907 g) was added at room temperature to a mixture of 6-bromo-2,2',4'-trifluoro-3-hydroxybiphenyl-4- carbaldehyde (1.41 g), potassium carbonate (1.18 g), and DMF (20 mL), and the resultant mixture was stirred at 60° C. for 3 hours in a nitrogen atmosphere. Water was added to the reaction mixture at room temperature, followed by extraction with ethyl acetate. The obtained organic layer was washed with water and saturated saline in this order and dried over anhydrous magnesium sulfate, and then, the solvent was distilled off under reduced pressure. The obtained residue was purified by silica gel column chromatography (hexane/ethyl acetate) to obtain the title compound (1.37 g).

$^1$H NMR (300 MHz, CDCl$_3$) δ 4.11 (3H, d, J=2.9 Hz), 6.92-7.07 (2H, m), 7.23-7.33 (1H, m), 7.93 (1H, d, J=1.9 Hz), 10.37 (1H, s).

F) 6-Cyclopropyl-2,2',4'-trifluoro-3-methoxybiphenyl-4-carbaldehyde

Cyclopropylboronic acid (1.01 g), dicyclohexyl(2',6'-dimethoxybiphenyl-2-yl)phosphine (0.323 g), a 2 M aqueous sodium carbonate solution (7.87 mL), and tris(dibenzylideneacetone)dipalladium(0) (0.360 g) were added at room temperature to a toluene (30 mL) solution of 6-bromo-2,2',4'-trifluoro-3-methoxybiphenyl-4-carbaldehyde (1.36 g), and the mixture was stirred at 100° C. for 16 hours in an argon atmosphere. Water was added to the reaction mixture at room temperature, and the mixture was filtered through celite. Then, the filtrate was subjected to extraction with ethyl acetate. The obtained organic layer was washed with water and saturated saline in this order and dried over anhydrous magnesium sulfate, and then, the solvent was distilled off under reduced pressure. The obtained residue was purified by silica gel column chromatography (hexane/ethyl acetate) to obtain the title compound (1.11 g).

$^1$H NMR (400 MHz, CDCl$_3$) δ 0.59-0.66 (1H, m), 0.69-0.75 (1H, m), 0.77-0.83 (2H, m), 1.53-1.61 (1H, m), 4.07 (3H, d, J=2.3 Hz), 6.93-7.05 (2H, m), 7.25 (1H, d, J=0.9 Hz), 7.27-7.35 (1H, m), 10.39 (1H, s).

G) Methyl 6-(1-((6-cyclopropyl-2,2',4'-trifluoro-3-methoxybiphenyl-4-yl)methyl)piperidin-4-yl)-5-oxo-2-propyl-5,6,7,8-tetrahydro-1,6-naphthyridine-3-carboxylate A mixture of methyl 6-(1-(tert-butoxycarbonyl)piperidin-4-yl)-5-oxo-2-propyl-5,6,7,8-tetrahydro-1,6-naphthyridine-3-carboxylate (313 mg) and formic acid (8 mL) was stirred at 70° C. for 30 minutes in a nitrogen atmosphere, and then, the solvent was distilled off under reduced pressure. Sodium triacetoxy borohydride (307 mg) was added at room temperature to a mixture of the obtained residue, 6-cyclopropyl-2,2',4'-trifluoro-3-methoxybiphenyl-4-carbaldehyde (244 mg), and THF (8 mL), and the resultant mixture was stirred at the same temperature as above for 15 hours in a nitrogen atmosphere. A saturated aqueous solution of sodium bicarbonate was added to the reaction mixture at room temperature, followed by extraction with ethyl acetate. The obtained organic layer was washed with water and saturated saline in this order and dried over anhydrous magnesium sulfate, and then, the solvent was distilled off under reduced pressure. The obtained residue was purified by silica gel column chromatography (hexane/ethyl acetate) to obtain the title compound (250 mg).

$^1$H NMR (400 MHz, CDCl$_3$) δ 0.53-0.59 (1H, m), 0.61-0.68 (1H, m), 0.73-0.79 (2H, m), 1.01 (3H, t, J=7.3 Hz), 1.55-1.62 (1H, m), 1.67-1.90 (6H, m), 2.19-2.30 (2H, m), 3.01 (2H, brs), 3.11-3.19 (4H, m), 3.55-3.62 (4H, m), 3.90 (3H, d, J=1.3 Hz), 3.92 (3H, s), 4.62-4.74 (1H, m), 6.76 (1H, s), 6.91-7.01 (2H, m), 7.27-7.35 (1H, m), 8.76 (1H, s)

H) 6-(1-((6-Cyclopropyl-2,2',4'-trifluoro-3-methoxybiphenyl-4-yl)methyl)piperidin-4-yl)-5-oxo-2-propyl-5,6,7,8-tetrahydro-1,6-naphthyridine-3-carboxylic acid A 2 M aqueous sodium hydroxide solution (1.5 mL) was added at room temperature to an ethanol (8 mL) solution of methyl 6-(1-((6-cyclopropyl-2,2',4'-trifluoro-3-methoxybiphenyl-4-yl)methyl)piperidin-4-yl)-5-oxo-2-propyl-5,6,7,8-tetrahydro-1,6-naphthyridine-3-carboxylate (244 mg), and the mixture was stirred at 80° C. for 2 hours in a nitrogen atmosphere. Then, the solvent was distilled off under reduced pressure. Water was added to the obtained residue, and the mixture was neutralized with 2 M hydrochloric acid, followed by extraction with a mixed solution of ethyl acetate and THF. The obtained organic layer was washed with water and saturated saline in this order and dried over anhydrous magnesium sulfate, and then, the solvent was distilled off under reduced pressure. The obtained residue was crystallized (hexane/ethyl acetate) and further recrystallized (hexane/ethanol) to obtain the title compound (160 mg).

$^1$H NMR (300 MHz, DMSO-d$_6$) δ 0.55-0.62 (2H, m), 0.72-0.80 (2H, m), 0.92 (3H, t, J=7.4 Hz), 1.47-1.72 (5H, m), 1.73-1.90 (2H, m), 2.16 (2H, t, J=11.6 Hz), 2.95 (2H, d, J=11.3 Hz), 3.03-3.14 (4H, m), 3.52-3.62 (4H, m), 3.82 (3H, d, J=0.9 Hz), 4.36-4.52 (1H, m), 6.84 (1H, s), 7.18-7.27 (1H, m), 7.40 (1H, td, J=9.7, 2.5 Hz), 7.50 (1H, td, J=8.5, 6.7 Hz), 8.49 (1H, s)

Example 66

6-(1-((2-Chloro-6-cyclopropyl-2',4'-difluoro-3-methoxybiphenyl-4-yl)methyl)piperidin-4-yl)-2-ethyl-5-oxo-5,6,7,8-tetrahydro-1,6-naphthyridine-3-carboxylic acid A) Methyl 3-(benzyloxy)-2',4'-difluorobiphenyl-4-carboxylate A mixture of methyl 2-hydroxy-4-iodobenzoate (22 g), (2,4-difluorophenyl)boronic acid (25 g), dicyclohexyl(2',6'-dimethoxybiphenyl-2-yl)phosphine (4.87 g), a 2 M aqueous sodium carbonate solution (119 mL), tris(dibenzylideneacetone)dipalladium(0) (5.07 g), and toluene (150 mL) was stirred at 100° C. for 2 hours. The reaction mixture was poured to water at room temperature, and the mixture was filtered through celite. Then, the filtrate was subjected to extraction with ethyl acetate. The obtained organic layer was washed with saturated saline and passed through a short silica gel (NH) column, and the solvent was distilled off under reduced pressure. Benzyl bromide (10.4 mL) was added to a mixture of the obtained residue, potassium carbonate (21.9 g), and DMF (100 mL), and the resultant mixture was stirred at 70° C. for 1 hour in a nitrogen atmosphere. Water was added to the reaction mixture at room temperature, followed by extraction with ethyl acetate. The obtained organic layer was washed with water and saturated saline in this order and dried over anhydrous magnesium sulfate, and then, the solvent was distilled off under reduced pressure. The obtained residue was purified by silica gel column chromatography (hexane/ethyl acetate) to obtain the title compound (30.5 g).

$^1$H NMR (300 MHz, CDCl$_3$) δ 3.92 (3H, s), 5.22 (2H, s), 6.85-7.02 (2H, m), 7.09-7.19 (2H, m), 7.28-7.45 (3H, m), 7.47-7.56 (2H, m), 7.62 (1H, dd, J=6.8, 2.9 Hz), 7.90 (1H, d, J=8.0 Hz).

B) Methyl 5-(benzyloxy)-2-bromo-2',4'-difluorobiphenyl-4-carboxylate

Dibromoisocyanuric acid (15.9 g) was added at room temperature to a DMF (150 mL) solution of methyl 3-(benzyloxy)-2',4'-difluorobiphenyl-4-carboxylate (28.0 g), and the mixture was stirred overnight at the same temperature as above. Water was added to the reaction mixture at room temperature, followed by extraction with ethyl acetate. The obtained organic layer was washed with water and saturated saline in this order and dried over anhydrous magnesium sulfate, and then, the solvent was distilled off under reduced pressure. The obtained residue was purified by silica gel column chromatography (hexane/ethyl acetate) to obtain the title compound (34.0 g).
$^1$H NMR (300 MHz, CDCl$_3$) δ 3.92 (3H, s), 5.15 (2H, s), 6.87-7.01 (3H, m), 7.10-7.55 (6H, m), 8.11 (1H, s).

C) Methyl 5-(benzyloxy)-2-cyclopropyl-2',4'-difluorobiphenyl-4-carboxylate

A mixture of methyl 5-(benzyloxy)-2-bromo-2',4'-difluorobiphenyl-4-carboxylate (34.3 g), cyclopropylboronic acid (17.0 g), dicyclohexyl(2',6'-dimethoxybiphenyl-2-yl)phosphine (4.87 g), a 2 M aqueous sodium carbonate solution (119 mL), tris(dibenzylideneacetone)dipalladium(0) (5.07 g), and toluene (150 mL) was stirred overnight at 100° C. The reaction mixture was poured to water at room temperature, followed by extraction with ethyl acetate. The obtained organic layer was washed with saturated saline and passed through a short silica gel (NH) column, and the solvent was distilled off under reduced pressure. The obtained residue was purified by silica gel column chromatography (hexane/ethyl acetate) to obtain the title compound (20.3 g).
$^1$H NMR (300 MHz, CDCl$_3$) δ 0.54-0.63 (2H, m), 0.70-0.80 (2H, m), 1.59-1.72 (1H, m), 3.87-3.93 (3H, m), 5.14 (2H, s), 6.83-7.01 (3H, m), 7.18-7.41 (4H, m), 7.44-7.51 (3H, m).

D) Methyl 2-cyclopropyl-2',4'-difluoro-5-hydroxybiphenyl-4-carboxylate

A mixture of methyl 5-(benzyloxy)-2-cyclopropyl-2',4'-difluorobiphenyl-4-carboxylate (20.3 g), 10% palladium carbon (containing 55% water, 10 g), and THF (100 mL) was stirred at room temperature for 1 hour in a hydrogen atmosphere. The catalyst was filtered off, and then, the filtrate was concentrated under reduced pressure. The obtained residue was purified by silica gel column chromatography (hexane/ethyl acetate) to obtain the title compound (15.0 g).
$^1$H NMR (300 MHz, CDCl$_3$) δ 0.48-0.58 (2H, m), 0.65-0.78 (2H, m), 1.57-1.70 (1H, m), 3.96 (3H, s), 6.85 (1H, s), 6.86-7.00 (2H, m), 7.19-7.34 (1H, m), 7.50 (1H, s), 10.58 (1H, s).

E) Methyl 2-chloro-6-cyclopropyl-2',4'-difluoro-3-hydroxybiphenyl-4-carboxylate N-Chlorosuccinimide (1.65 g) was added at room temperature to a DMF (40 mL) solution of methyl 2-cyclopropyl-2',4'-difluoro-5-hydroxybiphenyl-4-carboxylate (3.13 g), and the mixture was stirred at the same temperature as above for 3 hours in a nitrogen atmosphere. Then, N-chlorosuccinimide (0.549 g) was further added thereto, and the mixture was stirred at the same temperature as above for 16 hours in a nitrogen atmosphere. Water was added to the reaction mixture at room temperature, and the mixture was stirred at 0° C. for 1 hour. The deposited crystals were collected by filtration. The obtained crystals were dissolved in ethyl acetate and dried over anhydrous magnesium sulfate, and then, the solvent was distilled off under reduced pressure to obtain the title compound (3.17 g).
$^1$H NMR (300 MHz, CDCl$_3$) δ 0.48-0.72 (4H, m), 1.43-1.53 (1H, m), 3.99 (3H, s), 6.90-7.04 (2H, m), 7.14-7.25 (1H, m), 7.46 (1H, d, J=0.7 Hz), 11.26 (1H, s).

F) Methyl 2-chloro-6-cyclopropyl-2',4'-difluoro-3-methoxybiphenyl-4-carboxylate Iodomethane (1.04 g) was added at room temperature to a mixture of methyl 2-chloro-6-cyclopropyl-2',4'-difluoro-3-hydroxybiphenyl-4-carboxylate (1.66 g), potassium carbonate (1.36 g), and DMF (30 mL), and the resultant mixture was stirred at 60° C. for 3 hours in a nitrogen atmosphere. Water was added to the reaction mixture at room temperature, followed by extraction with ethyl acetate. The obtained organic layer was washed with water and saturated saline in this order and dried over anhydrous magnesium sulfate, and then, the solvent was distilled off under reduced pressure. The obtained residue was purified by silica gel column chromatography (hexane/ethyl acetate) to obtain the title compound (1.20 g).
$^1$H NMR (300 MHz, CDCl$_3$) δ 0.56-0.78 (4H, m), 1.45-1.55 (1H, m), 3.93 (3H, s), 3.94 (3H, s), 6.90-7.04 (2H, m), 7.14-7.25 (1H, m), 7.33 (1H, s)

G) (2-Chloro-6-cyclopropyl-2',4'-difluoro-3-methoxybiphenyl-4-yl)methanol

Diisobutylaluminum hydride (1.5 M toluene solution, 6 mL) was added at 0° C. to a THF (40 mL) solution of methyl 2-chloro-6-cyclopropyl-2',4'-difluoro-3-methoxybiphenyl-4-carboxylate (1.17 g), and the mixture was stirred at room temperature for 1 hour in a nitrogen atmosphere. Diisobutylaluminum hydride (1.5 M toluene solution, 2 mL) was added to the reaction mixture, and the mixture was stirred at room temperature for 30 minutes in a nitrogen atmosphere. Then, diisobutylaluminum hydride (1.5 M toluene solution, 2 mL) was further added thereto, and the mixture was stirred at room temperature for 30 minutes in a nitrogen atmosphere. Sodium sulfate decahydrate was added to the reaction mixture at 0° C., and the mixture was filtered through celite. Then, the filtrate was concentrated under reduced pressure. The obtained residue was purified by silica gel column chromatography (hexane/ethyl acetate) to obtain the title compound (1.07 g).
$^1$H NMR (300 MHz, CDCl$_3$) δ 0.54-0.76 (4H, m), 1.44-1.56 (1H, m), 2.07-2.16 (1H, m), 3.90 (3H, s), 4.67-4.82 (2H, m), 6.89-7.02 (3H, m), 7.15-7.24 (1H, m).

H) 2-Chloro-6-cyclopropyl-2',4'-difluoro-3-methoxybiphenyl-4-carbaldehyde

Manganese dioxide (2.29 g) was added at room temperature to a toluene (30 mL) solution of (2-chloro-6-cyclopropyl-2',4'-difluoro-3-methoxybiphenyl-4-yl)methanol (1.07 g), and the mixture was stirred at 80° C. for 1 hour in a nitrogen atmosphere. The reaction mixture was filtered through celite, and then, the filtrate was concentrated under reduced pressure. The obtained residue was purified by silica gel column chromatography (hexane/ethyl acetate) to obtain the title compound (978 mg).

$^1$H NMR (300 MHz, CDCl$_3$) δ 0.60-0.81 (4H, m), 1.45-1.56 (1H, m), 4.00 (3H, s), 6.93-7.06 (2H, m), 7.16-7.26 (1H, m), 7.40 (1H, s), 10.38 (1H, s).

I) Methyl 6-(1-((2-chloro-6-cyclopropyl-2',4'-difluoro-3-methoxybiphenyl-4-yl)methyl)piperidin-4-yl)-2-ethyl-5-oxo-5,6,7,8-tetrahydro-1,6-naphthyridine-3-carboxylate A mixture of methyl 6-(1-(tert-butoxycarbonyl)piperidin-4-yl)-2-ethyl-5-oxo-5,6,7,8-tetrahydro-1,6-naphthyridine-3-carboxylate (358 mg) and formic acid (6 mL) was stirred at 70° C. for 30 minutes in a nitrogen atmosphere, and then, the solvent was distilled off under reduced pressure. Sodium triacetoxy borohydride (364 mg) was added at room temperature to a mixture of the obtained residue, 2-chloro-6-cyclopropyl-2',4'-difluoro-3-methoxybiphenyl-4-carbaldehyde (304 mg), and THF (8 mL), and the resultant mixture was stirred at the same temperature as above for 48 hours in a nitrogen atmosphere. A saturated aqueous solution of sodium bicarbonate was added to the reaction mixture at room temperature, followed by extraction with ethyl acetate. The obtained organic layer was washed with water and saturated saline in this order and dried over anhydrous magnesium sulfate, and then, the solvent was distilled off under reduced pressure. The obtained residue was purified by silica gel column chromatography (hexane/ethyl acetate) to obtain the title compound (315 mg).

$^1$H NMR (300 MHz, CDCl$_3$) δ 0.52-0.68 (2H, m), 0.69-0.77 (2H, m), 1.30 (3H, t, J=7.5 Hz), 1.45-1.57 (1H, m), 1.66-1.92 (4H, m), 2.19-2.32 (2H, m), 2.97-3.08 (2H, m), 3.11-3.26 (4H, m), 3.55-3.63 (4H, m), 3.87 (3H, s), 3.93 (3H, s), 4.62-4.76 (1H, m), 6.89-7.02 (3H, m), 7.17-7.26 (1H, m), 8.76 (1H, s)

J) 6-(1-((2-Chloro-6-cyclopropyl-2',4'-difluoro-3-methoxybiphenyl-4-yl)methyl)piperidin-4-yl)-2-ethyl-5-oxo-5,6,7,8-tetrahydro-1,6-naphthyridine-3-carboxylic acid A 2 M aqueous sodium hydroxide solution (1.5 mL) was added at room temperature to an ethanol (8 mL) solution of methyl 6-(1-((2-chloro-6-cyclopropyl-2',4'-difluoro-3-methoxybiphenyl-4-yl)methyl)piperidin-4-yl)-2-ethyl-5-oxo-5,6,7,8-tetrahydro-1,6-naphthyridine-3-carboxylate (301 mg), and the mixture was stirred at 80° C. for 1 hour in a nitrogen atmosphere. Then, the solvent was distilled off under reduced pressure. Water was added to the obtained residue, and the mixture was neutralized with 2 M hydrochloric acid. Then, the deposited crystals were collected by filtration and dissolved in ethanol, and the solvent was distilled off under reduced pressure. The obtained residue was crystallized (hexane/ethyl acetate) and further recrystallized (hexane/ethanol) to obtain the title compound (241 mg).

$^1$H NMR (300 MHz, DMSO-d$_6$) δ 0.52-0.64 (2H, m), 0.67-0.78 (2H, m), 1.21 (3H, t, J=7.5 Hz), 1.38-1.50 (1H, m), 1.60 (2H, d, J=9.4 Hz), 1.73-1.90 (2H, m), 2.17 (2H, t, J=11.5 Hz), 2.96 (2H, d, J=11.0 Hz), 3.04-3.18 (4H, m), 3.53-3.62 (4H, m), 3.80 (3H, s), 4.38-4.53 (1H, m), 7.02 (1H, s), 7.16-7.25 (1H, m), 7.34-7.45 (2H, m), 8.49 (1H, s).

Example 67

6-(1-((6-Cyclopropyl-3-ethoxy-2,4'-difluorobiphenyl-4-yl)methyl)piperidin-4-yl)-5-oxo-2-propyl-5,6,7,8-tetrahydro-1,6-naphthyridine-3-carboxylic acid A) 4-Bromo-3-fluoro-2-methoxybenzaldehyde Sodium methoxide (28% methanol solution, 69.1 g) was added to a solution of 4-bromo-2,3-difluorobenzaldehyde (52.8 g) in methanol (600 mL) at room temperature. The mixture was refluxed under nitrogen atmosphere for 2 hours and concentrated in vacuo to about 1/4 volume. The mixture was diluted with ethyl acetate and water. The mixture was extracted with ethyl acetate. The organic layer was separated, washed with water and brine, dried over anhydrous magnesium sulfate and concentrated in vacuo to give the title compound (52.3 g).

$^1$H NMR (300 MHz, CDCl$_3$) δ 4.12 (3H, d, J=2.9 Hz), 7.34 (1H, dd, J=8.5, 5.7 Hz), 7.50 (1H, dd, J=8.5, 1.6 Hz), 10.34 (1H, s).

B) 4-Bromo-3-fluoro-2-hydroxybenzaldehyde

48% Hydrobromic acid (254 mL) was added to a solution of 4-bromo-3-fluoro-2-methoxybenzaldehyde (52.3 g) in acetic acid (350 mL) at room temperature. The mixture was stirred at 120° C. under nitrogen atmosphere for 16 hours and concentrated in vacuo. The residue was diluted with ethyl acetate and water. The mixture was extracted with ethyl acetate. The organic layer was separated, washed with water and brine, dried over anhydrous magnesium sulfate and concentrated in vacuo. The residue was triturated with diisopropyl ether and collected by filtration to give the title compound (34.6 g).

$^1$H NMR (300 MHz, DMSO-d$_6$) δ 7.26 (1H, dd, J=8.5, 5.9 Hz), 7.42 (1H, dd, J=8.5, 1.4 Hz), 10.25 (1H, s), 11.36 (1H, brs).

C) 2,4'-Difluoro-3-hydroxybiphenyl-4-carbaldehyde (4-Fluorophenyl)boronic acid (33.2 g), 2M aqueous sodium carbonate solution (237 mL), palladium (II) acetate (2.49 g) and dicyclohexylphosphino-2',6'-dimethoxy-1,1'-biphenyl (9.74 g) were added to a solution of 4-bromo-3-fluoro-2-hydroxybenzaldehyde (34.6 g) in DME (350 mL) at room temperature. The mixture was stirred at 100° C. under argon atmosphere for 16 hours. The mixture was cooled to room temperature. Water (700 mL) was added to the reaction mixture. The mixture was concentrated in vacuo to remove DME. The precipitate was collected by filtration and washed with water. The aqueous filtrate was set aside for further purification. Then the solid was washed with ethyl acetate. The solid was added to a mixture of ethyl acetate and 1M hydrochloric acid. The mixture was stirred at room temperature for 1 hour and filtrated through celite. The filtrate was extracted with ethyl acetate. The organic layer was separated, washed with water and brine, dried over anhydrous magnesium sulfate and concentrated in vacuo to give the title compound (20.6 g).

The aqueous filtrate was neutralized with 1M hydrochloric acid and extrated with ethyl acetate. The organic layer was separated, washed with water and brine, dried over anhydrous magnesium sulfate and concentrated in vacuo. The residue was purified by a silica gel column chromatography (hexane/ethyl acetate) to give the title compound (8.96 g).

¹H NMR (300 MHz, DMSO-d₆) δ 7.05-7.15 (1H, m), 7.30-7.42 (2H, m), 7.56 (1H, dd, J=8.2, 1.3 Hz), 7.61-7.72 (2H, m), 10.29 (1H, s), 11.02 (1H, brs).

D) 6-Bromo-2,4'-difluoro-3-hydroxybiphenyl-4-carbaldehyde

Dibromoisocyanuric acid (24.8 g) was added to a solution of 2,4'-difluoro-3-hydroxybiphenyl-4-carbaldehyde (33.7 g) in DMF (400 mL) at room temperature. The mixture was stirred at the same temperature under nitrogen atmosphere for 3 hours. The mixture was quenched with aqueous saturated sodium thiosulfate solution at room temperature and extracted with ethyl acetate. The organic layer was separated, washed with water and brine, dried over anhydrous magnesium sulfate and concentrated in vacuo. The residue was purified by a silica gel column chromatography (hexane/ethyl acetate) to give the title compound (33.1 g).

¹H NMR (300 MHz, DMSO-d₆) δ 7.32-7.48 (4H, m), 7.77 (1H, d, J=1.7 Hz), 10.27 (1H, s), 11.28 (1H, brs).

E) 6-Bromo-3-ethoxy-2,4'-difluorobiphenyl-4-carbaldehyde

Iodoethane (2.54 g) was added to a mixture of 6-Bromo-2,4'-difluoro-3-hydroxybiphenyl-4-carbaldehyde (3.40 g) and potassium carbonate (3.00 g) in DMF (35 mL) at room temperature. The mixture was stirred at 60° C. under nitrogen atmosphere for 5 hours. The mixture was quenched with water at room temperature and extracted with ethyl acetate. The organic layer was separated, washed with water and brine, dried over anhydrous magnesium sulfate and concentrated in vacuo. The residue was purified by a silica gel column chromatography (hexane/ethyl acetate) to give the title compound (3.55 g).

¹H NMR (300 MHz, DMSO-d₆) δ 1.37 (3H, t, J=7.0 Hz), 4.29 (2H, qd, J=7.0, 1.2 Hz), 7.32-7.42 (2H, m), 7.42-7.51 (2H, m), 7.83 (1H, d, J=1.8 Hz), 10.27 (1H, s).

F) 6-Cyclopropyl-3-ethoxy-2,4'-difluorobiphenyl-4-carbaldehyde

Cyclopropylboronic acid (1.79 g), dicyclohexyl(2',6'-dimethoxy-[1,1'-biphenyl]-2-yl)phosphine (854 mg), tris(dibenzylideneacetone)dipalladium (0) (953 mg) and 2M aqueous sodium carbonate solution (15.6 mL) were added to a solution of 6-bromo-3-ethoxy-2,4'-difluorobiphenyl-4-carbaldehyde (3.55 g) in toluene (35 mL) at room temperature. The mixture was stirred at 100° C. under argon atmosphere for 16 hours. The mixture was quenched with water at room temperature and filtrated through celite. The filtrate was extracted with ethyl acetate. The organic layer was separated, washed with water and brine, dried over anhydrous magnesium sulfate and concentrated in vacuo. The residue was purified by a silica gel column chromatography (hexane/ethyl acetate) to give the title compound (2.99 g).

¹H NMR (300 MHz, DMSO-d₆) δ 0.60-0.70 (2H, m), 0.75-0.85 (2H, m), 1.35 (3H, t, J=7.0 Hz), 1.59 (1H, tt, J=8.4, 5.3 Hz), 4.22 (2H, q, J=7.0 Hz), 7.15 (1H, d, J=1.1 Hz), 7.30-7.41 (2H, m), 7.42-7.52 (2H, m), 10.28 (1H, s).

G) Diethyl 2-hydroxy-6-propylpyridine-3,5-dicarboxylate

A mixture of ethyl 3-oxohexanoate (20.0 g) and 1,1-dimethoxy-N,N-dimethylmethanamine (15.8 g) in ethanol (40 mL) was stirred at 40 to 50° C. for 3 hours. After cooling to 25° C., ethyl cyanoacetate (15.7 g) was added to the mixture followed by addition of N-ethyl-N-isopropylpropan-2-amine (22.1 mL) at room temperature. The mixture was stirred at 50° C. for 16 hours. Acetic acid (9.11 g) and ethanol (40 mL) were added to the mixture at room temperature. The mixture was warmed to 50° C., and water (100 mL) was charged. The suspension was cooled to room temperature and stirred for 30 minutes. The precipitate was collected by filtration, washed with ethanol-water (20 mL-80 mL) and dried at 70° C. under vacuum to give a white solid. This solid was dissolved in ethanol (200 mL) at reflux temperature. Water (150 mL) was added to the mixture at the same temperature. The mixture was cooled gradually, stirred at 50 to 60° C. for 1 hour and at room temperature for 2 hours. The precipitate was collected by filtration, washed with ethanol-water (25 mL-25 mL) and dried at 70° C. under vacuum to give the title compound (17.5 g).

¹H NMR (300 MHz, DMSO-d₆) δ 0.92 (3H, t, J=7.4 Hz), 1.18-1.36 (6H, m), 1.50-1.68 (2H, m), 2.85-2.99 (2H, m), 4.15-4.32 (4H, m), 8.47 (1H, s), 12.49 (1H, brs).

H) Diethyl 2-propyl-6-vinylpyridine-3,5-dicarboxylate

Phosphoryl trichloride (7.95 mL) was added to a solution of diethyl 2-hydroxy-6-propylpyridine-3,5-dicarboxylate (12.0 g) in acetonitrile (120 mL) at room temperature. The mixture was stirred at 90° C. under a dry atmosphere with calcium chloride tube for 3 hours. After cooling to room temperature, the mixture was quenched with aqueous saturated sodium hydrogen carbonate solution at room temperature and extracted with ethyl acetate. The organic layer was separated, washed with brine and water, dried over anhydrous magnesium sulfate and concentrated in vacuo. A mixture of the residue, triethylamine (11.8 mL), potassium trifluoro(vinyl)borate (8.51 g) and dichloro[1,1'-bis(diphenylphosphino)ferrocene]palladium dichloromethane adduct (2.42 g) in ethanol (130 mL) was stirred at 90° C. overnight under nitrogen atmosphere. After cooling to room temperature, the mixture was concentrated in vacuo. The residue was diluted with ethyl acetate and water. The organic layer was separated, washed with brine, dried over anhydrous magnesium sulfate and concentrated in vacuo. The residue was passed through a silica gel-pad (hexane/ethyl acetate) to give the title compound (10.3 g).

¹H NMR (300 MHz, DMSO-d₆) δ 0.95 (3H, t, J=7.4 Hz), 1.34 (6H, td, J=7.1, 1.3 Hz), 1.65-1.80 (2H, m), 3.05-3.15 (2H, m), 4.29-4.40 (4H, m), 5.66-5.74 (1H, m), 6.58 (1H, dd, J=16.9, 2.5 Hz), 7.56 (1H, dd, J=16.9, 10.6 Hz), 8.50 (1H, s).

I) Ethyl 6-(1-(tert-butoxycarbonyl)piperidin-4-yl)-5-oxo-2-propyl-5,6,7,8-tetrahydro-1,6-naphthyridine-3-carboxylate A mixture of diethyl 2-propyl-6-vinylpyridine-3,5-dicarboxylate (9.00 g), tert-butyl 4-aminopiperidine-1-carboxylate (7.42 g) and N-ethyl-N-isopropylpropan-2-amine (8.09 mL) in DMA (45 mL) was stirred at 130 to 140° C. for 4.5 hours. The mixture was poured into water at room temperature and extracted with ethyl acetate. The organic layer was separated, washed with brine twice, dried over anhydrous magnesium sulfate and concentrated in vacuo. The residue was passed through a silica gel-pad (hexane/ethyl acetate), and concentrated in vacuo. The residue was purified by a silica gel column chromatography (hexane/ethyl acetate) to give the title compound (10.0 g).

¹H NMR (300 MHz, DMSO-d₆) δ 0.93 (3H, t, J=7.4 Hz), 1.34 (3H, t, J=7.1 Hz), 1.42 (9H, s), 1.53-1.73 (6H, m), 2.70-2.93 (2H, m), 3.00-3.15 (4H, m), 3.54 (2H, t, J=6.6 Hz), 3.97-4.15 (2H, m), 4.34 (2H, q, J=7.1 Hz), 4.51-4.67 (1H, m), 8.48 (1H, s).

J) Ethyl 5-oxo-6-(piperidin-4-yl)-2-propyl-5,6,7,8-tetrahydro-1,6-naphthyridine-3-carboxylate dihydrochloride monohydrate Ethyl 6-(1-(tert-butoxycarbonyl)piperidin-4-yl)-5-oxo-2-propyl-5,6,7,8-tetrahydro-1,6-naphthyridine-3-carboxylate (14.9 g) was added to 2M hydrogen chloride (ethanol solution, 167 mL) at room temperature. The mixture was stirred for 4 hours. Diisopropyl ether (1.00 L) was added to the reaction mixture. The mixture was stirred for 30 minutes. The precipitate was collected by filtration, washed with diisopropyl ether, dried under reduced pressure to give the title compound (13.7 g).

¹H NMR (300 MHz, DMSO-d₆) δ 0.93 (3H, t, J=7.4 Hz), 1.33 (3H, t, J=7.2 Hz), 1.59-1.81 (4H, m), 1.99-2.17 (2H, m), 2.97-3.11 (4H, m), 3.15 (2H, t, J=6.6 Hz), 3.35 (2H, d, J=12.1 Hz), 3.54 (2H, t, J=6.4 Hz), 4.35 (2H, q, J=7.1 Hz), 4.71 (1H, ddd, J=12.2, 8.2, 4.2 Hz), 6.81 (2H, brs), 8.50 (1H, s), 8.91 (2H, brs).

K) Ethyl 6-(1-((6-cyclopropyl-3-ethoxy-2,4'-difluorobiphenyl-4-yl)methyl)piperidin-4-yl)-5-oxo-2-propyl-5,6,7,8-tetrahydro-1,6-naphthyridine-3-carboxylate Triethylamine (3.26 g) was added to a mixture of ethyl 5-oxo-6-(piperidin-4-yl)-2-propyl-5,6,7,8-tetrahydro-1,6-naphthyridine-3-carboxylate dihydrochloride monohydrate (5.92 g) and 6-cyclopropyl-3-ethoxy-2,4'-difluorobiphenyl-4-carbaldehyde (5.35 g) in THF (100 mL) at room temperature. The mixture was stirred at the same temperature under nitrogen atmosphere for 10 minutes. Sodium triacetoxyhydroborate (6.82 g) was added to the reaction mixture at room temperature. The mixture was stirred at the same temperature under nitrogen atmosphere for 16 hours. The mixture was quenched with saturated sodium hydrogen carbonate aqueous solution at room temperature and extracted with ethyl acetate. The organic layer was separated, washed with water and brine, dried over anhydrous magnesium sulfate and concentrated in vacuo. The residue was purified by a silica gel column chromatography (hexane/ethyl acetate then NH silica gel, hexane/ethyl acetate) to give the title compound (7.98 g)

¹H NMR (300 MHz, CDCl₃) δ 0.58-0.67 (2H, m), 0.74-0.82 (2H, m), 0.97-1.05 (3H, m), 1.34-1.45 (6H, m), 1.63-1.91 (7H, m), 2.24 (2H, t, J=11.1 Hz), 3.02 (2H, d, J=11.1 Hz), 3.10-3.20 (4H, m), 3.54-3.62 (4H, m), 4.09 (2H, q, J=7.0 Hz), 4.38 (2H, qd, J=7.1, 1.5 Hz), 4.60-4.75 (1H, m), 6.71 (1H, s), 7.09-7.19 (2H, m), 7.30-7.40 (2H, m), 8.75 (1H, s).

L) 6-(1-((6-Cyclopropyl-3-ethoxy-2,4'-difluorobiphenyl-4-yl)methyl)piperidin-4-yl)-5-oxo-2-propyl-5,6,7,8-tetrahydro-1,6-naphthyridine-3-carboxylic acid 2M aqueous sodium hydroxide solution (25 mL) was added to a solution of ethyl 6-(1-((6-cyclopropyl-3-ethoxy-2,4'-difluorobiphenyl-4-yl)methyl)piperidin-4-yl)-5-oxo-2-propyl-5,6,7,8-tetrahydro-1,6-naphthyridine-3-carboxylate (7.98 g) in ethanol (65 mL) at room temperature. The mixture was stirred at 80° C. under nitrogen atmosphere for 2 hours and concentrated in vacuo. The residue was dissolved in water. The solution was adjusted to neutral with 2M hydrochloric acid to give colorless crystals. After filtration, the crystals was dissolved in ethanol. The solution was filtrated and the filtrate was concentrated in vacuo. The residue was crystallized from ethyl acetate-hexane to give a colorless solid. The solid was recrystallized from ethanol-hexane to give the title compound (7.16 g).

¹H NMR (300 MHz, DMSO-d₆) δ 0.55-0.65 (2H, m), 0.72-0.81 (2H, m), 0.92 (3H, t, J=7.4 Hz), 1.32 (3H, t, J=7.0 Hz), 1.54-1.87 (7H, m), 2.15 (2H, t, J=10.9 Hz), 2.95 (2H, d, J=10.8 Hz), 3.03-3.15 (4H, m), 3.50-3.61 (4H, m), 4.03 (2H, q, J=7.0 Hz), 4.37-4.52 (1H, m), 6.80 (1H, s), 7.26-7.35 (2H, m), 7.37-7.46 (2H, m), 8.48 (1H, s).

mp 221.3-222.0° C.

Example 68

6-(1-((6-Cyclopropyl-3-ethoxy-2,4'-difluorobiphenyl-4-yl)methyl)piperidin-4-yl)-2-methyl-5-oxo-5,6,7,8-tetrahydro-1,6-naphthyridine-3-carboxylic acid A) Methyl 6-(1-((6-cyclopropyl-3-ethoxy-2,4'-difluorobiphenyl-4-yl)methyl)piperidin-4-yl)-2-methyl-5-oxo-5,6,7,8-tetrahydro-1,6-naphthyridine-3-carboxylate Methyl 6-(1-(tert-butoxycarbonyl)piperidin-4-yl)-5-oxo-2-methyl-5,6,7,8-tetrahydro-1,6-naphthyridine-3-carboxylate (500 mg) was added to formic acid (2 mL), and the mixture was stirred at 60° C. for 30 minutes. Then, the solvent was distilled off under reduced pressure. 6-Cyclopropyl-3-ethoxy-2,4'-difluorobiphenyl-4-carbaldehyde (375 mg) was added to a mixture of the obtained residue and THF (6 mL), then sodium triacetoxy borohydride (368 mg) was added thereto, and the mixture was stirred overnight at room temperature. A saturated aqueous solution of sodium bicarbonate was added to the reaction mixture, followed by extraction with ethyl acetate. The solvent in the obtained organic layer was distilled off under reduced pressure. The obtained residue was purified by silica gel column chromatography (ethyl acetate/methanol) to obtain the title compound (461 mg).

MS (ESI+): [M+H]⁺ 590.4.

B) 6-(1-((6-Cyclopropyl-3-ethoxy-2,4'-difluorobiphenyl-4-yl)methyl)piperidin-4-yl)-2-methyl-5-oxo-5,6,7,8-tetrahydro-1,6-naphthyridine-3-carboxylic acid A 2 M aqueous sodium hydroxide solution (1.0 mL) was added at room temperature to a methanol (4 mL) solution of methyl 6-(1-((6-cyclopropyl-3-ethoxy-2,4'-difluorobiphenyl-4-yl)methyl)piperidin-4-yl)-2-methyl-5-oxo-5,6,7,8-tetrahydro-1,6-naphthyridine-3-carboxylate (460 mg), and the mixture was stirred at 50° C. for 30 minutes. The reaction mixture was neutralized with hydrochloric acid at room temperature and then stirred at room temperature for 2 hours, and then, the deposited solid was collected by filtration. The obtained solid was recrystallized (DMSO/ethanol/water) to obtain the title compound (385 mg).

Example 69

6-(1-((2,6-Diethoxy-2',4'-difluorobiphenyl-4-yl)methyl)piperidin-4-yl)-5-oxo-2-propyl-5,6,7,8-tetrahydro-1,6-naphthyridine-3-carboxylic acid

A) 2,6-Diethoxy-2',4'-difluorobiphenyl-4-carbaldehyde

The title compound was obtained in the same way as in step D of Example 8 and step E of Example 1 using methyl 3,5-diethoxy-4-iodobenzoate and (2,4-difluorophenyl)boronic acid.
$^1$H NMR (300 MHz, CDCl$_3$) δ 1.25-1.33 (6H, m), 3.98-4.14 (4H, m), 6.76-6.98 (2H, m), 7.19-7.34 (2H, m), 9.95 (1H, s).

B) 6-(1-((2,6-Diethoxy-2',4'-difluorobiphenyl-4-yl)methyl)piperidin-4-yl)-5-oxo-2-propyl-5,6,7,8-tetrahydro-1,6-naphthyridine-3-carboxylic acid The title compound was obtained in the same way as in steps K and L of Example 1 using methyl 6-(1-(tert-butoxycarbonyl)piperidin-4-yl)-5-oxo-2-propyl-5,6,7,8-tetrahydro-1,6-naphthyridine-3-carboxylate and 2,6-diethoxy-2',4'-difluorobiphenyl-4-carbaldehyde.

Example 70

6-(1-((6-Cyclopropyl-2,2',4'-trifluoro-3-methoxybiphenyl-4-yl)methyl)piperidin-4-yl)-2-ethyl-5-oxo-5,6,7,8-tetrahydro-1,6-naphthyridine-3-carboxylic acid The title compound was obtained in the same way as in steps K and L of Example 1 using methyl 6-(1-(tert-butoxycarbonyl)piperidin-4-yl)-2-ethyl-5-oxo-5,6,7,8-tetrahydro-1,6-naphthyridine-3-carboxylate and 6-cyclopropyl-2,2',4'-trifluoro-3-methoxybiphenyl-4-carbaldehyde.

Example 71

6-(1-((6-Cyclopropyl-3-ethoxy-2,2',4'-trifluorobiphenyl-4-yl)methyl)piperidin-4-yl)-2-ethyl-5-oxo-5,6,7,8-tetrahydro-1,6-naphthyridine-3-carboxylic acid

A) 6-Cyclopropyl-3-ethoxy-2,2',4'-trifluorobiphenyl-4-carbaldehyde

The title compound was obtained in the same way as in steps E and F of Example 65 using 6-bromo-2,2',4'-trifluoro-3-hydroxybiphenyl-4-carbaldehyde and iodoethane.
$^1$H NMR (300 MHz, CDCl$_3$) δ 0.59-0.67 (1H, m), 0.67-0.76 (1H, m), 0.77-0.83 (2H, m), 1.43 (3H, td, J=7.1, 0.7 Hz), 1.50-1.63 (1H, m), 4.28 (2H, qt, J=7.0, 1.3 Hz), 6.92-7.05 (2H, m), 7.24-7.36 (2H, m), 10.41 (1H, s).

B) 6-(1-((6-Cyclopropyl-3-ethoxy-2,2',4'-trifluorobiphenyl-4-yl)methyl)piperidin-4-yl)-2-ethyl-5-oxo-5,6,7,8-tetrahydro-1,6-naphthyridine-3-carboxylic acid The title compound was obtained in the same way as in steps K and L of Example 1 using methyl 6-(1-(tert-butoxycarbonyl)piperidin-4-yl)-2-ethyl-5-oxo-5,6,7,8-tetrahydro-1,6-naphthyridine-3-carboxylate and 6-cyclopropyl-3-ethoxy-2,2',4'-trifluorobiphenyl-4-carbaldehyde.

Example 72

6-(1-((6-Cyclopropyl-2,4'-difluoro-3-isopropoxybiphenyl-4-yl)methyl)piperidin-4-yl)-2-ethyl-5-oxo-5,6,7,8-tetrahydro-1,6-naphthyridine-3-carboxylic acid

A) 4-Bromo-3-fluoro-2-methoxybenzaldehyde

Sodium methoxide (28% methanol solution, 69.1 g) was added to a solution of 4-bromo-2,3-difluorobenzaldehyde (52.8 g) in methanol (600 mL) at room temperature. The mixture was refluxed under nitrogen atmosphere for 2 hours and concentrated in vacuo to about 1/4 volume. The mixture was diluted with ethyl acetate and water. The mixture was extracted with ethyl acetate. The organic layer was separated, washed with water and brine, dried over anhydrous magnesium sulfate and concentrated in vacuo to give the title compound (52.3 g).
$^1$H NMR (300 MHz, CDCl$_3$) δ 4.12 (3H, d, J=2.9 Hz), 7.34 (1H, dd, J=8.5, 5.7 Hz), 7.50 (1H, dd, J=8.5, 1.6 Hz), 10.34 (1H, s).

B) 4-Bromo-3-fluoro-2-hydroxybenzaldehyde

48% Hydrobromic acid (254 mL) was added to a solution of 4-bromo-3-fluoro-2-methoxybenzaldehyde (52.3 g) in acetic acid (350 mL) at room temperature. The mixture was stirred at 120° C. under nitrogen atmosphere for 16 hours and concentrated in vacuo. The residue was diluted with ethyl acetate and water. The mixture was extracted with ethyl acetate. The organic layer was separated, washed with water and brine, dried over anhydrous magnesium sulfate and concentrated in vacuo. The residue was triturated with diisopropyl ether and collected by filtration to give the title compound (34.6 g).
$^1$H NMR (300 MHz, DMSO-d$_6$) δ 7.26 (1H, dd, J=8.5, 5.9 Hz), 7.42 (1H, dd, J=8.5, 1.4 Hz), 10.25 (1H, s), 11.36 (1H, brs).

C) 2,4'-Difluoro-3-hydroxybiphenyl-4-carbaldehyde (4-Fluorophenyl)boronic acid (33.2 g), 2M aqueous sodium carbonate solution (237 mL), palladium (II) acetate (2.49 g) and dicyclohexylphosphino-2',6'-dimethoxy-1,1'-biphenyl (9.74 g) were added to a solution of 4-bromo-3-fluoro-2-hydroxybenzaldehyde (34.6 g) in DME (350 mL) at room temperature. The mixture was stirred at 100° C. under argon atmosphere for 16 hours. The mixture was cooled to room temperature. Water (700 mL) was added to the reaction mixture. The mixture was concentrated in vacuo to remove DME. The precipitate was collected by filtration and washed with water. The aqueous filtrate was set aside for further purification. Then the solid was washed with ethyl acetate. The solid was added to a mixture of ethyl acetate and 1M hydrochloric acid. The mixture was stirred at room temperature for 1 hour and filtrated through celite. The filtrate was extracted with ethyl acetate. The organic layer was separated, washed with water and brine, dried over anhydrous magnesium sulfate and concentrated in vacuo to give the title compound (20.6 g).

The aqueous filtrate was neutralized with 1M hydrochloric acid and extrated with ethyl acetate. The organic layer was separated, washed with water and brine, dried over anhydrous magnesium sulfate and concentrated in vacuo. The residue was purified by a silica gel column chromatography (hexane/ethyl acetate) to give the title compound (8.96 g).

¹H NMR (300 MHz, DMSO-d₆) δ 7.05-7.15 (1H, m), 7.30-7.42 (2H, m), 7.56 (1H, dd, J=8.2, 1.3 Hz), 7.61-7.72 (2H, m), 10.29 (1H, s), 11.02 (1H, brs).

D) 6-Bromo-2,4'-difluoro-3-hydroxybiphenyl-4-carbaldehyde

Dibromoisocyanuric acid (24.8 g) was added to a solution of 2,4'-difluoro-3-hydroxybiphenyl-4-carbaldehyde (33.7 g) in DMF (400 mL) at room temperature. The mixture was stirred at the same temperature under nitrogen atmosphere for 3 hours. The mixture was quenched with aqueous saturated sodium thiosulfate solution at room temperature and extracted with ethyl acetate. The organic layer was separated, washed with water and brine, dried over anhydrous magnesium sulfate and concentrated in vacuo. The residue was purified by a silica gel column chromatography (hexane/ethyl acetate) to give the title compound (33.1 g).
¹H NMR (300 MHz, DMSO-d₆) δ 7.32-7.48 (4H, m), 7.77 (1H, d, J=1.7 Hz), 10.27 (1H, s), 11.28 (1H, brs).

E) 6-Bromo-2,4'-difluoro-3-isopropoxybiphenyl-4-carbaldehyde

2-Iodopropane (21.7 g) was added to a mixture of 6-bromo-2,4'-difluoro-3-hydroxybiphenyl-4-carbaldehyde (26.7 g) and potassium carbonate (23.6 g) in DMF (250 mL) at room temperature. The mixture was stirred at 60° C. under nitrogen atmosphere for 3 hours. The mixture was quenched with water at room temperature and extracted with ethyl acetate. The organic layer was separated, washed with water and brine, dried over anhydrous magnesium sulfate and concentrated in vacuo. The residue was purified by a silica gel column chromatography (hexane/ethyl acetate) to give the title compound (28.5 g).
¹H NMR (300 MHz, DMSO-d₆) δ 1.34 (6H, d, J=6.0 Hz), 4.50-4.65 (1H, m), 7.32-7.42 (2H, m), 7.43-7.53 (2H, m), 7.83 (1H, d, J=1.7 Hz), 10.26 (1H, s).

F) 6-Cyclopropyl-2,4'-difluoro-3-isopropoxybiphenyl-4-carbaldehyde

Cyclopropylboronic acid (13.8 g), dicyclohexyl(2',6'-dimethoxy-[1,1'-biphenyl]-2-yl)phosphine (6.58 g), tris(dibenzylideneacetone)dipalladium (0) (7.34 g) and 2M aqueous sodium carbonate solution (120 mL) were added to a solution of 6-bromo-2,4'-difluoro-3-isopropoxybiphenyl-4-carbaldehyde (28.5 g) in toluene (250 mL) at room temperature. The mixture was stirred at 100° C. under argon atmosphere for 16 hours. The mixture was filtrated through celite. The filtrate was extracted with ethyl acetate. The organic layer was separated, washed with water and brine, dried over anhydrous magnesium sulfate and concentrated in vacuo. The residue was purified by a silica gel column chromatography (hexane/ethyl acetate) to give the title compound (24.8 g).
¹H NMR (300 MHz, DMSO-d₆) δ 0.61-0.70 (2H, m), 0.75-0.85 (2H, m), 1.31 (6H, d, J=6.1 Hz), 1.59 (1H, tt, J=8.4, 5.3 Hz), 4.41-4.56 (1H, m), 7.15 (1H, d, J=1.0 Hz), 7.30-7.41 (2H, m), 7.43-7.52 (2H, m), 10.28 (1H, s)

G) Dimethyl 2-ethyl-6-hydroxypyridine-3,5-dicarboxylate 1,1-Dimethoxy-N,N-dimethylmethanamine (24.4 g) was added to a solution of methyl 3-oxopentanoate (25.4 g) in methanol (50 mL) at room temperature. The mixture was stirred at 50° C. under nitrogen atmosphere for 3 hours. After cooling to room temperature, methyl cyanoacetate (21.3 g) and N-ethyl-N-isopropylpropan-2-amine (25.2 g) were added to the reaction mixture. The mixture was stirred at 50° C. under nitrogen atmosphere for 16 hours. After cooling to room temperature, acetic acid (14.1 g) was added to the reaction mixture at 50° C. The mixture was stirred at 50° C. under nitrogen atmosphere for 10 minutes. Water (150 mL) was added to the reaction mixture at 50° C. The mixture was stirred at room temperature for 2 hours. After filtration, the crystals were washed with methanol-water (1:4) and then diisopropyl ether. The crystals were dried at 70° C. under vacuum to give the title compound (22.3 g).
¹H NMR (400 MHz, DMSO-d₆) δ 1.17 (3H, t, J=7.4 Hz), 2.95 (2H, q, J=7.4 Hz), 3.75 (3H, s), 3.78 (3H, s), 8.50 (1H, s), 12.55 (1H, brs).

H) Dimethyl 2-chloro-6-ethylpyridine-3,5-dicarboxylate

Phosphoryl trichloride (17.3 ml) was added to a solution of dimethyl 2-ethyl-6-hydroxypyridine-3,5-dicarboxylate (22.3 g) in acetonitrile (250 mL) at room temperature. The mixture was stirred at 90° C. under nitrogen atmosphere for 3 hours. The mixture was neutralized with aqueous saturated sodium hydrogen carbonate solution at 0° C. and extracted with ethyl acetate. The organic layer was separated, washed with water and brine, dried over anhydrous magnesium sulfate and concentrated in vacuo to give the title compound (24.0 g).
¹H NMR (300 MHz, DMSO-d₆) δ 1.22 (3H, t, J=7.5 Hz), 3.10 (2H, q, J=7.5 Hz), 3.87-3.94 (6H, m), 8.59 (1H, s).

I) Methyl 6-(1-(tert-butoxycarbonyl)piperidin-4-yl)-2-ethyl-5-oxo-5,6,7,8-tetrahydro-1,6-naphthyridine-3-carboxylate Dichloro[1,1'-bis(diphenylphosphino)ferrocene]palladium dichloromethane adduct (5.32 g), potassium trifluoro(vinyl)borate (18.7 g) and triethylamine (18.8 g) were added to a solution of dimethyl 2-chloro-6-ethylpyridine-3,5-dicarboxylate (24.0 g) in methanol (230 mL) at room temperature. The mixture was stirred at 85° C. under argon atmosphere for 16 hours and concentrated in vacuo. The residue was diluted with ethyl acetate and water. The mixture was filtrated through celite. The filtrate was extracted with ethyl acetate. The organic layer was separated, washed with water and brine, dried over anhydrous magnesium sulfate and concentrated in vacuo. Tert-butyl 4-aminopiperidine-1-carboxylate (22.4 g) and N-ethyl-N-isopropylpropan-2-amine (18.0 g) were added to a solution of the residue in DMA (150 mL) at room temperature. The mixture was stirred at 140° C. under nitrogen atmosphere for 6 hours. The mixture was quenched with water at room temperature and filtrated through celite. The filtrate was extracted with ethyl acetate. The organic layer was separated, washed with water and brine, dried over anhydrous magnesium sulfate and concentrated in vacuo. The residue was purified by a silica gel column chromatography (hexane/ethyl acetate) to give the title compound (24.8 g).
¹H NMR (300 MHz, DMSO-d₆) δ 1.22 (3H, t, J=7.5 Hz), 1.41 (9H, s), 1.55-1.68 (4H, m), 2.84 (2H, brs), 3.03-3.17 (4H, m), 3.55 (2H, t, J=6.6 Hz), 3.88 (3H, s), 3.98-4.17 (2H, m), 4.50-4.70 (1H, m), 8.50 (1H, s)

J) Methyl 2-ethyl-5-oxo-6-(piperidin-4-yl)-5,6,7,8-tetrahydro-1,6-naphthyridine-3-carboxylate dihydrochloride A mixture of 2M hydrogen chloride (methanol solution, 236 mL) and methyl 6-(1-(tert-butoxycarbonyl)piperidin-4- yl)-2-ethyl-5-oxo-5,6,7,8-tetrahydro-1,6-naphthyridine-3-carboxylate (19.7 g) was stirred at room temperature under nitrogen atmosphere for 4 hours and concentrated in vacuo. The residue was crystallized from methanol and ethyl acetate. After filtration, the crystals were washed with ethyl acetate to give the title compound (18.5 g).

$^1$H NMR (300 MHz, DMSO-d$_6$) δ 1.23 (3H, t, J=7.5 Hz), 1.74 (2H, d, J=12.4 Hz), 2.07-2.25 (2H, m), 2.97-3.25 (6H, m), 3.34 (2H, d, J=12.3 Hz), 3.57 (2H, t, J=6.6 Hz), 3.89 (3H, s), 4.65-4.83 (1H, m), 8.55 (1H, s), 9.07-9.49 (2H, m).

K) Methyl 6-(1-((6-cyclopropyl-2,4'-difluoro-3-isopropoxybiphenyl-4-yl)methyl)piperidin-4-yl)-2-ethyl-5-oxo-5,6,7,8-tetrahydro-1,6-naphthyridine-3-carboxylate Triethylamine (2.59 g) was added to a suspension of methyl 2-ethyl-5-oxo-6-(piperidin-4-yl)-5,6,7,8-tetrahydro-1,6-naphthyridine-3-carboxylate dihydrochloride (5.00 g) in THF (60 mL) and DMA (20 mL) at room temperature. After being stirred at the same temperature for 30 minutes, 6-cyclopropyl-2,4'-difluoro-3-isopropoxybiphenyl-4-carbaldehyde (4.86 g) was added to the reaction mixture. The mixture was stirred at room temperature under nitrogen atmosphere for 30 minutes. Sodium triacetoxyhydroborate (4.07 g) and acetic acid (769 mg) were added to the reaction mixture at room temperature. The mixture was stirred at the same temperature under nitrogen atmosphere for 16 hours. The mixture was quenched with aqueous saturated sodium hydrogen carbonate solution at room temperature and extracted with ethyl acetate. The organic layer was separated, washed with water and brine, dried over anhydrous magnesium sulfate and concentrated in vacuo. The residue was purified by a silica gel column chromatography (ethyl acetate/methanol) to give the title compound (5.80 g).

$^1$H NMR (300 MHz, CDCl$_3$) δ 0.58-0.68 (2H, m), 0.74-0.82 (2H, m), 1.25-1.36 (9H, m), 1.56-1.74 (3H, m), 1.76-1.93 (2H, m), 2.16-2.33 (2H, m), 3.01 (2H, d, J=11.7 Hz), 3.09-3.27 (4H, m), 3.53-3.65 (4H, m), 3.92 (3H, s), 4.34-4.49 (1H, m), 4.60-4.76 (1H, m), 6.76 (1H, s), 7.08-7.19 (2H, m), 7.34 (2H, dd, J=8.6, 5.5 Hz), 8.76 (1H, s).

L) 6-(1-((6-Cyclopropyl-2,4'-difluoro-3-isopropoxybiphenyl-4-yl)methyl)piperidin-4-yl)-2-ethyl-5-oxo-5,6,7,8-tetrahydro-1,6-naphthyridine-3-carboxylic acid 2M aqueous sodium hydroxide solution (20 mL) was added to a solution of methyl 6-(1-((6-cyclopropyl-2,4'-difluoro-3-isopropoxybiphenyl-4-yl)methyl)piperidin-4-yl)-2-ethyl-5-oxo-5,6,7,8-tetrahydro-1,6-naphthyridine-3-carboxylate (8.03 g) in methanol (25 mL) at 70° C. The mixture was stirred at the same temperature under nitrogen atmosphere for 2 hours. The mixture was neutralized with 1M hydrochloric acid at room temperature and added to water (100 mL). The mixture was stirred at 70° C. for 30 minutes and at room temperature for 2 hours to give colorless crystals. After filtration, the crystals were dissolved in ethanol. The solution was filtrated and the filtrate was concentrated in vacuo to give a colorless solid. The solid was recrystallized from ethanol-water (45 mL-130 mL) to give the title compound (7.26 g).

$^1$H NMR (300 MHz, DMSO-d$_6$) δ 0.54-0.65 (2H, m), 0.72-0.84 (2H, m), 1.18-1.29 (9H, m), 1.52-1.68 (3H, m), 1.71-1.90 (2H, m), 2.14 (2H, t, J=11.3 Hz), 2.95 (2H, d, J=11.0 Hz), 3.05-3.18 (4H, m), 3.51-3.62 (4H, m), 4.28-4.54 (2H, m), 6.83 (1H, s), 7.25-7.36 (2H, m), 7.37-7.48 (2H, m), 8.49 (1H, s).

mp 148.1-148.9° C.

Example 73

6-(1-((6-cyclopropyl-2,4'-difluoro-3-isopropoxybiphenyl-4-yl)methyl)piperidin-4-yl)-2-methyl-5-oxo-5,6,7,8-tetrahydro-1,6-naphthyridine-3-carboxylic acid The title compound was obtained in the same way as in steps K and L of Example 1 using methyl 6-(1-(tert-butoxycarbonyl)piperidin-4-yl)-5-oxo-2-methyl-5,6,7,8-tetrahydro-1,6-naphthyridine-3-carboxylate and 6-cyclopropyl-3-isopropoxy-2,4'-difluorobiphenyl-4-carbaldehyde.

Example 74

6-(1-((6-Cyclopropyl-3-ethoxy-2,4'-difluorobiphenyl-4-yl)methyl)piperidin-4-yl)-2-ethyl-5-oxo-5,6,7,8-tetrahydro-1,6-naphthyridine-3-carboxylic acid A) 4-Bromo-3-fluoro-2-methoxybenzaldehyde Sodium methoxide (28% methanol solution, 69.1 g) was added to a solution of 4-bromo-2,3-difluorobenzaldehyde (52.8 g) in methanol (600 mL) at room temperature. The mixture was refluxed under nitrogen atmosphere for 2 hours and concentrated in vacuo to about 1/4 volume. The mixture was diluted with ethyl acetate and water. The mixture was extracted with ethyl acetate. The organic layer was separated, washed with water and brine, dried over anhydrous magnesium sulfate and concentrated in vacuo to give the title compound (52.3 g).

$^1$H NMR (300 MHz, CDCl$_3$) δ 4.12 (3H, d, J=2.9 Hz), 7.34 (1H, dd, J=8.5, 5.7 Hz), 7.50 (1H, dd, J=8.5, 1.6 Hz), 10.34 (1H, s).

B) 4-Bromo-3-fluoro-2-hydroxybenzaldehyde

48% Hydrobromic acid (254 mL) was added to a solution of 4-bromo-3-fluoro-2-methoxybenzaldehyde (52.3 g) in acetic acid (350 mL) at room temperature. The mixture was stirred at 120° C. under nitrogen atmosphere for 16 hours and concentrated in vacuo. The residue was diluted with ethyl acetate and water. The mixture was extracted with ethyl acetate. The organic layer was separated, washed with water and brine, dried over anhydrous magnesium sulfate and concentrated in vacuo. The residue was triturated with diisopropyl ether and collected by filtration to give the title compound (34.6 g).

$^1$H NMR (300 MHz, DMSO-d$_6$) δ 7.26 (1H, dd, J=8.5, 5.9 Hz), 7.42 (1H, dd, J=8.5, 1.4 Hz), 10.25 (1H, s), 11.36 (1H, brs).

C) 2,4'-Difluoro-3-hydroxybiphenyl-4-carbaldehyde (4-Fluorophenyl)boronic acid (33.2 g), 2M aqueous sodium carbonate solution (237 mL), palladium (II) acetate (2.49 g) and dicyclohexylphosphino-2',6'-dimethoxy-1,1'-biphenyl (9.74 g) were added to a solution of 4-bromo-3-fluoro-2-hydroxybenzaldehyde (34.6 g) in DME (350 mL) at room temperature. The mixture was stirred at 100° C. under argon atmosphere for 16 hours. The mixture was cooled to room temperature. Water (700 mL) was added to the reaction mixture. The mixture was concentrated in vacuo to remove DME. The precipitate was collected by filtration and washed with water. The aqueous filtrate was set aside for further purification. Then the solid was washed with ethyl acetate. The solid was added to a mixture of ethyl acetate and 1M hydrochloric acid. The mixture was stirred at room temperature for 1 hour and filtrated through celite. The filtrate was extracted with ethyl acetate. The organic layer was separated, washed with water and brine, dried over anhydrous magnesium sulfate and concentrated in vacuo to give the title compound (20.6 g).

The aqueous filtrate was neutralized with 1M hydrochloric acid and extrated with ethyl acetate. The organic layer was separated, washed with water and brine, dried over anhydrous magnesium sulfate and concentrated in vacuo. The residue was purified by a silica gel column chromatography (hexane/ethyl acetate) to give the title compound (8.96 g).

$^1$H NMR (300 MHz, DMSO-d$_6$) δ 7.05-7.15 (1H, m), 7.30-7.42 (2H, m), 7.56 (1H, dd, J=8.2, 1.3 Hz), 7.61-7.72 (2H, m), 10.29 (1H, s), 11.02 (1H, brs).

D) 6-Bromo-2,4'-difluoro-3-hydroxybiphenyl-4-carbaldehyde

Dibromoisocyanuric acid (24.8 g) was added to a solution of 2,4'-difluoro-3-hydroxybiphenyl-4-carbaldehyde (33.7 g) in DMF (400 mL) at room temperature. The mixture was stirred at the same temperature under nitrogen atmosphere for 3 hours. The mixture was quenched with aqueous saturated sodium thiosulfate solution at room temperature and extracted with ethyl acetate. The organic layer was separated, washed with water and brine, dried over anhydrous magnesium sulfate and concentrated in vacuo. The residue was purified by a silica gel column chromatography (hexane/ethyl acetate) to give the title compound (33.1 g).

$^1$H NMR (300 MHz, DMSO-d$_6$) δ 7.32-7.48 (4H, m), 7.77 (1H, d, J=1.7 Hz), 10.27 (1H, s), 11.28 (1H, brs).

E) 6-Bromo-3-ethoxy-2,4'-difluorobiphenyl-4-carbaldehyde

Iodoethane (2.54 g) was added to a mixture of 6-Bromo-2,4'-difluoro-3-hydroxybiphenyl-4-carbaldehyde (3.40 g) and potassium carbonate (3.00 g) in DMF (35 mL) at room temperature. The mixture was stirred at 60° C. under nitrogen atmosphere for 5 hours. The mixture was quenched with water at room temperature and extracted with ethyl acetate. The organic layer was separated, washed with water and brine, dried over anhydrous magnesium sulfate and concentrated in vacuo. The residue was purified by a silica gel column chromatography (hexane/ethyl acetate) to give the title compound (3.55 g).

$^1$H NMR (300 MHz, DMSO-d$_6$) δ 1.37 (3H, t, J=7.0 Hz), 4.29 (2H, qd, J=7.0, 1.2 Hz), 7.32-7.42 (2H, m), 7.42-7.51 (2H, m), 7.83 (1H, d, J=1.8 Hz), 10.27 (1H, s).

F) 6-Cyclopropyl-3-ethoxy-2,4'-difluorobiphenyl-4-carbaldehyde

Cyclopropylboronic acid (1.79 g), dicyclohexyl(2',6'-dimethoxy-[1,1'-biphenyl]-2-yl)phosphine (854 mg), tris(dibenzylideneacetone)dipalladium (0) (953 mg) and 2M aqueous sodium carbonate solution (15.6 mL) were added to a solution of 6-bromo-3-ethoxy-2,4'-difluorobiphenyl-4-carbaldehyde (3.55 g) in toluene (35 mL) at room temperature. The mixture was stirred at 100° C. under argon atmosphere for 16 hours. The mixture was quenched with water at room temperature and filtrated through celite. The filtrate was extracted with ethyl acetate. The organic layer was separated, washed with water and brine, dried over anhydrous magnesium sulfate and concentrated in vacuo. The residue was purified by a silica gel column chromatography (hexane/ethyl acetate) to give the title compound (2.99 g).

$^1$H NMR (300 MHz, DMSO-d$_6$) δ 0.60-0.70 (2H, m), 0.75-0.85 (2H, m), 1.35 (3H, t, J=7.0 Hz), 1.59 (1H, tt, J=8.4, 5.3 Hz), 4.22 (2H, q, J=7.0 Hz), 7.15 (1H, d, J=1.1 Hz), 7.30-7.41 (2H, m), 7.42-7.52 (2H, m), 10.28 (1H, s).

G) Dimethyl 2-ethyl-6-hydroxypyridine-3,5-dicarboxylate 1,1-Dimethoxy-N,N-dimethylmethanamine (24.4 g) was added to a solution of methyl 3-oxopentanoate (25.4 g) in methanol (50 mL) at room temperature. The mixture was stirred at 50° C. under nitrogen atmosphere for 3 hours. After cooling to room temperature, methyl cyanoacetate (21.3 g) and N-ethyl-N-isopropylpropan-2-amine (25.2 g) were added to the reaction mixture. The mixture was stirred at 50° C. under nitrogen atmosphere for 16 hours. After cooling to room temperature, acetic acid (14.1 g) was added to the reaction mixture at 50° C. The mixture was stirred at 50° C. under nitrogen atmosphere for 10 minutes. Water (150 mL) was added to the reaction mixture at 50° C. The mixture was stirred at room temperature for 2 hours. After filtration, the crystals were washed with methanol-water (1:4) and then diisopropyl ether. The crystals were dried at 70° C. under vacuum to give the title compound (22.3 g).

$^1$H NMR (400 MHz, DMSO-d$_6$) δ 1.17 (3H, t, J=7.4 Hz), 2.95 (2H, q, J=7.4 Hz), 3.75 (3H, s), 3.78 (3H, s), 8.50 (1H, s), 12.55 (1H, brs).

H) Dimethyl 2-chloro-6-ethylpyridine-3,5-dicarboxylate

Phosphoryl trichloride (17.3 ml) was added to a solution of dimethyl 2-ethyl-6-hydroxypyridine-3,5-dicarboxylate (22.3 g) in acetonitrile (250 mL) at room temperature. The mixture was stirred at 90° C. under nitrogen atmosphere for 3 hours. The mixture was neutralized with aqueous saturated sodium hydrogen carbonate solution at 0° C. and extracted with ethyl acetate. The organic layer was separated, washed with water and brine, dried over anhydrous magnesium sulfate and concentrated in vacuo to give the title compound (24.0 g).

$^1$H NMR (300 MHz, DMSO-d$_6$) δ 1.22 (3H, t, J=7.5 Hz), 3.10 (2H, q, J=7.5 Hz), 3.87-3.94 (6H, m), 8.59 (1H, s).

I) Methyl 6-(1-(tert-butoxycarbonyl)piperidin-4-yl)-2-ethyl-5-oxo-5,6,7,8-tetrahydro-1,6-naphthyridine-3-carboxylate Dichloro[1,1'-bis(diphenylphosphino)ferrocene]palladium dichloromethane adduct (5.32 g), potassium trifluoro(vinyl)borate (18.7 g) and triethylamine (18.8 g) were added to a solution of dimethyl 2-chloro-6-ethylpyridine-3,5-dicarboxylate (24.0 g) in methanol (230 mL) at room temperature. The mixture was stirred at 85° C. under argon atmosphere for 16 hours and concentrated in vacuo. The residue was diluted with ethyl acetate and water. The mixture was filtered through celite. The filtrate was extracted with ethyl acetate. The organic layer was separated, washed with water and brine, dried over anhydrous magnesium sulfate and concentrated in vacuo. Tert-butyl 4-aminopiperidine-1-carboxylate (22.4 g) and N-ethyl-N-isopropylpropan-2-amine (18.0 g) were added to a solution of the residue in DMA (150 mL) at room temperature. The mixture was stirred at 140° C. under nitrogen atmosphere for 6 hours. The mixture was quenched with water at room temperature and filtrated through celite. The filtrate was extracted with ethyl acetate. The organic layer was separated, washed with water and brine, dried over anhydrous magnesium sulfate and concentrated in vacuo. The residue was purified by a silica gel column chromatography (hexane/ethyl acetate) to give the title compound (24.8 g).

$^1$H NMR (300 MHz, DMSO-$d_6$) δ 1.22 (3H, t, J=7.5 Hz), 1.41 (9H, s), 1.55-1.68 (4H, m), 2.84 (2H, brs), 3.03-3.17 (4H, m), 3.55 (2H, t, J=6.6 Hz), 3.88 (3H, s), 3.98-4.17 (2H, m), 4.50-4.70 (1H, m), 8.50 (1H, s).

J) Methyl 2-ethyl-5-oxo-6-(piperidin-4-yl)-5,6,7,8-tetrahydro-1,6-naphthyridine-3-carboxylate dihydrochloride A mixture of 2M hydrogen chloride (methanol solution, 236 mL) and methyl 6-(1-(tert-butoxycarbonyl)piperidin-4-yl)-2-ethyl-5-oxo-5,6,7,8-tetrahydro-1,6-naphthyridine-3-carboxylate (19.7 g) was stirred at room temperature under nitrogen atmosphere for 4 hours and concentrated in vacuo. The residue was crystallized with methanol and ethyl acetate. After filtration, the crystals were washed with ethyl acetate to give the title compound (18.5 g).

$^1$H NMR (300 MHz, DMSO-$d_6$) δ 1.23 (3H, t, J=7.5 Hz), 1.74 (2H, d, J=12.4 Hz), 2.07-2.25 (2H, m), 2.97-3.25 (6H, m), 3.34 (2H, d, J=12.3 Hz), 3.57 (2H, t, J=6.6 Hz), 3.89 (3H, s), 4.65-4.83 (1H, m), 8.55 (1H, s), 9.07-9.49 (2H, m).

K) Methyl 6-(1-((6-cyclopropyl-3-ethoxy-2,4'-difluorobiphenyl-4-yl)methyl)piperidin-4-yl)-2-ethyl-5-oxo-5,6,7,8-tetrahydro-1,6-naphthyridine-3-carboxylate Triethylamine (3.84 g) was added to a suspension of methyl 2-ethyl-5-oxo-6-(piperidin-4-yl)-5,6,7,8-tetrahydro-1,6-naphthyridine-3-carboxylate dihydrochloride (7.41 g) in THF (90 mL) and DMA (30 mL) at room temperature. After being stirred at the same temperature for 30 minutes, 6-cyclopropyl-3-ethoxy-2,4'-difluorobiphenyl-4-carbaldehyde (6.89 g) was added to the reaction mixture. The mixture was stirred at room temperature under nitrogen atmosphere for 30 minutes. Sodium triacetoxyhydroborate (6.04 g) and acetic acid (1.141 g) were added to the reaction mixture at room temperature. The mixture was stirred at the same temperature under nitrogen atmosphere for 60 hours. The mixture was quenched with aqueous saturated sodium hydrogen carbonate solution at room temperature and extracted with ethyl acetate. The organic layer was separated, washed with water and brine, dried over anhydrous magnesium sulfate and concentrated in vacuo. The residue was purified by a silica gel column chromatography (ethyl acetate/methanol) to give the title compound (7.17 g).

$^1$H NMR (300 MHz, DMSO-$d_6$) δ 0.55-0.64 (2H, m), 0.71-0.82 (2H, m), 1.22 (3H, t, J=7.5 Hz), 1.32 (3H, t, J=7.0 Hz), 1.50-1.66 (3H, m), 1.70-1.91 (2H, m), 2.12 (2H, t, J=10.9 Hz), 2.89-3.01 (2H, m), 3.05-3.16 (4H, m), 3.51 (2H, s), 3.57 (2H, t, J=6.6 Hz), 3.88 (3H, s), 4.03 (2H, q, J=7.0 Hz), 4.35-4.52 (1H, m), 6.79 (1H, s), 7.25-7.36 (2H, m), 7.38-7.46 (2H, m), 8.50 (1H, s).

L) 6-(1-((6-Cyclopropyl-3-ethoxy-2,4'-difluorobiphenyl-4-yl)methyl)piperidin-4-yl)-2-ethyl-5-oxo-5,6,7,8-tetrahydro-1,6-naphthyridine-3-carboxylic acid 2M aqueous sodium hydroxide solution (20 mL) was added to a solution of methyl 6-(1-((6-cyclopropyl-3-ethoxy-2,4'-difluorobiphenyl-4-yl)methyl)piperidin-4-yl)-2-ethyl-5-oxo-5,6,7,8-tetrahydro-1,6-naphthyridine-3-carboxylate (6.94 g) in methanol (20 mL) at room temperature. The mixture was stirred at 70° C. under nitrogen atmosphere for 2 hours. The mixture was neutralized with 1M hydrochloric acid at room temperature and stirred at 70° C. for 1 hour and at room temperature for 16 hours to give colorless crystals. After filtration, the crystals were dissolved in ethanol. The solution was filtrated and the filtrate was concentrated in vacuo to give a colorless solid. The solid was recrystallized from ethanol-DMSO-water (45 mL-5 mL-130 mL) to give the title compound (6.24 g).

$^1$H NMR (300 MHz, DMSO-$d_6$) δ 0.54-0.67 (2H, m), 0.71-0.84 (2H, m), 1.21 (3H, t, J=7.5 Hz), 1.32 (3H, t, J=7.0 Hz), 1.51-1.68 (3H, m), 1.72-1.90 (2H, m), 2.10-2.26 (2H, m), 2.96 (2H, d, J=10.2 Hz), 3.05-3.17 (4H, m), 3.51-3.62 (4H, m), 4.03 (2H, q, J=7.0 Hz), 4.35-4.56 (1H, m), 6.80 (1H, s), 7.26-7.36 (2H, m), 7.37-7.47 (2H, m), 8.50 (1H, s).

mp 207.8-208.7° C.

Example 75

6-(1-((6-Cyclopropyl-2,4'-difluoro-3-isopropoxybiphenyl-4-yl)methyl)piperidin-4-yl)-5-oxo-2-propyl-5,6,7,8-tetrahydro-1,6-naphthyridine-3-carboxylic acid The title compound was obtained in the same way as in steps K and L of Example 1 using methyl 6-(1-(tert-butoxycarbonyl)piperidin-4-yl)-5-oxo-2-propyl-5,6,7,8-tetrahydro-1,6-naphthyridine-3-carboxylate and 6-cyclopropyl-3-isopropoxy-2,4'-difluorobiphenyl-4-carbaldehyde.

Example 76

6-(1-((2-Cyclopropyl-5-ethoxy-2'-fluorobiphenyl-4-yl)methyl)piperidin-4-yl)-5-oxo-2-propyl-5,6,7,8-tetrahydro-1,6-naphthyridine-3-carboxylic acid A) Methyl 2-ethoxy-4-iodobenzoate Iodoethane (2.75 g) was added to a DMF (40 mL) suspension of methyl 2-hydroxy-4-iodobenzoate (3.27 g) and potassium carbonate (3.25 g), and the mixture was stirred at 60° C. for 24 hours. The reaction mixture was allowed to cool to room temperature, and then, water was added thereto, followed by extraction with ethyl acetate. The obtained organic layer was washed with water and saturated saline and dried over anhydrous magnesium sulfate, and then, the solvent was distilled off under reduced pressure. The obtained residue was purified by silica gel column chromatography (hexane/ethyl acetate) to obtain the title compound (3.53 g).

$^1$H NMR (300 MHz, CDCl$_3$) δ 1.46 (3H, t, J=7.0 Hz), 3.87 (3H, s), 4.09 (2H, q, J=7.0 Hz), 7.28-7.34 (2H, m), 7.48 (1H, d, J=8.0 Hz).

B) Methyl 3-ethoxy-2'-fluorobiphenyl-4-carboxylate (2-Fluorophenyl)boronic acid (0.918 g), cesium fluoride (1.99 g), and a dichloromethane adduct of (1,1'-bis(diphenylphosphino)ferrocene)dichloropalladium(II) (0.714 g) were added to a mixture of methyl 2-ethoxy-4-iodobenzoate (1.34 g) and DME (20 mL), and the resultant mixture was stirred at 100° C. for 15 hours in an argon atmosphere. Water was added to the reaction mixture, and the mixture was filtered through celite. The filtrate was subjected to extraction with ethyl acetate. The organic layer was washed with water and saturated saline and dried over anhydrous magnesium sulfate, and then, the solvent was distilled off under reduced pressure. The obtained residue was purified by silica gel column chromatography (hexane/ethyl acetate) to obtain the title compound (1.15 g).

MS (ESI+): [M+H]$^+$ 275.2.

C) Methyl 2-bromo-5-ethoxy-2'-fluorobiphenyl-4-carboxylate

Dibromoisocyanuric acid (0.631 g) was added to a mixture of methyl 3-ethoxy-2'-fluorobiphenyl-4-carboxylate (1.14 g) and DMF (10 mL), and the resultant mixture was stirred at room temperature for 2 hours. Dibromoisocyanuric acid (0.238 g) was further added to the reaction mixture, and the mixture was stirred at room temperature for 1 hour. Water was added to the reaction mixture, followed by extraction with ethyl acetate. The obtained organic layer was washed with water and saturated saline and dried over anhydrous magnesium sulfate, and then, the solvent was distilled off under reduced pressure. The obtained residue was purified by silica gel column chromatography (hexane/ethyl acetate) to obtain the title compound (1.39 g).

$^1$H NMR (300 MHz, CDCl$_3$) δ 1.45 (3H, t, J=7.0 Hz), 3.91 (3H, s), 4.10 (2H, q, J=7.0 Hz), 6.92 (1H, s), 7.13-7.33 (3H, m), 7.36-7.47 (1H, m), 8.07 (1H, s).

D) (2-Cyclopropyl-5-ethoxy-2'-fluorobiphenyl-4-yl)methanol

Cyclopropylboronic acid (0.504 g), dicyclohexyl(2',6'-dimethoxybiphenyl-2-yl)phosphine (0.241 g), a 2 M aqueous sodium carbonate solution (5.86 mL), and tris(dibenzylideneacetone)dipalladium(0) (0.251 g) were added to a mixture of methyl 2-bromo-5-ethoxy-2'-fluorobiphenyl-4-carboxylate (1.38 g) and toluene (20 mL), and the resultant mixture was stirred at 100° C. for 6 hours in an argon atmosphere. Water was added to the reaction mixture, and the mixture was filtered through celite. The filtrate was subjected to extraction with ethyl acetate. The organic layer was washed with water and saturated saline and dried over anhydrous magnesium sulfate, and then, the solvent was distilled off under reduced pressure. The obtained residue was purified by silica gel column chromatography (hexane/ethyl acetate). A THF (5 mL) solution of the purified product was added at 0° C. to a THF (5 mL) suspension of lithium aluminum hydride (0.326 g). After stirring at the same temperature as above for 2 hours, water (0.5 mL), a 1 M aqueous sodium hydroxide solution (0.5 mL), and water (1.5 mL) were added thereto in this order. The reaction mixture was filtered, and the filtrate was concentrated under reduced pressure. The obtained residue was purified by silica gel column chromatography (hexane/ethyl acetate) to obtain the title compound (1.07 g).

$^1$H NMR (300 MHz, CDCl$_3$) δ 0.52-0.60 (2H, m), 0.67-0.76 (2H, m), 1.42 (3H, t, J=6.9 Hz), 1.62-1.75 (1H, m), 2.41 (1H, t, J=6.6 Hz), 4.07 (2H, q, J=7.0 Hz), 4.70 (2H, d, J=6.5 Hz), 6.73 (1H, s), 6.90 (1H, s), 7.10-7.23 (2H, m), 7.28-7.40 (2H, m)

E) 2-Cyclopropyl-5-ethoxy-2'-fluorobiphenyl-4-carbaldehyde

Manganese dioxide (1.61 g) was added to a toluene (10 mL) solution of (2-cyclopropyl-5-ethoxy-2'-fluorobiphenyl-4-yl)methanol (1.06 g), and the mixture was stirred at 60° C. for 1 hour. Manganese dioxide (0.965 g) was further added to the reaction mixture, and the mixture was stirred at 60° C. for 30 minutes. The reaction mixture was filtered, and then, the solvent was distilled off under reduced pressure. The obtained residue was purified by silica gel column chromatography (hexane/ethyl acetate) to obtain the title compound (955 mg).

MS (ESI+): [M+H]$^+$ 285.2.

F) Methyl 6-(1-((2-cyclopropyl-5-ethoxy-2'-fluorobiphenyl-4-yl)methyl)piperidin-4-yl)-5-oxo-2-propyl-5,6,7,8-tetrahydro-1,6-naphthyridine-3-carboxylate A mixture of methyl 6-(1-(tert-butoxycarbonyl)piperidin-4-yl)-5-oxo-2-propyl-5,6,7,8-tetrahydro-1,6-naphthyridine-3-carboxylate (395 mg) and formic acid (5 mL) was stirred at 60° C. for 30 minutes, and then, the solvent was distilled off under reduced pressure. Toluene was added to the obtained residue, and the solvent was distilled off under reduced pressure. A THF (5 mL) solution of the obtained residue and 2-cyclopropyl-5-ethoxy-2'-fluorobiphenyl-4-carbaldehyde (260 mg) was stirred at room temperature for 10 minutes. Then, sodium triacetoxy borohydride (291 mg) was added thereto, and the mixture was stirred at room temperature for 2 hours. A saturated aqueous solution of sodium bicarbonate was added to the reaction mixture, followed by extraction with ethyl acetate. The obtained organic layer was dried over anhydrous magnesium sulfate, and then, the solvent was distilled off under reduced pressure. The obtained residue was purified by silica gel column chromatography (hexane/ethyl acetate/methanol) to obtain the title compound (260 mg).

MS (ESI+): [M+H]$^+$ 600.3.

G) 6-(1-((2-cyclopropyl-5-ethoxy-2'-fluorobiphenyl-4-yl)methyl)piperidin-4-yl)-5-oxo-2-propyl-5,6,7,8-tetrahydro-1,6-naphthyridine-3-carboxylic acid A 2 M aqueous sodium hydroxide solution (1.50 mL) was added at room temperature to a methanol (5 mL)-THF (5 mL) solution of methyl 6-(1-((2-cyclopropyl-5-ethoxy-2'-fluorobiphenyl-4-yl)methyl)piperidin-4-yl)-5-oxo-2-propyl-5,6,7,8-tetrahydro-1,6-naphthyridine-3-carboxylate (250 mg), and the mixture was stirred at 60° C. for 30 minutes. The reaction mixture was neutralized with 2 M hydrochloric acid at room temperature. Then, ethyl acetate was added thereto, and the solvent was distilled off under reduced pressure. The deposited solid was collected by filtration. The obtained solid was recrystallized (DMSO/ethanol/hexane) to obtain the title compound (153 mg).

$^1$H NMR (300 MHz, CDCl$_3$) δ 0.43-0.55 (2H, m), 0.65-0.77 (2H, m), 0.92 (3H, t, J=7.4 Hz), 1.31 (3H, t, J=6.9 Hz), 1.53-1.74 (5H, m), 1.76-1.93 (2H, m), 2.09-2.25 (2H, m), 2.98 (2H, d, J=10.7 Hz), 3.04-3.15 (4H, m), 3.50-3.64 (4H, m), 4.01 (2H, q, J=6.9 Hz), 4.32-4.53 (1H, m), 6.75 (1H, s), 6.97 (1H, s), 7.23-7.33 (2H, m), 7.35-7.51 (2H, m), 8.47 (1H, s).

Example 77

6-(1-((2-Chloro-6-cyclopropyl-3-ethoxy-2',4'-difluorobiphenyl-4-yl)methyl)piperidin-4-yl)-5-oxo-2-propyl-5,6,7,8-tetrahydro-1,6-naphthyridine-3-carboxylic acid

A) 2-Chloro-6-cyclopropyl-3-ethoxy-2',4'-difluorobiphenyl-4-carbaldehyde

The title compound was obtained in the same way as in steps A, B, C, and G of Example 2, steps B and C of Example 15, and step D of Example 2 using methyl 2-hydroxy-4-iodobenzoate.

¹H NMR (300 MHz, CDCl₃) δ 0.54-0.85 (4H, m), 1.40-1.55 (4H, m), 4.13-4.24 (2H, m), 6.84-7.08 (2H, m), 7.20 (1H, td, J=8.2, 6.4 Hz), 7.39 (1H, s), 10.38 (1H, s).

B) 6-(1-((2-Chloro-6-cyclopropyl-3-ethoxy-2',4'-difluorobiphenyl-4-yl)methyl)piperidin-4-yl)-5-oxo-2-propyl-5,6,7,8-tetrahydro-1,6-naphthyridine-3-carboxylic acid The title compound was obtained in the same way as in steps K and L of Example 1 using methyl 6-(1-((2-cyclopropyl-4'-fluoro-6-propoxybiphenyl-4-yl)methyl)piperidin-4-yl)-5-oxo-2-propyl-5,6,7,8-tetrahydro-1,6-naphthyridine-3-carboxylate and 2-chloro-6-cyclopropyl-3-ethoxy-2',4'-difluorobiphenyl-4-carbaldehyde.

Example 78

6-(1-((2-Cyclopropyl-5-ethoxy-3'-fluorobiphenyl-4-yl)methyl)piperidin-4-yl)-5-oxo-2-propyl-5,6,7,8-tetrahydro-1,6-naphthyridine-3-carboxylic acid A) 7-(Benzyloxy)-6-bromo-2,2-dimethyl-4H-1,3-benzodioxin-4-one Benzyl bromide (4.88 mL) was added to a DMF (50 mL) suspension of 6-bromo-7-hydroxy-2,2-dimethyl-4H-1,3-benzodioxin-4-one (9.34 g) and potassium carbonate (7.09 g), and the mixture was stirred at room temperature for 30 minutes. The reaction mixture was allowed to cool to room temperature, and then, water was added thereto, followed by extraction with ethyl acetate. The obtained organic layer was washed with saturated saline and dried over anhydrous magnesium sulfate, and then, the solvent was distilled off under reduced pressure. The obtained solid was washed with diethyl ether to obtain the title compound (9.95 g).
¹H NMR (300 MHz, CDCl₃) δ 1.72 (6H, s), 5.18 (2H, s), 6.50 (1H, s), 7.30-7.51 (5H, m), 8.14 (1H, s).

B) Methyl 4-(benzyloxy)-5-bromo-2-ethoxybenzoate

Potassium carbonate (7.57 g) was added to a mixture of 7-(benzyloxy)-6-bromo-2,2-dimethyl-4H-1,3-benzodioxin-4-one (9.95 g) and methanol (50 mL), and the resultant mixture was stirred overnight at room temperature. The reaction mixture was filtered through celite, and then, the solvent was distilled off under reduced pressure. Iodoethane (3.29 mL) was added to a DMF (50 mL) suspension of the obtained residue and potassium carbonate (7.57 g), and the mixture was stirred at room temperature for 30 minutes. The reaction mixture was allowed to cool to room temperature, and then, water was added thereto, followed by extraction with ethyl acetate. The obtained organic layer was washed with saturated saline and dried over anhydrous magnesium sulfate, and then, the solvent was distilled off under reduced pressure. The obtained residue was purified by silica gel column chromatography (hexane/ethyl acetate) to obtain the title compound (9.80 g).
¹H NMR (300 MHz, CDCl₃) δ 1.38-1.47 (3H, m), 3.85 (3H, s), 3.97-4.09 (2H, m), 5.20 (2H, s), 6.50 (1H, s), 7.29-7.49 (5H, m), 7.95-8.23 (1H, m).

C) Methyl 4-(benzyloxy)-5-cyclopropyl-2-ethoxybenzoate

A mixture of methyl 4-(benzyloxy)-5-bromo-2-ethoxybenzoate (9.80 g), cyclopropylboronic acid (5.76 g), dicyclohexyl(2',6'-dimethoxybiphenyl-2-yl)phosphine (1.65 g), a 2 M aqueous sodium carbonate solution (40.2 mL), tris(dibenzylideneacetone)dipalladium(0) (1.72 g), and toluene (100 mL) was stirred overnight at 100° C. in an argon atmosphere. The reaction mixture was filtered, and then, the filtrate was poured to water, followed by extraction with ethyl acetate. The obtained organic layer was dried over anhydrous magnesium sulfate, and then, the solvent was distilled off under reduced pressure. The obtained residue was purified by silica gel column chromatography (hexane/ethyl acetate) to obtain the title compound (8.76 g).
¹H NMR (300 MHz, CDCl₃) δ 0.56-0.70 (2H, m), 0.82-0.95 (2H, m), 1.42 (3H, t, J=6.9 Hz), 2.04-2.15 (1H, m), 3.84 (3H, s), 4.04 (2H, q, J=7.0 Hz), 5.15 (2H, s), 6.48 (1H, s), 7.28-7.51 (6H, m)

D) Methyl 5-cyclopropyl-2-ethoxy-4-(((trifluoromethyl)sulfonyl)oxy)benzoate

A mixture of methyl 4-(benzyloxy)-5-cyclopropyl-2-ethoxybenzoate (8.76 g), 10% palladium carbon (containing 55% water, 4 g), and THF (100 mL) was stirred at room temperature for 2 hours in a hydrogen atmosphere. The catalyst was filtered off, and then, the obtained filtrate was concentrated under reduced pressure. The obtained residue was purified by silica gel column chromatography (hexane/ethyl acetate). 4-Dimethylaminopyridine (282 mg) and N-phenyl-trifluoromethanesulfonimide (11.6 g) were added to a mixture of the obtained purified product, N,N'-diisopropylethylamine (8.07 mL), and THF (50 mL), and the resultant mixture was stirred at 70° C. for 4 hours. The solvent in the reaction mixture was distilled off under reduced pressure. The obtained residue was purified by silica gel column chromatography (hexane/ethyl acetate) to obtain the title compound (8.51 g).
¹H NMR (300 MHz, CDCl₃) δ 0.66-0.77 (2H, m), 0.94-1.08 (2H, m), 1.46 (3H, t, J=6.9 Hz), 1.92-2.02 (1H, m), 3.88 (3H, s), 4.08 (2H, q, J=7.0 Hz), 6.82 (1H, s), 7.47 (1H, s).

E) (2-Cyclopropyl-5-ethoxy-3'-fluorobiphenyl-4-yl)methanol

A mixture of methyl 5-cyclopropyl-2-ethoxy-4-(((trifluoromethyl)sulfonyl)oxy)benzoate (2.50 g), (3-fluorophenyl)boronic acid (1.90 g), dicyclohexyl(2',6'-dimethoxybiphenyl-2-yl)phosphine (0.418 g), a 2 M aqueous sodium carbonate solution (10.2 mL), tris(dibenzylideneacetone)dipalladium (0) (435 mg), and toluene (20 mL) was stirred overnight at 100° C. in an argon atmosphere. Water was added to the reaction mixture, and then, the mixture was filtered through celite, followed by extraction with ethyl acetate. The organic layer was passed through a short silica gel (NH) column, and the solvent was distilled off under reduced pressure. The obtained residue was purified by silica gel column chromatography (hexane/ethyl acetate). A THF (10 mL) solution of the obtained purified product was added to a THF (20 mL) suspension of lithium aluminum hydride (500 mg) under ice cooling in a nitrogen atmosphere. After stirring at the same temperature as above for 30 minutes, water (0.5 mL) and a 15% aqueous sodium hydroxide solution (0.5 mL) were added thereto, and the mixture was stirred for 5 minutes. Water (1.5 mL) was further added to the reaction mixture, and the mixture was stirred for 30 minutes and then filtered. The filtrate was concentrated under reduced pressure. The obtained residue was purified by silica gel column chromatography (hexane/ethyl acetate) to obtain the title compound (1.80 g).

¹H NMR (300 MHz, CDCl₃) δ 0.54-0.67 (2H, m), 0.73-0.83 (2H, m), 1.43 (3H, t, J=7.0 Hz), 1.65-1.87 (1H, m), 2.39 (1H, brs), 4.08 (2H, q, J=7.0 Hz), 4.69 (2H, brs), 6.73 (1H, s), 6.88 (1H, s), 6.98-7.08 (1H, m), 7.10-7.23 (2H, m), 7.32-7.43 (1H, m).

F) 2-Cyclopropyl-5-ethoxy-3'-fluorobiphenyl-4-carbaldehyde

Manganese dioxide (5.47 g) was added to a toluene (80 mL) solution of (2-cyclopropyl-5-ethoxy-3'-fluorobiphenyl-4-yl)methanol (1.80 g), and the mixture was stirred at 60° C. for 1 hour in a nitrogen atmosphere. The reaction mixture was filtered, and then, the solvent was distilled off under reduced pressure. The obtained residue was purified by silica gel column chromatography (hexane/ethyl acetate) to obtain the title compound (1.14 g).
¹H NMR (300 MHz, CDCl₃) δ 0.62-0.71 (2H, m), 0.77-0.85 (2H, m), 1.46 (3H, t, J=7.0 Hz), 1.74 (1H, tt, J=8.4, 5.4 Hz), 4.14 (2H, q, J=7.0 Hz), 6.82 (1H, s), 7.01-7.24 (3H, m), 7.41 (1H, td, J=7.9, 5.9 Hz), 7.46 (1H, s), 10.49 (1H, s).

G) Methyl 6-(1-((2-cyclopropyl-5-ethoxy-3'-fluorobiphenyl-4-yl)methyl)piperidin-4-yl)-5-oxo-2-propyl-5,6,7,8-tetrahydro-1,6-naphthyridine-3-carboxylate Methyl 6-(1-(tert-butoxycarbonyl)piperidin-4-yl)-5-oxo-2-propyl-5,6,7,8-tetrahydro-1,6-naphthyridine-3-carboxylate (500 mg) was added to formic acid (5 mL), and the mixture was stirred at 60° C. for 30 minutes. Then, the solvent was distilled off under reduced pressure. Toluene was added to the residue, and the solvent was further distilled off under reduced pressure. 2-Cyclopropyl-5-ethoxy-3'-fluorobiphenyl-4-carbaldehyde (395 mg) was added to a mixture of the obtained residue and THF (5 mL), and the mixture was stirred for 10 minutes. Then, sodium triacetoxy borohydride (368 mg) was added thereto, and the mixture was stirred at room temperature for 2 hours. A saturated aqueous solution of sodium bicarbonate was added to the reaction mixture, followed by extraction with ethyl acetate twice. The obtained organic layer was dried over anhydrous magnesium sulfate, and then, the solvent was distilled off under reduced pressure. The obtained residue was purified by silica gel column chromatography (hexane/ethyl acetate/methanol) to obtain the title compound (300 mg).
MS (ESI+): [M+H]⁺ 600.3.

H) 6-(1-((2-Cyclopropyl-5-ethoxy-3'-fluorobiphenyl-4-yl)methyl)piperidin-4-yl)-5-oxo-2-propyl-5,6,7,8-tetrahydro-1,6-naphthyridine-3-carboxylic acid A 2 M aqueous sodium hydroxide solution (1.50 mL) was added at room temperature to a methanol (5 mL)-THF (5 mL) solution of methyl 6-(1-((2-cyclopropyl-5-ethoxy-3'-fluorobiphenyl-4-yl)methyl)piperidin-4-yl)-5-oxo-2-propyl-5,6,7,8-tetrahydro-1,6-naphthyridine-3-carboxylate (300 mg), and the mixture was stirred at 60° C. for 30 minutes. The reaction mixture was neutralized with 2 M hydrochloric acid at room temperature. Then, ethyl acetate was added thereto, and the solvent was distilled off under reduced pressure. The deposited solid was collected by filtration and washed with diethyl ether. The obtained solid was recrystallized (ethanol/hexane) to obtain the title compound (173 mg).
¹H NMR (300 MHz, DMSO-d₆) δ 0.47-0.60 (2H, m), 0.73-0.83 (2H, m), 0.92 (3H, t, J=7.4 Hz), 1.33 (3H, t, J=6.9 Hz), 1.52-1.95 (7H, m), 2.18 (2H, t, J=11.0 Hz), 2.98 (2H, d, J=11.3 Hz), 3.04-3.15 (4H, m), 3.49-3.65 (4H, m), 4.04 (2H, q, J=6.9 Hz), 4.33-4.52 (1H, m), 6.79 (1H, s), 7.00 (1H, s), 7.13-7.34 (3H, m), 7.42-7.55 (1H, m), 8.47 (1H, s).

Example 79

6-(1-((2-Cyclopropyl-5-ethoxy-2'-methoxybiphenyl-4-yl)methyl)piperidin-4-yl)-5-oxo-2-propyl-5,6,7,8-tetrahydro-1,6-naphthyridine-3-carboxylic acid A) 2-Cyclopropyl-5-ethoxy-2'-methoxybiphenyl-4-carbaldehyde The title compound was obtained in the same way as in step B of Example 7 and step E of Example 1 using methyl 5-cyclopropyl-2-ethoxy-4-(((trifluoromethyl)sulfonyl)oxy)benzoate and (2-methoxyphenyl)boronic acid.
¹H NMR (300 MHz, CDCl₃) δ 0.51-0.77 (4H, m), 1.44 (3H, t, J=7.0 Hz), 1.55-1.66 (1H, m), 3.78 (3H, s), 4.11 (2H, q, J=7.0 Hz), 6.82 (1H, s), 6.96-7.11 (2H, m), 7.21 (1H, dd, J=7.5, 1.8 Hz), 7.31-7.47 (2H, m), 10.48 (1H, s).

B) 6-(1-((2-Cyclopropyl-5-ethoxy-2'-methoxybiphenyl-4-yl)methyl)piperidin-4-yl)-5-oxo-2-propyl-5,6,7,8-tetrahydro-1,6-naphthyridine-3-carboxylic acid The title compound was obtained in the same way as in steps K and L of Example 1 using methyl 6-(1-(tert-butoxycarbonyl)piperidin-4-yl)-5-oxo-2-propyl-5,6,7,8-tetrahydro-1,6-naphthyridine-3-carboxylate and 2-cyclopropyl-5-ethoxy-2'-methoxybiphenyl-4-carbaldehyde.

Example 80

6-(1-((2-Cyclopropyl-5-ethoxybiphenyl-4-yl)methyl)piperidin-4-yl)-5-oxo-2-propyl-5,6,7,8-tetrahydro-1,6-naphthyridine-3-carboxylic acid A) Methyl 2-cyclopropyl-5-ethoxybiphenyl-4-carboxylate A mixture of methyl 5-cyclopropyl-2-ethoxy-4-(((trifluoromethyl)sulfonyl)oxy)benzoate (2.5 g), phenylboronic acid (1.66 g), dicyclohexyl(2',6'-dimethoxybiphenyl-2-yl)phosphine (0.418 g), a 2 M aqueous sodium carbonate solution (10.2 mL), tris(dibenzylideneacetone)dipalladium(0) (0.435 g), and toluene (20 mL) was stirred overnight at 100° C. in an argon atmosphere. The reaction mixture was allowed to cool to room temperature. Then, the organic layer was separated and passed through a short silica gel (NH) column, and the solvent was distilled off under reduced pressure. The obtained residue was purified by silica gel column chromatography (hexane/ethyl acetate) to obtain the title compound (1.80 g).
¹H NMR (300 MHz, CDCl₃) δ 0.57-0.69 (2H, m), 0.73-0.85 (2H, m), 1.43 (3H, t, J=6.9 Hz), 1.69-1.86 (1H, m), 3.89 (3H, s), 4.05-4.14 (2H, m), 6.84 (1H, s), 7.26 (1H, d, J=1.7 Hz), 7.33-7.58 (5H, m).

B) 2-Cyclopropyl-5-ethoxybiphenyl-4-carbaldehyde

A THF (10 mL) solution of methyl 2-cyclopropyl-5-ethoxybiphenyl-4-carboxylate (1.80 g) was added to a THF (20 mL) suspension of lithium aluminum hydride (500 mg) under ice cooling in a nitrogen atmosphere. After stirring at the same temperature as above for 30 minutes, water (0.5 mL) and a 15% aqueous sodium hydroxide solution (0.5 mL) were added thereto, and the mixture was stirred for 5 minutes.

Water (1.5 mL) was further added to the reaction mixture, and the mixture was stirred for 30 minutes and then filtered. The filtrate was concentrated under reduced pressure. The obtained residue was purified by silica gel column chromatography (hexane/ethyl acetate). Manganese dioxide (4.73 g) was added to a toluene (80 mL) solution of the obtained purified product, and the mixture was stirred at 60° C. for 1 hour in a nitrogen atmosphere. The reaction mixture was filtered, and then, the solvent was distilled off under reduced pressure. The obtained residue was purified by silica gel column chromatography (hexane/ethyl acetate) to obtain the title compound (1.13 g).

$^1$H NMR (300 MHz, CDCl$_3$) δ 0.62-0.71 (2H, m), 0.75-0.86 (2H, m), 1.46 (3H, t, J=6.9 Hz), 1.67-1.83 (1H, m), 4.14 (2H, q, J=7.0 Hz), 6.84 (1H, s), 7.34-7.51 (6H, m), 10.49 (1H, s).

C) Methyl 6-(1-((2-cyclopropyl-5-ethoxybiphenyl-4-yl)methyl)piperidin-4-yl)-5-oxo-2-propyl-5,6,7,8-tetrahydro-1,6-naphthyridine-3-carboxylate Methyl 6-(1-(tert-butoxycarbonyl)piperidin-4-yl)-5-oxo-2-propyl-5,6,7,8-tetrahydro-1,6-naphthyridine-3-carboxylate (500 mg) was added to formic acid (5 mL), and the mixture was stirred at 60° C. for 30 minutes. Then, the solvent was distilled off under reduced pressure. Toluene was added to the residue, and the solvent was further distilled off under reduced pressure. 2-Cyclopropyl-5-ethoxybiphenyl-4-carbaldehyde (370 mg) was added to a mixture of the obtained residue and THF (5 mL), and the resultant mixture was stirred for 10 minutes. Then, sodium triacetoxy borohydride (368 mg) was added thereto, and the mixture was stirred at room temperature for 2 hours. A saturated aqueous solution of sodium bicarbonate was added to the reaction mixture, followed by extraction with ethyl acetate twice. The obtained organic layer was dried over anhydrous magnesium sulfate, and then, the solvent was distilled off under reduced pressure. The obtained residue was purified by silica gel column chromatography (hexane/ethyl acetate/methanol) to obtain the title compound (471 mg).

MS (ESI+) [M+H]$^+$ 582.3.

D) 6-(1-((2-Cyclopropyl-5-ethoxybiphenyl-4-yl)methyl)piperidin-4-yl)-5-oxo-2-propyl-5,6,7,8-tetrahydro-1,6-naphthyridine-3-carboxylic acid A 2 M aqueous sodium hydroxide solution (1.50 mL) was added at room temperature to a methanol (5 mL)-THF (5 mL) solution of methyl 6-(1-((2-cyclopropyl-5-ethoxybiphenyl-4-yl)methyl)piperidin-4-yl)-5-oxo-2-propyl-5,6,7,8-tetrahydro-1,6-naphthyridine-3-carboxylate (460 mg), and the mixture was stirred at 60° C. for 30 minutes. The reaction mixture was neutralized with hydrochloric acid at room temperature. Then, ethyl acetate was added thereto, and the solvent was distilled off under reduced pressure. The deposited solid was collected by filtration and washed with diethyl ether. The obtained solid was recrystallized (DMSO/ethanol/hexane) to obtain the title compound (397 mg).

$^1$H NMR (300 MHz, DMSO-d$_6$) δ 0.45-0.61 (2H, m), 0.71-0.82 (2H, m), 0.92 (3H, t, J=7.4 Hz), 1.32 (3H, t, J=6.9 Hz), 1.49-1.98 (7H, m), 2.19 (2H, t, J=11.0 Hz), 2.92-3.14 (6H, m), 3.52-3.62 (4H, m), 4.03 (2H, q, J=6.9 Hz), 4.36-4.52 (1H, m), 6.76 (1H, s), 6.96 (1H, s), 7.29-7.42 (1H, m), 7.42-7.49 (4H, m), 8.47 (1H, s).

Example 81

6-(1-((6-Cyclopropyl-2,4'-difluoro-3-methoxybiphenyl-4-yl)methyl)piperidin-4-yl)-5-oxo-2-propyl-5,6,7,8-tetrahydro-1,6-naphthyridine-3-carboxylic acid A) 2,3,4'-Trifluorobiphenyl-4-carbaldehyde (4-Fluorophenyl)boronic acid (6.67 g), dicyclohexyl(2',6'-dimethoxybiphenyl-2-yl)phosphine (1.96 g), a 2 M aqueous sodium carbonate solution (47.6 mL), and tris(dibenzylideneacetone)dipalladium(0) (2.04 g) were added at room temperature to a toluene (200 mL) solution of 4-bromo-2,3-difluorobenzaldehyde (7.02 g), and the mixture was stirred at 100° C. for 16 hours in an argon atmosphere. Water was added to the reaction mixture at room temperature, and the mixture was filtered through celite. Then, the filtrate was subjected to extraction with ethyl acetate. The obtained organic layer was washed with water and saturated saline in this order and dried over anhydrous magnesium sulfate, and then, the solvent was distilled off under reduced pressure. The obtained residue was passed through a short silica gel column (hexane/ethyl acetate), and the solvent was distilled off under reduced pressure. The obtained residue was crystallized (hexane/ethyl acetate) and further recrystallized (hexane/ethyl acetate) to obtain the title compound (6.01 g).

$^1$H NMR (300 MHz, CDCl$_3$) δ 7.15-7.23 (2H, m), 7.28-7.34 (1H, m), 7.53-7.61 (2H, m), 7.69 (1H, ddd, J=8.2, 6.2, 1.8 Hz), 10.37 (1H, d, J=0.7 Hz).

B) 2,4'-Difluoro-3-methoxybiphenyl-4-carbaldehyde

Sodium methoxide (28% methanol solution, 7.37 g) was added at room temperature to a methanol (160 mL) solution of 2,3,4'-trifluorobiphenyl-4-carbaldehyde (6.01 g), and the mixture was heated to reflux for 18 hours in a nitrogen atmosphere. The reaction mixture was cooled to room temperature, and then, the solvent was distilled off under reduced pressure. The obtained residue was diluted with ethyl acetate and water, followed by extraction with ethyl acetate. The obtained organic layer was washed with water and saturated saline in this order and dried over anhydrous magnesium sulfate, and then, the solvent was distilled off under reduced pressure to obtain the title compound (6.18 g).

$^1$H NMR (300 MHz, CDCl$_3$) δ 4.13 (3H, d, J=2.5 Hz), 7.14-7.22 (3H, m), 7.51-7.58 (2H, m), 7.66 (1H, dd, J=8.2, 1.4 Hz), 10.41 (1H, d, J=0.8 Hz).

C) 2,4'-Difluoro-3-hydroxybiphenyl-4-carbaldehyde

48% hydrobromic acid (28.4 mL) was added at room temperature to an acetic acid (150 mL) solution of 2,4'-difluoro-3-methoxybiphenyl-4-carbaldehyde (6.18 g), and the mixture was stirred at 120° C. for 18 hours in a nitrogen atmosphere. The reaction mixture was cooled to room temperature, and then, the solvent was distilled off under reduced pressure. The obtained residue was diluted with ethyl acetate and water. The organic layer was separated, and then, the obtained aqueous layer was neutralized with a 1 M aqueous sodium hydroxide solution, followed by extraction with ethyl acetate. Combined organic layers were washed with water and saturated saline in this order and dried over anhydrous magnesium sulfate, and then, the solvent was distilled off under reduced pressure. The obtained residue was passed through a short silica gel column (hexane/ethyl acetate) to obtain the title compound (5.51 g).

¹H NMR (300 MHz, DMSO-d₆) δ 7.06-7.13 (1H, m), 7.31-7.41 (2H, m), 7.56 (1H, dd, J=8.2, 1.4 Hz), 7.62-7.70 (2H, m), 10.29 (1H, s), 11.02 (1H, brs).

D) 6-Bromo-2,4'-difluoro-3-hydroxybiphenyl-4-carbaldehyde

Dibromoisocyanuric acid (1.49 g) was added at room temperature to a DMF (50 mL) solution of 2,4'-difluoro-3-hydroxybiphenyl-4-carbaldehyde (2.02 g), and the mixture was stirred at the same temperature as above for 3 hours in a nitrogen atmosphere. A saturated aqueous solution of sodium thiosulfate was added to the reaction mixture at room temperature, followed by extraction with ethyl acetate. The obtained organic layer was washed with water and saturated saline in this order and dried over anhydrous magnesium sulfate, and then, the solvent was distilled off under reduced pressure. The obtained residue was purified by silica gel column chromatography (hexane/ethyl acetate) to obtain the title compound (1.99 g).

¹H NMR (300 MHz, CDCl₃) δ 7.15-7.23 (2H, m), 7.28-7.36 (2H, m), 7.70 (1H, d, J=1.8 Hz), 9.90 (1H, d, J=1.9 Hz), 10.90 (1H, s).

E) 6-Bromo-2,4'-difluoro-3-methoxybiphenyl-4-carbaldehyde

Iodomethane (1.35 g) was added at room temperature to a mixture of 6-bromo-2,4'-difluoro-3-hydroxybiphenyl-4-carbaldehyde (1.99 g), potassium carbonate (1.76 g), and DMF (40 mL), and the resultant mixture was stirred at 60° C. for 3 hours in a nitrogen atmosphere. Water was added to the reaction mixture at room temperature, followed by extraction with ethyl acetate. The obtained organic layer was washed with water and saturated saline in this order and dried over anhydrous magnesium sulfate, and then, the solvent was distilled off under reduced pressure. The obtained residue was purified by silica gel column chromatography (hexane/ethyl acetate) to obtain the title compound (2.03 g).

¹H NMR (300 MHz, CDCl₃) δ 4.10 (3H, d, J=2.7 Hz), 7.14-7.23 (2H, m), 7.28-7.35 (2H, m), 7.92 (1H, d, J=1.8 Hz), 10.36 (1H, s).

F) 6-Cyclopropyl-2,4'-difluoro-3-methoxybiphenyl-4-carbaldehyde

Cyclopropylboronic acid (1.07 g), dicyclohexyl(2',6'-dimethoxybiphenyl-2-yl)phosphine (0.510 g), a 2 M aqueous sodium carbonate solution (9.31 mL), and tris(dibenzylideneacetone)dipalladium(0) (0.568 g) were added at room temperature to a toluene (50 mL) solution of 6-bromo-2,4'-difluoro-3-methoxybiphenyl-4-carbaldehyde (2.03 g), and the mixture was stirred at 100° C. for 16 hours in an argon atmosphere. Water was added to the reaction mixture at room temperature, and the mixture was filtered through celite. Then, the filtrate was subjected to extraction with ethyl acetate. The obtained organic layer was washed with water and saturated saline in this order and dried over anhydrous magnesium sulfate, and then, the solvent was distilled off under reduced pressure. The obtained residue was purified by silica gel column chromatography (hexane/ethyl acetate) to obtain the title compound (1.68 g).

¹H NMR (300 MHz, CDCl₃) δ 0.65-0.73 (2H, m), 0.77-0.86 (2H, m), 1.54-1.65 (1H, m), 4.06 (3H, d, J=2.4 Hz), 7.14-7.22 (3H, m), 7.31-7.39 (2H, m), 10.38 (1H, s).

G) Methyl 6-(1-((6-cyclopropyl-2,4'-difluoro-3-methoxybiphenyl-4-yl)methyl)piperidin-4-yl)-5-oxo-2-propyl-5,6,7,8-tetrahydro-1,6-naphthyridine-3-carboxylate A mixture of methyl 6-(1-(tert-butoxycarbonyl)piperidin-4-yl)-5-oxo-2-propyl-5,6,7,8-tetrahydro-1,6-naphthyridine-3-carboxylate (393 mg) and formic acid (8 mL) was stirred at 70° C. for 30 minutes in a nitrogen atmosphere, and then, the solvent was distilled off under reduced pressure. Sodium triacetoxy borohydride (386 mg) was added at room temperature to a mixture of the obtained residue, 6-cyclopropyl-2,4'-difluoro-3-methoxybiphenyl-4-carbaldehyde (289 mg), and THF (8 mL), and the resultant mixture was stirred at the same temperature as above for 16 hours in a nitrogen atmosphere. A saturated aqueous solution of sodium bicarbonate was added to the reaction mixture at room temperature, followed by extraction with ethyl acetate. The obtained organic layer was washed with water and saturated saline in this order and dried over anhydrous magnesium sulfate, and then, the solvent was distilled off under reduced pressure. The obtained residue was purified by silica gel column chromatography (hexane/ethyl acetate) to obtain the title compound (352 mg).

¹H NMR (300 MHz, CDCl₃) δ 0.59-0.66 (2H, m), 0.74-0.82 (2H, m), 1.01 (3H, t, J=7.3 Hz), 1.57-1.65 (1H, m), 1.67-1.92 (6H, m), 2.25 (2H, td, J=11.6, 2.2 Hz), 3.02 (2H, d, J=11.7 Hz), 3.11-3.20 (4H, m), 3.54-3.62 (4H, m), 3.89 (3H, d, J=1.3 Hz), 3.92 (3H, s), 4.60-4.75 (1H, m), 6.70 (1H, d, J=1.3 Hz), 7.10-7.19 (2H, m), 7.31-7.39 (2H, m), 8.76 (1H, s)

H) 6-(1-((6-Cyclopropyl-2,4'-difluoro-3-methoxybiphenyl-4-yl)methyl)piperidin-4-yl)-5-oxo-2-propyl-5,6,7,8-tetrahydro-1,6-naphthyridine-3-carboxylic acid A 2 M aqueous sodium hydroxide solution (2 mL) was added at room temperature to an ethanol (8 mL) solution of methyl 6-(1-((6-cyclopropyl-2,4'-difluoro-3-methoxybiphenyl-4-yl)methyl)piperidin-4-yl)-5-oxo-2-propyl-5,6,7,8-tetrahydro-1,6-naphthyridine-3-carboxylate (335 mg), and the mixture was stirred at 80° C. for 3 hours in a nitrogen atmosphere. Then, the solvent was distilled off under reduced pressure. Water was added to the obtained residue, and the mixture was neutralized with 2 M hydrochloric acid. The deposited crystals were collected by filtration and dissolved in ethanol, and then, the solvent was distilled off under reduced pressure. The obtained residue was crystallized (hexane/ethyl acetate) and further recrystallized (hexane/ethanol) to obtain the title compound (276 mg).

¹H NMR (300 MHz, DMSO-d₆) δ 0.56-0.63 (2H, m), 0.73-0.80 (2H, m), 0.92 (3H, t, J=7.4 Hz), 1.52-1.89 (7H, m), 2.07-2.24 (2H, m), 2.95 (2H, d, J=11.2 Hz), 3.03-3.14 (4H, m), 3.51-3.61 (4H, m), 3.82 (3H, d, J=0.9 Hz), 4.36-4.53 (1H, m), 6.80 (1H, s), 7.27-7.36 (2H, m), 7.38-7.47 (2H, m), 8.48 (1H, s).

Example 82

6-(1-(5-Cyclopropyl-2-ethoxy-4-(pyridin-2-yl)benzyl)piperidin-4-yl)-5-oxo-2-propyl-5,6,7,8-tetrahydro-1,6-naphthyridine-3-carboxylic acid A) Methyl 5-cyclopropyl-2-ethoxy-4-(pyridin-2-yl)benzoate A mixture of methyl 5-cyclopropyl-2-ethoxy-4-(((trifluoromethyl)sulfonyl)oxy)benzoate (2.5 g), 2-(tributylstannyl)

pyridine (3.75 g), tetrakis(triphenylphosphine)palladium (0.784 g), and DMF (20 mL) was stirred overnight at 100° C. The reaction mixture was poured to water, followed by extraction with ethyl acetate. The obtained organic layer was washed with saturated saline and then dried over anhydrous magnesium sulfate, and the solvent was distilled off under reduced pressure. The obtained residue was purified by silica gel column chromatography (hexane/ethyl acetate) to obtain the title compound (480 mg).

$^1$H NMR (300 MHz, CDCl$_3$) δ 0.58-0.67 (2H, m), 0.72-0.84 (2H, m), 1.44 (3H, t, J=7.0 Hz), 1.86-2.01 (1H, m), 3.90 (3H, s), 4.14 (2H, q, J=7.0 Hz), 7.07 (1H, s), 7.27-7.33 (1H, m), 7.49 (1H, s), 7.58 (1H, dt, J=7.9, 1.1 Hz), 7.76 (1H, td, J=7.7, 1.9 Hz), 8.59-8.78 (1H, m).

B) 5-Cyclopropyl-2-ethoxy-4-(pyridin-2-yl)benzaldehyde

The title compound was obtained in the same way as in step E of Example 1 using methyl 5-cyclopropyl-2-ethoxy-4-(pyridin-2-yl)benzoate.

$^1$H NMR (300 MHz, CDCl$_3$) δ 0.52-0.64 (2H, m), 0.71-0.83 (2H, m), 1.42 (3H, t, J=7.0 Hz), 1.87-2.02 (1H, m), 2.36-2.53 (1H, m), 4.12 (2H, q, J=7.0 Hz), 4.70 (2H, d, J=6.4 Hz), 6.94 (1H, s), 6.98 (1H, s), 7.17-7.30 (1H, m), 7.57 (1H, dt, J=7.9, 1.1 Hz), 7.69-7.82 (1H, m), 8.64-8.76 (1H, m).

C) 6-(1-(5-Cyclopropyl-2-ethoxy-4-(pyridin-2-yl) benzyl)piperidin-4-yl)-5-oxo-2-propyl-5,6,7,8-tetrahydro-1,6-naphthyridine-3-carboxylic acid The title compound was obtained in the same way as in steps K and L of Example 1 using methyl 6-(1-(tert-butoxycarbonyl)piperidin-4-yl)-5-oxo-2-propyl-5,6,7,8-tetrahydro-1,6-naphthyridine-3-carboxylate and 5-cyclopropyl-2-ethoxy-4-(pyridin-2-yl)benzaldehyde.

Example 83

6-(1-((2-Cyclopropyl-5-ethoxy-2',4'-difluorobiphenyl-4-yl)methyl)piperidin-4-yl)-5-oxo-2-propyl-5,6, 7,8-tetrahydro-1,6-naphthyridine-3-carboxylic acid A) 2',4'-Difluoro-3-hydroxybiphenyl-4-carbaldehyde A mixture of 4-bromo-2-hydroxybenzaldehyde (7.5 g), (2,4-difluorophenyl)boronic acid (8.84 g), tris(dibenzylideneacetone)dipalladium (0) (1.367 g), 2M aqueous sodium carbonate solution (56.0 mL) and dicyclohexyl(2',6'-dimethoxy-[1,1'-biphenyl]-2-yl)phosphine (1.53 g) in toluene (70 mL) was stirred at 100° C. under nitrogen atmosphere overnight. The mixture was diluted with ethyl acetate and water. The organic layer was separated and concentrated in vacuo. The residue was passed through a silica gel pad and concentrated in vacuo. The residue was crystallized from methanol-water (80 mL-20 mL) to give the title compound (8.50 g).

$^1$H NMR (300 MHz, DMSO-d$_6$) δ 7.08-7.17 (2H, m), 7.19-7.28 (1H, m), 7.36-7.46 (1H, m), 7.63 (1H, td, J=8.9, 6.5 Hz), 7.75 (1H, d, J=8.0 Hz), 10.30 (1H, s), 10.89 (1H, brs).

B) 3-Ethoxy-2',4'-difluorobiphenyl-4-carbaldehyde

A mixture of 2',4'-difluoro-3-hydroxybiphenyl-4-carbaldehyde (8.00 g), iodoethane (8.98 g) and potassium carbonate (6.19 g) in acetone (70 mL) was stirred at 60° C. for 3 hours. The mixture was filtered through celite. The filtrate was concentrated in vacuo. The residue was diluted with ethyl acetate and water. The organic layer was separated and concentrated in vacuo. The residue was refluxed for 30 minutes in methanol (30 mL), cooled to room temperature, and further stirred for 1 hour. The solid was collected by filtration, washed with methanol (10 mL) and dried at 70° C. to give the title compound (5.16 g).

$^1$H NMR (400 MHz, DMSO-d$_6$) δ 1.41 (3H, t, J=7.0 Hz), 4.27 (2H, q, J=7.0 Hz), 7.20-7.28 (2H, m), 7.33 (1H, s), 7.38-7.46 (1H, m), 7.66-7.74 (1H, m), 7.77 (1H, d, J=8.0 Hz), 10.41 (1H, d, J=0.6 Hz).

C) 2-Bromo-5-ethoxy-2',4'-difluorobiphenyl-4-carbaldehyde

Dibromoisocyanuric acid (3.39 g) was added to a solution of 3-ethoxy-2',4'-difluorobiphenyl-4-carbaldehyde (5.16 g) in DMF (30 mL) at room temperature. The mixture was stirred at room temperature for 4 hours. Water (6 mL) was added to the mixture. Then the crystalline seed was added to the mixture. The mixture was stirred at room temperature for 1 hour. The precipitate was collected by filtration, washed with DMF-water (8 mL-2 mL), and dried at 70° C. to give the title compound (6.00 g).

$^1$H NMR (300 MHz, DMSO-d$_6$) δ 1.38 (3H, t, J=6.9 Hz), 4.23 (2H, q, J=7.0 Hz), 7.15-7.61 (4H, m), 7.90 (1H, s), 10.33 (1H, s).

D) 2-Cyclopropyl-5-ethoxy-2',4'-difluorobiphenyl-4-carbaldehyde

A mixture of 2-bromo-5-ethoxy-2',4'-difluorobiphenyl-4-carbaldehyde (5.70 g), cyclopropylboronic acid (2.15 g), dicyclohexyl(2',6'-dimethoxy-[1,1'-biphenyl]-2-yl)phosphine (549 mg), tris(dibenzylideneacetone)dipalladium (0) (612 mg) and 2 M aqueous sodium carbonate solution (25.1 mL) in toluene (50 mL) was stirred at 100° C. for 2 hours under nitrogen atmosphere. The mixture was poured into water at room temperature and extracted with ethyl acetate. The organic layer was separated, washed with brine, dried over anhydrous magnesium sulfate. Activated carbon (600 mg) was added to the filtrate. The mixture was stirred for 20 minutes at room temperature. After filtration, the filtrate was concentrated in vacuo. The residue was purified by a silica gel column chromatography (hexane/ethyl acetate) to give the title compound (4.62 g).

$^1$H NMR (300 MHz, DMSO-d$_6$) δ 0.49-0.57 (2H, m), 0.70-0.79 (2H, m), 1.37 (3H, t, J=6.9 Hz), 1.53-1.64 (1H, m), 4.18 (2H, q, J=7.0 Hz), 7.06 (1H, s), 7.18-7.27 (1H, m), 7.32 (1H, s), 7.34-7.54 (2H, m), 10.37 (1H, s).

E) Diethyl 2-hydroxy-6-propylpyridine-3,5-dicarboxylate

A mixture of ethyl 3-oxohexanoate (20.0 g) and 1,1-dimethoxy-N,N-dimethylmethanamine (15.8 g) in ethanol (40 mL) was stirred at 40 to 50° C. for 3 hours. After cooling to 25° C., ethyl cyanoacetate (15.7 g) was added to the mixture followed by addition of N-ethyl-N-isopropylpropan-2-amine (22.1 mL) at room temperature. The mixture was stirred at 50° C. for 16 hours. Acetic acid (9.11 g) and ethanol (40 mL) were added to the mixture at room temperature. The mixture was warmed to 50° C., and water (100 mL) was charged. The suspension was cooled to room temperature and stirred for 30 minutes. The precipitate was collected by filtration, washed with ethanol-water (20 mL-80 mL) and dried at 70° C. under vacuum to give a white solid. This solid was dissolved in ethanol (200 mL) at reflux temperature. Water (150 mL) was added to the mixture at the same temperature. The mixture was cooled gradually, stirred at 50 to 60° C. for 1 hour and at room temperature for 2 hours. The precipitate was collected by filtration, washed with ethanol-water (25 mL-25 mL) and dried at 70° C. under vacuum to give the title compound (17.5 g).

$^1$H NMR (300 MHz, DMSO-d$_6$) δ 0.92 (3H, t, J=7.4 Hz), 1.18-1.36 (6H, m), 1.50-1.68 (2H, m), 2.85-2.99 (2H, m), 4.15-4.32 (4H, m), 8.47 (1H, s), 12.49 (1H, brs).

F) Diethyl 2-propyl-6-vinylpyridine-3,5-dicarboxylate

Phosphoryl trichloride (7.95 mL) was added to a solution of diethyl 2-hydroxy-6-propylpyridine-3,5-dicarboxylate (12.0 g) in acetonitrile (120 mL) at room temperature. The mixture was stirred at 90° C. under a dry atmosphere with calcium chloride tube for 3 hours. After cooling to room temperature, the mixture was quenched with aqueous saturated sodium hydrogen carbonate solution at room temperature and extracted with ethyl acetate. The organic layer was separated, washed with brine and water, dried over anhydrous magnesium sulfate and concentrated in vacuo. A mixture of the residue, triethylamine (11.8 mL), potassium trifluoro(vinyl)borate (8.51 g) and dichloro[1,1'-bis(diphenylphosphino) ferrocene]palladium dichloromethane adduct (2.42 g) in ethanol (130 mL) was stirred at 90° C. overnight under nitrogen atmosphere. After cooling to room temperature, the mixture was concentrated in vacuo. The residue was diluted with ethyl acetate and water. The organic layer was separated, washed with brine, dried over anhydrous magnesium sulfate and concentrated in vacuo. The residue was passed through a silica gel-pad (hexane/ethyl acetate) to give the title compound (10.3 g).

$^1$H NMR (300 MHz, DMSO-d$_6$) δ 0.95 (3H, t, J=7.4 Hz), 1.34 (6H, td, J=7.1, 1.3 Hz), 1.65-1.80 (2H, m), 3.05-3.15 (2H, m), 4.29-4.40 (4H, m), 5.66-5.74 (1H, m), 6.58 (1H, dd, J=16.9, 2.5 Hz), 7.56 (1H, dd, J=16.9, 10.6 Hz), 8.50 (1H, s).

G) Ethyl 6-(1-(tert-butoxycarbonyl)piperidin-4-yl)-5-oxo-2-propyl-5,6,7,8-tetrahydro-1,6-naphthyridine-3-carboxylate A mixture of diethyl 2-propyl-6-vinylpyridine-3,5-dicarboxylate (9.00 g), tert-butyl 4-aminopiperidine-1-carboxylate (7.42 g) and N-ethyl-N-isopropylpropan-2-amine (8.09 mL) in DMA (45 mL) was stirred at 130 to 140° C. for 4.5 hours. The mixture was poured into water at room temperature and extracted with ethyl acetate. The organic layer was separated, washed with brine twice, dried over anhydrous magnesium sulfate and concentrated in vacuo. The residue was passed through a silica gel-pad (hexane/ethyl acetate), and concentrated in vacuo. The residue was purified by a silica gel column chromatography (hexane/ethyl acetate) to give the title compound (10.0 g).

$^1$H NMR (300 MHz, DMSO-d$_6$) δ 0.93 (3H, t, J=7.4 Hz), 1.34 (3H, t, J=7.1 Hz), 1.42 (9H, s), 1.53-1.73 (6H, m), 2.70-2.93 (2H, m), 3.00-3.15 (4H, m), 3.54 (2H, t, J=6.6 Hz), 3.97-4.15 (2H, m), 4.34 (2H, q, J=7.1 Hz), 4.51-4.67 (1H, m), 8.48 (1H, s).

H) Ethyl 5-oxo-6-(piperidin-4-yl)-2-propyl-5,6,7,8-tetrahydro-1,6-naphthyridine-3-carboxylate dihydrochloride monohydrate Ethyl 6-(1-(tert-butoxycarbonyl)piperidin-4-yl)-5-oxo-2-propyl-5,6,7,8-tetrahydro-1,6-naphthyridine-3-carboxylate (14.9 g) was added to 2M hydrogen chloride (ethanol solution, 167 mL) at room temperature. The mixture was stirred for 4 hours. Diisopropyl ether (1.00 L) was added to the reaction mixture. The mixture was stirred for 30 minutes. The precipitate was collected by filtration, washed with diisopropyl ether, dried under reduced pressure to give the title compound (13.7 g).

$^1$H NMR (300 MHz, DMSO-d$_6$) δ 0.93 (3H, t, J=7.4 Hz), 1.33 (3H, t, J=7.2 Hz), 1.59-1.81 (4H, m), 1.99-2.17 (2H, m), 2.97-3.11 (4H, m), 3.15 (2H, t, J=6.6 Hz), 3.35 (2H, d, J=12.1 Hz), 3.54 (2H, t, J=6.4 Hz), 4.35 (2H, q, J=7.1 Hz), 4.71 (1H, ddd, J=12.2, 8.2, 4.2 Hz), 6.81 (2H, brs), 8.50 (1H, s), 8.91 (2H, brs).

I) Ethyl 6-(1-((2-cyclopropyl-5-ethoxy-2',4'-difluoro-biphenyl-4-yl)methyl)piperidin-4-yl)-5-oxo-2-propyl-5,6,7,8-tetrahydro-1,6-naphthyridine-3-carboxylate To a suspension of Ethyl 5-oxo-6-(piperidin-4-yl)-2-propyl-5,6,7,8-tetrahydro-1,6-naphthyridine-3-carboxylate dihydrochloride monohydrate (10.1 g) in THF (203 mL) was added triethylamine (6.49 mL). The mixture was stirred for 30 minutes. 2-Cyclopropyl-5-ethoxy-2',4'-difluorobiphenyl-4-carbaldehyde (7.73 g) was added to the mixture. The mixture was stirred for 30 minutes. Then Sodium triacetoxyborohydride (7.39 g) and acetic acid (1.33 mL) was added to the reaction mixture. The mixture was stirred at room temperature for overnight. The mixture was added to aqueous saturated sodium hydrogen carbonate solution (135 mL) and water (135 mL) at room temperature. The mixture was extracted with ethyl acetate (1.35 L). The organic layer was separated, washed with brine, dried over anhydrous sodium sulfate and concentrated in vacuo. The residue was purified by a silica gel column chromatography (hexane/ethyl acetate) to give the title compound (13.3 g).

$^1$H NMR (300 MHz, CDCl$_3$) δ 0.51-0.59 (2H, m), 0.67-0.77 (2H, m), 1.01 (3H, t, J=7.4 Hz), 1.40 (6H, t, J=7.2 Hz), 1.61-1.78 (5H, m), 1.78-1.95 (2H, m), 2.21-2.34 (2H, m), 3.05 (2H, d, J=11.7 Hz), 3.10-3.20 (4H, m), 3.55-3.63 (4H, m), 4.00 (2H, q, J=6.8 Hz), 4.38 (2H, q, J=7.2 Hz), 4.67 (1H, tt, J=12.1, 4.2 Hz), 6.68 (1H, s), 6.85-6.98 (2H, m), 6.99 (1H, s), 7.27-7.36 (1H, m), 8.75 (1H, s).

J) 6-(1-((2-Cyclopropyl-5-ethoxy-2',4'-difluorobiphenyl-4-yl)methyl)piperidin-4-yl)-5-oxo-2-propyl-5,6,7,8-tetrahydro-1,6-naphthyridine-3-carboxylic acid To a solution of ethyl 6-(1-((2-cyclopropyl-5-ethoxy-2',4'-difluorobiphenyl-4-yl)methyl)piperidin-4-yl)-5-oxo-2-propyl-5,6,7,8-tetrahydro-1,6-naphthyridine-3-carboxylate (13.2 g) in THF (33 mL)-ethanol (33 mL) was added 2M aqueous sodium hydroxide solution (31.2 mL). The mixture was stirred for 1 hour at 50° C. The mixture was cooled to room temperature. 2M hydrochloric acid (31.2 mL) was added to the reaction mixture. Then water (62.5 mL) was added to the reaction mixture. After cooled to 0° C., the precipitate was collected by filtration, washed with water, dried by airstream to give the title compound (12.4 g).

$^1$H NMR (300 MHz, DMSO-d$_6$) δ 0.45-0.53 (2H, m), 0.67-0.76 (2H, m), 0.92 (3H, t, J=7.4 Hz), 1.32 (3H, t, J=7.0 Hz), 1.52-1.74 (5H, m), 1.77-1.94 (2H, m), 2.23 (2H, t, J=11.3 Hz), 2.95-3.15 (6H, m), 3.52-3.62 (4H, m), 4.01 (2H, q, J=6.8 Hz), 4.46 (1H, t, J=11.9 Hz), 6.77 (1H, s), 7.01 (1H, s), 7.13-7.22 (1H, m), 7.33 (1H, td, J=9.7, 2.5 Hz), 7.44 (1H, td, J=8.5, 6.8 Hz), 8.48 (1H, s).

K) 6-(1-((2-Cyclopropyl-5-ethoxy-2',4'-difluorobiphenyl-4-yl)methyl)piperidin-4-yl)-5-oxo-2-propyl-5,6,7,8-tetrahydro-1,6-naphthyridine-3-carboxylic acid 6-(1-((2-Cyclopropyl-5-ethoxy-2',4'-difluorobiphenyl-4-yl)methyl)piperidin-4-yl)-5-oxo-2-propyl-5,6,7,8-tetrahydro-1,6-naphthyridine-3-carboxylic acid (23.1 g) was crystallized from DMSO-ethanol to give the title compound (15.0 g).
$^1$H NMR (300 MHz, DMSO-$d_6$) δ 0.37-0.56 (2H, m), 0.68-0.77 (2H, m), 0.92 (3H, t, J=7.4 Hz), 1.31 (3H, t, J=6.9 Hz), 1.53-1.74 (5H, m), 1.75-1.93 (2H, m), 2.17 (2H, t, J=11.9 Hz), 2.98 (2H, d, J=11.3 Hz), 3.03-3.14 (4H, m), 3.50-3.63 (4H, m), 4.01 (2H, q, J=7.0 Hz), 4.34-4.51 (1H, m), 6.76 (1H, s), 6.99 (1H, s), 7.18 (1H, s), 7.28-7.38 (1H, m), 7.40-7.51 (1H, m), 8.47 (1H, s).
mp 262-264° C.

Example 84

6-(1-((2-Cyclopropyl-5-ethoxy-2',4'-difluorobiphenyl-4-yl)methyl)piperidin-4-yl)-5-oxo-2-propyl-5,6,7,8-tetrahydro-1,6-naphthyridine-3-carboxylic acid 1/2 fumarate Fumaric acid (36.1 mg) was added to a mixture of 6-(1-((2-cyclopropyl-5-ethoxy-2',4'-difluorobiphenyl-4-yl)methyl)piperidin-4-yl)-5-oxo-2-propyl-5,6,7,8-tetrahydro-1,6-naphthyridine-3-carboxylic acid (125 mg) in ethanol (10 mL). The suspension was filtered and the solvent was concentrated to ca.2 mL. Then acetonitrile was added to the mixture. The mixture was stirred at room temperature for 30 minutes. The precipitate was collected by filtration and washed with ethyl acetate to give the title compound (12.1 mg).
Anal. Calcd for $C_{35}H_{39}N_3O_4F_2 \cdot 1/2 C_4H_4O_4$: C, 67.16; H, 6.25; N, 6.35. Found: C, 67.19; H, 6.34; N, 6.49.

Example 85

6-(1-((2-Cyclopropyl-5-ethoxy-2',4'-difluorobiphenyl-4-yl)methyl)piperidin-4-yl)-5-oxo-2-propyl-5,6,7,8-tetrahydro-1,6-naphthyridine-3-carboxylic acid maleate Maleic acid (36.1 mg) was added to a mixture of 6-(1-((2-cyclopropyl-5-ethoxy-2',4'-difluorobiphenyl-4-yl)methyl)piperidin-4-yl)-5-oxo-2-propyl-5,6,7,8-tetrahydro-1,6-naphthyridine-3-carboxylic acid (125 mg) in ethanol (10 mL). The suspension was filtered and the solvent was removed under reduced pressure. The residue was crystallized from ethyl acetate-hexane to give the title compound (100 mg).
$^1$H NMR (300 MHz, DMSO-$d_6$) δ 0.51-0.64 (2H, m), 0.76 (2H, d, J=8.0 Hz), 0.92 (3H, t, J=7.3 Hz), 1.36 (3H, t, J=6.9 Hz), 1.51-1.75 (3H, m), 1.76-1.90 (2H, m), 1.97-2.20 (2H, m), 3.03-3.63 (12H, m), 4.10 (2H, q, J=7.0 Hz), 4.15-4.28 (1H, m), 4.59-4.80 (1H, m), 6.03 (2H, s), 6.93 (1H, s), 7.08-7.29 (2H, m), 7.30-7.52 (2H, m), 8.51 (1H, s)

Table 1 shows the compound names, structural formulas, and actual MS measurement values of the compounds of Examples. The actual MS measurement values are indicated by values found in a positive mode (ESI+) or a negative mode (ESI−).

TABLE 1

| Example # | IUPAC NAME | Structure | MS |
|---|---|---|---|
| 1 | 6-(1-((2-cyclopropyl-6-ethoxy-4'-fluorobiphenyl-4-yl)methyl)piperidin-4-yl)-2-methyl-5-oxo-5,6,7,8-tetrahydro-1,6-naphthyridine-3-carboxylic acid | 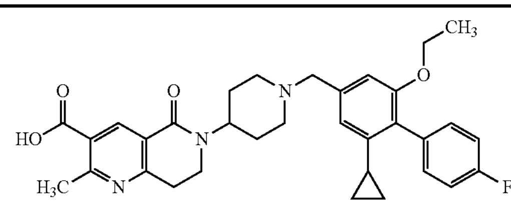 | 558.5 |
| 2 | 6-(1-((2-cyclopropyl-5-ethoxy-4'-fluorobiphenyl-4-yl)methyl)piperidin-4-yl)-2-ethyl-5-oxo-5,6,7,8-tetrahydro-1,6-naphthyridine-3-carboxylic acid | 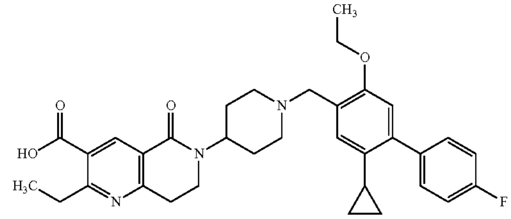 [SMILES: CCOc1cc(-c2ccc(F)cc2)c(C2CC2)cc1CN1CCC(N2CCc3nc(CC)c(C(=O)O)cc3C2=O)CC1] | 572.5 |
| 3 | 2-cyclopropyl-6-(1-((2-cyclopropyl-5-ethoxy-4'-fluorobiphenyl-4-yl)methyl)piperidin-4-yl)-5-oxo-5,6,7,8-tetrahydro-1,6-naphthyridine-3-carboxylic acid | 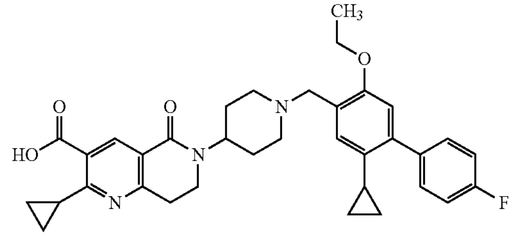 [SMILES: CCOc1cc(-c2ccc(F)cc2)c(C2CC2)cc1CN1CCC(N2CCc3nc(C4CC4)c(C(=O)O)cc3C2=O)CC1] | 584.5 |

TABLE 1-continued

| Example # | IUPAC NAME | Structure | MS |
|---|---|---|---|
| 4 | 6-(1-((2-cyclopropyl-5-ethoxy-4'-fluorobiphenyl-4-yl)methyl)piperidin-4-yl)-5-oxo-2-propyl-5,6,7,8-tetrahydro-1,6-naphthyridine-3-carboxylic acid | 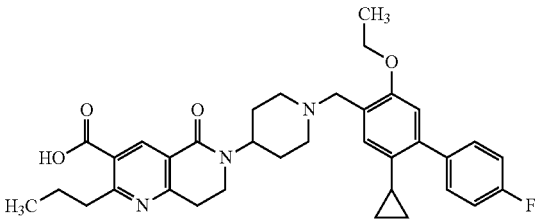 | 586.5 |
| 5 | 6-(1-((2-cyclopropyl-5-ethoxy-4'-fluorobiphenyl-4-yl)methyl)piperidin-4-yl)-2-methyl-5-oxo-5,6,7,8-tetrahydro-1,6-naphthyridine-3-carboxylic acid | 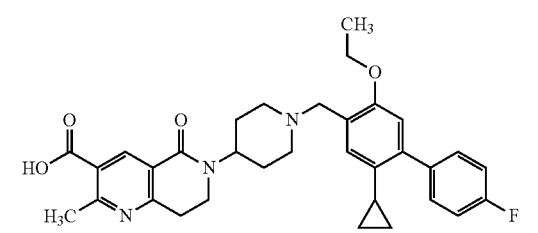 [SMILES: CCOc1cc(-c2ccc(F)cc2)c(C2CC2)cc1CN1CCC(N2CCc3nc(C)c(C(=O)O)cc3C2=O)CC1] | 558.5 |
| 6 | 6-(1-((5-cyclopropyl-6-(4-fluorophenyl)-2-isopropoxypyridin-3-yl)methyl)piperidin-4-yl)-2-methyl-5-oxo-5,6,7,8-tetrahydro-1,6-naphthyridine-3-carboxylic acid | 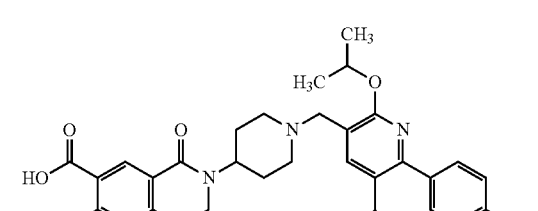 | 573.5 |
| 7 | 6-(1-((2-cyclopropyl-4'-fluoro-5-isopropoxybiphenyl-4-yl)methyl)piperidin-4-yl)-2-methyl-5-oxo-5,6,7,8-tetrahydro-1,6-naphthyridine-3-carboxylic acid | 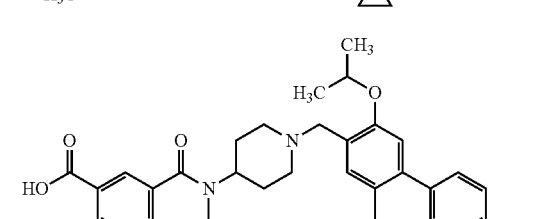 | 572.5 |
| 8 | 6-(1-((2-cyclopropyl-6-ethoxy-3',4'-difluorobiphenyl-4-yl)methyl)piperidin-4-yl)-2-methyl-5-oxo-5,6,7,8-tetrahydro-1,6-naphthyridine-3-carboxylic acid | 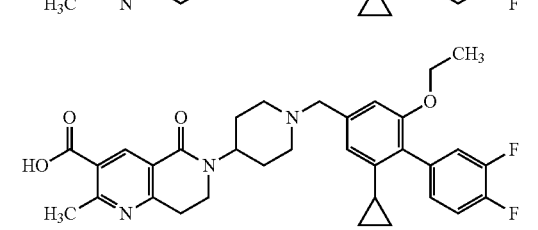 | 576.4 |
| 9 | 6-(1-((2-cyclopropyl-4'-fluoro-6-propoxybiphenyl-4-yl)methyl)piperidin-4-yl)-2-methyl-5-oxo-5,6,7,8-tetrahydro-1,6-naphthyridine-3-carboxylic acid | 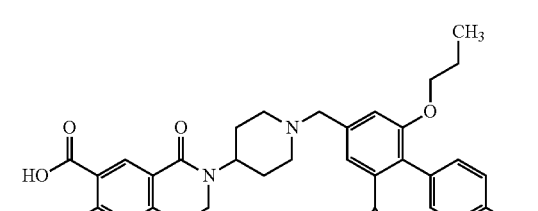 | 572.5 |
| 10 | 6-(1-(4-cyclobutyl-3-cyclopropyl-5-ethoxybenzyl)piperidin-4-yl)-2-methyl-5-oxo-5,6,7,8-tetrahydro-1,6-naphthyridine-3-carboxylic acid | 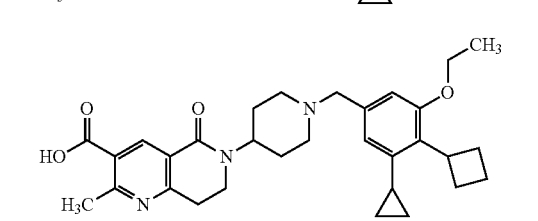 | 518.5 |

TABLE 1-continued

| Example # | IUPAC NAME | Structure | MS |
|---|---|---|---|
| 11 | 6-(1-(3-cyclopropyl-4-(cyclopropylmethoxy)-5-ethoxybenzyl)piperidin-4-yl)-2-methyl-5-oxo-5,6,7,8-tetrahydro-1,6-naphthyridine-3-carboxylic acid | 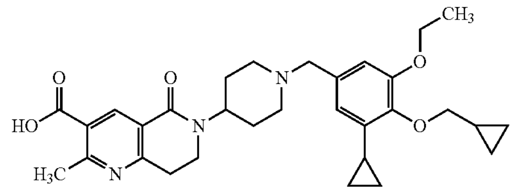 [SMILES: CCOc1cc(CN2CCC(N3CCc4nc(C)c(C(=O)O)cc4C3=O)CC2)cc(C2CC2)c1OCC1CC1] | 534.5 |
| 12 | 6-(1-(4-cyclopentyl-3-cyclopropyl-5-ethoxybenzyl)piperidin-4-yl)-2-methyl-5-oxo-5,6,7,8-tetrahydro-1,6-naphthyridine-3-carboxylic acid | 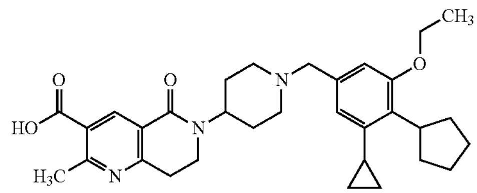 [SMILES: CCOc1cc(CN2CCC(N3CCc4nc(C)c(C(=O)O)cc4C3=O)CC2)cc(C2CC2)c1C1CCCC1] | 532.5 |
| 13 | 6-(1-((1-tert-butyl-3-(3-chloro-4-fluorophenyl)-1H-pyrazol-4-yl)methyl)piperidin-4-yl)-2-methyl-5-oxo-5,6,7,8-tetrahydro-1,6-naphthyridine-3-carboxylic acid | 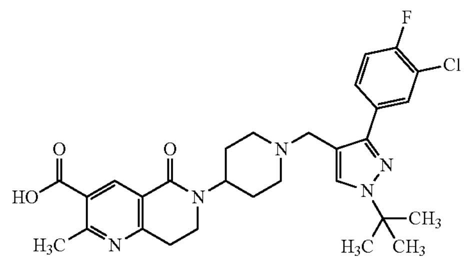 [SMILES: Cc1nc2c(cc1C(=O)O)C(=O)N(C1CCN(Cc3cn(C(C)(C)C)nc3-c3ccc(F)c(Cl)c3)CC1)CC2] | 554.4 |
| 14 | 6-(1-((2-cyclopropyl-6-ethoxy-2',4'-difluorobiphenyl-4-yl)methyl)piperidin-4-yl)-2-methyl-5-oxo-5,6,7,8-tetrahydro-1,6-naphthyridine-3-carboxylic acid | 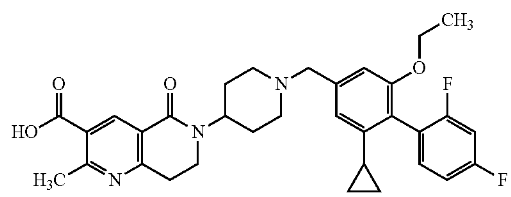 [SMILES: CCOc1cc(CN2CCC(N3CCc4nc(C)c(C(=O)O)cc4C3=O)CC2)cc(C2CC2)c1-c1ccc(F)cc1F] | 576.4 |
| 15 | 6-(1-((2-chloro-6-cyclopropyl-4'-fluoro-3-isopropoxybiphenyl-4-yl)methyl)piperidin-4-yl)-2-methyl-5-oxo-5,6,7,8-tetrahydro-1,6-naphthyridine-3-carboxylic acid | 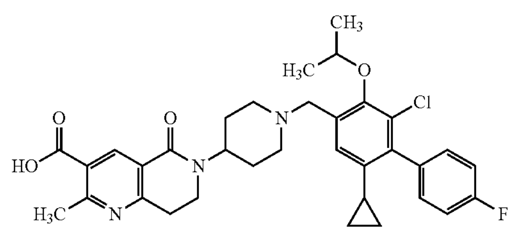 [SMILES: Cc1nc2c(cc1C(=O)O)C(=O)N(C1CCN(Cc3cc(C4CC4)c(-c4ccc(F)cc4)c(Cl)c3OC(C)C)CC1)CC2] | 606.4 |
| 16 | 6-(1-((2-cyclopropyl-2',4'-difluoro-5-isopropoxybiphenyl-4-yl)methyl)piperidin-4-yl)-2-methyl-5-oxo-5,6,7,8-tetrahydro-1,6-naphthyridine-3-carboxylic acid | 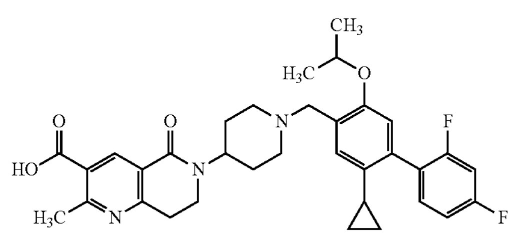 [SMILES: Cc1nc2c(cc1C(=O)O)C(=O)N(C1CCN(Cc3cc(C4CC4)c(-c4ccc(F)cc4F)cc3OC(C)C)CC1)CC2] | 590.5 |
| 17 | 6-(1-((2-cyclopropyl-4'-fluoro-6-isopropoxybiphenyl-4-yl)methyl)piperidin-4-yl)-2-methyl-5-oxo-5,6,7,8-tetrahydro-1,6-naphthyridine-3-carboxylic acid | 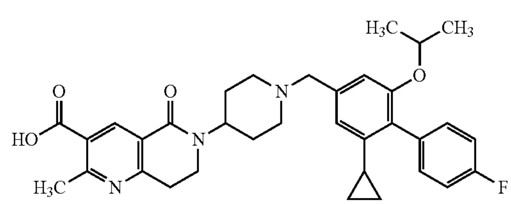 [SMILES: Cc1nc2c(cc1C(=O)O)C(=O)N(C1CCN(Cc3cc(OC(C)C)c(-c4ccc(F)cc4)c(C4CC4)c3)CC1)CC2] | 572.5 |

TABLE 1-continued

| Example # | IUPAC NAME | Structure | MS |
|---|---|---|---|
| 18 | 6-(1-(4-cyclobutyl-5-cyclopropyl-2-isopropoxybenzyl)piperidin-4-yl)-2-methyl-5-oxo-5,6,7,8-tetrahydro-1,6-naphthyridine-3-carboxylic acid | 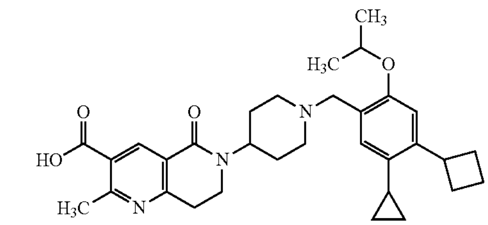 [SMILES: Cc1nc2c(cc1C(=O)O)C(=O)N(C1CCN(Cc3cc(C4CC4)c(C4CCC4)cc3OC(C)C)CC1)CC2] | 532.5 |
| 19 | 6-(1-((2-cyclopropyl-3',4'-difluoro-5-isopropoxybiphenyl-4-yl)methyl)piperidin-4-yl)-2-methyl-5-oxo-5,6,7,8-tetrahydro-1,6-naphthyridine-3-carboxylic acid | 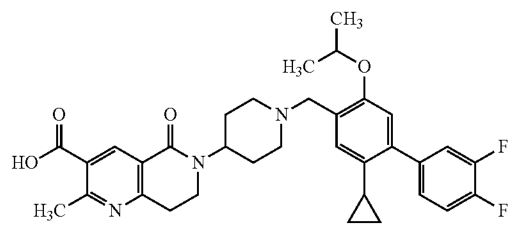 [SMILES: Cc1nc2c(cc1C(=O)O)C(=O)N(C1CCN(Cc3cc(C4CC4)c(-c4ccc(F)c(F)c4)cc3OC(C)C)CC1)CC2] | 590.5 |
| 20 | 6-(1-((2,6-diethoxy-4'-fluorobiphenyl-4-yl)methyl)piperidin-4-yl)-2-methyl-5-oxo-5,6,7,8-tetrahydro-1,6-naphthyridine-3-carboxylic acid | 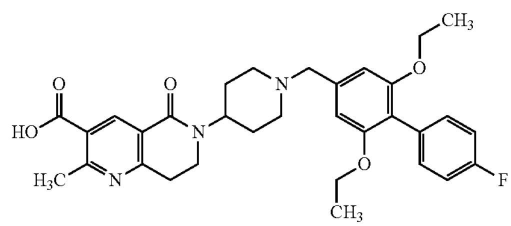 [SMILES: CCOc1cc(CN2CCC(N3CCc4nc(C)c(C(=O)O)cc4C3=O)CC2)cc(OCC)c1-c1ccc(F)cc1] | 562.5 |
| 21 | 6-(1-(4-cyclopentyl-5-cyclopropyl-2-isopropoxybenzyl)piperidin-4-yl)-2-methyl-5-oxo-5,6,7,8-tetrahydro-1,6-naphthyridine-3-carboxylic acid | 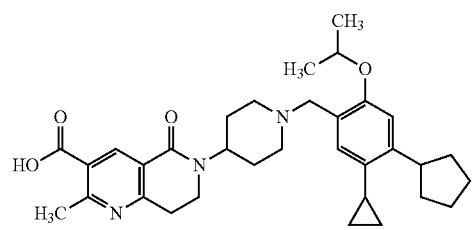 [SMILES: Cc1nc2c(cc1C(=O)O)C(=O)N(C1CCN(Cc3cc(C4CC4)c(C4CCCC4)cc3OC(C)C)CC1)CC2] | 546.5 |
| 22 | 6-(1-((2-ethoxy-4'-fluoro-6-isopropoxybiphenyl-4-yl)methyl)piperidin-4-yl)-2-methyl-5-oxo-5,6,7,8-tetrahydro-1,6-naphthyridine-3-carboxylic acid | 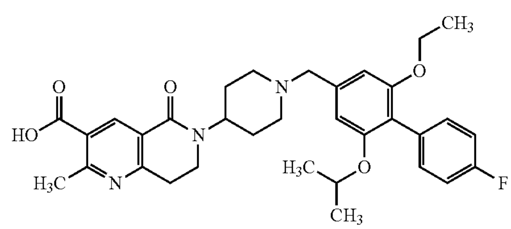 [SMILES: CCOc1cc(CN2CCC(N3CCc4nc(C)c(C(=O)O)cc4C3=O)CC2)cc(OC(C)C)c1-c1ccc(F)cc1] | 576.5 |
| 23 | 6-(1-((2-ethoxy-4'-fluoro-6-propoxybiphenyl-4-yl)methyl)piperidin-4-yl)-2-methyl-5-oxo-5,6,7,8-tetrahydro-1,6-naphthyridine-3-carboxylic acid | 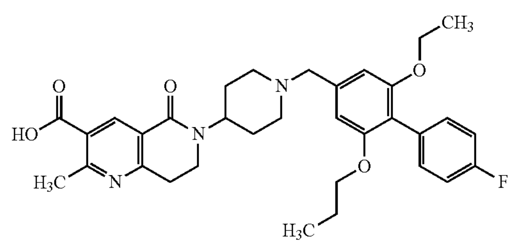 [SMILES: CCCOc1cc(CN2CCC(N3CCc4nc(C)c(C(=O)O)cc4C3=O)CC2)cc(OCC)c1-c1ccc(F)cc1] | 576.4 |

TABLE 1-continued

| Example # | IUPAC NAME | Structure | MS |
|---|---|---|---|
| 24 | 6-(1-(4,5-dicyclopropyl-2-isopropoxybenzyl)piperidin-4-yl)-2-methyl-5-oxo-5,6,7,8-tetrahydro-1,6-naphthyridine-3-carboxylic acid | 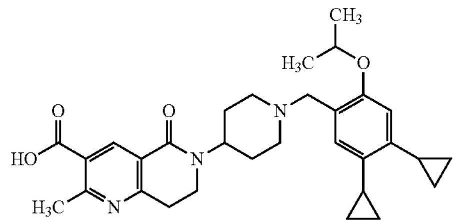 [SMILES: Cc1nc2c(cc1C(=O)O)C(=O)N(C1CCN(Cc3cc(C4CC4)c(C4CC4)cc3OC(C)C)CC1)CC2] | 518.5 |
| 25 | 6-(1-((2-diethoxy-4'-fluorobiphenyl-4-yl)methyl)piperidin-4-yl)-5-oxo-5,6,7,8-tetrahydro-1,6-naphthyridine-3-carboxylic acid | 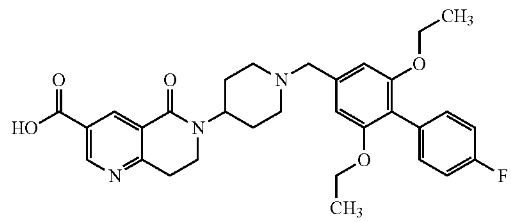 [SMILES: CCOc1cc(CN2CCC(N3CCc4ncc(C(=O)O)cc4C3=O)CC2)cc(OCC)c1-c1ccc(F)cc1] | 548.4 |
| 26 | 6-(1-((2-cyclopropyl-6-ethoxy-4'-fluorobiphenyl-4-yl)methyl)piperidin-4-yl)-5-oxo-5,6,7,8-tetrahydro-1,6-naphthyridine-3-carboxylic acid | 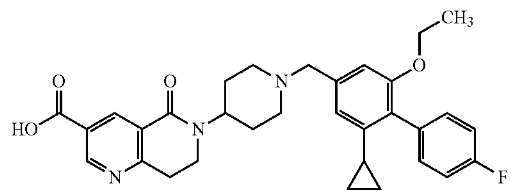 [SMILES: CCOc1cc(CN2CCC(N3CCc4ncc(C(=O)O)cc4C3=O)CC2)cc(C2CC2)c1-c1ccc(F)cc1] | 544.4 |
| 27 | 6-(1-((2-cyclopropyl-5-ethoxy-4'-fluorobiphenyl-4-yl)methyl)piperidin-4-yl)-5-oxo-5,6,7,8-tetrahydro-1,6-naphthyridine-3-carboxylic acid | 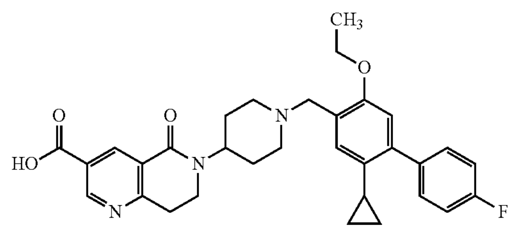 [SMILES: CCOc1cc(-c2ccc(F)cc2)c(C2CC2)cc1CN1CCC(N2CCc3ncc(C(=O)O)cc3C2=O)CC1] | 544.5 |
| 28 | 6-(1-((5-cyclopropyl-2-ethoxy-6-(4-fluorophenyl)pyridin-3-yl)methyl)piperidin-4-yl)-5-oxo-5,6,7,8-tetrahydro-1,6-naphthyridine-3-carboxylic acid | 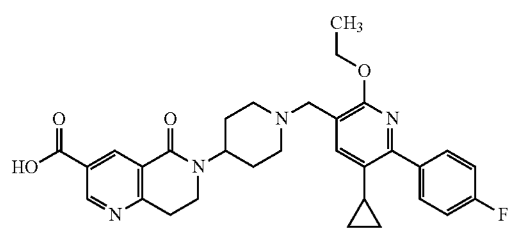 | 545.4 |
| 29 | 6-(1-((2,6-diethoxy-4'-fluorobiphenyl-4-yl)methyl)azetidin-3-yl)-5-oxo-5,6,7,8-tetrahydro-1,6-naphthyridine-3-carboxylic acid | 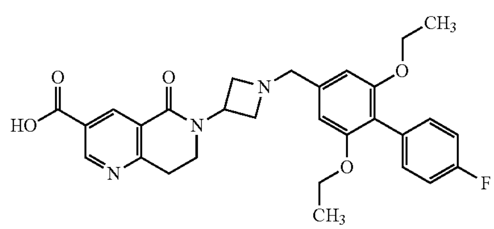 [SMILES: CCOc1cc(CN2CC(N3CCc4ncc(C(=O)O)cc4C3=O)C2)cc(OCC)c1-c1ccc(F)cc1] | 520.4 |
| 30 | 6-(1-(4-cyclobutyl-5-cyclopropyl-2-ethoxybenzyl)piperidin-4-yl)-5-oxo-5,6,7,8-tetrahydro-1,6-naphthyridine-3-carboxylic acid | 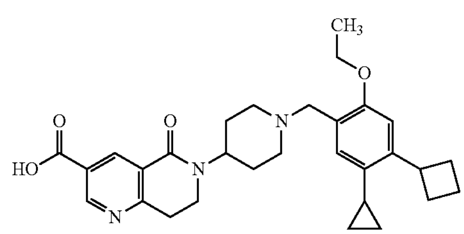 [SMILES: CCOc1cc(C2CCC2)c(C2CC2)cc1CN1CCC(N2CCc3ncc(C(=O)O)cc3C2=O)CC1] | 504.5 |

TABLE 1-continued

| Example # | IUPAC NAME | Structure | MS |
|---|---|---|---|
| 31 | 7-(1-((2-cyclopropyl-5-ethoxy-4'-fluorobiphenyl-4-yl)methyl)piperidin-4-yl)-8-oxo-5,6,7,8-tetrahydro-1,7-naphthyridine-2-carboxylic acid | 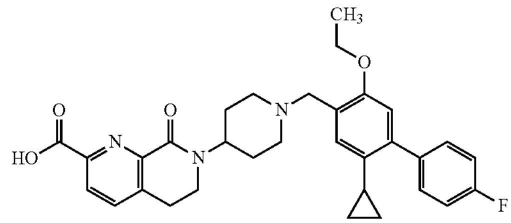 [SMILES: CCOc1cc(-c2ccc(F)cc2)c(C2CC2)cc1CN1CCC(N2CCc3ccc(C(=O)O)nc3C2=O)CC1] | 544.4 |
| 32 | 6-(1-((4-cyclopropyl-1-ethyl-1H-indol-6-yl)methyl)piperidin-4-yl)-5-oxo-5,6,7,8-tetrahydro-1,6-naphthyridine-3-carboxylic acid | 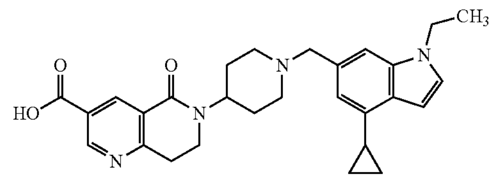 [SMILES: CCn1ccc2c(C3CC3)cc(CN3CCC(N4CCc5ncc(C(=O)O)cc5C4=O)CC3)cc21] | 473.4 |
| 33 | 6-(1-((5-cyclopropyl-2-ethoxy-6-(4-fluorophenyl)pyridin-3-yl)methyl)piperidin-4-yl)-2-ethyl-5-oxo-5,6,7,8-tetrahydro-1,6-naphthyridine-3-carboxylic acid | 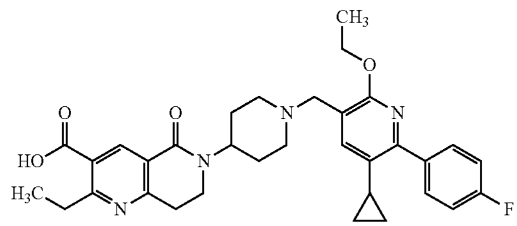 [SMILES: CCOc1nc(-c2ccc(F)cc2)c(C2CC2)cc1CN1CCC(N2CCc3nc(CC)c(C(=O)O)cc3C2=O)CC1] | 573.5 |
| 34 | 6-(1-((2,6-diethoxy-4'-fluorobiphenyl-4-yl)methyl)pyrrolidin-3-yl)-5-oxo-5,6,7,8-tetrahydro-1,6-naphthyridine-3-carboxylic acid | 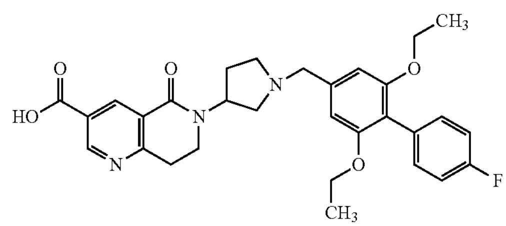 [SMILES: CCOc1cc(CN2CCC(N3CCc4ncc(C(=O)O)cc4C3=O)C2)cc(OCC)c1-c1ccc(F)cc1] | 534.4 |
| 35 | 6-(1-((2-cyclopropyl-5-ethoxy-2',4'-difluorobiphenyl-4-yl)methyl)piperidin-4-yl)-5-oxo-2-propyl-5,6,7,8-tetrahydro-1,6-naphthyridine-3-carboxylic acid | 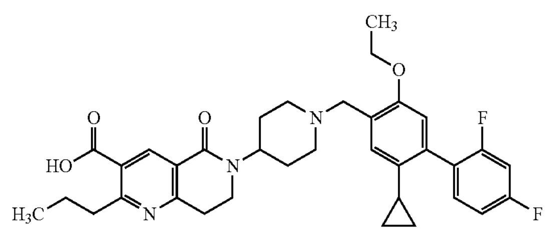 [SMILES: CCCc1nc2c(cc1C(=O)O)C(=O)N(C1CCN(Cc3cc(C4CC4)c(-c4ccc(F)cc4F)cc3OCC)CC1)CC2] | 604.5 |
| 36 | 6-(1-((2-cyclopropyl-6-ethoxy-4'-fluorobiphenyl-4-yl)methyl)piperidin-4-yl)-5-oxo-2-propyl-5,6,7,8-tetrahydro-1,6-naphthyridine-3-carboxylic acid | 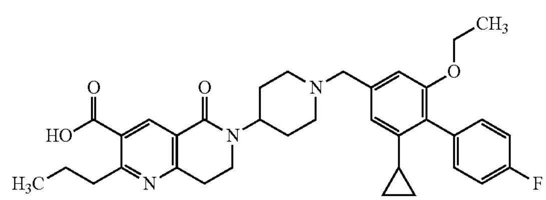 [SMILES: CCCc1nc2c(cc1C(=O)O)C(=O)N(C1CCN(Cc3cc(OCC)c(-c4ccc(F)cc4)c(C4CC4)c3)CC1)CC2] | 586.5 |
| 37 | 6-(1-((2-cyclopropyl-4'-fluoro-5-isopropoxybiphenyl-4-yl)methyl)piperidin-4-yl)-5-oxo-2-propyl-5,6,7,8-tetrahydro-1,6-naphthyridine-3-carboxylic acid | 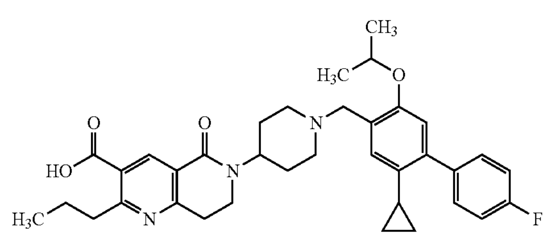 [SMILES: CCCc1nc2c(cc1C(=O)O)C(=O)N(C1CCN(Cc3cc(C4CC4)c(-c4ccc(F)cc4)cc3OC(C)C)CC1)CC2] | 600.6 |

TABLE 1-continued

| Example # | IUPAC NAME | Structure | MS |
|---|---|---|---|
| 38 | 6-(1-((2,6-diethoxy-4'-fluorobiphenyl-4-yl)methyl)piperidin-4-yl)-5-oxo-2-propyl-5,6,7,8-tetrahydro-1,6-naphthyridine-3-carboxylic acid | 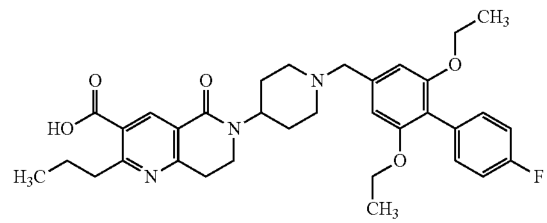 [SMILES: CCCc1nc2c(cc1C(=O)O)C(=O)N(C1CCN(Cc3cc(OCC)c(-c4ccc(F)cc4)c(OCC)c3)CC1)CC2] | 590.5 |
| 39 | 6-(1-((2-cyclopropyl-3',4'-difluoro-5-isopropoxybiphenyl-4-yl)methyl)piperidin-4-yl)-5-oxo-2-propyl-5,6,7,8-tetrahydro-1,6-naphthyridine-3-carboxylic acid | 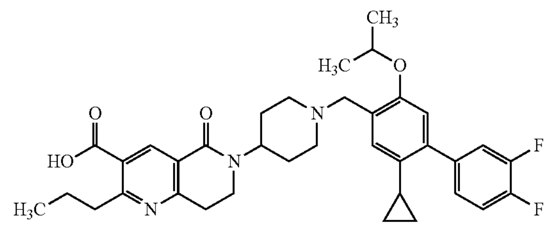 [SMILES: CCCc1nc2c(cc1C(=O)O)C(=O)N(C1CCN(Cc3cc(C4CC4)c(-c4ccc(F)c(F)c4)cc3OC(C)C)CC1)CC2] | 618.5 |
| 40 | 6-(1-((2-cyclopropyl-2',4'-difluoro-5-isopropoxybiphenyl-4-yl)methyl)piperidin-4-yl)-5-oxo-2-propyl-5,6,7,8-tetrahydro-1,6-naphthyridine-3-carboxylic acid | 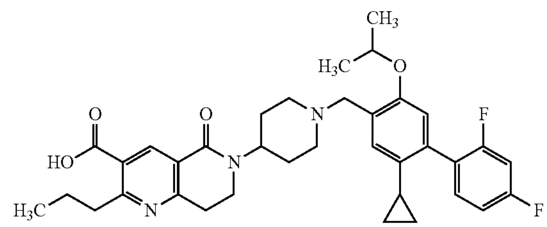 [SMILES: CCCc1nc2c(cc1C(=O)O)C(=O)N(C1CCN(Cc3cc(C4CC4)c(-c4ccc(F)cc4F)cc3OC(C)C)CC1)CC2] | 618.5 |
| 41 | 6-(1-(4-cyclobutyl-5-cyclopropyl-2-isopropoxybenzyl)piperidin-4-yl)-5-oxo-2-propyl-5,6,7,8-tetrahydro-1,6-naphthyridine-3-carboxylic acid | 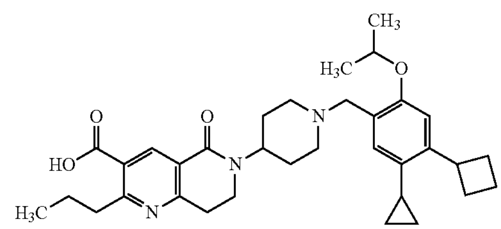 [SMILES: CCCc1nc2c(cc1C(=O)O)C(=O)N(C1CCN(Cc3cc(C4CC4)c(C4CCC4)cc3OC(C)C)CC1)CC2] | 560.5 |
| 42 | 6-(1-((2-cyclopropyl-4'-fluoro-5-methoxybiphenyl-4-yl)methyl)piperidin-4-yl)-5-oxo-2-propyl-5,6,7,8-tetrahydro-1,6-naphthyridine-3-carboxylic acid | 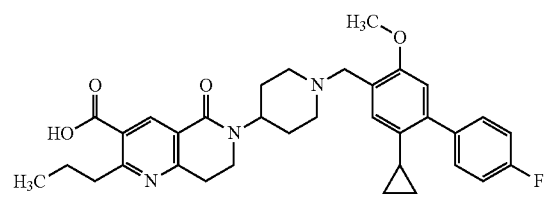 [SMILES: CCCc1nc2c(cc1C(=O)O)C(=O)N(C1CCN(Cc3cc(C4CC4)c(-c4ccc(F)cc4)cc3OC)CC1)CC2] | 572.5 |
| 43 | 6-(1-((2-cyclopropyl-5-ethoxy-3',4'-difluorobiphenyl-4-yl)methyl)piperidin-4-yl)-5-oxo-2-propyl-5,6,7,8-tetrahydro-1,6-naphthyridine-3-carboxylic acid | 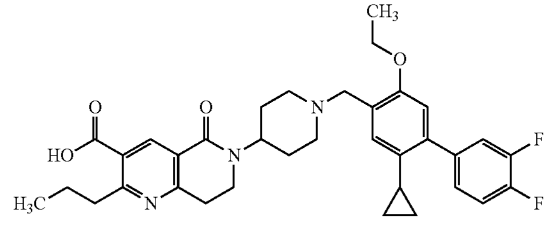 [SMILES: CCCc1nc2c(cc1C(=O)O)C(=O)N(C1CCN(Cc3cc(C4CC4)c(-c4ccc(F)c(F)c4)cc3OCC)CC1)CC2] | 604.5 |
| 44 | 6-(1-((2-cyclopropyl-4'-fluoro-5-isopropoxybiphenyl-4-yl)methyl)piperidin-4-yl)-2-ethyl-5-oxo-5,6,7,8-tetrahydro-1,6-naphthyridine-3-carboxylic acid | 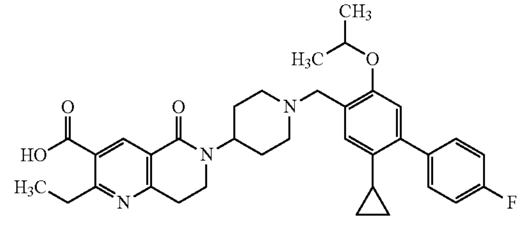 [SMILES: CCc1nc2c(cc1C(=O)O)C(=O)N(C1CCN(Cc3cc(C4CC4)c(-c4ccc(F)cc4)cc3OC(C)C)CC1)CC2] | 586.5 |

TABLE 1-continued

| Example # | IUPAC NAME | Structure | MS |
|---|---|---|---|
| 45 | 6-(1-((2-cyclopropyl-6-ethoxy-4'-fluorobiphenyl-4-yl)methyl)piperidin-4-yl)-2-ethyl-5-oxo-5,6,7,8-tetrahydro-1,6-naphthyridine-3-carboxylic acid | 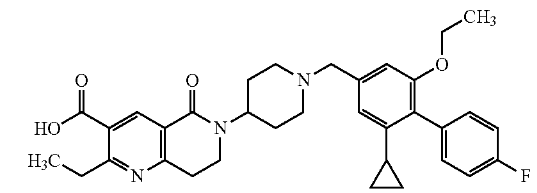 [SMILES: CCOc1cc(CN2CCC(N3CCc4nc(CC)c(C(=O)O)cc4C3=O)CC2)cc(C2CC2)c1-c1ccc(F)cc1] | 572.5 |
| 46 | 6-(1-((2-cyclopropyl-2',4'-difluoro-5-isopropoxybiphenyl-4-yl)methyl)piperidin-4-yl)-2-ethyl-5-oxo-5,6,7,8-tetrahydro-1,6-naphthyridine-3-carboxylic acid | 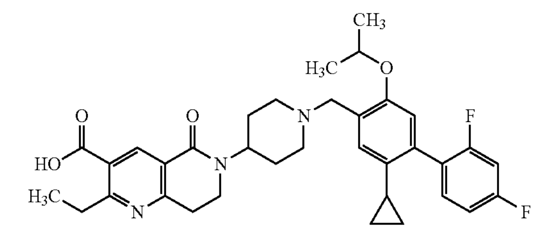 [SMILES: CCc1nc2c(cc1C(=O)O)C(=O)N(C1CCN(Cc3cc(C4CC4)c(-c4ccc(F)cc4F)cc3OC(C)C)CC1)CC2] | 604.3 |
| 47 | 6-(1-((2-cyclopropyl-5-ethoxy-4'-fluorobiphenyl-4-yl)methyl)piperidin-4-yl)-2-(methoxymethyl)-5-oxo-5,6,7,8-tetrahydro-1,6-naphthyridine-3-carboxylic acid | 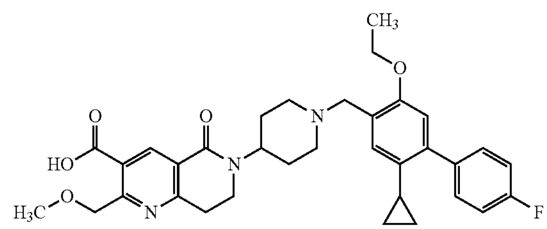 [SMILES: CCOc1cc(-c2ccc(F)cc2)c(C2CC2)cc1CN1CCC(N2CCc3nc(COC)c(C(=O)O)cc3C2=O)CC1] | 588.4 |
| 48 | 6-(1-((2-cyclopropyl-5-ethoxy-2',4'-difluorobiphenyl-4-yl)methyl)piperidin-4-yl)-2-(methoxymethyl)-5-oxo-5,6,7,8-tetrahydro-1,6-naphthyridine-3-carboxylic acid | 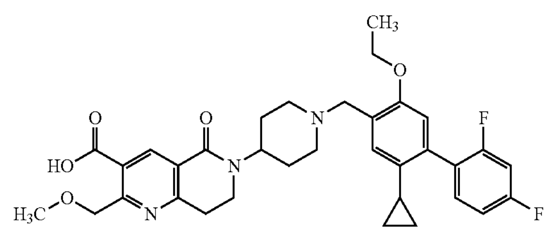 | 606.5 |
| 49 | 6-(1-((2-cyclopropyl-5-ethoxy-4'-fluorobiphenyl-4-yl)methyl)piperidin-4-yl)-2-isopropyl-5-oxo-5,6,7,8-tetrahydro-1,6-naphthyridine-3-carboxylic acid | 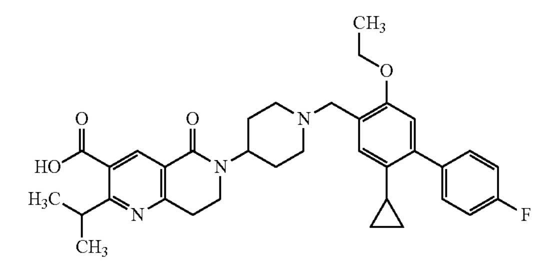 [SMILES: CCOc1cc(-c2ccc(F)cc2)c(C2CC2)cc1CN1CCC(N2CCc3nc(C(C)C)c(C(=O)O)cc3C2=O)CC1] | 586.5 |
| 50 | 6-(1-((2-cyclopropyl-4'-fluoro-5-isopropoxybiphenyl-4-yl))methyl)piperidin-4-yl)-2-isopropyl-5-oxo-5,6,7,8-tetrahydro-1,6-naphthyridine-3-carboxylic acid | 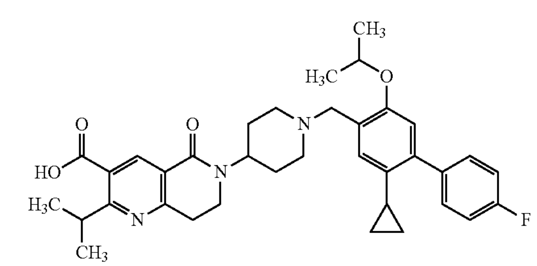 [SMILES: CC(C)Oc1cc(-c2ccc(F)cc2)c(C2CC2)cc1CN1CCC(N2CCc3nc(C(C)C)c(C(=O)O)cc3C2=O)CC1] | 600.5 |

TABLE 1-continued

| Example # | IUPAC NAME | Structure | MS |
|---|---|---|---|
| 51 | 6-(1-(4,5-dicyclopropyl-2-ethoxybenzyl)piperidin-4-yl)-5-oxo-2-propyl-5,6,7,8-tetrahydro-1,6-naphthyridine-3-carboxylic acid | 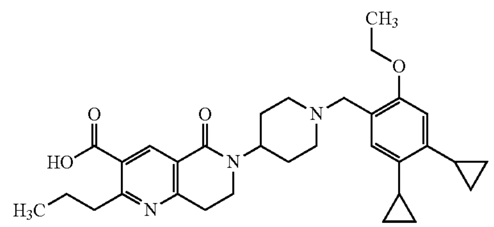 [SMILES: CCCc1nc2c(cc1C(=O)O)C(=O)N(C1CCN(Cc3cc(C4CC4)c(C4CC4)cc3OCC)CC1)CC2] | 532.5 |
| 52 | 6-(1-(4-cyclobutyl-5-cyclopropyl-2-ethoxybenzyl)piperidin-4-yl)-5-oxo-2-propyl-5,6,7,8-tetrahydro-1,6-naphthyridine-3-carboxylic acid | 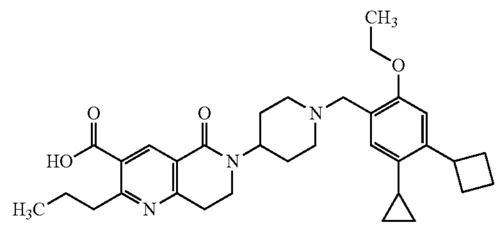 [SMILES: CCCc1nc2c(cc1C(=O)O)C(=O)N(C1CCN(Cc3cc(C4CC4)c(C4CCC4)cc3OCC)CC1)CC2] | 546.2 |
| 53 | 6-(1-((2,6-diethoxy-4'-fluorobiphenyl-4-yl)methyl)piperidin-4-yl)-5-oxo-5,6,7,8-tetrahydro-1,6-naphthyridine-2-carboxylic acid | 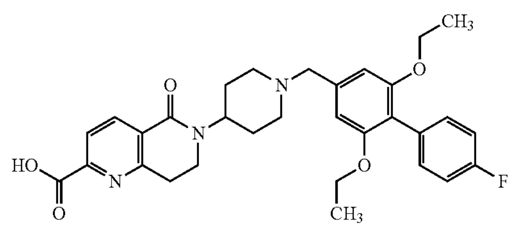 [SMILES: CCOc1cc(CN2CCC(N3CCc4nc(C(=O)O)ccc4C3=O)CC2)cc(OCC)c1-c1ccc(F)cc1] | 548.4 |
| 54 | 6-(1-((2-cyclopropyl-5-ethoxy-4'-fluorobiphenyl-4-yl)methyl)piperidin-4-yl)-5-oxo-5,6,7,8-tetrahydro-1,6-naphthyridine-2-carboxylic acid | 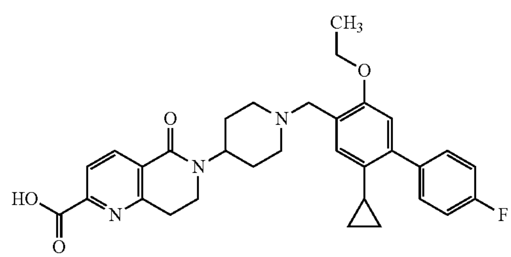 [SMILES: CCOc1cc(-c2ccc(F)cc2)c(C2CC2)cc1CN1CCC(N2CCc3nc(C(=O)O)ccc3C2=O)CC1] | 544.4 |
| 55 | 6-(1-((5-cyclopropyl-6-(4-fluorophenyl)-2-isopropoxypyridin-3-yl)methyl)piperidin-4-yl)-5-oxo-5,6,7,8-tetrahydro-1,6-naphthyridine-2-carboxylic acid | 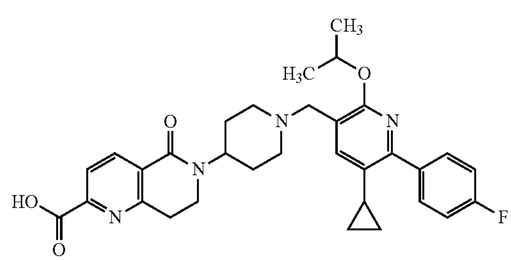 [SMILES: CC(C)Oc1nc(-c2ccc(F)cc2)c(C2CC2)cc1CN1CCC(N2CCc3nc(C(=O)O)ccc3C2=O)CC1] | 559.5 |
| 56 | 6-(1-((2-cyclopropyl-4'-fluoro-5-isopropoxybiphenyl-4-yl)methyl)piperidin-4-yl)-5-oxo-5,6,7,8-tetrahydro-1,6-naphthyridine-2-carboxylic acid | 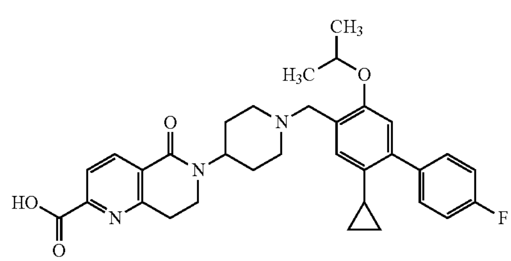 | 558.5 |

TABLE 1-continued

| Example # | IUPAC NAME | Structure | MS |
|---|---|---|---|
| 57 | 6-(1-((2-cyclopropyl-4'-fluoro-5-methoxybiphenyl-4-yl)methyl)piperidin-4-yl)-5-oxo-5,6,7,8-tetrahydro-1,6-naphthyridine-2-carboxylic acid | 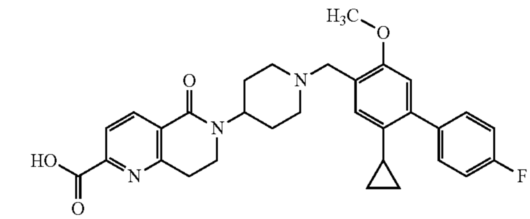 [SMILES: COc1cc(-c2ccc(F)cc2)c(C2CC2)cc1CN1CCC(N2CCc3nc(C(=O)O)ccc3C2=O)CC1] | 530.4 |
| 58 | 6-(1-((5-cyclopropyl-2-ethoxy-6-(4-fluorophenyl)pyridin-3-yl)methyl)piperidin-4-yl)-5-oxo-5,6,7,8-tetrahydro-1,6-naphthyridine-2-carboxylic acid | 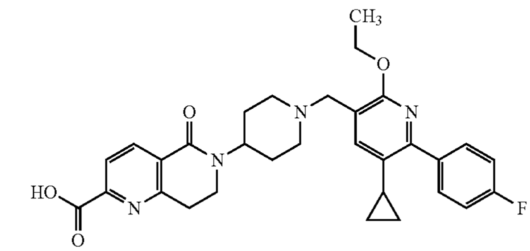 | 545.4 |
| 59 | 6-(1-((2-cyclopropyl-6-ethoxy-4'-fluorobiphenyl-4-yl)methyl)piperidin-4-yl)-5-oxo-5,6,7,8-tetrahydro-1,6-naphthyridine-2-carboxylic acid | 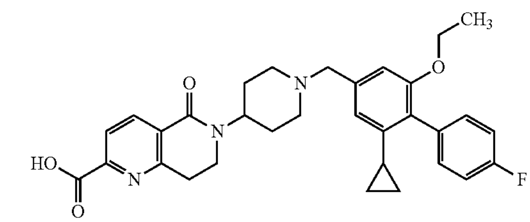 [SMILES: CCOc1cc(CN2CCC(N3CCc4nc(C(=O)O)ccc4C3=O)CC2)cc(C2CC2)c1-c1ccc(F)cc1] | 544.5 |
| 60 | methyl 6-(1-((2,6-diethoxy-4'-fluorobiphenyl-4-yl)methyl)piperidin-4-yl)-5-oxo-5,6,7,8-tetrahydro-5H-pyrido[3,2-c]azepine-2-carboxylate | 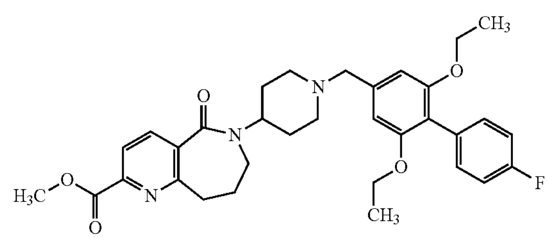 [SMILES: CCOc1cc(CN2CCC(N3CCCc4nc(C(=O)OC)ccc4C3=O)CC2)cc(OCC)c1-c1ccc(F)cc1] | 576.4 |
| 61 | 6-(1-((2-cyclopropyl-4'-fluoro-6-propoxybiphenyl-4-yl)methyl)piperidin-4-yl)-5-oxo-2-propyl-5,6,7,8-tetrahydro-1,6-naphthyridine-3-carboxylic acid | 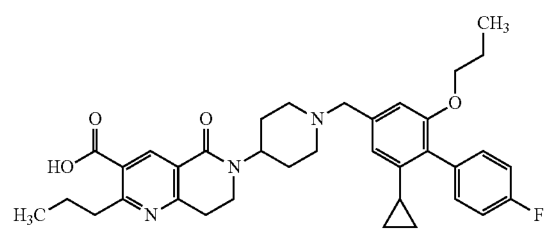 [SMILES: CCCOc1cc(CN2CCC(N3CCc4nc(CCC)c(C(=O)O)cc4C3=O)CC2)cc(C2CC2)c1-c1ccc(F)cc1] | 600.1 |
| 62 | 6-(1-((2-cyclopropyl-6-ethoxy-3',4'-difluorobiphenyl-4-yl)methyl)piperidin-4-yl)-5-oxo-2-propyl-5,6,7,8-tetrahydro-1,6-naphthyridine-3-carboxylic acid | 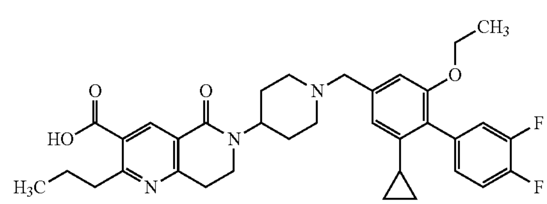 [SMILES: CCCc1nc2c(cc1C(=O)O)C(=O)N(C1CCN(Cc3cc(OCC)c(-c4ccc(F)c(F)c4)c(C4CC4)c3)CC1)CC2] | 604.2 |
| 63 | 6-(1-((2-cyclopropyl-4'-fluoro-6-isopropoxybiphenyl-4-yl)methyl)piperidin-4-yl)-5-oxo-2-propyl-5,6,7,8-tetrahydro-1,6-naphthyridine-3-carboxylic acid | 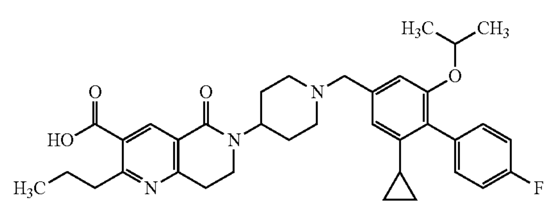 [SMILES: CCCc1nc2c(cc1C(=O)O)C(=O)N(C1CCN(Cc3cc(OC(C)C)c(-c4ccc(F)cc4)c(C4CC4)c3)CC1)CC2] | 600.2 |

TABLE 1-continued

| Example # | IUPAC NAME | Structure | MS |
|---|---|---|---|
| 64 | 6-(1-((2-cyclopropyl-6-ethoxy-2',4'-difluorobiphenyl-4-yl)methyl)piperidin-4-yl)-5-oxo-2-propyl-5,6,7,8-tetrahydro-1,6-naphthyridine-3-carboxylic acid | 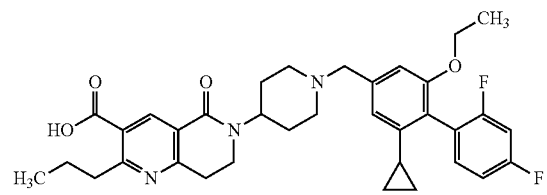 [SMILES: CCCc1nc2c(cc1C(=O)O)C(=O)N(C1CCN(Cc3cc(OCC)c(-c4ccc(F)cc4F)c(C4CC4)c3)CC1)CC2] | 604.3 |
| 65 | 6-(1-((6-cyclopropyl-2,2',4'-trifluoro-3-methoxybiphenyl-4-yl)methyl)piperidin-4-yl)-5-oxo-2-propyl-5,6,7,8-tetrahydro-1,6-naphthyridine-3-carboxylic acid | 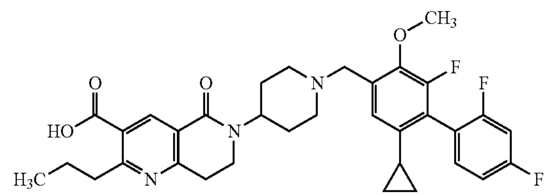 [SMILES: CCCc1nc2c(cc1C(=O)O)C(=O)N(C1CCN(Cc3cc(C4CC4)c(-c4ccc(F)cc4F)c(F)c3OC)CC1)CC2] | 608.1 |
| 66 | 6-(1-((2-chloro-6-cyclopropyl-2',4'-difluoro-3-methoxybiphenyl-4-yl)methyl)piperidin-4-yl)-2-ethyl-5-oxo-5,6,7,8-tetrahydro-1,6-naphthyridine-3-carboxylic acid | 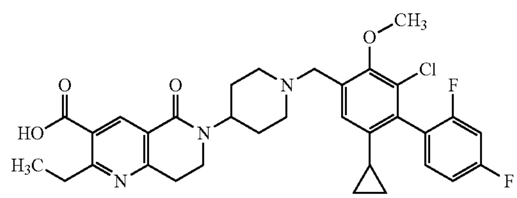 | 610.1 |
| 67 | 6-(1-((6-cyclopropyl-3-ethoxy-2,4'-difluorobiphenyl-4-yl)methyl)piperidin-4-yl)-5-oxo-2-propyl-5,6,7,8-tetrahydro-1,6-naphthyridine-3-carboxylic acid | 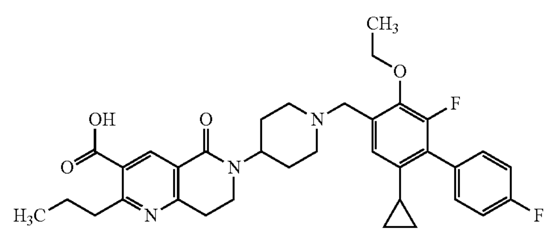 [SMILES: CCCc1nc2c(cc1C(=O)O)C(=O)N(C1CCN(Cc3cc(C4CC4)c(-c4ccc(F)cc4)c(F)c3OCC)CC1)CC2] | 604.3 |
| 68 | 6-(1-((6-cyclopropyl-3-ethoxy-2,4'-difluorobiphenyl-4-yl)methyl)piperidin-4-yl)-2-methyl-5-oxo-5,6,7,8-tetrahydro-1,6-naphthyridine-3-carboxylic acid | 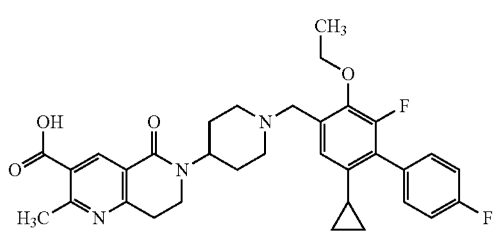 [SMILES: CCOc1c(CN2CCC(N3CCc4nc(C)c(C(=O)O)cc4C3=O)CC2)cc(C2CC2)c(-c2ccc(F)cc2)c1F] | 576.1 |
| 69 | 6-(1-((2,6-diethoxy-2',4'-difluorobiphenyl-4-yl)methyl)piperidin-4-yl)-5-oxo-2-propyl-5,6,7,8-tetrahydro-1,6-naphthyridine-3-carboxylic acid | 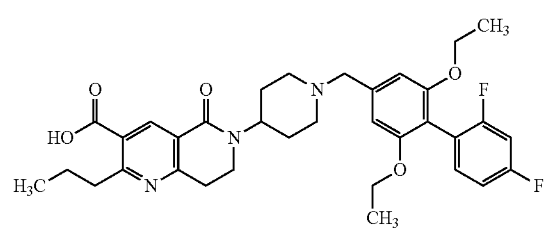 [SMILES: CCCc1nc2c(cc1C(=O)O)C(=O)N(C1CCN(Cc3cc(OCC)c(-c4ccc(F)cc4F)c(OCC)c3)CC1)CC2] | 608.2 |
| 70 | 6-(1-((6-diethoxy-2,2',4'-trifluoro-3-methoxybiphenyl-4-yl)methyl)piperidin-4-yl)-2-ethyl-5-oxo-5,6,7,8-tetrahydro-1,6-naphthyridine-3-carboxylic acid | 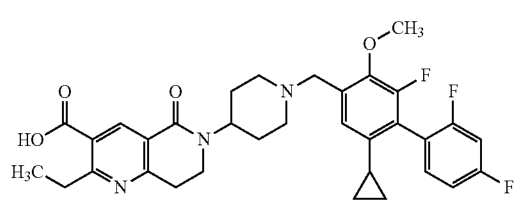 [SMILES: CCc1nc2c(cc1C(=O)O)C(=O)N(C1CCN(Cc3cc(C4CC4)c(-c4ccc(F)cc4F)c(F)c3OC)CC1)CC2] | 594.1 |

TABLE 1-continued

| Example # | IUPAC NAME | Structure | MS |
|---|---|---|---|
| 71 | 6-(1-((6-cyclopropyl-3-ethoxy-2,2',4'-trifluorobiphenyl-4-yl)methyl)piperidin-4-yl)-2-ethyl-5-oxo-5,6,7,8-tetrahydro-1,6-naphthyridine-3-carboxylic acid | 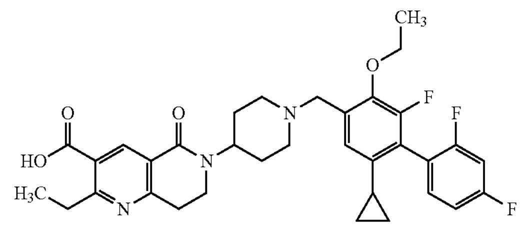 [SMILES: CCOc1c(CN2CCC(N3CCc4nc(CC)c(C(=O)O)cc4C3=O)CC2)cc(C2CC2)c(-c2ccc(F)cc2F)c1F] | 608.2 |
| 72 | 6-(1-((6-cyclopropyl-2,4'-difluoro-3-isopropoxybiphenyl-4-yl)methyl)piperidin-4-yl)-2-ethyl-5-oxo-5,6,7,8-tetrahydro-1,6-naphthyridine-3-carboxylic acid | 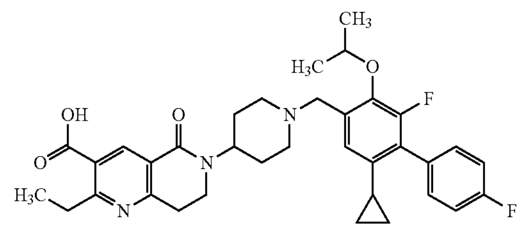 [SMILES: CCc1nc2c(cc1C(=O)O)C(=O)N(C1CCN(Cc3cc(C4CC4)c(-c4ccc(F)cc4)c(F)c3OC(C)C)CC1)CC2] | 604.3 |
| 73 | 6-(1-((6-cyclopropyl-2,4'-difluoro-3-isopropoxybiphenyl-4-yl)methyl)piperidin-4-yl)-2-methyl-5-oxo-5,6,7,8-tetrahydro-1,6-naphthyridine-3-carboxylic acid | 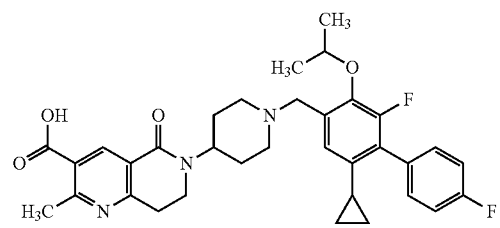 [SMILES: Cc1nc2c(cc1C(=O)O)C(=O)N(C1CCN(Cc3cc(C4CC4)c(-c4ccc(F)cc4)c(F)c3OC(C)C)CC1)CC2] | 590.2 |
| 74 | 6-(1-((6-cyclopropyl-3-ethoxy-2,4'-difluorobiphenyl-4-yl)methyl)piperidin-4-yl)-2-ethyl-5-oxo-5,6,7,8-tetrahydro-1,6-naphthyridine-3-carboxylic acid | 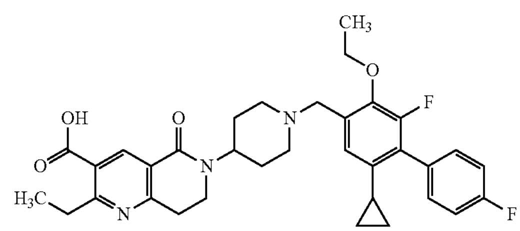 [SMILES: CCOc1c(CN2CCC(N3CCc4nc(CC)c(C(=O)O)cc4C3=O)CC2)cc(C2CC2)c(-c2ccc(F)cc2)c1F] | 590.2 |
| 75 | 6-(1-((6-cyclopropyl-2,4'-difluoro-3-isopropoxybiphenyl-4-yl)methyl)piperidin-4-yl)-5-oxo-2-propyl-5,6,7,8-tetrahydro-1,6-naphthyridine-3-carboxylic acid | 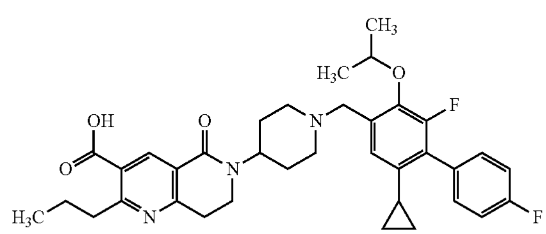 [SMILES: CCCc1nc2c(cc1C(=O)O)C(=O)N(C1CCN(Cc3cc(C4CC4)c(-c4ccc(F)cc4)c(F)c3OC(C)C)CC1)CC2] | 618.2 |
| 76 | 6-(1-((2-cyclopropyl-5-ethoxy-2'-fluorobiphenyl-4-yl)methyl)piperidin-4-yl)-5-oxo-2-propyl-5,6,7,8-tetrahydro-1,6-naphthyridine-3-carboxylic acid | 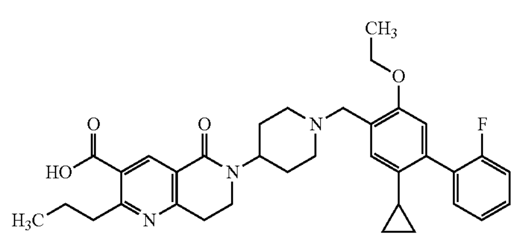 [SMILES: CCCc1nc2c(cc1C(=O)O)C(=O)N(C1CCN(Cc3cc(C4CC4)c(-c4ccccc4F)cc3OCC)CC1)CC2] | 586.2 |

TABLE 1-continued

| Example # | IUPAC NAME | Structure | MS |
|---|---|---|---|
| 77 | 6-(1-((2-chloro-6-cyclopropyl-3-ethoxy-2',4'-difluorobiphenyl-4-yl)methyl)piperidin-4-yl)-2-methyl-5-oxo-5,6,7,8-tetrahydro-1,6-naphthyridine-3-carboxylic acid | 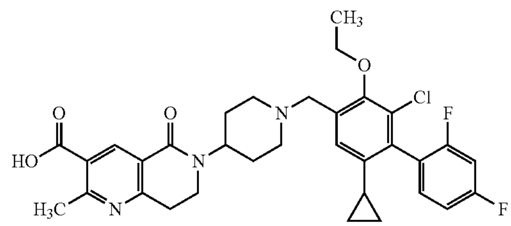 [SMILES: CCOc1c(CN2CCC(N3CCc4nc(C)c(C(=O)O)cc4C3=O)CC2)cc(C2CC2)c(-c2ccc(F)cc2F)c1Cl] | 610.1 |
| 78 | 6-(1-((2-cyclopropyl-5-ethoxy-3'-fluorobiphenyl-4-yl)methyl)piperidin-4-yl)-5-oxo-2-propyl-5,6,7,8-tetrahydro-1,6-naphthyridine-3-carboxylic acid | 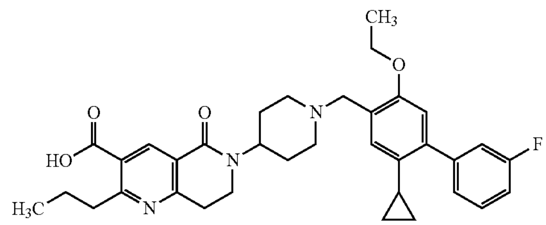 [SMILES: CCCc1nc2c(cc1C(=O)O)C(=O)N(C1CCN(Cc3cc(C4CC4)c(-c4cccc(F)c4)cc3OCC)CC1)CC2] | 586.2 |
| 79 | 6-(1-((2-cyclopropyl-5-ethoxy-2'-methoxybiphenyl-4-yl)methyl)piperidin-4-yl)-5-oxo-2-propyl-5,6,7,8-tetrahydro-1,6-naphthyridine-3-carboxylic acid | 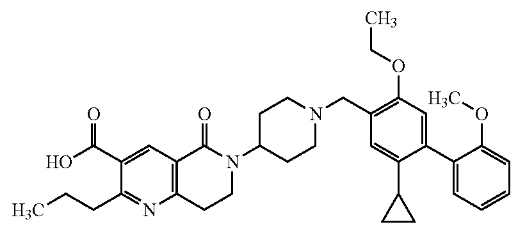 [SMILES: CCCc1nc2c(cc1C(=O)O)C(=O)N(C1CCN(Cc3cc(C4CC4)c(-c4ccccc4OC)cc3OCC)CC1)CC2] | 598.2 |
| 80 | 6-(1-((2-cyclopropyl-5-ethoxybiphenyl-4-yl)methyl)piperidin-4-yl)-5-oxo-2-propyl-5,6,7,8-tetrahydro-1,6-naphthyridine-3-carboxylic acid | 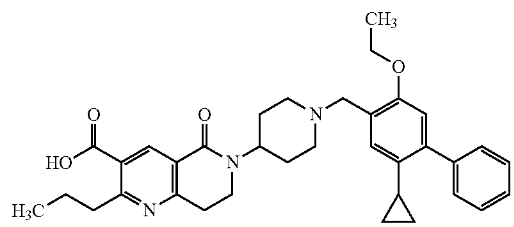 [SMILES: CCCc1nc2c(cc1C(=O)O)C(=O)N(C1CCN(Cc3cc(C4CC4)c(-c4ccccc4)cc3OCC)CC1)CC2] | 568.2 |
| 81 | 6-(1-((6-cyclopropyl-2,4'-difluoro-3-methoxybiphenyl-4-yl)methyl)piperidin-4-yl)-5-oxo-2-propyl-5,6,7,8-tetrahydro-1,6-naphthyridine-3-carboxylic acid | 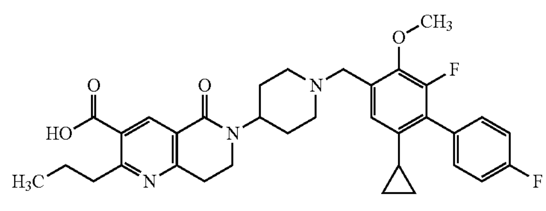 [SMILES: CCCc1nc2c(cc1C(=O)O)C(=O)N(C1CCN(Cc3cc(C4CC4)c(-c4ccc(F)cc4)c(F)c3OC)CC1)CC2] | 590.2 |
| 82 | 6-(1-(5-cyclopropyl-2-ethoxy-4-(pyridin-2-yl)benzyl)piperidin-4-yl)-5-oxo-2-propyl-5,6,7,8-tetrahydro-1,6-naphthyridine-3-carboxylic acid | 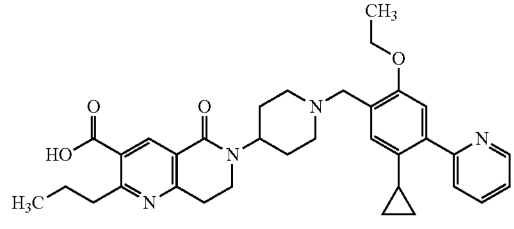 [SMILES: CCCc1nc2c(cc1C(=O)O)C(=O)N(C1CCN(Cc3cc(C4CC4)c(-c4ccccn4)cc3OCC)CC1)CC2] | 569.1 |
| 83 | 6-(1-((2-cyclopropyl-5-ethoxy-2',4'-difluorobiphenyl-4-yl)methyl)piperidin-4-yl)-5-oxo-2-propyl-5,6,7,8-tetrahydro-1,6-naphthyridine-3-carboxylic acid | 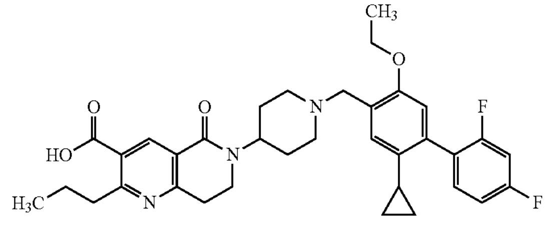 [SMILES: CCCc1nc2c(cc1C(=O)O)C(=O)N(C1CCN(Cc3cc(C4CC4)c(-c4ccc(F)cc4F)cc3OCC)CC1)CC2] | 604.3 |

TABLE 1-continued

| Example # | IUPAC NAME | Structure | MS |
|---|---|---|---|
| 84 | 6-(1-((2-cyclopropyl-5-ethoxy-2',4'-difluorobiphenyl-4-yl)methyl)piperidin-4-yl)-5-oxo-2-propyl-5,6,7,8-tetrahydro-1,6-naphthyridine-3-carboxylic acid ½ fumarate | 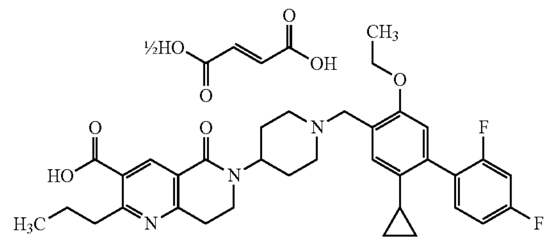 | 604.3 |
| 85 | 6-(1-((2-cyclopropyl-5-ethoxy-2',4'-difluorobiphenyl-4-yl)methyl)piperidin-4-yl)-5-oxo-2-propyl-5,6,7,8-tetrahydro-1,6-naphthyridine-3-carboxylic acid maleate | 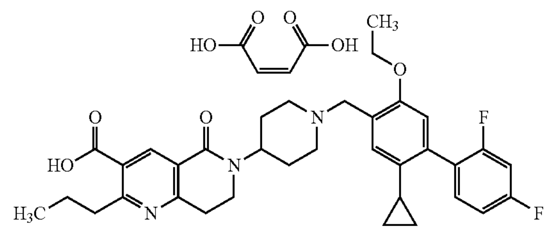 | 604.3 |

Test Example 1

Evaluation of Human SSTR5 Antagonist Activity Using Intracellular cAMP Concentration as Index The intracellular cAMP concentration was measured using HTRF cAMP dynamic 2 kit (Cisbio Bioassays). Each test compound diluted with an assay buffer (HBSS (Invitrogen Corp.) containing 5 mM HEPES (pH 7.5) (Invitrogen Corp.), 0.1% fatty-acid free BSA (Sigma-Aldrich Corp.), and 500 µM IBMX (Wako Pure Chemical Industries, Ltd.)) was added at a concentration of 2 µL/well to a 384-well white plate (Greiner Bio-One Co., Ltd.) to give the final concentration of 1 µM. A frozen stock of CHO (dhfr–) cells stably expressing the human SSTR5 gene (Accession No. NM_001053) was thawed in a thermostat bath of 37° C. and suspended in a subculture medium (MEM alpha (Wako Pure Chemical Industries, Ltd.), 10% dialyzed serum (Gemini Bio-Products), and 50 µg/mL gentamicin (Invitrogen Corp.). After centrifugation of the cell suspension, the cells were resuspended in an assay buffer and added at a concentration of 2 µL/well (about 4,000 cells/well) to the plate. The compound and the cells were incubated for 15 minutes, and then, an assay buffer containing 0.1 nM (final concentration) somatostatin 28 (Toray Research Center) and 0.3 µM (final concentration) forskolin (Wako Pure Chemical Industries, Ltd.) was added thereto at a concentration of 2 µL/well, followed by incubation at room temperature for 30 minutes. cAMP-d2 and anti-cAMP-cryptate were each added thereto at a concentration of 3 µL/well. The plate was left standing at room temperature for 60 minutes. Then, the fluorescence resonance energy transfer (FRET) intensity was measured using Multi-label reader Envision (PerkinElmer). The FRET intensity of the wells supplemented with the test compound group was converted to a cAMP concentration using a calibration curve prepared from the FRET intensity of a well group containing an assay buffer supplemented with an arbitrary concentration of cAMP. The inhibitory activity of each compound was calculated according to the following expression:

Inhibitory activity (%)=(C−B)/(A−B)×100

A: cAMP concentration calculated from the wells supplemented with 0.3 µM forskolin
B: cAMP concentration calculated from the wells supplemented with 0.3 µM forskolin and 0.1 nM somatostatin 28
C: cAMP concentration calculated from the wells supplemented with 0.3 µM forskolin, 0.1 nM somatostatin 28, and 1 µM test compound Table 2 shows the inhibition rate (%) against SSTR5 at the concentration 1 µM of the test compound.

TABLE 2

| Example No. | Inhibition rate against SSTR5 at 1 µM |
|---|---|
| 1 | 91 |
| 2 | 86 |
| 3 | 115 |
| 4 | 87 |
| 5 | 132 |
| 6 | 88 |
| 7 | 88 |
| 8 | 97 |
| 30 | 110 |
| 31 | 118 |
| 33 | 123 |
| 34 | 102 |
| 35 | 125 |
| 36 | 94 |
| 37 | 97 |
| 38 | 97 |
| 39 | 112 |
| 40 | 148 |
| 41 | 99 |
| 42 | 136 |
| 43 | 95 |
| 44 | 111 |
| 45 | 99 |
| 46 | 86 |
| 47 | 106 |
| 48 | 99 |
| 49 | 91 |
| 50 | 99 |
| 51 | 103 |
| 52 | 114 |
| 53 | 108 |
| 54 | 123 |
| 61 | 96 |

TABLE 2-continued

| Example No. | Inhibition rate against SSTR5 at 1 μM |
|---|---|
| 62 | 92 |
| 63 | 97 |
| 64 | 89 |
| 65 | 86 |
| 66 | 64 |
| 67 | 85 |
| 72 | 97 |
| 74 | 95 |
| 81 | 82 |

As is evident from Table 2, the compound of the present invention exhibited a superior SSTR5 antagonist action.

Test Example 2

Glucose Tolerance Test in Mice

Oral glucose tolerance test was performed in high fat diet-fed male C57BL6J mice (Clea Japan Inc.). 8 weeks old mice were fasted overnight and divided into separate groups (n=6) based on plasma glucose levels and body weight. Vehicle (0.5% (w/v) methylcellulose) or the compound of Example 72 (1 mg/kg) (suspended in vehicle) were orally given to animals and glucose was loaded (5 g/kg) 1 h after drug administration. Blood was collected from tail vein and blood glucose levels (mg/dL) were measured by ACCU-CHEK (Roche Inc.) at time 0 (just before glucose load), 10, 30, 60 and 120 min after glucose load.

TABLE 3

| Group | 0 min | 10 min | 30 min | 60 min | 120 min | $AUC_{pre-120\,min}$ |
|---|---|---|---|---|---|---|
| vehicle | 148 | 301 | 449 | 445 | 186 | 701 |
| Example 72 | 123 | 283 | 269 | 267 | 140 | 463 |

As is evident from Table 3, the compound of the present invention exhibited a superior blood glucose lowering action.

Test Example 3

Antidiabetic Effect in Mice (1)

Male KK-Ay/Ta mice (Clea Japan Inc.), a type 2 diabetes model, were used in this study. At the age of 7-week old, blood samples were collected from tail vein at 8:00 am, and animals were divided into separate groups (n=8) based on glycated hemoglobin (GHb), plasma glucose, insulin, triglyceride levels and body weight. Vehicle (0.5% (w/v) methylcellulose) or the compound of Example 67 (10 mg/kg) (suspended in vehicle) were orally administered once a day for 2 weeks. After 2 weeks of treatment, GHb was determined by auto-analyzer HLC-723G8 (TOSOH, Japan).

TABLE 4

| Group | Average of delta GHb (%) |
|---|---|
| vehicle | 0.93 |
| Example 67 | 0.40 |

As is evident from Table 4, the compound of the present invention exhibited a superior antidiabetic effect (GHb lowering action).

Test Example 4

Antidiabetic Effect in Mice (2)

Male KK-Ay/Ta mice (Clea Japan Inc.), a type 2 diabetes model, were used in this study. At the age of 7-week old, blood samples were collected from tail vein at 8:00 am, and animals were divided into separate groups (n=7) based on glycated hemoglobin (GHb), plasma glucose, insulin, triglyceride levels and body weight. The Compound of Example 35 (0.03% (weight % of the compound in the food admixture)) was administered by food admixture with CE-2 diet (Clea Japan Inc.) for 2 weeks. After 2 weeks of treatment, GHb was determined by auto-analyzer HLC-723G8 (TOSOH, Japan).

TABLE 5

| Group | Average of delta GHb (%) |
|---|---|
| vehicle | 1.31 |
| Example 35 | 0.60 |

As is evident from Table 5, the compound of the present invention exhibited a superior antidiabetic effect (GHb lowering action).

Formulation Example 1

Production of Capsule

| 1) Compound of Example 1 | 30 mg |
|---|---|
| 2) Fine cellulose powder | 10 mg |
| 3) Lactose | 19 mg |
| 4) Magnesium stearate | 1 mg |
| Total: | 60 mg |

Ingredients 1), 2), 3), and 4) are mixed and filled in a gelatin capsule shell.

Formulation Example 2

Production of Tablet

| 1) Compound of Example 1 | 30 g |
|---|---|
| 2) Lactose | 50 g |
| 3) Corn starch | 15 g |
| 4) Carboxymethylcellulose calcium | 44 g |
| 5) Magnesium stearate | 1 g |
| Total of 1000 tablets: | 140 g |

The whole amounts of ingredients 1), 2), and 3) and 30 g of ingredient 4) are kneaded with water and granulated after vacuum drying. The granulated powders are mixed with 14 g of ingredient 4) and 1 g of ingredient 5). The mixture is compressed using a tableting machine. In this way, 1000 tablets each containing 30 mg of the compound of Example 1 are obtained.

INDUSTRIAL APPLICABILITY

The compound of the present invention has a somatostatin receptor subtype 5 antagonist action and is useful in the prophylaxis or treatment of diabetes mellitus, obesity, and the like.

All the publications, patents, and the patent applications cited herein are incorporated herein by reference in their entireties.

The invention claimed is:

1. A compound selected from the group consisting of
6-(1-((2-cyclopropyl-5-ethoxy-2',4'-difluorobiphenyl-4-yl)methyl)piperidin-4-yl)-5-oxo-2-propyl-5,6,7,8-tetrahydro-1,6-naphthyridine-3-carboxylic acid,
6-(1-((6-cyclopropyl-3-ethoxy-2,4'-difluorobiphenyl-4-yl)methyl)piperidin-4-yl)-5-oxo-2-propyl-5,6,7,8-tetrahydro-1,6-naphthyridine-3-carboxylic acid,
6-(1-((6-cyclopropyl-2,4'-difluoro-3-isopropoxybiphenyl-4-yl)methyl)piperidin-4-yl)-2-ethyl-5-oxo-5,6,7,8-tetrahydro-1,6-naphthyridine-3-carboxylic acid, and
6-(1-((6-cyclopropyl-3-ethoxy-2,4'-difluorobiphenyl-4-yl)methyl)piperidin-4-yl)-2-ethyl-5-oxo-5,6,7,8-tetrahydro-1,6-naphthyridine-3-carboxylic acid,
or a salt thereof.

2. 6-(1-((2-Cyclopropyl-5-ethoxy-2',4'-difluorobiphenyl-4-yl)methyl)piperidin-4-yl)-5-oxo-2-propyl-5,6,7,8-tetrahydro-1,6-naphthyridine-3-carboxylic acid or a salt thereof.

3. 6-(1-((6-Cyclopropyl-3-ethoxy-2,4'-difluorobiphenyl-4-yl)methyl)piperidin-4-yl)-5-oxo-2-propyl-5,6,7,8-tetrahydro-1,6-naphthyridine-3-carboxylic acid or a salt thereof.

4. 6-(1-((6-Cyclopropyl-2,4'-difluoro-3-isopropoxybiphenyl-4-yl)methyl)piperidin-4-yl)-2-ethyl-5-oxo-5,6,7,8-tetrahydro-1,6-naphthyridine-3-carboxylic acid or a salt thereof.

5. 6-(1-((6-Cyclopropyl-3-ethoxy-2,4'-difluorobiphenyl-4-yl)methyl)piperidin-4-yl)-2-ethyl-5-oxo-5,6,7,8-tetrahydro-1,6-naphthyridine-3-carboxylic acid or a salt thereof.

6. A medicament comprising the compound of claim 1 or a salt thereof.

7. A method for treating diabetes mellitus in a mammal, comprising administering to the mammal an effective amount of the compound according to claim 1 or a salt thereof.

8. A method for antagonizing somatostatin receptor subtype 5 in a mammal, comprising administering to the mammal an effective amount of the compound according to claim 1 or a salt thereof.

* * * * *